United States Patent
Douty et al.

(10) Patent No.: US 10,738,057 B2
(45) Date of Patent: Aug. 11, 2020

(54) TERTIARY ALCOHOLS AS PI3K-γ INHIBITORS

(71) Applicant: Incyte Corporation, Wilmington, DE (US)

(72) Inventors: Brent Douty, Fallowfield, PA (US); Andrew W. Buesking, Wilmington, DE (US); David M. Burns, Plymouth Meeting, PA (US); Andrew P. Combs, Kennett Square, PA (US); Nikoo Falahatpisheh, Wilmington, DE (US); Ravi Kumar Jalluri, Avondale, PA (US); Daniel Levy, Philadelphia, PA (US); Padmaja Polam, Kennett Square, PA (US); Lixin Shao, Wilmington, DE (US); Stacey Shepard, Wilmington, DE (US); Artem Shvartsbart, Kennett Square, PA (US); Richard B. Sparks, Wilmington, DE (US); Eddy W. Yue, Landenberg, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 16/163,341

(22) Filed: Oct. 17, 2018

(65) Prior Publication Data

US 2019/0152975 A1    May 23, 2019

Related U.S. Application Data

(60) Provisional application No. 62/574,057, filed on Oct. 18, 2017, provisional application No. 62/608,897, filed on Dec. 21, 2017, provisional application No. 62/727,316, filed on Sep. 5, 2018.

(51) Int. Cl.
```
C07D 487/04    (2006.01)
A61P 35/00     (2006.01)
A61P 25/28     (2006.01)
```
(52) U.S. Cl.
CPC ............ C07D 487/04 (2013.01); A61P 25/28 (2018.01); A61P 35/00 (2018.01); *C07B 2200/07* (2013.01); *C07B 2200/13* (2013.01)

(58) Field of Classification Search
CPC ...... A61P 25/28; A61P 35/00; C07B 2200/07; C07B 2200/13; C07D 487/04
See application file for complete search history.

(56) References Cited

U.S. PATENT DOCUMENTS

| | | | |
|---|---|---|---|
| 4,269,846 A | 5/1981 | Huang et al. | |
| 5,137,876 A | 8/1992 | MacCoss et al. | |
| 5,521,184 A | 5/1996 | Zimmermann | |
| 7,186,832 B2 | 3/2007 | Sun | |
| 7,511,145 B2 | 3/2009 | Schmitz et al. | |
| 8,329,697 B2 | 12/2012 | Garbaccio et al. | |
| 8,680,108 B2 | 3/2014 | Li et al. | |
| 8,759,359 B2 | 6/2014 | Combs et al. | |
| 8,940,752 B2 | 1/2015 | Li et al. | |
| 9,062,055 B2 | 6/2015 | Li et al. | |
| 9,096,600 B2 | 8/2015 | Li et al. | |
| 9,108,984 B2 | 8/2015 | Combs et al. | |
| 9,126,948 B2 | 9/2015 | Combs et al. | |
| 9,193,721 B2 | 11/2015 | Combs et al. | |
| 9,199,982 B2 | 12/2015 | Li et al. | |
| 9,586,949 B2 | 3/2017 | Zou et al. | |
| 10,022,387 B2 | 7/2018 | Zou et al. | |
| 10,065,963 B2 | 9/2018 | Shvartsbart et al. | |
| 10,138,248 B2 | 11/2018 | Buesking et al. | |
| 10,472,368 B2 | 11/2019 | Shvartsbart et al. | |
| 10,479,795 B2 | 11/2019 | Buesking et al. | |
| 2004/0220189 A1 | 11/2004 | Sun et al. | |
| 2005/0009832 A1 | 1/2005 | Sun et al. | |
| 2007/0099925 A1 | 5/2007 | Calderwood et al. | |
| 2007/0225286 A1 | 9/2007 | Ren et al. | |

(Continued)

FOREIGN PATENT DOCUMENTS

| | | |
|---|---|---|
| EP | 2044051 | 1/2010 |
| WO | WO 00/009495 | 2/2000 |

(Continued)

OTHER PUBLICATIONS

Atzrodt et al., "The Renaissance of H/D Exchange," Angew Chem Int Ed., Oct. 4, 2007, 46(41):7744-7765.

(Continued)

*Primary Examiner* — Erich A Leeser
(74) *Attorney, Agent, or Firm* — Fish & Richardson P.C.

(57) ABSTRACT

This application relates to compounds of Formula (I):

(I)

or pharmaceutically acceptable salts thereof, which are inhibitors of PI3K-γ which are useful for the treatment of disorders such as autoimmune diseases, cancer, cardiovascular diseases, and neurodegenerative diseases.

38 Claims, 17 Drawing Sheets

(56) References Cited

U.S. PATENT DOCUMENTS

| | | |
|---|---|---|
| 2010/0298334 A1 | 11/2010 | Rodgers et al. |
| 2011/0015212 A1 | 1/2011 | Li et al. |
| 2011/0059951 A1 | 3/2011 | Rodgers et al. |
| 2011/0224190 A1 | 9/2011 | Huang et al. |
| 2012/0149681 A1 | 6/2012 | Rodgers et al. |
| 2012/0149682 A1 | 6/2012 | Rodgers et al. |
| 2012/0157430 A1 | 6/2012 | Li et al. |
| 2012/0238564 A1 | 9/2012 | Luk et al. |
| 2012/0329792 A1 | 12/2012 | Bartolome-Nebreda et al. |
| 2013/0018034 A1 | 1/2013 | Yao et al. |
| 2013/0045963 A1 | 2/2013 | Rodgers et al. |
| 2013/0059835 A1 | 3/2013 | Li et al. |
| 2013/0261101 A1 | 10/2013 | Combs et al. |
| 2014/0005166 A1 | 1/2014 | Rodgers et al. |
| 2014/0121198 A1 | 5/2014 | Li et al. |
| 2014/0249132 A1 | 9/2014 | Li et al. |
| 2014/0275127 A1 | 9/2014 | Combs et al. |
| 2014/0343030 A1 | 11/2014 | Li et al. |
| 2015/0005309 A1 | 1/2015 | Barfacker et al. |
| 2015/0284390 A1 | 10/2015 | Li et al. |
| 2015/0361094 A1 | 12/2015 | Li et al. |
| 2016/0000795 A1 | 1/2016 | Scherle et al. |
| 2016/0022685 A1 | 1/2016 | Li et al. |
| 2016/0024117 A1 | 1/2016 | Li et al. |
| 2017/0129899 A1 | 5/2017 | Shvartsbart et al. |
| 2017/0190689 A1 | 7/2017 | Sparks et al. |
| 2018/0009816 A1 | 1/2018 | Buesking et al. |
| 2018/0057469 A1 | 3/2018 | Wu et al. |
| 2019/0060331 A1 | 2/2019 | Zou et al. |
| 2019/0062336 A1 | 2/2019 | Shvartsbart et al. |
| 2019/0119287 A1 | 4/2019 | Buesking et al. |
| 2019/0359592 A1 | 11/2019 | Sparks et al. |
| 2020/0071335 A1 | 3/2020 | Douty et al. |

FOREIGN PATENT DOCUMENTS

| | | |
|---|---|---|
| WO | WO 00/053595 | 9/2000 |
| WO | WO 01/014402 | 3/2001 |
| WO | WO 01/064655 | 9/2001 |
| WO | WO 2001/085724 | 11/2001 |
| WO | WO 2002/000196 | 1/2002 |
| WO | WO 03/024967 | 3/2003 |
| WO | WO 03/037347 | 5/2003 |
| WO | WO 2003/035065 | 5/2003 |
| WO | WO 2003/035644 | 5/2003 |
| WO | WO 2003/068225 | 8/2003 |
| WO | WO 03/099771 | 12/2003 |
| WO | WO 2004/005281 | 1/2004 |
| WO | WO 2004/046120 | 6/2004 |
| WO | WO 2004/056786 | 7/2004 |
| WO | WO 2004/078943 | 9/2004 |
| WO | WO 2004/080980 | 9/2004 |
| WO | WO 2005/012288 | 2/2005 |
| WO | WO 2005/028444 | 3/2005 |
| WO | WO 2005/118580 | 12/2005 |
| WO | WO 2006/056399 | 6/2006 |
| WO | WO 2007/019416 | 2/2007 |
| WO | WO 2007/019417 | 2/2007 |
| WO | WO 2007/028051 | 3/2007 |
| WO | WO 2009/005551 | 1/2009 |
| WO | WO 2009/016118 | 2/2009 |
| WO | WO 2009/024585 | 2/2009 |
| WO | WO 2009/064835 | 5/2009 |
| WO | WO 2009/079011 | 6/2009 |
| WO | WO 2009/114512 | 9/2009 |
| WO | WO 2009/123776 | 10/2009 |
| WO | WO 2009/133127 | 11/2009 |
| WO | WO 2009/158118 | 12/2009 |
| WO | WO 2010/051245 | 5/2010 |
| WO | WO 2010/061903 | 6/2010 |
| WO | WO 2010/069684 | 6/2010 |
| WO | WO 2010/135014 | 11/2010 |
| WO | WO 2011/099832 | 8/2011 |
| WO | WO 2011/123609 | 10/2011 |
| WO | WO 2011/149856 | 12/2011 |
| WO | WO 2011/149874 | 12/2011 |
| WO | WO 2012/051410 | 4/2012 |
| WO | WO 2012/074126 | 6/2012 |
| WO | WO 2012/143796 | 10/2012 |
| WO | WO 2012/170867 | 12/2012 |
| WO | WO 2013/104610 | 7/2013 |
| WO | WO 2013/129674 | 9/2013 |
| WO | WO 2013/180193 | 12/2013 |
| WO | WO 2014/009295 | 1/2014 |
| WO | WO 2014/149207 | 9/2014 |
| WO | WO 2014/153529 | 9/2014 |
| WO | WO 2014/182954 | 11/2014 |
| WO | WO 2015/008872 | 1/2015 |
| WO | WO 2015/051241 | 4/2015 |
| WO | WO 2015/154878 | 10/2015 |
| WO | WO 2016/044342 | 3/2016 |
| WO | WO 2016/064957 | 4/2016 |
| WO | WO 2016/075130 | 5/2016 |
| WO | WO 2016/166239 | 10/2016 |
| WO | WO 2017/223414 | 12/2017 |
| WO | WO 2018/038265 | 3/2018 |

OTHER PUBLICATIONS

Bather et al., "PI3Kgamma inhibition blocks glomerulonephritis and extends lifespan in a mouse model of systemic lupus," Nat Medicine., Sep. 2005, 11(9):933-935.

Berge et al., "Pharmaceutical Salts", Journal of Pharmaceutical Science, 1977, 66(2):1-19.

Berod et al., "PI3Kγ deficiency delays the onset of experimental autoimmune encephalomyelitis and ameliorates its clinical outcome," Euro J Immunol., Mar. 2011, 41(3):833-844.

Blom et al., "Two-Pump at Column Dilution Configuration for Preparative LC-MS," J Comb. Chem., Jul.-Aug. 2002, 4(295):295-301.

Blomb et al., "Optimizing Preparative Lc-Ms Configurations and Methods for Parallel Synthesis Purification," J Comb Chem., 2003, 5(5):670-683.

Blom et al., "Preparative LC-MS Purification: Improved Compound Specific Method Optimization," J Comb Chem., 2004, 6(6):874-883.

Buesking et al., "Asymmetric Synthesis of Protected α-Amino Boronic Acid Derivatives with an Air- and Moisture-Stable Cu(II) Catalyst," J Org Chem., Mar. 31, 2014, 79(8):3671-3677.

Brock et al., "Roles of G beta gamma in membrane recruitment and activation of p110 gamma/p101 phosphoinositide 3-kinase gamma," J Biol Chem., Jan. 6, 2003, 160(1):89-99.

Bruneau et al., "2-Aminobiphenyl Palladacycles: The "Most Powerful" Precatalysts in C—C and C-Heteroatom Cross-Couplings," ACS Catal., 2015, 5(2):1386-1396.

Cantley, "The phosphoinositide 3-kinase pathway," Science, May 31, 2002, 296(5573):1655-1657.

Camps et al., "Blockade of PI3Kγ suppresses joint inflammation and damage in mouse models of rheumatoid arthritis," Nat Medicine., 2005, 11(9):939-943.

Carter et al., "Prioritization of driver mutations in pancreatic cancer using cancer-specific high-throughput annotation of somatic mutations (CHASM)," Cancer Biol Ther., Sep. 15, 2010, 10(6):582-587.

Choudhury-Mukherjee et al., "Design, synthesis, and evaluation of analogues of 3,3,3-trifluoro-2-hydroxy-2-phenyl-propionamide as orally available general anesthetics," J Med Chem, Jun. 5, 2003, 46(12):2494-2501.

Comerford et al., "PI3Kγ Drives Primin and Survival of Autoreactive CD4+ T Cells during Experimental Autoimmune Encephalomyelitis," PLOS one, Sep. 2012, 7(9):e450095.

Doukas et al., "Aerosolized phosphoinositide 3-kinase gamma/delta inhibitor TG100-115 [3-[2,4-diamino-6-(3-hydroxyphenyl)pteridin-7-yl]phenol] as a therapeutic candidate for asthma and chronic obstructive pulmonary disease," J Pharmacol Exp Ther., Mar. 2009, 328(3):758-765.

Doukas et al., "Phosphoinositide 3-kinase gamma/delta inhibition limits infarct size after myocardial ischemia/reperfusion injury," Proc Natl Acad Sci USA., Dec. 26, 2006, 103(52):19866-19871.

(56) References Cited

OTHER PUBLICATIONS

El Khoury et al., "Ccr2 deficiency impairs microglial accumulation and accelerates progression of Alzheimer-like disease," Nat Med, 2007, 13(4):432-438.
Falasca and Mufficci, Targeting p110gamma in gastrointestinal cancers: attack on multiple fronts, Frontiers in Physiology, Oct. 15, 2014, 5:1-10.
Garamvolgyi et al., "Design and Synthesis of new imidazo[1,2-a]pyridine and imidazo [1,2-A]pyrazine derivates with antiproliferative activity against melanoma cells," Eur J Med Chem., Jan. 27, 2018, 108:623-643.
Giri et al "Mechanism of amyloid peptide induced CCR5 expression in monocytes and its inhibition by siRNA for Egr-1," Am J Physiol Cell Physiol., Aug. 2005, 289:C264-C276.
Gonzalez-Garcia et al., "Phosphatidylinositol 3-kinase gamma inhibition ameliorates inflammation and tumor growth in a model of colitis-associated cancer," Gastroenterology, Apr. 2010, 138(4):1373-1384.
Hayer et al., "PI3Kgamma regulates cartilage damage in chronic inflammatory arthritis," FASB J, 2009, 23(12):4288-4298.
Hannahan and Weinberg, "Hallmarks of cancer: the next generation," Cell, Mar. 4, 2011, 144(5):646-674.
International Search Report and Written Opinion in International Application No. PCT/US2018/056311, dated Jan. 1, 2019, 14 pages.
Jimenez et al., "The p85 regulatory subunit controls sequential activation of phosphoinositide 3-kinase by Tyr kinases and Ras," J Biol Chem., Nov. 1, 2002, 277(44):41556-415562.
Kaneda et al., "Abstract 3650: PI3-kinase gamma controls the macrophage M1-M2 switch, thereby promoting tumor immunosuppression and progression," Presented at the Proceedings of the AACR Annual Meeting 2014, San Diego, CA, Apr. 5-9, 2014, Cancer Res., 74(Suppl 19): 2 pages.
Kerekes et al., "Aurora kinase inhibitors based on the imidazo[1,2-a]pyrazine core: fluorine and deuterium incorporation improve oral absorption and exposure," J Med Chem., Jan. 13, 2011, 54(1):201-210.
Kolb et al., "Catalytic Asymmetric Dihydroxylation," Chem Rev., 1994, 94(8):2483-2547.
Laffargue et al., "Phosphoinositide 3-kinase gamma is an essential amplifier of mast cell function," Immunity, 2002, 16(3):441-451.
Li et al., "PI3Kγ inhibition alleviates symptoms and increases axon number in experimental autoimmune encephalomyelitis mice," Neuroscience, 2013, 253:89-99.
Lupia et al., "Ablation of phosphoinositide 3-kinase-gamma reduces the severity of acute pancreatitis," Am J Pathology., Dec. 2004, 165(6):2003-2011.
Manning et al., "An innovative and efficient synthesis of stable isotope labelled 1-methyl-5-(4,4,5,5-tetramethyl-1,3,2-dioxaborolan-2-yl)-1H-pyrazole via [13C42H3] N-methylpyrazole," J Label Compd Radiopharm., Nov. 2012, 55(13):467-469.
Martin et al., "PI3Kγ mediates kaposi's sarcoma-associated herpesvirus vGPCR-induced sarcomagenesis," Cancer Cell, 2011, 19(6):805-813.
Moreno-Dorado et al., "Enantioselective synthesis of arylmethoxyacetic acid derivatives," Tetrahedron:Asymmetry, Feb. 21, 2003, 14(4):503-510.
Organic Synthesis, "Bromopropionic Acid," 1941, Coll. vol. 1, p. 131.
Organic Synthesis, "Glutaric Acid," 1941, Coll. vol. 1, p. 289.
Organic Synthesis, "Hydroxypropionic Acid," 1941, Coll. vol. 1, p. 321.
Passos et al., "Involvement of phosphoinositide 3-kinase gamma in the neuro-inflammatory response and cognitive impairments induced by beta-amyloid 1-40 peptide in mice," Brain Behav Immun, Mar. 2010, 24(3):493-501.
Pinho et al., "Phosphoinositide-3 kinases critically regulate the recruitment and survival of eosinophils in vivo: importance for the resolution of allergic inflammation," L Leukocyte Biology., May 2005, 77(5):800-810.

Prete et al., "Defective dendritic cell migration and activation of adaptive immunity in PI3Kgamma-deficient mice," The EMBO Journal, Sep. 1, 2004, 23(17):3505-3515.
Randis et al., "Role of PI3Kdelta and PI3Kgamma in inflammatory arthritis and tissue localization of neutrophils," Eur J Immunol., May 2008, 38(5):1215-1224.
Remington's Pharmaceutical Sciences, Mack Publishing Company, Easton, 1985, 17th ed., p. 1418.
Ruckle et al., "PI3Kgamma inhibition: towards an 'aspirin of the 21st century'?" Nat Rev Drug Discov., Nov. 2006, 5(11):903-918.
Ruiz-Castillo et al., "Applications of Palladium-Catalyzed C—N Cross-Coupling Reactions," Chem Rev., Oct. 12, 2016, 116(19):12564-12649.
Rodrigues et al., "Absence of PI3Kgamma leads to increased leukocyte apoptosis and diminished severity of experimental autoimmune encephalomyelitis," J Neuroimmunol, May 2010, 222(1-2):90-94.
Schmid et al., "Receptor tyrosine kinases and TLR/IL1Rs unexpectedly activate myeloid cell PI3kγ, a single convergent point promoting tumor inflammation and progression," Cancer Cell, 2011, 19:715-727.
Schmidt et al., "Abstract 411: PI3 Kinase gamma Control of Arginase-1 expression promotes tumor immunosupression," Cancer Res., Apr. 15, 2012, 72(Suppl 1).
Sharpless et al., "The osmium-catalyzed asymmetric dihydroxylation: a new ligand class and a process improvement," J Org. Chem., 1992, 57(10):2768-2771.
Subramaniam et al., "Targeting nonclassical oncogenes for therapy in T-ALL," Cancer Cell, 2012, 21(4):459-472.
Thomas et al., "Airway inflammation. chemokine-induced neutrophilia and the class I phosphoinositide 3-kinases," Eur J Immunol., Apr. 2005, 35(4):1283-1291.
Vanhaesebroeck et al., "Signalling by PI3K isoforms: insights from gene-targeted mice," Trends Biochem Sci, Apr. 2005, 30(4):194-204.
Vecchione et al., "Protection from angiotensin Ii-mediated vasculotoxic and hypertensive response in mice lacking PI3Kgamma," J Exp Med., 2005, 201:1217-1228.
Xu et al., "Design, synthesis and biological evaluation of deuterated nintedanib for improving pharmacokinetic properties," J Label Compd Radiopharma., Jun. 15, 2015, 58(7):308-312.
Winterfeldt "Applications of Diisobutylaluminium Hydride (DIBAH) and Triisobutylaluminium (TIBA) as Reducing Agents in Organic Synthesis," Synthesis 1975, 10:617-630.
Bala et al., "Highly efficient water-mediated approach to access benzazoles: metal catalyst and base-free synthesis of 2-substituted benzimidazoles, benzoxazoles, and benzothiazoles," Molecular Diversity, Mar. 2015, 19(2): 263-272.
Collier et al., "Discovery of Highly Isoform Selective Thiazolopiperidine Inhibitors of Phosphoinositide 3-Kinase γ," Journal of Medicinal Chemistry, Jul. 26, 2015, 58: 5684-5688.
Collier et al., "Structural Basis for Isoform Selectivity in a Class of Benzothiazole Inhibitors of Phosphoinositide 3-Kinase [gamma]," Journal of Medicinal Chemistry, Jan. 2015, 58(1): 517-521.
Cossy et al., "Formation of optically active 3-hydroxypiperidines," Tetrahedron Letters, Jan. 23, 1995, 36(4):549-552.
Cushing et al., "PI3Kδ and PI3Kγ as Targets for Autoimmune and Inflammatory Diseases," Journal of Medicinal Chemistry, Sep. 13, 2012, 55: 8559-8581.
Database Registry [online], Chemical Abstracts Service, Columbus, OH, US, Jun. 1, 2015, Chemical Catalog; Supplier: Aurora Fine Chemicals: XP002755361, Database Accession No. 1770353-29-1.
Database Registry [online], Chemical Abstracts Service, Columbus, OH, US, Jun. 4, 2015, Chemical Catalog; Supplier: Aurora Fine Chemicals: XP002755362, Database Accession No. 1773443-64-3.
Database Registry [online], Chemical Abstracts Service, Columbus, OH, US, May 29, 2015, Chemical Catalog; Supplier: Aurora Fine Chemicals: XP002755360, Database Accession No. 1715195-44-0.
Database Registry [online], Chemical Abstracts Service, Columbus, OH, US; Aug. 2012, CAS client services: XP002755356, Database accession No. 1391828-67-3.

(56) References Cited

OTHER PUBLICATIONS

Database Registry [online], Chemical Abstracts Service, Columbus, OH, US; Dec. 2011, Chemical Catalog; Supplier: Ukrorgsyntez ltd.: XP002755357, Database accession No. 1347088-145.
Database Registry [online], Chemical Abstracts Service, Columbus, OH, US; Dec. 2012, Chemical Catalog; Supplier: Aurora Fine Chemicals: XP002755355, Database accession No. 1411464-90-8.
Database Registry [online], Chemical Abstracts Service, Columbus, OH, US; Feb. 2014, Chemical Catalog; Supplier: Aurora Fine Chemicals: XP002755346, Database accession No. 1554931-95-1.
Database Registry [online], Chemical Abstracts Service, Columbus, OH, US; Feb. 2014, Chemical Catalog; Supplier: Aurora Fine Chemicals: XP002755347, Database accession No. 1540856-06-1.
Database Registry [online], Chemical Abstracts Service, Columbus, OH, US; Feb. 2014, Chemical Catalog; Supplier: Aurora Fine Chemicals: XP002755349, Database accession No. 1538237-68-1.
Database Registry [online], Chemical Abstracts Service, Columbus, OH, US; Feb. 2014, Chemical Catalog; Supplier: Aurora Fine Chemicals: XP002755350, Database accession No. 1536955-67-5.
Database Registry [online], Chemical Abstracts Service, Columbus, OH, US; Jan. 2014, Chemical Catalog; Supplier: Aurora Fine Chemicals: XP002755351, Database accession No. 1528719-88-1.
Database Registry [online], Chemical Abstracts Service, Columbus, OH, US; Jan. 2014, Chemical Catalog; Supplier: Aurora Fine Chemicals: XP002755352, Database accession No. 1526778-80-2.
Database Registry [online], Chemical Abstracts Service, Columbus, OH, US; Jan. 2014, Chemical Catalog; Supplier: Aurora Fine Chemicals: XP002755353, Database accession No. 1522493-70-4.
Database Registry [online], Chemical Abstracts Service, Columbus, OH, US; Jan. 2014, Chemical Catalog; Supplier: Aurora Fine Chemicals: XP002755354, Database accession No. 1520181-20-7.
Database Registry [online], Chemical Abstracts Service, Columbus, OH, US; Oct. 2005, Chemical Library; Supplier: interchim: XP002755358, Database accession No. 866138-38-7.
Database Registry [online], Chemical Abstracts Service, Columbus, OH, US; Oct. 2005, Chemical Library; Supplier: interchim: XP002755359, Database accession No. 864939-76-4.
Database Registry [online], Chemical Abstracts Service, Columbus, Ohio, US, Feb. 2010, Chemical Catalog; Supplier: Aurora Fine Chemicals: XP002755348, Database accession No. 1540777-22-7.
Elger et al., "Novel alpha-amino-3-hydroxy-5-methyl-4-isoxazole propionate (AMPA) receptor antagonists of 2,3-benzodiazepine type: chemical synthesis, in vitro characterization, and in vivo prevention of acute neurodegeneration," J. Med. Chem., Jul. 2005, 48(14): 4618-4627.
International Preliminary Report on Patentability in International Application No. PCT/US2016/017073, dated Aug. 15, 2017, 11 pages.
International Preliminary Report on Patentability in International Application No. PCT/US2016/060468, dated May 8, 2018, 9 pages.
International Preliminary Report on Patentability in International Application No. PCT/US2017/012135, dated Jul. 19, 2018, 10 pages.
International Preliminary Report on Patentability in International Application No. PCT/US2017/038955, dated Dec. 25, 2018, 8 pages.
International Search Report and Written Opinion in International Application No. PCT/US2016/017073, dated Apr. 15, 2016, 21 pages.
International Search Report and Written Opinion in International Application No. PCT/US2016/060468, dated Jan. 25, 2017, 11 pages.
International Search Report and Written Opinion in International Application No. PCT/US2017/012135, dated May 19, 2017, 17 pages.
International Search Report and Written Opinion in International Application No. PCT/US2017/038955, dated Aug. 8, 2017, 15 pages.
International Search Report and Written Opinion in International Application No. PCT/US2019/49419, dated Jan. 31, 2020, 10 pages.
Invitation to Pay Additional Fees in International Application No. PCT/US19/49419, dated Dec. 5, 2019, 10 pages.
Kumar et al., "Discovery and optimization of a new class of pyruvate kinase inhibitors as potential therapeutics for the treatment of methicillin-resistant Staphylococcus aureus infections," Bioorganic & Medicinal Chemistry, Jan. 2014, 22(5): 1708-1725.
Liu et al., "Discovery of Novel Small Molecule Mer Kinase Inhibitors for the Treatment of Pediatric Acute Lymphoblastic Leukemia," ACS Med. Chem. Lett., Feb. 9, 2012, 3(2):129-134.
Mamedov et al., "Acid-catalyzed rearrangement of 3-(beta-2-aminostyryl)quinoxalin-2(1H)ones-a new and efficient method for the synthesis of 2-benzimidazol-2-ylquinolines," Tetrahedron Letters, Dec. 2010, 51(50): 6503-6506.
Mejdrova et al., "Highly selective Phosphatidylinositol 4-Kinase III[beta] Inhibitors and Structural Insight into Their Mode of Action," Journal of Medicinal Chemistry, May 2015, 58(9): 3767-3793.
Park et al., "Homogenous proximity tyrosine kinase assays: scintillation proximity assay versus homogenous time-resolved fluorescence," Anal. Biochem., Apr. 1999, 269(1): 94-104.
Pomel et al., "Furan-2-ylmethylene thiazolidinediones as novel, potent, and selective inhibitors of phosphoinositide 3-kinase gamma," J Med. Chem., Jun. 2006, 49(13): 3857-71.
Vaillard et al., "Synthesis of 6-substituted 2-pyrrolyl and Indolyl Benzoxazoles by Intramolecular O-Arylation in Photostimulated Reactions," The Journal of Organic Chemistry, Feb. 2012, 77(3): 1507-1519.
Venable et al., "Phosphoinositide 3-Kinase Gamma (PI3K[gamma]) Inhibitors for the Treatment of Inflammation and Autoimmune Disease," Recent Patents on Inflammation & Allergy Drug Discovery, Jan. 2010, 4(1): 1-15.
International Preliminary Report on Patentability in International Application No. PCT/US2018/056311, dated Apr. 30, 2020, 8 pages.

XRPD Form I

DSC Form I

TGA Form I

XRPD Form II

DSC Form II

XRPD Form III

DSC Form III

TGA Form III

DSC Form I

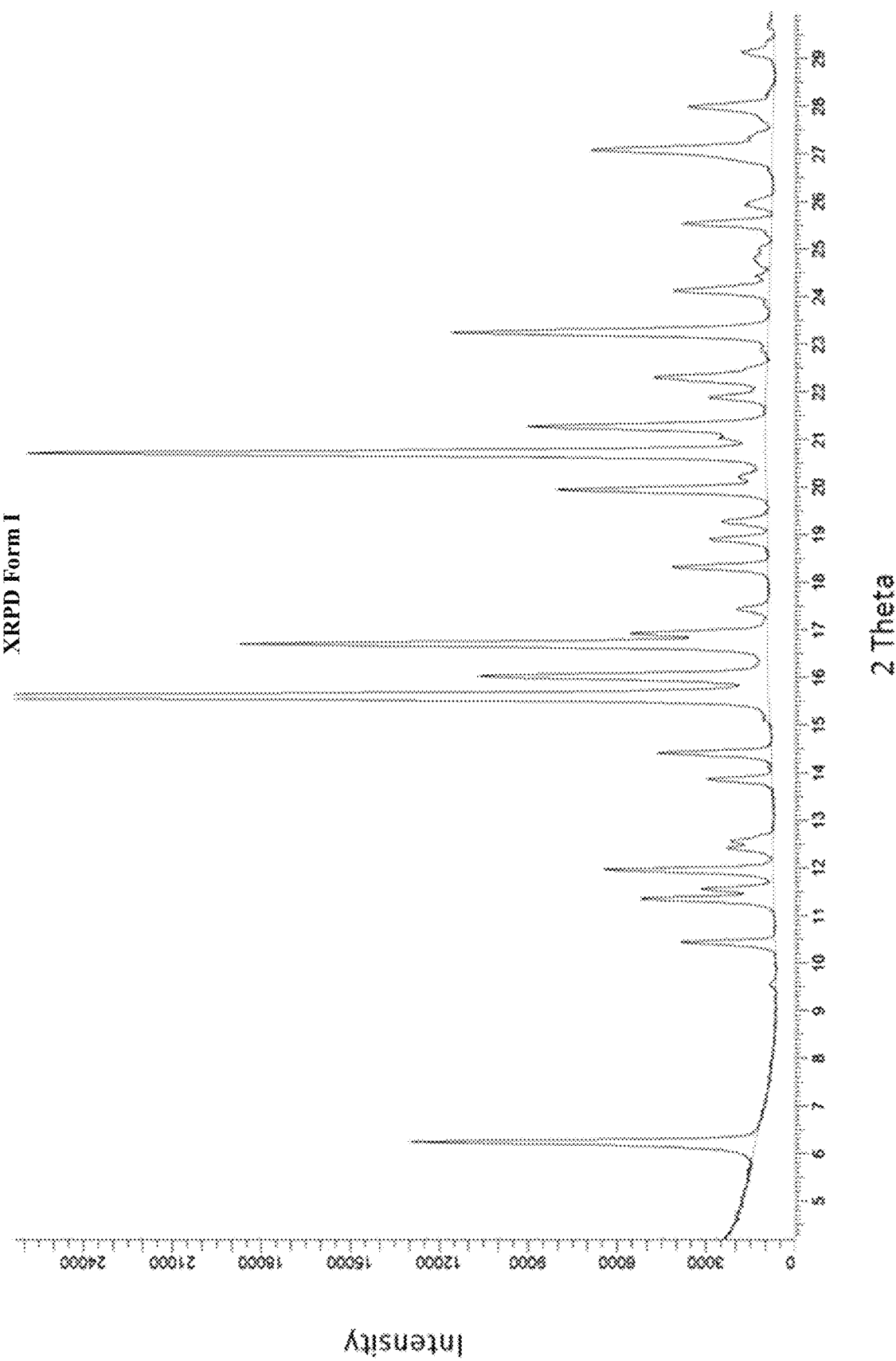

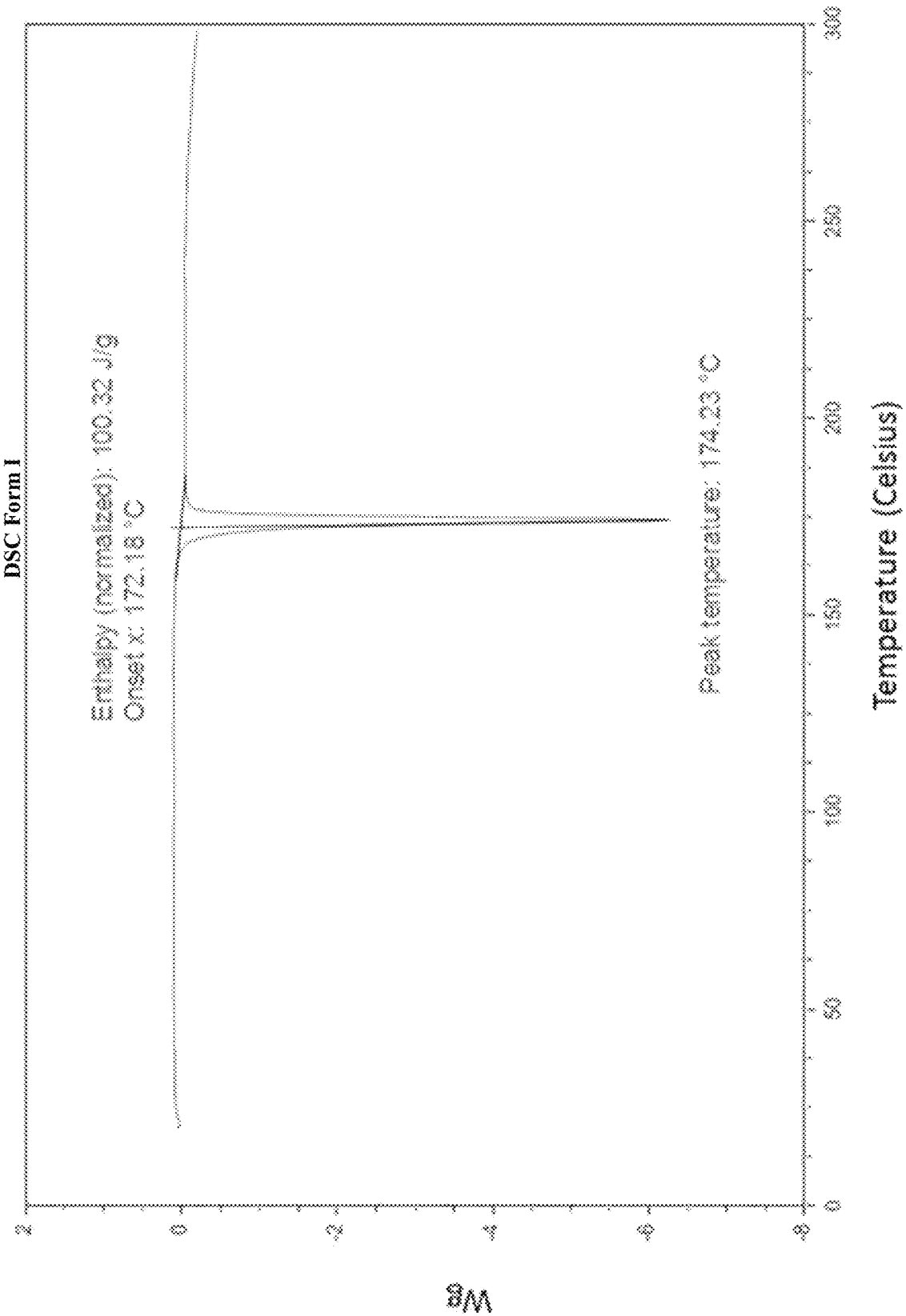

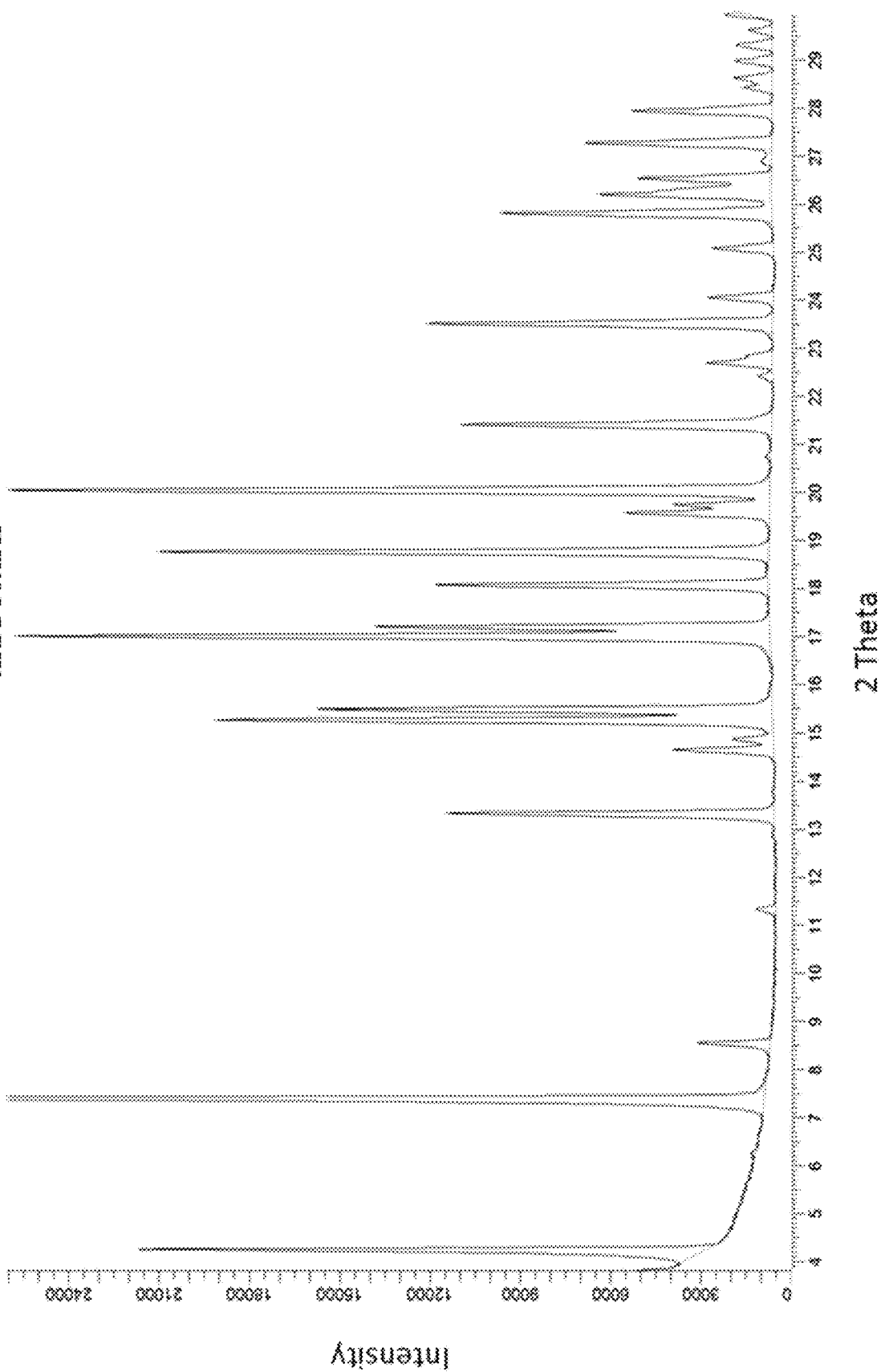

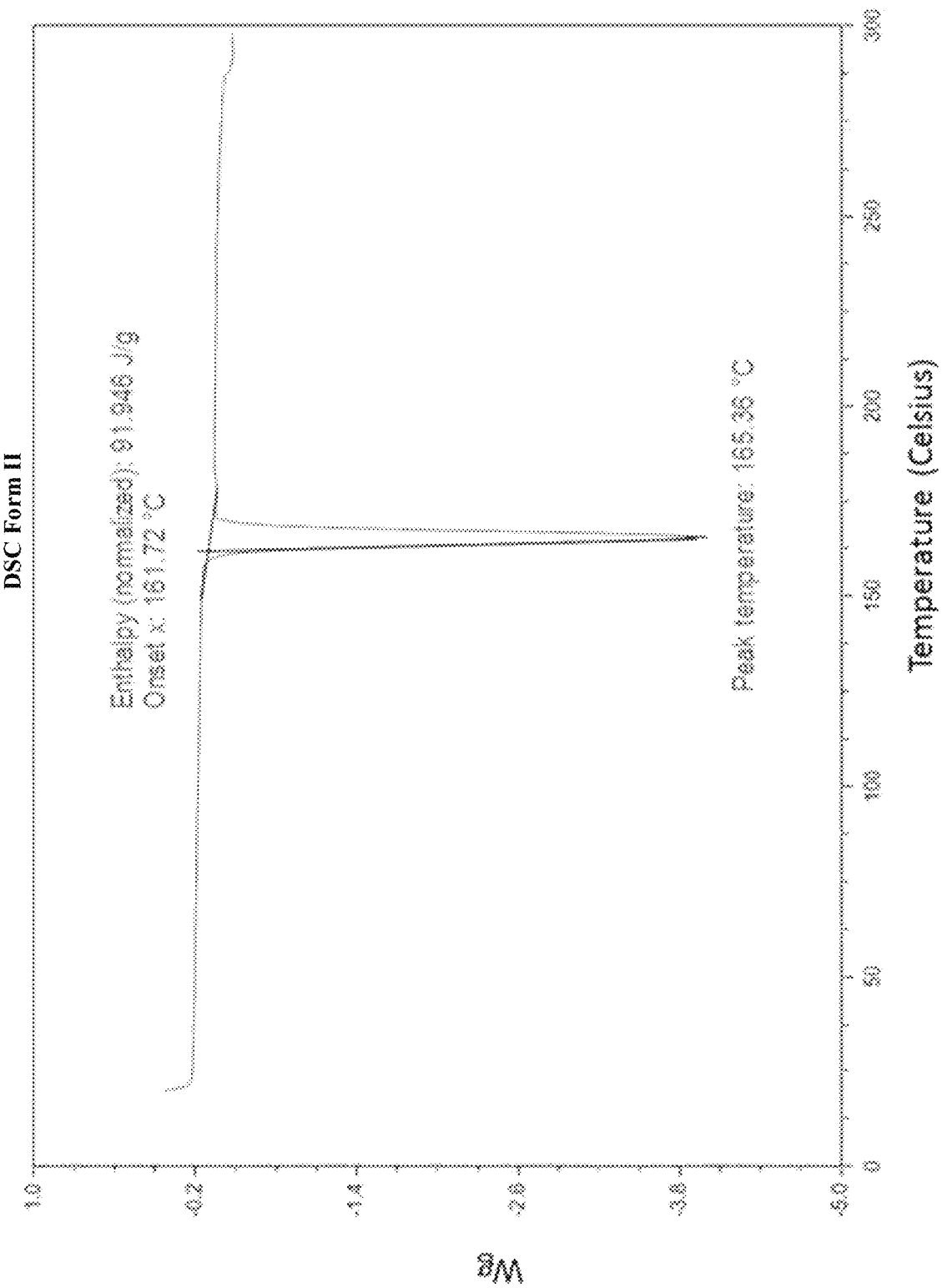

TERTIARY ALCOHOLS AS PI3K-γ INHIBITORS

FIELD OF THE INVENTION

The present invention provides tertiary alcohol compounds that modulate the activity of phosphoinositide 3-kinases-gamma (PI3Kγ) and are useful in the treatment of diseases related to the activity of PI3Kγ including, for example, autoimmune diseases, cancer, cardiovascular diseases, and neurodegenerative diseases.

BACKGROUND

The phosphoinositide 3-kinases (PI3Ks) belong to a large family of lipid signaling kinases that phosphorylate phosphoinositides at the D3 position of the inositol ring (Cantley, Science, 2002, 296(5573):1655-7). PI3Ks are divided into three classes (class I, II, and III) according to their structure, regulation and substrate specificity. Class I PI3Ks, which include PI3Kα, PI3Kβ, PI3Kγ, and PI3Kδ, are a family of dual specificity lipid and protein kinases that catalyze the phosphorylation of phosphatidylinosito-4,5-bisphosphate ($PIP_2$) giving rise to phosphatidylinosito-3,4,5-trisphosphate ($PIP_3$). $PIP_3$ functions as a second messenger that controls a number of cellular processes, including growth, survival, adhesion and migration. All four class I PI3K isoforms exist as heterodimers composed of a catalytic subunit (p110) and a tightly associated regulatory subunit that controls their expression, activation, and subcellular localization. PI3Kα, PI3Kβ, and PI3Kδ associate with a regulatory subunit known as p85 and are activated by growth factors and cytokines through a tyrosine kinase-dependent mechanism (Jimenez, et al., J Biol Chem., 2002, 277(44):41556-62) whereas PI3Kγ associates with two regulatory subunits (p101 and p84) and its activation is driven by the activation of G-protein-coupled receptors (Brock, et al., J Cell Biol., 2003, 160(1):89-99). PI3Kα and PI3Kβ are ubiquitously expressed. In contrast, PI3Kγ and PI3Kδ are predominantly expressed in leukocytes (Vanhaesebroeck, et al., Trends Biochem Sci., 2005, 30(4):194-204).

Expression of PI3Kγ is mainly restricted to hematopoietic system, although it can be also detected at lower level in endothelium, heart and brain. PI3Kγ knock-out or kinase dead knock in mice are normal and fertile and do not present any overt adverse phenotypes. Analysis at the cellular level indicates that PI3Kγ is required for GPCR ligand-induced PtdINs (3,4,5)P3 production, chemotaxis and respiratory burst in neutrophils. PI3Kγ-null macrophages and dendritic cell exhibit reduced migration towards various chemoattractants. T-cells deficient in PI3Kγ show impaired cytokine production in response to anti-CD3 or Con A stimulation. PI3Kγ working downstream of adenosine A3A receptor is critical for sustained degranulation of mast cells induced by FCεRI cross-linking with IgE. PI3Kγ is also essential for survival of eosinophils (Ruckle et al., Nat. Rev. Drug Discovery, 2006, 5, 903-918)

Given its unique expression pattern and cellular functions, the potential role of PI3Kγ in various autoimmune and inflammatory disease models has been investigated with genetic and pharmacological tools. In asthma and allergy models, PI3Kγ$^{-/-}$ mice or mice treated with PI3Kγ inhibitor showed a defective capacity to mount contact hypersensitivity and delayed-type hypersensitivity reactions. In these models, PI3Kγ was shown to be important for recruitment of neutrophils and eosinopohils to airways and degranulation of mast cells (see e.g. Laffargue et al., Immunity, 2002, 16, 441-451; Prete et al., The EMBO Journal, 2004, 23, 3505-3515; Pinho et al., L. Leukocyte Biology, 2005, 77, 800-810; Thomas et al., Eur. J. Immunol. 2005, 35, 1283-1291; Doukas et al., J. Pharmacol. Exp Ther. 2009, 328, 758-765).

In two different acute pancreatitis models, genetic ablation of PI3Kγ significantly reduced the extent of acinar cell injury/necrosis and neutrophil infiltration without any impact on secretive function of isolated pancreatic acini (Lupia et al., Am. J. Pathology, 2004, 165, 2003-2011). PI3Kγ$^{-/-}$ mice were largely protected in four different models of rheumatoid arthritis (CIA, α-CII-IA, K/B×N serum transfer and TNF transgenic) and PI3Kγ inhibition suppressed the progression of joint inflammation and damage in the CIA and α-CII-IA models (see e.g., Camps et al., Nat. Medicine, 2005, 11, 939-943; Randis et al., Eur. J. Immunol, 2008, 38, 1215-1224; Hayer et al., FASB J., 2009, 4288-4298). In the MRL-lpr mouse model of human systemic lupus erythematous, inhibition of PI3Kγ reduced glomerulonephritis and prolonged life span (Barber et al., Nat. Medicine, 2005, 9, 933-935).

There is evidence suggesting that chronic inflammation due to infiltration by myeloid-derived cells is a key component in the progression of neurodegeneration diseases, such as Alzheimer's disease (AD) (Giri et al., Am. J. Physiol. Cell Physiol., 2005, 289, C264-C276; El Khoury et al., Nat. Med., 2007, 13, 432-438). In line with this suggestion, PI3Kγ inhibition was shown to attenuate Aβ(1-40)-induced accumulation of activated astrocytes and microglia in the hippocampus and prevent the peptide-induced congnitive deficits and synaptic dysfunction in a mouse model of AD (Passos et al., Brain Behav. Immun. 2010, 24, 493-501). PI3Kγ deficiency or inhibition also was shown to delay onset and alleviate symptoms in experimental autoimmune encephalomyelitis in mice, a mouse model of human multiple sclerosis, which is another form of neurodegeneration disease (see e.g., Rodrigues et al., J. Neuroimmunol. 2010, 222, 90-94; Berod et al., Euro. J. Immunol. 2011, 41, 833-844; Comerford et al., PLOS one, 2012, 7, e45095; Li et al., Neuroscience, 2013, 253, 89-99).

Chronic inflammation has been formally recognized as one of the hallmarks for many different types of cancers. Accordingly, selective anti-inflammatory drugs represent a novel class of anti-cancer therapies (Hanahan and Weinberg, Cell, 2011, 144, 646-674). Since PI3Kγ is reported to mediate various inflammatory processes, its role as an immune oncology target has also been investigated. A recent study reported that PI3Kγ deficiency suppressed tumor growth in the syngeneic models of lung cancer, pancreatic cancer and melanoma (LLC, PAN02 and B16). PI3Kγ deficiency or inhibition also inhibited tumor growth in a spontaneous breast cancer model (Schmid et al., Cancer Cell, 2011, 19, 715-727). A further study reported that PI3Kγ deficiency could ameliorate inflammation and tumor growth in mice having colitis-associated colon cancer, (Gonzalez-Garcia et al., Gastroenterology, 2010, 138, 1373-1384). Detailed mechanistic analysis indicates that tumor infiltration by CD11b$^+$ myeloid cells can cause protumorigenic inflammation at tumor sites and PI3Kγ in the myeloid cells is critical in mediating signaling of various chemoattractants in bring the cells to the tumor (Schmid et al., Cancer Cell, 2011, 19, 715-727). Other studies suggest that PI3Kγ is also required for differentiation of nave myeloid cells into M2 macrophges at tumor sites. M2 macrophages promote tumor growth and progression by secreting immunosuppressive factors such arginase 1, which depletes the tumor microenvironment of arginine, thereby promoting T-cell death and NK cell inhibition (Schmidt et al., *Cancer Res.* 2012, 72 (Suppl 1: Abstract, 411; Kaneda et al., *Cancer Res.*, 74 (Suppl 19: Abstract 3650)).

In addition to its potential role in promoting protumorigenic microenvironment, PI3Kγ may play a direct role in cancer cells. PI3Kγ is reported to be required for signaling from the Kaposi's sarcoma-associated herpevirus encoded vGPCR oncogene and tumor growth in a mouse model of sarcoma (Martin et al., *Cancer Cell*, 2011, 19, 805-813). PI3Kγ was also suggested to be required for growth of T-ALL (Subramanjam et al., *Cancer Cell*, 2012, 21, 459-472), PDAC and HCC cells (Falasca and Maffucci, *Frontiers in Physiology*, 2014, 5, 1-10). Moreover, in a survey of driver mutations in pancreatic cancer, PI3Kγ gene was found to contain second highest scoring predicted driven mutation (R839C) among the set of genes not previously identified as a driver in pancreatic cancer (Carter et al., *Cancer Biol. Ther.* 2010, 10, 582-587).

Finally, PI3Kγ deficiency also has been reported to offer protection to experimental animals in different cardiovascular disease models. For examples, lack of PI3Kγ would reduce angiotension-evoked smooth muscle contraction and, therefore, protect mice from angiotension-induced hypertension (Vecchione et al., *J. Exp. Med.* 2005, 201, 1217-1228). In rigorous animal myocardial infarction models, PI3Kγ inhibition provided potent cardioprotection, reducing infarct development and preserving myocardial function (Doukas et al., *Proc. Natl. Acad. Sci. USA*, 2006, 103, 19866-19871).

For these reasons, there is a need to develop new PI3Kγ inhibitors that can be used for the treatment of diseases such as cancer, autoimmune disorders, and inflammatory and cardiac diseases. This application is directed to this need and others.

SUMMARY

The present invention relates to, inter alia, compounds of Formula (I):

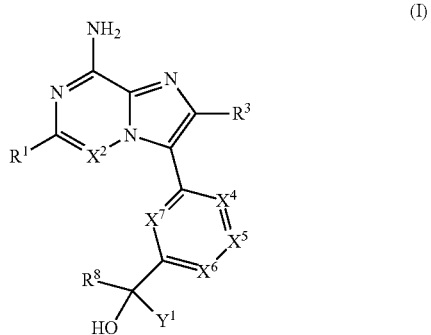

(I)

or a pharmaceutically acceptable salt thereof, wherein constituent members are defined herein.

The present invention further provides pharmaceutical compositions comprising a compound of Formula (I), or a pharmaceutically acceptable salt thereof, and a pharmaceutically acceptable carrier.

The present invention further provides methods of inhibiting an activity of PI3Kγ kinase comprising contacting the kinase with a compound of Formula (I), or a pharmaceutically acceptable salt thereof.

The present invention further provides methods of treating a disease or a disorder associated with abnormal PI3Kγ kinase expression or activity in a patient by administering to the patient a therapeutically effective amount of a compound of Formula (I), or a pharmaceutically acceptable salt thereof.

The present invention further provides a compound of Formula (I), or a pharmaceutically acceptable salt thereof, for use in any of the methods described herein.

The present invention further provides use of a compound of Formula (I), or a pharmaceutically acceptable salt thereof, for the preparation of a medicament for use in any of the methods described herein.

BRIEF DESCRIPTION OF THE DRAWINGS

FIG. 12 shows an XRPD pattern for crystalline Form I of Example P5.

FIG. 13 shows the results of a DSC experiment for crystalline Form I of Example P5.

FIG. 14 shows an XRPD pattern for crystalline Form II of Example P6.

FIG. 15 shows the results of a DSC experiment for crystalline Form II of Example P6.

DETAILED DESCRIPTION

Compounds

Figure 1:
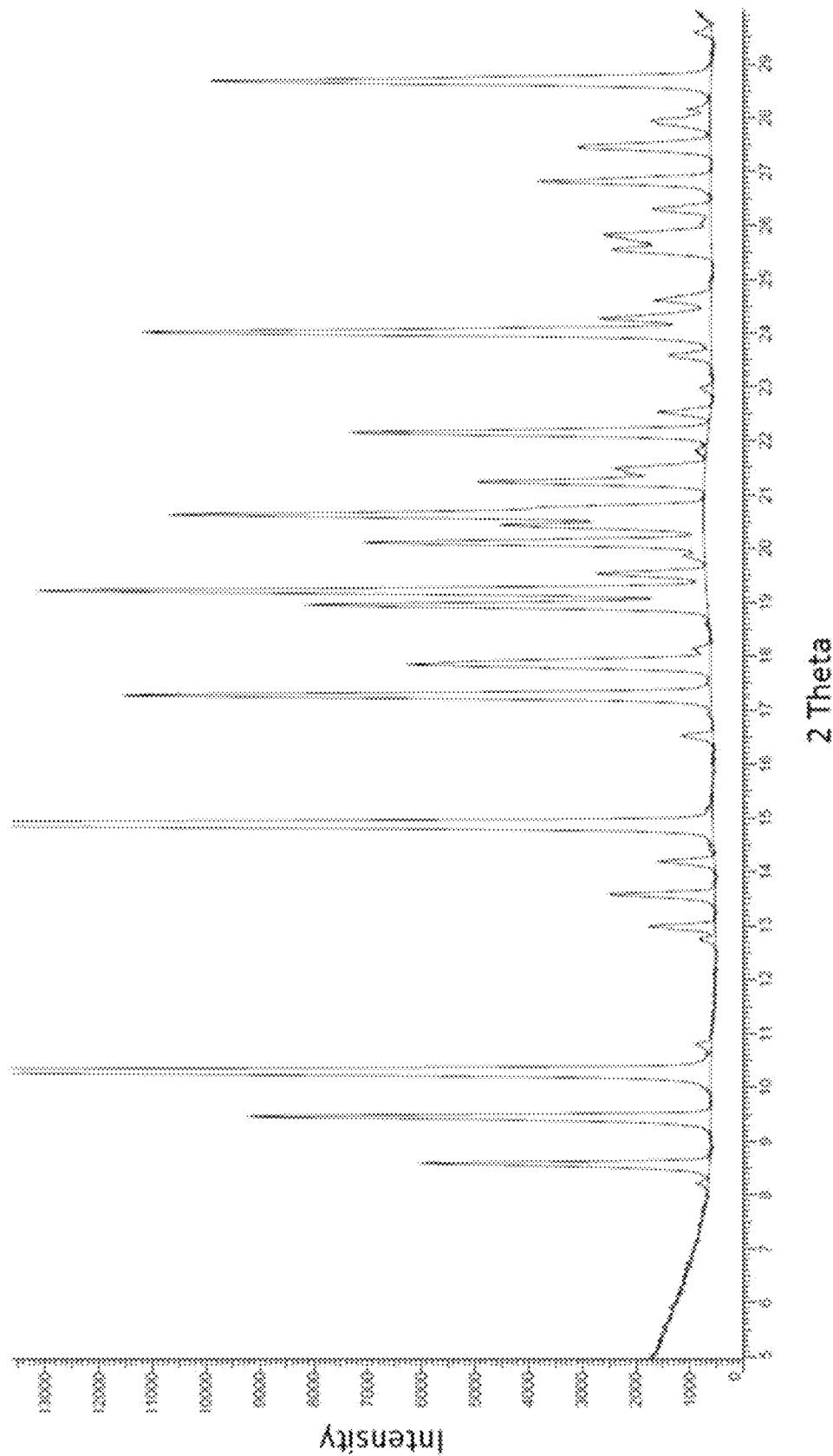
FIG. 1 shows an XRPD pattern for crystalline Form I of Example P1.

The present application provides, inter alia, compounds of Formula (I):

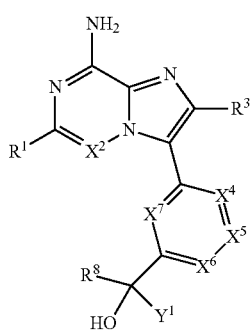

or a pharmaceutically acceptable salt thereof; wherein:
$X^2$ is N or $CR^2$;
$X^4$ is N or $CR^4$;
$X^5$ is N or $CR^5$;
$X^6$ is N or $CR^6$;
$X^7$ is N or $CR^7$;
provided that $X^4$, $X^5$, and $X^6$ are not all N;

$Y^1$ is a $C_{1-6}$ haloalkyl, wherein each halogen is selected from F or Cl, wherein the haloalkyl is optionally substituted with 1 or 2 independently selected $Y^2$ substituents;

$R^1$ is selected from H, D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NR^aR^a$, $NR^aNR^aR^a$, $NR^aC(O)R^a$, $NR^aC(O)OR^a$, $NR^aC(O)NR^aR^a$, $C(=NR^i)R^a$, $C(=NR^i)NR^aR^a$, $NR^aC(=NR^i)NR^aR^a$, $NR^aC(=NOH)NR^aR^a$, $NR^aC(=NCN)NR^aR^a$, $NR^aS(O)R^a$, $NR^aS(O)_2R^a$, $NR^aS(O)(=NR^i)R^a$, $NR^aS(O)_2NR^aR^a$, $S(O)R^a$, $S(O)NR^aR^a$, $S(O)_2R^a$, $OS(O)(=NR^i)R^a$, $SF_5$, $P(O)R^aR^a$, $P(O)(OR^a)(OR^a)$, $B(OR^a)_2$, and $S(O)_2NR^aR^a$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^1$ are each optionally substituted with 1, 2, 3, 4, 5, 6, 7, or 8 independently selected $R^b$ substituents;

$R^2$, $R^3$, $R^4$, $R^5$, $R^6$ and $R^7$ are each independently selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl, OH, $NO_2$, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^2$, $R^3$, $R^4$, $R^5$, $R^6$ and $R^7$ are each optionally substituted with 1, 2, 3, or 4 independently selected $R^h$ substituents;

$R^8$ is selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, $NO_2$, $C(O)R^a$, $C(O)NR^aR^a$, $C(O)OR^a$, $C(=NR^i)R^a$, $C(=NR^i)NR^aR^a$, $SF_5$, —$P(O)R^aR^a$, —$P(O)(OR^a)(OR^a)$, $B(OR^a)_2$, and $S(O)_2NR^aR^a$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^8$ are each optionally substituted with 1, 2, 3, or 4 independently selected $R^9$ substituents;

or any two $R^4$, $R^5$, $R^6$ and $R^7$ substituents, together with the ring atoms to which they attached form a 4-, 5-, 6-, or 7-membered aryl, cycloalkyl, heteroaryl, or heterocycloalkyl group optionally substituted with 1, 2, 3, or 4 independently selected $R^b$ substituents;

or $Y^1$ and $R^8$, together with the carbon atom to which they are attached, form a 4-, 5-, 6-, or 7-membered cycloalkyl or heterocycloalkyl group optionally substituted with 1, 2, 3, or 4 independently selected $R^9$ substituents;

each $R^i$ is independently selected from H, CN, OH, $C_{1-4}$ alkyl, and $C_{1-4}$ alkoxy;

each $Y^2$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^a$ is independently selected from H, D, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl- and 4-10 membered heterocycloalkyl-$C_{1-6}$ alkyl- of $R^a$ is each optionally substituted with 1, 2, 3, or 4 independently selected $R^b$ substituents;

each $R^b$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^c$, $SR^c$, $NHOR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, NR$^c$C(O)OR$^c$, NR$^c$C(O)NR$^c$R$^c$, C(=NR$^i$)R$^c$, C(=NR$^i$)NR$^c$R$^c$, NR$^c$C(=NR$^i$)NR$^c$R$^c$, NR$^c$C(=NOH)NR$^c$R$^c$, NR$^c$C(=NCN)NR$^c$R$^c$, NR$^c$S(O)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$, SF$_5$, —P(O)R$^c$R$^c$, —P(O)(OR$^c$)(OR$^c$), B(OR$^c$)$_2$, and S(O)$_2$NR$^c$R$^c$, wherein the C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, and 4-10 membered heterocycloalkyl-C$_{1-6}$ alkyl- of R$^b$ is each optionally substituted with 1, 2, 3, or 4 independently selected R$^d$ substituents;

each R$^9$ is independently selected from D, halo, C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, 4-10 membered heterocycloalkyl-C$_{1-6}$ alkyl-, CN, NO$_2$, OR$^k$, SR$^k$, NHOR$^k$, C(O)R$^k$, C(O)NR$^k$R$^k$, C(O)OR$^k$, OC(O)R$^k$, OC(O)NR$^k$R$^k$, NR$^k$R$^k$, NR$^k$C(O)R$^k$, NR$^k$C(O)OR$^k$, NR$^k$C(O)NR$^k$R$^k$, C(=NR$^i$)R$^k$, C(=NR$^i$)NR$^k$R$^k$, NR$^k$C(=NR$^i$)NR$^k$R$^k$, NR$^k$C(=NOH)NR$^k$R$^k$, NR$^k$C(=NCN)NR$^k$R$^k$, NR$^k$S(O)R$^k$, NR$^k$S(O)$_2$R$^k$, NR$^k$S(O)$_2$NR$^k$R$^k$, S(O)R$^k$, S(O)NR$^k$R$^k$, S(O)$_2$R$^k$, SF$_5$, —P(O)R$^k$R$^k$, —P(O)(OR$^k$)(OR$^k$), B(OR$^k$)$_2$, and S(O)$_2$NR$^k$R$^k$, wherein the C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, and 4-10 membered heterocycloalkyl-C$_{1-6}$ alkyl- of R$^9$ is each optionally substituted with 1, 2, 3, or 4 independently selected R$^q$ substituents;

each R$^c$ is independently selected from H, D, C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, and 4-10 membered heterocycloalkyl-C$_{1-6}$ alkyl-, wherein the C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl- and 4-10 membered heterocycloalkyl-C$_{1-6}$ alkyl- of R$^c$ is each optionally substituted with 1, 2, 3, or 4 independently selected R$^d$ substituents;

or two R$^c$ substituents, together with the nitrogen atom to which they attached form a 4-, 5-, 6-, or 7-membered heteroaryl or heterocycloalkyl group optionally substituted with 1, 2, 3, or 4 independently selected R$^d$ substituents;

each R$^d$ is independently selected from D, halo, C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, 4-10 membered heterocycloalkyl-C$_{1-6}$ alkyl-, CN, NO$_2$, OR$^e$, SR$^e$, NHOR$^e$, C(O)R$^e$, C(O)NR$^e$R$^e$, C(O)OR$^e$, OC(O)R$^e$, OC(O)NR$^e$R$^e$, NR$^e$R$^e$, NR$^e$C(O)R$^e$, NR$^e$C(O)OR$^e$, NR$^e$C(O)NR$^e$R$^e$, C(=NR$^i$)R$^e$, C(=NR$^i$)NR$^e$R$^e$, NR$^e$C(=NR$^i$)NR$^e$R$^e$, NR$^e$C(=NOH)NR$^e$R$^e$, NR$^e$C(=NCN)NR$^e$R$^e$, NR$^e$S(O)R$^e$, NR$^e$S(O)$_2$R$^e$, NR$^e$S(O)$_2$NR$^e$R$^e$, S(O)R$^e$, S(O)NR$^e$R$^e$, S(O)$_2$R$^e$, SF$_5$, —P(O)R$^e$R$^e$, —P(O)(OR$^e$)(OR$^e$), B(OR$^e$)$_2$, and S(O)$_2$NR$^e$R$^e$, wherein the C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, and 4-10 membered heterocycloalkyl-C$_{1-6}$ alkyl- of R$^d$ is each optionally substituted with 1, 2, 3 or 4 independently selected R$^f$ substituents;

each R$^e$ is independently selected from H, D, C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, 5-6 membered heteroaryl-C$_{1-6}$ alkyl-, and 4-7 membered heterocycloalkyl-C$_{1-6}$ alkyl-, wherein the C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, 5-6 membered heteroaryl-C$_{1-6}$ alkyl- and 4-7 membered heterocycloalkyl-C$_{1-6}$ alkyl- of R$^e$ is each optionally substituted with 1, 2, 3 or 4 independently selected R$^f$ substituents;

each R$^f$ is independently selected from D, halo, C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, 5-6 membered heteroaryl-C$_{1-6}$ alkyl-, 4-7 membered heterocycloalkyl-C$_{1-6}$ alkyl-, CN, NO$_2$, OR$^g$, SR$^g$, NHOR$^g$, C(O)R$^g$, C(O)NR$^g$R$^g$, C(O)OR$^g$, OC(O)R$^g$, OC(O)NR$^g$R$^g$, NR$^g$R$^g$, NR$^g$C(O)R$^g$, NR$^g$C(O)OR$^g$, NR$^g$C(O)NR$^g$R$^g$, C(=NR$^i$)R$^g$, C(=NR$^i$)NR$^g$R$^g$, NR$^g$C(=NR$^i$)NR$^g$R$^g$, NR$^g$C(=NOH)NR$^g$R$^g$, NR$^g$C(=NCN)NR$^g$R$^g$, NR$^g$S(O)R$^g$, NR$^g$S(O)$_2$R$^g$, NR$^g$S(O)$_2$NR$^g$R$^g$, S(O)R$^g$, S(O)NR$^g$R$^g$, S(O)$_2$R$^g$, SF$_5$, —P(O)R$^g$R$^g$, —P(O)(OR$^g$)(OR$^g$), B(OR$^g$)$_2$, and S(O)$_2$NR$^g$R$^g$, wherein the C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, 5-6 membered heteroaryl-C$_{1-6}$ alkyl-, and 4-7 membered heterocycloalkyl-C$_{1-6}$ alkyl- of R$^f$ is each optionally substituted with 1, 2, 3 or 4 independently selected R$^h$ substituents;

each R$^g$ is independently selected from H, D, C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, 5-6 membered heteroaryl-C$_{1-6}$ alkyl-, and 4-7 membered heterocycloalkyl-C$_{1-6}$ alkyl-, wherein the C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, 5-6 membered heteroaryl-C$_{1-6}$ alkyl- and 4-7 membered heterocycloalkyl-C$_{1-6}$ alkyl- of R$^g$ is each optionally substituted with 1, 2, 3 or 4 independently selected R$^h$ substituents;

each R$^h$ is independently selected from OH, NO$_2$, CN, halo, C$_{1-6}$ alkyl, C$_{2-6}$ alkenyl, C$_{2-6}$ alkynyl, C$_{1-6}$ haloalkyl, cyano-C$_{1-6}$ alkyl, HO—C$_{1-6}$ alkyl, C$_{1-6}$ alkoxy-C$_{1-6}$ alkyl, C$_{3-7}$ cycloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

each R$^k$ is independently selected from H, D, C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, and 4-10 membered heterocycloalkyl- $C_{1-6}$ alkyl-, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl- and 4-10 membered heterocycloalkyl-$C_{1-6}$ alkyl- of $R^k$ is each optionally substituted with 1, 2, 3, or 4 independently selected $R^q$ substituents;

each $R^q$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^m$, $SR^m$, $NHOR^m$, $C(O)R^m$, $C(O)NR^mR^m$, $C(O)OR^m$, $OC(O)R^m$, $OC(O)NR^mR^m$, $NHR^m$, $NR^mR^m$, $NR^mC(O)R^m$, $NR^mC(O)OR^m$, $NR^mC(O)NR^mR^m$, $C(=NR^i)R^m$, $C(=NR^i)NR^mR^m$, $NR^mC(=NR^i)NR^mR^m$, $NR^mC(=NOH)NR^mR^m$, $NR^mC(=NCN)NR^mR^m$, $NR^mS(O)R^m$, $NR^mS(O)_2R^m$, $NR^mS(O)_2NR^mR^m$, $S(O)R^m$, $S(O)NR^mR^m$, $S(O)_2R^m$, $SF_5$, $-P(O)R^mR^m$, $-P(O)(OR^m)(OR^m)$, $B(OR^m)_2$, and $S(O)_2NR^mR^m$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^q$ is each optionally substituted with 1, 2, 3 or 4 independently selected $R^n$ substituents;

each $R^m$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl- and 4-7 membered heterocycloalkyl-$C_{1-6}$ alkyl- of $R^m$ is each optionally substituted with 1, 2, 3 or 4 independently selected $R^n$ substituents;

each $R^n$ is independently selected from D, halo, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, 4-7 membered heterocycloalkyl-$C_{1-6}$ alkyl-, CN, $NO_2$, $OR^o$, $SR^o$, $NHOR^o$, $C(O)R^o$, $C(O)NR^oR^o$, $C(O)OR^o$, $OC(O)R^o$, $OC(O)NR^oR^o$, $NR^oR^o$, $NR^oC(O)R^o$, $NR^oC(O)OR^o$, $NR^oC(O)NR^oR^o$, $C(=NR^i)R^o$, $C(=NR^i)NR^oR^o$, $NR^oC(=NR^i)NR^oR^o$, $NR^oC(=NOH)NR^oR^o$, $NR^oC(=NCN)NR^oR^o$, $NR^oS(O)R^o$, $NR^oS(O)_2R^o$, $NR^oS(O)_2NR^oR^o$, $S(O)R^o$, $S(O)NR^oR^o$, $S(O)_2R^o$, and $S(O)_2NR^oR^o$, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl- of $R^n$ is each optionally substituted with 1, 2, 3 or 4 independently selected $R^h$ substituents; and each $R^o$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl- and 4-7 membered heterocycloalkyl-$C_{1-6}$ alkyl- of $R^o$ is each optionally substituted with 1, 2, 3 or 4 independently selected $R^h$ substituents.

In some embodiments:
$X^2$ is N or $CR^2$;
$X^4$ is N or $CR^4$;
$X^5$ is N or $CR^5$;
$X^6$ is N or $CR^6$;
$X^7$ is N or $CR^7$;
provided that $X^4$, $X^5$, and $X^6$ are not all N;

$Y^1$ is a $C_{1-6}$ haloalkyl, wherein each halogen is selected from F or Cl, wherein the haloalkyl is optionally substituted with 1 or 2 independently selected $Y^2$ substituents;

$R^1$ is selected from H, D, halo, $C_{1-6}$ alkyl, $C_{2-6}$ alkenyl, $C_{2-6}$ alkynyl, $C_{1-6}$ haloalkyl, 6-10 membered aryl, $C_{3-10}$cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NR^aR^a$, $NR^aNR^aR^a$, $NR^aC(O)R^a$, $NR^aC(O)OR^a$, $NR^aC(O)NR^aR^a$, $C(=NR^i)R^a$, $C(=NR^i)NR^aR^a$, $NR^aC(=NR^i)NR^aR^a$, $NR^aC(=NOH)NR^aR^a$, $NR^aC(=NCN)NR^aR^a$, $NR^aS(O)R^a$, $NR^aS(O)_2R^a$, $NR^aS(O)(=NR^i)R^a$, $NR^aS(O)_2NR^aR^a$, $S(O)R^a$, $S(O)NR^aR^a$, $S(O)_2R^a$, $OS(O)(=NR^i)R^a$, $SF_5$, $P(O)R^aR^a$, $P(O)(OR^a)(OR^a)$, $B(OR^a)_2$, and $S(O)_2NR^aR^a$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^1$ are each optionally substituted with 1, 2, 3, or 4 independently selected $R^b$ substituents;

$R^2$, $R^3$, $R^4$, $R^5$, $R^6$ and $R^7$ are each independently selected from H, D, $CD_3$, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl, OH, $NO_2$, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^2$, $R^3$, $R^4$, $R^5$, $R^6$ and $R^7$ are each optionally substituted with 1, 2, 3, or 4 independently selected $R^h$ substituents;

$R^8$ is selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$cycloalkyl-$C_{1-6}$ alkyl-, 5-10 membered heteroaryl-$C_{1-6}$ alkyl-, 4-10 membered heterocycloalkyl-$C_{1-6}$ alkyl-, $NO_2$, $C(O)R^a$, $C(O)NR^aR^a$, $C(O)OR^a$, $C(=NR^i)R^a$, $C(=NR^i)NR^aR^a$, $SF_5$, —$P(O)R^aR^a$, —$P(O)(OR^a)(OR^a)$, $B(OR^a)_2$, and $S(O)_2NR^aR^a$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^8$ are each optionally substituted with 1, 2, 3, or 4 independently selected $R^9$ substituents;

or any two $R^4$, $R^5$, $R^6$ and $R^7$ substituents, together with the ring atoms to which they attached form a 4-, 5-, 6-, or 7-membered aryl, cycloalkyl, heteroaryl, or heterocycloalkyl group optionally substituted with 1, 2, 3, or 4 independently selected $R^b$ substituents;

or $Y^1$ and $R^8$, together with the carbon atom to which they are attached, form a 4-, 5-, 6-, or 7-membered cycloalkyl or heterocycloalkyl group optionally substituted with 1, 2, 3, or 4 independently selected $R^9$ substituents;

each $R^i$ is independently selected from H, CN, OH, $C_{1-4}$ alkyl, and $C_{1-4}$ alkoxy;

each $Y^2$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^a$ is independently selected from H, D, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl- and 4-10 membered heterocycloalkyl-$C_{1-6}$ alkyl- of $R^a$ is each optionally substituted with 1, 2, 3, or 4 independently selected $R^b$ substituents;

each $R^b$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^c$, $SR^c$, $NHOR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^cC(O)OR^c$, $NR^cC(O)NR^cR^c$, $C(=NR^i)R^c$, $C(=NR^i)NR^cR^c$, $NR^cC(=NR^i)NR^cR^c$, $NR^cC(=NOH)NR^cR^c$, $NR^cC(=NCN)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$, $SF_5$, —$P(O)R^cR^c$, —$P(O)(OR^c)(OR^c)$, $B(OR^c)_2$, and $S(O)_2NR^cR^c$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^b$ is each optionally substituted with 1, 2, 3, or 4 independently selected $R^d$ substituents;

each $R^9$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^k$, $SR^k$, $NHOR^k$, $C(O)R^k$, $C(O)NR^kR^k$, $C(O)OR^k$, $OC(O)R^k$, $OC(O)NR^kR^k$, $NR^kR^k$, $NR^kC(O)R^k$, $NR^kC(O)OR^k$, $NR^kC(O)NR^kR^k$, $C(=NR^i)R^k$, $C(=NR^i)NR^kR^k$, $NR^kC(=NR^i)NR^kR^k$, $NR^kC(=NOH)NR^kR^k$, $NR^kC(=NCN)NR^kR^k$, $NR^kS(O)R^k$, $NR^kS(O)_2R^k$, $NR^kS(O)_2NR^kR^k$, $S(O)R^k$, $S(O)NR^kR^k$, $S(O)_2R^k$, $SF_5$, —$P(O)R^kR^k$, —$P(O)(OR^k)(OR^k)$, $B(OR^k)_2$, and $S(O)_2NR^kR^k$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^9$ is each optionally substituted with 1, 2, 3, or 4 independently selected $R^q$ substituents;

each $R^c$ is independently selected from H, D, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl- and 4-10 membered heterocycloalkyl-$C_{1-6}$ alkyl- of $R^c$ is each optionally substituted with 1, 2, 3, or 4 independently selected $R^d$ substituents;

or two $R^c$ substituents, together with the nitrogen atom to which they attached form a 4-, 5-, 6-, or 7-membered heteroaryl or heterocycloalkyl group optionally substituted with 1, 2, 3, or 4 independently selected $R^d$ substituents;

each $R^d$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^e$, $SR^e$, $NHOR^e$, $C(O)R^e$, $C(O)NR^eR^e$, $C(O)OR^e$, $OC(O)R^e$, $OC(O)NR^eR^e$, $NR^eR^e$, $NR^eC(O)R^e$, $NR^eC(O)OR^e$, $NR^eC(O)NR^eR^e$, $C(=NR^i)R^e$, $C(=NR^i)NR^eR^e$, $NR^eC(=NR^i)NR^eR^e$, $NR^eC(=NOH)NR^eR^e$, $NR^eC(=NCN)NR^eR^e$, $NR^eS(O)R^e$, $NR^eS(O)_2R^e$, $NR^eS(O)_2NR^eR^e$, $S(O)R^e$, $S(O)NR^eR^e$, $S(O)_2R^e$, $SF_5$, —$P(O)R^eR^e$, —$P(O)(OR^e)(OR^e)$, $B(OR^e)_2$, and $S(O)_2NR^eR^e$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^d$ is each optionally substituted with 1, 2, 3 or 4 independently selected $R^f$ substituents;

each $R^e$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl- and 4-7 membered heterocycloalkyl-$C_{1-6}$ alkyl- of $R^e$ is each optionally substituted with 1, 2, 3 or 4 independently selected $R^f$ substituents;

each $R^f$ is independently selected from D, halo, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, 4-7 membered heterocycloalkyl-$C_{1-6}$ alkyl-, CN, $NO_2$, $OR^g$, $SR^g$, $NHOR^g$, $C(O)R^g$, $C(O)NR^gR^g$, $C(O)OR^g$, $OC(O)R^g$, $OC(O)NR^gR^g$, $NR^gR^g$, $NR^gC(O)R^g$, $NR^gC(O)OR^g$, $NR^gC(O)NR^gR^g$, $C(=NR^i)R^g$, $C(=NR^i)NR^gR^g$, $NR^gC(=NR^i)NR^gR^g$, $NR^gC(=NOH)NR^gR^g$, $NR^gC(=NCN)NR^gR^g$, $NR^gS(O)R^g$, $NR^gS(O)_2R^g$, $NR^gS(O)_2NR^gR^g$, $S(O)R^g$, $S(O)NR^gR^g$, $S(O)_2R^g$, $SF_5$, —$P(O)R^gR^g$, —$P(O)(OR^g)(OR^g)$, $B(OR^g)_2$, and $S(O)_2NR^gR^g$, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl- of $R^f$ is each optionally substituted with 1, 2, 3 or 4 independently selected $R^h$ substituents;

each $R^g$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl- and 4-7 membered heterocycloalkyl-$C_{1-6}$ alkyl- of $R^g$ is each optionally substituted with 1, 2, 3 or 4 independently selected $R^h$ substituents;

each $R^h$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^k$ is independently selected from H, D, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl- and 4-10 membered heterocycloalkyl-$C_{1-6}$ alkyl- of $R^k$ is each optionally substituted with 1, 2, 3, or 4 independently selected $R^q$ substituents;

each $R^q$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^m$, $SR^m$, $NHOR^m$, $C(O)R^m$, $C(O)NR^mR^m$, $C(O)OR^m$, $OC(O)R^m$, $OC(O)NR^mR^m$, $NHR^m$, $NR^mR^m$, $NR^mC(O)R^m$, $NR^mC(O)OR^m$, $NR^mC(O)NR^mR^m$, $C(=NR^i)R^m$, $C(=NR^i)NR^mR^m$, $NR^mC(=NR^i)NR^mR^m$, $NR^mC(=NOH)NR^mR^m$, $NR^mC(=NCN)NR^mR^m$, $NR^mS(O)R^m$, $NR^mS(O)_2R^m$, $NR^mS(O)_2NR^mR^m$, $S(O)R^m$, $S(O)NR^mR^m$, $S(O)_2R^m$, $SF_5$, —$P(O)R^mR^m$, —$P(O)(OR^m)(OR^m)$, $B(OR^m)_2$, and $S(O)_2NR^mR^m$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^q$ is each optionally substituted with 1, 2, 3 or 4 independently selected $R^n$ substituents;

each $R^m$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl- and 4-7 membered heterocycloalkyl-$C_{1-6}$ alkyl- of $R^m$ is each optionally substituted with 1, 2, 3 or 4 independently selected $R^n$ substituents;

each $R^n$ is independently selected from D, halo, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, 4-7 membered heterocycloalkyl-$C_{1-6}$ alkyl-, CN, $NO_2$, $OR^o$, $SR^o$, $NHOR^o$, $C(O)R^o$, $C(O)NR^oR^o$, $C(O)OR^o$, $OC(O)R^o$, $OC(O)NR^oR^o$, $NR^oR^o$, $NR^oC(O)R^o$, $NR^oC(O)OR^o$, $NR^oC(O)NR^oR^o$, $C(=NR^i)R^o$, $C(=NR^i)NR^oR^o$, $NR^oC(=NR^i)NR^oR^o$, $NR^oC(=NOH)NR^oR^o$, $NR^oC(=NCN)NR^oR^o$, $NR^oS(O)R^o$, $NR^oS(O)_2R^o$, $NR^oS(O)_2NR^oR^o$, $S(O)R^o$, $S(O)NR^oR^o$, $S(O)_2R^o$, and $S(O)_2NR^oR^o$, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl- of $R^n$ is each optionally substituted with 1, 2, 3 or 4 independently selected $R^h$ substituents; and each $R^o$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl- and 4-7 membered heterocycloalkyl-$C_{1-6}$ alkyl- of $R^o$ is each optionally substituted with 1, 2, 3 or 4 independently selected $R^h$ substituents.

In some embodiments:

$X^2$ is N or $CR^2$;
$X^4$ is N or $CR^4$;
$X^5$ is N or $CR^5$;
$X^6$ is N or $CR^6$;
$X^7$ is N or $CR^7$;
provided that $X^4$, $X^5$, and $X^6$ are not all N;

$Y^1$ is a $C_{1-6}$ haloalkyl, wherein each halogen is selected from F or Cl, wherein the haloalkyl is optionally substituted with 1 or 2 independently selected $Y^2$ substituents;

$R^1$ is selected from H, D, halo, $C_{1-6}$ alkyl, $C_{2-6}$ alkenyl, $C_{2-6}$ alkynyl, $C_{1-6}$ haloalkyl, 6-10 membered aryl, $C_{3-10}$cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NR^aR^a$, $NR^aNR^aR^a$, $NR^aC(O)R^a$, $NR^aC(O)OR^a$, $NR^aC(O)NR^aR^a$, $C(=NR^i)R^a$, $C(=NR^i)NR^aR^a$, $NR^aC(=NR^i)NR^aR^a$, $NR^aC(=NOH)NR^aR^a$, $NR^aC(=NCN)NR^aR^a$, $NR^aS(O)R^a$, $NR^aS(O)_2R^a$, $NR^aS(O)(=NR^i)R^a$, $NR^aS(O)_2NR^aR^a$, $S(O)R^a$, $S(O)NR^aR^a$, $S(O)_2R^a$, $OS(O)(=NR^i)R^a$, $SF_5$, $P(O)R^aR^a$, $P(O)(OR^a)(OR^a)$, $B(OR^a)_2$, and $S(O)_2NR^aR^a$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^1$ are each optionally substituted with 1, 2, 3, or 4 independently selected $R^b$ substituents;

$R^2$, $R^3$, $R^4$, $R^5$, $R^6$ and $R^7$ are each independently selected from H, D, $CD_3$, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl, OH, $NO_2$, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^2$, $R^3$, $R^4$, $R^5$, $R^6$ and $R^7$ are each optionally substituted with 1, 2, 3, or 4 independently selected $R^h$ substituents;

$R^8$ is selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$cycloalkyl-$C_{1-6}$ alkyl-, 5-10 membered heteroaryl-$C_{1-6}$ alkyl-, 4-10 membered heterocycloalkyl-$C_{1-6}$ alkyl-, $NO_2$, $C(O)R^a$, $C(O)NR^aR^a$, $C(O)OR^a$, $C(=NR^i)R^a$, $C(=NR^i)NR^aR^a$, $SF_5$, $-P(O)R^aR^a$, $-P(O)(OR^a)(OR^a)$, $B(OR^a)_2$, and $S(O)_2NR^aR^a$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^8$ are each optionally substituted with 1, 2, 3, or 4 independently selected $R^9$ substituents;

or any two $R^4$, $R^5$, $R^6$ and $R^7$ substituents, together with the ring atoms to which they attached form a 4-, 5-, 6-, or 7-membered aryl, cycloalkyl, heteroaryl, or heterocycloalkyl group optionally substituted with 1, 2, 3, or 4 independently selected $R^b$ substituents;

or $Y^1$ and $R^8$, together with the carbon atom to which they are attached, form a 4-, 5-, 6-, or 7-membered cycloalkyl or heterocycloalkyl group optionally substituted with 1, 2, 3, or 4 independently selected $R^9$ substituents;

each $R^i$ is independently selected from H, CN, OH, $C_{1-4}$ alkyl, and $C_{1-4}$ alkoxy;

each $Y^2$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^a$ is independently selected from H, D, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl- and 4-10 membered heterocycloalkyl-$C_{1-6}$ alkyl- of $R^a$ is each optionally substituted with 1, 2, 3, or 4 independently selected $R^b$ substituents;

each $R^b$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^c$, $SR^c$, $NHOR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^cC(O)OR^c$, $NR^cC(O)NR^cR^c$, $C(=NR^i)R^c$, $C(=NR^i)NR^cR^c$, $NR^cC(=NR^i)NR^cR^c$, $NR^cC(=NOH)NR^cR^c$, $NR^cC(=NCN)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$, $SF_5$, $-P(O)R^cR^c$, $-P(O)(OR^c)(OR^c)$, $B(OR^c)_2$, and $S(O)_2NR^cR^c$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^b$ is each optionally substituted with 1, 2, 3, or 4 independently selected $R^d$ substituents;

each $R^9$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^k$, $SR^k$, $NHOR^k$, $C(O)R^k$, $C(O)NR^kR^k$, $C(O)OR^k$, $OC(O)R^k$, $OC(O)NR^kR^k$, $NR^kR^k$, $NR^kC(O)R^k$, $NR^kC(O)OR^k$, $NR^kC(O)NR^kR^k$, $C(=NR^i)R^k$, $C(=NR^i)NR^kR^k$, $NR^kC(=NR^i)NR^kR^k$, $NR^kC(=NOH)NR^kR^k$, $NR^kC(=NCN)NR^kR^k$, $NR^kS(O)R^k$, $NR^kS(O)_2R^k$, $NR^kS(O)_2NR^kR^k$, $S(O)R^k$, $S(O)NR^kR^k$, $S(O)_2R^k$, $SF_5$, —$P(O)R^kR^k$, —$P(O)(OR^k)(OR^k)$, $B(OR^k)_2$, and $S(O)_2NR^kR^k$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^9$ is each optionally substituted with 1, 2, 3, or 4 independently selected $R^q$ substituents;

each $R^c$ is independently selected from H, D, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl- and 4-10 membered heterocycloalkyl-$C_{1-6}$ alkyl- of $R^c$ is each optionally substituted with 1, 2, 3, or 4 independently selected $R^d$ substituents;

each $R^d$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^e$, $SR^e$, $NHOR^e$, $C(O)R^e$, $C(O)NR^eR^e$, $C(O)OR^e$, $OC(O)R^e$, $OC(O)NR^eR^e$, $NR^eR^e$, $NR^eC(O)R^e$, $NR^eC(O)OR^e$, $NR^eC(O)NR^eR^e$, $C(=NR^i)R^e$, $C(=NR^i)NR^eR^e$, $NR^eC(=NR^i)NR^eR^e$, $NR^eC(=NOH)NR^eR^e$, $NR^eC(=NCN)NR^eR^e$, $NR^eS(O)R^e$, $NR^eS(O)_2R^e$, $NR^eS(O)_2NR^eR^e$, $S(O)R^e$, $S(O)NR^eR^e$, $S(O)_2R^e$, $SF_5$, —$P(O)R^eR^e$, —$P(O)(OR^e)(OR^e)$, $B(OR^e)_2$, and $S(O)_2NR^eR^e$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^d$ is each optionally substituted with 1, 2, 3 or 4 independently selected $R^f$ substituents;

each $R^e$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl- and 4-7 membered heterocycloalkyl-$C_{1-6}$ alkyl- of $R^e$ is each optionally substituted with 1, 2, 3 or 4 independently selected $R^f$ substituents;

each $R^f$ is independently selected from D, halo, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, 4-7 membered heterocycloalkyl-$C_{1-6}$ alkyl-, CN, $NO_2$, $OR^g$, $SR^g$, $NHOR^g$, $C(O)R^g$, $C(O)NR^gR^g$, $C(O)OR^g$, $OC(O)R^g$, $OC(O)NR^gR^g$, $NR^gR^g$, $NR^gC(O)R^g$, $NR^gC(O)OR^g$, $NR^gC(O)NR^gR^g$, $C(=NR^i)R^g$, $C(=NR^i)NR^gR^g$, $NR^gC(=NR^i)NR^gR^g$, $NR^gC(=NOH)NR^gR^g$, $NR^gC(=NCN)NR^gR^g$, $NR^gS(O)R^g$, $NR^gS(O)_2R^g$, $NR^gS(O)_2NR^gR^g$, $S(O)R^g$, $S(O)NR^gR^g$, $S(O)_2R^g$, $SF_5$, —$P(O)R^gR^g$, —$P(O)(OR^g)(OR^g)$, $B(OR^g)_2$, and $S(O)_2NR^gR^g$, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl- of $R^f$ is each optionally substituted with 1, 2, 3 or 4 independently selected $R^h$ substituents;

each $R^g$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl- and 4-7 membered heterocycloalkyl-$C_{1-6}$ alkyl- of $R^g$ is each optionally substituted with 1, 2, 3 or 4 independently selected $R^h$ substituents;

each $R^h$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^k$ is independently selected from H, D, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl- and 4-10 membered heterocycloalkyl-$C_{1-6}$ alkyl- of $R^k$ is each optionally substituted with 1, 2, 3, or 4 independently selected $R^q$ substituents;

each $R^q$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^m$, $SR^m$, $NHOR^m$, $C(O)R^m$, $C(O)NR^mR^m$, $C(O)OR^m$, $OC(O)R^m$, $OC(O)NR^mR^m$, $NHR^m$, $NR^mR^m$, $NR^mC(O)R^m$, $NR^mC(O)OR^m$, $NR^mC(O)NR^mR^m$, $C(=NR^i)R^m$, $C(=NR^i)NR^mR^m$, $NR^mC(=NR^i)NR^mR^m$, $NR^mC(=NOH)NR^mR^m$, $NR^mC(=NCN)NR^mR^m$, $NR^mS(O)$ $R'''$, $NR'''S(O)_2R'''$, $NR'''S(O)_2NR'''R'''$, $S(O)R'''$, $S(O)NR'''R'''$, $S(O)_2R'''$, $SF_5$, —$P(O)R'''R'''$, —$P(O)(OR''')(OR''')$, $B(OR''')_2$, and $S(O)_2NR'''R'''$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^q$ is each optionally substituted with 1, 2, 3 or 4 independently selected $R^n$ substituents;

each $R'''$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl- and 4-7 membered heterocycloalkyl-$C_{1-6}$ alkyl- of $R'''$ is each optionally substituted with 1, 2, 3 or 4 independently selected $R^n$ substituents;

each $R^n$ is independently selected from D, halo, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, 4-7 membered heterocycloalkyl-$C_{1-6}$ alkyl-, CN, $NO_2$, $OR^o$, $SR^o$, $NHOR^o$, $C(O)R^o$, $C(O)NR^oR^o$, $C(O)OR^o$, $OC(O)R^o$, $OC(O)NR^oR^o$, $NR^oR^o$, $NR^oC(O)R^o$, $NR^oC(O)OR^o$, $NR^oC(O)NR^oR^o$, $C(=NR^i)R^o$, $C(=NR^i)NR^oR^o$, $NR^oC(=NR^i)NR^oR^o$, $NR^oC(=NOH)NR^oR^o$, $NR^oC(=NCN)NR^oR^o$, $NR^oS(O)R^o$, $NR^oS(O)_2R^o$, $NR^oS(O)_2NR^oR^o$, $S(O)R^o$, $S(O)NR^oR^o$, $S(O)_2R^o$, and $S(O)_2NR^oR^o$, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl- of $R^n$ is each optionally substituted with 1, 2, 3 or 4 independently selected $R^h$ substituents; and each $R^o$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl- and 4-7 membered heterocycloalkyl-$C_{1-6}$ alkyl- of $R^o$ is each optionally substituted with 1, 2, 3 or 4 independently selected $R^h$ substituents.

In some embodiments:
$X^2$ is N or $CR^2$;
$X^4$ is N or $CR^4$;
$X^5$ is N or $CR^5$;
$X^6$ is N or $CR^6$;
$X^7$ is N or $CR^7$;
provided that $X^4$, $X^5$, and $X^6$ are not all N;
$Y^1$ is a $C_{1-6}$ haloalkyl, wherein each halogen is selected from F or Cl, wherein the haloalkyl is optionally substituted with 1 or 2 independently selected $Y^2$ substituents;
$R^1$ is selected from H, D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NR^aR^a$, $NR^aNR^aR^a$, $NR^aC(O)R^a$, $NR^aC(O)OR^a$, $NR^aC(O)NR^aR^a$, $C(=NR^i)R^a$, $C(=NR^i)NR^aR^a$, $NR^aC(=NR^i)NR^aR^a$, $NR^aC(=NOH)NR^aR^a$, $NR^aC(=NCN)NR^aR^a$, $NR^aS(O)R^a$, $NR^aS(O)_2R^a$, $NR^aS(O)(=NR^i)R^a$, $NR^aS(O)_2NR^aR^a$, $S(O)R^a$, $S(O)NR^aR^a$, $S(O)_2R^a$, $OS(O)(=NR^i)R^a$, $SF_5$, $P(O)R^aR^a$, $P(O)(OR^a)(OR^a)$, $B(OR^a)_2$, and $S(O)_2NR^aR^a$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^1$ are each optionally substituted with 1, 2, 3, or 4 independently selected $R^b$ substituents;

$R^2$, $R^3$, $R^4$, $R^5$, $R^6$ and $R^7$ are each independently selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl, OH, $NO_2$, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^2$, $R^3$, $R^4$, $R^5$, $R^6$ and $R^7$ are each optionally substituted with 1, 2, 3, or 4 independently selected $R^h$ substituents;

$R^8$ is selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$cycloalkyl-$C_{1-6}$ alkyl-, 5-10 membered heteroaryl-$C_{1-6}$ alkyl-, 4-10 membered heterocycloalkyl-$C_{1-6}$ alkyl-, $NO_2$, $C(O)R^a$, $C(O)NR^aR^a$, $C(O)OR^a$, $C(=NR^i)R^a$, $C(=NR^i)NR^aR^a$, $SF_5$, —$P(O)R^aR^a$, —$P(O)(OR^a)(OR^a)$, $B(OR^a)_2$, and $S(O)_2NR^aR^a$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^8$ are each optionally substituted with 1, 2, 3, or 4 independently selected $R^9$ substituents;

or any two $R^4$, $R^5$, $R^6$ and $R^7$ substituents, together with the ring atoms to which they attached form a 4-, 5-, 6-, or 7-membered aryl, cycloalkyl, heteroaryl, or heterocycloalkyl group optionally substituted with 1, 2, 3, or 4 independently selected $R^b$ substituents;

or Y$^1$ and R$^8$, together with the carbon atom to which they are attached, form a 4-, 5-, 6-, or 7-membered cycloalkyl or heterocycloalkyl group optionally substituted with 1, 2, 3, or 4 independently selected R$^9$ substituents;

each R$^i$ is independently selected from H, CN, OH, C$_{1-4}$ alkyl, and C$_{1-4}$ alkoxy;

each Y$^2$ is independently selected from OH, NO$_2$, CN, halo, C$_{1-6}$ alkyl, C$_{2-6}$ alkenyl, C$_{2-6}$ alkynyl, C$_{1-6}$ haloalkyl, cyano-C$_{1-6}$ alkyl, HO—C$_{1-6}$ alkyl, C$_{1-6}$ alkoxy-C$_{1-6}$ alkyl, C$_{3-10}$ cycloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

each R$^a$ is independently selected from H, D, C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, and 4-10 membered heterocycloalkyl-C$_{1-6}$ alkyl-, wherein the C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl- and 4-10 membered heterocycloalkyl-C$_{1-6}$ alkyl- of R$^a$ is each optionally substituted with 1, 2, 3, or 4 independently selected R$^b$ substituents;

each R$^b$ is independently selected from D, halo, C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, 4-10 membered heterocycloalkyl-C$_{1-6}$ alkyl-, CN, NO$_2$, OR$^c$, SR$^c$, NHOR$^c$, C(O)R$^c$, C(O)NR$^c$R$^c$, C(O)OR$^c$, OC(O)R$^c$, OC(O)NR$^c$R$^c$, NR$^c$R$^c$, NR$^c$C(O)R$^c$, NR$^c$C(O)OR$^c$, NR$^c$C(O)NR$^c$R$^c$, C(=NR$^i$)R$^c$, C(=NR$^i$)NR$^c$R$^c$, NR$^c$C(=NR$^i$)NR$^c$R$^c$, NR$^c$C(=NOH)NR$^c$R$^c$, NR$^c$C(=NCN)NR$^c$R$^c$, NR$^c$S(O)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$, SF$_5$, —P(O)R$^c$R$^c$, —P(O)(OR$^c$)(OR$^c$), B(OR$^c$)$_2$, and S(O)$_2$NR$^c$R$^c$, wherein the C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, and 4-10 membered heterocycloalkyl-C$_{1-6}$ alkyl- of R$^b$ is each optionally substituted with 1, 2, 3, or 4 independently selected R$^d$ substituents;

each R$^9$ is independently selected from D, halo, C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, 4-10 membered heterocycloalkyl-C$_{1-6}$ alkyl-, CN, NO$_2$, OR$^k$, SR$^k$, NHOR$^k$, C(O)R$^k$, C(O)NR$^k$R$^k$, C(O)OR$^k$, OC(O)R$^k$, OC(O)NR$^k$R$^k$, NR$^k$R$^k$, NR$^k$C(O)R$^k$, NR$^k$C(O)OR$^k$, NR$^k$C(O)NR$^k$R$^k$, C(=NR$^i$)R$^k$, C(=NR$^i$)NR$^k$R$^k$, NR$^k$C(=NR$^i$)NR$^k$R$^k$, NR$^k$C(=NOH)NR$^k$R$^k$, NR$^k$C(=NCN)NR$^k$R$^k$, NR$^k$S(O)R$^k$, NR$^k$S(O)$_2$R$^k$, NR$^k$S(O)$_2$NR$^k$R$^k$, S(O)R$^k$, S(O)NR$^k$R$^k$, S(O)$_2$R$^k$, SF$_5$, —P(O)R$^k$R$^k$, —P(O)(OR$^k$)(OR$^k$), B(OR$^k$)$_2$, and S(O)$_2$NR$^k$R$^k$, wherein the C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, and 4-10 membered heterocycloalkyl-C$_{1-6}$ alkyl- of R$^9$ is each optionally substituted with 1, 2, 3, or 4 independently selected R$^q$ substituents;

each R$^c$ is independently selected from H, D, C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, and 4-10 membered heterocycloalkyl-C$_{1-6}$ alkyl-, wherein the C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl- and 4-10 membered heterocycloalkyl-C$_{1-6}$ alkyl- of R$^c$ is each optionally substituted with 1, 2, 3, or 4 independently selected R$^d$ substituents;

each R$^d$ is independently selected from D, halo, C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, 4-10 membered heterocycloalkyl-C$_{1-6}$ alkyl-, CN, NO$_2$, OR$^e$, SR$^e$, NHOR$^e$, C(O)R$^e$, C(O)NR$^e$R$^e$, C(O)OR$^e$, OC(O)R$^e$, OC(O)NR$^e$R$^e$, NR$^e$R$^e$, NR$^e$C(O)R$^e$, NR$^e$C(O)OR$^e$, NR$^e$C(O)NR$^e$R$^e$, C(=NR$^i$)R$^e$, C(=NR$^i$)NR$^e$R$^e$, NR$^e$C(=NR$^i$)NR$^e$R$^e$, NR$^e$C(=NOH)NR$^e$R$^e$, NR$^e$C(=NCN)NR$^e$R$^e$, NR$^e$S(O)R$^e$, NR$^e$S(O)$_2$R$^e$, NR$^e$S(O)$_2$NR$^e$R$^e$, S(O)R$^e$, S(O)NR$^e$R$^e$, S(O)$_2$R$^e$, SF$_5$, —P(O)R$^e$R$^e$, —P(O)(OR$^e$)(OR$^e$), B(OR$^e$)$_2$, and S(O)$_2$NR$^e$R$^e$, wherein the C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, and 4-10 membered heterocycloalkyl-C$_{1-6}$ alkyl- of R$^d$ is each optionally substituted with 1, 2, 3 or 4 independently selected R$^f$ substituents;

each R$^e$ is independently selected from H, D, C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, 5-6 membered heteroaryl-C$_{1-6}$ alkyl-, and 4-7 membered heterocycloalkyl-C$_{1-6}$ alkyl-, wherein the C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, 5-6 membered heteroaryl-C$_{1-6}$ alkyl- and 4-7 membered heterocycloalkyl-C$_{1-6}$ alkyl- of R$^e$ is each optionally substituted with 1, 2, 3 or 4 independently selected R$^f$ substituents;

each R$^f$ is independently selected from D, halo, C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, 5-6 membered heteroaryl-C$_{1-6}$ alkyl-, 4-7 membered heterocycloalkyl-C$_{1-6}$ alkyl-, CN, NO$_2$, OR$^g$, SR$^g$, NHOR$^g$, C(O)R$^g$, C(O)NR$^g$R$^g$, C(O)OR$^g$, OC(O)R$^g$, OC(O)NR$^g$R$^g$, NR$^g$R$^g$, NR$^g$C(O)R$^g$, NR$^g$C(O)OR$^g$, NR$^g$C(O)NR$^g$R$^g$, C(=NR$^i$)R$^g$, C(=NR$^i$)NR$^g$R$^g$, NR$^g$C(=NR$^i$)NR$^g$R$^g$, NR$^g$C(=NOH)NR$^g$R$^g$, NR$^g$C(=NCN)NR$^g$R$^g$, NR$^g$S(O)R$^g$, NR$^g$S(O)$_2$R$^g$, NR$^g$S(O)$_2$NR$^g$R$^g$, S(O)R$^g$, S(O)NR$^g$R$^g$, S(O)$_2$R$^g$, SF$_5$, —P(O)R$^g$R$^g$, —P(O)(OR$^g$)(OR$^g$), B(OR$^g$)$_2$, and S(O)$_2$NR$^g$R$^g$, wherein the C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl- of $R^f$ is each optionally substituted with 1, 2, 3 or 4 independently selected $R^h$ substituents;

each $R^g$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl- and 4-7 membered heterocycloalkyl-$C_{1-6}$ alkyl- of $R^g$ is each optionally substituted with 1, 2, 3 or 4 independently selected $R^h$ substituents;

each $R^h$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^k$ is independently selected from H, D, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl- and 4-10 membered heterocycloalkyl-$C_{1-6}$ alkyl- of $R^k$ is each optionally substituted with 1, 2, 3, or 4 independently selected $R^q$ substituents;

each $R^q$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^m$, $SR^m$, $NHOR^m$, $C(O)R^m$, $C(O)NR^mR^m$, $C(O)OR^m$, $OC(O)R^m$, $OC(O)NR^mR^m$, $NHR^m$, $NR^mR^m$, $NR^mC(O)R^m$, $NR^mC(O)OR^m$, $NR^mC(O)NR^mR^m$, $C(=NR^i)R^m$, $C(=NR^i)NR^mR^m$, $NR^mC(=NR^i)NR^mR^m$, $NR^mC(=NOH)NR^mR^m$, $NR^mC(=NCN)NR^mR^m$, $NR^mS(O)R^m$, $NR^mS(O)_2R^m$, $NR^mS(O)_2NR^mR^m$, $S(O)R^m$, $S(O)NR^mR^m$, $S(O)_2R^m$, $SF_5$, —$P(O)R^mR^m$, —$P(O)(OR^m)(OR^m)$, $B(OR^m)_2$, and $S(O)_2NR^mR^m$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^q$ is each optionally substituted with 1, 2, 3 or 4 independently selected $R^n$ substituents;

each $R^m$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl- and 4-7 membered heterocycloalkyl-$C_{1-6}$ alkyl- of $R^m$ is each optionally substituted with 1, 2, 3 or 4 independently selected $R^n$ substituents;

each $R^n$ is independently selected from D, halo, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, 4-7 membered heterocycloalkyl-$C_{1-6}$ alkyl-, CN, $NO_2$, $OR^o$, $SR^o$, $NHOR^o$, $C(O)R^o$, $C(O)NR^oR^o$, $C(O)OR^o$, $OC(O)R^o$, $OC(O)NR^oR^o$, $NR^oR^o$, $NR^oC(O)R^o$, $NR^oC(O)OR^o$, $NR^oC(O)NR^oR^o$, $C(=NR^i)R^o$, $C(=NR^i)NR^oR^o$, $NR^oC(=NR^i)NR^oR^o$, $NR^oC(=NOH)NR^oR^o$, $NR^oC(=NCN)NR^oR^o$, $NR^oS(O)R^o$, $NR^oS(O)_2R^o$, $NR^oS(O)_2NR^oR^o$, $S(O)R^o$, $S(O)NR^oR^o$, $S(O)_2R^o$, and $S(O)_2NR^oR^o$, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl- of $R^n$ is each optionally substituted with 1, 2, 3 or 4 independently selected $R^h$ substituents; and each $R^o$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl- and 4-7 membered heterocycloalkyl-$C_{1-6}$ alkyl- of $R^o$ is each optionally substituted with 1, 2, 3 or 4 independently selected $R^h$ substituents.

In some embodiments:
$X^2$ is N or $CR^2$;
$X^4$ is N or $CR^4$;
$X^5$ is N or $CR^5$;
$X^6$ is N or $CR^6$;
$X^7$ is N or $CR^7$;
provided that $X^4$, $X^5$, and $X^6$ are not all N;

$Y^1$ is a $C_{1-6}$ haloalkyl, wherein each halogen is selected from F or Cl, wherein the haloalkyl is optionally substituted with 1 or 2 independently selected $Y^2$ substituents;

$R^1$ is selected from H, D, halo, $C_{1-6}$ alkyl, $C_{2-6}$ alkenyl, $C_{2-6}$ alkynyl, $C_{1-6}$ haloalkyl, 6-10 membered aryl, $C_{3-10}$cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NR^aR^a$, $NR^aNR^aR^a$, $NR^aC(O)R^a$, $NR^aC(O)OR^a$, $NR^aC(O)NR^aR^a$, $C(=NR^i)R^a$, $C(=NR^i)NR^aR^a$, $NR^aC(=NR^i)NR^aR^a$, $NR^aC(=NOH)NR^aR^a$, $NR^aC(=NCN)NR^aR^a$, $NR^aS(O)R^a$, $NR^aS(O)_2R^a$, $NR^aS(O)(=NR^i)R^a$, $NR^aS(O)_2NR^aR^a$, $S(O)R^a$, $S(O)NR^aR^a$, $S(O)_2R^a$, $OS(O)(=NR^i)R^a$, and $S(O)_2NR^aR^a$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^1$ are each optionally substituted with 1, 2, 3, or 4 independently selected $R^b$ substituents;

$R^2$, $R^3$, $R^4$, $R^5$, $R^6$ and $R^7$ are each independently selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, OH, $NO_2$, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^2$, $R^3$, $R^4$, $R^5$, $R^6$ and $R^7$ are each optionally substituted with 1, 2, 3, or 4 independently selected $R^h$ substituents;

$R^8$ is selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$cycloalkyl-$C_{1-6}$ alkyl-, 5-10 membered heteroaryl-$C_{1-6}$ alkyl-, 4-10 membered heterocycloalkyl-$C_{1-6}$ alkyl-, $NO_2$, $C(O)R^a$, $C(O)NR^aR^a$, $C(O)OR^a$, $C(=NR^i)R^a$, $C(=NR^i)NR^aR^a$, and $S(O)_2NR^aR^a$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^8$ are each optionally substituted with 1, 2, 3, or 4 independently selected $R^9$ substituents;

or any two $R^4$, $R^5$, $R^6$ and $R^7$ substituents, together with the ring atoms to which they attached form a 4-, 5-, 6-, or 7-membered aryl, cycloalkyl, heteroaryl, or heterocycloalkyl group optionally substituted with 1, 2, 3, or 4 independently selected $R^b$ substituents;

or $Y^1$ and $R^8$, together with the carbon atom to which they are attached, form a 4-, 5-, 6-, or 7-membered cycloalkyl or heterocycloalkyl group optionally substituted with 1, 2, 3, or 4 independently selected $R^9$ substituents;

each $R^i$ is independently selected from H, CN, OH, $C_{1-4}$ alkyl, and $C_{1-4}$ alkoxy;

each $Y^2$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^a$ is independently selected from H, D, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl- and 4-10 membered heterocycloalkyl-$C_{1-6}$ alkyl- of $R^a$ is each optionally substituted with 1, 2, 3, or 4 independently selected $R^b$ substituents;

each $R^b$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^c$, $SR^c$, $NHOR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^cC(O)OR^c$, $NR^cC(O)NR^cR^c$, $C(=NR^i)R^c$, $C(=NR^i)NR^cR^c$, $NR^cC(=NR^i)NR^cR^c$, $NR^cC(=NOH)NR^cR^c$, $NR^cC(=NCN)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$, and $S(O)_2NR^cR^c$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^b$ is each optionally substituted with 1, 2, 3, or 4 independently selected $R^d$ substituents;

each $R^9$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^k$, $SR^k$, $NHOR^k$, $C(O)R^k$, $C(O)NR^kR^k$, $C(O)OR^k$, $OC(O)R^k$, $OC(O)NR^kR^k$, $NR^kR^k$, $NR^kC(O)R^k$, $NR^kC(O)OR^k$, $NR^kC(O)NR^kR^k$, $C(=NR^i)R^k$, $C(=NR^i)NR^kR^k$, $NR^kC(=NR^i)NR^kR^k$, $NR^kC(=NOH)NR^kR^k$, $NR^kC(=NCN)NR^kR^k$, $NR^kS(O)R^k$, $NR^kS(O)_2R^k$, $NR^kS(O)_2NR^kR^k$, $S(O)R^k$, $S(O)NR^kR^k$, $S(O)_2R^k$, and $S(O)_2NR^kR^k$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^9$ is each optionally substituted with 1, 2, 3, or 4 independently selected $R^q$ substituents;

each $R^c$ is independently selected from H, D, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl- and 4-10 membered heterocycloalkyl-$C_{1-6}$ alkyl- of $R^c$ is each optionally substituted with 1, 2, 3, or 4 independently selected $R^d$ substituents;

or two $R^c$ substituents, together with the nitrogen atom to which they attached form a 4-, 5-, 6-, or 7-membered heteroaryl or heterocycloalkyl group optionally substituted with 1, 2, 3, or 4 independently selected $R^d$ substituents;

each $R^d$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, NO$_2$, OR$^e$, SR$^e$, NHOR$^e$, C(O)R$^e$, C(O)NR$^e$R$^e$, C(O)OR$^e$, OC(O)R$^e$, OC(O)NR$^e$R$^e$, NR$^e$R$^e$, NR$^e$C(O)R$^e$, NR$^e$C(O)OR$^e$, NR$^e$C(O)NR$^e$R$^e$, C(=NR$^i$)R$^e$, C(=NR$^i$)NR$^e$R$^e$, NR$^e$C(=NR$^i$)NR$^e$R$^e$, NR$^e$C(=NOH)NR$^e$R$^e$, NR$^e$C(=NCN)NR$^e$R$^e$, NR$^e$S(O)R$^e$, NR$^e$S(O)$_2$R$^e$, NR$^e$S(O)$_2$NR$^e$R$^e$, S(O)R$^e$, S(O)NR$^e$R$^e$, S(O)$_2$R$^e$, and S(O)$_2$NR$^e$R$^e$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^d$ is each optionally substituted with 1, 2, 3 or 4 independently selected $R^f$ substituents;

each $R^e$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl- and 4-7 membered heterocycloalkyl-$C_{1-6}$ alkyl- of $R^e$ is each optionally substituted with 1, 2, 3 or 4 independently selected $R^f$ substituents;

each $R^f$ is independently selected from D, halo, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-74}$ cycloalkyl-$C_{1-6}$ alkyl-, 5-6 membered heteroaryl-$C_{1-6}$ alkyl-, 4-7 membered heterocycloalkyl-$C_{1-6}$ alkyl-, CN, NO$_2$, OR$^g$, SR$^g$, NHOR$^g$, C(O)R$^g$, C(O)NR$^g$R$^g$, C(O)OR$^g$, OC(O)R$^g$, OC(O)NR$^g$R$^g$, NR$^g$R$^g$, NR$^g$C(O)R$^g$, NR$^g$C(O)OR$^g$, NR$^g$C(O)NR$^g$R$^g$, C(=NR$^i$)R$^g$, C(=NR$^i$)NR$^g$R$^g$, NR$^g$C(=NR$^i$)NR$^g$R$^g$, NR$^g$C(=NOH)NR$^g$R$^g$, NR$^g$C(=NCN)NR$^g$R$^g$, NR$^g$S(O)R$^g$, NR$^g$S(O)$_2$R$^g$, NR$^g$S(O)$_2$NR$^g$R$^g$, S(O)R$^g$, S(O)NR$^g$R$^g$, S(O)$_2$R$^g$, and S(O)$_2$NR$^g$R$^g$, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl- of $R^f$ is each optionally substituted with 1, 2, 3 or 4 independently selected $R^h$ substituents;

each $R^g$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl- and 4-7 membered heterocycloalkyl-$C_{1-6}$ alkyl- of $R^g$ is each optionally substituted with 1, 2, 3 or 4 independently selected $R^h$ substituents;

each $R^h$ is independently selected from OH, NO$_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^k$ is independently selected from H, D, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl- and 4-10 membered heterocycloalkyl-$C_{1-6}$ alkyl- of $R^k$ is each optionally substituted with 1, 2, 3, or 4 independently selected $R^q$ substituents;

each $R^q$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, NO$_2$, OR$^m$, SR$^m$, NHOR$^m$, C(O)R$^m$, C(O)NR$^m$R$^m$, C(O)OR$^m$, OC(O)R$^m$, OC(O)NR$^m$R$^m$, NHR$^m$, NR$^m$R$^m$, NR$^m$C(O)R$^m$, NR$^m$C(O)OR$^m$, NR$^m$C(O)NR$^m$R$^m$, C(=NR$^i$)R$^m$, C(=NR$^i$)NR$^m$R$^m$, NR$^m$C(=NR$^i$)NR$^m$R$^m$, NR$^m$C(=NOH)NR$^m$R$^m$, NR$^m$C(=NCN)NR$^m$R$^m$, NR$^m$S(O)R$^m$, NR$^m$S(O)$_2$R$^m$, NR$^m$S(O)$_2$NR$^m$R$^m$, S(O)R$^m$, S(O)NR$^m$R$^m$, S(O)$_2$R$^m$, and S(O)$_2$NR$^m$R$^m$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^q$ is each optionally substituted with 1, 2, 3 or 4 independently selected $R^n$ substituents;

each $R^m$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl- and 4-7 membered heterocycloalkyl-$C_{1-6}$ alkyl- of $R'''$ is each optionally substituted with 1, 2, 3 or 4 independently selected $R''$ substituents;

each $R''$ is independently selected from D, halo, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, 4-7 membered heterocycloalkyl-$C_{1-6}$ alkyl-, CN, $NO_2$, $OR^o$, $SR^o$, $NHOR^o$, $C(O)R^o$, $C(O)NR^oR^o$, $C(O)OR^o$, $OC(O)R^o$, $OC(O)NR^oR^o$, $NR^oR^o$, $NR^oC(O)R^o$, $NR^oC(O)OR^o$, $NR^oC(O)NR^oR^o$, $C(=NR^i)R^o$, $C(=NR^i)NR^oR^o$, $NR^oC(=NR^i)NR^oR^o$, $NR^oC(=NOH)NR^oR^o$, $NR^oC(=NCN)NR^oR^o$, $NR^oS(O)R^o$, $NR^oS(O)_2R^o$, $NR^oS(O)_2NR^oR^o$, $S(O)R^o$, $S(O)NR^oR^o$, $S(O)_2R^o$, and $S(O)_2NR^oR^o$, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl- of $R''$ is each optionally substituted with 1, 2, 3 or 4 independently selected $R^h$ substituents; and each $R^o$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl- and 4-7 membered heterocycloalkyl-$C_{1-6}$ alkyl- of $R^o$ is each optionally substituted with 1, 2, 3 or 4 independently selected $R^h$ substituents.

In some embodiments:

$X^2$ is N or $CR^2$;
$X^4$ is N or $CR^4$;
$X^5$ is N or $CR^5$;
$X^6$ is N or $CR^6$;
$X^7$ is N or $CR^7$;
provided that $X^4$, $X^5$, and $X^6$ are not all N;
$Y^1$ is a $C_{1-6}$ haloalkyl, wherein each halogen is selected from F or Cl;
$R^1$ is independently selected from H, D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NR^aR^a$, $NR^aNR^aR^a$, $NR^aC(O)R^a$, $NR^aC(O)OR^a$, $NR^aC(O)NR^aR^a$, $C(=NR^i)R^a$, $C(=NR^i)NR^aR^a$, $NR^aC(=NR^i)NR^aR^a$, $NR^aC(=NOH)NR^aR^a$, $NR^aC(=NCN)NR^aR^a$, $NR^aS(O)R^a$, $NR^aS(O)_2R^a$, $NR^aS(O)(=NR^i)R^a$, $NR^aS(O)_2NR^aR^a$, $S(O)R^a$, $S(O)NR^aR^a$, $S(O)_2R^a$, and $S(O)_2NR^aR^a$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-4}$ alkyl- of $R^1$ are each optionally substituted with 1, 2, 3, or 4 independently selected $R^b$ substituents;

$R^2$, $R^3$, $R^4$, $R^5$, $R^6$ and $R^7$ are each independently selected from H, D, halo, $C_{1-6}$ alkyl, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, OH, $NO_2$, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-4}$ alkyl- of $R^2$, $R^3$, $R^4$, $R^5$, $R^6$ and $R^7$ are each optionally substituted with 1, 2, 3, or 4 independently selected $R^h$ substituents;

$R^8$ is selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$cycloalkyl-$C_{1-6}$ alkyl-, 5-10 membered heteroaryl-$C_{1-6}$ alkyl-, 4-10 membered heterocycloalkyl-$C_{1-6}$ alkyl-, $NO_2$, $C(O)R^a$, $C(O)NR^aR^a$, $C(O)OR^a$, $C(=NR^i)R^a$, $C(=NR^i)NR^aR^a$, and $S(O)_2NR^aR^a$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-4}$ alkyl- of $R^8$ are each optionally substituted with 1, 2, 3, or 4 independently selected $R^9$ substituents;

or $Y^1$ and $R^8$, together with the carbon atom to which they are attached, form a 4-, 5-, 6-, or 7-membered cycloalkyl or heterocycloalkyl group optionally substituted with 1, 2, 3, or 4 independently selected $R^9$ substituents;

each $R^i$ is independently selected from H, CN, OH, $C_{1-4}$ alkyl, and $C_{1-4}$ alkoxy;

each $R^a$ is independently selected from H, D, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-4}$ alkyl-, 5-10 membered heteroaryl-$C_{1-6}$ alkyl- and 4-10 membered heterocycloalkyl-$C_{1-6}$ alkyl- of $R^a$ is each optionally substituted with 1, 2, 3, or 4 independently selected $R^b$ substituents;

each $R^b$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^c$, $SR^c$, $NHOR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^cC(O)OR^c$, $NR^cC(O)NR^cR^c$, $C(=NR^i)R^c$, $C(=NR^i)NR^cR^c$, $NR^cC(=NR^i)NR^cR^c$, $NR^cC(=NOH)NR^cR^c$, $NR^cC(=NCN)NR^cR^c$, $NR^cS(O)R^c$, $NR^cS(O)_2R^c$, NR$^c$S(O)$_2$NR$^c$R$^c$, S(O)R$^c$, S(O)NR$^c$R$^c$, S(O)$_2$R$^c$, and S(O)$_2$NR$^c$R$^c$, wherein the C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heterocycloalkyl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, and 4-10 membered heterocycloalkyl-C$_{1-4}$ alkyl- of R$^b$ is each optionally substituted with 1, 2, 3, or 4 independently selected R$^d$ substituents;

each R$^g$ is independently selected from D, halo, C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, 4-10 membered heterocycloalkyl-C$_{1-6}$ alkyl-, CN, NO$_2$, OR$^k$, SR$^k$, NHOR$^k$, C(O)R$^k$, C(O)NR$^k$R$^k$, C(O)OR$^k$, OC(O)R$^k$, OC(O)NR$^k$R$^k$, NR$^k$R$^k$, NR$^k$C(O)R$^k$, NR$^k$C(O)OR$^k$, NR$^k$C(O)NR$^k$R$^k$, C(=NR$^i$)R$^k$, C(=NR$^i$)NR$^k$R$^k$, NR$^k$C(=NR$^i$)NR$^k$R$^k$, NR$^k$C(=NOH)NR$^k$R$^k$, NR$^k$C(=NCN)NR$^k$R$^k$, NR$^k$S(O)R$^k$, NR$^k$S(O)$_2$R$^k$, NR$^k$S(O)$_2$NR$^k$R$^k$, S(O)R$^k$, S(O)NR$^k$R$^k$, S(O)$_2$R$^k$, and S(O)$_2$NR$^k$R$^k$, wherein the C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, and 4-10 membered heterocycloalkyl-C$_{1-4}$ alkyl- of R$^g$ is each optionally substituted with 1, 2, 3, or 4 independently selected R$^q$ substituents;

each R$^c$ is independently selected from H, D, C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, and 4-10 membered heterocycloalkyl-C$_{1-6}$ alkyl-, wherein the C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-4}$ alkyl-, 5-10 membered heteroaryl-C$_{1-6}$ alkyl- and 4-10 membered heterocycloalkyl-C$_{1-6}$ alkyl- of R$^c$ is each optionally substituted with 1, 2, 3, or 4 independently selected R$^d$ substituents;

or two R$^c$ substituents, together with the nitrogen atom to which they attached form a 4-, 5-, 6-, or 7-membered heteroaryl or heterocycloalkyl group optionally substituted with 1, 2, 3, or 4 independently selected R$^d$ substituents;

each R$^d$ is independently selected from D, halo, C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, 4-10 membered heterocycloalkyl-C$_{1-6}$ alkyl-, CN, NO$_2$, OR$^e$, SR$^e$, NHOR$^e$, C(O)R$^e$, C(O)NR$^e$R$^e$, C(O)OR$^e$, OC(O)R$^e$, OC(O)NR$^e$R$^e$, NR$^e$R$^e$, NR$^e$C(O)R$^e$, NR$^e$C(O)OR$^e$, NR$^e$C(O)NR$^e$R$^e$, C(=NR$^i$)R$^e$, C(=NR$^i$)NR$^e$R$^e$, NR$^e$C(=NR$^i$)NR$^e$R$^e$, NR$^e$C(=NOH)NR$^e$R$^e$, NR$^e$C(=NCN)NR$^e$R$^e$, NR$^e$S(O)R$^e$, NR$^e$S(O)$_2$R$^e$, NR$^e$S(O)$_2$NR$^e$R$^e$, S(O)R$^e$, S(O)NR$^e$R$^e$, S(O)$_2$R$^e$, and S(O)$_2$NR$^e$R$^e$, wherein the C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, and 4-10 membered heterocycloalkyl-C$_{1-4}$ alkyl- of R$^d$ is each optionally substituted with 1, 2, 3 or 4 independently selected R$^f$ substituents;

each R$^e$ is independently selected from H, D, C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, 5-6 membered heteroaryl-C$_{1-6}$ alkyl-, and 4-7 membered heterocycloalkyl-C$_{1-6}$ alkyl-;

each R$^h$ is independently selected from OH, NO$_2$, CN, halo, C$_{1-6}$ alkyl, C$_{2-6}$ alkenyl, C$_{2-6}$ alkynyl, C$_{1-6}$ haloalkyl, cyano-C$_{1-6}$ alkyl, HO—C$_{1-6}$ alkyl, C$_{1-6}$ alkoxy-C$_{1-6}$ alkyl, C$_{3-7}$ cycloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino; and each R$^k$ is independently selected from H, D, C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, and 4-10 membered heterocycloalkyl-C$_{1-6}$ alkyl-.

In some embodiments:

$X^2$ is N or CR$^2$;
$X^4$ is N or CR$^4$;
$X^5$ is N or CR$^5$;
$X^6$ is N or CR$^6$;
$X^7$ is N or CR$^7$;
provided that $X^4$, $X^5$, and $X^6$ are not all N;

$Y^1$ is a C$_{1-6}$ haloalkyl, wherein each halogen is selected from F or Cl, wherein the haloalkyl is optionally substituted with 1 or 2 independently selected $Y^2$ substituents;

$R^1$ is selected from H, D, halo, C$_{1-6}$ alkyl, C$_{2-6}$ alkenyl, C$_{2-6}$ alkynyl, C$_{1-6}$ haloalkyl, 6-10 membered aryl, C$_{3-10}$cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, 4-10 membered heterocycloalkyl-C$_{1-6}$ alkyl-, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NR$^a$R$^a$, NR$^a$NR$^a$R$^a$, NR$^a$C(O)R$^a$, NR$^a$C(O)OR$^a$, NR$^a$C(O)NR$^a$R$^a$, C(=NR$^i$)R$^a$, C(=NR$^i$)NR$^a$R$^a$, NR$^a$C(=NR$^i$)NR$^a$R$^a$, NR$^a$C(=NOH)NR$^a$R$^a$, NR$^a$C(=NCN)NR$^a$R$^a$, NR$^a$S(O)R$^a$, NR$^a$S(O)$_2$R$^a$, NR$^a$S(O)(=NR$^i$)R$^a$, NR$^a$S(O)$_2$NR$^a$R$^a$, S(O)R$^a$, S(O)NR$^a$R$^a$, S(O)$_2$R$^a$, OS(O)(=NR$^i$)R$^a$, and S(O)$_2$NR$^a$R$^a$, wherein the C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, and 4-10 membered heterocycloalkyl-C$_{1-6}$ alkyl- of $R^1$ are each optionally substituted with 1, 2, 3, or 4 independently selected R$^b$ substituents;

$R^2$, $R^3$, $R^4$, $R^5$, $R^6$ and $R^7$ are each independently selected from H, D, halo, C$_{1-6}$ alkyl, C$_{1-6}$ alkoxy, C$_{2-6}$ alkenyl, C$_{2-6}$ alkynyl, C$_{1-6}$ haloalkyl, C$_{1-6}$ haloalkoxy, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, 4-10 membered heterocycloalkyl-C$_{1-6}$ alkyl, OH, NO$_2$, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^2$, $R^3$, $R^4$, $R^5$, $R^6$ and $R^7$ are each optionally substituted with 1, 2, 3, or 4 independently selected $R^h$ substituents;

$R^8$ is selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$cycloalkyl-$C_{1-6}$ alkyl-, 5-10 membered heteroaryl-$C_{1-6}$ alkyl-, 4-10 membered heterocycloalkyl-$C_{1-6}$ alkyl-, $NO_2$, $C(O)R^a$, $C(O)NR^aR^a$, $C(O)OR^a$, $C(=NR^i)R^a$, $C(=NR^i)NR^aR^a$, and $S(O)_2NR^aR^a$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^8$ are each optionally substituted with 1, 2, 3, or 4 independently selected $R^9$ substituents;

or any two $R^4$, $R^5$, $R^6$ and $R^7$ substituents, together with the ring atoms to which they attached form a 4-, 5-, 6-, or 7-membered aryl, cycloalkyl, heteroaryl, or heterocycloalkyl group optionally substituted with 1, 2, 3, or 4 independently selected $R^b$ substituents;

or $Y^1$ and $R^8$, together with the carbon atom to which they are attached, form a 4-, 5-, 6-, or 7-membered cycloalkyl or heterocycloalkyl group optionally substituted with 1, 2, 3, or 4 independently selected $R^9$ substituents;

each $R^i$ is independently selected from H, CN, OH, $C_{1-4}$ alkyl, and $C_{1-4}$ alkoxy;

each $Y^2$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^a$ is independently selected from H, D, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl- and 4-10 membered heterocycloalkyl-$C_{1-6}$ alkyl- of $R^a$ is each optionally substituted with 1, 2, 3, or 4 independently selected $R^b$ substituents;

each $R^b$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^c$, $SR^c$, $NHOR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^cC(O)OR^c$, $NR^cC(O)NR^cR^c$, $C(=NR^i)R^c$, $C(=NR^i)NR^cR^c$, $NR^cC(=NR^i)NR^cR^c$, $NR^cC(=NOH)NR^cR^c$, $NR^cC(=NCN)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$, and $S(O)_2NR^cR^c$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^b$ is each optionally substituted with 1, 2, 3, or 4 independently selected $R^d$ substituents;

each $R^9$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^k$, $SR^k$, $NHOR^k$, $C(O)R^k$, $C(O)NR^kR^k$, $C(O)OR^k$, $OC(O)R^k$, $OC(O)NR^kR^k$, $NR^kR^k$, $NR^kC(O)R^k$, $NR^kC(O)OR^k$, $NR^kC(O)NR^kR^k$, $C(=NR^i)R^k$, $C(=NR^i)NR^kR^k$, $NR^kC(=NR^i)NR^kR^k$, $NR^kC(=NOH)NR^kR^k$, $NR^kC(=NCN)NR^kR^k$, $NR^kS(O)R^k$, $NR^kS(O)_2R^k$, $NR^kS(O)_2NR^kR^k$, $S(O)R^k$, $S(O)NR^kR^k$, $S(O)_2R^k$, and $S(O)_2NR^kR^k$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^9$ is each optionally substituted with 1, 2, 3, or 4 independently selected $R^q$ substituents;

each $R^c$ is independently selected from H, D, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl- and 4-10 membered heterocycloalkyl-$C_{1-6}$ alkyl- of $R^c$ is each optionally substituted with 1, 2, 3, or 4 independently selected $R^d$ substituents;

each $R^d$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^e$, $SR^e$, $NHOR^e$, $C(O)R^e$, $C(O)NR^eR^e$, $C(O)OR^e$, $OC(O)R^e$, $OC(O)NR^eR^e$, $NR^eR^e$, $NR^eC(O)R^e$, $NR^eC(O)OR^e$, $NR^eC(O)NR^eR^e$, $C(=NR^i)R^e$, $C(=NR^i)NR^eR^e$, $NR^eC(=NR^i)NR^eR^e$, $NR^eC(=NOH)NR^eR^e$, $NR^eC$ (=NCN)NR$^e$R$^e$, NR$^e$S(O)R$^e$, NR$^e$S(O)$_2$R$^e$, NR$^e$S(O)$_2$NR$^e$R$^e$, S(O)R$^e$, S(O)NR$^e$R$^e$, S(O)$_2$R$^e$, and S(O)$_2$NR$^e$R$^e$, wherein the C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, and 4-10 membered heterocycloalkyl-C$_{1-6}$ alkyl- of R$^d$ is each optionally substituted with 1, 2, 3 or 4 independently selected R$^f$ substituents;

each R$^e$ is independently selected from H, D, C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, 5-6 membered heteroaryl-C$_{1-6}$ alkyl-, and 4-7 membered heterocycloalkyl-C$_{1-6}$ alkyl-, wherein the C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, 5-6 membered heteroaryl-C$_{1-6}$ alkyl- and 4-7 membered heterocycloalkyl-C$_{1-6}$ alkyl- of R$^e$ is each optionally substituted with 1, 2, 3 or 4 independently selected R$^f$ substituents;

each R$^f$ is independently selected from D, halo, C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, 5-6 membered heteroaryl-C$_{1-6}$ alkyl-, 4-7 membered heterocycloalkyl-C$_{1-6}$ alkyl-, CN, NO$_2$, OR$^g$, SR$^g$, NHOR$^g$, C(O)R$^g$, C(O)NR$^g$R$^g$, C(O)OR$^g$, OC(O)R$^g$, OC(O)NR$^g$R$^g$, NR$^g$R$^g$, NR$^g$C(O)R$^g$, NR$^g$C(O)OR$^g$, NR$^g$C(O)NR$^g$R$^g$, C(=NR$^i$)R$^g$, C(=NR$^i$)NR$^g$R$^g$, NR$^g$C(=NR$^i$)NR$^g$R$^g$, NR$^g$C(=NOH)NR$^g$R$^g$, NR$^g$C(=NCN)NR$^g$R$^g$, NR$^g$S(O)R$^g$, NR$^g$S(O)$_2$R$^g$, NR$^g$S(O)$_2$NR$^g$R$^g$, S(O)R$^g$, S(O)NR$^g$R$^g$, S(O)$_2$R$^g$, and S(O)$_2$NR$^g$R$^g$, wherein the C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, 5-6 membered heteroaryl-C$_{1-6}$ alkyl-, and 4-7 membered heterocycloalkyl-C$_{1-6}$ alkyl- of R$^f$ is each optionally substituted with 1, 2, 3 or 4 independently selected R$^h$ substituents;

each R$^g$ is independently selected from H, D, C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, 5-6 membered heteroaryl-C$_{1-6}$ alkyl-, and 4-7 membered heterocycloalkyl-C$_{1-6}$ alkyl-, wherein the C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, 5-6 membered heteroaryl-C$_{1-6}$ alkyl- and 4-7 membered heterocycloalkyl-C$_{1-6}$ alkyl- of R$^g$ is each optionally substituted with 1, 2, 3 or 4 independently selected R$^h$ substituents;

each R$^h$ is independently selected from OH, NO$_2$, CN, halo, C$_{1-6}$ alkyl, C$_{2-6}$ alkenyl, C$_{2-6}$ alkynyl, C$_{1-6}$ haloalkyl, cyano-C$_{1-6}$ alkyl, HO—C$_{1-6}$ alkyl, C$_{1-6}$ alkoxy-C$_{1-6}$ alkyl, C$_{3-7}$ cycloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

each R$^k$ is independently selected from H, D, C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, and 4-10 membered heterocycloalkyl-C$_{1-6}$ alkyl-, wherein the C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl- and 4-10 membered heterocycloalkyl-C$_{1-6}$ alkyl- of R$^k$ is each optionally substituted with 1, 2, 3, or 4 independently selected R$^q$ substituents;

each R$^q$ is independently selected from D, halo, C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, 4-10 membered heterocycloalkyl-C$_{1-6}$ alkyl-, CN, NO$_2$, OR$^m$, SR$^m$, NHOR$^m$, C(O)R$^m$, C(O)NR$^m$R$^m$, C(O)OR$^m$, OC(O)R$^m$, OC(O)NR$^m$R$^m$, NHR$^m$, NR$^m$R$^m$, NR$^m$C(O)R$^m$, NR$^m$C(O)OR$^m$, NR$^m$C(O)NR$^m$R$^m$, C(=NR$^i$)R$^m$, C(=NR$^i$)NR$^m$R$^m$, NR$^m$C(=NR$^i$)NR$^m$R$^m$, NR$^m$C(=NOH)NR$^m$R$^m$, NR$^m$C(=NCN)NR$^m$R$^m$, NR$^m$S(O)R$^m$, NR$^m$S(O)$_2$R$^m$, NR$^m$S(O)$_2$NR$^m$R$^m$, S(O)R$^m$, S(O)NR$^m$R$^m$, S(O)$_2$R$^m$, and S(O)$_2$NR$^m$R$^m$, wherein the C$_{1-6}$ alkyl, C$_{2-6}$ alkenyl, C$_{2-6}$ alkynyl, C$_{1-6}$ haloalkyl, 6-10 membered aryl, C$_{3-10}$ cycloalkyl, 5-10 membered heteroaryl, 4-10 membered heterocycloalkyl, 6-10 membered aryl-C$_{1-6}$ alkyl-, C$_{3-10}$ cycloalkyl-C$_{1-6}$ alkyl-, 5-10 membered heteroaryl-C$_{1-6}$ alkyl-, and 4-10 membered heterocycloalkyl-C$_{1-6}$ alkyl- of R$^q$ is each optionally substituted with 1, 2, 3 or 4 independently selected R$^n$ substituents;

each R$^m$ is independently selected from H, D, C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, 5-6 membered heteroaryl-C$_{1-6}$ alkyl-, and 4-7 membered heterocycloalkyl-C$_{1-6}$ alkyl-, wherein the C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, 5-6 membered heteroaryl-C$_{1-6}$ alkyl- and 4-7 membered heterocycloalkyl-C$_{1-6}$ alkyl- of R$^m$ is each optionally substituted with 1, 2, 3 or 4 independently selected R$^n$ substituents;

each R$^n$ is independently selected from D, halo, C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, 5-6 membered heteroaryl-C$_{1-6}$ alkyl-, 4-7 membered heterocycloalkyl-C$_{1-6}$ alkyl-, CN, NO$_2$, OR$^o$, SR$^o$, NHOR$^o$, C(O)R$^o$, C(O)NR$^o$R$^o$, C(O)OR$^o$, OC(O)R$^o$, OC(O)NR$^o$R$^o$, NR$^o$R$^o$, NR$^o$C(O)R$^o$, NR$^o$C(O)OR$^o$, NR$^o$C(O)NR$^o$R$^o$, C(=NR$^i$)R$^o$, C(=NR$^i$)NR$^o$R$^o$, NR$^o$C(=NR$^i$)NR$^o$R$^o$, NR$^o$C(=NOH)NR$^o$R$^o$, NR$^o$C(=NCN)NR$^o$R$^o$, NR$^o$S(O)R$^o$, NR$^o$S(O)$_2$R$^o$, NR$^o$S(O)$_2$NR$^o$R$^o$, S(O)R$^o$, S(O)NR$^o$R$^o$, S(O)$_2$R$^o$, and S(O)$_2$NR$^o$R$^o$, wherein the C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, 5-6 membered heteroaryl-C$_{1-6}$ alkyl-, and 4-7 membered heterocycloalkyl-C$_{1-6}$ alkyl- of R$^n$ is each optionally substituted with 1, 2, 3 or 4 independently selected R$^h$ substituents; and each $R^o$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl- and 4-7 membered heterocycloalkyl-$C_{1-6}$ alkyl- of $R^o$ is each optionally substituted with 1, 2, 3 or 4 independently selected $R^h$ substituents.

In some embodiments:

$X^2$ is N or $CR^2$;

$X^4$ is N or $CR^4$;

$X^5$ is N or $CR^5$;

$X^6$ is N or $CR^6$;

$X^7$ is N or $CR^7$;

provided that $X^4$, $X^5$, and $X^6$ are not all N;

$Y^1$ is a $C_{1-6}$ haloalkyl, wherein each halogen is selected from F or Cl;

$R^1$ is independently selected from H, D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NR^aR^a$, $NR^aNR^aR^a$, $NR^aC(O)R^a$, $NR^aC(O)OR^a$, $NR^aC(O)NR^aR^a$, $C(=NR^i)R^a$, $C(=NR^i)NR^aR^a$, $NR^aC(=NR^i)NR^aR^a$, $NR^aC(=NOH)NR^aR^a$, $NR^aC(=NCN)NR^aR^a$, $NR^aS(O)R^a$, $NR^aS(O)_2R^a$, $NR^aS(O)(=NR^i)R^a$, $NR^aS(O)_2NR^aR^a$, $S(O)R^a$, $S(O)NR^aR^a$, $S(O)_2R^a$, and $S(O)_2NR^aR^a$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-4}$ alkyl- of $R^1$ are each optionally substituted with 1, 2, 3, or 4 independently selected $R^b$ substituents;

$R^2$, $R^3$, $R^4$, $R^5$, $R^6$ and $R^7$ are each independently selected from H, D, halo, $C_{1-6}$ alkyl, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl, OH, $NO_2$, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-4}$ alkyl- of $R^2$, $R^3$, $R^4$, $R^5$, $R^6$ and $R^7$ are each optionally substituted with 1, 2, 3, or 4 independently selected $R^h$ substituents;

$R^8$ is selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$cycloalkyl-$C_{1-6}$ alkyl-, 5-10 membered heteroaryl-$C_{1-6}$ alkyl-, 4-10 membered heterocycloalkyl-$C_{1-6}$ alkyl-, $NO_2$, $C(O)R^a$, $C(O)NR^aR^a$, $C(O)OR^a$, $C(=NR^i)R^a$, $C(=NR^i)NR^aR^a$, and $S(O)_2NR^aR^a$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-4}$ alkyl- of $R^8$ are each optionally substituted with 1, 2, 3, or 4 independently selected $R^9$ substituents;

or $Y^1$ and $R^8$, together with the carbon atom to which they are attached, form a 4-, 5-, 6-, or 7-membered cycloalkyl or heterocycloalkyl group optionally substituted with 1, 2, 3, or 4 independently selected $R^9$ substituents;

each $R^i$ is independently selected from H, CN, OH, $C_{1-4}$ alkyl, and $C_{1-4}$ alkoxy;

each $R^a$ is independently selected from H, D, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-4}$ alkyl-, 5-10 membered heteroaryl-$C_{1-6}$ alkyl- and 4-10 membered heterocycloalkyl-$C_{1-6}$ alkyl- of $R^a$ is each optionally substituted with 1, 2, 3, or 4 independently selected $R^b$ substituents;

each $R^b$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^c$, $SR^c$, $NHOR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^cC(O)OR^c$, $NR^cC(O)NR^cR^c$, $C(=NR^i)R^c$, $C(=NR^i)NR^cR^c$, $NR^cC(=NR^i)NR^cR^c$, $NR^cC(=NOH)NR^cR^c$, $NR^cC(=NCN)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$, and $S(O)_2NR^cR^c$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-4}$ alkyl- of $R^b$ is each optionally substituted with 1, 2, 3, or 4 independently selected $R^d$ substituents;

each $R^9$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^k$, $SR^k$, $NHOR^k$, $C(O)R^k$, $C(O)NR^kR^k$, $C(O)OR^k$, $OC(O)R^k$, $OC(O)NR^kR^k$, $NR^kR^k$, $NR^kC(O)R^k$, $NR^kC(O)OR^k$, $NR^kC(O)NR^kR^k$, $C(=NR^i)R^k$, $C(=NR^i)NR^kR^k$, $NR^kC(=NR^i)NR^kR^k$, $NR^kC(=NOH)NR^kR^k$, $NR^kC(=NCN)NR^kR^k$, $NR^kS(O)R^k$, $NR^kS(O)_2R^k$, $NR^kS(O)_2NR^kR^k$, $S(O)R^k$, $S(O)NR^kR^k$, $S(O)_2R^k$, and $S(O)_2NR^kR^k$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-4}$ alkyl- of $R^9$ is each optionally substituted with 1, 2, 3, or 4 independently selected $R^q$ substituents;

each $R^c$ is independently selected from H, D, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-4}$ alkyl-, 5-10 membered heteroaryl-$C_{1-6}$ alkyl- and 4-10 membered heterocycloalkyl-$C_{1-6}$ alkyl- of $R^c$ is each optionally substituted with 1, 2, 3, or 4 independently selected $R^d$ substituents;

each $R^d$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^e$, $SR^e$, $NHOR^e$, $C(O)R^e$, $C(O)NR^eR^e$, $C(O)OR^e$, $OC(O)R^e$, $OC(O)NR^eR^e$, $NR^eR^e$, $NR^eC(O)R^e$, $NR^eC(O)OR^e$, $NR^eC(O)NR^eR^e$, $C(=NR^i)R^e$, $C(=NR^i)NR^eR^e$, $NR^eC(=NR^i)NR^eR^e$, $NR^eC(=NOH)NR^eR^e$, $NR^eC(=NCN)NR^eR^e$, $NR^eS(O)R^e$, $NR^eS(O)_2R^e$, $NR^eS(O)_2NR^eR^e$, $S(O)R^e$, $S(O)NR^eR^e$, $S(O)_2R^e$, and $S(O)_2NR^eR^e$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-4}$ alkyl- of $R^d$ is each optionally substituted with 1, 2, 3 or 4 independently selected $R^f$ substituents;

each $R^e$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-;

each $R^h$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and each $R^k$ is independently selected from H, D, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl-.

In some embodiments, $X^2$ is N

In some embodiments, $X^2$ is $CR^2$.

In some embodiments, $R^2$ is selected from H, D, halo, $C_{1-6}$ alkyl, $C_{2-6}$ alkenyl, $C_{2-6}$ alkynyl, and $C_{1-6}$ haloalkyl.

In some embodiments, $R^2$ is selected from H, D, and $C_{1-6}$ alkyl.

In some embodiments, $R^2$ is H.

In some embodiments, $X^2$ is N or CH.

In some embodiments, $R^3$ is H or D.

In some embodiments, $R^3$ is H.

In some embodiments, $X^4$ is $CR^4$.

In some embodiments, $R^4$ is selected from H, D, halo, $C_{1-6}$ alkyl, $C_{2-6}$ alkenyl, $C_{2-6}$ alkynyl, and $C_{1-6}$ haloalkyl.

In some embodiments, $R^4$ is selected from H, D, halo and $C_{1-6}$ alkyl.

In some embodiments, $R^4$ is selected from H, D, fluoro, methyl, and $CD_3$.

In some embodiments, $R^4$ is selected from H, fluoro, methyl, and $CD_3$.

In some embodiments, $R^4$ is selected from H, fluoro, and methyl.

In some embodiments, $X^4$ is N.

In some embodiments, $X^5$ is $CR^5$.

In some embodiments, $R^5$ is selected from H, D, halo, $C_{1-6}$ alkyl, $C_{2-6}$ alkenyl, $C_{2-6}$ alkynyl, and $C_{1-6}$ haloalkyl.

In some embodiments, $R^5$ is selected from H, D, and $C_{1-6}$ alkyl.

In some embodiments, $R^5$ is H.

In some embodiments, $X^5$ is N.

In some embodiments, $X^5$ is N or CH.

In some embodiments, $X^6$ is $CR^6$.

In some embodiments, $R^6$ is selected from H, D, halo, $C_{1-6}$ alkyl, $C_{2-6}$ alkenyl, $C_{2-6}$ alkynyl, and $C_{1-6}$ haloalkyl.

In some embodiments, $R^6$ is selected from H, D, and halo.

In some embodiments, $R^6$ is selected from H and halo.

In some embodiments, $R^6$ is selected from H and fluoro.

In some embodiments, $X^6$ is N.

In some embodiments, $X^7$ is $CR^7$.

In some embodiments, $R^7$ is selected from H, D, halo, $C_{1-6}$ alkyl, $C_{2-6}$ alkenyl, $C_{2-6}$ alkynyl, and $C_{1-6}$ haloalkyl.

In some embodiments, $R^7$ is selected from H, D, and $C_{1-6}$ alkyl.

In some embodiments, $R^7$ is H.

In some embodiments, $X^7$ is N.

In some embodiments, $X^7$ is N or CH.

In some embodiments, $R^2$, $R^3$, $R^4$, $R^5$, $R^6$ and $R^7$ are each independently selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, $OR^a$, and $SR^a$, wherein the $C_{1-6}$ alkyl, $C_{1-6}$ alkoxy, $C_{2-6}$ alkenyl, $C_{2-6}$ alkynyl, $C_{1-6}$ haloalkyl and $C_{1-6}$ haloalkoxy of $R^2$, $R^3$, $R^4$, $R^5$, $R^6$ and $R^7$ are each optionally substituted with 1, 2, 3, or 4 independently selected $R^h$ substituents.

In some embodiments, $R^2$, $R^3$, $R^4$, $R^5$, $R^6$ and $R^7$ are each independently selected from H, halo, CN, $C_{1-6}$ alkyl, and $C_{1-6}$ haloalkyl.

In some embodiments, $R^4$, $R^5$, $R^6$, and $R^7$ are each independently selected from H, D, halo, $C_{1-6}$ alkyl, $C_{2-6}$ alkenyl, $C_{2-6}$ alkynyl, and $C_{1-6}$ haloalkyl.

In some embodiments, $R^2$, $R^3$, $R^5$, and $R^7$ are each H.

In some embodiments, $R^3$, $R^5$, and $R^7$ are each H.

In some embodiments, any two $R^4$, $R^5$, and $R^6$ substituents, together with the ring atoms to which they attached form a 4-, 5-, 6-, or 7-membered aryl, cycloalkyl, heteroaryl, or heterocycloalkyl group optionally substituted with 1, 2, 3, or 4 independently selected $R^b$ substituents.

In some embodiments, $R^1$ is optionally substituted with 1, 2, 3, or 4 independently selected $R^b$ substituents In some embodiments, $R^1$ is selected from H, D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, $OR^a$, $C(O)R^a$, $C(O)NR^aR^a$, $C(O)OR^a$, $NR^aR^a$, $NR^aC(O)R^a$, $NR^aC(O)OR^a$, $NR^aC(O)NR^aR^a$, $NR^aS(O)_2NR^aR^a$, $NR^aS(O)_2R^a$, $S(O)_2R^a$, and $S(O)_2NR^aR^a$, wherein the $C_{1-6}$ alkyl, $C_{2-6}$ alkenyl, $C_{2-6}$ alkynyl, 6-10 membered aryl, $C_{3-10}$ cycloalkyl, 5-10 membered heteroaryl, and 4-10 membered heterocycloalkyl are each optionally substituted with 1, 2, 3, or 4 independently selected $R^b$ substituents.

In some embodiments, $R^1$ is selected from H, D, halo, $C_{1-6}$ alkyl, $C_{1-6}$ haloalkyl, 6-10 membered aryl, $C_{3-10}$ cycloalkyl, 5-10 membered heteroaryl, 4-10 membered heterocycloalkyl, $OR^a$, $C(O)NR^aR^a$, and $C(O)OR^a$, wherein the $C_{1-6}$ alkyl, 6-10 membered aryl, $C_{3-10}$ cycloalkyl, 5-10 membered heteroaryl, and 4-10 membered heterocycloalkyl are each optionally substituted with 1, 2, 3, or 4 independently selected $R^b$ substituents.

In some embodiments, $R^1$ is selected from H, $C_{1-6}$ alkyl, $C_{1-6}$ haloalkyl, phenyl, 3-6 membered cycloalkyl, 5-6 membered heteroaryl, 5-6 membered heterocycloalkyl, $C(O)NR^aR^a$, and $C(O)OR^a$, wherein the $C_{1-6}$ alkyl, phenyl, 3-6 membered cycloalkyl, 5-6 membered heteroaryl, and 5-6 membered heterocycloalkyl are each optionally substituted with 1 or 2 independently selected $R^b$ substituents.

In some embodiments, $R^1$ is selected from H, $C_{1-6}$ alkyl, $C_{1-6}$ haloalkyl, phenyl, 5-6 membered heteroaryl, $C(O)NR^aR^a$, and $C(O)OR^a$, wherein the $C_{1-6}$ alkyl, phenyl, and 5-6 membered heteroaryl are each optionally substituted with 1 or 2 independently selected $R^b$ substituents.

In some embodiments, $R^1$ is selected from H, methyl, $CF_3$, $C(O)OR^a$, $C(O)NR^aR^a$, phenyl, cyclopropyl, thiazolyl, pyrazolyl, oxazolyl, pyrimidinyl, pyridinyl, isoxazolyl, 1,2,4-triazolyl, and piperidinyl, wherein the phenyl, cyclopropyl, thiazolyl, pyrazolyl, oxazolyl, pyrimidinyl, pyridinyl, isoxazolyl, 1,2,4-triazolyl, and piperidinyl are each optionally substituted by 1 or 2 independently selected $R^b$ substituents.

In some embodiments, $R^1$ is selected from H, methyl, $CF_3$, $C(O)OR^a$, $C(O)NR^aR^a$, phenyl, thiazolyl, pyrazolyl, oxazolyl, pyrimidinyl, pyridinyl, isoxazolyl, and 1,2,4-triazolyl, wherein the phenyl, thiazolyl, pyrazolyl, oxazolyl, pyrimidinyl, pyridinyl, isoxazolyl, and 1,2,4-triazolyl are each optionally substituted by 1 or 2 independently selected $R^b$ substituents.

In some embodiments, $R^1$ is selected from H, methyl, $CF_3$, $C(O)OR^a$, $C(O)NR^aR^a$, phenyl, cyclopropyl, thiazolyl, pyrazolyl, oxazolyl, pyrimidinyl, pyridinyl, isoxazolyl, 1,2,4-triazolyl, and piperidinyl, wherein the phenyl, cyclopropyl, thiazolyl, pyrazolyl, oxazolyl, pyrimidinyl, pyridinyl, isoxazolyl, 1,2,4-triazolyl, and piperidinyl are each optionally substituted by 1 or 2 independently selected $R^b$ substituents; and each $R^a$ is selected from H, $C_{1-6}$ alkyl, isoxazol-5-ylmethyl, tetrahydrofuran-3-yl, tetrahydro-2H-pyran-4-yl, 5,6-dihydro-4H-pyrrolo[1,2-b]pyrazol-3-yl, wherein said isoxazol-5-ylmethyl, tetrahydrofuran-3-yl, and tetrahydro-2H-pyran-4-yl are each optionally substituted by 1 or 2 substituents independently selected from methyl, trifluoromethyl, and cyclopropyl, and wherein said $C_{1-6}$ alkyl is optionally substituted by OH.

In some embodiments, $R^1$ is selected from H, methyl, $CF_3$, $C(O)OR^a$, $C(O)NR^aR^a$, phenyl, thiazolyl, pyrazolyl, oxazolyl, pyrimidinyl, pyridinyl, isoxazolyl, 1,2, 4-triazolyl, and piperidinyl, wherein the phenyl, cyclopropyl, thiazolyl, pyrazolyl, oxazolyl, pyrimidinyl, pyridinyl, isoxazolyl, 1,2,4-triazolyl, and piperidinyl are each optionally substituted by 1 or 2 independently selected $R^b$ substituents; and each $R^a$ is selected from H, $C_{1-6}$ alkyl, and isoxazol-5-ylmethyl; wherein said isoxazol-5-ylmethyl is substituted by methyl and said $C_{1-6}$ alkyl is optionally substituted by OH.

In some embodiments, $R^1$ is selected from H, methyl, $CF_3$, $C(O)OR^a$, $C(O)NR^aR^a$, phenyl, thiazolyl, pyrazolyl, oxazolyl, pyrimidinyl, pyridinyl, isoxazolyl, and 1,2,4-triazolyl, wherein the phenyl, thiazolyl, pyrazolyl, oxazolyl, pyrimidinyl, pyridinyl, isoxazolyl, and 1,2,4-triazolyl are each optionally substituted by 1 or 2 independently selected $R^b$ substituents; and each $R^a$ is selected from H, $C_{1-6}$ alkyl, and isoxazol-5-ylmethyl; wherein said isoxazol-5-ylmethyl is substituted by methyl and said $C_{1-6}$ alkyl is optionally substituted by OH.

In some embodiments, $R^1$ is selected from H, methyl, $CF_3$, $C(O)OR^a$, $C(O)NR^aR^a$, phenyl, thiazolyl, pyrazolyl, oxazolyl, pyrimidinyl, pyridinyl, isoxazolyl, and 1,2,4-triazolyl, wherein the phenyl, thiazolyl, pyrazolyl, oxazolyl, pyrimidinyl, pyridinyl, isoxazolyl, and 1,2,4-triazolyl are each optionally substituted by 1 or 2 independently selected $R^b$ substituents; and each $R^a$ is selected from H, $C_{1-6}$ alkyl, isoxazol-5-ylmethyl, tetrahydrofuran-3-yl, tetrahydro-2H-pyran-4-yl, 5,6-dihydro-4H-pyrrolo[1,2-b]pyrazol-3-yl, wherein said isoxazol-5-ylmethyl, tetrahydrofuran-3-yl, and tetrahydro-2H-pyran-4-yl are each optionally substituted by 1 or 2 substituents independently selected from methyl, trifluoromethyl, and cyclopropyl, and wherein said $C_{1-6}$ alkyl is optionally substituted by OH.

In some embodiments, $R^1$ is selected from H, methyl, $CF_3$, $C(O)OR^a$, $C(O)NR^aR^a$, phenyl, cyclopropyl, thiazol-5-yl, thiazol-2-yl, pyrazol-3-yl, pyrazol-4-yl, pyrazol-5-yl, oxazol-5-yl, pyrimidin-5-yl, pyridin-3-yl, pyridin-4-yl, isoxazol-5-yl, 1,2,4-triazol-1-yl, and piperidin-1-yl, wherein the phenyl, thiazol-5-yl, thiazol-2-yl, pyrazol-3-yl, pyrazol-4-yl, pyrazol-5-yl, oxazol-5-yl, pyrimidin-5-yl, pyridin-3-yl, pyridin-4-yl, isoxazol-5-yl, 1,2,4-triazol-1-yl, and piperidin-1-yl are each optionally substituted by 1 or 2 independently selected $R^b$ substituents; and each $R^a$ is selected from H, $C_{1-6}$ alkyl, and isoxazol-5-ylmethyl; wherein said isoxazol-5-ylmethyl is substituted by methyl and said $C_{1-6}$ alkyl is optionally substituted by OH.

In some embodiments, $R^1$ is selected from H, methyl, $CF_3$, $C(O)OR^a$, $C(O)NR^aR^a$, phenyl, thiazol-5-yl, thiazol-2-yl, pyrazol-3-yl, pyrazol-4-yl, pyrazol-5-yl, oxazol-5-yl, pyrimidin-5-yl, pyridin-3-yl, pyridin-4-yl, isoxazol-5-yl, and 1,2,4-triazol-1-yl, wherein the phenyl, thiazol-5-yl, thiazol-2-yl, pyrazol-3-yl, pyrazol-4-yl, pyrazol-5-yl, oxazol-5-yl, pyrimidin-5-yl, pyridin-3-yl, pyridin-4-yl, isoxazol-5-yl, and 1,2,4-triazol-1-yl are each optionally substituted by 1 or 2 independently selected $R^b$ substituents; and each $R^a$ is selected from H, $C_{1-6}$ alkyl, and isoxazol-5-ylmethyl; wherein said isoxazol-5-ylmethyl is substituted by methyl and said $C_{1-6}$ alkyl is optionally substituted by OH.

In some embodiments, $R^1$ is selected from H, methyl, $CF_3$, $C(O)OCH_3$, $C(O)NHCH_3$, $C(O)NHCH_2$-(3-methyl-isoxazol-5-yl), $C(O)NHCH_2C(CH_3)_2OH$, 4-fluorobenzamide-3-yl, 2-cyclopropylthiazol-5-yl, 5-methoxythiazol-2-yl, 2-(hydroxymethyl)pyridin-4-yl, 1-(methyl-$d_3$)-1H-pyrazol-5-yl, 2-methyloxazol-5-yl, 1-methyl-1H-pyrazol-5-yl, pyrimidin-3-yl, 2-methoxypyridin-3-yl, 2-methylthiazol-5-yl, 3-fluoro-2-methylpyridin-4-yl, 1,5-dimethyl-1H-pyrazol-4-yl, 1-methyl-1H-pyrazol-4-yl, 1,3-dimethyl-1H-pyrazol-4-yl, 3,5-dimethyl-1H-pyrazol-4-yl, 1H-pyrazol-4-yl, 1,3-dimethyl-1H-pyrazol-5-yl, 1,4-dimethyl-1H-pyrazol- 5-yl, 1-methyl-1H-pyrazol-3-yl, 6-(hydroxymethyl)pyridin-3-yl, 3-methyl-1H-pyrazol-4-yl, 3-methylisoxazol-5-yl, 1H-1,2,4-triazol-1-yl, 4-cyanopiperidin-1-yl, 4-hydroxypiperidin-1-yl, 1-(methyl-d$_3$)-1H-pyrazol-5-yl, oxazol-5-yl, 1-(hydroxymethyl)cycloprop-2-yl, 1-(ethoxycarbonyl)cycloprop-2-yl, 1-(N-methylaminocarbonyl)cycloprop-2-yl, 1-(4-methylpiperazin-1-yl)cycloprop-2-yl, and 1-(N-(2-hydroxy-1,1-dimethylethyl)aminocarbonyl)cycloprop-2-yl.

In some embodiments, $R^1$ is selected from H, methyl, $CF_3$, C(O)OCH$_3$, C(O)NHCH$_3$, C(O)NHCH$_2$-(3-methylisoxazol-5-yl), C(O)NHCH$_2$C(CH$_3$)$_2$OH, 4-fluorobenzamide-3-yl, 2-cyclopropylthiazol-5-yl, 5-methoxythiazol-2-yl, 2-(hydroxymethyl)pyridin-4-yl, 1-(methyl-d$_3$)-1H-pyrazol-5-yl, 2-methyloxazol-5-yl, 1-methyl-1H-pyrazol-5-yl, pyrimidin-3-yl, 2-methoxypyridin-3-yl, 2-methylthiazol-5-yl, 3-fluoro-2-methylpyridin-4-yl, 1,5-dimethyl-1H-pyrazol-4-yl, 1-methyl-1H-pyrazol-4-yl, 1,3-dimethyl-1H-pyrazol-4-yl, 3,5-dimethyl-1H-pyrazol-4-yl, 1H-pyrazol-4-yl, 1,3-dimethyl-1H-pyrazol-5-yl, 1,4-dimethyl-1H-pyrazol-5-yl, 1-methyl-1H-pyrazol-3-yl, 6-(hydroxymethyl)pyridin-3-yl, 3-methyl-1H-pyrazol-4-yl, 3-methylisoxazol-5-yl, 1H-1,2,4-triazol-1-yl, 3-cyclopropyltetrahydrofuran-3-yl, 2,3-dimethyltetrahydrofuran-3-yl, 4-(trifluoromethyl)tetrahydro-2H-pyran-4-yl, and 5,6-dihydro-4H-pyrrolo[1,2-b]pyrazol-3-yl.

In some embodiments, $R^1$ is selected from H, methyl, $CF_3$, C(O)OCH$_3$, C(O)NHCH$_3$, C(O)NHCH$_2$-(3-methylisoxazol-5-yl), C(O)NHCH$_2$C(CH$_3$)$_2$OH, 4-fluorobenzamide-3-yl, 2-cyclopropylthiazol-5-yl, 5-methoxythiazol-2-yl, 2-(hydroxymethyl)pyridin-4-yl, 1-(methyl-d$_3$)-1H-pyrazol-5-yl, 2-methyloxazol-5-yl, 1-methyl-1H-pyrazol-5-yl, pyrimidin-3-yl, 2-methoxypyridin-3-yl, 2-methylthiazol-5-yl, 3-fluoro-2-methylpyridin-4-yl, 1,5-dimethyl-1H-pyrazol-4-yl, 1-methyl-1H-pyrazol-4-yl, 1,3-dimethyl-1H-pyrazol-4-yl, 3,5-dimethyl-1H-pyrazol-4-yl, 1H-pyrazol-4-yl, 1,3-dimethyl-1H-pyrazol-5-yl, 1,4-dimethyl-1H-pyrazol-5-yl, 1-methyl-1H-pyrazol-3-yl, 6-(hydroxymethyl)pyridin-3-yl, 3-methyl-1H-pyrazol-4-yl, 3-methylisoxazol-5-yl, and 1H-1,2,4-triazol-1-yl.

In some embodiments, $R^1$ is selected from H, methyl, $CF_3$, and C(O)NHCH$_2$C(CH$_3$)$_2$OH.

In some embodiments, $R^1$ is $CF_3$.

In some embodiments, $R^1$ is C(O)NHCH$_2$C(CH$_3$)$_2$OH.

In some embodiments, $Y^1$ is $C_{1-6}$ haloalkyl, wherein each halogen is F, wherein the haloalkyl is optionally substituted with 1 or 2 independently selected $Y^2$ substituents.

In some embodiments, $Y^1$ is selected from $CF_3$, $CCl_3$, $CF_2H$, $CCl_2H$, $CF_2Y^2$, $CCl_2Y^2$, $CFH_2$, $CClH_2$, $CFHY^2$, $CClHY^2$, $CF(Y^2)_2$ and $CCl(Y^2)_2$.

In some embodiments, $Y^1$ is selected from $CF_3$, $CF_2H$, $CF_2Y^2$, $CFH_2$, $CFHY^2$, and $CF(Y^2)_2$.

In some embodiments, $Y^1$ is $C_{1-6}$ haloalkyl, wherein each halogen is F.

In some embodiments, $Y^1$ is $C_{1-6}$ haloalkyl, wherein each halogen is Cl.

In some embodiments, $Y^1$ is selected from $CH_2F$, $CHF_2$, $CF_3$, and $CF_2CF_3$.

In some embodiments, $Y^1$ is $CF_3$.

In some embodiments, $Y^1$ is $CH_2F$.

In some embodiments, $Y^1$ is $CHF_2$.

In some embodiments, $Y^1$ is $CF_2CF_3$.

In some embodiments, $Y^2$ is selected from D, halo, $C_{1-6}$ alkyl, and $C_{1-6}$ haloalkyl.

In some embodiments, $Y^2$ is selected from halo and $C_{1-6}$ haloalkyl.

In some embodiments, at least one of $R^1$ and $Y^1$ is $CF_3$.

In some embodiments, $R^1$ is selected from H, methyl, $CF_3$, and C(O)NHCH$_2$C(CH$_3$)$_2$OH, and $Y^1$ is selected from $CH_2F$, $CHF_2$, $CF_3$, and $CF_2CF_3$.

In some embodiments, $R^1$ is selected from H, methyl, and $CF_3$, and $Y^1$ is selected from $CH_2F$, $CHF_2$, $CF_3$, and $CF_2CF_3$.

In some embodiments, $R^1$ is $CF_3$ and $Y^1$ is selected from $CH_2F$, $CHF_2$, $CF_3$, and $CF_2CF_3$.

In some embodiments, $R^1$ is C(O)NHCH$_2$C(CH$_3$)$_2$OH and $Y^1$ is selected from $CH_2F$, $CHF_2$, $CF_3$, and $CF_2CF_3$.

In some embodiments, $R^8$ is selected from H, D, $C_{1-6}$ alkyl, $C_{1-6}$ alkoxy, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, and C(O)NR$^a$R$^a$, wherein the $C_{1-6}$ alkyl, $C_{1-6}$ alkoxy, $C_{2-6}$ alkenyl, $C_{2-6}$ alkynyl, haloalkyl, $C_{1-6}$haloalkoxy, 6-10 membered aryl, $C_{3-10}$ cycloalkyl, 5-10 membered heteroaryl, and 4-10 membered heterocycloalkyl are each optionally substituted with 1, 2, 3, or 4 independently selected $R^9$ substituents.

In some embodiments, $R^8$ is selected from H, D, $C_{1-6}$ alkyl, $C_{1-6}$ alkoxy, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, and 4-10 membered heterocycloalkyl, wherein the $C_{1-6}$ alkyl, $C_{1-6}$ alkoxy, $C_{2-6}$ alkenyl, $C_{2-6}$ alkynyl, haloalkyl, $C_{1-6}$haloalkoxy, 6-10 membered aryl, $C_{3-10}$ cycloalkyl, 5-10 membered heteroaryl, and 4-10 membered heterocycloalkyl are each optionally substituted with 1, 2, 3, or 4 independently selected $R^9$ substituents.

In some embodiments, $R^8$ is selected from H, $C_{1-6}$ alkyl, 6-10 membered aryl, $C_{3-10}$ cycloalkyl, 5-10 membered heteroaryl, 4-10 membered heterocycloalkyl, and C(O)NR$^a$R$^a$, wherein the $C_{1-6}$ alkyl, 6-10 membered aryl, $C_{3-10}$ cycloalkyl, 5-10 membered heteroaryl, and 4-10 membered heterocycloalkyl are each optionally substituted with 1, 2, 3, or 4 independently selected $R^9$ substituents.

In some embodiments, $R^8$ is selected from H, $C_{1-6}$ alkyl, 6-10 membered aryl, $C_{3-10}$ cycloalkyl, 5-10 membered heteroaryl, and 4-10 membered heterocycloalkyl, wherein the $C_{1-6}$ alkyl, 6-10 membered aryl, $C_{3-10}$ cycloalkyl, 5-10 membered heteroaryl, and 4-10 membered heterocycloalkyl are each optionally substituted with 1, 2, 3, or 4 independently selected $R^9$ substituents.

In some embodiments, $R^8$ is selected from H, $C_{1-6}$ alkyl, phenyl, $C_{3-6}$ cycloalkyl, 5-6 membered heteroaryl, 4-6 membered heterocycloalkyl, and C(O)NH$_2$, wherein the $C_{1-6}$ alkyl, phenyl, $C_{3-6}$ cycloalkyl, 5-6 membered heteroaryl, and 4-6 membered heterocycloalkyl are each optionally substituted with 1 or 2 independently selected $R^9$ substituents.

In some embodiments, $R^8$ is selected from H, $C_{1-6}$ alkyl, phenyl, $C_{3-6}$ cycloalkyl, 5-6 membered heteroaryl, and 4-6 membered heterocycloalkyl, wherein the $C_{1-6}$ alkyl, phenyl, $C_{3-6}$ cycloalkyl, 5-6 membered heteroaryl, and 4-6 membered heterocycloalkyl are each optionally substituted with 1 or 2 independently selected $R^9$ substituents.

In some embodiments, $R^8$ is selected from H, $C_{1-6}$ alkyl, $C_{3-6}$ cycloalkyl, 5-6 membered heteroaryl, and C(O)NH$_2$, wherein the $C_{1-6}$ alkyl, $C_{3-6}$ cycloalkyl, and 5-6 membered heteroaryl are each optionally substituted with 1 or 2 independently selected $R^9$ substituents.

In some embodiments, $R^8$ is selected from H, $C_{1-6}$ alkyl, $C_{3-6}$ cycloalkyl, 5-6 membered heteroaryl, wherein the $C_{1-6}$ alkyl, $C_{3-6}$ cycloalkyl, and 5-6 membered heteroaryl are each optionally substituted with 1 or 2 independently selected $R^9$ substituents.

In some embodiments, $R^8$ is selected from H, methyl, hydroxymethyl, ethyl, 1-hydroxyethyl, 2-hydroxyethyl, 2-aminoethyl, 2-(N-methylamino)ethyl, 2-(N-{tetrahydro- 2H-pyran-4-yl}amino)ethyl, 1-hydroxypropyl, 2-hydroxypropyl, 3-hydroxpropyl, cyclopropyl, 1-methyl-1H-tetrazol-5-yl, and aminocarbonyl.

In some embodiments, $R^8$ is selected from H, methyl, hydroxymethyl, ethyl, 1-hydroxyethyl, 2-hydroxyethyl, 2-aminoethyl, 2-(N-methylamino)ethyl, 2-(N-{tetrahydro-2H-pyran-4-yl}amino)ethyl, 1-hydroxypropyl, 2-hydroxypropyl, 3-hydroxpropyl, cyclopropyl, and 1-methyl-1H-tetrazol-5-yl.

In some embodiments, $R^8$ is selected from H, methyl, ethyl, 2-hydroxyethyl, 2-aminoethyl, 2-(N-methylamino)ethyl, 2-(N-{tetrahydro-2H-pyran-4-yl}amino)ethyl, cyclopropyl, 1-methyl-1H-tetrazol-5-yl, and aminocarbonyl.

In some embodiments, $R^8$ is selected from H, methyl, ethyl, 2-hydroxyethyl, 2-aminoethyl, 2-(N-methylamino)ethyl, 2-(N-{tetrahydro-2H-pyran-4-yl}amino)ethyl, cyclopropyl, and 1-methyl-1H-tetrazol-5-yl.

In some embodiments, $R^8$ is selected from H, methyl, hydroxymethyl, ethyl, 2-hydroxyethyl, 2-(N-methylamino)ethyl, 2-(N-{tetrahydro-2H-pyran-4-yl}amino)ethyl, cyclopropyl, 1-methyl-1H-tetrazol-5-yl, and amino carbonyl.

In some embodiments, $R^8$ is selected from H, methyl, hydroxymethyl, ethyl, 2-hydroxyethyl, 2-(N-methylamino)ethyl, 2-(N-{tetrahydro-2H-pyran-4-yl}amino)ethyl, cyclopropyl, and 1-methyl-1H-tetrazol-5-yl.

In some embodiments, $R^8$ is selected from H, methyl, ethyl, 2-hydroxyethyl, 2-(N-methylamino)ethyl, 2-(N-{tetrahydro-2H-pyran-4-yl}amino)ethyl, cyclopropyl, 1-methyl-1H-tetrazol-5-yl, and aminocarbonyl.

In some embodiments, $R^8$ is selected from H, methyl, ethyl, 2-hydroxyethyl, 2-(N-methylamino)ethyl, 2-(N-{tetrahydro-2H-pyran-4-yl}amino)ethyl, cyclopropyl, and 1-methyl-1H-tetrazol-5-yl.

In some embodiments, $Y^1$ and $R^8$, together with the carbon atom to which they are attached, form a 4-, 5-, 6-, or 7-membered cycloalkyl or heterocycloalkyl group which is optionally substituted by 1 or 2 independently selected halo substituents.

In some embodiments, $Y^1$ and $R^8$, together with the carbon atom to which they are attached, form a 4-, 5-, 6-, or 7-membered cycloalkyl or heterocycloalkyl group which is optionally substituted by 1 or 2 substituents independently selected from Cl and F.

In some embodiments, $Y^1$ and $R^8$, together with the carbon atom to which they are attached, form a 4-, 5-, 6-, or 7-membered cycloalkyl group which is optionally substituted by 1 or 2 substituents independently selected from Cl and F.

In some embodiments, $Y^1$ and $R^8$, together with the carbon atom to which they are attached, form a 2-fluorocyclopentyl group.

In some embodiments, each $R^9$ is independently selected from halo, $C_{1-6}$ alkyl, $C_{1-6}$ haloalkyl, phenyl, $C_{3-6}$ cycloalkyl, 5-6 membered heteroaryl, 4-6 membered heterocycloalkyl, phenyl-$C_{1-3}$ alkyl-, $C_{3-6}$ cycloalkyl-$C_{1-3}$ alkyl-, 5-6 membered heteroaryl-$C_{1-3}$ alkyl-, 4-6 membered heterocycloalkyl-$C_{1-3}$ alkyl-, CN, $OR^k$, $C(O)R^k$, $C(O)NR^kR^k$, $C(O)OR^k$, $NR^kR^k$, $NR^kC(O)R^k$, $NR^kC(O)OR^k$, $NR^kC(O)NR^kR^k$, $NR^kS(O)_2R^k$, $NR^kS(O)_2NR^kR^k$, $S(O)_2R^k$, and $S(O)_2NR^kR^k$, wherein the $C_{1-6}$ alkyl, $C_{1-6}$ haloalkyl, phenyl, $C_{3-6}$ cycloalkyl, 5-6 membered heteroaryl, 4-6 membered heterocycloalkyl, phenyl-$C_{1-3}$ alkyl-, $C_{3-6}$ cycloalkyl-$C_{1-3}$ alkyl-, 5-6 membered heteroaryl-$C_{1-3}$ alkyl-, and 4-6 membered heterocycloalkyl-$C_{1-3}$ alkyl- of $R^9$ is each optionally substituted with 1, 2, 3, or 4 independently selected $R^q$ substituents.

In some embodiments, each $R^9$ is independently selected from halo, $C_{1-6}$ alkyl, $C_{1-6}$ haloalkyl, phenyl, $C_{3-6}$ cycloalkyl, 5-6 membered heteroaryl, 4-6 membered heterocycloalkyl, $OR^k$, $C(O)R^k$, $C(O)NR^kR^k$, $C(O)OR^k$, and $NR^kR^k$, wherein the $C_{1-6}$ alkyl, $C_{1-6}$ haloalkyl, phenyl, $C_{3-6}$ cycloalkyl, 5-6 membered heteroaryl, and 4-6 membered heterocycloalkyl of $R^9$ is each optionally substituted with 1 or 2 independently selected $R^q$ substituents.

In some embodiments, each $R^9$ is independently selected from halo, $C_{1-6}$ alkyl, $C_{1-6}$ haloalkyl, CN, $OR^k$, and $NR^kR^k$; wherein the $C_{1-6}$ alkyl of $R^9$ is each optionally substituted with 1, 2, 3, or 4 independently selected $R^q$ substituents.

In some embodiments, each $R^9$ is independently selected from halo, $C_{1-6}$ alkyl, $C_{1-6}$ haloalkyl, CN, $OR^k$, and $NR^kR^k$; wherein the $C_{1-6}$ alkyl of $R^9$ is each optionally substituted with 1, or 2 independently selected $R^q$ substituents.

In some embodiments, each $R^9$ is independently selected from $C_{1-6}$ alkyl, $OR^k$, and $NR^kR^k$.

In some embodiments, each $R^9$ is independently selected from methyl, OH, N-methylamino, and N-(tetrahydropyran-4-yl)amino.

In some embodiments, each $R^a$ is independently selected from H, D, $C_{1-6}$ alkyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl- of $R^a$ is each optionally substituted with 1, 2, or 3 independently selected $R^b$ substituents.

In some embodiments, each $R^a$ is independently selected from H, $C_{1-6}$ alkyl, $C_{1-6}$ haloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{1-6}$ haloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl- of $R^a$ is each optionally substituted with 1, 2, or 3 independently selected $R^b$ substituents.

In some embodiments, each $R^a$ is independently selected from H, $C_{1-6}$ alkyl, $C_{1-6}$ haloalkyl, and 4-7 membered heterocycloalkyl-$C_{1-6}$ alkyl-, wherein the $C_{1-6}$ alkyl, $C_{1-6}$ haloalkyl, and 4-7 membered heterocycloalkyl-$C_{1-6}$ alkyl- of $R^a$ is each optionally substituted with 1 or 2 independently selected $R^b$ substituents.

In some embodiments, each $R^a$ is selected from H, $C_{1-6}$ alkyl, and isoxazol-5-ylmethyl; wherein said isoxazol-5-ylmethyl is substituted by methyl.

In some embodiments, each $R^a$ is H.

In some embodiments, each $R^b$ is independently selected from halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, $OR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^cC(O)OR^c$, $NR^cC(O)NR^cR^c$, $S(O)R^c$, $S(O)NR^cR^c$, $S(O)_2R^c$, and $S(O)_2NR^cR^c$, wherein the $C_{1-6}$ alkyl, $C_{2-6}$ alkenyl, $C_{2-6}$ alkynyl, phenyl, $C_{3-10}$ cycloalkyl, 5-10 membered heteroaryl, and 4-10 membered heterocycloalkyl are each optionally substituted with 1 or 2 independently selected $R^d$ substituents.

In some embodiments, each $R^b$ is independently selected from halo, $C_{1-6}$ alkyl, $C_{2-6}$ alkenyl, $C_{2-6}$ alkynyl, $C_{1-6}$ haloalkyl, phenyl, $C_{3-6}$ cycloalkyl, 5-6 membered heteroaryl, 4-6 membered heterocycloalkyl, $OR^c$, $C(O)R^c$, C(O)NR$^c$R$^c$, C(O)OR$^c$, and NR$^c$R$^c$, wherein the C$_{1-6}$ alkyl, C$_{2-6}$ alkenyl, C$_{2-6}$ alkynyl, phenyl, C$_{3-6}$ cycloalkyl, 5-6 membered heteroaryl, and 4-6 membered heterocycloalkyl are each optionally substituted with 1 or 2 independently selected R$^d$ substituents.

In some embodiments, each R$^b$ is independently selected from halo, C$_{1-6}$ alkyl, C$_{3-6}$ cycloalkyl, OR$^c$, and C(O)NR$^c$R$^c$, wherein the C$_{1-6}$ alkyl and C$_{3-6}$ cycloalkyl are each optionally substituted with 1 or 2 independently selected R$^d$ substituents selected from D, C$_{1-6}$ alkyl and OH; and each R$^c$ group is independently selected from H and C$_{1-6}$ alkyl.

In some embodiments, each R$^b$ is independently selected from fluoro, methyl, CD$_3$, hydroxymethyl, methoxy, C(O)NH$_2$, cyclopropyl, and 3-methylisoxazol-5-yl.

In some embodiments:

each R$^c$ is independently selected from H, D, C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-4}$ alkyl-, C$_{3-7}$ cycloalkyl-C$_{1-4}$ alkyl-, 5-6 membered heteroaryl-C$_{1-4}$ alkyl-, and 4-7 membered heterocycloalkyl-C$_{1-4}$ alkyl-, wherein the C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-4}$ alkyl-, C$_{3-7}$ cycloalkyl-C$_{1-4}$ alkyl-, 5-6 membered heteroaryl-C$_{1-4}$ alkyl-, and 4-7 membered heterocycloalkyl-C$_{1-4}$ alkyl- of R$^c$ is each optionally substituted with 1, 2, 3, or 4 independently selected R$^d$ substituents;

each R$^d$ is independently selected from D, halo, C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, 5-6 membered heteroaryl-C$_{1-6}$ alkyl-, 4-7 membered heterocycloalkyl-C$_{1-6}$ alkyl-, OH, NO$_2$, CN, halo, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino, wherein the C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, 5-6 membered heteroaryl-C$_{1-6}$ alkyl-, 4-7 membered heterocycloalkyl-C$_{1-6}$ alkyl- of R$^d$ is each optionally substituted with 1, 2, 3 or 4 independently selected R$^f$ substituents; and each R$^f$ is independently selected from OH, NO$_2$, CN, halo, C$_{1-6}$ alkyl, C$_{2-6}$ alkenyl, C$_{2-6}$ alkynyl, C$_{1-6}$ haloalkyl, cyano-C$_{1-6}$ alkyl, HO—C$_{1-6}$ alkyl, C$_{1-6}$ alkoxy-C$_{1-6}$ alkyl, C$_{3-7}$ cycloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino.

In some embodiments, each R$^c$ is independently selected from H, C$_{1-6}$ alkyl, and C$_{1-6}$ haloalkyl, wherein the C$_{1-6}$ alkyl and C$_{1-6}$ haloalkyl of R$^c$ is each optionally substituted with 1, 2, 3, or 4 independently selected R$^d$ substituents; and each R$^d$ is independently selected from D, halo, C$_{1-6}$ alkyl, C$_{1-6}$ haloalkyl, OH, CN, C$_{1-6}$ alkoxy, C$_{1-6}$ haloalkoxy, amino, C$_{1-6}$ alkylamino, and di(C$_{1-6}$ alkyl)amino.

In some embodiments, each R$^c$ group is independently selected from H and C$_{1-6}$ alkyl; and each R$^d$ is independently selected from selected from D, C$_{1-6}$ alkyl and OH.

In some embodiments, two R$^c$ substituents, together with the nitrogen atom to which they attached form a 4-, 5-, 6-, or 7-membered heteroaryl or heterocycloalkyl group optionally substituted with 1, 2, 3, or 4 independently selected R$^d$ substituents.

In some embodiments, two R$^c$ substituents, together with the nitrogen atom to which they attached form a 5- or 6-membered heteroaryl or heterocycloalkyl group optionally substituted with 1 or 2 independently selected R$^d$ substituents.

In some embodiments, two R$^c$ substituents, together with the nitrogen atom to which they attached form a 5- or 6-membered heterocycloalkyl group optionally substituted with 1 or 2 independently selected R$^d$ substituents.

In some embodiments, two R$^c$ substituents, together with the nitrogen atom to which they attached form a 5- or 6-membered heterocycloalkyl group optionally substituted with 1 or 2 independently selected R$^d$ substituents selected from D and C$_{1-6}$ alkyl.

In some embodiments, two R$^c$ substituents, together with the nitrogen atom to which they attached form a 5- or 6-membered heterocycloalkyl group optionally substituted with methyl.

In some embodiments:

each R$^k$ is independently selected from H, D, C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-4}$ alkyl-, C$_{3-7}$ cycloalkyl-C$_{1-4}$ alkyl-, 5-6 membered heteroaryl-C$_{1-4}$ alkyl-, and 4-7 membered heterocycloalkyl-C$_{1-4}$ alkyl-, wherein the C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-4}$ alkyl-, C$_{3-7}$ cycloalkyl-C$_{1-4}$ alkyl-, 5-6 membered heteroaryl-C$_{1-4}$ alkyl-, and 4-7 membered heterocycloalkyl-C$_{1-4}$ alkyl- of R$^k$ is each optionally substituted with 1, 2, 3, or 4 independently selected R$^q$ substituents;

each R$^q$ is independently selected from D, halo, C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, 5-6 membered heteroaryl-C$_{1-6}$ alkyl-, 4-7 membered heterocycloalkyl-C$_{1-6}$ alkyl-, OH, NO$_2$, CN, halo, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, alkyl)carbamyl, carboxy, C$_{1-6}$ alkylcarbonyl, C$_{1-6}$ alkoxycarbonyl, alkylcarbonylamino, alkylsulfonylamino, aminosulfonyl, C$_{1-6}$ alkylaminosulfonyl, di(C$_{1-6}$ alkyl)aminosulfonyl, aminosulfonylamino, alkylaminosulfonylamino, di(C$_{1-6}$ alkyl)aminosulfonylamino, aminocarbonylamino, alkylaminocarbonylamino, and di(C$_{1-6}$ alkyl)aminocarbonylamino, wherein the C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, 5-6 membered heteroaryl-C$_{1-6}$ alkyl-, 4-7 membered heterocycloalkyl-C$_{1-6}$ alkyl- of R$^q$ is each optionally substituted with 1, 2, 3 or 4 independently selected R$^n$ substituents; and each R$^n$ is independently selected from OH, NO$_2$, CN, halo, C$_{1-6}$ alkyl, C$_{2-6}$ alkenyl, C$_{2-6}$ alkynyl, C$_{1-6}$ haloalkyl, cyano-$C_{1-6}$ alkyl, HO—$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments:

each $R^k$ is independently selected from H, $C_{1-6}$ alkyl, $C_{1-6}$ haloalkyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, 5-6 membered heteroaryl-$C_{1-4}$ alkyl-, and 4-7 membered heterocycloalkyl-$C_{1-4}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, 5-6 membered heteroaryl-$C_{1-4}$ alkyl-, and 4-7 membered heterocycloalkyl-$C_{1-4}$ alkyl- of $R^k$ is each optionally substituted with 1, 2, 3, or 4 independently selected $R^q$ substituents; and each $R^q$ is independently selected halo, $C_{1-6}$ alkyl, $C_{1-6}$ haloalkyl, OH, CN, $C_{1-6}$ alkoxy, $C_{1-6}$ haloalkoxy, amino, $C_{1-6}$ alkylamino, di($C_{1-6}$alkyl)amino, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, and di($C_{1-6}$ alkyl)aminosulfonyl.

In some embodiments, each $R^k$ is independently selected from H, $C_{1-6}$ alkyl, $C_{3-7}$ cycloalkyl, and 4-7 membered heterocycloalkyl, wherein the $C_{1-6}$ alkyl, $C_{3-7}$ cycloalkyl, and 4-7 membered heterocycloalkyl of $R^k$ is each optionally substituted with 1 or 2 independently selected $C_{1-6}$ alkyl groups.

In some embodiments:

$X^2$ is N or $CR^2$;
$X^4$ is N or $CR^4$;
$X^5$ is N or $CR^5$;
$X^6$ is N or $CR^6$;
$X^7$ is N or $CR^7$;
$Y^1$ is $C_{1-6}$ haloalkyl, wherein each halogen is F;
$R^1$ is selected from H, D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, $OR^a$, $C(O)R^a$, $C(O)NR^aR^a$, $C(O)OR^a$, $NR^aR^a$, $NR^aC(O)R^a$, $NR^aC(O)OR^a$, $NR^aC(O)NR^aR^a$, $S(O)R^a$, $S(O)_2R^a$, and $S(O)_2NR^aR^a$, wherein the $C_{1-6}$ alkyl, $C_{2-6}$ alkenyl, $C_{2-6}$ alkynyl, 6-10 membered aryl, $C_{3-10}$ cycloalkyl, 5-10 membered heteroaryl, and 4-10 membered heterocycloalkyl are each optionally substituted with 1, 2, 3, or 4 independently selected $R^b$ substituents;

$R^2$, $R^3$, $R^4$, $R^5$, $R^6$ and $R^7$ are each independently selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, CN, $OR^a$, and $SR^a$, wherein the $C_{1-6}$ alkyl, $C_{1-6}$ alkoxy, $C_{2-6}$ alkenyl, $C_{2-6}$ alkynyl, and $C_{1-6}$ haloalkyl of $R^2$, $R^3$, $R^4$, $R^5$, $R^6$ and $R^7$ are each optionally substituted with 1, 2, 3, or 4 independently selected $R^h$ substituents;

$R^8$ is selected from H, D, $C_{1-6}$ alkyl, $C_{1-6}$ alkoxy, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, and 4-10 membered heterocycloalkyl, wherein the $C_{1-6}$ alkyl, $C_{1-6}$ alkoxy, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, and 4-10 membered heterocycloalkyl are each optionally substituted with 1, 2, 3, or 4 independently selected $R^9$ substituents;

or $Y^1$ and $R^8$, together with the carbon atom to which they are attached, form a 4-, 5-, 6-, or 7-membered cycloalkyl group which is optionally substituted by 1 or 2 independently selected $R^9$ groups;

each $R^9$ is independently selected from halo, $C_{1-6}$ alkyl, $C_{1-6}$ haloalkyl, CN, $OR^k$, and $NR^kR^k$; wherein the $C_{1-6}$ alkyl of $R^9$ is each optionally substituted with 1, 2, 3, or 4 independently selected $R^q$ substituents;

each $R^b$ is independently selected from halo, $C_{1-6}$ alkyl, $C_{2-6}$ alkenyl, $C_{2-6}$ alkynyl, $C_{1-6}$ haloalkyl, 6-10 membered aryl, $C_{3-10}$cycloalkyl, 5-10 membered heteroaryl, 4-10 membered heterocycloalkyl, $OR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^cC(O)OR^c$, $NR^cC(O)NR^cR^c$, $S(O)R^c$, $S(O)NR^cR^c$, $S(O)_2R^c$, and $S(O)_2NR^cR^c$, wherein the $C_{1-6}$ alkyl, $C_{2-6}$ alkenyl, $C_{2-6}$ alkynyl, phenyl, $C_{3-10}$ cycloalkyl, 5-10 membered heteroaryl, and 4-10 membered heterocycloalkyl are each optionally substituted with 1 or 2 independently selected $R^d$ substituents;

each $R^c$ is independently selected from H, $C_{1-6}$ alkyl, and $C_{1-6}$ haloalkyl, wherein the $C_{1-6}$ alkyl and $C_{1-6}$ haloalkyl of $R^c$ is each optionally substituted with 1, 2, 3, or 4 independently selected $R^d$ substituents;

each $R^d$ is independently selected from D, halo, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, 4-7 membered heterocycloalkyl-$C_{1-6}$ alkyl-, OH, $NO_2$, CN, halo, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^e$ is independently selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl;

each $R^k$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, 5-6 membered heteroaryl-$C_{1-4}$ alkyl-, and 4-7 membered heterocycloalkyl-$C_{1-4}$ alkyl-;

each $R^q$ is independently selected from D, halo, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, 4-7 membered heterocycloalkyl-$C_{1-6}$ alkyl-, OH, $NO_2$, CN, halo, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments:

$X^2$ is N or $CR^2$;

$X^4$ is $CR^4$;

$X^5$ is $CR^5$ or N;

$X^6$ is N or $CR^6$;

$X^7$ is $CR^7$;

$Y^1$ is a $C_{1-6}$ haloalkyl, wherein each halogen is selected from F, wherein the haloalkyl is optionally substituted with 1 or 2 independently selected $Y^2$ substituents;

$R^1$ is selected from H, D, halo, $C_{1-6}$ alkyl, $C_{1-6}$ haloalkyl, $C_{5-10}$ membered heteroaryl, $C_{5-10}$ membered heteroaryl-$C_{1-6}$ alkyl-, $C(O)NR^aR^a$, and $C(O)OR^a$, wherein the $C_{1-6}$ alkyl, $C_{1-6}$ haloalkyl, $C_{5-10}$ membered heteroaryl, $C_{5-10}$ membered heteroaryl-$C_{1-6}$ alkyl- of $R^1$ are each optionally substituted with 1, 2, 3 or 4 independently selected $R^b$ substituents, $R^2$, $R^3$, $R^4$, $R^5$, $R^6$ and $R^7$ are each independently selected from H, D, halo, $C_{1-6}$ alkyl and $C_{1-6}$ haloalkyl, wherein the $C_{1-6}$ alkyl and $C_{1-6}$ haloalkyl of $R^2$, $R^3$, $R^4$, $R^5$, $R^6$ and $R^7$ are each optionally substituted with 1, 2, 3 or 4 independently selected $R^h$ substituents;

or $Y^1$ and $R^8$ form a 4-, 5-, 6-, or 7-membered cycloalkyl or heterocycloalkyl group optionally substituted with 1, 2, 3, or 4 independently selected $R^9$ substituents; and $R^8$ is selected from H, $C_{1-6}$ alkyl, $C_{3-10}$ cycloalkyl, $C_{5-10}$ membered heteroaryl, $C_{5-10}$ membered heteroaryl-$C_{1-6}$ alkyl-, wherein the $C_{1-6}$ alkyl, $C_{3-10}$ cycloalkyl, $C_{5-10}$ membered heteroaryl, $C_{5-10}$ membered heteroaryl-$C_{1-6}$ alkyl- of $R^8$ are each optionally substituted with 1, 2, 3 or 4 independently selected $R^9$ substituents.

In some embodiments:

$X^2$ is N or $CR^2$;

$X^4$ is $CR^4$;

$X^5$ is CH or N;

$X^6$ is N or $CR^6$;

$X^7$ is CH;

$Y^1$ is $CF_3$, $CF_2H$, $CFH_2$, $CF_2CF_3$, $CFHY^2$ or $CF(Y^2)_2$;

$Y^2$ is D or $C_{1-6}$ alkyl;

$R^1$ is selected from H, D, halo, $C_{1-6}$ alkyl, $C_{1-6}$ haloalkyl, 5-10 membered heteroaryl, 5-10 membered heteroaryl-$C_{1-6}$ alkyl-, $C(O)NR^aR^a$, and $C(O)OR^a$, wherein the $C_{1-6}$ alkyl, $C_{1-6}$ haloalkyl, 5-10 membered heteroaryl, 5-10 membered heteroaryl-$C_{1-6}$ alkyl- is optionally substituted with 1, 2, 3 or 4 independently selected $R^h$ substituents;

or $Y^1$ and $R^8$ form a 4-, 5-, 6-, or 7-membered cycloalkyl heterocycloalkyl group optionally substituted with 1, 2, 3, or 4 independently selected $R^9$ substituents;

$R^2$ is H;

$R^3$ is H;

$R^4$ is H or halo;

$R^6$ is H or halo; and $R^8$ is selected from H, $C_{1-6}$ alkyl, $C_{3-10}$ cycloalkyl, 5-10 membered heteroaryl, 5-10 membered heteroaryl-$C_{1-6}$ alkyl-, wherein the $C_{1-6}$ alkyl, $C_{3-10}$ cycloalkyl, 5-10 membered heteroaryl, 5-10 membered heteroaryl-$C_{1-6}$ alkyl- of $R^8$ are each optionally substituted with 1, 2, 3 or 4 independently selected $R^9$ substituents.

In some embodiments:

$X^2$ is N or $CR^2$;

$X^4$ is $CR^4$;

$X^5$ is N or $CR^5$;

$X^6$ is N or $CR^6$;

$X^7$ is $CR^7$;

wherein 0 or 1 of $X^5$ and $X^6$ are N;

$R^2$ is H, halo, CN, $C_{1-6}$ alkyl, or $C_{1-6}$ haloalkyl;

$R^3$ is H, halo, CN, $C_{1-6}$ alkyl, or $C_{1-6}$ haloalkyl;

$R^4$ is H, halo, CN, $C_{1-6}$ alkyl, or $C_{1-6}$ haloalkyl;

$R^5$ is H, halo, CN, $C_{1-6}$ alkyl, or $C_{1-6}$ haloalkyl;

$R^6$ is H, halo, CN, $C_{1-6}$ alkyl, or $C_{1-6}$ haloalkyl;

$R^7$ is H, halo, CN, $C_{1-6}$ alkyl, or $C_{1-6}$ haloalkyl;

$R^1$ is selected from H, D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, $OR^a$, $C(O)R^a$, $C(O)NR^aR^a$, $C(O)OR^a$, $NR^aR^a$, $NR^aC(O)R^a$, $NR^aC(O)OR^a$, $NR^aC(O)NR^aR^a$, $NR^aS(O)_2NR^aR^a$, $NR^aS(O)_2R^a$, $S(O)_2R^a$, and $S(O)_2NR^aR^a$, wherein the $C_{1-6}$ alkyl, $C_{2-6}$ alkenyl, $C_{2-6}$ alkynyl, 6-10 membered aryl, $C_{3-10}$ cycloalkyl, 5-10 membered heteroaryl, and 4-10 membered heterocycloalkyl are each optionally substituted with 1, 2, 3, or 4 independently selected $R^b$ substituents;

$Y^1$ is $C_{1-6}$ haloalkyl, wherein each halo is independently selected from Cl and F;

$R^8$ is selected from H, D, $C_{1-6}$ alkyl, $C_{1-6}$ alkoxy, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, and 4-10 membered heterocycloalkyl, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, and 4-10 membered heterocycloalkyl are each optionally substituted with 1, 2, 3, or 4 independently selected $R^9$ substituents; or $Y^1$ and $R^8$, together with the carbon atom to which they are attached, form a 4-, 5-, 6-, or 7-membered cycloalkyl group which is optionally substituted by 1 or 2 substituents independently selected from Cl and F;

each $R^9$ is independently selected from halo, $C_{1-6}$ alkyl, $C_{1-6}$ haloalkyl, phenyl, $C_{3-6}$ cycloalkyl, 5-6 membered heteroaryl, 4-6 membered heterocycloalkyl, phenyl-$C_{1-3}$ alkyl-, $C_{3-6}$ cycloalkyl-$C_{1-3}$ alkyl-, 5-6 membered heteroaryl-$C_{1-3}$ alkyl-, 4-6 membered heterocycloalkyl-$C_{1-3}$ alkyl-, CN, $OR^k$, $C(O)R^k$, $C(O)NR^kR^k$, $C(O)OR^k$, $NR^kR^k$, $NR^kC(O)R^k$, $NR^kC(O)OR^k$, $NR^kC(O)NR^kR^k$, $NR^kS(O)_2R^k$, $NR^kS(O)_2NR^kR^k$, $S(O)_2R^k$, and $S(O)_2NR^kR^k$, wherein the $C_{1-6}$ alkyl, $C_{1-6}$ haloalkyl, phenyl, $C_{3-6}$ cycloalkyl, 5-6 membered heteroaryl, 4-6 membered heterocycloalkyl, phenyl-$C_{1-3}$ alkyl-, $C_{3-6}$ cycloalkyl-$C_{1-3}$ alkyl-, 5-6 membered heteroaryl-$C_{1-3}$ alkyl-, and 4-6 membered heterocycloalkyl-$C_{1-3}$ alkyl- of $R^9$ is each optionally substituted with 1, 2, 3, or 4 independently selected $R^q$ substituents;

each $R^a$ is independently selected from H, D, $C_{1-6}$ alkyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl- of $R^a$ is each optionally substituted with 1, 2, or 3 independently selected $R^b$ substituents;

each $R^b$ is independently selected from halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, $OR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^cC(O)OR^c$, $NR^cC(O)NR^cR^c$, $S(O)R^c$, $S(O)NR^cR^c$, $S(O)_2R^c$, and $S(O)_2NR^cR^c$, wherein the $C_{1-6}$ alkyl, $C_{2-6}$ alkenyl, $C_{2-6}$ alkynyl, phenyl, $C_{3-10}$ cycloalkyl, 5-10 membered heteroaryl, and 4-10 membered heterocycloalkyl are each optionally substituted with 1 or 2 independently selected $R^d$ substituents;

each $R^d$ is independently selected from D, halo, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, 4-7 membered heterocycloalkyl-$C_{1-6}$ alkyl-, OH, $NO_2$, CN, halo, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, 4-7 membered heterocycloalkyl-$C_{1-6}$ alkyl- of $R^d$ is each optionally substituted with 1, 2, 3 or 4 independently selected $R^f$ substituents;

each $R^f$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^k$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, 5-6 membered heteroaryl-$C_{1-4}$ alkyl-, and 4-7 membered heterocycloalkyl-$C_{1-4}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, 5-6 membered heteroaryl-$C_{1-4}$ alkyl-, and 4-7 membered heterocycloalkyl-$C_{1-4}$ alkyl- of $R^k$ is each optionally substituted with 1, 2, 3, or 4 independently selected $R^q$ substituents;

each $R^q$ is independently selected from D, halo, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, 4-7 membered heterocycloalkyl-$C_{1-6}$ alkyl-, OH, $NO_2$, CN, halo, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, 4-7 membered heterocycloalkyl-$C_{1-6}$ alkyl- of $R^q$ is each optionally substituted with 1, 2, 3 or 4 independently selected $R^n$ substituents; and each $R^n$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments:

$X^2$ is N or $CR^2$;

$X^4$ is $CR^4$;

$X^5$ is N or $CR^5$;

$X^6$ is N or $CR^6$;

$X^7$ is $CR^7$;

wherein 0 or 1 of $X^5$ and $X^6$ are N;

$R^2$ is H;

$R^3$ is H;

$R^4$ is H, halo, or $C_{1-6}$ alkyl;

$R^5$ is H;

$R^6$ is H or halo;

$R^7$ is H;

$R^1$ is selected from H, $C_{1-6}$ alkyl, $C_{1-6}$ haloalkyl, phenyl, 5-6 membered heteroaryl, $C(O)NR^aR^a$, and $C(O)OR^a$, wherein the $C_{1-6}$ alkyl, phenyl, and 5-6 membered heteroaryl are each optionally substituted with 1 or 2 independently selected $R^b$ substituents;

$Y^1$ is $C_{1-6}$ haloalkyl, wherein each halo is F;

$R^8$ is selected from H, $C_{1-6}$ alkyl, 6-10 membered aryl, $C_{3-10}$ cycloalkyl, 5-10 membered heteroaryl, and 4-10 membered heterocycloalkyl, wherein the $C_{1-6}$ alkyl, 6-10 membered aryl, $C_{3-10}$ cycloalkyl, 5-10 membered heteroaryl, and 4-10 membered heterocycloalkyl are each optionally substituted with 1, 2, 3, or 4 independently selected $R^9$ substituents; or $Y^1$ and $R^8$, together with the carbon atom to which they are attached, form a 4-, 5-, or 6-membered cycloalkyl group which is optionally substituted by 1 or 2 F;

each $R^9$ is independently selected from halo, $C_{1-6}$ alkyl, $C_{1-6}$ haloalkyl, CN, $OR^k$, and $NR^kR^k$; wherein the $C_{1-6}$ alkyl of $R^9$ is each optionally substituted with 1, 2, 3, or 4 independently selected $R^q$ substituents;

each $R^a$ is independently selected from H, $C_{1-6}$ alkyl, $C_{1-6}$ haloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{1-6}$ haloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl- of $R^a$ is each optionally substituted with 1, 2, or 3 independently selected $R^b$ substituents;

each $R^b$ is independently selected from halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, $OR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^cC(O)OR^c$, $NR^cC(O)NR^cR^c$, $S(O)R^c$, $S(O)NR^cR^c$, $S(O)_2R^c$, and $S(O)_2NR^cR^c$, wherein the $C_{1-6}$ alkyl, $C_{2-6}$ alkenyl, $C_{2-6}$ alkynyl, phenyl, $C_{3-10}$ cycloalkyl, 5-10 membered heteroaryl, and 4-10 membered heterocycloalkyl are each optionally substituted with 1 or 2 independently selected $R^d$ substituents;

each $R^c$ is independently selected from H, $C_{1-6}$ alkyl, and $C_{1-6}$ haloalkyl, wherein the $C_{1-6}$ alkyl and $C_{1-6}$ haloalkyl of $R^c$ is each optionally substituted with 1, 2, 3, or 4 independently selected $R^d$ substituents;

each $R^d$ is independently selected from D, halo, $C_{1-6}$ alkyl, $C_{1-6}$ haloalkyl, OH, CN, $C_{1-6}$ alkoxy, $C_{1-6}$ haloalkoxy, amino, $C_{1-6}$ alkylamino, and di($C_{1-6}$ alkyl)amino;

each $R^k$ is independently selected from H, $C_{1-6}$ alkyl, $C_{1-6}$ haloalkyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, 5-6 membered heteroaryl-$C_{1-4}$ alkyl-, and 4-7 membered heterocycloalkyl-$C_{1-4}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, 5-6 membered heteroaryl-$C_{1-4}$ alkyl-, and 4-7 membered heterocycloalkyl-$C_{1-4}$ alkyl- of $R^k$ is each optionally substituted with 1, 2, 3, or 4 independently selected $R^q$ substituents; and each $R^q$ is independently selected halo, $C_{1-6}$ alkyl, $C_{1-6}$ haloalkyl, OH, CN, $C_{1-6}$ alkoxy, $C_{1-6}$ haloalkoxy, amino, $C_{1-6}$ alkylamino, di($C_{1-6}$ alkyl)amino, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, and di($C_{1-6}$ alkyl)aminosulfonyl.

In some embodiments:
$X^2$ is N or $CR^2$;
$X^4$ is $CR^4$;
$X^5$ is N or $CR^5$;
$X^6$ is N or $CR^6$;
$X^7$ is $CR^7$;
wherein 0 or 1 of $X^5$ and $X^6$ are N;
$R^2$ is H;
$R^3$ is H;
$R^4$ is H, halo, or $C_{1-6}$ alkyl;
$R^5$ is H;
$R^6$ is H or halo;
$R^7$ is H;
$R^1$ is selected from H, $C_{1-6}$ alkyl, $C_{1-6}$ haloalkyl, C(O)OR$^a$, C(O)NR$^a$R$^a$, phenyl, thiazolyl, pyrazolyl, oxazolyl, pyrimidinyl, pyridinyl, isoxazolyl, and 1,2,4-triazolyl; wherein said $C_{1-6}$ alkyl, $C_{1-6}$ haloalkyl, phenyl, thiazolyl, pyrazolyl, oxazolyl, pyrimidinyl, pyridinyl, isoxazolyl, and 1,2,4-triazolyl are each optionally substituted by 1, 2, 3, or 4 independently selected $R^b$ substituents;
$Y^1$ is $C_{1-6}$ haloalkyl, wherein each halo is F;
$R^8$ is selected from H, $C_{1-6}$ alkyl, $C_{3-6}$ cycloalkyl, 5-6 membered heteroaryl, wherein the $C_{1-6}$ alkyl, $C_{3-6}$ cycloalkyl, and 5-6 membered heteroaryl are each optionally substituted with 1 or 2 independently selected $R^9$ substituents; or
$Y^1$ and $R^8$, together with the carbon atom to which they are attached, form a 4-, 5-, or 6-membered cycloalkyl group which is optionally substituted by one F;
each $R^9$ is independently selected from $C_{1-6}$ alkyl, OR$^k$, and NR$^k$R$^k$;
each $R^a$ is selected from H, $C_{1-6}$ alkyl, and isoxazol-5-ylmethyl; wherein said isoxazol-5-ylmethyl is substituted by methyl and said $C_{1-6}$ alkyl is optionally substituted by OH;
each $R^b$ is independently selected from halo, $C_{1-6}$ alkyl, $C_{3-6}$ cycloalkyl, OR$^c$, and C(O)NR$^c$R$^c$, wherein the $C_{1-6}$ alkyl and $C_{3-6}$ cycloalkyl are each optionally substituted with 1 or 2 independently selected $R^d$ substituents;

each $R^c$ group is independently selected from H and $C_{1-6}$ alkyl;

each $R^d$ is independently selected from D, $C_{1-6}$ alkyl and OH; and each $R^k$ is independently selected from H, $C_{1-6}$ alkyl, $C_{3-7}$ cycloalkyl, and 4-7 membered heterocycloalkyl, wherein the $C_{1-6}$ alkyl, $C_{3-7}$ cycloalkyl, and 4-7 membered heterocycloalkyl of $R^k$ is each optionally substituted with 1 or 2 independently selected $C_{1-6}$ alkyl groups.

In some embodiments:
$X^2$ is N or $CR^2$;
$X^4$ is $CR^4$;
$X^5$ is N or $CR^5$;
$X^6$ is N or $CR^6$;
$X^7$ is $CR^7$;
wherein 0 or 1 of $X^5$ and $X^6$ are N;
$R^2$ is H;
$R^3$ is H;
$R^4$ is H, F, or methyl;
$R^5$ is H;
$R^6$ is H or F;
$R^7$ is H;
$Y^1$ is $CF_3$, $CHF_2$, $CH_2F$, or $CF_2CF_3$;
$R^1$ is selected from H, methyl, $CF_3$, C(O)OR$^a$, C(O)NR$^a$R$^a$, phenyl, thiazolyl, pyrazolyl, oxazolyl, pyrimidinyl, pyridinyl, isoxazolyl, and 1,2,4-triazolyl, wherein the phenyl, thiazolyl, pyrazolyl, oxazolyl, pyrimidinyl, pyridinyl, isoxazolyl, and 1,2,4-triazolyl are each optionally substituted by 1 or 2 independently selected $R^b$ substituents;
$R^8$ is selected from H, methyl, ethyl, 2-hydroxyethyl, 2-(N-methylamino)ethyl, 2-(N-{tetrahydro-2H-pyran-4-yl}amino)ethyl, cyclopropyl, and 1-methyl-1H-tetrazol-5-yl;
or $Y^1$ and $R^8$, together with the carbon atom to which they are attached, form a 2-flourocyclopentyl ring;
each $R^a$ is independently selected from H, methyl, 2-hydroxy-2-methylpropyl, and (3-methylisoxazol-5-yl)methyl; and
each $R^b$ is independently selected from fluoro, methyl, $CD_3$, hydroxymethyl, methoxy, C(O)NH$_2$, and cyclopropyl.

In some embodiments:
$X^2$ is N or $CR^2$;
$X^4$ is $CR^4$;
$X^5$ is N or $CR^5$;
$X^6$ is N or $CR^6$;
$X^7$ is $CR^7$;
wherein 0 or 1 of $X^5$ and $X^6$ are N;
$R^2$ is H;
$R^3$ is H;
$R^4$ is H, F, or methyl;
$R^5$ is H;
$R^6$ is H or F;
$R^7$ is H;
$Y^1$ is $CF_3$, $CHF_2$, $CH_2F$, or $CF_2CF_3$;
$R^1$ is selected from H, methyl, $CF_3$, C(O)OR$^a$, C(O)NR$^a$R$^a$, phenyl, thiazol-5-yl, thiazol-2-yl, pyrazol-3-yl, pyrazol-4-yl, pyrazol-5-yl, oxazol-5-yl, pyrimidin-5-yl, pyridin-3-yl, pyridin-4-yl, isoxazol-5-yl, and 1,2,4-triazol-1-yl, wherein the phenyl, thiazol-5-yl, thiazol-2-yl, pyrazol-3-yl, pyrazol-4-yl, pyrazol-5-yl, oxazol-5-yl, pyrimidin-5-yl, pyridin-3-yl, pyridin-4-yl, isoxazol-5-yl, and 1,2,4-triazol-1-yl are each optionally substituted by 1 or 2 independently selected $R^b$ substituents;

R⁸ is selected from H, methyl, ethyl, 2-hydroxyethyl, 2-(N-methylamino)ethyl, 2-(N-{tetrahydro-2H-pyran-4-yl}amino)ethyl, cyclopropyl, and 1-methyl-1H-tetrazol-5-yl;

or $Y^1$ and $R^8$, together with the carbon atom to which they are attached, form a 2-flourocyclopentyl ring;

each $R^a$ is independently selected from H, methyl, 2-hydroxy-2-methylpropyl, and (3-methylisoxazol-5-yl)methyl; and each $R^b$ is independently selected from fluoro, methyl, $CD_3$, hydroxymethyl, methoxy, $C(O)NH_2$, and cyclopropyl.

In some embodiments:

$X^2$ is N or $CR^2$;
$X^4$ is $CR^4$;
$X^5$ is N or $CR^5$;
$X^6$ is N or $CR^6$;
$X^7$ is $CR^7$;
wherein 0 or 1 of $X^5$ and $X^6$ are N;
$R^2$ is H;
$R^3$ is H;
$R^4$ is H, halo, or $C_{1-6}$ alkyl;
$R^5$ is H;
$R^6$ is H or halo;
$R^7$ is H;
$R^1$ is selected from H, $C_{1-6}$ alkyl, $C_{1-6}$ haloalkyl, phenyl, 3-6 membered cycloalkyl, 5-6 membered heteroaryl, 5-6 membered heterocycloalkyl, $C(O)NR^aR^a$, and $C(O)OR^a$, wherein the $C_{1-6}$ alkyl, phenyl, 3-6 membered cycloalkyl, 5-6 membered heteroaryl, 5-6 membered heterocycloalkyl are each optionally substituted with 1 or 2 independently selected $R^b$ substituents;

$Y^1$ is $C_{1-6}$ haloalkyl, wherein each halo is F;

$R^8$ is selected from H, $C_{1-6}$ alkyl, 6-10 membered aryl, $C_{3-10}$ cycloalkyl, 5-10 membered heteroaryl, and 4-10 membered heterocycloalkyl, wherein the $C_{1-6}$ alkyl, 6-10 membered aryl, $C_{3-10}$ cycloalkyl, 5-10 membered heteroaryl, and 4-10 membered heterocycloalkyl are each optionally substituted with 1, 2, 3, or 4 independently selected $R^9$ substituents; or $Y^1$ and $R^8$, together with the carbon atom to which they are attached, form a 4-, 5-, or 6-membered cycloalkyl group which is optionally substituted by 1 or 2 F;

each $R^9$ is independently selected from halo, $C_{1-6}$ alkyl, $C_{1-6}$ haloalkyl, CN, $OR^k$, and $NR^kR^k$; wherein the $C_{1-6}$ alkyl of $R^9$ is each optionally substituted with 1, 2, 3, or 4 independently selected $R^q$ substituents;

each $R^a$ is independently selected from H, $C_{1-6}$ alkyl, $C_{1-6}$ haloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{1-6}$ haloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl- of $R^a$ is each optionally substituted with 1, 2, or 3 independently selected $R^b$ substituents;

each $R^b$ is independently selected from halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, $OR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^cC(O)OR^c$, $NR^cC(O)NR^cR^c$, $S(O)R^c$, $S(O)NR^cR^c$, $S(O)_2R^c$, and $S(O)_2NR^cR^c$, wherein the $C_{1-6}$ alkyl, $C_{2-6}$ alkenyl, $C_{2-6}$ alkynyl, 6-10 membered aryl, $C_{3-10}$ cycloalkyl, 5-10 membered heteroaryl, and 4-10 membered heterocycloalkyl are each optionally substituted with 1 or 2 independently selected $R^d$ substituents;

each $R^c$ is independently selected from H, $C_{1-6}$ alkyl, and $C_{1-6}$ haloalkyl, wherein the $C_{1-6}$ alkyl and $C_{1-6}$ haloalkyl of $R^c$ is each optionally substituted with 1, 2, 3, or 4 independently selected $R^d$ substituents;

each $R^d$ is independently selected from D, halo, $C_{1-6}$ alkyl, $C_{1-6}$ haloalkyl, OH, CN, $C_{1-6}$ alkoxy, $C_{1-6}$ haloalkoxy, amino, $C_{1-6}$ alkylamino, and di($C_{1-6}$ alkyl)amino;

each $R^k$ is independently selected from H, $C_{1-6}$ alkyl, $C_{1-6}$ haloalkyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, 5-6 membered heteroaryl-$C_{1-4}$ alkyl-, and 4-7 membered heterocycloalkyl-$C_{1-4}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, 5-6 membered heteroaryl-$C_{1-4}$ alkyl-, and 4-7 membered heterocycloalkyl-$C_{1-4}$ alkyl- of $R^k$ is each optionally substituted with 1, 2, 3, or 4 independently selected $R^q$ substituents; and each $R^q$ is independently selected halo, $C_{1-6}$ alkyl, $C_{1-6}$ haloalkyl, OH, CN, $C_{1-6}$ alkoxy, $C_{1-6}$ haloalkoxy, amino, $C_{1-6}$ alkylamino, di($C_{1-6}$ alkyl)amino, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, and di($C_{1-6}$ alkyl)aminosulfonyl.

In some embodiments:

$X^2$ is N or $CR^2$;
$X^4$ is $CR^4$;
$X^5$ is N or $CR^5$;
$X^6$ is N or $CR^6$;
$X^7$ is $CR^7$;
wherein 0 or 1 of $X^5$ and $X^6$ are N;
$R^2$ is H;
$R^3$ is H;
$R^4$ is H, halo, or $C_{1-6}$ alkyl;
$R^5$ is H;
$R^6$ is H or halo;
$R^7$ is H;
$R^1$ is selected from H, $C_{1-6}$ alkyl, $C_{1-6}$ haloalkyl, $C(O)OR^a$, $C(O)NR^aR^a$, phenyl, cyclopropyl, thiazolyl, pyrazolyl, oxazolyl, pyrimidinyl, pyridinyl, isoxazolyl, 1,2,4-triazolyl, and piperidinyl; wherein said $C_{1-6}$ alkyl, $C_{1-6}$ haloalkyl, phenyl, cyclopropyl, thiazolyl, pyrazolyl, oxazolyl, pyrimidinyl, pyridinyl, isoxazolyl, 1,2,4-triazolyl, and piperidinyl are each optionally substituted by 1, 2, 3, or 4 independently selected $R^b$ substituents;

$Y^1$ is $C_{1-6}$ haloalkyl, wherein each halo is F;

$R^8$ is selected from H, $C_{1-6}$ alkyl, $C_{3-6}$ cycloalkyl, 5-6 membered heteroaryl, wherein the $C_{1-6}$ alkyl, $C_{3-6}$ cycloalkyl, and 5-6 membered heteroaryl are each optionally substituted with 1 or 2 independently selected $R^9$ substituents; or $Y^1$ and $R^8$, together with the carbon atom to which they are attached, form a 4-, 5-, or 6-membered cycloalkyl group which is optionally substituted by one F;

each $R^9$ is independently selected from $C_{1-6}$ alkyl, $OR^k$, and $NR^kR^k$;

each $R^a$ is selected from H, $C_{1-6}$ alkyl, and isoxazol-5-ylmethyl; wherein said isoxazol-5-ylmethyl is substituted by methyl and said $C_{1-6}$ alkyl is optionally substituted by OH;

each $R^b$ is independently selected from halo, $C_{1-6}$ alkyl, $C_{3-6}$ cycloalkyl, $OR^c$, and $C(O)NR^cR^c$, wherein the $C_{1-6}$ alkyl and $C_{3-6}$ cycloalkyl are each optionally substituted with 1 or 2 independently selected $R^d$ substituents;

each $R^c$ group is independently selected from H and $C_{1-6}$ alkyl;

each $R^d$ is independently selected from D, $C_{1-6}$ alkyl and OH; and each $R^k$ is independently selected from H, $C_{1-6}$ alkyl, $C_{3-7}$ cycloalkyl, and 4-7 membered heterocycloalkyl, wherein the $C_{1-6}$ alkyl, $C_{3-7}$ cycloalkyl, and 4-7 membered heterocycloalkyl of $R^k$ is each optionally substituted with 1 or 2 independently selected $C_{1-6}$ alkyl groups.

In some embodiments:

$X^2$ is N or $CR^2$;

$X^4$ is $CR^4$;

$X^5$ is N or $CR^5$;

$X^6$ is N or $CR^6$;

$X^7$ is $CR^7$;

wherein 0 or 1 $X^5$ and $X^6$ are N;

$R^2$ is H;

$R^3$ is H;

$R^4$ is H, F, methyl, or $CD_3$;

$R^5$ is H;

$R^6$ is H or F;

$R^7$ is H;

$Y^1$ is $CF_3$, $CHF_2$, $CH_2F$, or $CF_2CF_3$;

$R^1$ is selected from H, methyl, $CF_3$, $C(O)OR^a$, $C(O)NR^aR^a$, phenyl, cyclopropyl, thiazolyl, pyrazolyl, oxazolyl, pyrimidinyl, pyridinyl, isoxazolyl, 1,2,4-triazolyl, and piperindinyl, wherein the phenyl, cyclopropyl, thiazolyl, pyrazolyl, oxazolyl, pyrimidinyl, pyridinyl, isoxazolyl, 1,2,4-triazolyl, and piperidinyl are each optionally substituted by 1 or 2 independently selected $R^b$ substituents;

$R^8$ is selected from H, methyl, hydroxymethyl, ethyl, 2-hydroxyethyl, 2-(N-methylamino)ethyl, 2-(N-{tetrahydro-2H-pyran-4-yl}amino)ethyl, cyclopropyl, and 1-methyl-1H-tetrazol-5-yl;

or $Y^1$ and $R^8$, together with the carbon atom to which they are attached, form a 2-flourocyclopentyl ring;

each $R^a$ is independently selected from H, methyl, 2-hydroxy-2-methylpropyl, and (3-methylisoxazol-5-yl)methyl; and each $R^b$ is independently selected from fluoro, methyl, $CD_3$, hydroxymethyl, methoxy, $C(O)NH_2$, and cyclopropyl.

In some embodiments, the compound of Formula (I) is a compound of Formula (II):

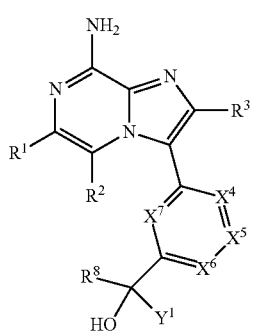

(II)

or a pharmaceutically acceptable salt thereof, wherein variables $R^1$, $R^2$, $R^3$, $X^4$, $X^5$, $X^6$, $X^7$, $R^8$, and $Y^1$ are defined according to the definitions provided herein for compounds of Formula (I).

In some embodiments, the compound of Formula (I) is a compound of Formula (III):

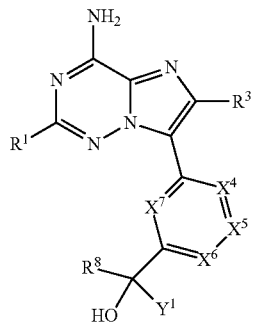

(III)

or a pharmaceutically acceptable salt thereof, wherein variables $R^1$, $R^3$, $X^4$, $X^5$, $X^6$, $X^7$, $R^8$, and $Y^1$ are defined according to the definitions provided herein for compounds of Formula (I).

In some embodiments, the compound of Formula (I) is a compound of Formula (IV):

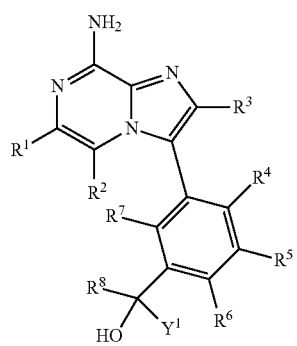

(IV)

or a pharmaceutically acceptable salt thereof, wherein variables $R^1$, $R^2$, $R^3$, $R^4$, $R^5$, $R^6$, $R^7$, $R^8$, and $Y^1$ are defined according to the definitions provided herein for compounds of Formula (I).

In some embodiments, the compound of Formula (I) is a compound of Formula (V):

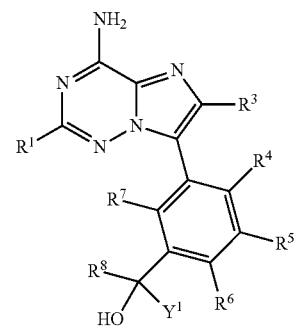

(V)

or a pharmaceutically acceptable salt thereof, wherein variables $R^1$, $R^3$, $R^4$, $R^5$, $R^6$, $R^7$, $R^8$, and $Y^1$ are defined according to the definitions provided herein for compounds of Formula (I).

In some embodiments, the compound of Formula (I) is a compound of Formula (VI):

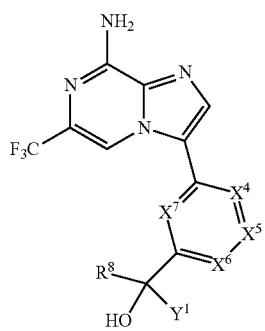

(VI)

or a pharmaceutically acceptable salt thereof, wherein variables $X^4, X^5, X^6, X^7, R^8$, and $Y^1$ are defined according to the definitions provided herein for compounds of Formula (I).

In some embodiments, the compound of Formula (I) is a compound of Formula (VII):

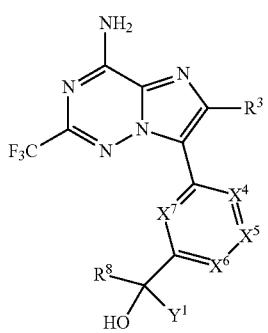

(VII)

or a pharmaceutically acceptable salt thereof, wherein variables $X^4, X^5, X^6, X^7, R^8$, and $Y^1$ are defined according to the definitions provided herein for compounds of Formula (I).

In some embodiments, the compound of Formula (I) is a compound of Formula (VIII):

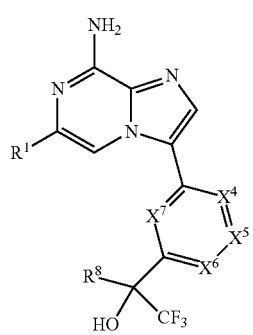

(VIII)

or a pharmaceutically acceptable salt thereof, wherein variables $R^1, X^4, X^5, X^6, X^7$, and $R^8$ are defined according to the definitions provided herein for compounds of Formula (I).

In some embodiments, the compound of Formula (I) is a compound of Formula (VIIIa):

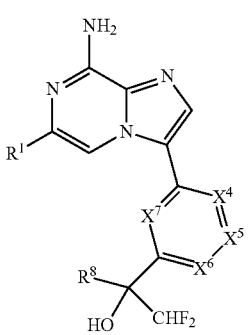

(VIIIa)

or a pharmaceutically acceptable salt thereof, wherein variables $R^1, X^4, X^5, X^6, X^7$, and $R^8$ are defined according to the definitions provided herein for compounds of Formula (I).

In some embodiments, the compound of Formula (I) is a compound of Formula (IX):

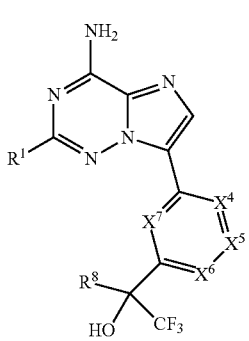

(IX)

or a pharmaceutically acceptable salt thereof, wherein variables $R^1, X^4, X^5, X^6, X^7$, and $R^8$ are defined according to the definitions provided herein for compounds of Formula (I).

In some embodiments, the compound of Formula (I) is a compound of Formula (IXa):

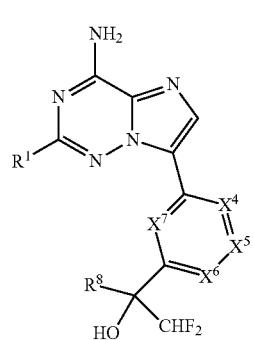

(IXa)

or a pharmaceutically acceptable salt thereof, wherein variables $R^1, X^4, X^5, X^6, X^7$, and $R^8$ are defined according to the definitions provided herein for compounds of Formula (I).

In some embodiments, the compound of Formula (I) is a compound of Formula (X):

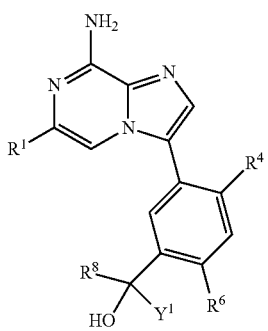

(X)

or a pharmaceutically acceptable salt thereof, wherein variables $R^1$, $R^4$, $R^6$, $R^8$, and $Y^1$ are defined according to the definitions provided herein for compounds of Formula (I).

In some embodiments, the compound of Formula (I) is a compound of Formula (XI):

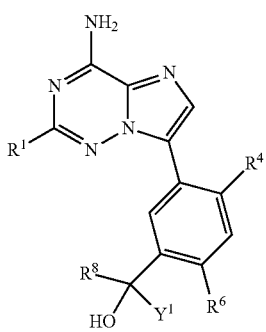

(XI)

or a pharmaceutically acceptable salt thereof, wherein variables $R^1$, $R^4$, $R^6$, $R^8$, and $Y^1$ are defined according to the definitions provided herein for compounds of Formula (I).

In some embodiments, the compound of Formula (I) is a compound of Formula (XII):

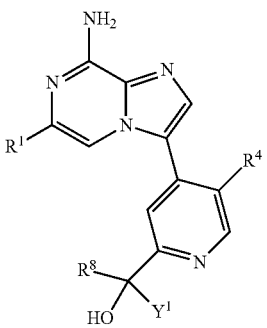

(XII)

or a pharmaceutically acceptable salt thereof, wherein variables $R^1$, $R^4$, $R^8$, and $Y^1$ are defined according to the definitions provided herein for compounds of Formula (I).

In some embodiments, the compound of Formula (I) is a compound of Formula (XIII):

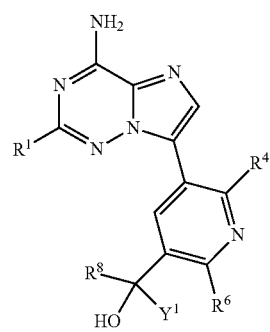

(XIII)

or a pharmaceutically acceptable salt thereof, wherein variables $R^1$, $X^4$, $X^6$, $R^8$, and $Y^1$ are defined according to the definitions provided herein for compounds of Formula (I).

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "each 'variable' is independently selected from" means substantially the same as wherein "at each occurrence 'variable' is selected from."

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl (Me), ethyl (Et), n-propyl (n-Pr), isopropyl (iPr), n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and iso-propoxy), butoxy (e.g., n-butoxy and tert-butoxy), and the like. In some embodiments, the alkyl group has 1 to 6, 1 to 4, or 1 to 3 carbon atoms.

As used herein, the term "amino" refers to a group of formula $NH_2$.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, the aryl group has from 5 to 10 carbon atoms. In some embodiments, the aryl group is phenyl or naphthyl. In some embodiments, the aryl group is phenyl.

As used herein, "halo" refers to F, Cl, Br, or I. In some embodiments, a halo is F, Cl, or Br. In some embodiments, a halo is F or Cl. In some embodiments, a halo is Cl.

As used herein, "$C_{n-m}$ haloalkoxy" refers to a group of formula —O-haloalkyl having n to m carbon atoms. Example haloalkoxy groups include $OCF_3$ and $OCHF_2$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms. Example haloalkyl groups include $CF_3$, $C_2F_5$, $CHF_2$, $CH_2F$, $CCl_3$, $CHCl_2$, $C_2Cl_5$ and the like.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "carbamyl" to a group of formula —C(O)NH$_2$.

As used herein, the term "carbonyl", employed alone or in combination with other terms, refers to a —C(O)— group.

As used herein, the term "cyano-$C_{1-3}$ alkyl" refers to a group of formula —($C_{1-6}$ alkylene)-CN.

As used herein, the term "HO—$C_{1-6}$ alkyl" refers to a group of formula —($C_{1-6}$ alkylene)-OH.

As used herein, the term "HO—$C_{1-3}$ alkyl" refers to a group of formula —($C_{1-3}$ alkylene)-OH. As used herein, the term "$C_{1-6}$ alkoxy-$C_{1-6}$ alkyl" refers to a group of formula —($C_{1-6}$ alkylene)-O($C_{1-6}$ alkyl).

As used herein, the term "$C_{1-3}$ alkoxy-$C_{1-3}$ alkyl" refers to a group of formula —($C_{1-3}$ alkylene)-O($C_{1-3}$ alkyl). As used herein, the term "carboxy" refers to a group of formula —C(O)OH.

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, "cycloalkyl" refers to non-aromatic cyclic hydrocarbons including cyclized alkyl and/or alkenyl groups. Cycloalkyl groups can include mono- or polycyclic (e.g., having 2 fused rings) groups, spirocycles, and bridged rings (e.g., a bridged bicycloalkyl group). Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons ($C_{3-10}$). In some embodiments, the cycloalkyl is a $C_{3-10}$ monocyclic or bicyclic cycloalkyl. In some embodiments, the cycloalkyl is a $C_{3-10}$ monocyclic or bicyclic cycloalkyl which is optionally substituted by $CH_2F$, $CHF_2$, $CF_3$, and $CF_2CF_3$. In some embodiments, the cycloalkyl is a $C_{3-7}$ monocyclic cycloalkyl. In some embodiments, the cycloalkyl is a $C_{4-10}$ spirocycle or bridged cycloalkyl. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1] pentyl, bicyclo[2.1.1]hexyl, bicyclo[2.2.1]heptanyl, bicyclo[3.1.1]heptanyl, bicyclo[2.2.2]octanyl, spiro[3.3]heptanyl, and the like. In some embodiments, cycloalkyl is cyclopropyl, cyclobutyl, cyclopentyl, or cyclohexyl.

As used herein, "heteroaryl" refers to a monocyclic or polycyclic aromatic heterocycle having at least one heteroatom ring member selected from N, O, S or B, wherein any ring forming N is optionally an N-oxide group. In some embodiments, the heteroaryl ring has 1, 2, 3, or 4 heteroatom ring members independently selected from N, O, S and B. In some embodiments, any ring-forming N in a heteroaryl moiety can be an N-oxide. In some embodiments, the heteroaryl is a 5-10 membered monocyclic or bicyclic heteroaryl having 1, 2, 3 or 4 heteroatom ring members independently selected from N, O, S and B. In some embodiments, the heteroaryl is a 5-6 monocyclic heteroaryl having 1 or 2 heteroatom ring members independently selected from N, O, S and B. In some embodiments, the heteroaryl is a 5-6 monocyclic heteroaryl ring having 1 or 2 heteroatom ring members independently selected from N, O or S. In some embodiments, the heteroaryl group has 1 to 4 ring-forming heteroatoms, 1 to 3 ring-forming heteroatoms, 1 to 2 ring-forming heteroatoms or 1 ring-forming heteroatom. When the heteroaryl group contains more than one heteroatom ring member, the heteroatoms may be the same or different. Example heteroaryl groups include, but are not limited to, pyridine, pyrimidine, pyrazine, pyridazine, pyrrole, pyrazole, oxazole, isoxazole, thiazole, isothiazole, imidazole, furan, thiophene, triazole, tetrazole, thiadiazole, quinoline, isoquinoline, indole, benzothiophene, benzofuran, benzisoxazole, imidazo[1, 2-b]thiazole, purine, triazine, thieno[3,2-b]pyridine, imidazo[1,2-a]pyridine, 1,5-naphthyridine, 1H-pyrazolo[4,3-b]pyridine and the like.

A five-membered heteroaryl ring is a heteroaryl group having five ring-forming atoms wherein one or more (e.g., 1, 2, or 3) ring atoms are independently selected from N, O, S and B. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl and 1,2-dihydro-1,2-azaborine.

A six-membered heteroaryl ring is a heteroaryl group having six ring-forming atoms wherein one or more (e.g., 1, 2, or 3) ring atoms are independently selected from N, O, S and B. Exemplary six-membered ring heteroaryls are pyridyl, pyrazinyl, pyrimidinyl, triazinyl and pyridazinyl.

As used herein, "heterocycloalkyl" refers to monocyclic or polycyclic heterocycles having at least one non-aromatic ring (saturated or partially unsaturated ring), wherein one or more of the ring-forming carbon atoms of the heterocycloalkyl is replaced by a heteroatom selected from N, O, S and B, and wherein the ring-forming carbon atoms and heteroatoms of the heterocycloalkyl group can be optionally substituted by one or more oxo or sulfido (e.g., C(O), S(O), C(S), or S(O)$_2$, etc.). Heterocycloalkyl groups include monocyclic and polycyclic (e.g., having 2 fused rings) systems. Included in heterocycloalkyl are monocyclic and polycyclic 3-10, 4-10, 3-7, 4-7, and 5-6 membered heterocycloalkyl groups. Heterocycloalkyl groups can also include spirocycles and bridged rings (e.g., a 5-10 membered bridged biheterocycloalkyl ring having one or more of the ring-forming carbon atoms replaced by a heteroatom independently selected from N, O, S and B). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds.

Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl group contains 3 to 10 ring-forming atoms, 4 to 10 ring-forming atoms, 3 to 7 ring-forming atoms, or 5 to 6 ring-forming atoms. In some embodiments, the heterocycloalkyl group has 1 to 4 heteroatoms, 1 to 3 heteroatoms, 1 to 2 heteroatoms or 1 heteroatom. In some embodiments, the heterocycloalkyl is a monocyclic 4-6 membered heterocycloalkyl having 1 or 2 heteroatoms independently selected from N, O, S and B and having one or more oxidized ring members.

Example heterocycloalkyl groups include pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, 1,2,3,4-tetrahydroisoquinoline, azabicyclo[3.1.0]hexanyl, diazabicyclo[3.1.0]hexanyl, oxabicyclo[2.1.1]hexanyl, azabicyclo[2.2.1]heptanyl, diazabicyclo[2.2.1]heptanyl, azabicyclo[3.1.1]heptanyl, diazabicyclo[3.1.1]heptanyl, azabicyclo[3.2.1]octanyl, diazabicyclo[3.2.1]octanyl, oxabicyclo[2.2.2]octanyl, azabicyclo[2.2.2]octanyl, azaadamantanyl, diazaadamantanyl, oxa-adamantanyl, azaspiro[3.3]heptanyl, diazaspiro[3.3]heptanyl, oxa-azaspiro[3.3]heptanyl, azaspiro[3.4]octanyl, diazaspiro[3.4]octanyl, oxa-azaspiro[3.4]octanyl, azaspiro[2.5]octanyl, diazaspiro[2.5]octanyl, azaspiro[4.4]nonanyl, diazaspiro[4.4]nonanyl, oxa-azaspiro[4.4]nonanyl, azaspiro[4.5]decanyl, diazaspiro[4.5]decanyl, diazaspiro[4.4]nonanyl, oxa-diazaspiro[4.4]nonanyl and the like.

As used herein, "$C_{o-p}$ cycloalkyl-$C_{n-m}$ alkyl-" refers to a group of formula cycloalkyl-alkylene-, wherein the cycloalkyl has o to p carbon atoms and the alkylene linking group has n to m carbon atoms.

As used herein "$C_{o-p}$ aryl-$C_{n-m}$ alkyl-" refers to a group of formula aryl-alkylene-, wherein the aryl has o to p carbon atoms and the alkylene linking group has n to m carbon atoms.

As used herein, "heteroaryl-$C_{n-m}$ alkyl-" refers to a group of formula heteroaryl-alkylene-, wherein alkylene linking group has n to m carbon atoms.

As used herein "heterocycloalkyl-$C_{n-m}$ alkyl-" refers to a group of formula heterocycloalkyl-alkylene-, wherein alkylene linking group has n to m carbon atoms.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom (i.e., =O) as a divalent substituent, forming a carbonyl group when attached to a carbon (e.g., C=O or C(O)), or attached to a nitrogen or sulfur heteroatom forming a nitroso, sulfinyl or sulfonyl group.

As used herein, the term "independently selected from" means that each occurrence of a variable or substituent are independently selected at each occurrence from the applicable list.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration. The Formulas (e.g., Formula (I), (II), etc.) provided herein include stereoisomers of the compounds.

Formulas (I)-(XIII) herein include stereoisomers of the compounds. In some embodiments, the carbon atom to which $R^8$ and $Y^1$ are attached is in the (R)-configuration. In some embodiments, the carbon atom to which $R^8$ and $Y^1$ are attached is in the (S)-configuration.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Synthesis

As will be appreciated by those skilled in the art, the compounds provided herein, including salts and stereoisomers thereof, can be prepared using known organic synthesis techniques and can be synthesized according to any of numerous possible synthetic routes.

Compounds of Formula (I) can be prepared from optionally protected (e.g., P=acetyl or p-methoxybenzyl) bicycles 1-1 where $Y^9$ is halogen (e.g., Cl, Br, or I) or pseudohalogen (e.g., OTf or OMs) as shown in Scheme I. Bicycle 1-1 can be coupled with 1-2, where $M^1$ is a boronic acid, boronate ester, potassium trifluoroborate, or an appropriately substituted metal, such as $Sn(Bu)_3$ or Zn, under standard Suzuki conditions (e.g., in the presence of a palladium catalyst, such as tetrakis(triphenylphosphine)palladium(0) or [1,1'-bis(diphenylphosphino)ferrocene]dichloropalladium (II), complex with dichloromethane and a base (e.g., a carbonate base)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give compound 1-3. After coupling, optionally chosen protecting groups can be removed under conditions suitable for their removal that are also compatible with the functionality present in 1-3 (e.g., exposure to aqueous HCl or trifluoroacetic acid) to afford the resulting compounds of Formula (I).

Alternatively, the $Y^9$ group can be converted to an appropriate substituted metal 1-4 (e.g., $M^2$ is $B(OH)_2$, Bpin, $BF_3K$, $Sn(Bu)_3$, or Zn) and then coupled to 1-5 where W is halogen (e.g., Cl, Br, or I) or pseudohalogen (e.g., OTf or OMs) under standard Suzuki conditions (e.g., in the presence of a palladium catalyst, such as tetrakis(triphenylphosphine)palladium(0) or [1,1'-bis(diphenylphosphino)ferrocene]dichloropalladium (II), complex with dichloromethane and a base (e.g., a carbonate base)) or standard Stille conditions (e.g., in the presence of a palladium(0) catalyst, such as tetrakis(triphenylphosphine)palladium(0)) or standard Negishi conditions (e.g., in the presence of a palladium (0) catalyst, such as tetrakis(triphenylphosphine)palladium (0) or [1,1'-bis(diphenylphosphino)ferrocene] dichloropalladium (II)) to give to give compound 1-3. After coupling, optionally chosen protecting groups can be removed under conditions suitable for their removal that are also compatible with the functionality present in 1-3 (e.g., exposure to aqueous HCl or trifluoroacetic acid) to afford the resulting compounds of Formula (I).

Scheme I.

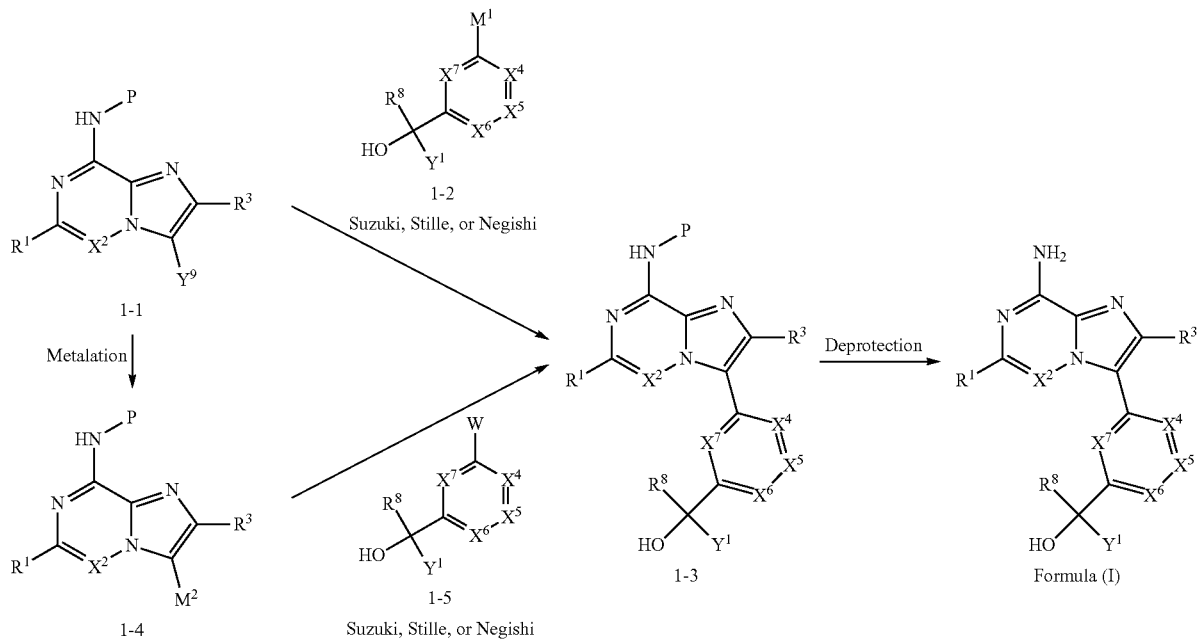

Intermediates for making compounds provided herein can be prepared as shown in Scheme II. For example, ketone 2-1 can be converted to tertiary alcohol 2-3 ($Y^1$=e.g., $CF_3$, $CF_2H$) with silane 2-2 where $Z^1$ is a halogen (e.g., F or Br or H) under standard conditions (e.g., in the presence of TBAF or $PPh_3$ and DMPU). The W halo (e.g., Cl, Br, or I) or pseudohalo group (e.g., OTf or OMs) of alcohol 2-3 can be converted to an appropriate substituted metal 2-4 (e.g., $M^1$ is $B(OH)_2$, Bpin, $BF_3K$, $Sn(Bu)_3$, or Zn) under standard conditions (e.g., in the presence of a diboron reagent such as bis(pinacolato)diboron, a palladium catalyst, such as dichloro[bis(triphenylphosphoranyl)]palladium or bis(diphenylphosphino)ferrocene]dichloropalladium(II), complex with dichloromethane, and a base, such as potassium acetate). Compounds provided herein can be synthesized from intermediates 2-4 using the methods described in Scheme I.

Scheme II.

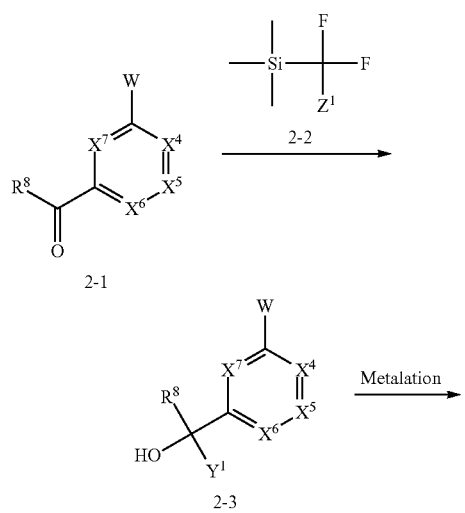

-continued

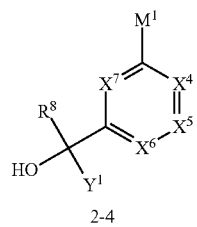

2-4

Intermediates for making compounds provided herein can be prepared as shown in Scheme III. For example, aldehyde 3-1 can be reacted with a nucleophile (e.g., a Grignard reagent or alkyllithium reagent) to afford secondary alcohol 3-2. The secondary alcohol 3-2 can be oxidized to ketone 3-3. Ketone 3-3 can be converted to tertiary alcohol 3-5 ($Y^1$=e.g., $CF_3$ or $CF_2H$) with silane 3-4 where $Z^1$ is a halogen (e.g., F or Br or H) under standard conditions (e.g., in the presence of TBAF or $PPh_3$ and DMPU). The $Y^2$ halo (e.g., Cl, Br, or I) or pseudohalo group (e.g., OTf or OMs) of alcohol 3-5 can be converted to an appropriate substituted metal 3-6 (e.g., $M^1$ is $B(OH)_2$, Bpin, $BF_3K$, $Sn(Bu)_3$, or Zn) under standard conditions (e.g., in the presence of a diboron reagent such as bis(pinacolato)diboron, a palladium catalyst, such as dichloro[bis(triphenylphosphoranyl)]palladium or bis(diphenylphosphino)ferrocene]dichloropalladium(II), complex with dichloromethane, and a base, such as potassium acetate). Compounds provided herein can be synthesized from intermediates 3-6 using the methods described in Scheme I.

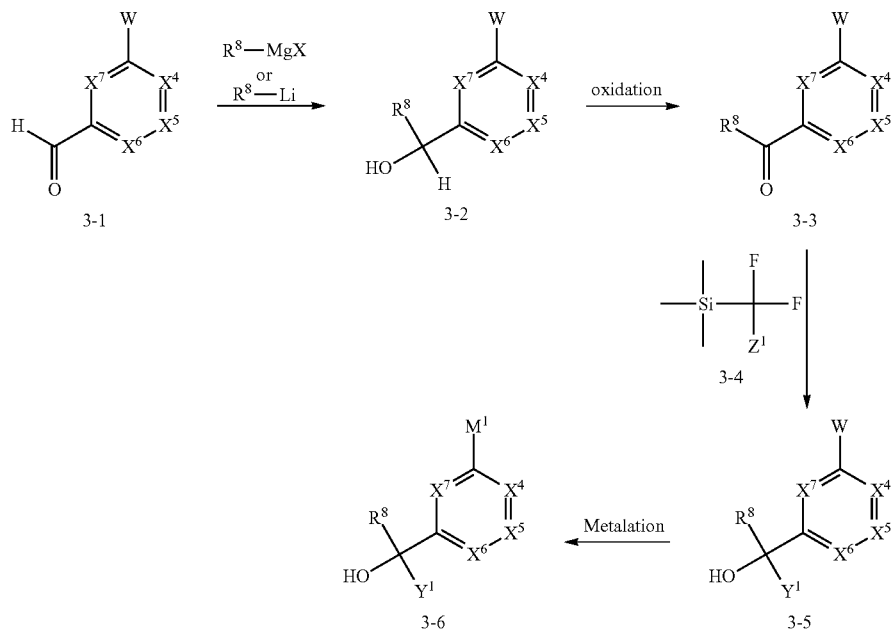

Intermediates for making compounds provided herein can be prepared as shown in Scheme IV. For example, aldehyde 4-1 can be converted to secondary alcohol 4-3 ($Y^1$=e.g., $CF_3$ or $CF_2H$) with silane 4-2 where $Z^1$ is a halogen (e.g., F or Br or H) under standard conditions (e.g., in the presence of TBAF or $PPh_3$ and DMPU). The secondary alcohol 4-3 can be oxidized to ketone 4-4. Ketone 4-4 can be reacted with a nucleophile (e.g., a Grignard reagent or alkyllithium reagent) to afford tertiary alcohol 4-5. The W halo (e.g., Cl, Br, or I) or pseudohalo group (e.g., OTf or OMs) of alcohol 4-5 can be converted to an appropriate substituted metal 4-6 (e.g., $M^1$ is $B(OH)_2$, Bpin, $BF_3K$, $Sn(Bu)_3$, or Zn) under standard conditions (e.g., in the presence of a diboron reagent such as bis(pinacolato)diboron, a palladium catalyst, such as dichloro[bis(triphenylphosphoranyl)]palladium or bis(diphenylphosphino)ferrocene]dichloropalladium(II), complex with dichloromethane, and a base, such as potassium acetate). Compounds provided herein can be synthesized from intermediates 4-6 using the methods described in Scheme I.

Alternatively the W halo (e.g., Cl, Br, or I) or pseudohalo group (e.g., OTf or OMs) of alcohol 4-3 can be converted to an appropriate substituted metal 4-6 wherein $R^8$ is H (e.g., $M^1$ is $B(OH)_2$, Bpin, $BF_3K$, $Sn(Bu)_3$, or Zn) under standard conditions (e.g., in the presence of a diboron reagent such as bis(pinacolato)diboron, a palladium catalyst, such as dichloro[bis(triphenylphosphoranyl)]palladium or bis(diphenylphosphino)ferrocene]dichloropalladium(II), complex with dichloromethane, and a base, such as potassium acetate). Compounds provided herein can be synthesized from intermediates 4-6 using the methods described in Scheme I.

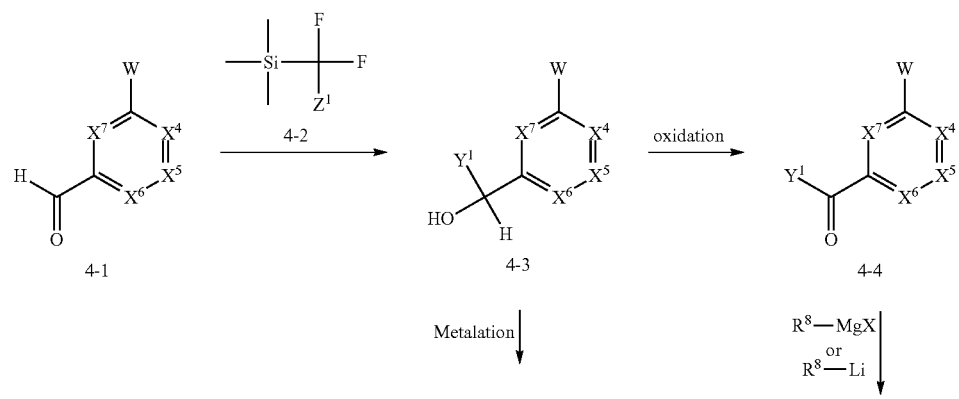

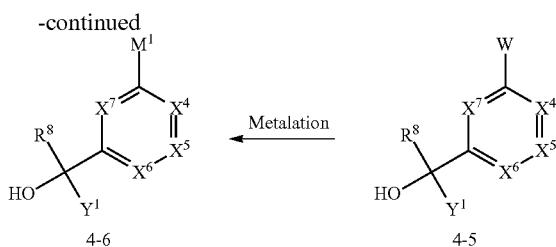

Intermediates for making compounds provided herein can be prepared as shown in Scheme V. For example, acid 5-1 can be converted to Weinreb amide 5-2. Weinreb amide 5-2 can be reacted with a nucleophile (e.g., a Grignard reagent or alkyllithium reagent) to afford ketone 5-3. Ketone 5-3 can be converted to tertiary alcohol 5-5 ($Y^1$=e.g., $CF_3$ or $CF_2H$) with silane 5-4 where $Z^1$ is a halogen (e.g., F or Br or H) under standard conditions (e.g., in the presence of TBAF or $PPh_3$ and DMPU). The W halo (e.g., Cl, Br, or I) or pseudohalo group (e.g., OTf or OMs) of alcohol 5-5 can be converted to an appropriate substituted metal 5-6 (e.g., $M^1$ is $B(OH)_2$, Bpin, $BF_3K$, $Sn(Bu)_3$, or Zn) under standard conditions (e.g., in the presence of a diboron reagent such as bis(pinacolato)diboron, a palladium catalyst, such as dichloro[bis(triphenylphosphoranyl)]palladium or bis(diphenylphosphino)ferrocene]dichloropalladium(II), complex with dichloromethane, and a base, such as potassium acetate). Compounds provided herein can be synthesized from intermediates 5-6 using the methods described in Scheme I.

presence of acetyl chloride or acetic anhydride, a base (e.g., triethylamine), and optionally a catalyst (e.g., 4-dimethylaminopyridine)) to give the protected amine 6-4. Compound 6-4 can be halogenated with suitable reagents, such as N-chlorosuccinimide, N-bromosuccinimide, or N-iodosuccinimide, to give halide 6-5 where $Y^9$ is a halo group (e.g., Cl, Br, or I). Halide 6-5 can be selectively coupled with 1-2, where $M^1$ is a boronic acid, boronate ester, potassium trifluoroborate, or an appropriately substituted metal such as $Sn(Bu)_3$ or Zn, under standard Suzuki conditions (e.g., in the presence of a palladium catalyst, such as tetrakis(triphenylphosphine)palladium(0) and a base (e.g., a carbonate base)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give compound 6-6. Compound 6-6 can be coupled with 6-7, where $M^4$ is a

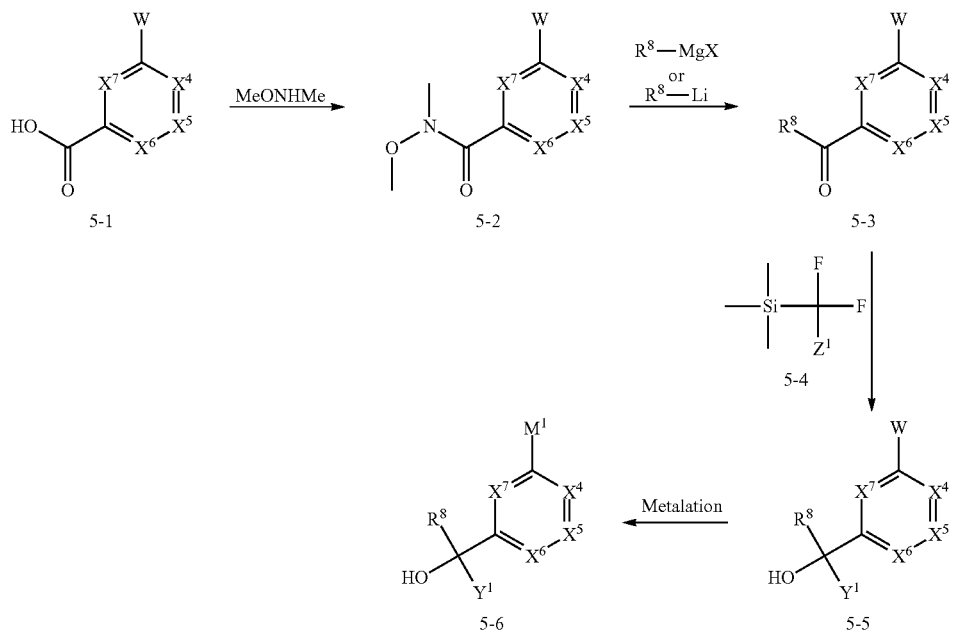

Scheme V.

Compounds of Formula (I) can also be prepared as shown in Scheme VI. For example, heteroaromatic amine 6-1, where $Y^4$ is a halogen (e.g., Cl, Br, or I), can be reacted with alpha-halo carbonyl derivative 6-2 where $Y^5$ is a halogen (e.g., Cl or Br), to give heterocycle 6-3. The amino group of 6-3 can be optionally protected with a suitable protecting group P, (e.g., acetyl), under standard conditions (e.g., in the boronic acid, boronate ester, potassium trifluoroborate, or an appropriately substituted metal, such as $Sn(Bu)_3$ or Zn, under standard Suzuki conditions (e.g., in the presence of a palladium catalyst, such as bis(diphenylphosphino)ferrocene]dichloropalladium(II), complex with dichloromethane or bis(di-tert-butyl(4-dimethylaminophenyl)phosphine)dichloropalladium(II) and a base (e.g., a carbonate base or cesium fluoride)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give compound 6-8. The optionally chosen protecting group can be removed according to Scheme I to afford the resulting compounds of Formula (I).

Alternatively, halide 6-5 can be selectively coupled with 6-7, where M⁴ is a boronic acid, boronate ester, potassium trifluoroborate, or an appropriately substituted metal such as Sn(Bu)₃ or Zn, under standard Suzuki conditions (e.g., in the presence of a palladium catalyst, such as bis(diphenylphosphino)ferrocene]dichloropalladium(II), complex with dichloromethane or bis(di-tert-butyl(4-dimethylaminophenyl)phosphine)dichloropalladium(II) and a base (e.g., a carbonate base or cesium fluoride)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give compound 6-9, which can be further coupled according to Scheme I to afford the resulting compounds of Formula (I).

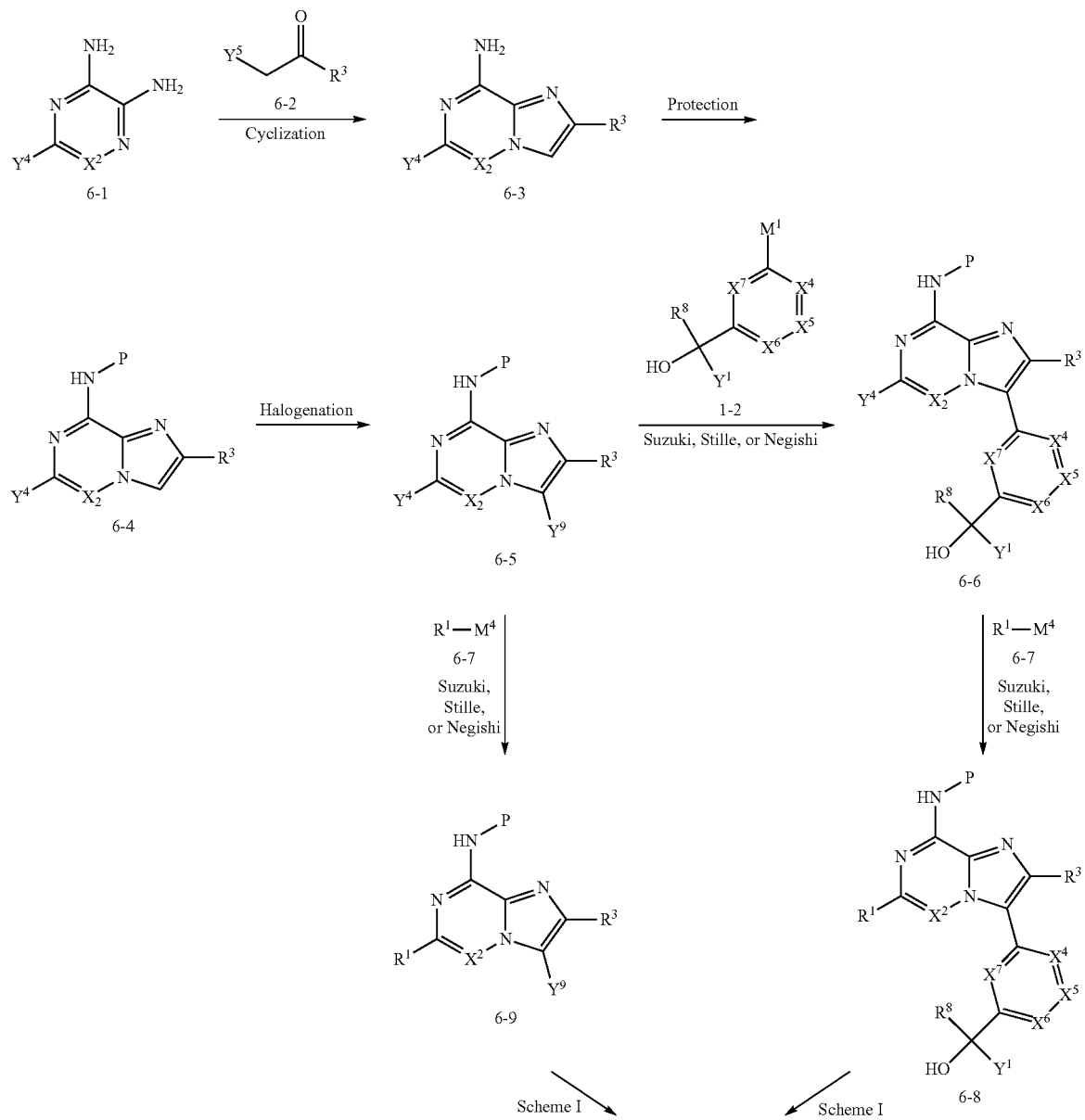

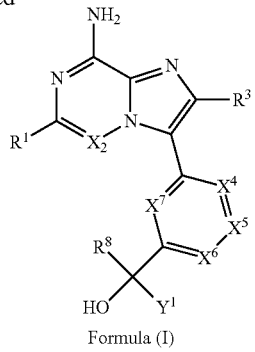

Formula (I)

Compounds of Formula (I) can also be prepared as shown in Scheme VII. For example, hetereoaromatic amine 7-1, where $Y^4$ and $Y^6$ are halo groups, can be reacted with alpha-halo carbonyl derivatives 6-2 where $Y^5$ is a halogen (e.g., Cl or Br), to give heterocycle 7-2. Halogenation of heterocycle 7-2 with suitable reagents, such as N-chlorosuccinimide, N-bromosuccinimide, or N-iodosuccinimide can give halide 7-3 where $Y^9$ is a halo group (e.g., Cl, Br, or I). Nucleophilic aromatic substitution of the halide of 7-3 with amine 7-4 (e.g., $NH_3$ or p-methoxybenzylamine) can provide halide 7-5. Halide 7-5 can be selectively coupled with 1-2, where $M^1$ is a boronic acid, boronate ester, potassium trifluoroborate, or an appropriately substituted metal such as $Sn(Bu)_3$ or Zn, under standard Suzuki conditions (e.g., in the presence of a palladium catalyst, such as tetrakis(triphenylphosphine)palladium(0) and a base (e.g., a carbonate base)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give compound 7-6. Compound 7-6 can be coupled with 7-7, where $M^4$ is a boronic acid, boronate ester, potassium trifluoroborate, or an appropriately substituted metal such as $Sn(Bu)_3$ or Zn, under standard Suzuki conditions (e.g., in the presence of a palladium catalyst, such as bis(diphenylphosphino)ferrocene]dichloropalladium(II), complex with dichloromethane or bis(di-tert-butyl(4-dimethylaminophenyl)phosphine)dichloropalladium(II) and a base (e.g., a carbonate base or cesium fluoride)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), followed by removal of the protecting group according to Scheme I can afford the resulting compounds of Formula (I).

Alternatively, selective coupling of halide 7-5 with 7-7, under standard Suzuki conditions (e.g., in the presence of a palladium catalyst, such as bis(diphenylphosphino)ferrocene]dichloropalladium(II), complex with dichloromethane or bis(di-tert-butyl(4-dimethylaminophenyl)phosphine)dichloropalladium(II) and a base (e.g., a carbonate base or cesium fluoride)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), can afford compound 7-8, which can be further reacted according to Scheme I to afford the resulting compounds of Formula (I).

Scheme VII.

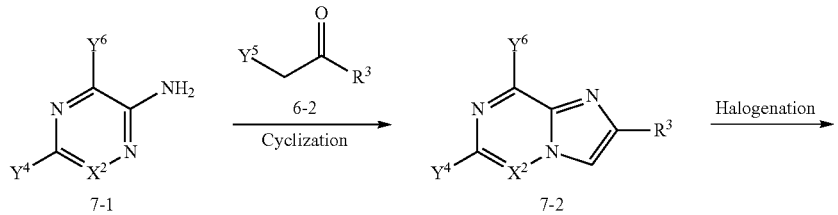

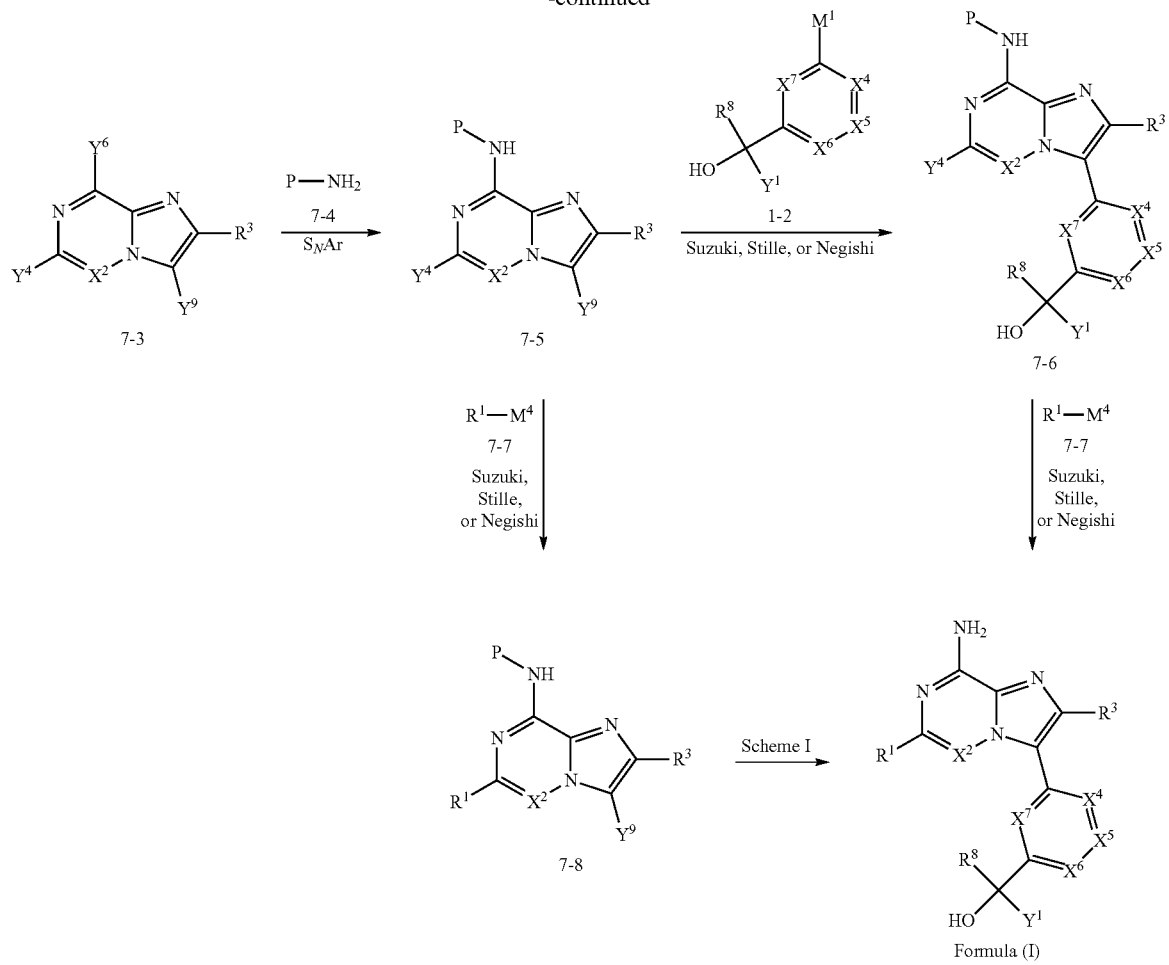

Compounds of Formula (I) can also be prepared as shown in Scheme VIII. For example, hetereoaromatic amine 8-1, where $Y^6$ is a halogen group, can be reacted with alpha-halo carbonyl derivatives 6-2 where $Y^5$ is a halogen (e.g., Cl or Br), to give heterocycle 8-2. Halogenation of heterocycle 8-2 with suitable reagents, such as N-chlorosuccinimide, N-bromosuccinimide, or N-iodosuccinimide, can give halide 8-3 where $Y^9$ is a halo group (e.g., Cl, Br, or I). Nucleophilic aromatic substitution of the halide 8-3 with amine 8-4 (e.g., NH₃ or p-methoxybenzylamine) can provide halide 8-5 with an optionally protected amine. Halide 8-5 can be further reacted according to Scheme I to afford the resulting compounds of Formula (I).

Scheme VIII.

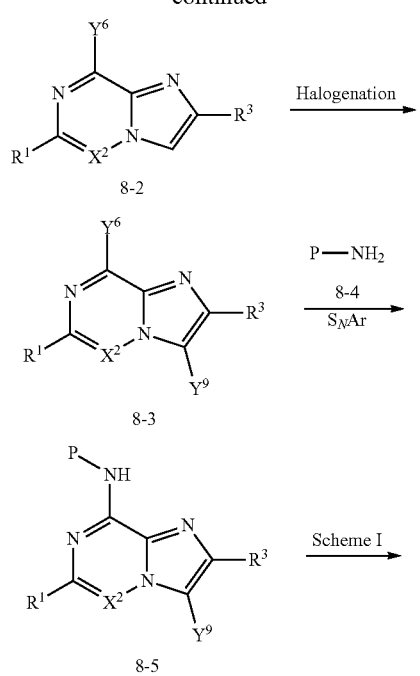

-continued

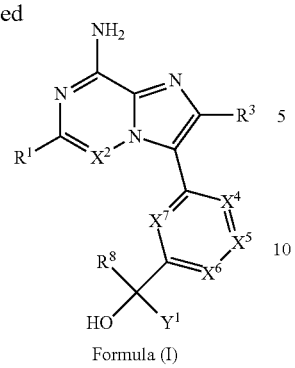

Formula (I)

Compounds of Formula (I) can also be prepared as shown in Scheme IX. Preparation of intermediate 9-5 from imidazole 9-1 can be achieved by methods analogous to those described in International App. No. WO 2016/183094, the disclosure of which is incorporated herein by reference in its entirety. Amination of 9-1 (e.g., $R^{12}$ can be alkyl) under standard conditions (e.g., in the presence of an $NH_2$-transfer agent such as chloramine, O-(diphenylphosphinyl)hydroxylamine, or O-(4-nitrobenzoyl)hydroxylamine and a base such as sodium hydride, lithium hexamethyldisilazane, or potassium tert-butoxide) and then condensation with an alkyl chloroformate $ClCO_2R^{13}$, where $R^{13}$ can be an alkyl group, under standard conditions (e.g., treatment with an appropriate base such as pyridine or sodium bicarbonate) can give compound 9-2. Cyclization of 9-2 in the presence of a suitable ammonia source (e.g., $NH_3$ or $NH_4OH$) can provide bicycle 9-3. The bicycle 9-3 can be halogenated with suitable reagents, such as N-chlorosuccinimide, N-bromosuccinimide, or N-iodosuccinimide, to give a halide 9-4 where $Y^9$ is a halo group (e.g., Cl, Br, or I). Dehydrative halogenation (e.g., by treating with a reagent such as $POCl_3$ or $POBr_3$) can afford compound 9-5, where $Y^4$ and $Y^6$ are each halogens (e.g., Cl or Br). Nucleophilic aromatic substitution of the halide of 9-5 with amine 9-6 (e.g., $NH_3$ or p-methoxybenzylamine) can provide intermediate 9-7 with an optionally protected amine.

Intermediate 9-7 can be selectively coupled with 1-2, where $M^1$ is a boronic acid, boronate ester, potassium trifluoroborate, or an appropriately substituted metal such as $Sn(Bu)_3$ or Zn, under standard Suzuki conditions (e.g., in the presence of a palladium catalyst, such as tetrakis(triphenylphosphine)palladium(0) and a base (e.g., a carbonate base)) or standard Stille conditions (e.g., in the presence of a palladium(0) catalyst, such as tetrakis(triphenylphosphine) palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give compound 9-8. Coupling of compound 9-8 with 9-9, where $M^4$ is a boronic acid, boronate ester, potassium trifluoroborate, or an appropriately substituted metal such as $Sn(Bu)_3$ or Zn, under standard Suzuki conditions (e.g., in the presence of a palladium catalyst, such as bis(diphenylphosphino)ferrocene]dichloropalladium(II), complex with dichloromethane or bis(di-tert-butyl(4-dimethylaminophenyl)phosphine)dichloropalladium(II) and a base (e.g., a carbonate base or cesium fluoride)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), followed by removal of the optional protecting group according to Scheme I can afford the resulting compounds of Formula (I), wherein $X^2$ is N.

Scheme IX.

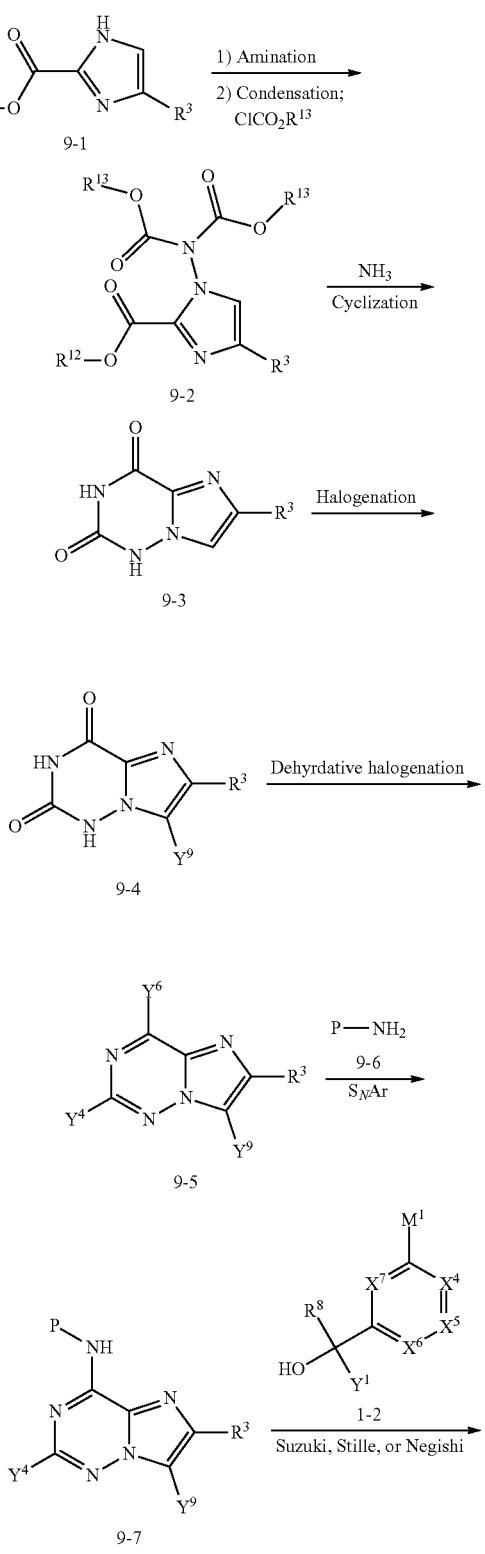

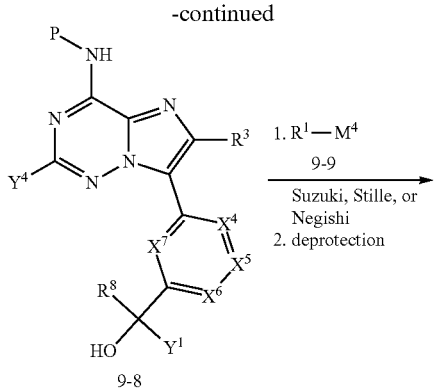

9-8

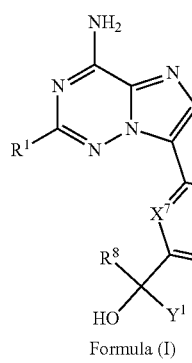

10-1

Intermediates for making compounds provided herein can be prepared as shown in Scheme X. Bis-halogenation of heteroaromatic amine 10-1 with suitable reagents, such as N-chlorosuccinimide, N-bromosuccinimide, Br$_2$, or N-iodosuccinimide can give halide 10-2 where $Y^4$ and $Y^6$ are each halogens (e.g., Cl, Br, or I). Nucleophilic aromatic substitution of halide 10-2 with amine 10-3 (e.g., NH$_3$ or p-methoxybenzylamine) can provide compound 10-4 with an optionally protected amine. Compounds provided herein can be synthesized from intermediates 10-2 and 10-4 using the methods described in Scheme VII and Scheme VI, respectively.

Intermediates for making compounds provided herein can be prepared as shown in Scheme XI. For example, ketone 11-1 can be converted to alkene 11-3 under standard olefination conditions such as reactions with ylides 11-2 (e.g., methylenetriphenylphosphorane). Alkene 11-3 can be converted to the fluorinated alcohol 11-4 with a reagent such as Selectfluor® and water. The W halo (e.g., Cl, Br, or I) or pseudohalo group (e.g., OTf or OMs) of alcohol 11-4 can be converted to an appropriate substituted metal 11-5 (e.g., M$^1$ is B(OH)$_2$, Bpin, BF$_3$K, Sn(Bu)$_3$, or Zn) under standard conditions (e.g., in the presence of a diboron reagent such as bis(pinacolato)diboron, a palladium catalyst, such as dichloro[bis(triphenylphosphoranyl)]palladium or bis(diphenylphosphino)ferrocene]dichloropalladium(II), complex with dichloromethane, and a base, such as potassium acetate). Compounds provided herein can be synthesized from intermediates 11-5 using the methods described in Scheme I.

Intermediates for making compounds provided herein can be prepared as shown in Scheme XII. Nucleophilic aromatic substitution of halide 12-1, where $Y^8$ is a halogen (e.g., Cl or Br), with ammonia can provide heteroaromatic amine 12-2. Halogenation of heteroaromatic amine 12-2 with suitable reagents, such as N-chlorosuccinimide, N-bromosuccinimide, Br$_2$, or N-iodosuccinimide, optionally in the presence of a base, such sodium bicarbonate or sodium carbonate, can give compound 12-3, where $Y^6$ is a halo group (e.g., Cl, Br, or I). Nucleophilic aromatic substitution of compound 12-3 with amine 12-4 (e.g., NH$_3$ or p-methoxybenzylamine) can provide compound 12-5 with an optionally protected amine. Compounds provided herein can be synthesized from intermediates 12-3 and 12-5 using the methods described in Scheme VII and Scheme VI, respectively.

Scheme XII.

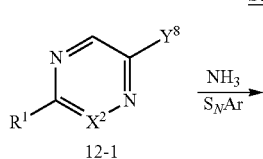

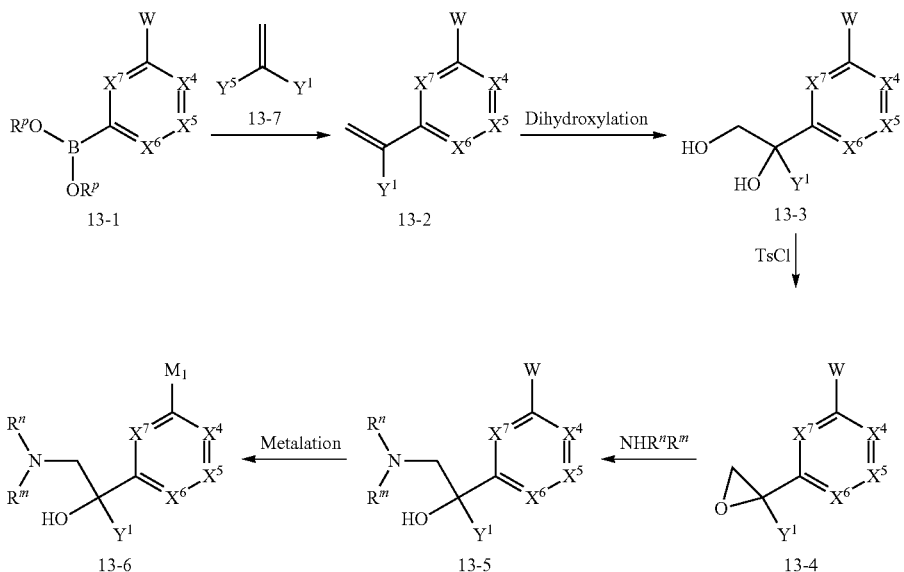

OMs) of alcohol 13-5 can be converted to an appropriate substituted metal 13-6 (e.g., $M^1$ is $B(OH)_2$, Bpin, $BF_3K$, $Sn(Bu)_3$, or Zn) under standard conditions (e.g., in the presence of a diboron reagent such as bis(pinacolato)diboron, a palladium catalyst, such as dichloro[bis(triphenylphosphoranyl)]palladium or bis(diphenylphosphino)ferrocene]dichloropalladium(II), complex with dichloromethane, and a base, such as potassium acetate). Compounds provided herein can be synthesized from intermediates 13-6 using the methods described in Scheme I.

Scheme XIII.

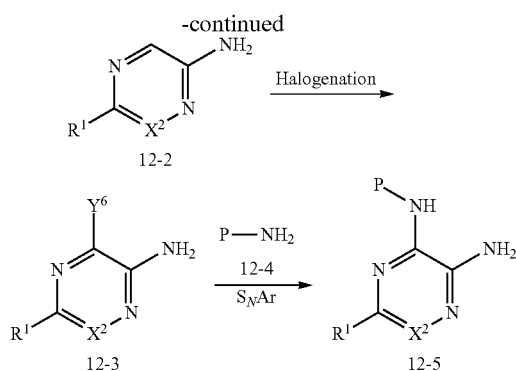

Intermediates for making compounds provided herein can be prepared as shown in Scheme XIII. For example, boron reagent 13-1 (e.g., $R^p$ can be alkyl) can be coupled with haloalkene 13-7 (where $Y^5$ is a halogen and $Y^1$ can be $CF_3$) to give alkene 13-2. Dihydroxylation of alkene 13-2 using reagents suitable for dihydroxylation (e.g., osmium tetroxide and a re-oxidant such as N-methylmorpholine-N-oxide, or AD-mix α or AD-mix β), can afford diol-containing intermediate 13-3. Diol 13-3 can be converted to epoxide 13-4 using tosyl chloride and a suitable base (e.g., triethylamine). Epoxide 13-4 can be treated with a variety of amines (e.g., $R^m$ and $R^n$ can be $R^b$ or $R^c$) to give amino alcohols 13-5. The W halo (e.g., Cl, Br, or I) or pseudohalo group (e.g., OTf or OMs) of alcohol 13-5 can be converted to an appropriate substituted metal 13-6 (e.g., $M^1$ is $B(OH)_2$, Bpin, $BF_3K$, $Sn(Bu)_3$, or Zn) under standard conditions (e.g., in the presence of a diboron reagent such as bis(pinacolato)diboron, a palladium catalyst, such as dichloro[bis(triphenylphosphoranyl)]palladium or bis(diphenylphosphino)ferrocene]dichloropalladium(II), complex with dichloromethane, and a base, such as potassium acetate). Compounds provided herein can be synthesized from intermediates 13-6 using the methods described in Scheme I.

Diol-containing compounds of Formula (I) can be prepared as shown in Scheme 13b. For example, boron reagent 13b-1 (e.g., $R^p$ can be alkyl) can be coupled with haloalkene 13b-2 (where $Y^5$ is a halogen and $Y^1$ can be $CF_3$) to give alkene 13b-3 (e.g., wherein $R^{10}$ and $R^{11}$ can each be $R^9$). Dihydroxylation with an appropriate oxidizing agent (e.g., osmium tetroxide and a re-oxidant such as N-methylmorpholine-N-oxide, or AD-mix α or AD-mix β) can afford diol 13b-4. The W halo (e.g., Cl, Br, or I) or pseudohalo group (e.g., OTf or OMs) of diol 13b-4 can be converted to an appropriate substituted metal 13b-5 (e.g., $M^1$ is $B(OH)_2$, Bpin, $BF_3K$, $Sn(Bu)_3$, or Zn) under standard conditions (e.g., in the presence of a diboron reagent such as bis(pinacolato)diboron, a palladium catalyst, such as dichloro[bis(triphenylphosphoranyl)]palladium or bis(diphenylphosphino)ferrocene]dichloropalladium(II), complex with dichloromethane, and a base, such as potassium acetate). Compounds provided herein can be synthesized from intermediates 13b-5 using the methods described in Scheme I or Scheme VI.

Scheme XIIIb.

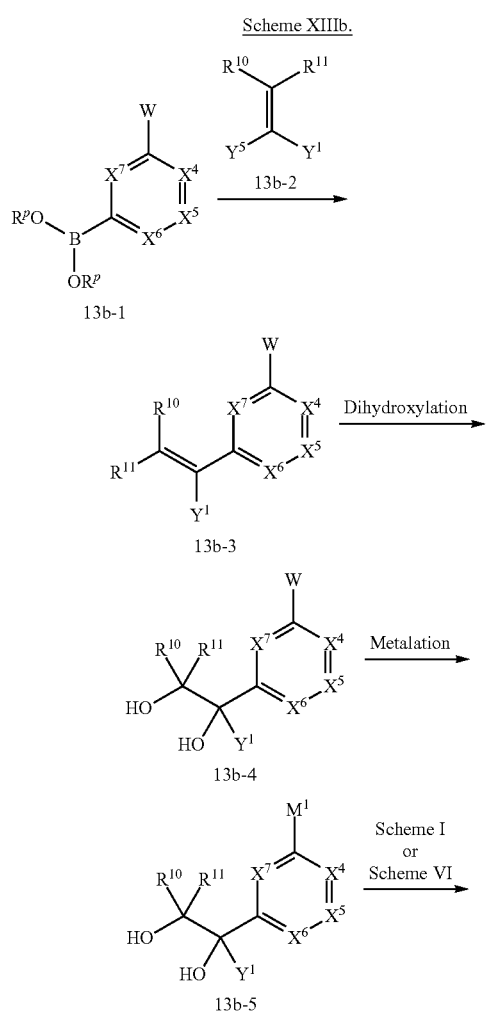

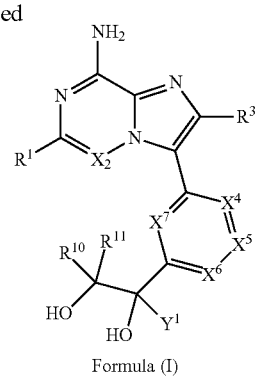

Formula (I)

Intermediates for making compounds provided herein can be prepared as shown in Scheme XIV. For example, nitrile 14-1 can be converted to ketone 14-2 (e.g., wherein $R^b$ can be $R^9$) with addition of a Grignard reagent. Ketone 14-2 can be brominated (e.g., $Br_2$) to give bromoketone 14-3. The bromine of 14-3 can be displaced with a variety of amines to give 14-4. Ketone 14-4 (e.g., wherein $R^m$ and $R^n$ can each be $R^k$) can be converted to tertiary alcohol 14-5 ($Y^1$=e.g., $CF_3$ or $CF_2H$) with silane 14-7 where $Z^1$ is a halogen (e.g., F or Br or H) under standard conditions (e.g., in the presence of TBAF or $PPh_3$ and DMPU). The W halo (e.g., Cl, Br, or I) or pseudohalo group (e.g., OTf or OMs) of alcohol 14-5 can be converted to an appropriate substituted metal 14-6 (e.g., $M^1$ is $B(OH)_2$, Bpin, $BF_3K$, $Sn(Bu)_3$, or Zn) under standard conditions (e.g., in the presence of a diboron reagent such as bis(pinacolato)diboron, a palladium catalyst, such as dichloro[bis(triphenylphosphoranyl)]palladium or bis(diphenylphosphino)ferrocene]dichloropalladium(II), complex with dichloromethane, and a base, such as potassium acetate). Compounds provided herein can be synthesized from intermediates 14-6 using the methods described in Scheme I.

Scheme XIV.

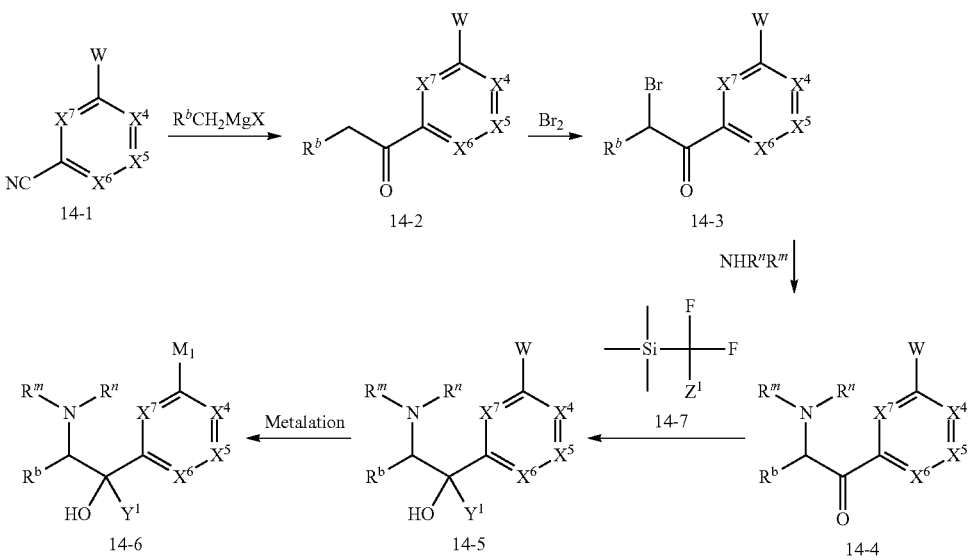

Intermediates for making compounds provided herein can be prepared as shown in Scheme XV. For example, aryl bishalide 15-1 where $Y^9$ is halogen (e.g., Cl, Br, or I) and W is halogen (e.g., Cl, Br, or I) or pseudohalogen (e.g., OTf or OMs) can be selectively lithiated and treated with Weinreb amide 15-5 to give ketone 15-2. Ketone 15-2 can be converted to tertiary alcohol 15-3 ($Y^1$=e.g., $CF_3$ or $CF_2H$) with silane 15-6 where $Z^1$ is a halogen (e.g., F or Br or H) under standard conditions (e.g., in the presence of TBAF or $PPh_3$ and DMPU). The W halo (e.g., Cl, Br, or I) or pseudohalo group (e.g., OTf or OMs) of alcohol 15-3 can be converted to an appropriate substituted metal 15-4 (e.g., $M^1$ is $B(OH)_2$, Bpin, $BF_3K$, $Sn(Bu)_3$, or Zn) under standard conditions (e.g., in the presence of a diboron reagent such as bis(pinacolato)diboron, a palladium catalyst, such as dichloro[bis(triphenylphosphoranyl)]palladium or bis(diphenylphosphino)ferrocene]dichloropalladium(II), complex with dichloromethane, and a base, such as potassium acetate). Compounds provided herein can be synthesized from intermediates 15-4 using the methods described in Scheme I.

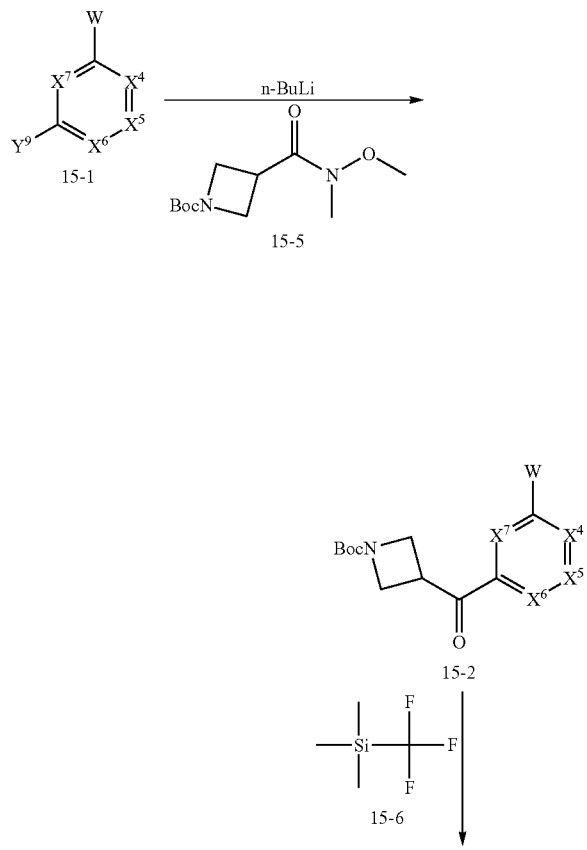

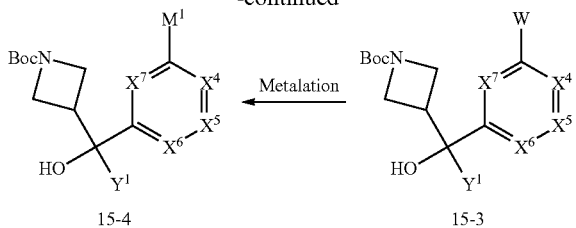

Compounds of Formula (I) can be prepared as shown in Scheme XVI. For example, ketone 4-4 can be reacted with a nucleophile (e.g., a Grignard reagent or alkyllithium reagent) to afford tertiary alcohol 16-1. The W halo (e.g., Cl, Br, or I) or pseudohalo group (e.g., OTf or OMs) of alcohol 16-1 can be converted to an appropriate substituted metal 16-2 (e.g., $M^1$ is $B(OH)_2$, Bpin, $BF_3K$, $Sn(Bu)_3$, or Zn) under standard conditions (e.g., in the presence of a diboron reagent such as bis(pinacolato)diboron, a palladium catalyst, such as dichloro[bis(triphenylphosphoranyl)]palladium or bis(diphenylphosphino)ferrocene]dichloropalladium(II), complex with dichloromethane, and a base, such as potassium acetate). Bicycle 16-6 (where $Y^9$ is halogen (e.g., Cl, Br, or I) or pseudohalogen (e.g., OTf or OMs)) can be coupled with 16-2 (where $M^1$ is a boronic acid, boronate ester, potassium trifluoroborate, or an appropriately substituted metal, such as $Sn(Bu)_3$ or Zn) under standard Suzuki conditions (e.g., in the presence of a palladium catalyst, such as tetrakis(triphenylphosphine)palladium(0) or [1,1'-bis(diphenylphosphino)ferrocene]dichloropalladium (II), complex with dichloromethane and a base (e.g., a carbonate base)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give compound 16-3. Deprotection of acetal 16-3 under acidic conditions (e.g., aqueous HCl) can give aldehyde 16-4. Aldehyde 16-4 can undergo reductive amination with a variety of amines (e.g., $R^m$ and $R^n$ can each be $R^k$) under standard conditions (e.g., methylamine) to give compounds 16-5.

Scheme XVI.

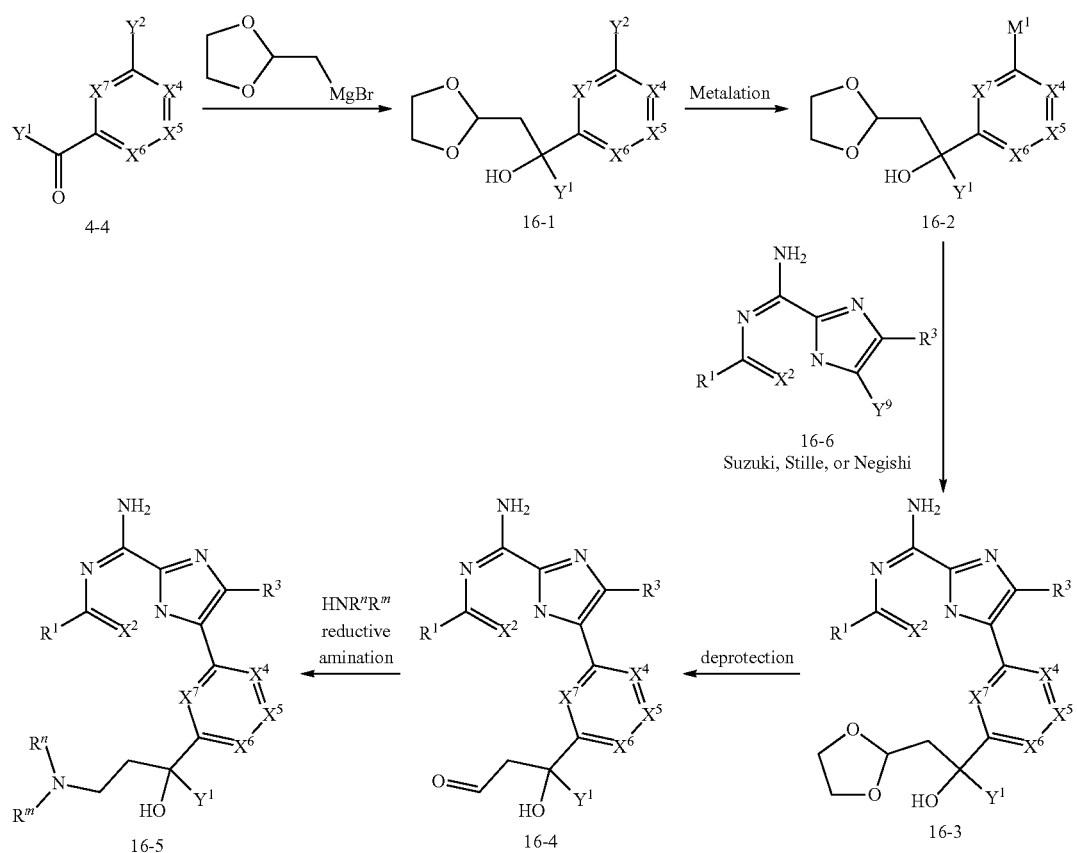

Compounds of Formula (I) can also be prepared as shown in Scheme XVII. For example, halide in 17-1 can be converted to ester 17-2 via carbonylation conditions (e.g., in the presence of a palladium catalyst, such as [1,1'-bis (diphenylphosphino)ferrocene]dichloropalladium, carbon monoxide, and an alcohol such as methanol). Ester 17-2 can be converted to amides 17-4 (e.g., wherein $R^m$ and $R^n$ can each be $R^a$) using amination conditions (e.g., AlMe$_3$) with appropriate amines. Alternatively, ester 17-2 can be hydrolyzed to acid 17-3 under standard conditions, (e.g., LiOH) and coupling of acid 17-3 with amines (e.g., methylamine) using standard amide coupling conditions (e.g., HATU or HOAt) can afford amides 17-4.

Scheme XVII.

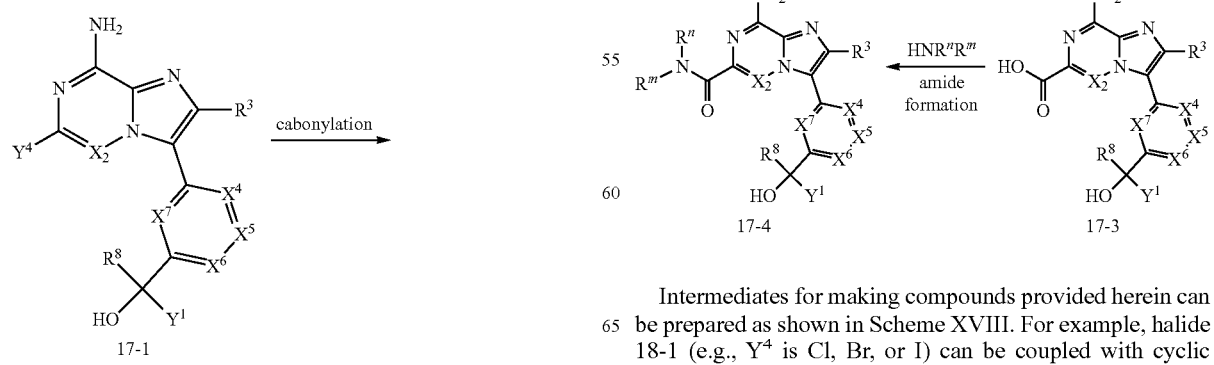

Intermediates for making compounds provided herein can be prepared as shown in Scheme XVIII. For example, halide 18-1 (e.g., $Y^4$ is Cl, Br, or I) can be coupled with cyclic alkene 18-2 where $M^2$ is a boronic acid, boronate ester, potassium trifluoroborate, or an appropriately substituted metal, such as Sn(Bu)$_3$ or Zn, under standard Suzuki conditions (e.g., in the presence of a palladium catalyst, such as tetrakis(triphenylphosphine)palladium(0) or [1,1'-bis(diphenylphosphino)ferrocene]dichloropalladium (II), complex with dichloromethane and a base (e.g., a carbonate base)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give compound 18-3. Cyclic alkene 18-3 can be converted to the fluorinated alcohol 18-4 with a reagent such as Selectfluor® and water. The W halo (e.g., Cl, Br, or I) or pseudohalo group (e.g., OTf or OMs) of alcohol 18-4 can be converted to an appropriate substituted metal 18-5 (e.g., M$^1$ is B(OH)$_2$, Bpin, BF$_3$K, Sn(Bu)$_3$, or Zn) under standard conditions (e.g., in the presence of a diboron reagent such as bis(pinacolato)diboron, a palladium catalyst, such as dichloro[bis(triphenylphosphoranyl)]palladium or bis(diphenylphosphino)ferrocene]dichloropalladium(II), complex with dichloromethane, and a base, such as potassium acetate). Compounds provided herein can be synthesized from intermediates 18-5 using the methods described in Scheme I.

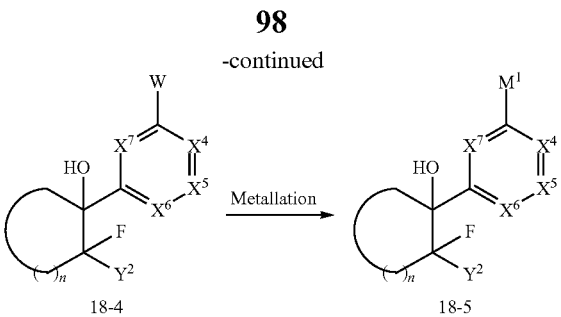

Compounds of Formula (I) can also be prepared as shown in Scheme XIX. Compound 19-1, where Y$^4$ is a halogen (e.g., Cl, Br, or I), can be coupled with 19-2, where M$^5$ is a boronic acid, boronate ester, potassium trifluoroborate, or an appropriately substituted metal such as Sn(Bu)$_3$, under standard Suzuki conditions (e.g., in the presence of a palladium catalyst, such as [1,1'-bis(diphenylphosphino)ferrocene]dichloropalladium(II), complex with dichloromethane and a base (e.g., a carbonate base) or standard Stille conditions (e.g., in the presence of a palladium(0) catalyst, such as tetrakis(triphenylphosphine)palladium(0)) to give compound 19-3, where R$^{b1}$, R$^{b2}$, and R$^{b3}$ can be independently H or R$^b$. Cyclopropanation in the presence of diazo compound 19-4, where R$^{14}$ is an alkyl group (e.g., ethyl or tert-butyl) and R$^{b4}$ can be H or R$^b$, and optionally an appropriate catalyst (e.g., Rh$_2$(OAc)$_4$, Rh$_2$(S-DOSP)$_4$, Cu(OTf)$_2$, or cobalt(II) meso-tetraphenylporphine) can give compound 19-5. Ester 19-5 can be hydrolyzed to acid 19-6 under standard conditions (e.g., aqueous NaOH), and coupling of acid 19-6 with amines 19-7, where R$^{c1}$ and R$^{c2}$ can be independently R$^c$, using standard amide coupling conditions (e.g., HATU or HOAt in the presence of an amine base such as N,N-diisopropylethylamine) can afford amides 19-8.

Alternatively, reduction of ester 19-5 with a suitable reagent (e.g., LiAlH$_4$ or LiAlD$_4$) can afford alcohols 19-9, where V$^1$ can be H or D.

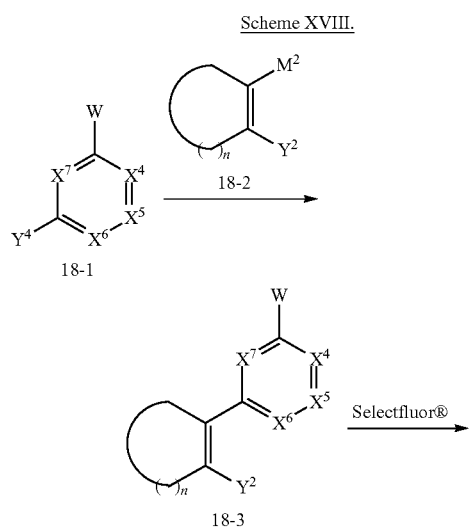

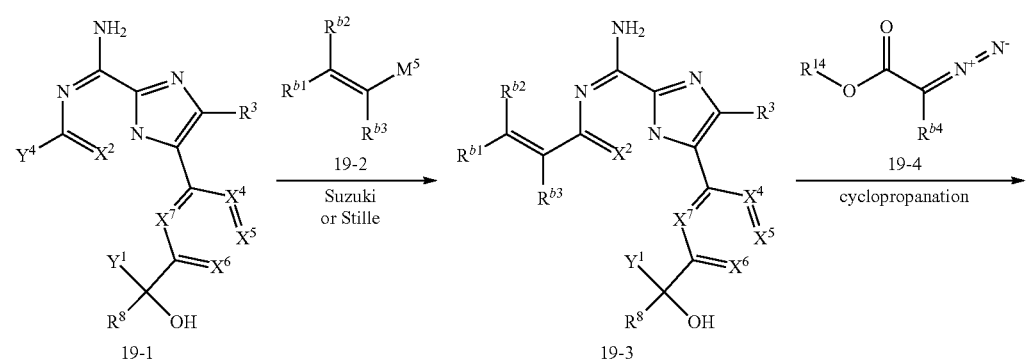

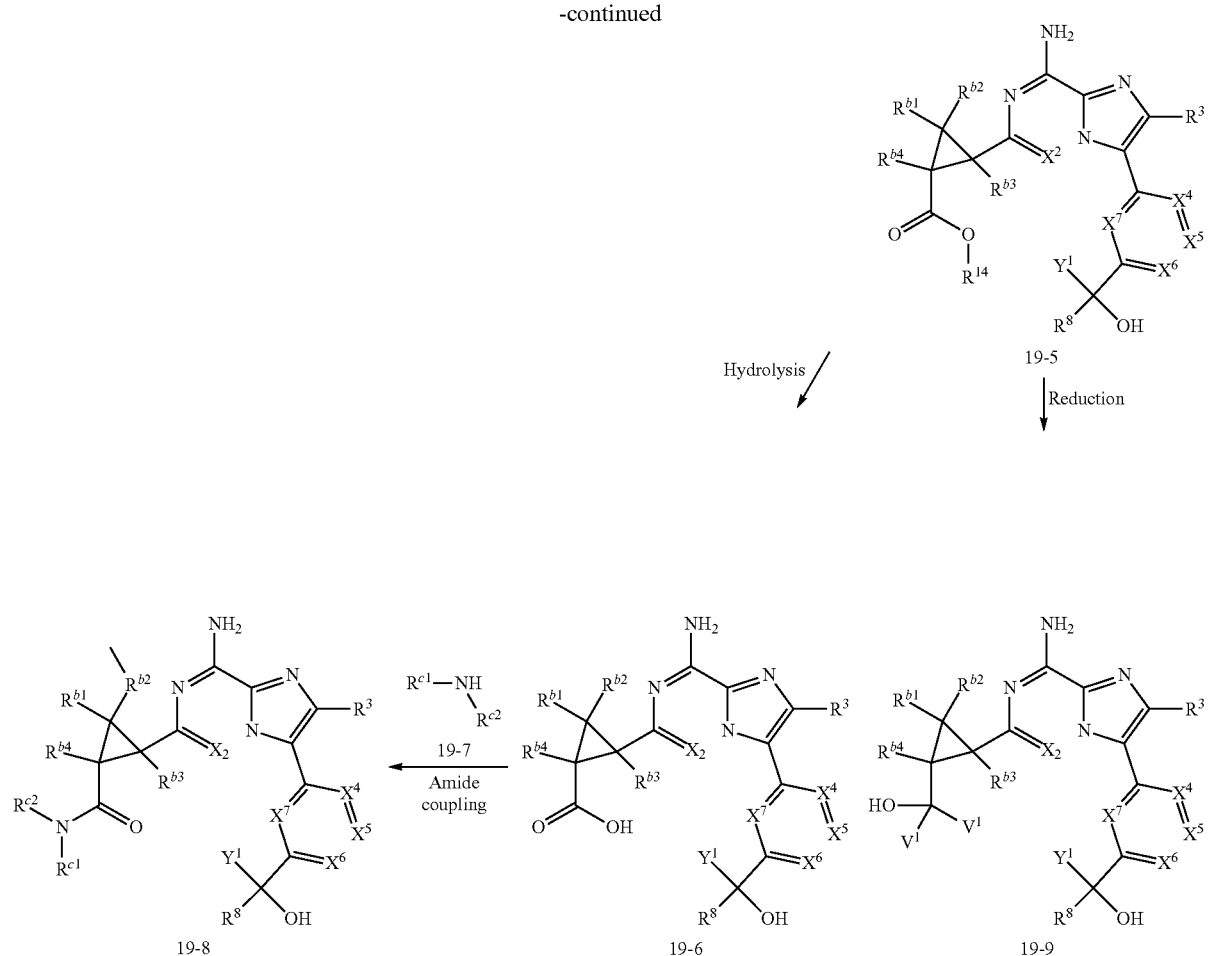

Compounds of Formula (I) can also be prepared as shown in Scheme XX. The alcohol moiety of general structure 20-1 can be protected with a suitable protecting group ($P^2$), such as a silyl protecting group (e.g. tert-butyldimethylsilyl) to afford the protected alcohol 20-2. The nitrogen of the imidazo[1,2-a]pyrazin-8-amine core can be protected with a suitable protecting group, such as a mono- or di-Boc group to afford 20-3. The C—N bond of 20-4 (e.g., wherein $R^m$ and $R^n$ can each be W) could be constructed using metal catalyzed cross-coupling conditions, such as Buchwald-Hartwig coupling conditions (Buchwald, S. L., Ruiz-Castillo, P. *Chem. Rev.* 2016, 116, 12564.; Messaoudi, S., et al. *ACS Catal.* 2015, 5 (2), 1386.). For example, 20-3 could be coupled with an amine, aniline, heteroaniline, or amide in the presence of a base ($Cs_2CO_3$, NaOt-Bu, etc.) and a catalyst, such as palladium in combination with a Buchwald ligand or the use of a Buchwald pre-catalyst system. Following C—N coupling, the protecting groups can be removed using standard conditions either sequentially or in one pot, such as TFA/DCM or 4 N HCl in 1,4-dioxane for removal of a silyl protected alcohol and Boc-protected heteroaniline.

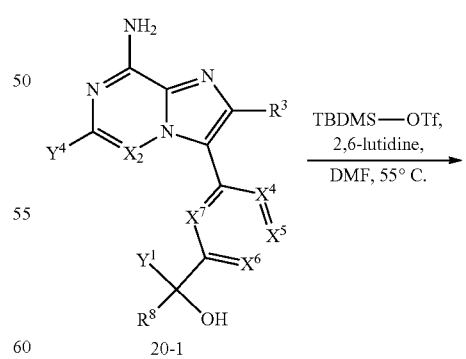

Scheme XX.

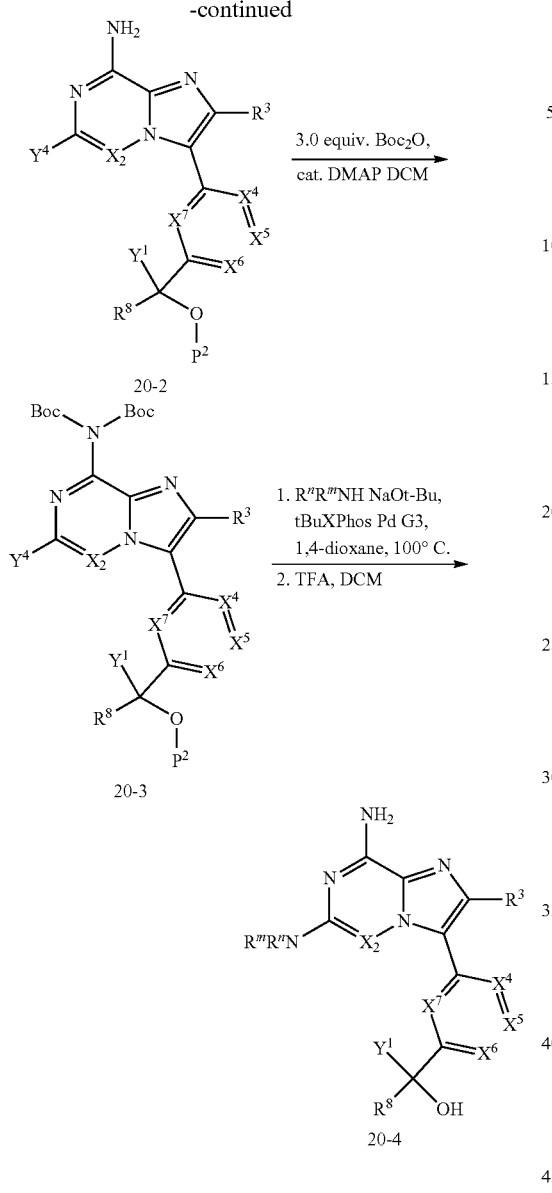

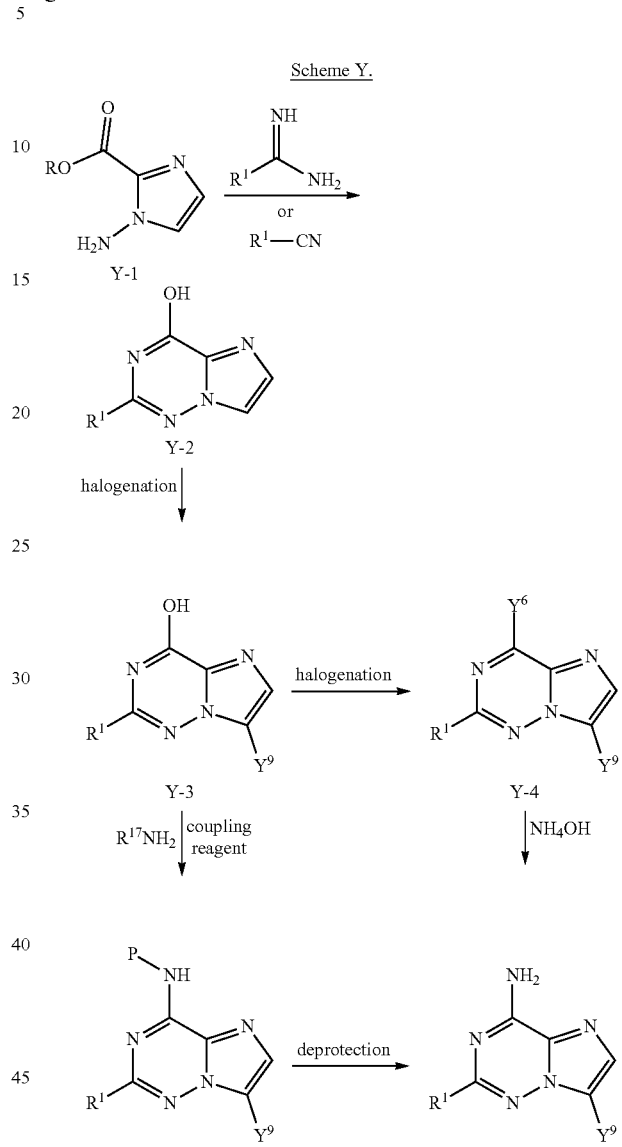

Intermediates 1-1 (Scheme I) useful for preparing compounds of Formula (I), such as wherein $X^2$ is N and of varying substitution at $R^1$, can be prepared via the method shown in Scheme Y. Condensation of Y-1 with an amidine at elevated temperature (e.g., 80 to 95° C.) in a suitable solvent (e.g., EtOH) affords bicyclic intermediate Y-2. Alternatively, Y-1 can be treated with a nitrile and acid (e.g., HCl) in a suitable solvent (e.g., dioxane) at elevated temperature (e.g., 100 to 110° C.) to afford Y-2. In some cases of cyclization the use of nitriles requires that the reaction mixture is made basic in the second step to facilitate cyclization. Intermediate Y-2 can be halogenated with suitable reagents, such as N-chlorosuccinimide, N-bromosuccinimide, $Br_2$ or N-iodosuccinimide to afford halide Y-3 where $Y^9$ is a halo group (e.g., Cl, Br, or I). Dehydrative halogenation (e.g., by treating with a reagent such as $POCl_3$ or $POBr_3$) can afford compound Y-4 where $Y^6$ is a halogen (e.g., Cl or Br). Nucleophilic aromatic substitution of the halide of Y-4 with ammonia (e.g., using aq. $NH_4OH$ solution) can provide intermediates Y-5, useful for preparing compounds of Formula (I). Alternatively, intermediate Y-3 can be condensed with an amine $R^{17}NH_2$ (e.g., p-methoxybenzylamine) with a coupling reagent (e.g., BOP) to give intermediate Y-6. Deprotection of Y-6 (e.g., using TFA) can give Y-5.

Alternatively, intermediates 1-1 (Scheme I) useful for preparing compounds of Formula (I), such as wherein $X^2$ is N and of varying substitution at $R^1$, can be prepared via the method shown in Scheme Y-B. Condensation of Y-7 with an amidine at elevated temperature (e.g., 80 to 95° C.) in a suitable solvent (e.g., EtOH) affords bicyclic intermediate Y-8. Alternatively, Y-7 can be treated with a nitrile and acid (e.g., HCl) in a suitable solvent (e.g., dioxane) at elevated temperature (e.g., 100 to 110° C.) to afford Y-8. In some cases of cyclization the use of nitriles requires that the reaction mixture is made basic in the second step to facilitate cyclization. Intermediate Y-8 can be halogenated with suitable reagents, such as N-chlorosuccinimide, N-bromosuccinimide, $Br_2$ or N-iodosuccinimide to afford intermediates Y-5, useful for preparing compounds of Formula (I).

Scheme Y-B.

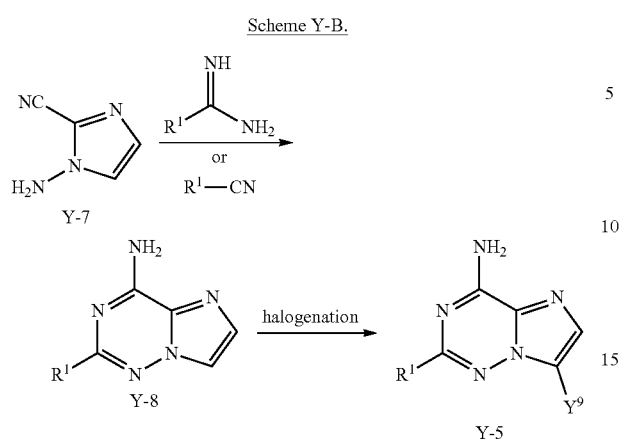

Substituents at $R^3$ may be introduced following the procedure shown in Scheme Z. Intermediate Z-1 can be halogenated with suitable reagents, such as N-chlorosuccinimide, N-bromosuccinimide, $Br_2$ or N-iodosuccinimide to afford halide Z-2 where $Y^9$ is a halo group (e.g., Cl, Br, or I). The $Y^9$ halo group of Z-2 can be coupled to $R^3$-M (Z-3) (e.g., M is $B(OH)_2$, Bpin, $BF_3K$, $Sn(Bu)_3$, Zn or Al) under standard conditions for Suzuki, Stille, Negishi and the like, in the presence of a palladium catalyst, and where appropriate, a base, to afford compounds of Formula (I).

Scheme Z.

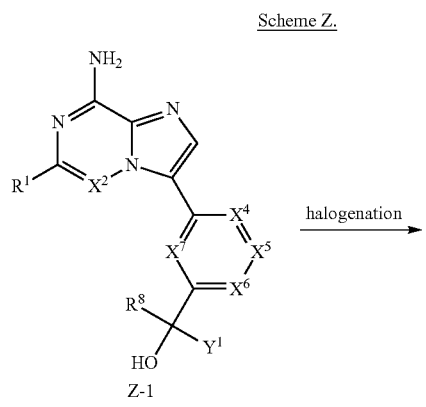

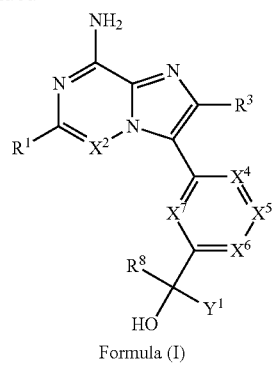

Formula (I)

Substituents at $R^4$ may be introduced following the procedure outlined in Scheme Q. Intermediate Q-1 can be selectively coupled with Q-2 bearing a halogen substituent $Y^4$ (e.g., Cl) to afford intermediate Q-3. The $Y^4$ halo group of Q-3 can be coupled to $R^4$-M (Q-4) (e.g., M is $B(OH)_2$, Bpin, $BF_3K$, $Sn(Bu)_3$, Zn or Al) under standard conditions for Suzuki, Stille, Negishi and the like, in the presence of a palladium catalyst and where appropriate, a base, to afford compounds of Formula (I), wherein $X^4$ is $CR^4$.

Scheme Q.

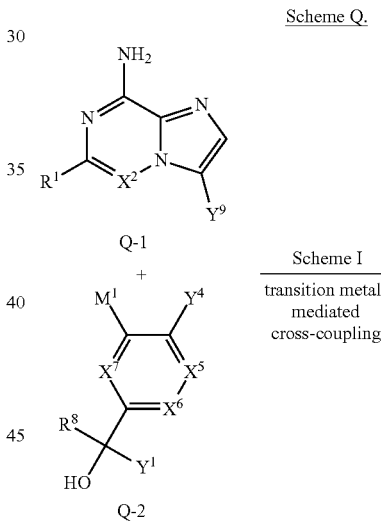

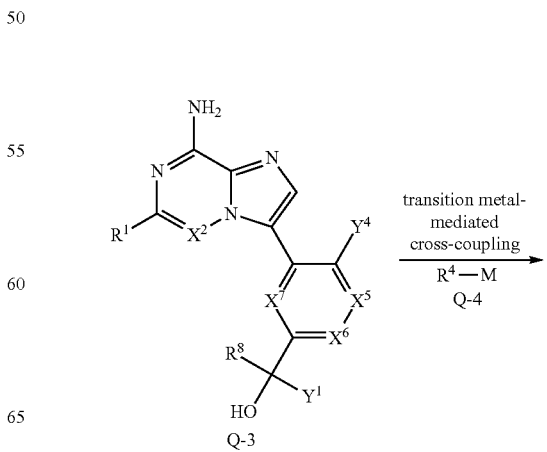

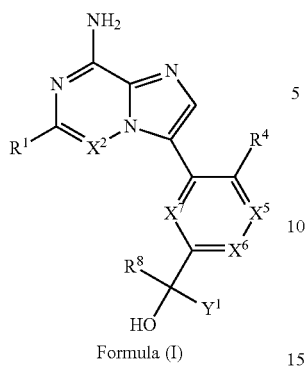

Formula (I)

Intermediates for making compounds provided herein can be prepared as shown in Scheme Y1. Suitable starting materials Y1-1, where $Y^8$ is a halogen (e.g., Cl, Br, or I) or pseudohalogen (e.g., OTf or OMs), can be converted with silane Y1-2 where $Z^1$ is a halogen (e.g., F or Br or H) under standard conditions (e.g., in the presence of TBAF or PPh$_3$ and DMPU) to give secondary alcohol Y1-3 (e.g., $Y^1$ is CF$_3$ or CHF$_2$). Oxidation of secondary alcohol Y1-3 under standard conditions (e.g., Swern oxidation or Dess-Martin oxidation) can give ketone Y1-4. Ketone Y1-4 can be converted to cyanohydrin Y1-5 under standard conditions (e.g., in the presence of KCN, TMSCN, and 18-crown-6). Cyanohydrin Y1-5 can be converted to carboxylic acid Y1-6 under standard acidic hydrolysis conditions (e.g., HCl or HBr in water (*Org. Syn. Coll. Vol.* 1 1941, 289 and 131)) or standard basic hydrolysis conditions (e.g., NaOH in water (*Org. Syn. Coll. Vol.* 1 1941, 321)). Carboxylic acid Y1-6 can be coupled with amine Y1-7 under standard amide formation conditions (e.g., conversion of acid Y1-6 to the acid chloride (e.g., with oxalyl chloride) and condensing with amine Y1-7) to give amide Y1-8. Alternatively, cyanohydrin Y1-5 can be converted directly to primary amide Y1-8 (where $R^k$ is H) with concentrated HCl and HCl gas (*J. Med. Chem.* 2003, 46, 2494-2501). The $Y^8$ group of Y1-8 can be converted to an appropriately substituted metal Y1-9 (e.g., $M^1$ is B(OH)$_2$, Bpin, BF$_3$K, Sn(Bu)$_3$, or Zn) under standard conditions (e.g., in the presence of a diboron reagent such as bis(pinacolato)diboron, a palladium catalyst, such as dichlorobis(triphenylphosphine)palladium(II) or [1,1'-bis(diphenylphosphino)ferrocene]dichloropalladium(II) complex with dichloromethane, and a base, such as potassium acetate). Compounds provided herein can be synthesized from intermediates Y3-6 using the methods described in the schemes herein (e.g., Scheme I).

Scheme Y1.

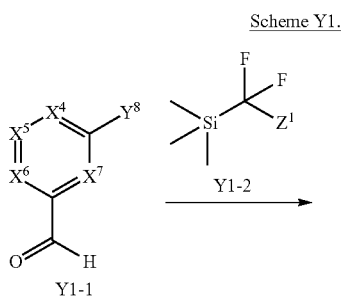

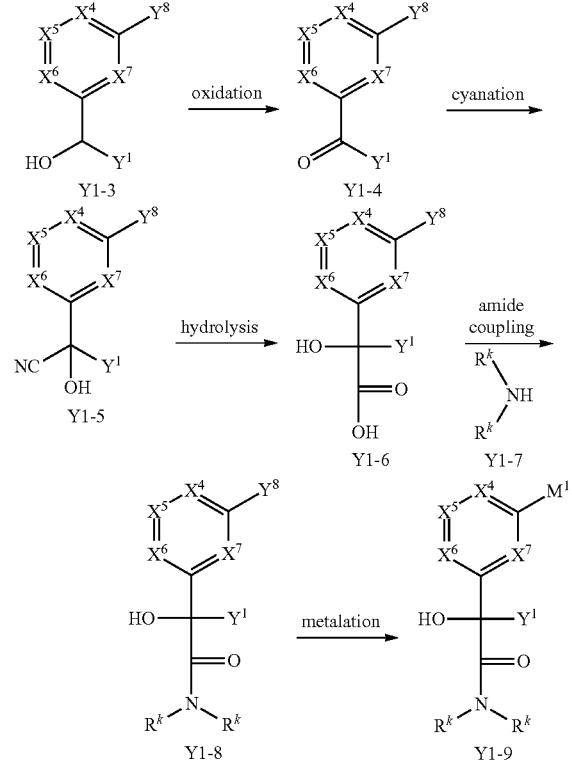

Compounds of Formula (I) can also be prepared as shown in Scheme Y2. Cyanohydrin Y1-5 (from Scheme Y1) can be converted to aldehyde Y2-1 upon reduction (e.g., in the presence of a reducing agent such as DIBAL-H (for a review see *Synthesis* 1975, 10, 617-630)). Aldehyde Y2-1 can be converted to amine Y2-3 under standard reductive amination conditions with amine Y2-2 and an appropriate reducing agent (e.g., sodium borohydride, sodium triacetoxyborohydride, or sodium cyanoborohydride). Alternatively, cyanohydrin Y1-5 can be reduced directly to amine Y2-3 where $R^k$ is hydrogen under standard conditions (e.g., LiAlH$_4$ in Et$_2$O). The $Y^8$ group of Y2-3 can be converted to an appropriately substituted metal Y2-4 (e.g., $M^1$ is B(OH)$_2$, Bpin, BF$_3$K, Sn(Bu)$_3$, or Zn) under standard conditions (e.g., in the presence of a diboron reagent such as bis(pinacolato)diboron, a palladium catalyst, such as dichlorobis(triphenylphosphine)palladium(II) or [1,1'-bis(diphenylphosphino)ferrocene]dichloropalladium(II) complex with dichloromethane, and a base, such as potassium acetate) and then coupled to Y2-5 where $Y^9$ is a halogen (e.g., Cl, Br, or I) or pseudohalogen (e.g., OTf or OMs) under standard Suzuki conditions (e.g., in the presence of a palladium catalyst, such as tetrakis(triphenylphosphine)palladium(0), dichlorobis(triphenylphosphine)palladium(II), or [1,1'-bis(diphenylphosphino)ferrocene]dichloropalladium(II) complex with dichloromethane, and a base (e.g., a carbonate base, such as sodium carbonate or potassium carbonate)) or standard Stille conditions (e.g., in the presence of a palladium(0) catalyst, such as tetrakis(triphenylphosphine)palladium(0)), or standard Negishi conditions (e.g., in the presence of a palladium(0) catalyst, such as tetrakis(triphenylphosphine)palladium(0) or [1,1'-bis(diphenylphosphino)ferrocene]dichloropalladium(II)) to give Y2-6. Amine Y2-6 can be coupled with carboxylic acid Y2-7 under standard amide formation conditions (e.g., in the presence of a coupling reagent, such as HATU, and amine, such as diisopropylethylamine) to give compounds of Formula (I).

Scheme Y2.

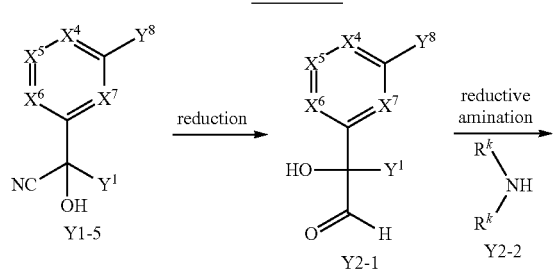

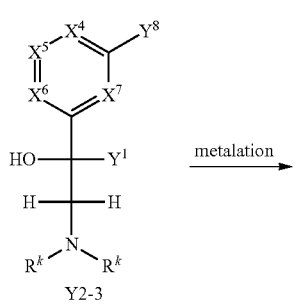

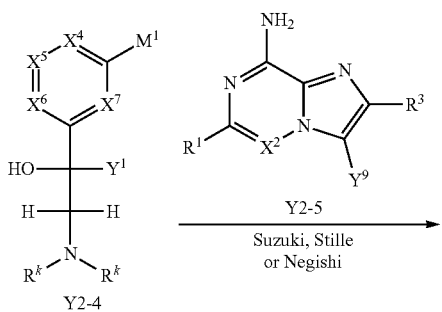

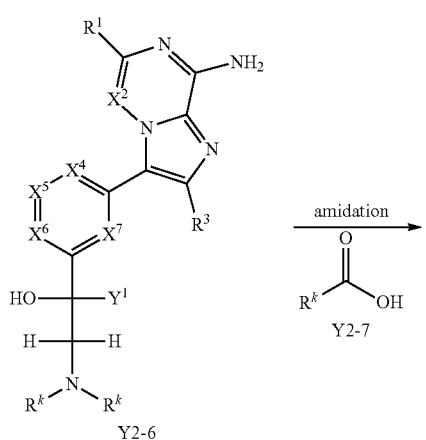

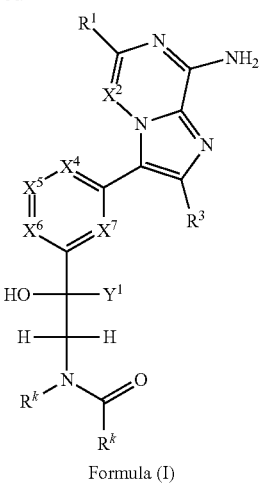

Formula (I)

Intermediates for making compounds provided herein can be prepared as shown in Scheme Y3. Keto-ester Y3-1 can be halogenated with suitable reagents, such as N-chlorosuccinimide, N-bromosuccinimide, or N-iodosuccinimide to give Y3-2 where W is a halo group (e.g., Cl, Br, or I). Ketone Y3-2 can be converted to tertiary alcohol Y3-4 with silane Y3-3 where $Z^1$ is a halogen (e.g., F or Br or H) under standard conditions (e.g., in the presence of TBAF or PPh$_3$ and DMPU). In some instances $Z^1$ can be H wherein a CHF$_2$ group ($Y^1$) can be formed. Ester Y3-4 can be converted to primary amide (Y3-5, $R^k$ is hydrogen) under standard conditions (e.g., ammonia in methanol and optionally a base, such as cesium carbonate) or secondary and tertiary amides (Y3-5) under standard conditions (e.g., AlMe$_3$ and an appropriate amine NHR$^k$R$^k$, wherein each $R^k$ can be $R^a$). The W group of Y3-5 can be converted to an appropriately substituted metal Y3-6 (e.g., $M^1$ is B(OH)$_2$, Bpin, BF$_3$K, Sn(Bu)$_3$, or Zn) under standard conditions (e.g., in the presence of a diboron reagent such as bis(pinacolato)diboron; a base, such as potassium acetate; a palladium catalyst, such as tris(dibenzylideneacetone)dipalladium(0); and optionally a ligand, such as 2-dicyclohexylphosphino-2',4',6'-triisopropylbiphenyl). Compounds provided herein can be synthesized from intermediates Y3-6 using the methods described in the schemes herein (e.g., Scheme I).

Scheme Y3.

-continued

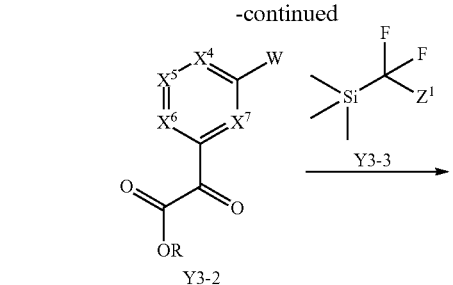

Y3-2

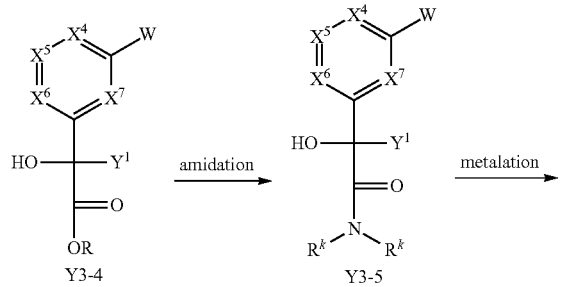

Y3-4 → Y3-5

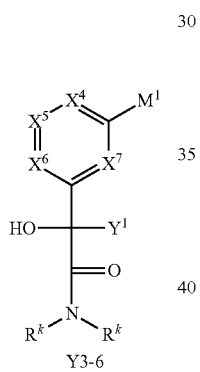

Y3-6

Intermediates for making compounds provided herein can be prepared as shown in Scheme XXI. Diol 13-3 where W is a halogen (e.g., Cl, Br, or I) or pseudohalogen (e.g., OTf or OMs) can be oxidized under standard conditions (e.g., in the presence of a transition metal catalyst, such as platinum on carbon in the presence of an oxygen source, such as air) to give α-hydroxy carboxylic acid 21-1. Coupling of acid 21-1 with amine 21-2 where $R^{a1}$ and $R^{a2}$ can be independently W using standard amide coupling conditions (e.g., formation of the acid chloride with an appropriate reagent, such as oxalyl chloride, and subsequent in situ quenching with amine 21-2) can afford amide 21-3. The W group of 21-3 can be converted to an appropriately substituted metal 21-4 (e.g., $M^1$ is $B(OH)_2$, Bpin, $BF_3K$, $Sn(Bu)_3$, or Zn) under standard conditions (e.g., in the presence of a diboron reagent such as bis(pinacolato)diboron; a base, such as potassium acetate; a palladium catalyst, such as tris(dibenzylideneacetone)dipalladium(0); and optionally a ligand, such as 2-dicyclohexylphosphino-2',4',6'-triisopropylbiphenyl). Compounds provided herein can be synthesized from intermediates 21-4 using the methods described in the schemes herein (e.g., Scheme I).

Scheme XXI.

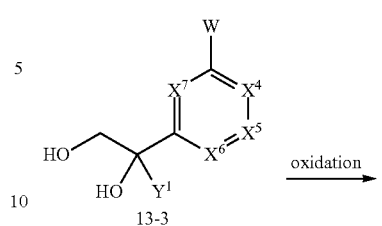

13-3 oxidation →

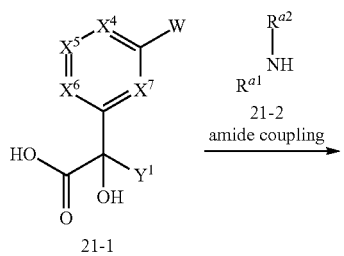

21-1 amide coupling →

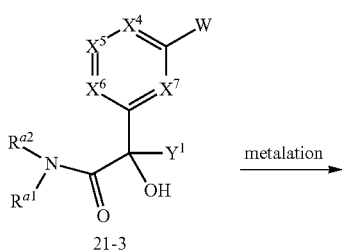

21-3 metalation →

21-4

Compounds of Formula (I) can also be prepared as shown in Scheme XXII. Hydrolysis of amide 22-1 where $R^{a1}$ and $R^{a2}$ can be independently W under standard conditions (e.g., heating in the presence of aqueous HCl) can give acid 22-2. Coupling of acid 22-2 with amine 22-3 where $R^{a3}$ and $R^{a4}$ can be independently $R^a$ using standard amide coupling conditions (e.g., formation of the acid chloride with an appropriate reagent, such as oxalyl chloride, and subsequent in situ quenching with amine 22-3) can afford amide 22-4.

Scheme XXII.

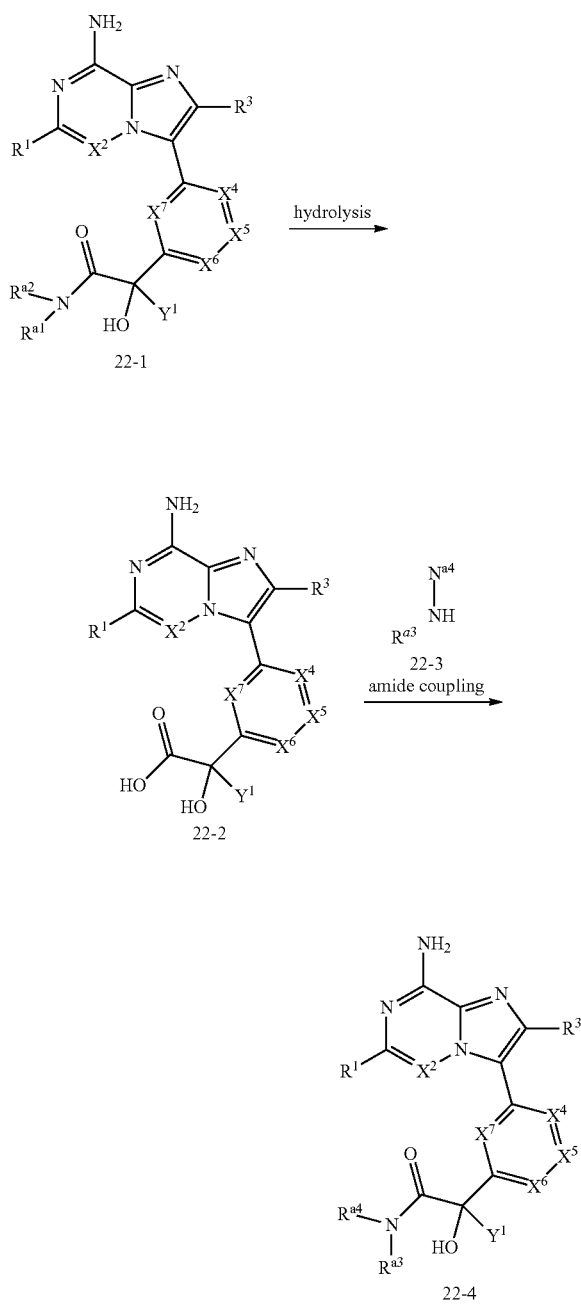

Compounds of Formula (I) can also be prepared as shown in Scheme XXIII. Ketone 23-1 where W is halogen (e.g., Cl, Br, or I) or pseudohalo group (e.g., OTf or OMs) can be converted to alcohol 23-3 via standard Reformatsky conditions (e.g., in the presence of a metal, such as zinc or indium, and an ahaloester 23-2 where $W^2$ is halogen (e.g., Cl, Br, or I) and W is a $C_{1-6}$ alkyl group). The W halo (e.g., Cl, Br, or I) or pseudohalo group (e.g., OTf or OMs) of alcohol 23-3 can be converted to an appropriate substituted metal 23-4 (e.g., $M^1$ is $B(OH)_2$, Bpin, $BF_3K$, $Sn(Bu)_3$, or Zn) under standard conditions (e.g., in the presence of a diboron reagent such as bis(pinacolato)diboron, a palladium catalyst, such as dichloro[bis(triphenylphosphoranyl)]palladium or bis(diphenylphosphino)ferrocene]dichloropalladium(II), complex with dichloromethane, and a base, such as potassium acetate). Optionally protected (e.g., P=acetyl, tert-butoxycarbonyl, or p-methoxybenzyl) bicycle 6-5 can be coupled with metal 23-4 under standard Suzuki conditions (e.g., in the presence of a palladium catalyst, such as tetrakis(triphenylphosphine)palladium(0) or [1,1'-bis(diphenylphosphino)ferrocene]dichloropalladium (II), complex with dichloromethane and a base (e.g., a carbonate base)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis (triphenylphosphine)palladium(0) or [1,1'-bis (diphenylphosphino)ferrocene]dichloropalladium (II)), to give compound 23-5. In some cases, subsequent hydrolysis of the ester (—$CO_2R^z$) under standard conditions (e.g., in the presence of a base such as sodium hydroxide or an acid such as HCl or trifluoracetic acid) may be required to give acid 23-5. Coupling of acid 23-5 with amines 23-6 where $R^{a5}$ and $R^{a6}$ can be independently $R^a$ using standard amide coupling conditions (e.g., in the presence of a peptide coupling reagent, such as N,N,N',N'-tetramethyl-O-(7-azabenzotriazol-1-yl)uronium hexafluorophosphate, and an amine base, such as N,N-diisopropylethylamine) can afford amide 23-7. Compound 23-7 can be coupled with metal 23-8 under standard Suzuki conditions (e.g., in the presence of a palladium catalyst, such as tetrakis(triphenylphosphine)palladium(0) or [1,1'-bis(diphenylphosphino)ferrocene]dichloropalladium (II), complex with dichloromethane and a base (e.g., a carbonate base)) or standard Stille conditions (e.g., in the presence of a palladium(0) catalyst, such as tetrakis (triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give compound 23-9.

Alternatively, compound 23-5 can be coupled with metal 23-8 under standard Suzuki conditions (e.g., in the presence of a palladium catalyst, such as tetrakis(triphenylphosphine) palladium(0) or [1,1'-bis(diphenylphosphino)ferrocene]dichloropalladium (II), complex with dichloromethane and a base (e.g., a carbonate base)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give compound 23-10. Coupling of acid 23-10 with amine 23-6 using standard amide coupling conditions (e.g., in the presence of a peptide coupling reagent, such as N,N,N',N'-tetramethyl-O-(7-azabenzotriazol-1-yl)uronium hexafluorophosphate, and an amine base, such as N,N-diisopropylethylamine) can afford amide 23-9.

After coupling, optionally chosen protecting groups can be removed under conditions suitable for their removal that are also compatible with the functionality present in 23-9 (e.g., exposure to aqueous HCl or trifluoroacetic acid) to afford the resulting compound 23-10.

Scheme XXIII.
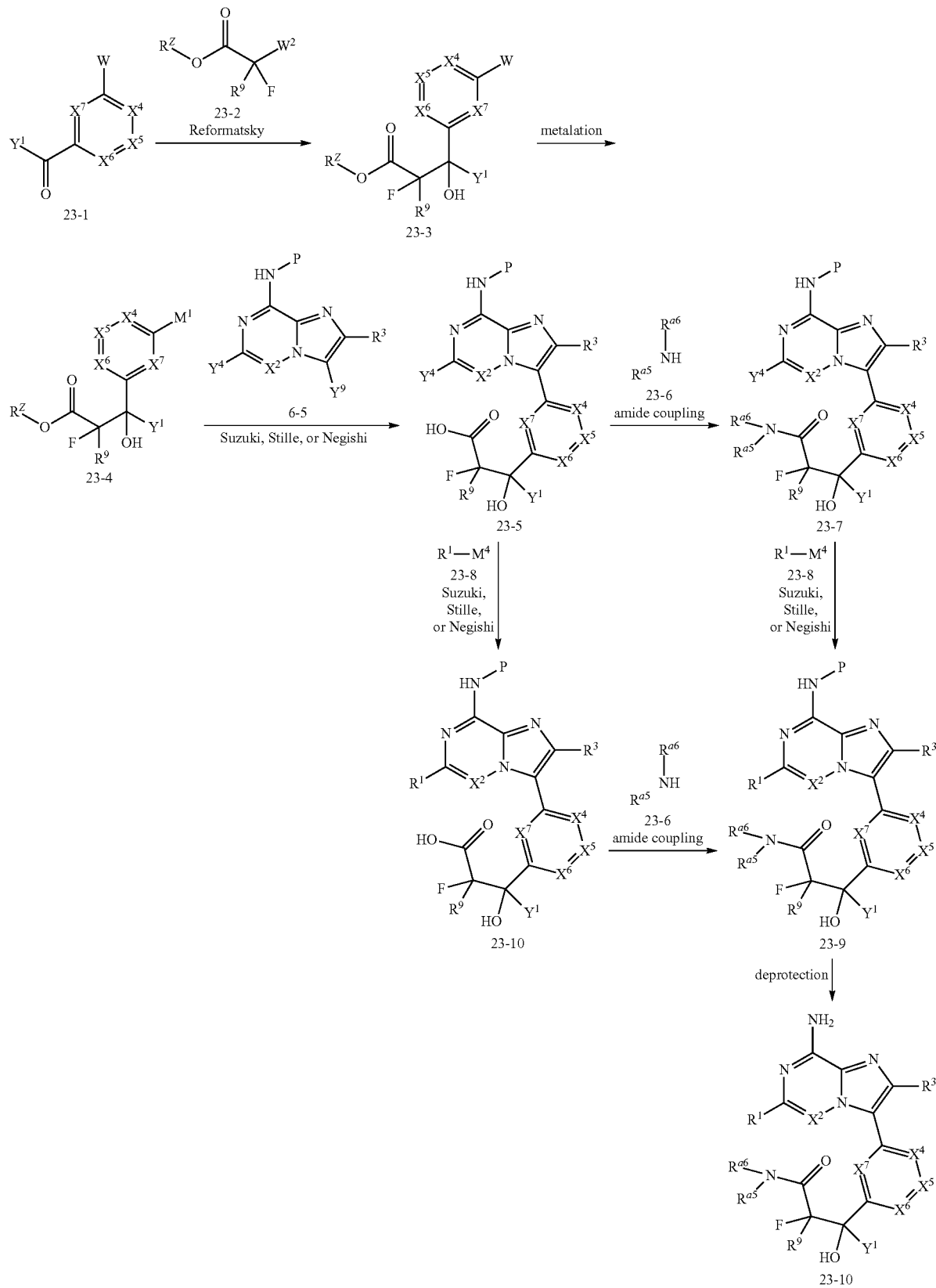

Intermediates for making compounds provided herein can be prepared as shown in Scheme XXIV. Ester 23-3 where W is a halogen (e.g., Cl, Br, or I) or pseudohalogen (e.g., OTf or OMs) can be reduced with a suitable reagent (e.g., NaBH$_4$ or NaBD$_4$) to afford alcohol 24-2 where V$^2$ can be H or D. The W group of 24-2 can be converted to an appropriately substituted metal 24-3 (e.g., M$^1$ is B(OH)$_2$, Bpin, BF$_3$K, Sn(Bu)$_3$, or Zn) under standard conditions (e.g., in the presence of a diboron reagent such as bis(pinacolato)diboron; a base, such as potassium acetate; and a palladium catalyst, such as dichloro[bis(triphenylphosphoranyl)]palladium or bis(diphenylphosphino)ferrocene]dichloropalladium(II), complex with dichloromethane). Compounds provided herein can be synthesized from intermediates 24-3 using the methods described in the schemes herein (e.g., Scheme I).

Scheme XXIV.

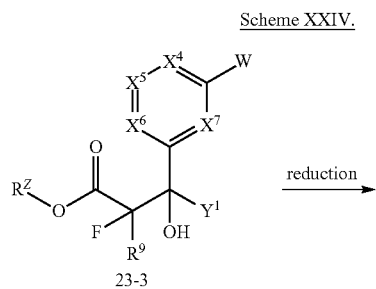

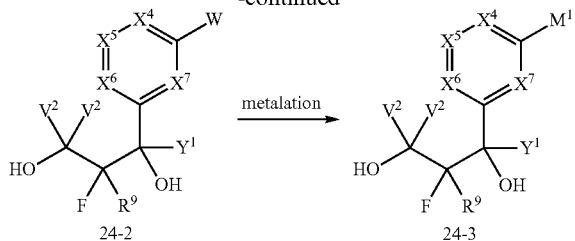

Intermediates for making compounds provided herein can be prepared as shown in Scheme XXV. For example, bromide 25-1 can be converted to vinyl ether 25-3 under standard conditions for Suzuki or Negishi coupling (e.g., in the presence of a palladium catalyst, such as [1,1'-bis(diphenylphosphino)ferrocene]dichloropalladium, and a organoborane or organozinc such as 25-2). Vinyl ether 25-3 can be converted to aldehyde 25-4 under acid treatment (e.g., in the presence of HCl in THF). Aldehyde 25-4 can be converted to carboxylic acid 25-5 under standard Pinnick oxidation condition (e.g., in the presence of NaClO$_2$ and 2-methyl-2-butene). Acid 25-5 can be converted to amide 25-7 using standard amide synthesis conditions (e.g., coupling of 25-5 with amine 25-6 using coupling reagent such as HATU). Aldehyde 25-4 can also be converted to alcohol 25-9 utilizing nucleophilc addition (e.g., in the presence of organomagnesium or organolithium such as Grignard reagent). Aldehyde 25-4 can also be converted to amine 25-11 under standard conditions for reductive amination (e.g., in the presence of amine such as 25-10, and reducing reagent such as NaBH(OAc)$_3$).

Scheme XXV.

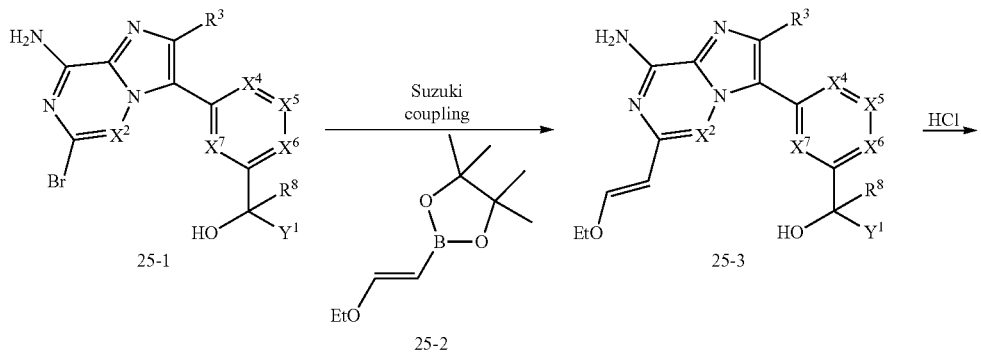

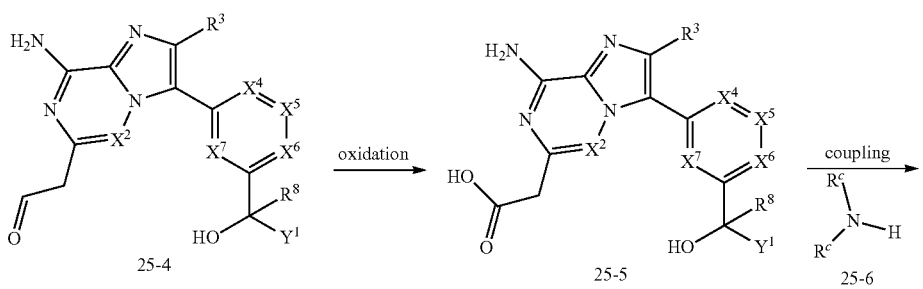

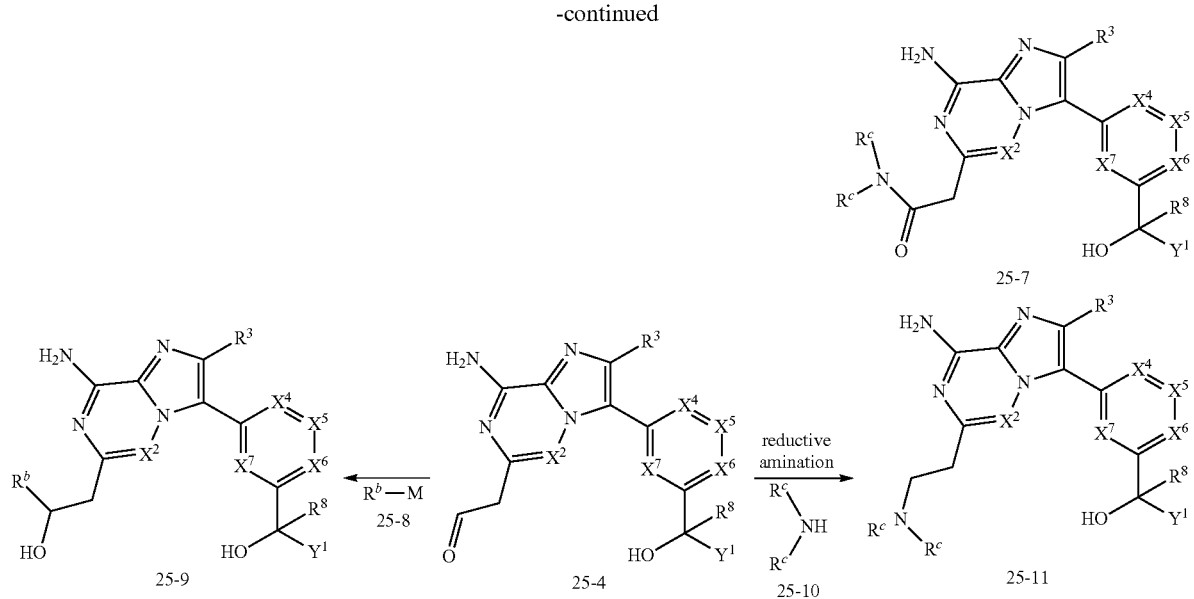

Intermediates for making compounds provided herein can be prepared as shown in Scheme XXVI. For example, bromide 26-1 can be converted to ester 26-3 under a Negishi coupling conditions (e.g., in the presence of a palladium catalyst, such as [1,3-bis(2,6-diisopropylphenyl)imidazol-2-ylidene](3-chloropyridyl)palladium(II) dichloride, and a organozinc such as 26-2). Ester 26-3 can be converted to carboxylic acid 26-4 under hydrolysis conditions (e.g., in the presence of water and base such as LiOH). Acid 26-4 can be converted to amide 26-6 using standard amide synthesis conditions (e.g., coupling of 26-5 with amine 26-6 using coupling reagent such as HATU). Ester 26-3 can also be converted to alcohol 26-8 utilizing nucleophilic addition (e.g., in the presence of organomagnesium or organolithium such as Grignard reagent).

Scheme XXVI.

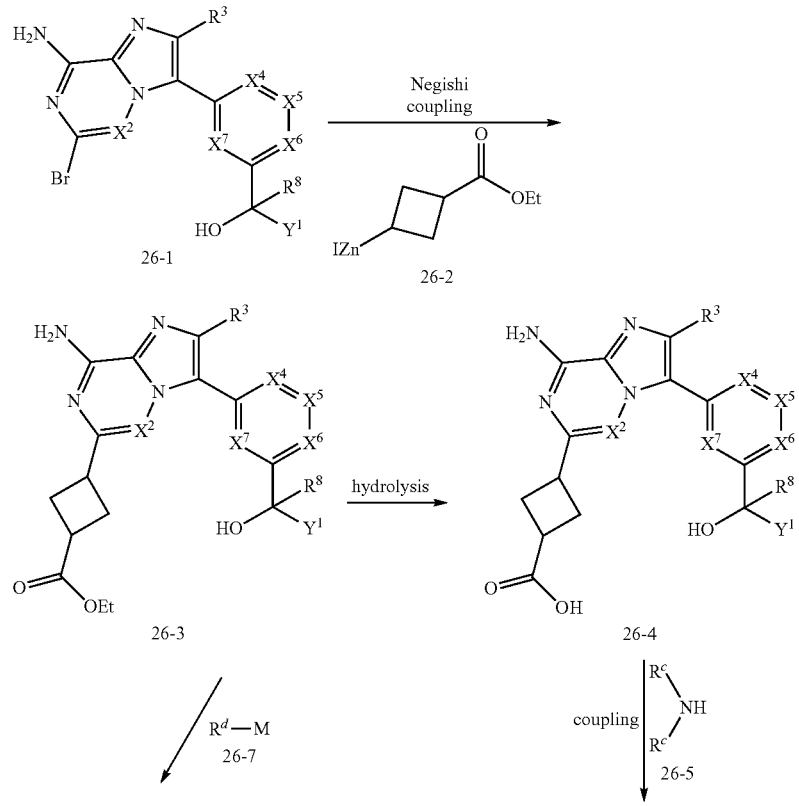

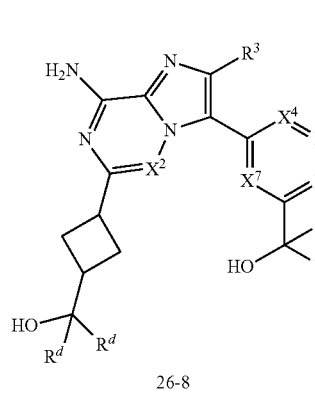

26-8

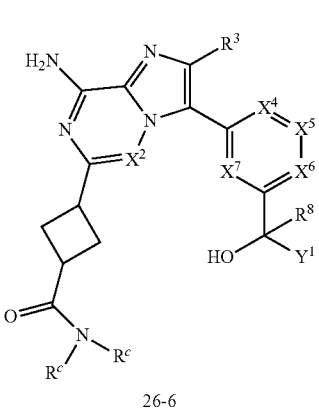

26-6

Intermediates for making compounds provided herein can be prepared as shown in Scheme XXVII. For example, bromide 27-1 can be converted to amine 27-3 under standard conditions for Suzuki or Negishi coupling (e.g., in the presence of a palladium catalyst, such as [1,1'-bis(diphenylphosphino)ferrocene]dichloropalladium, and a organoborane or organozinc such as 27-2). Amine 27-3 can be converted to amide 27-5 using standard acylation conditions (e.g., coupling of amine 27-3 with a carboxylic acid using coupling reagent such as HATU).

Scheme XXVII.

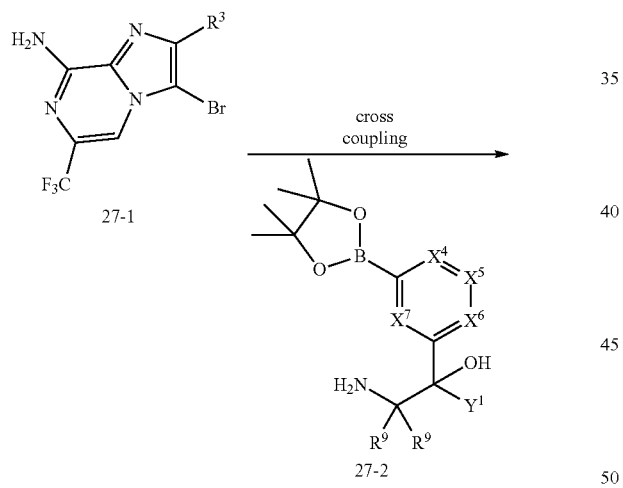

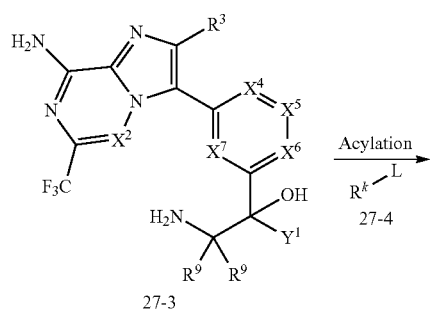

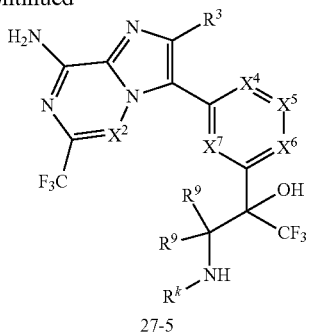

27-5

Intermediates for making compounds provided herein can be prepared as shown in Scheme XXVIII. For example, iodide 28-1 can be converted to amino bromide 28-3 under standard conditions for Suzuki or Negishi coupling (e.g., in the presence of a palladium catalyst, such as [1,1'-bis(diphenylphosphino)ferrocene]dichloropalladium, and a organoborane or organozinc such as 28-2). Amino bromide can be converted to amino amide 28-5 under carbonylation conditions (e.g., in the presence of a palladium catalyst, such as [1,1'-bis(diphenylphosphino)ferrocene]dichloropalladium, carbon monoxide, and amine 28-4). Amino amide 28-5 can be converted to bis-amide 28-7 using standard amide synthesis conditions (e.g., coupling of 28-5 with carboxylic acid 28-6 using coupling reagent such as HATU). Amino amide 28-5 can be converted to amide 28-7 using standard acylation conditions (e.g., coupling of amine 4-5 with a carboxylic acid using coupling reagent such as HATU).

Scheme XXVIII.

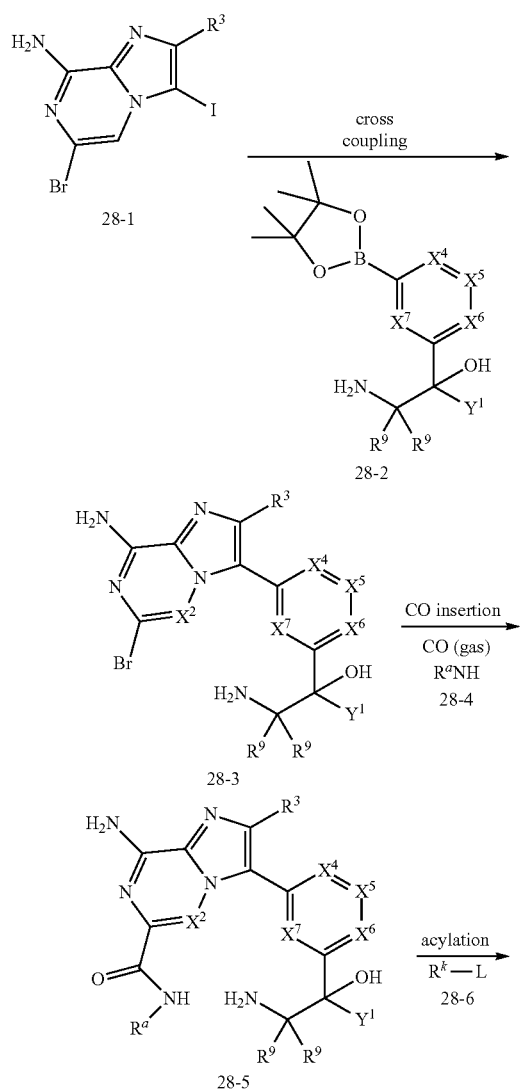

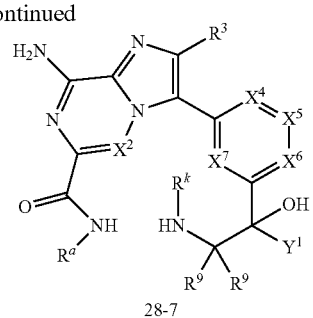

Compounds of Formula (I) wherein $R^1$ is a hydroxyl-substituted alkyl can be prepared as shown in Scheme XXIX. Ester SS-3 can be hydrolyzed under standard conditions for hydrolysis (e.g, LiOH or NaOH in water with a cosolvent such as THF or MeOH) to provide a carboxylic acid, which can be coupled with N,O-dimethyl hydroxylamine under standard amide coupling conditions (e.g., HATU and N,N-diisopropylethylamine) to afford Weinreb amide SS-1. Weinreb amide SS-1 can be reacted with two different nucleophiles sequentially (e.g., $R^{10}$-M and $R^{11}$-M are Grignard reagents or alkyllithium reagents) to provide SS-2. Alternatively, reaction of SS-3 with an excess of a nucleophilic reagent ($R^{10}$-M) can provide SS-4 wherein both R groups ($R^{10}$) are the same. Another method for preparing SS-2 wherein $R^{10}$ and $R^{11}$ are different is shown in Scheme XXIX. Ester SS-3 can be converted to an aldehyde by reduction to the alcohol using a suitable reducing agent (e.g., LiAlH$_4$), followed by oxidation (e.g., with Dess-Martin periodinane) to the aldehyde SS-5. Aldehyde SS-5 can be treated with a suitable nucleophile, $R^{10}$-M to afford secondary alcohol, SS-6. Alcohol SS-6 can be oxidized to the ketone SS-7 (e.g., with Dess-Martin periodinane), which can be treated with a second nucleophile, to afford SS-2. In some embodiments, $R^{10}$ and/or $R^{11}$ are independently $R^a$.

Scheme XXIX.

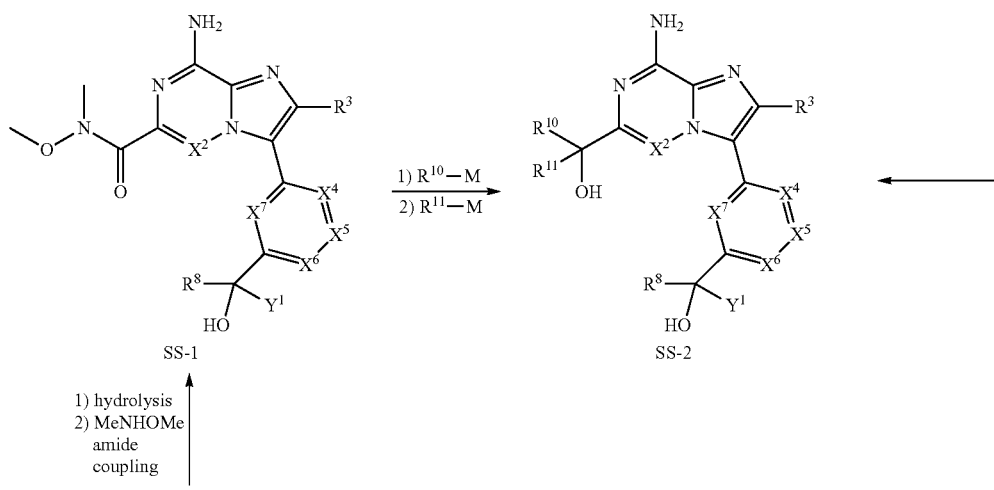

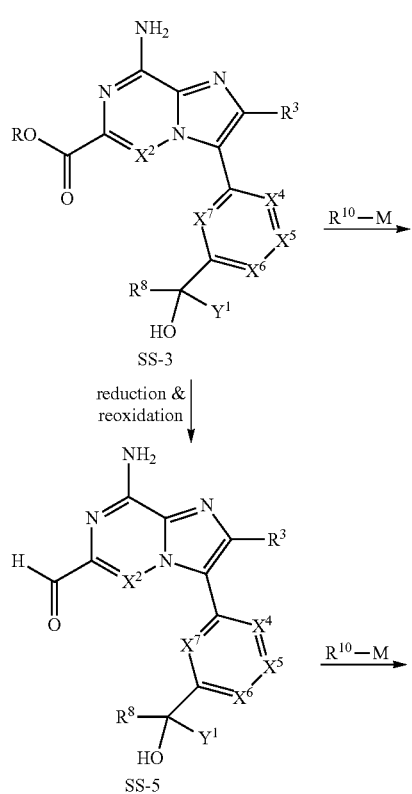

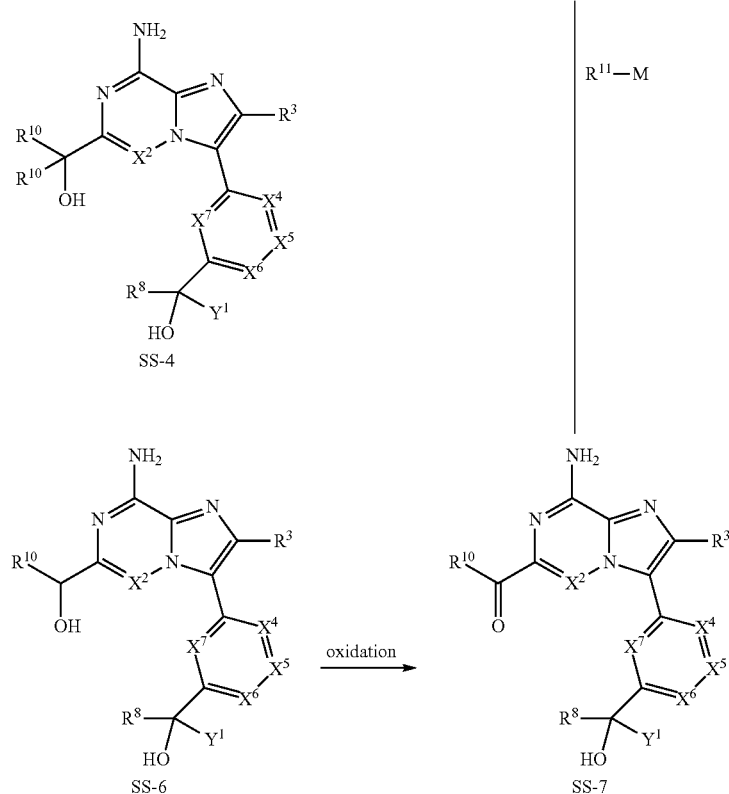

Compounds of Formula (I) wherein $R^1$ is an N-linked heterocycle can be prepared as shown in Scheme XXX. Intermediate SS-II-1, wherein $Y^4$ is a suitable leaving group such as halogen (e.g., Cl or Br) can be reacted with an amine ($R^aR^aNH$, where each $R^a$ is independently selected) under $S_NAr$ conditions (e.g., heating in the presence of base, such as $Cs_2CO_3$), to afford compound SS-II-2.

Scheme XXX.

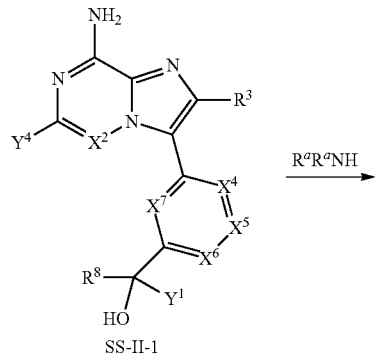

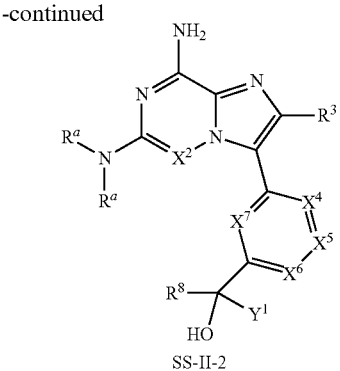

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

The expressions, "ambient temperature" or "room temperature" or "rt" as used herein, are understood in the art, and refer generally to a temperature, e.g., a reaction temperature, that is about the temperature of the room in which the reaction is carried out, for example, a temperature from about 20° C. to about 30° C.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3$^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

Methods of Use

The compounds, salts or stereoisomers thereof described herein inhibit activity of PI3Kγ kinase. Accordingly, the compounds, salts or stereoisomers described herein can be used in methods of inhibiting PI3Kγ kinase by contacting the kinase with any one or more of the compounds, salts, or compositions described herein. In some embodiments, the compounds or salts can be used in methods of inhibiting activity of PI3Kγ in an individual/patient in need of the inhibition by administering an effective amount of a compound or salt of described herein. In some embodiments, modulating is inhibiting. In some embodiments, the contacting is in vivo. In some embodiments, the contacting is ex vivo. Advantageously, the compounds as described herein demonstrate better efficacy and favorable safety and toxicity profiles in animal studies.

In some embodiments, the PI3Kγ includes a mutation. A mutation can be a replacement of one amino acid for another, or a deletion of one or more amino acids. In such embodiments, the mutation can be present in the kinase domain of the PI3Kγ.

In some embodiments, the compound or salt further inhibits PI3Kδ.

The compounds or salts described herein can be selective. By "selective" is meant that the compound binds to or inhibits PI3Kγ with greater affinity or potency, respectively, compared to at least one other kinase. In some embodiments, the compounds of the disclosure are selective inhibitors of PI3Kγ over PI3Kδ, PI3Kα, and PI3Kβ. In some embodiments, the compounds of the disclosure are selective inhibitors of PI3Kγ over PI3Kα and PI3Kβ. In some embodiments, selectivity can be at least about 2-fold, 3-fold, 5-fold, 10-fold, at or 20-fold over PI3Kδ as measured by the assays described herein. In some embodiments, selectivity can be tested at the 2 μM ATP concentration of each enzyme. In some embodiments, the selectivity of compounds of the disclosure can be determined by cellular assays associated with particular PI3K kinase activity.

Another aspect of the present disclosure pertains to methods of treating a kinase PI3Kγ-associated disease or disorder in an individual (e.g., patient) by administering to the individual in need of such treatment a therapeutically effective amount or dose of one or more compounds of the present disclosure or a pharmaceutical composition thereof. A PI3Kγ-associated disease or disorder can include any disease, disorder or condition that is directly or indirectly linked to expression or activity of the PI3Kγ, including overexpression and/or abnormal activity levels.

In some embodiments, the disease or disorder is an autoimmune disease or disorder, cancer, cardiovascular disease, or neurodegenerative disease.

In some embodiments, the disease or disorder is lung cancer (e.g., non-small cell lung cancer), melanoma, pancreatic cancer, breast cancer, prostate cancer, liver cancer, color cancer, endometrial cancer, bladder cancer, skin cancer, cancer of the uterus, renal cancer, gastric cancer, or sarcoma. In some embodiments, the sarcoma is Askin's tumor, sarcoma botryoides, chondrosarcoma, Ewing's sarcoma, malignant hemangioendothelioma, malignant schwannoma, osteosarcoma, alveolar soft part sarcoma, angiosarcoma, cystosarcoma phyllodes, dermatofibrosarcoma protuberans, desmoid tumor, desmoplastic small round cell tumor, epithelioid sarcoma, extraskeletal chondrosarcoma, extraskeletal osteosarcoma, fibrosarcoma, gastrointestinal stromal tumor (GIST), hemangiopericytoma, hemangiosarcoma, Kaposi's sarcoma, leiomyosarcoma, liposarcoma, lymphangiosarcoma, lymphosarcoma, malignant peripheral nerve sheath tumor (MPNST), neurofibrosarcoma, rhabdomyosarcoma, synovial sarcoma, or undifferentiated pleomorphic sarcoma.

In some embodiments, the disease or disorder is mesothelioma or adrenocarcinoma. In some embodiments, the disease or disorder is mesothelioma. In some embodiments, the disease or disorder is adrenocarcinoma.

In some embodiments, the disease or disorder is acute myeloid leukemia (e.g., acute monocytic leukemia), small lymphocytic lymphoma, chronic lymphocytic leukemia (CLL), chronic myelogenous leukemia (CML), multiple myeloma, T-cell actute lymphoblasic leukemia (T-ALL), cutaneous T-cell lymphoma, large granular lymphocytic leukemia, mature (peripheral) t-cell neoplasm (PTCL), anaplastic large cell lymphoma (ALCL), or lymphoblastic lymphoma. In some embodiments, the mature (peripheral) t-cell neoplasm (PTCL) is T-cell prolymphocytic leukemia, T-cell granular lymphocytic leukemia, aggressive NK-cell leukemia, mycosis fungoides/Sezary syndrome, naplastic large cell lymphoma (T-cell type), enteropathy type T-cell lymphoma, adult T-cell leukemia/lymphoma, or angioimmunoblastic T-cell lymphoma. In some embodiments, the anaplastic large cell lymphoma (ALCL) is systemic ALCL or primary cutaneous ALCL.

In some embodiments, the disease or disorder is Burkitt's lymphoma, acute myeloblastic leukemia, chronic myeloid leukemia, non-Hodgkin's lymphoma, Hodgkin's lymphoma, hairy cell leukemia, Mantle cell lymphoma, small lymphocytic lymphoma, follicular lymphoma, xenoderoma pigmentosum, keratoctanthoma, lymphoplasmacytic lymphoma, extranodal marginal zone lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), monoclonal gammopathy of undetermined significance (MGUS), or diffuse large B cell lymphoma.

MDSC (myeloid-derived suppressor cells) are a heterogenous group of immune cells from the myeloid lineage (a family of cells that originate from bone marrow stem cells). MDSCs strongly expand in pathological situations such as chronic infections and cancer, as a result of an altered haematopoiesis. MDSCs are discriminated from other myeloid cell types in which they possess strong immunosuppressive activities rather than immunostimulatory properties. Similar to other myeloid cells, MDSCs interact with other immune cell types including T cells, dendritic cells, macrophages and natural killer cells to regulate their functions. In some embodiments, the compounds, etc. described herein can be used in methods related to cancer tissue (e.g., tumors) with high infiltration of MDSCs, including solid tumors with high basal level of macrophage and/or MDSC infiltration.

In some embodiments, the disease or disorder is Burkitt's lymphoma, acute myeloblastic leukemia, chronic myeloid leukemia, non-Hodgkin's lymphoma, Hodgkin's lymphoma, hairy cell leukemia, Mantle cell lymphoma, small lymphocytic lymphoma, follicular lymphoma, lymphoplasmacytic lymphoma, extranodal marginal zone lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), monoclonal gammopathy of undetermined significance (MGUS), or diffuse large B cell lymphoma.

In some embodiments, the non-Hodgkin's lymphoma (NHL) is relapsed NHL, refractory NHL, recucurrent follicular NHL, indolent NHL (iNHL), or aggressive NHL (aNHL).

In some embodiments, the diffuse large B cell lymphoma is activated B-cell like (ABC) diffuse large B cell lymphoma, or germinal center B cell (GCB) diffuse large B cell lymphoma.

In some embodiments, the Burkitt's lymphoma is endemic Burkitt's lymphoma, sporadic Burkitt's lymphoma, or Burkitt's-like lymphoma.

In some embodiments, the disease or disorder is rheumatoid arthritis, multiple sclerosis, systemic lupus erythematous, asthma, allergy (e.g, allergic rhinitis), pancreatitis, psoriasis, anaphylaxis, glomerulonephritis, inflammatory bowel disease (e.g., Crohn's disease and ulcerative colitis), thrombosis, meningitis, encephalitis, diabetic retinopathy, benign prostatic hypertrophy, myasthenia gravis, Sjögren's syndrome, osteoarthritis, restenosis, or atherosclerosis.

In some embodiments, the disease or disorder is heart hypertropy, cardiac myocyte dysfunction, acute coronary syndrome, chronic obstructive pulmonary disease (COPD), chronic bronchitis, elevated blood pressure, ischemia, ischemia-reperfusion, vasoconstriction, anemia (e.g., hemolytic anemia, aplastic anemia, or pure red cell anemia), bacterial infection, viral infection, graft rejection, kidney disease, anaphylactic shock fibrosis, skeletal muscle atrophy, skeletal muscle hypertrophy, angiogenesis, sepsis, graft-versus-host disease, allogeneic or xenogeneic transplantation, glomerulosclerosis, progressive renal fibrosis, idiopathic thrombocytopenic purpura (ITP), idiopathic pulmonary fibrosis, autoimmune hemolytic anemia, vasculitis, lupus nephritis, pemphigus, or membranous nephropathy.

In some embodiments, disease or disorder is heart hypertropy, cardiac myocyte dysfunction, chronic obstructive pulmonary disease (COPD), elevated blood pressure, ischemia, ischemia-reperfusion, vasoconstriction, anemia (e.g., hemolytic anemia, aplastic anemia, or pure red cell anemia), bacterial infection, viral infection, graft rejection, kidney disease, anaphylactic shock fibrosis, skeletal muscle atrophy, skeletal muscle hypertrophy, angiogenesis, sepsis, graft rejection, glomerulosclerosis, progressive renal fibrosis, idiopathic thrombocytopenic purpura (ITP), autoimmune hemolytic anemia, vasculitis, systemic lupus erythematosus, lupus nephritis, pemphigus, or membranous nephropathy.

In some embodiments, the disease or disorder is Alzheimer's disease, central nervous system trauma, or stroke.

In some embodiments, the idiopathic thrombocytopenic purpura (ITP) is relapsed ITP or refractory ITP.

In some embodiments, the vasculitis is Behcet's disease, Cogan's syndrome, giant cell arteritis, polymyalgia rheumatica (PMR), Takayasu's arteritis, Buerger's disease (thromboangiitis obliterans), central nervous system vasculitis, Kawasaki disease, polyarteritis nodosa, Churg-Strauss syndrome, mixed cryoglobulinemia vasculitis (essential or hepatitis C virus (HCV)-induced), Henoch-Schönlein purpura (HSP), hypersensitivity vasculitis, microscopic polyangiitis, Wegener's granulomatosis, or anti-neutrophil cytoplasm antibody associated (ANCA) systemic vasculitis (AASV).

The present disclosure further provides a compound described herein, or a pharmaceutically acceptable salt thereof, for use in any of the methods described herein.

The present disclosure further provides use of a compound described herein, or a pharmaceutically acceptable salt thereof, for the preparation of a medicament for use in any of the methods described herein.

As used herein, the term "contacting" refers to the bringing together of indicated moieties in an in vitro system or an in vivo system. For example, "contacting" a PI3K with a compound of the disclosure includes the administration of a compound of the present disclosure to an individual or patient, such as a human, having a PI3K, as well as, for example, introducing a compound of the disclosure into a sample containing a cellular or purified preparation containing the PI3K.

It is believed that compounds of the present disclosure as provided herein (e.g., compounds of Formula (I), or pharmaceutically acceptable salts thereof) or any of the embodiments thereof, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" can refer to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

I. Immune-Checkpoint Therapies

In some embodiments, the PI3Kγ inhibitors provided herein can be used in combination with one or more immune checkpoint inhibitors for the treatment of cancer as described herein. In one embodiment, the combination with one or more immune checkpoint inhibitors as described herein can be used for the treatment of melanoma. Compounds of the present disclosure can be used in combination with one or more immune checkpoint inhibitors. Exemplary immune checkpoint inhibitors include inhibitors against immune checkpoint molecules such as CD20, CD28, CD40, CD122, CD96, CD73, CD47, GITR, CSF1R, JAK, PI3K delta, PI3K gamma, TAM, arginase, HPK1, CD137 (also known as 4-1BB), ICOS, B7-H3, B7-H4, BTLA, CTLA-4, LAG3, TIM3, VISTA, TIGIT, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds of the disclosure provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the PI3Kγ inhibitors provided herein can be used in combination with one or more agonists of immune checkpoint molecules, e.g., OX40, CD27, OX40, GITR, and CD137 (also known as 4-1BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), durvalumab (Imfinzi®), pidilizumab, SHR-1210, PDR001, MGA012, PDR001, AB122, or AMP-224. In some embodiments, the anti-PD-1 monoclonal antibody is nivolumab or pembrolizumab. In some embodiments, the anti-PD1 antibody is pembrolizumab. In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g. urelumab, utomilumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of PD-1 and PD-L1, e.g., an anti-PD-1/PD-L1 monoclonal antibody. In some embodiments, the anti-PD-1/PD-L1 is MCLA-136.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the PI3Kγ inhibitors provided herein can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

As provided throughout, the additional compounds, inhibitors, agents, etc. can be combined with the present compound in a single or continuous dosage form, or they can be administered simultaneously or sequentially as separate dosage forms.

II. Cancer Therapies

Cancer cell growth and survival can be impacted by multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

The compounds of the present disclosure can be used in combination with one or more other enzyme/protein/receptor inhibitors or one or more therapies for the treatment of diseases, such as cancer. Examples of diseases and indications treatable with combination therapies include those as described herein. Examples of cancers include solid tumors and liquid tumors, such as blood cancers.

One or more additional pharmaceutical agents such as, for example, chemotherapeutics, anti-inflammatory agents, steroids, immunosuppressants, immune-oncology agents, metabolic enzyme inhibitors, chemokine receptor inhibitors, and phosphatase inhibitors, as well as targeted therapies such as Bcr-Abl, EGFR, HER2, JAK, c-MET, VEGFR, PDGFR, c-Kit, IGF-1R, RAF and FAK kinase inhibitors such as, for example, those described in WO 2006/056399. Other agents such as therapeutic antibodies can be used in combination with the compounds of the present disclosure for treatment of PI3K-associated diseases, disorders or conditions. The one or more additional pharmaceutical agents can be administered to a patient simultaneously or sequentially.

For example, the compounds as disclosed herein can be combined with one or more inhibitors of the following kinases for the treatment of cancer and other diseases or disorders described herein: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Non-limiting examples of inhibitors that can be combined with the compounds of the present disclosure for treatment of cancer and other diseases and disorders described herein include an FGFR inhibitor (FGFR1, FGFR2, FGFR3 or FGFR4, e.g., INCB54828, INCB62079 and INCB63904), a JAK inhibitor (JAK1 and/or JAK2, e.g., ruxolitinib, baricitinib or INCB39110), an IDO inhibitor (e.g., epacadostat, NLG919, or BMS-986205), an LSD1 inhibitor (e.g., INCB59872 and INCB60003), a TDO inhibitor, a PI3K-delta inhibitor (e.g., INCB50797 and INCB50465), a Pim inhibitor, a CSF1R inhibitor, a TAM receptor tyrosine kinases (Tyro-3, Axl, and Mer), a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643) and an adenosine receptor antagonist or combinations thereof.

In some embodiments, the compound or salt described herein is administered with a PI3Kδ inhibitor. In some embodiments, the compound or salt described herein is administered with a JAK inhibitor. In some embodiments, the compound or salt described herein is administered with a JAK1 or JAK2 inhibitor (e.g., baricitinib or ruxolitinib). In some embodiments, the compound or salt described herein is administered with a JAK1 inhibitor. In some embodiments, the compound or salt described herein is administered with a JAK1 inhibitor, which is selective over JAK2.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds of the present disclosure and are presented as a non-limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, IRESSA™ (gefitinib), TARCEVA™ (erlotinib), antibodies to EGFR, intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, leucovirin, ELOXATIN™ (oxaliplatin), pentostatine, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide 17.alpha.-ethinylestradiol, diethylstilbestrol, testosterone, Prednisone, Fluoxymesterone, Dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, avastin, HERCEPTIN™ (trastuzumab), BEXXAR™ (tositumomab), VELCADE™ (bortezomib), ZEVALIN™ (ibritumomab tiuxetan), TRISENOX™ (arsenic trioxide), XELODA™ (capecitabine), vinorelbine, porfimer, ERBITUX™ (cetuximab), thiotepa, altretamine, melphalan, trastuzumab, lerozole, fulvestrant, exemestane, ifosfomide, rituximab, C225 (cetuximab), Campath, (alemtuzumab), clofarabine, cladribine, aphidicolon, rituxan, sunitinib, dasatinib, tezacitabine, Sml1, fludarabine, pentostatin, triapine, didox, trimidox, amidox, 3-AP, and MDL-101,731.

The compounds of the present disclosure can further be used in combination with other methods of treating cancers, for example by chemotherapy, irradiation therapy, tumortargeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, Toll receptor agonists, STING agonists, oncolytic virotherapy and immunomodulating small molecules, including thalidomide or JAK1/2 inhibitor and the like. The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, olapariboxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, rucaparib, streptozocin, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, niraparib, veliparib, talazoparib, and zoledronate.

Additional examples of chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include imatinib mesylate (GLEEVAC™), nilotinib, dasatinib, bosutinib, and ponatinib, and pharmaceutically acceptable salts. Other example suitable Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include midostaurin, lestaurtinib, linifanib, sunitinib, sunitinib, maleate, sorafenib, quizartinib, crenolanib, pacritinib, tandutinib, PLX3397 and ASP2215, and their pharmaceutically acceptable salts. Other example suitable Flt-3 inhibitors include compounds, and their pharmaceutically acceptable salts, as disclosed in WO 03/037347, WO 03/099771, and WO 04/046120.

Example suitable RAF inhibitors include dabrafenib, sorafenib, and vemurafenib, and their pharmaceutically acceptable salts. Other example suitable RAF inhibitors include compounds, and their pharmaceutically acceptable salts, as disclosed in WO 00/09495 and WO 05/028444.

Example suitable FAK inhibitors include VS-4718, VS-5095, VS-6062, VS-6063, BI853520, and GSK2256098, and their pharmaceutically acceptable salts. Other example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the compounds of the disclosure can be used in combination with one or more other kinase inhibitors including imatinib, particularly for treating patients resistant to imatinib or other kinase inhibitors.

In some embodiments, the compounds of the disclosure can be used in combination with a chemotherapeutic in the treatment of cancer, and may improve the treatment response as compared to the response to the chemotherapeutic agent alone, without exacerbation of its toxic effects. In some embodiments, the compounds of the disclosure can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM). Additive or synergistic effects are desirable outcomes of combining a PI3K inhibitor of the present disclosure with an additional agent.

In some embodiments, the compounds of the disclosure can be used in combination with an inhibitor of JAK or PI3Kδ.

The agents can be combined with the present compound in a single or continuous dosage form, or the agents can be administered simultaneously or sequentially as separate dosage forms.

The compounds of the present disclosure can be used in combination with one or more other inhibitors or one or more therapies for the treatment of infections. Examples of infections include viral infections, bacterial infections, fungus infections or parasite infections.

In some embodiments, a corticosteroid such as dexamethasone is administered to a patient in combination with the compounds of the disclosure where the dexamethasone is administered intermittently as opposed to continuously.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fc alpha or Fc gamma receptor-expressing effectors cells to tumor cells. The compounds of the present disclosure can also be combined with macrocyclic peptides that activate host immune responsiveness.

In some further embodiments, combinations of the compounds of the disclosure with other therapeutic agents can be administered to a patient prior to, during, and/or after a bone marrow transplant or stem cell transplant. The compounds of the present disclosure can be used in combination with bone marrow transplant for the treatment of a variety of tumors of hematopoietic origin.

The compounds of Formula (I) or any of the formulas as described herein, a compound as recited in any of the claims and described herein, or salts thereof can be used in combination with vaccines, to stimulate the immune response to pathogens, toxins, and self antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, Giardia, Malaria, *Leishmania, Staphylococcus aureus, Pseudomonas aeruginosa*.

Viruses causing infections treatable by methods of the present disclosure include, but are not limit to human papillomavirus, influenza, hepatitis A, B, C or D viruses, adenovirus, poxvirus, herpes simplex viruses, human cytomegalovirus, severe acute respiratory syndrome virus, ebola virus, measles virus, herpes virus (e.g., VZV, HSV-1, HAV-6, HSV-II, and CMV, Epstein Barr virus), flaviviruses, echovirus, rhinovirus, coxsackie virus, cornovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lyme's disease bacteria.

Pathogenic fungi causing infections treatable by methods of the disclosure include, but are not limited to, *Candida* (*albicans, krusei, glabrata, tropicalis*, etc.), *Cryptococcus neoformans, Aspergillus* (*fumigatus, niger,* etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*. Pathogenic parasites causing infections treatable by methods of the disclosure include, but are not limited to, *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi,* and *Nippostrongylus brasiliensis*.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds of the disclosure can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compound of the disclosure or a pharmaceutically acceptable salt thereof, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the disclosure contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the disclosure contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the disclosure contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the disclosure.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the disclosure. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the disclosure can further include one or more additional pharmaceutical agents such as a chemotherapeutic, steroid, anti-inflammatory compound, or immunosuppressant, examples of which are listed herein.

Labeled Compounds and Assay Methods

Another aspect of the present disclosure relates to labeled compounds of the disclosure (radio-labeled, fluorescent-labeled, etc.) that would be useful not only in imaging techniques but also in assays, both in vitro and in vivo, for localizing and quantitating PI3K in tissue samples, including human, and for identifying PI3K ligands by inhibition binding of a labeled compound. Substitution of one or more of the atoms of the compounds of the present disclosure can also be useful in generating differentiated ADME (Adsorption, Distribution, Metabolism and Excretion.) Accordingly, the present disclosure includes PI3K assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as —CD$_3$ being substituted for —CH$_3$). In some embodiments, alkyl groups of the disclosed Formulas (e.g., Formula (I), (II), etc.), can be perdeuterated.

One or more constituent atoms of the compounds presented herein can be replaced or substituted with isotopes of the atoms in natural or non-natural abundance. In some embodiments, the compound includes at least one deuterium atom. For example, one or more hydrogen atoms in a compound presented herein can be replaced or substituted by deuterium (e.g., one or more hydrogen atoms of a $C_{1-6}$ alkyl group can be replaced by deuterium atoms, such as —CD$_3$ being substituted for —CH$_3$). In some embodiments, the compound includes two or more deuterium atoms. In some embodiments, the compound includes 1, 1-2, 1-3, 1-4, 1-5, or 1-6 deuterium atoms. In some embodiments, all of the hydrogen atoms in a compound can be replaced or substituted by deuterium atoms.

In some embodiments, 1, 2, 3, 4, 5, 6, 7, or 8 hydrogen atoms, attached to carbon atoms of any alkyl, alkenyl, alkynyl, aryl, phenyl, cycloalkyl, heterocycloalkyl, or heteroaryl substituents, or —$C_{1-6}$ alkyl-, alkylene, alkenylene, and alkynylene linking groups, as described herein, are each optionally replaced by a deuterium atom.

Synthetic methods for including isotopes into organic compounds are known in the art (Deuterium Labeling in Organic Chemistry by Alan F Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. *J. Med. Chem.* 2011, 54, 201-210; R. Xu et. al. *J. Label Compd. Radiopharm.* 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro PI3K labeling and competition assays, compounds that incorporate $^3$H, $^{14}$C, $^{82}$Br, $^{125}$I, $^{131}$I or $^{35}$S can be useful. For radio-imaging applications $^{11}$C, $^{18}$F, $^{125}$I, $^{123}$I, $^{124}$I, $^{131}$I, $^{75}$Br or $^{77}$Br can be useful.

It is understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the disclosure can be used in a screening assay to identify/evaluate compounds. For example, a newly synthesized or identified compound (i.e., test compound) which is labeled can be evaluated for its ability to bind a PI3K by monitoring its concentration variation when contacting with the PI3K, through tracking of the labeling. For example, a test compound (labeled) can be evaluated for its ability to reduce binding of another compound which is known to bind to a PI3K (i.e., standard compound). Accordingly, the ability of a test compound to compete with the standard compound for binding to the PI3K directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, for example, in the treatment or prevention of PI3K-associated diseases or disorders, such as cancer, which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be PI3Kγ inhibitors according to at least one assay described herein.

EXAMPLES

Preparatory LC-MS purifications of some of the compounds prepared were performed on Waters mass directed fractionation systems. The basic equipment setup, protocols, and control software for the operation of these systems have been described in detail in the literature (see e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Hague, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004)). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 μm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm, 30×100 mm or Waters XBridge™ $C_{18}$ 5 μm, 30×100 mm column, eluting with mobile phase A: 0.1% TFA (trifluoroacetic acid) in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)).

pH=6.5 purifications: Waters XBridge™ $C_{18}$ 5 μm, 30×100 mm column, eluting with mobile phase A: 100 mM ammonium acetate ($NH_4OAc$) in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)).

pH=10 purifications: Waters XBridge™ $C_{18}$ 5 μm, 30×100 mm column, eluting with mobile phase A: 0.1% $NH_4OH$ in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)).

Stereochemical Rationale

The Sharpless asymmetric dihydroxylation of olefins has been studied extensively, and its basis as a model for enantioselectivity is well established (Sharpless, K. B.; Amberg, W.; Bennani, Y. L.; Crispino, G. A.; Hartung, J.; Jeong, K.-S.; Kwong, H.-L.; Morikawa, K.; Wang, Z.-M.; Xu, D.; Zhang, X.-L. *J. Org. Chem.*, 1992, 57, 2768-2771; and Kolb, H. C.; VanNieuwenhze, M. S.; Sharpless, K. B. Chem. Rev., 1994, 94, 2483-2547. Briefly, the application of AD-mix-α (containing $(DHQ)_2$-PHAL) in the dihydroxylation of prop-1-en-2-ylbenzene affords (S)-2-phenylpropane-1,2-diol. Application of AD-mix-β (containing $(DHQD)_2$-PHAL) in the dihydroxylation of prop-1-en-2-ylbenzene affords (R)-2-phenylpropane-1,2-diol (Sharpless and Kolb, supra). Moreno-Dorado et al. extended the method to the trifluoromethyl case (e.g., (3,3,3-trifluoroprop-1-en-2-yl)benzene affords (S)-3,3,3-trifluoro-2-phenylpropane-1,2-diol when treated with AD-mix-α and affords (R)-3,3,3-trifluoro-2-phenylpropane-1,2-diol when treated with AD-mix-β) and the stereochemical outcome was verified by subsequent conversion to well known compounds whose specific rotations were found to be in agreement with the literature values (Moreno-Dorado, F. J.; Guerra, F. M.; Ortega, M. J.; Zubia, E.; Massanet, G. M. Tetrahedron: *Asymmetry*, 2003, 14, 503-510). While not wishing to be bound by any one theory, in the dihydroxylations performed on vinyl arenes in the Examples, we expect to obtain the (S)-configuration with AD-mix-α and the (R)-configuration with AD-mix-β.

Intermediate 1. 3-Amino-1,1,1-trifluoro-2-(4-methyl-3-(4,4,5,5-tetramethyl-1,3,2-dioxaborolan-2-yl)phenyl)propan-2-ol

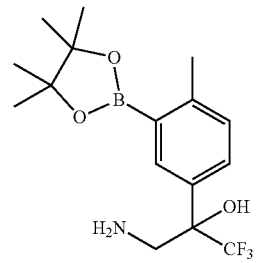 [SMILES: Cc1ccc(C(O)(CN)C(F)(F)F)cc1B1OC(C)(C)C(C)(C)O1]

Step 1. 1-(3-Bromo-4-methylphenyl)-2,2,2-trifluoroethan-1-ol

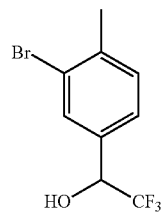

A solution of 3-bromo-4-methylbenzaldehyde (6.51 g, 32.7 mmol) [Combi-Blocks, HC-3454] in dry tetrahydrofuran (65.4 mL) was cooled to 0° C. followed by the addition of trimethyl(trifluoromethyl)silane (6.28 mL, 42.5 mmol). The yellow mixture was treated with 1.0 M tetra-n-butylammonium fluoride in tetrahydrofuran (0.654 mL, 0.654 mmol) at 0° C. and stirred for a few minutes at 0° C. The ice bath was removed and the resulting reaction mixture was stirred for 1.5 h. The reaction mixture was cooled back to 0° C. and treated with water (6.48 mL, 360 mmol) and 1.0 M tetra-n-butylammonium fluoride in tetrahydrofuran (6.54 mL, 6.54 mmol). The ice bath was removed and the reaction mixture was stirred at ambient temperature for 30 min. The yellow reaction mixture was diluted with brine (150 mL) and extracted with ethyl acetate (200 mL). The organic layer was washed with saturated ammonium chloride (100 mL), dried over sodium sulfate, filtered, and concentrated to give a tan oil. Purification by flash column chromatography using methyl tert-butyl ether (MTBE) in hexanes (0% to 50%) gave the desired product (8.42 g, 95.7%) as a yellow oil. LCMS for $C_9H_7BrF_3$ (M-OH)$^+$: m/z=251.0, 253.0; Found: 250.9, 252.8.

Step 2. 1-(3-Bromo-4-methylphenyl)-2,2,2-trifluoroethan-1-one

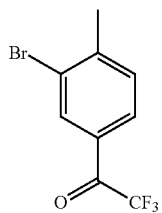

A mixture of 1-(3-bromo-4-methylphenyl)-2,2,2-trifluoroethan-1-ol (8.41 g, 31.3 mmol) in dichloromethane (125 mL) at 0° C. was treated with Dess-Martin periodinane (19.9 g, 46.9 mmol) and stirred at room temperature (rt) for 2.5 h. The reaction mixture was concentrated (by rotary evaporation with the water bath set at 30° C.) to an oily solid that was diluted with diethyl ether (200 mL) which precipitated more solids. This mixture was filtered over Celite® and the Celite® was rinsed with additional diethyl ether (200 mL). The filtrate was washed with saturated sodium bicarbonate solution (3×200 mL) and brine, dried over sodium sulfate, filtered, and concentrated to give an oily solid. The oily solid was partioned between diethyl ether (150 mL) and water (100 mL). The organic layer was separated and washed with saturated sodium bicarbonate solution (2×75 mL) and brine, dried over sodium sulfate, filtered, and concentrated to give the desired product (7.93 g, 95.0%) as an oil that was used without further purification. LCMS for $C_9H_7BrF_3O$ (M+H)$^+$: m/z=267.0, 269.0; Found: 267.1, 268.9.

Step 3. 2-(3-Bromo-4-methylphenyl)-3,3,3-trifluoro-2-hydroxypropanenitrile

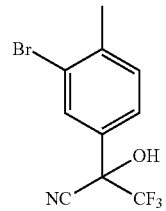

A solution of 1-(3-bromo-4-methylphenyl)-2,2,2-trifluoroethan-1-one (7.92 g, 29.7 mmol) in dichloromethane (29.7 mL) was treated with trimethylsilyl cyanide (8.70 mL, 65.2 mmol), potassium cyanide (0.29 g, 4.45 mmol), and 18-crown-6 (0.29 g, 1.10 mmol) and stirred for 1 h. The reaction can be cooled with an ice bath due to an exotherm after the addition of 18-crown-6. The reaction mixture was concentrated (by rotary evaporation with the water bath set at 28° C.) to give a rust colored solid. The solid was dissolved in THF (29.6 mL), cooled to 0° C., treated with 1.8 M HCl (10.9 mL, 19.6 mmol), and stirred at room temperature (rt) for 1.5 h. The reaction mixture was diluted with water (75 mL) and extracted with diethyl ether (3×75 mL). The combined organic extracts were washed with brine, dried over sodium sulfate, filtered, and concentrated. Reconcentration from hexanes to give the desired product (8.70 g, 99.8%) as an orange solid that was used without further purification. LCMS for $C_9H_7BrF_3O$ (M-CN)$^+$: m/z=267.0, 269.0; Found: 266.9, 269.0.

Step 4. 2-(3-bromo-4-methylphenyl)-3,3,3-trifluoro-2-hydroxypropanamide

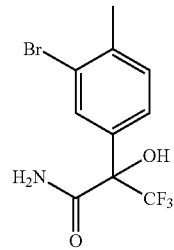 [SMILES: Cc1ccc(C(O)(C(N)=O)C(F)(F)F)cc1Br]

A solution of 2-(3-bromo-4-methylphenyl)-3,3,3-trifluoro-2-hydroxypropanenitrile (8.70 g, 29.6 mmol) in dioxane (59.2 mL) at 0° C. was treated with concentrated HCl (9.00 mL, 108 mmol) that had been pre-cooled in an ice bath. While stirring at 0° C., the reaction mixture was bubbled with HCl gas for 45 min. The cooling bath was removed and the reaction mixture was stirred at rt for 61 h. The reaction mixture was bubbled with nitrogen for 10 min to remove some of the HCl, cooled to 0° C., and diluted with brine (200 mL), water (50 mL), and ethyl acetate (200 mL). The organic layer was separated and the aqueous layer was diluted with water (100 mL) to dissolve the remaining solids. The aqueous layer was extracted with ethyl acetate (100 mL). The combined organic extracts were washed with brine, dried over sodium sulfate, filtered, and concentrated to give a brown oil. Purification by flash column chromatography using MTBE in hexanes (0% to 60%) gave the desired product as a yellow oily solid. The racemic mixture was separated via preparative chiral HPLC (Phenomenex Lux Amylose-1 [21.2×250 mm, 5 micron], eluting with 95% ethanol in hexanes, at flow rate of 18 mL/min, loading about 100 mg in 2 mL ethanol) to give the desired second eluting enantiomer (4.50 g, 48.8%) as a viscous yellow oil. The first enantiomer that eluted had a retention time of 4.0 min. The second enantiomer that eluted had a retention time of 5.3 min. Second eluting enantiomer: LCMS for $C_{10}H_{10}BrF_3NO_2$ (M+H)$^+$: m/z=312.0, 314.0; Found: 312.0, 314.0.

Step 5. 3-amino-1,1,1-trifluoro-2-(4-methyl-3-(4,4,5,5-tetramethyl-1,3,2-dioxaborolan-2-yl)phenyl)propan-2-ol A solution of 2-(3-bromo-4-methylphenyl)-3,3,3-trifluoro-2-hydroxypropanamide (racemic mixture, 350 mg, 1.17 mmol) in dioxane (6 mL) was treated with bis(pinacolato)diboron (350 mg, 1.37 mmol), and potassium acetate (370 mg, 3.78 mmol) and degassed with nitrogen for 5 min. The reaction mixture was treated with bis(triphenylphosphine)palladium(II)chloride (0.048 g, 0.069 mmol), degassed for 5 min, and stirred at 100° C. for 2.5 h. The reaction mixture was diluted with ethyl acetate (5 mL), filtered over CELITE®, and rinsed with additional ethyl acetate (10 mL). The filtrate was washed with brine, dried over sodium sulfate, filtered, and concentrated to a brown foam. Purification by flash column chromatography using MTBE in hexanes (30% to 100%) gave the desired product (300 mg, 0.87 mmol, 63%) as a thick yellow foam. LCMS for $C_{16}H_{24}BF_3NO_3$ (M+H)$^+$: m/z=346.2; Found: 346.2.

Example 1. 2-(3-(4-Amino-2-(trifluoromethyl)imidazo[2,1-f][1,2,4]triazin-7-yl)-4-methylphenyl)-1,1,1-trifluoropropan-2-ol

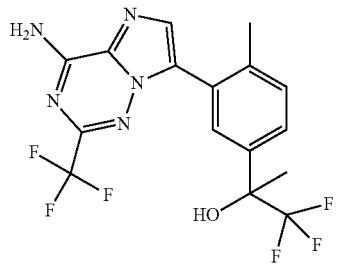 [SMILES: Cc1ccc(C(C)(O)C(F)(F)F)cc1-c1cnc2c(N)nc(C(F)(F)F)nn12]

Step 1. 2-(3-Bromo-4-methylphenyl)-1,1,1-trifluoropropan-2-ol

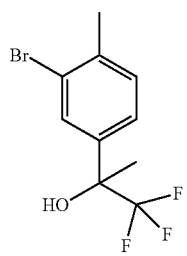

A solution of 1-(3-bromo-4-methylphenyl)ethan-1-one (1.20 g, 5.63 mmol) [Aldrich, 579734] in tetrahydrofuran (22.5 mL) at 0° C. was treated with trimethyl(trifluoromethyl)silane (1.00 mL, 6.76 mmol) [Aldrich, 488712] and stirred at 0° C. for 5 min. The reaction mixture was treated with 1.0 M tetra-n-butylammonium fluoride in tetrahydrofuran (0.282 mL, 0.282 mmol) at 0° C. and stirred at room temperature for 1 h. The reaction mixture was cooled to 0° C., treated with additional 1.0 M tetra-n-butylammonium fluoride in tetrahydrofuran (6.76 mL, 6.76 mmol), and stirred at room temperature for 30 min. The reaction mixture was diluted with ethyl acetate (100 mL) and washed with brine (2×75 mL). The organic layer was separated, dried over sodium sulfate, filtered, and concentrated to give a crude residue. Purification by flash column chromatography using ethyl acetate in hexanes (0%-30%) gave the desired product (1.54 g, 96.7%) as a yellow oil. LCMS for $C_{10}H_9BrF_3$ (M-OH)$^+$: m/z=265.0, 267.0; Found: 264.9, 267.0.

Step 2. 1,1,1-Trifluoro-2-(4-methyl-3-(4,4,5,5-tetramethyl-1,3,2-dioxaborolan-2-yl)phenyl)propan-2-ol

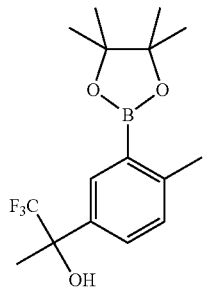 [SMILES: Cc1ccc(C(C)(O)C(F)(F)F)cc1B1OC(C)(C)C(C)(C)O1]

A mixture of 2-(3-bromo-4-methylphenyl)-1,1,1-trifluoropropan-2-ol (0.252 g, 0.890 mmol), bis(pinacolato)diboron (0.294 g, 1.16 mmol) and potassium acetate (0.288 g, 2.94 mmol) in tetrahydrofuran (4.95 mL) was degassed with nitrogen for 5 min. The reaction mixture was treated with triphenylphosphine palladium chloride (0.025 g, 0.036 mmol), degassed with nitrogen for another 5 min, and heated at 135° C. in the microwave for 20 min. The reaction mixture was diluted with ethyl acetate and filtered through a 0.5 micrometer cartridge that was rinsed with ethyl acetate. The filtrate was washed with water and brine, dried over sodium sulfate, filtered, and concentrated to give a crude residue. Purification by flash column chromatography using ether in hexanes (0%-50%) gave the desired product (272 mg, 92.5%) as a colorless oil. LCMS for $C_{16}H_{23}BF_3O_3$ (M+H)$^+$: m/z=331.2; Found: 331.2.

Step 3. 2-(Trifluoromethyl)imidazo[1,2-f][1,2,4]triazin-4-ol

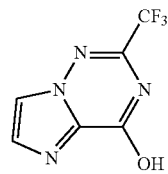 [SMILES: Oc1nc(C(F)(F)F)nn2ccnc12]

Ethyl 1-amino-1H-imidazole-2-carboxylate (3.22 g, 20.8 mmol) (Example 2, step 1) and trifluoroacetamidine (9.36 mL, 125 mmol, Oakwood) in EtOH (86 mL) were stirred in an oil bath held at 95° C. for 96 hours. The reaction mixture was cooled to room temperature and the white solid product was isolated by filtration (1.42 g, 34%). LCMS for $C_6H_4F_3N_4O$ (M+H)$^+$: calculated m/z=205.0; found 205.1. $^1$H NMR (400 MHz, CD$_3$OD) δ 7.77 (s, 1H), 7.49 (s, 1H).

Step 4. 7-Bromo-2-(trifluoromethyl)imidazo[1,2-f][1,2,4]triazin-4-ol

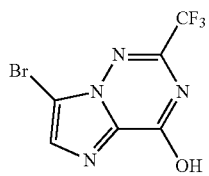 [SMILES: Oc1nc(C(F)(F)F)nn2c(Br)cnc12]

A solution of 2-(trifluoromethyl)imidazo[2,1-f][1,2,4]triazin-4-ol (1.46 g, 7.19 mmol) in DMF (25 mL) was treated with N-bromosuccinimide (NBS, 1.41 g, 7.91 mmol) for 1 h. The reaction mixture was diluted with water (100 mL), acidified to pH=2 using 1 N HCl, and was extracted with ethyl acetate (EtOAc) twice. The combined organic extracts were washed with water (3×100 mL) and brine (100 mL), dried over Na$_2$SO$_4$, filtered, and concentrated to afford a white solid (1.92 g, 95%). LCMS for $C_6H_3BrF_3N_4O$ (M+H)$^+$: calculated m/z=282.9, 284.9; found 283.0, 285.0. $^1$H NMR (400 MHz, CD$_3$OD) δ 7.67 (s, 1H).

Step 5. 7-Bromo-4-chloro-2-(trifluoromethyl)imidazo[1,2-f][1,2,4]triazine

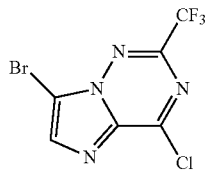

7-Bromo-2-(trifluoromethyl)imidazo[2,1-f][1,2,4]triazin-4-ol (1.92 g, 6.80 mmol) was heated at 110° C. in POCl$_3$ (20.0 mL, 215 mmol) for 30 minutes. Upon cooling to room temperature, POCl$_3$ was removed in vacuo. The residue was poured into a mixture of ice water. The aqueous mixture was made basic by the addition of sat'd NaHCO$_3$ solution (aq.), and the mixture was extracted with EtOAc (3×). The combined organic extracts were dried over sodium sulfate, filtered, and concentrated. The product was used without further purification in the next step (2.0 g, 98%). LCMS for $C_6H_2BrClF_3N_4$ (M+H)$^+$: calculated m/z=300.9, 302.9; found 301.0, 303.0.

Step 6. 7-Bromo-2-(trifluoromethyl)imidazo[1,2-f][1,2,4]triazin-4-amine

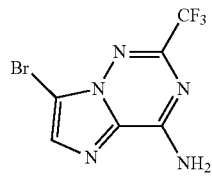 [SMILES: Nc1nc(C(F)(F)F)nn2c(Br)cnc12]

A suspension of 7-bromo-4-chloro-2-(trifluoromethyl)imidazo[2,1-f][1,2,4]triazine (2.0 g, 6.6 mmol) in ammonium hydroxide (23 mL, 330 mmol, 14.8 M NH$_4$OH) was heated to 80° C. in oil bath for 45 minutes. Upon cooling to room temperature, water was added and the mixture was extracted with EtOAc (3×). The combined organic extracts were dried over Na$_2$SO$_4$, filtered, and concentrated to afford an off-white solid (1.7 g, 92%). LCMS for $C_6H_4BrF_3N_5$ (M+H)$^+$: calculated m/z=282.0, 284.0; found 282.0, 284.0. $^1$H NMR (400 MHz, CDCl$_3$) δ 7.72 (s, 1H), 6.75 (br s, 1H), 6.46 (br s, 1H).

Step 7. 2-(3-(4-Amino-2-(trifluoromethyl)imidazo[2,1-f][1,2,4]triazin-7-yl)-4-methylphenyl)-1,1,1-trifluoropropan-2-ol A mixture of 7-bromo-2-(trifluoromethyl)imidazo[2,1-f][1,2,4]triazin-4-amine (0.014 g, 0.050 mmol) and 1,1,1-trifluoro-2-(4-methyl-3-(4,4,5,5-tetramethyl-1,3,2-dioxaborolan-2-yl)phenyl)propan-2-ol (Example 1, Step 2; 0.020 g, 0.060 mmol) in tetrahydrofuran (0.735 ml) was treated with 1.0 M potassium carbonate in water (0.125 ml, 0.125 mmol), degassed with nitrogen for 5 min, treated with dichloro[1,1'-bis(diphenylphosphino)ferrocene]palladium (II) dichloromethane adduct (6.12 mg, 7.50 µmol), degassed with nitrogen for an additional 5 min, and stirred at 80° C. for 14 h. The reaction mixture was diluted with ethyl acetate and filtered through a 0.5 micrometer cartridge that was rinsed with ethyl acetate. The filtrate was concentrated to give a crude residue that was purified via preparative LCMS (XBridge® C18 column, eluting with a gradient of acetonitrile/water 0.1% ammonium hydroxide, at flow rate of 60 mL/min) to give the desired product (3.90 mg, 19.2%) as a white solid. $^1$H NMR (400 MHz, DMSO-d$_6$) δ 8.88 (s, 2H), 7.85 (s, 1H), 7.69 (s, 1H), 7.61 (d, J=8.1 Hz, 1H), 7.41 (d, J=8.1 Hz, 1H), 6.60 (s, 1H), 2.24 (s, 3H), 1.68 (s, 3H). LCMS for $C_{16}H_{14}F_6N_5O$ (M+H)$^+$: m/z=406.1; Found: 406.1.

Example 2. 2-(3-(4-Amino-2-methylimidazo[2,1-f][1,2,4]triazin-7-yl)-4-methylphenyl)-1,1,1-trifluoropropan-2-ol

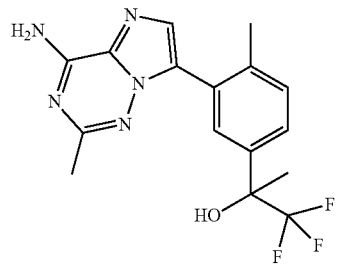 [SMILES: Cc1nc(N)c2ncc(-c3cc(C(C)(O)C(F)(F)F)ccc3C)n2n1]

149

Step 1. Ethyl 1-amino-1H-imidazole-2-carboxylate

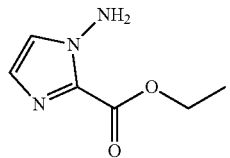

A solution of ethyl 1H-imidazole-2-carboxylate (10.0 g, 71.4 mmol) [Combi-Blocks, SS-7811] in N,N-dimethylformamide (357 mL) was treated with potassium tert-butoxide (74.9 mL, 74.9 mmol, 1.0 M in tetrahydrofuran) dropwise and stirred at 20° C. for 1 h. The reaction mixture was then treated with a solution of O-(4-nitrobenzoyl)hydroxylamine (13.7 g, 74.9 mmol) in N,N-dimethylformamide (120 mL) dropwise via an addition funnel and stirred at 20° C. for 3 h. The reaction mixture was filtered and the solid was washed with acetonitrile. The filtrate was evaporated to give the crude product as a slightly oily red solid that was used without further purification.

Step 2. 2-Methylimidazo[2,1-f][1,2,4]triazin-4-ol

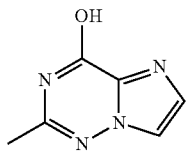

A solution of ethyl 1-amino-1H-imidazole-2-carboxylate (11.1 g, 71.4 mmol) in acetonitrile (179 mL) in a 3-neck round bottom flask equipped with a reflux condenser was cooled to 0° C. and bubbled with HCl gas for 10 min. The reaction mixture was then stirred at 80° C. for 1 h. The reaction mixture was concentrated and the resultant solid was triturated with diethyl ether to give crude intermediate amidine that was used immediately without further purification. A solution of the crude intermediate amidine in dioxane (179 mL) was treated carefully with 1.0 M sodium bicarbonate in water (71.4 mL, 71.4 mmol) and stirred at 100° C. for 1 h. The reaction mixture was concentrated and the resultant solid was diluted with acetonitrile and filtered to give the desired product (15.1 g) as an off-white solid that used without further purification. LCMS for $C_6H_7N_4O$ $(M+H)^+$: m/z=151.1; Found: 151.0.

Step 3. 7-Bromo-2-methylimidazo[2,1-f][1,2,4]triazin-4-ol

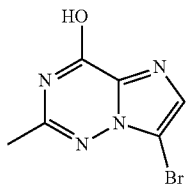

150

A suspension of 2-methylimidazo[2,1-f][1,2,4]triazin-4-ol (10.7 g, 71.4 mmol) in DMF (238 mL) was treated with N-bromosuccinimide (15.3 g, 86.0 mmol) and stirred at 80° C. for 1 h. The reaction mixture was concentrated and the residue was diluted with DCM, filtered, washed with additional DCM, and dried to give the desired product (14.7 g) as a white solid that was used without further purification. LCMS for $C_6H_6BrN_4O$ $(M+H)^+$: m/z=229.0, 231.0; Found: 229.0, 230.9.

Step 4. 7-Bromo-N-(4-methoxybenzyl)-2-methylimidazo[2,1-f][1,2,4]triazin-4-amine

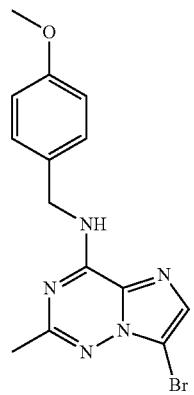 [SMILES: COc1ccc(CNc2nc(C)nn3c(Br)cnc23)cc1]

A heterogeneous mixture of 7-bromo-2-methylimidazo[2,1-f][1,2,4]triazin-4-ol (9.30 g, 40.6 mmol) and (benzotriazol-1-yloxy)tris(dimethylamino)phosphonium hexafluorophosphate (31.1 g, 70.2 mmol) in DCE (203 mL) was treated with 4-methoxybenzylamine (23.1 mL, 177 mmol) and 1,8-diazabicyclo[5.4.0]undec-7-ene (DBU, 4.41 mL, 29.2 mmol) and stirred at 20° C. for 20.5 h. The reaction mixture was treated with N,N-diisopropylethylamine (6.84 mL, 39.3 mmol) and stirred at 20° C. for 67 h. The reaction mixture was filtered and washed with DCM. The filtrate was concentrated to give a crude orange oil. Purification by flash column chromatography using ethyl acetate in hexanes (0%-30%) gave the desired product (4.80 g, 33.9%) as a yellow solid. LCMS for $C_{14}H_{15}BrN_5O$ $(M+H)^+$: m/z=348.0, 350.0; Found: 348.0, 350.0.

Step 5. 7-Bromo-2-methylimidazo[2,1-f][1,2,4]triazin-4-amine 2,2,2-trifluoroacetate

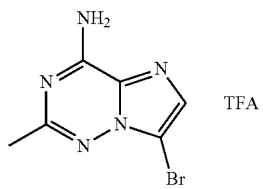

A solution of 7-bromo-N-(4-methoxybenzyl)-2-methylimidazo[2,1-f][1,2,4]triazin-4-amine (8.52 g, 24.5 mmol) in TFA (12.4 mL, 161 mmol) was stirred at 80° C. for 18 h. The reaction mixture was treated with additional TFA (12.4 mL, 161 mmol) and stirred at 80° C. for 5 h. The reaction mixture was concentrated and then diluted with toluene and re-concentrated (3×) to give 13.7 g of a crude green solid. The crude material was diluted with ethyl acetate (82 mL) and stirred at 80° C. for 45 min. This material did not completely dissolve. The mixture was cooled to 20° C., diluted with hexanes (82 mL) over 5 min, and stirred overnight. The solids were filtered and washed with hexanes to give the desired product (8.43 g, >99%) as a green solid. LCMS for $C_6H_7BrN_5$ (M+H)$^+$: m/z=228.0, 230.0; Found: 228.0, 230.0.

Step 6. 2-(3-(4-Amino-2-methylimidazo[2,1-f][1,2,4]triazin-7-yl)-4-methylphenyl)-1,1,1-trifluoropropan-2-ol The desired compound was prepared according to the procedure of Example 1, step 7, using 7-bromo-2-methylimidazo[2,1-f][1,2,4]triazin-4-amine 2,2,2-trifluoroacetate as the starting material. $^1$H NMR (400 MHz, DMSO-$d_6$) δ 8.11 (br s, 1H), 8.05 (br s, 1H), 7.68-7.47 (m, 3H), 7.38 (d, J=8.1 Hz, 1H), 6.58 (s, 1H), 2.25 (s, 3H), 2.20 (s, 3H), 1.69 (s, 3H). LCMS for $C_{16}H_{17}F_3N_5O$ (M+H)$^+$: m/z=352.1; Found: 352.1.

Example 3. 2-(3-(4-Aminoimidazo[2,1-f][1,2,4]triazin-7-yl)-4-methylphenyl)-1,1,1-trifluoropropan-2-ol

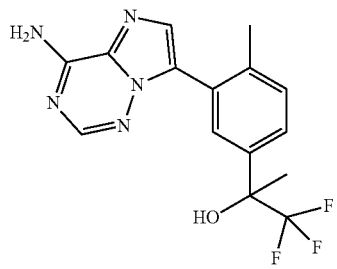 [SMILES: Cc1ccc(C(C)(O)C(F)(F)F)cc1-c1cnc2c(N)ncnn12]

The desired compound was prepared according to the procedure of Example 1 using 7-bromoimidazo[2,1-f][1,2,4]triazin-4-amine [Synthonix, A8092] as the starting material in step 7. $^1$H NMR (400 MHz, DMSO-$d_6$) δ 8.23 (br s, 1H), 8.18 (br s, 1H), 8.03 (s, 1H), 7.66 (s, 1H), 7.62 (s, 1H), 7.57 (d, J=8.1 Hz, 1H), 7.38 (d, J=8.1 Hz, 1H), 6.60 (br s, 1H), 2.19 (s, 3H), 1.68 (s, 3H). LCMS for $C_{15}H_{15}F_3N_5O$ (M+H)$^+$: m/z=338.1; Found: 338.1.

Example 4. 2-(3-(8-Amino-6-(trifluoromethyl)imidazo[1,2-a]pyrazin-3-yl)-4-methylphenyl)-1,1,1-trifluoropropan-2-ol (Mixture of Isomers)

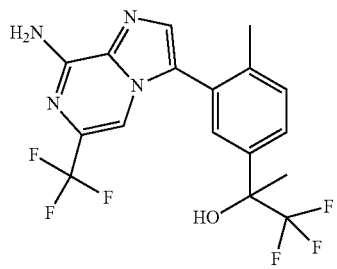 [SMILES: Cc1ccc(C(C)(O)C(F)(F)F)cc1-c1cnc2c(N)nc(C(F)(F)F)cn12]

Step 1. 5-(Trifluoromethyl)pyrazin-2-amine

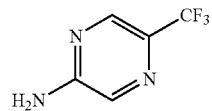

2-Chloro-5-(trifluoromethyl)pyrazine (5.0 g, 27 mmol) (Oakwood Products, 075803) was stirred in concentrated ammonium hydroxide (190 mL, 2.7 mol) and heated to 80° C. for 3.5 h in a sealed pressure vessel. After cooling to room temperature (rt), the aqueous mixture was extracted with DCM (4x). The extracts were combined, dried over sodium sulfate, filtered, and concentrated to afford the title compound as a white solid (4.0 g, 90%). $^1$H NMR (400 MHz, CDCl$_3$) δ 8.34 (s, 1H), 8.01 (s, 1H), 5.01 (br s, 2H). LCMS for $C_5H_5F_3N_3$ (M+H)$^+$: calculated m/z=164.0; found 164.1.

Step 2. 3-Chloro-5-(trifluoromethyl)pyrazin-2-amine

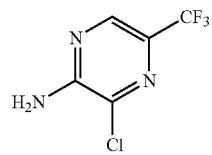

5-(Trifluoromethyl)pyrazin-2-amine (4.56 g, 28.0 mmol) was stirred in N-methyl-2-pyrrolidone (NMP, 135 mL, 1400 mmol) and N-chlorosuccinimide (3.73 g, 28.0 mmol) was added. The reaction mixture was stirred at rt for 6 h. The reaction mixture was poured into sat. sodium thiosulfate (100 mL) and diluted with water (500 mL). The mixture was extracted with ethyl acetate (4x200 mL). The combined extracts were washed with brine (3x), dried over sodium sulfate, filtered, and concentrated. Purification via silica gel column (0-35% EtOAc/hexanes) afforded the title compound as a white solid (2.32 g, 42.0%). LCMS for $C_5H_4ClF_3N_3$ (M+H)$^+$: calculated m/z=198.0; found 198.0.

Step 3. 8-Chloro-6-(trifluoromethyl)imidazo[1,2-a]pyrazine

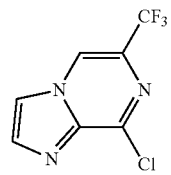 [SMILES: FC(F)(F)c1cn2ccnc2c(Cl)n1]

To a solution of 3-chloro-5-(trifluoromethyl)pyrazin-2-amine (2.32 g, 11.7 mmol) in EtOH (84 mL) was slowly added chloroacetaldehyde (37.3 mL, 294 mmol, 50% in H$_2$O). The reaction mixture was portioned into seven 20-mL microwave vials, and then each was heated at 150° C. for 20 min in a microwave reactor. The reaction mixtures were combined and concentrated, the residue was diluted with DCM, and triethylamine was added to adjust pH≥7. Purification via silica gel chromatography (0-50% EtOAc/ hexanes) afforded the title compound as a brown oil (1.93 g, 74.2%). LCMS for $C_7H_4ClF_3N_3$ (M+H)$^+$: calculated m/z=222.0; found 221.9.

Step 4. 3-Bromo-8-chloro-6-(trifluoromethyl)imidazo[1,2-a]pyrazine

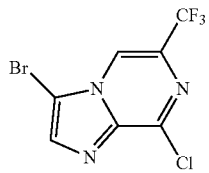 [SMILES: FC(F)(F)c1cn2c(Br)cnc2c(Cl)n1]

To a solution of 8-chloro-6-(trifluoromethyl)imidazo[1,2-a]pyrazine (0.37 g, 1.7 mmol) in DMF (11 mL) was added N-bromosuccinimide (0.30 g, 1.7 mmol). The reaction mixture was heated at 60° C. for 2 h. The reaction mixture was cooled to rt and poured into 40% sat. $Na_2S_2O_3$ (50 mL). The aqueous mixture was then extracted with DCM (3×40 mL). The combined organic layers were washed with brine (75 mL), dried over $Na_2SO_4$, filtered, and concentrated. Purification via silica gel chromatography (10-40% EtOAc/hexanes) afforded the title compound as a white solid (0.41 g, 82%). LCMS for $C_7H_3BrClF_3N_3$ (M+H)$^+$: calculated m/z=299.9, 301.9; found 299.9, 301.8.

Step 5. 3-Bromo-N-(4-methoxybenzyl)-6-(trifluoromethyl)imidazo[1,2-a]pyrazin-8-amine

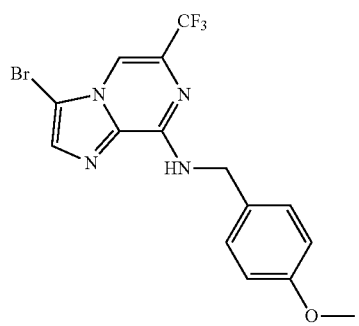 [SMILES: COc1ccc(CNc2nc(C(F)(F)F)cn3c(Br)cnc23)cc1]

A mixture of 3-bromo-8-chloro-6-(trifluoromethyl)imidazo[1,2-a]pyrazine (0.35 g, 1.2 mmol), N,N-diisopropylethylamine (0.40 mL, 2.3 mmol), and 4-methoxybenzylamine (0.17 mL, 1.3 mmol) in iPrOH (5.0 mL) was heated at 110° C. for 15 min in a microwave. The resulting white suspension was filtered and washed with water (3×). The resulting white solid was dried in vacuo overnight to afford the title compound as a white solid (0.53 g, >99%). $^1$H NMR (400 MHz, DMSO-d$_6$) δ 8.71 (t, J=6.0 Hz, 1H), 7.97 (s, 1H), 7.80 (s, 1H), 7.32 (d, J=8.6 Hz, 2H), 6.85 (d, J=8.6 Hz, 2H), 4.59 (d, J=6.0 Hz, 2H), 3.70 (s, 3H). $^{19}$F NMR (376 MHz, DMSO-d$_6$) δ -66.99. LCMS for $C_{15}H_{13}BrF_3N_4O$ (M+H)$^+$: calculated m/z=401.0, 403.0; found 401.0, 403.0.

Step 6. 3-Bromo-6-(trifluoromethyl)imidazo[1,2-a]pyrazin-8-amine

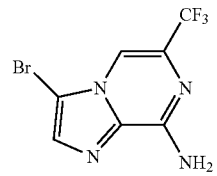

A solution of 3-bromo-N-(4-methoxybenzyl)-6-(trifluoromethyl)imidazo[1,2-a]pyrazin-8-amine (0.53 g, 1.2 mmol) in TFA (2.9 mL) was heated at 55° C. for 1 h. The reaction mixture was concentrated and then diluted with water (3.0 mL). With the reaction vial in a 0° C. bath, the aqueous mixture was basified with 1.0 M NaOH (7.5 mL). The bath was removed, and the aqueous mixture was stirred for 5 min. The resulting white precipitate was collected via filtration, washed with water (2×10 mL) and dried to afford the crude product as a white solid (0.440 g). Purification via silica gel chromatography (5-40% EtOAc/DCM) afforded the title compound as a white solid (0.25 g, 77%). $^1$H NMR (400 MHz, DMSO-d$_6$) δ 7.98 (s, 1H), 7.81 (s, 1H), 7.73 (br s, 2H). $^{19}$F NMR (376 MHz, DMSO-d$_6$) δ -66.77. LCMS for $C_7H_5BrF_3N_4$ (M+H)$^+$: calculated m/z=281.0, 283.0; found 280.9, 282.9.

Step 7. 2-(3-(8-Amino-6-(trifluoromethyl)imidazo[1,2-a]pyrazin-3-yl)-4-methylphenyl)-1,1,1-trifluoropropan-2-ol The desired compound was prepared according to the procedure of Example 1 using 3-bromo-6-(trifluoromethyl)imidazo[1,2-a]pyrazin-8-amine as the starting material in step 7. $^1$H NMR (400 MHz, DMSO-d$_6$) δ 7.77 (s, 1H), 7.69-7.58 (m, 4H), 7.55 (s, 1H), 7.47 (d, J=8.1 Hz, 1H), 6.66 (s, 1H), 2.21 (s, 3H), 1.70 (s, 3H). LCMS for $C_{17}H_{15}F_6N_4O$ (M+H)$^+$: m/z=405.1; Found: 405.1.

Examples 5-6. 2-(3-(8-Amino-6-(trifluoromethyl)imidazo[1,2-a]pyrazin-3-yl)-4-methylphenyl)-1,1,1-trifluoropropan-2-ol (Enantiomers 1-2)

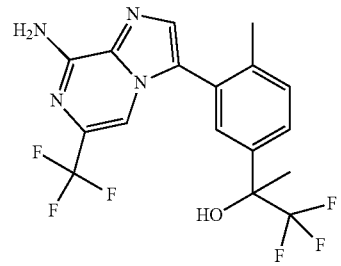 [SMILES: Cc1ccc(C(C)(O)C(F)(F)F)cc1-c1cnc2c(N)nc(C(F)(F)F)cn12]

The racemic mixture of Example 4, (2-(3-(8-Amino-6-(trifluoromethyl)imidazo[1,2-a]pyrazin-3-yl)-4-methylphenyl)-1,1,1-trifluoropropan-2-ol), was separated via preparative chiral HPLC (Phenomenex Lux Amylose-1 [21.2×250 mm, 5 micron], eluting with 10% ethanol in hexanes, at flow rate of 18 mL/min, loading ~9 mg in 900 μL ethanol). The first peak that eluted (Example 5) had a retention time of 18.2 min. The second peak that eluted (Example 6) had a retention time of 23.0 min.

Example 5 (Enantiomer 1): $^1$H NMR (500 MHz, DMSO-$d_6$) δ 7.77 (s, 1H), 7.69-7.58 (m, 4H), 7.55 (s, 1H), 7.47 (d, J=8.1 Hz, 1H), 6.65 (s, 1H), 2.21 (s, 3H), 1.70 (s, 3H). LCMS for $C_{17}H_{15}F_6N_4O$ (M+H)$^+$: m/z=405.1; Found: 405.1.

Example 6 (Enantiomer 2): $^1$H NMR (500 MHz, DMSO-$d_6$) δ 7.77 (s, 1H), 7.70-7.58 (m, 4H), 7.55 (s, 1H), 7.47 (d, J=8.1 Hz, 1H), 6.65 (s, 1H), 2.21 (s, 3H), 1.70 (s, 3H). LCMS for $C_{17}H_{15}F_6N_4O$ (M+H)$^+$: m/z=405.1; Found: 405.1.

Example 7. 2-(3-(8-Amino-6-methylimidazo[1,2-a]pyrazin-3-yl)-4-methylphenyl)-1,1,1-trifluoropropan-2-ol

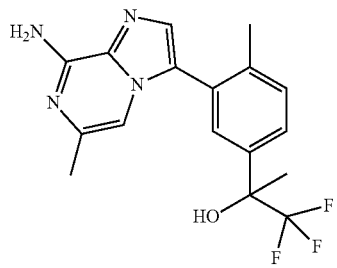 [SMILES: Cc1cn2c(-c3cc(C(C)(O)C(F)(F)F)ccc3C)cnc2c(N)n1]

Step 1. 8-Bromo-3-iodo-6-methylimidazo[1,2-a]pyrazine

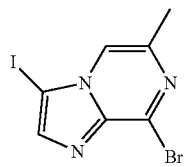

A solution of 8-bromo-6-methylimidazo[1,2-a]pyrazine (0.881 g, 4.15 mmol) [Frontier, B12886] in DMF (27.7 mL) was treated with N-iodosuccinimide (1.03 g, 4.57 mmol) and stirred at 60° C. overnight. The reaction mixture was cooled to rt and poured into 50% sat. $Na_2S_2O_3$ (50 mL). The aqueous mixture was extracted with DCM (3×50 mL). The combined organic layers were washed with water (100 mL) and then a 1:1 mixture of brine and sat. $Na_2S_2O_3$ (100 mL), dried over magnesium sulfate, filtered, and concentrated to afford the desired product (1.30 g, 93%) as a brown solid that was used without further purification. LCMS for $C_7H_6BrIN_3$ (M+H)$^+$: calculated m/z=337.9, 339.9; found 337.9, 339.9.

Step 2. 3-Iodo-6-methylimidazo[1,2-a]pyrazin-8-amine

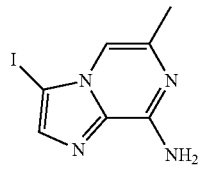

A suspension of 8-bromo-3-iodo-6-methylimidazo[1,2-a]pyrazine (107 mg, 0.317 mmol) in 14.5 M ammonium hydroxide in water (40 mmol) (conc. $NH_4OH$) was heated at 150° C. for 15 min in a microwave. After cooling to 0° C., the reaction mixture was diluted with cold water and filtered. The collected solid was then washed with cold water to afford the desired product (65.1 mg, 75%) as an off-white solid that was used without further purification. $^1$H NMR (400 MHz, DMSO-$d_6$) δ 7.58 (s, 1H), 7.38 (s, 1H), 6.95 (s, 2H), 2.23 (s, 3H). LCMS for $C_7H_8IN_4$ (M+H)$^+$: calculated m/z=275.0; found 275.0.

Step 3. 2-(3-(8-Amino-6-methylimidazo[1,2-a]pyrazin-3-yl)-4-methylphenyl)-1,1,1-trifluoropropan-2-ol The desired compound was prepared according to the procedure of Example 1 using 3-iodo-6-methylimidazo[1,2-a]pyrazin-8-amine as the starting material in step 7. $^1$H NMR (400 MHz, DMSO-$d_6$) δ 7.60 (d, J=8.1 Hz, 1H), 7.52 (s, 2H), 7.44 (d, J=8.2 Hz, 1H), 6.99 (s, 1H), 6.92 (s, 2H), 6.63 (br s, 1H), 2.15 (s, 3H), 2.13 (s, 3H), 1.70 (s, 3H). LCMS for $C_{17}H_{18}F_3N_4O$ (M+H)$^+$: m/z=351.1; Found: 351.2.

Example 8. Methyl 8-amino-3-(2-methyl-5-(1,1,1-trifluoro-2-hydroxypropan-2-yl)phenyl)imidazo[1,2-a]pyrazine-6-carboxylate

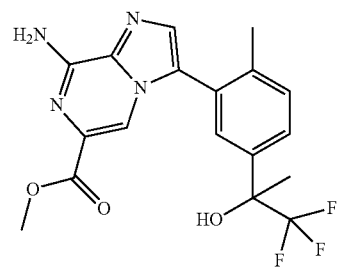 [SMILES: COC(=O)c1cn2c(-c3cc(C(C)(O)C(F)(F)F)ccc3C)cnc2c(N)n1]

Step 1. 6,8-Dibromo-3-iodoimidazo[1,2-a]pyrazine

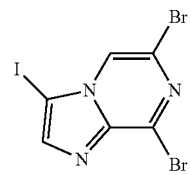 [SMILES: Brc1cn2c(I)cnc2c(Br)n1]

To a solution of 6,8-dibromoimidazo[1,2-a]pyrazine (0.50 g, 1.8 mmol) [Combi-Blocks, OR-7964] in DMF (12 mL) was added N-iodosuccinimide (0.45 g, 2.0 mmol). The reaction mixture was then heated at 60° C. for 15.5 h. The reaction mixture was concentrated in vacuo. The resulting solid was taken up into dichloromethane (DCM). The organic layer was washed sequentially with water and sat. $Na_2S_2O_3$ (aq). The organic layer was then dried over $Na_2SO_4$, filtered, and concentrated to afford the title compound as a light yellow solid (0.64 g, 88%). LCMS for $C_6H_3Br_2IN_3$ (M+H)$^+$: calculated m/z=401.8, 403.8, 405.8; found 401.8, 403.7, 405.6.

Step 2. 6-Bromo-3-iodo-N-(4-methoxybenzyl)imidazo[1,2-a]pyrazin-8-amine

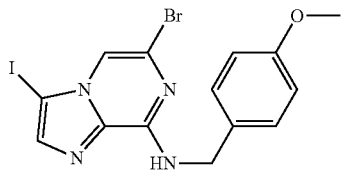 [SMILES: COc1ccc(CNc2nc(Br)cn3c(I)cnc23)cc1]

A solution of 6,8-dibromo-3-iodoimidazo[1,2-a]pyrazine (1.67 g, 3.57 mmol), N,N-diisopropylethylamine (1.24 mL, 7.13 mmol), and (4-methoxyphenyl)methanamine (0.512 mL, 3.92 mmol) in iPrOH (11.9 mL) was heated in a microwave at 110° C. for 1 h. After cooling to room temperature, the solidified reaction mixture was diluted with isopropanol (75 mL) and water (19 mL) and stirred for 10 min. The solids were collected by filtration to give the desired product (1.41 g, 86.1%) that was used without further purification. LCMS for $C_{14}H_{13}BrIN_4O$ $(M+H)^+$: calculated m/z=458.9, 460.9; found 459.0, 461.0.

Step 3. 6-Bromo-3-iodoimidazo[1,2-a]pyrazin-8-amine trifluoroacetate

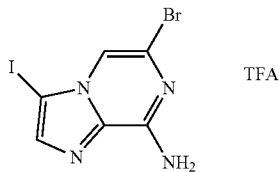 [SMILES: Nc1nc(Br)cn2c(I)cnc12]

A solution of 6-bromo-3-iodo-N-(4-methoxybenzyl)imidazo[1,2-a]pyrazin-8-amine (2.72 g, 5.92 mmol) in trifluoroacetic acid (TFA, 14.8 mL) was stirred at 55° C. for 5.5 h. The reaction mixture was concentrated and re-concentrated after diluting with acetonitrile (2×). The solid was diluted with ethyl acetate (12 mL) and stirred at room temperature for 1 h. The slurry was diluted with hexanes (12 mL) dropwise and stirred at room temperature for 75 min. The solids were collected by filtration to give the desired product (2.03 g, 75.7%) that was used without further purification. LCMS for $C_6H_5BrIN_4$ $(M+H)^+$: calculated m/z=338.9, 340.9; found 338.8, 340.8.

Step 4. 2-(3-(8-Amino-6-bromoimidazo[1,2-a]pyrazin-3-yl)-4-methylphenyl)-1,1,1-trifluoropropan-2-ol

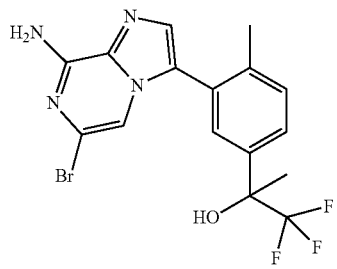 [SMILES: Cc1ccc(C(C)(O)C(F)(F)F)cc1-c1cnc2c(N)nc(Br)cn12]

A mixture of 6-bromo-3-iodoimidazo[1,2-a]pyrazin-8-amine trifluoroacetate (0.855 g, 1.89 mmol), 1,1,1-trifluoro-2-(4-methyl-3-(4,4,5,5-tetramethyl-1,3,2-dioxaborolan-2-yl)phenyl)propan-2-ol (Example 1, Step 2; 0.623 g, 1.89 mmol), and tetrakis(triphenylphosphine)palladium(0) (0.131 g, 0.113 mmol) in ethanol (12.6 ml) was treated with 2.0 M sodium carbonate in water (1.89 ml, 3.77 mmol), degassed with nitrogen for 5 min, and heated in a microwave reactor at 130° C. for 2 h. The reaction mixture was partially concentrated to remove ethanol and diluted with ethyl acetate and water. The solids were removed with filtration and the aqueous layer of the filtrate was separated and extracted with ethyl acetate (2×). The combined organic layers were washed with brine, dried over magnesium sulfate, filtered, and concentrated to give a crude residue. Purification by flash column chromatography using methanol in dichloromethane (0%-2%) gave the desired product (610 mg, 77.8%) as a white foam. LCMS for $C_{16}H_{15}BrF_3N_4O$ $(M+H)^+$: m/z=415.0, 417.0; Found: 415.0, 417.0.

Step 5. Methyl 8-amino-3-(2-methyl-5-(1,1,1-trifluoro-2-hydroxypropan-2-yl)phenyl)imidazo[1,2-a]pyrazine-6-carboxylate A solution of 2-(3-(8-amino-6-bromoimidazo[1,2-a]pyrazin-3-yl)-4-methylphenyl)-1,1,1-trifluoropropan-2-ol (Example 8, Step 4; 0.250 g, 0.602 mmol) in methanol (16.1 ml) was treated with triethylamine (0.336 ml, 2.41 mmol), and degassed with nitrogen for 5 min. The reaction mixture was treated with $Pd(dppf)_2CH_2Cl_2$ (0.049 g, 0.060 mmol), degassed with nitrogen for another 5 min, saturated with CO by bubbling the gas through the reaction subsurface for 3 min, and heated at 60° C. overnight. The reaction mixture was concentrated and the resultant red oil was diluted with ethyl acetate, water, and saturated sodium bicarbonate. The aqueous layer was separated and re-extracted with ethyl acetate (2×). The combined organic layers were washed with brine, dried over magnesium sulfate, filtered, and concentrated to a brown oil. Purification by flash column chromatography using methanol in dichloromethane (0%-4%) gave the desired product (158 mg, 66.5%) as an amber oily solid. LCMS for $C_{18}H_{18}F_3N_4O_3$ $(M+H)^+$: m/z=395.1; Found: 395.1.

Example 9. 8-Amino-N-methyl-3-(2-methyl-5-(1,1,1-trifluoro-2-hydroxypropan-2-yl)phenyl)imidazo[1,2-a]pyrazine-6-carboxamide

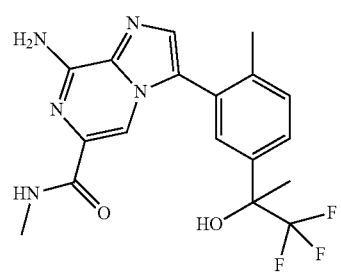 [SMILES: CNC(=O)c1cn2c(-c3cc(C(C)(O)C(F)(F)F)ccc3C)cnc2c(N)n1]

A solution of methyl 8-amino-3-(2-methyl-5-(1,1,1-trifluoro-2-hydroxypropan-2-yl)phenyl)imidazo[1,2-a]pyrazine-6-carboxylate (Example 8, 0.010 g, 0.025 mmol) in tetrahydrofuran (0.423 ml) in a sealable tube was treated with methanamine (0.127 ml, 0.254 mmol) (2.0 M in THF)

followed by trimethylaluminum (0.063 ml, 0.127 mmol) (2M in toluene) and heated at 80° C. overnight in the sealed tube. After cooling to room temperature the reaction mixture was diluted with methanol and stirred at room temperature for 90 min before passing through a 0.45 μm filter. The filtrate was concentrated to give a crude residue that was purified via preparative LCMS (XBridge® C18 column, eluting with a gradient of acetonitrile/water 0.1% ammonium hydroxide, at flow rate of 60 mL/min) to give the desired product (2.20 mg, 22.1%) as a white solid. $^1$H NMR (400 MHz, DMSO-$d_6$) δ 8.11 (d, J=5.2 Hz, 1H), 7.74-7.62 (m, 3H), 7.57 (s, 1H), 7.49 (d, J=8.2 Hz, 1H), 7.19 (s, 2H), 6.65 (s, 1H), 2.78 (d, J=4.9 Hz, 3H), 2.15 (s, 3H), 1.70 (s, 3H). LCMS for $C_{18}H_{19}F_3N_5O_2$ (M+H)$^+$: m/z=394.1; Found: 394.1.

Example 10. 2-(3-(8-Amino-6-(2-(hydroxymethyl)pyridin-4-yl)imidazo[1,2-a]pyrazin-3-yl)-4-methylphenyl)-1,1,1-trifluoropropan-2-ol (Mixture of Isomers)

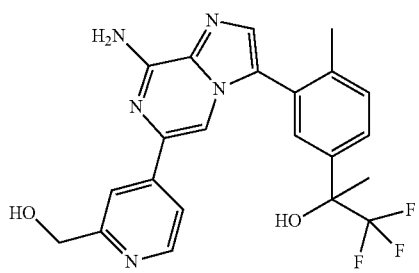 [SMILES: Cc1ccc(C(C)(O)C(F)(F)F)cc1-c1cnc2c(N)nc(-c3ccnc(CO)c3)cn12]

A solution of (2-(hydroxymethyl)pyridin-4-yl)boronic acid (10.6 mg, 0.069 mmol) [Combi-Blocks, FA-5835] and 2-(3-(8-amino-6-bromoimidazo[1,2-a]pyrazin-3-yl)-4-methylphenyl)-1,1,1-trifluoropropan-2-ol (Example 8, Step 4; 0.020 g, 0.035 mmol) in tetrahydrofuran (0.694 ml) in a sealable tube was stirred for 5 min, treated with 1.0 M potassium carbonate in water (0.104 ml, 0.104 mmol), degassed with nitrogen for 5 min, treated with dichloro[1,1'-bis(diphenylphosphino)ferrocene]palladium (II) dichloromethane adduct (5.66 mg, 6.94 μmol), degassed with nitrogen for another 5 min, and heated at 80° C. for 15 h in the sealed tube. The reaction mixture was diluted with ethyl acetate and filtered through a 0.5 micrometer cartridge that was rinsed with ethyl acetate. The filtrate was concentrated and purified via preparative LCMS (XBridge® C18 column, eluting with a gradient of acetonitrile/water 0.1% ammonium hydroxide, at flow rate of 60 mL/min) to give the desired product (2.70 mg, 17.6%) as a white solid. $^1$H NMR (400 MHz, DMSO-$d_6$) δ 8.45 (d, J=5.2 Hz, 1H), 7.97 (s, 1H), 7.79 (s, 1H), 7.72-7.56 (m, 4H), 7.49 (d, J=7.9 Hz, 1H), 7.29 (s, 2H), 6.65 (s, 1H), 5.39 (t, J=5.7 Hz, 1H), 4.57 (d, J=5.6 Hz, 2H), 2.23 (s, 3H), 1.72 (s, 3H). LCMS for $C_{22}H_{21}F_3N_5O_2$ (M+H)$^+$: m/z=444.2; Found: 444.1.

Examples 11-12. 2-(3-(8-amino-6-(2-(hydroxymethyl)pyridin-4-yl)imidazo[1,2-a]pyrazin-3-yl)-4-methylphenyl)-1,1,1-trifluoropropan-2-ol (Enantiomers 1-2)

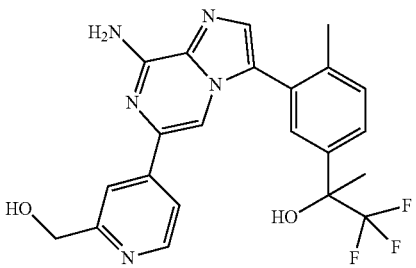 [SMILES: Cc1ccc(C(C)(O)C(F)(F)F)cc1-c1cnc2c(N)nc(-c3ccnc(CO)c3)cn12]

The racemic mixture of Example 10, 2-(3-(8-amino-6-(2-(hydroxymethyl)pyridin-4-yl)imidazo[1,2-a]pyrazin-3-yl)-4-methylphenyl)-1,1,1-trifluoropropan-2-ol, was separated via preparative chiral HPLC (Phenomenex Lux Amylose-1 [21.2×250 mm, 5 micron], eluting with 20% ethanol in hexanes, at flow rate of 18 mL/min, loading ~3.6 mg in 900 μL ethanol). The first peak that eluted (Example 11) had a retention time of 7.8 min. The second peak that eluted (Example 12) had a retention time of 12.6 min.

Example 11 (Enantiomer 1): $^1$H NMR (400 MHz, DMSO-$d_6$) δ 8.45 (d, J=5.1 Hz, 1H), 7.97 (s, 1H), 7.79 (s, 1H), 7.72-7.57 (m, 4H), 7.49 (d, J=7.9 Hz, 1H), 7.29 (s, 2H), 6.65 (s, 1H), 5.39 (t, J=5.5 Hz, 1H), 4.57 (d, J=5.1 Hz, 2H), 2.23 (s, 3H), 1.72 (s, 3H). LCMS for $C_{22}H_{21}F_3N_5O_2$ (M+H)$^+$: m/z=444.2; Found: 444.1.

Example 12 (Enantiomer 2): $^1$H NMR (400 MHz, DMSO-$d_6$) δ 8.45 (d, J=5.2 Hz, 1H), 7.97 (s, 1H), 7.79 (s, 1H), 7.73-7.57 (m, 4H), 7.49 (d, J=7.9 Hz, 1H), 7.29 (s, 2H), 6.65 (s, 1H), 5.39 (t, J=5.6 Hz, 1H), 4.57 (d, J=5.2 Hz, 2H), 2.23 (s, 3H), 1.72 (s, 3H). LCMS for $C_{22}H_{21}F_3N_5O_2$ (M+H)$^+$: m/z=444.2; Found: 444.1.

Example 13. 1-(3-(8-Amino-6-(trifluoromethyl)imidazo[1,2-a]pyrazin-3-yl)-4-methylphenyl)-2,2,2-trifluoro-1-(1-methyl-1H-tetrazol-5-yl)ethan-1-ol trifluoroacetate

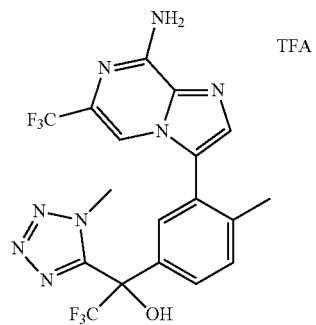 [SMILES: Cc1ccc(C(O)(c2nnnn2C)C(F)(F)F)cc1-c1cnc2c(N)nc(C(F)(F)F)cn12]

Step 1. (3-Bromo-4-methylphenyl)(1-methyl-1H-tetrazol-5-yl)methanol

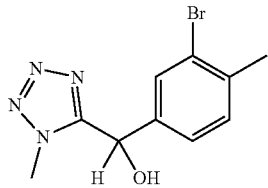 [SMILES: Cc1ccc(C(O)c2nnnn2C)cc1Br]

A solution of 1-methyl-1H-tetrazole (0.110 g, 1.31 mmol) [TCI, M2451] in tetrahydrofuran (3.0 mL) at −78° C. was treated with 1.6 M n-butyllithium in hexanes (0.785 ml, 1.26 mmol) dropwise and stirred for 10 min. The reaction mixture was treated with a solution of 3-bromo-4-methylbenzaldehyde (0.20 g, 1.01 mmol) [Combi-Blocks, HC-3454] in tetrahydrofuran (1.0 mL) dropwise and stirred at −78° C. for 15 min. The reaction mixture was warmed to room temperature and quenched with saturated ammonium chloride. The reaction mixture was diluted with water and extracted with ethyl acetate (2×). The combined organic layers were washed with brine, dried over magnesium sulfate, filtered, and concentrated to a crude residue. Purification by flash column chromatography using methanol in dichloromethane (0%-5%) gave the desired product (137 mg, 48.2%) as an amber oily solid. LCMS for $C_{10}H_{12}BrN_4O$ $(M+H)^+$: m/z=283.0, 285.0; Found: 283.0, 285.0.

Step 2. (3-Bromo-4-methylphenyl)(1-methyl-1H-tetrazol-5-yl)methanone

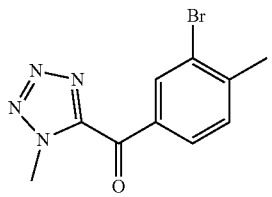 [SMILES: Cc1ccc(C(=O)c2nnnn2C)cc1Br]

A solution of (3-bromo-4-methylphenyl)(1-methyl-1H-tetrazol-5-yl)methanol (0.117 g, 0.413 mmol) in dichloromethane (1.65 mL) at 0° C. was treated with Dess-Martin periodinane (0.263 g, 0.62 mmol) and stirred at room temperature overnight. The reaction mixture was diluted with saturated sodium bicarbonate, ethyl acetate, and water. The mixture was filtered to remove solids. The aqueous layer of the filtrate was separated and extracted with ethyl acetate (2×). The combined organic layers were washed with saturated sodium bicarbonate (2×) and brine, dried over magnesium sulfate, filtered, and concentrated to give the desired product (113 mg, 97.4%) as a white solid that was used without further purification. LCMS for $C_{10}H_{10}BrN_4O$ $(M+H)^+$: m/z=281.0, 283.0; Found: 280.9, 282.9.

Step 3. 1-(3-Bromo-4-methylphenyl)-2,2,2-trifluoro-1-(1-methyl-1H-tetrazol-5-yl)ethan-1-ol

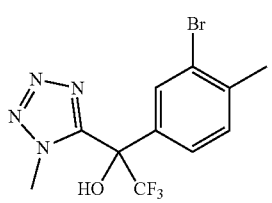 [SMILES: Cc1ccc(C(O)(c2nnnn2C)C(F)(F)F)cc1Br]

The desired compound was prepared according to the procedure of Example 1, step 1, using (3-bromo-4-methylphenyl)(1-methyl-1H-tetrazol-5-yl)methanone as the starting material. LCMS for $C_{11}H_{11}BrF_3N_4O$ $(M+H)^+$: m/z=351.0, 353.0; Found: 350.9, 352.9.

Step 4. 2,2,2-Trifluoro-1-(1-methyl-1H-tetrazol-5-yl)-1-(4-methyl-3-(4,4,5,5-tetramethyl-1,3,2-dioxaborolan-2-yl)phenyl)ethan-1-ol

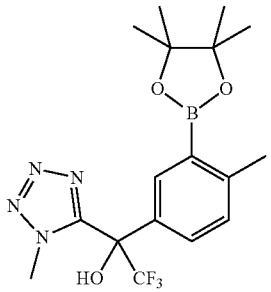 [SMILES: Cc1ccc(C(O)(c2nnnn2C)C(F)(F)F)cc1B1OC(C)(C)C(C)(C)O1]

The desired compound was prepared according to the procedure of Example 1, step 2, using 1-(3-bromo-4-methylphenyl)-2,2,2-trifluoro-1-(1-methyl-1H-tetrazol-5-yl)ethan-1-ol as the starting material. LCMS for $C_{17}H_{23}BF_3N_4O_3$ $(M+H)^+$: m/z=399.2; Found: 399.1.

Step 5. 1-(3-(8-Amino-6-(trifluoromethyl)imidazo[1,2-a]pyrazin-3-yl)-4-methylphenyl)-2,2,2-trifluoro-1-(1-methyl-1H-tetrazol-5-yl)ethan-1-ol, TFA The desired compound was prepared according to the procedure of Example 1, step 7, using 2,2,2-trifluoro-1-(1-methyl-1H-tetrazol-5-yl)-1-(4-methyl-3-(4,4,5,5-tetramethyl-1,3,2-dioxaborolan-2-yl)phenyl)ethan-1-ol and 3-bromo-6-(trifluoromethyl)imidazo[1,2-a]pyrazin-8-amine (Example 4, Step 6) as the starting materials. $^1$H NMR (400 MHz, DMSO-d$_6$) δ 8.58 (s, 1H), 7.78 (s, 1H), 7.64 (br s, 2H), 7.57-7.48 (m, 2H), 7.42-7.31 (m, 2H), 3.77 (s, 3H), 2.24 (s, 3H). LCMS for $C_{18}H_{15}F_6N_8O$ $(M+H)^+$: m/z=473.1; Found: 473.1.

Example 14. 2-(3-(8-Amino-6-(trifluoromethyl)imidazo[1,2-a]pyrazin-3-yl)-4-methylphenyl)-1,1,1-trifluoro-4-(methylamino)butan-2-ol bis(2,2,2-trifluoroacetate) (Mixture of Isomers)

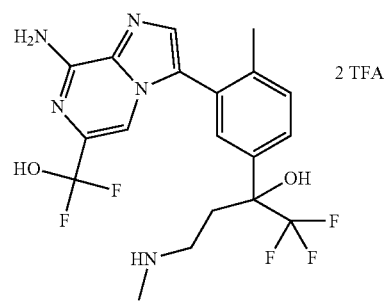 [SMILES: CNCCC(O)(c1ccc(C)c(-c2cnc3c(N)nc(C(O)(F)F)cn23)c1)C(F)(F)F]

Step 1. 1-(3-Bromo-4-methylphenyl)-2,2,2-trifluoroethan-1-ol

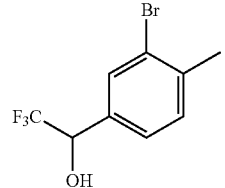

The desired compound was prepared according to the procedure of Example 1, step 1, using 3-bromo-4-methylbenzaldehyde [Aldrich, 750573] as the starting material. LCMS for $C_9H_7BrF_3$ (M-OH)$^+$: m/z=251.0, 253.0; Found: 250.9, 252.9.

Step 2. 1-(3-Bromo-4-methylphenyl)-2,2,2-trifluoroethan-1-one

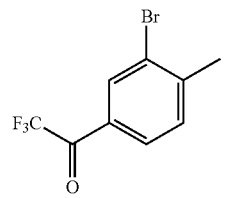

The desired compound was prepared according to the procedure of Example 13, step 2, using 1-(3-bromo-4-methylphenyl)-2,2,2-trifluoroethan-1-ol as the starting material. LCMS for $C_9H_7BrF_3O$ (M+H)$^+$: m/z=267.0, 269.0; Found: 266.9, 268.9.

Step 3. 2-(3-Bromo-4-methylphenyl)-3-(1,3-dioxolan-2-yl)-1,1,1-trifluoropropan-2-ol

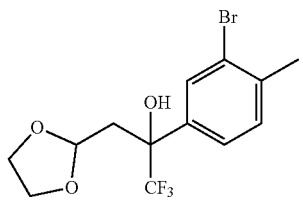 [SMILES: Cc1ccc(C(O)(CC2OCCO2)C(F)(F)F)cc1Br]

A solution of 1-(3-bromo-4-methylphenyl)-2,2,2-trifluoroethan-1-one (0.520 g, 1.95 mmol) in tetrahydrofuran (1.95 ml) in an oven dried flask was treated with (1,3-dioxolan-2-ylmethyl)magnesium bromide (0.5 M in THF) (9.74 mL, 4.87 mmol) [Aldrich, 472611] dropwise and stirred at 60° C. for 5 h. The reaction mixture was cooled to 0° C. and quenched with saturated ammonium chloride (20 mL) and with ethyl acetate (50 mL). A small amount of water was added to dissolve all solids. The organic layer was washed with brine, dried over sodium sulfate, filtered, and concentrated to give a crude residue. Purification by flash column chromatography using MTBE in hexanes (0%-40%) gave the desired product (0.528 g, 76.3%) as a white solid. LCMS for $C_{13}H_{18}BrF_3NO_3$ (M+NH$_4$)$^+$: m/z=372.0, 374.0; Found: 372.1, 374.1.

Step 4. 3-(1,3-Dioxolan-2-yl)-1,1,1-trifluoro-2-(4-methyl-3-(4,4,5,5-tetramethyl-1,3,2-dioxaborolan-2-yl)phenyl)propan-2-ol

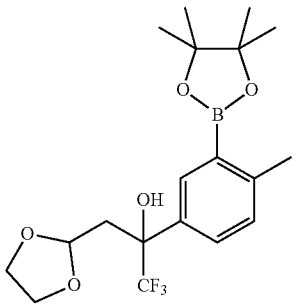 [SMILES: Cc1ccc(C(O)(CC2OCCO2)C(F)(F)F)cc1B1OC(C)(C)C(C)(C)O1]

The desired compound was prepared according to the procedure of Example 1, step 2, using 2-(3-bromo-4-methylphenyl)-3-(1,3-dioxolan-2-yl)-1,1,1-trifluoropropan-2-ol as the starting material. LCMS for $C_{19}H_{30}BF_3NO_5$ (M+NH$_4$)$^+$: m/z=420.2; Found: 420.2.

Step 5. 2-(3-(8-Amino-6-(trifluoromethyl)imidazo[1,2-a]pyrazin-3-yl)-4-methylphenyl)-3-(1,3-dioxolan-2-yl)-1,1,1-trifluoropropan-2-ol

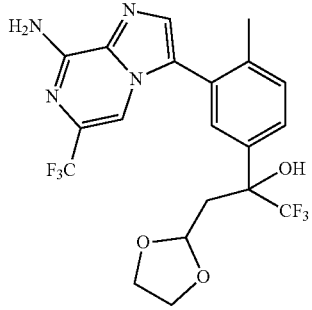 [SMILES: Cc1ccc(C(O)(CC2OCCO2)C(F)(F)F)cc1-c1cnc2c(N)nc(C(F)(F)F)cn12]

The desired compound was prepared according to the procedure of Example 1, step 7, using 3-(1,3-dioxolan-2-yl)-1,1,1-trifluoro-2-(4-methyl-3-(4,4,5,5-tetramethyl-1,3,2-dioxaborolan-2-yl)phenyl)propan-2-ol and 3-bromo-6-(trifluoromethyl)imidazo[1,2-a]pyrazin-8-amine (Example 4, Step 6) as the starting materials. LCMS for $C_{20}H_{19}F_6N_4O_3$ (M+H)$^+$: m/z=477.1; Found: 477.1.

Step 6. 3-(3-(8-Amino-6-(trifluoromethyl)imidazo[1,2-a]pyrazin-3-yl)-4-methylphenyl)-4,4,4-trifluoro-3-hydroxybutanal

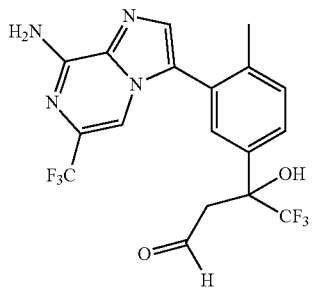 [SMILES: Cc1ccc(C(O)(CC=O)C(F)(F)F)cc1-c1cnc2c(N)nc(C(F)(F)F)cn12]

A solution of 2-(3-(8-amino-6-(trifluoromethyl)imidazo[1,2-a]pyrazin-3-yl)-4-methylphenyl)-3-(1,3-dioxolan-2-yl)-1,1,1-trifluoropropan-2-ol (0.207 g, 0.435 mmol) in tetrahydrofuran (2.90 mL) was treated with 6.0 M hydrogen chloride in water (1.45 ml, 8.69 mmol) dropwise and stirred at 60° C. for 1 h. The reaction mixture was added dropwise to ice cooled saturated sodium bicarbonate solution (25 ml) and extracted with ethyl acetate (50 mL). The organic layer was washed with brine, dried over sodium sulfate, filtered, and concentrated to give the desired product (207 mg, quantitative) as a white foam that was used without further purification. LCMS for $C_{18}H_{15}F_6N_4O_2$ (M+H)$^+$: m/z=433.1; Found: 433.1.

Step 7. 2-(3-(8-Amino-6-(trifluoromethyl)imidazo [1,2-a]pyrazin-3-yl)-4-methylphenyl)-1,1,1-trifluoro-4-(methylamino)butan-2-ol bis(2,2,2-trifluoroacetate)

A solution of 3-(3-(8-amino-6-(trifluoromethyl)imidazo [1,2-a]pyrazin-3-yl)-4-methylphenyl)-4,4,4-trifluoro-3-hydroxybutanal (22.5 mg, 0.052 mmol) in methanol (1.04 ml) was treated with methylamine (2M in THF) (0.156 ml, 0.312 mmol) and stirred for 1 h. The reaction mixture was treated with sodium cyanoborohydride (6.54 mg, 0.104 mmol) and stirred for 14 h. The reaction mixture was concentrated and the crude residue was purified via preparative LCMS (XBridge® C18 Column, eluting with a gradient of acetonitrile in water with 0.1% trifluoroacetic acid, at flow rate of 60 mL/min) to give the desired product (7.30 mg, 20.8%) as a white solid. $^1$H NMR (400 MHz, DMSO-d$_6$) δ 8.35 (br s, 2H), 7.80 (s, 1H), 7.73-7.47 (m, 5H), 7.07 (s, 1H), 2.98-2.82 (m, 1H), 2.69-2.51 (m, 5H), 2.40-2.28 (m, 1H), 2.24 (s, 3H). LCMS for $C_{19}H_{20}F_6N_5O$ (M+H)$^+$: m/z=448.1; Found: 448.1.

Examples 15-16. 2-(3-(8-amino-6-(trifluoromethyl) imidazo[1,2-a]pyrazin-3-yl)-4-methylphenyl)-1,1,1-trifluoro-4-(methylamino)butan-2-ol (Enantiomers 1-2)

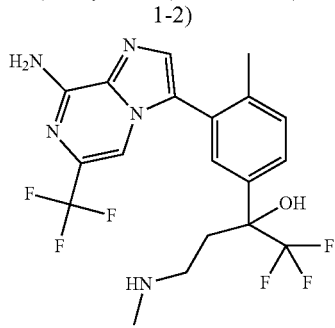

Step 1. tert-Butyl (3-(3-(8-amino-6-(trifluoromethyl)imidazo[1,2-a]pyrazin-3-yl)-4-methylphenyl)-4,4,4-trifluoro-3-hydroxybutyl)(methyl)carbamate

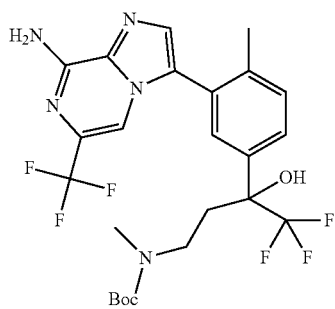 [SMILES: Cc1ccc(C(O)(CCN(C)C(=O)OC(C)(C)C)C(F)(F)F)cc1-c1cnc2c(N)nc(C(F)(F)F)cn12]

A solution of 2-(3-(8-amino-6-(trifluoromethyl)imidazo [1,2-a]pyrazin-3-yl)-4-methylphenyl)-1,1,1-trifluoro-4-(methylamino)butan-2-ol (Example 14, 0.375 g, 0.838 mmol) in ethanol (5.59 mL) was treated with di-tert-butyl-dicarbonate (0.231 ml, 1.01 mmol) and stirred for 1 h. The reaction mixture was concentrated to a crude residue. Purification by flash column chromatography using ethyl acetate in hexanes (0%-70%) gave the desired product (0.453 g, 98.7%) as a white foam. LCMS for $C_{24}H_{28}F_6N_5O_3$ (M+H)$^+$: m/z=548.2; Found: 548.2.

Step 2. tert-butyl (3-(3-(8-amino-6-(trifluoromethyl) imidazo[1,2-a]pyrazin-3-yl)-4-methylphenyl)-4,4,4-trifluoro-3-hydroxybutyl)(methyl)carbamate (Enantiomers 1-2)

The racemic mixture of tert-butyl (3-(3-(8-amino-6-(trifluoromethyl)imidazo[1,2-a]pyrazin-3-yl)-4-methylphenyl)-4,4,4-trifluoro-3-hydroxybutyl)(methyl)carbamate was separated via preparative chiral HPLC (Phenomenex Lux Amylose-1 [21.2×250 mm, 5 micron], eluting with 10% ethanol in hexanes, at flow rate of 18 mL/min, loading ~90 mg in 1800 μL ethanol). The first peak that eluted had a retention time of 6.0 min (Enantiomer 1). The second peak that eluted had a retention time of 12.4 min (Enantiomer 2).
Peak 1 (Enantiomer 1): LCMS for $C_{24}H_{28}F_6N_5O_3$ (M+H)$^+$: m/z=548.2; Found: 548.2.
Peak 2 (Enantiomer 2): LCMS for $C_{24}H_{28}F_6N_5O_3$ (M+H)$^+$: m/z=548.2; Found: 548.2.

Step 3. 2-(3-(8-Amino-6-(trifluoromethyl)imidazo [1,2-a]pyrazin-3-yl)-4-methylphenyl)-1,1,1-trifluoro-4-(methylamino)butan-2-ol (Example 15; Enantiomer 1)

A solution of tert-butyl (3-(3-(8-amino-6-(trifluoromethyl)imidazo[1,2-a]pyrazin-3-yl)-4-methylphenyl)-4,4,4-trifluoro-3-hydroxybutyl)(methyl)carbamate (0.204 g, 0.373 mmol) (peak 1 from step 2) in dichloromethane (2.48 mL) was treated with trifluoroacetic acid (2.50 mL, 32.4 mmol) and stirred for 30 min. The reaction mixture was concentrated and reconcentrated from dichloromethane (2×) to a viscous oil. The oil was cooled to 0° C., treated with saturated sodium bicarbonate, and extracted with dichloromethane (3×30 mL). The combined organic extracts were dried over sodium sulfate, filtered, and concentrated to give a colorless foam. This foam was dissolved in a minimal amount of acetonitrile and water and lyophilized to give the desired product (147 mg, 88.0%) as a white solid. $^1$H NMR (600 MHz, DMSO-d$_6$) δ 7.79 (s, 1H), 7.68-7.62 (m, 3H), 7.61 (s, 1H), 7.55 (s, 1H), 7.49 (d, J=8.2 Hz, 1H), 2.64-2.56 (m, 1H), 2.48-2.39 (m, 1H), 2.29-2.24 (m, 1H), 2.24 (s, 3H), 2.20-2.17 (m, 1H), 2.16 (s, 3H). LCMS for $C_{19}H_{20}F_6N_5O$ (M+H)$^+$: m/z=448.1; Found: 448.1.

Step 4. 2-(3-(8-Amino-6-(trifluoromethyl)imidazo [1,2-a]pyrazin-3-yl)-4-methylphenyl)-1,1,1-trifluoro-4-(methylamino)butan-2-ol (Example 16; Enantiomer 2)

The desired compound was prepared according to the procedure of step 3, using peak 2 from step 2 as the starting material. $^1$H NMR (500 MHz, DMSO-d$_6$) δ 7.79 (s, 1H), 7.68-7.62 (m, 3H), 7.61 (s, 1H), 7.55 (s, 1H), 7.49 (d, J=8.2 Hz, 1H), 2.64-2.55 (m, 1H), 2.47-2.39 (m, 1H), 2.32-2.25

(m, 1H), 2.24 (s, 3H), 2.21-2.17 (m, 1H), 2.16 (s, 3H). LCMS for $C_{19}H_{20}F_6N_5O$ (M+H)$^+$: m/z=448.1; Found: 448.1.

Example 17. 2-(3-(8-Amino-6-(trifluoromethyl) imidazo[1,2-a]pyrazin-3-yl)-4-methylphenyl)-1,1,1-trifluoro-4-((tetrahydro-2H-pyran-4-yl)amino)butan-2-ol bis(2,2,2-trifluoroacetate)

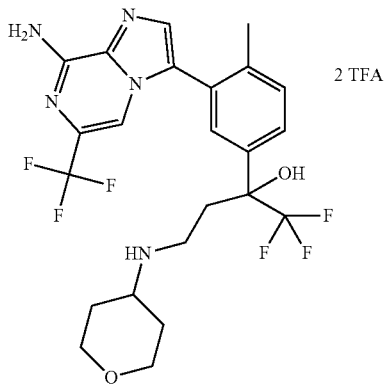 [SMILES: Cc1ccc(C(O)(CCNC2CCOCC2)C(F)(F)F)cc1-c1cnc2c(N)nc(C(F)(F)F)cn12]

The desired compound was prepared according to the procedure of Example 14, step 7, using tetrahydro-2H-pyran-4-amine [Combi-Blocks, AM-1004] as the starting material. $^1$H NMR (400 MHz, DMSO-d$_6$) δ 8.51 (br s, 2H), 7.79 (s, 1H), 7.74-7.60 (m, 2H), 7.60-7.49 (m, 3H), 7.08 (s, 1H), 3.90-3.79 (m, 2H), 3.34-3.10 (m, 3H), 3.11-2.88 (m, 1H), 2.64-2.51 (m, 2H), 2.44-2.29 (m, 1H), 2.23 (s, 3H), 1.88-1.64 (m, 2H), 1.60-1.26 (m, 2H). LCMS for $C_{23}H_{26}F_6N_5O_2$ (M+H)$^+$: m/z=518.2; Found: 518.2.

Example 18. 3-(3-(8-Amino-6-(trifluoromethyl) imidazo[1,2-a]pyrazin-3-yl)-4-methylphenyl)-4,4,4-trifluorobutane-1,3-diol

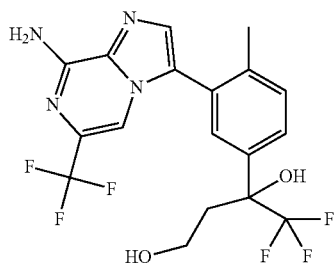 [SMILES: Cc1ccc(C(O)(CCO)C(F)(F)F)cc1-c1cnc2c(N)nc(C(F)(F)F)cn12]

Step 1. 3-(3-Bromo-4-methylphenyl)-4,4,4-trifluoro-3-hydroxybutanal

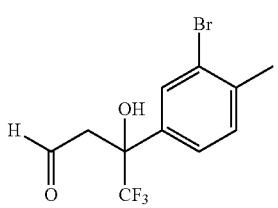 [SMILES: Cc1ccc(C(O)(CC=O)C(F)(F)F)cc1Br]

The desired compound was prepared according to the procedure of Example 14, step 6, using 2-(3-bromo-4-methylphenyl)-3-(1,3-dioxolan-2-yl)-1,1,1-trifluoropropan-2-ol (Example 14, Step 3) as the starting material. LCMS for $C_{11}H_{10}BrF_3O_2$ (M)$^+$: m/z=310.0, 312.0; Found: 310.0, 312.0.

Step 2. 3-(3-Bromo-4-methylphenyl)-4,4,4-trifluorobutane-1,3-diol

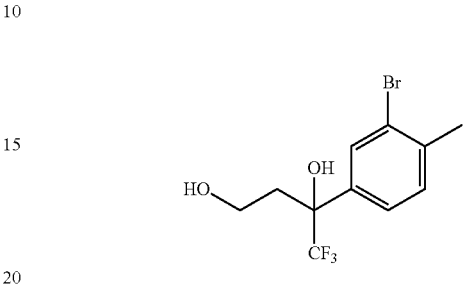

A solution of crude 3-(3-bromo-4-methylphenyl)-4,4,4-trifluoro-3-hydroxybutanal (0.280 g, 0.774 mmol) in methanol (5.16 mL) at 0° C. was treated with sodium tetrahydroborate (0.062 ml, 1.55 mmol) and stirred at 0° C. for 30 min. The reaction mixture was quenched with water at 0° C., warmed to rt, diluted with saturated sodium bicarbonate (20 mL), and extracted with ethyl acetate (30 mL). The aqueous layer was separated and extracted with additional ethyl acetate (30 mL). The combined organic extracts were washed with brine, dried over sodium sulfate, filtered, and concentrated to give a crude oil. Purification by flash column chromatography using methyl tert-butyl ether (MTBE) in hexanes (0%-80%) gave the desired product (0.209 g, 86.4%) as a colorless oil. LCMS for $C_{11}H_{12}BrF_3O_2Na$ (M+Na)$^+$: m/z=335.0, 337.0; Found: 334.9, 336.9.

Step 3. 4,4,4-Trifluoro-3-(4-methyl-3-(4,4,5,5-tetramethyl-1,3,2-dioxaborolan-2-yl)phenyl)butane-1, 3-diol

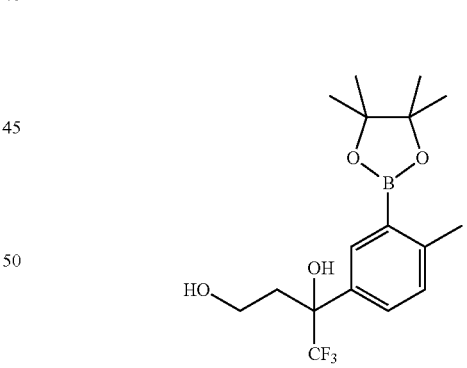

The desired compound was prepared according to the procedure of Example 1, step 2, using 3-(3-bromo-4-methylphenyl)-4,4,4-trifluorobutane-1,3-diol as the starting material. LCMS for $C_{17}H_{28}BF_3NO_4$ (M+NH$_4$)$^+$: m/z=378.2; Found: 378.2.

Step 4. 3-(3-(8-Amino-6-(trifluoromethyl)imidazo [1,2-a]pyrazin-3-yl)-4-methylphenyl)-4,4,4-trifluorobutane-1,3-diol The desired compound was prepared according to the procedure of Example 1, step 7, using 4,4,4-trifluoro-3-(4- methyl-3-(4,4,5,5-tetramethyl-1,3,2-dioxaborolan-2-yl)phenyl)butane-1,3-diol and 3-bromo-6-(trifluoromethyl)imidazo[1,2-a]pyrazin-8-amine (Example 4, Step 6) as the starting materials. $^1$H NMR (400 MHz, DMSO-d$_6$) δ 7.79 (s, 1H), 7.68-7.53 (m, 5H), 7.48 (d, J=8.2 Hz, 1H), 6.59 (s, 1H), 4.59 (t, J=5.0 Hz, 1H), 3.62-3.40 (m, 1H), 3.28-3.16 (m, 1H), 2.43-2.30 (m, 1H), 2.29-2.23 (m, 1H), 2.22 (s, 3H). LCMS for $C_{18}H_{17}F_6N_4O_2$ (M+H)$^+$: m/z=435.1; Found: 435.1.

Example 19. 1-(3-(8-Amino-6-(trifluoromethyl)imidazo[1,2-a]pyrazin-3-yl)-4-methylphenyl)-1-cyclopropyl-2,2,2-trifluoroethan-1-ol

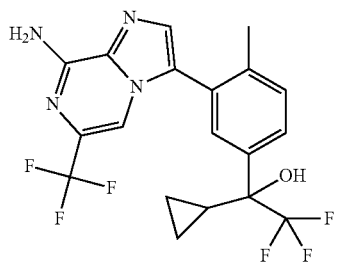 [SMILES: Cc1ccc(C(O)(C2CC2)C(F)(F)F)cc1-c1cnc2c(N)nc(C(F)(F)F)cn12]

Step 1.
3-Bromo-N-methoxy-N,4-dimethylbenzamide

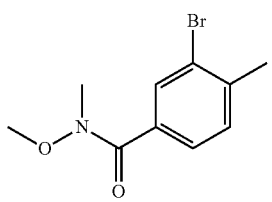

A solution of 3-bromo-4-methylbenzoic acid (2.50 g, 11.6 mmol) [Combi-Blocks, CA-5008] in N,N-dimethylformamide (11.6 mL) at 0° C. was treated with triethylamine (4.86 ml, 34.9 mmol) followed by O-(benzotriazol-1-yl)-N,N,N,N-tetramethyluronium hexafluorophosphate (5.29 g, 14.0 mmol) and stirred for 5 min. The reaction mixture was treated with N,O-dimethylhydroxylamine hydrochloride (1.35 mL, 15.1 mmol) and stirred at room temperature for 1 h. The reaction mixture was poured into a mixture of saturated sodium bicarbonate (75 mL) and water (75 mL) and extracted with ethyl acetate (200 mL). The organic layer was separated and washed with 1M HCl (150 mL) and brine (50 mL), dried over sodium sulfate, filtered, and concentrated to give a tan oil. Purification by flash column chromatography using ethyl acetate in hexanes (0%-40%) gave the desired product (2.80 g, 93.3%) as a colorless oil. LCMS for $C_{10}H_{13}BrNO_2$ (M+H)$^+$: m/z=258.0, 260.0; Found: 258.0, 260.0.

Step 2.
(3-Bromo-4-methylphenyl)(cyclopropyl)methanone

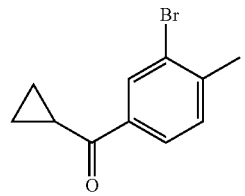

A solution of 3-bromo-N-methoxy-N,4-dimethylbenzamide (0.353 g, 1.37 mmol) in tetrahydrofuran (5.47 mL) at 0° C. was treated with cyclopropylmagnesium bromide (8.21 ml, 4.10 mmol) (0.5 M in THF) dropwise and stirred at room temperature for 1 h. The reaction mixture was cooled to 0° C., quenched with saturated ammonium chloride (20 mL), and extracted with ethyl acetate (50 mL) (a few drops of water were added to dissolve all solids). The organic layer was separated and washed with brine, dried over sodium sulfate, filtered, and concentrated to give a yellow oil. Purification by flash column chromatography using MTBE in hexanes (0%-30%) gave the desired product (0.313 g, 95.7%) as a colorless oil. LCMS for $C_{11}H_{12}BrO$ (M+H)$^+$: m/z=239.0, 241.0; Found: 239.0, 241.0.

Step 3. 1-(3-Bromo-4-methylphenyl)-1-cyclopropyl-2,2,2-trifluoroethan-1-ol

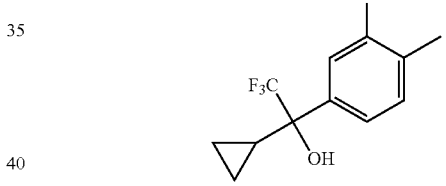

The desired compound was prepared according to the procedure of Example 1, step 1, using (3-bromo-4-methylphenyl)(cyclopropyl)methanone as the starting material. LCMS for $C_{12}H_{11}BrF_3$ (M-OH)$^+$: m/z=291.0, 293.0; Found: 291.0, 293.0.

Step 4. 1-Cyclopropyl-2,2,2-trifluoro-1-(4-methyl-3-(4,4,5,5-tetramethyl-1,3,2-dioxaborolan-2-yl)phenyl)ethan-1-ol

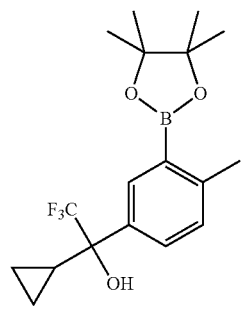 [SMILES: Cc1ccc(C(O)(C2CC2)C(F)(F)F)cc1B1OC(C)(C)C(C)(C)O1]

The desired compound was prepared according to the procedure of Example 1, step 2, using 1-(3-bromo-4-methylphenyl)-1-cyclopropyl-2,2,2-trifluoroethan-1-ol as the starting material. LCMS for $C_{18}H_{25}BF_3O_3$ (M+H)⁺: m/z=357.2; Found: 357.1.

Step 5. 1-(3-(8-Amino-6-(trifluoromethyl)imidazo[1,2-a]pyrazin-3-yl)-4-methylphenyl)-1-cyclopropyl-2,2,2-trifluoroethan-1-ol The desired compound was prepared according to the procedure of Example 1, step 7, using 1-cyclopropyl-2,2,2-trifluoro-1-(4-methyl-3-(4,4,5,5-tetramethyl-1,3,2-dioxaborolan-2-yl)phenyl)ethan-1-ol and 3-bromo-6-(trifluoromethyl)imidazo[1,2-a]pyrazin-8-amine (Example 4, Step 6) as the starting materials. ¹H NMR (400 MHz, DMSO-d₆) δ 7.80 (s, 1H), 7.72-7.62 (m, 4H), 7.59 (s, 1H), 7.48 (d, J=8.0 Hz, 1H), 6.13 (s, 1H), 2.25 (s, 3H), 1.82-1.62 (m, 1H), 0.89-0.72 (m, 1H), 0.65-0.48 (m, 1H), 0.44-0.31 (m, 1H), 0.31-0.17 (m, 1H). LCMS for $C_{19}H_{17}F_6N_4O$ (M+H)⁺: m/z=431.1; Found: 431.1.

Examples 20-21

Examples 20-21 listed in Table 1 were synthesized according to procedures analogous to the synthesis of Example 10.

TABLE 1

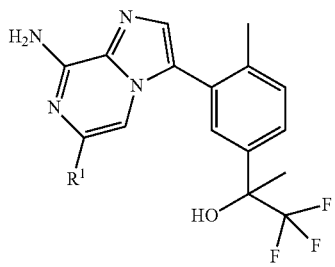

| Ex. No. | Name | R¹ | LCMS [M+H]⁺ | NMR Spectra |
|---|---|---|---|---|
| 20 | 2-(3-(8-Amino-6-(2-cyclopropylthiazol-5-yl)imidazo[1,2-a]pyrazin-3-yl)-4-methylphenyl)-1,1,1-trifluoropropan-2-ol, TFA | | 460.1 | |
| 21 | 2-(3-(8-Amino-6-(5-methoxythiazol-2-yl)imidazo[1,2-a]pyrazin-3-yl)-4-methylphenyl)-1,1,1-trifluoropropan-2-ol, TFA | | 450.1 | ¹H NMR (400 MHz, DMSO-d₆) δ 7.69-7.63 (m, 2H), 7.59-7.52 (m, 2H), 7.47 (d, J = 8.1 Hz, 1H), 7.37 (s, 1H), 7.27 (br s, 1H), 6.64 (br s, 1H), 3.24 (s, 3H), 2.18 (s, 3H), 1.71 (s, 3H). |

Example 22

Example 22 listed in Table 2 was synthesized according to procedures analogous to the synthesis of Example 9.

TABLE 2

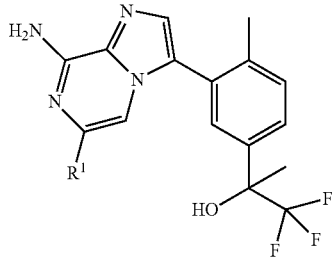

| Ex. No. | Name | R¹ | LCMS [M + H]⁺ | NMR Spectra |
|---|---|---|---|---|
| 22 | 8-Amino-3-(2-methyl-5-(1,1,1-trifluoro-2-hydroxypropan-2-yl)phenyl)-N-((3-methylisoxazol-5-yl)methyl)imidazo[1,2-a]pyrazine-6- | | 475.2 | |

173

TABLE 2-continued

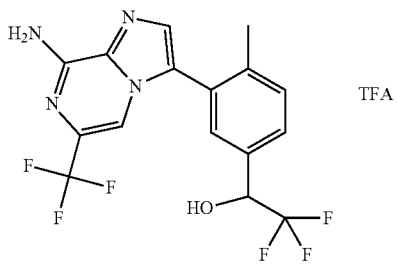 [SMILES: Cc1ccc(C(O)C(F)(F)F)cc1-c1cnc2c(N)nc(C(F)(F)F)cn12]

| Ex. No. Name | R[1] | LCMS [M + H]+ | NMR Spectra |
|---|---|---|---|
| carboxamide, TFA | | | |

Example 23. 1-(3-(8-Amino-6-(trifluoromethyl)imidazo[1,2-a]pyrazin-3-yl)-4-methylphenyl)-2,2,2-trifluoroethan-1-ol trifluoroacetate salt

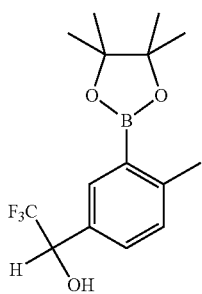 [SMILES: Cc1ccc(C(O)C(F)(F)F)cc1B1OC(C)(C)C(C)(C)O1]

TFA

Step 1. 2,2,2-Trifluoro-1-(4-methyl-3-(4,4,5,5-tetramethyl-1,3,2-dioxaborolan-2-yl)phenyl)ethan-1-ol

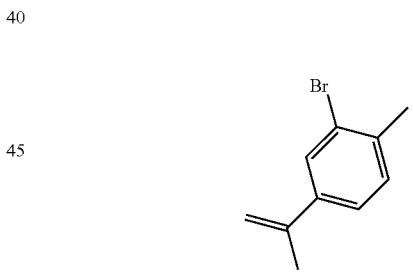

The desired compound was prepared according to the procedure of Example 1, step 2, using 1-(3-bromo-4-methylphenyl)-2,2,2-trifluoroethan-1-ol (Example 14, Step 1) as the starting material. LCMS for $C_{15}H_{21}BF_3O_3$ (M+H)+: m/z=317.1; Found: 317.1.

174

Step 2. 1-(3-(8-Amino-6-(trifluoromethyl)imidazo[1,2-a]pyrazin-3-yl)-4-methylphenyl)-2,2,2-trifluoroethan-1-ol trifluoroacetate salt The desired compound was prepared according to the procedure of Example 1, step 7, using 2,2,2-trifluoro-1-(4-methyl-3-(4,4,5,5-tetramethyl-1,3,2-dioxaborolan-2-yl)phenyl)ethan-1-ol and 3-bromo-6-(trifluoromethyl)imidazo[1,2-a]pyrazin-8-amine (Example 4, Step 6) as the starting materials. $^1$H NMR (400 MHz, DMSO-$d_6$) δ 7.78 (s, 1H), 7.66 (br s, 2H), 7.59-7.41 (m, 5H), 5.40-5.02 (m, 1H), 2.22 (s, 3H). LCMS for $C_{16}H_{13}F_6N_4O$ (M+H)+: m/z=391.1; Found: 391.1.

Example 24. 2-(3-(8-Amino-6-(trifluoromethyl)imidazo[1,2-a]pyrazin-3-yl)-4-methylphenyl)-1-fluoropropan-2-ol trifluoroacetate salt (Racemic Mixture of Isomers)

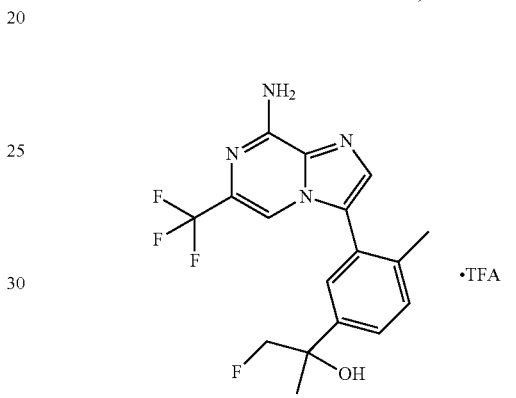

Step 1. 2-Bromo-1-methyl-4-(prop-1-en-2-yl)benzene

Potassium tert-butoxide solution (1.0 M, 5.6 mL, 5.6 mmol) was added to a stirred mixture of methyltriphenylphosphonium bromide (2.0 g, 5.6 mmol) in anhydrous ether (20 mL). The resulting yellow mixture was allowed to stir for 1 hour, after which time a solution of 1-(3-bromo-4-methylphenyl)ethan-1-one (1.0 g, 4.7 mmol, Combi-Blocks) in anhydrous ether (10.0 mL) was added dropwise. The reaction mixture was stirred overnight and was then passed through a pad of Celite® and washed with hexanes. Solvent was removed from the filtrate under reduced pressure. The product was purified by flash column chromatography, eluting with hexanes as the eluent to afford the product as a colorless oil (0.50 g, 51%). $^1$H NMR (400 MHz, CDCl$_3$) δ 7.65 (d, J=1.5 Hz, 1H), 7.33 (dd, J=7.9, 1.6 Hz, 1H), 7.20 (d, J=7.9 Hz, 1H), 5.37 (s, 1H), 5.10 (s, 1H), 2.41 (s, 3H), 2.14 (s, 3H).

Step 2. 2-(3-Bromo-4-methylphenyl)-1-fluoropropan-2-ol (Racemic Mixture of Isomers)

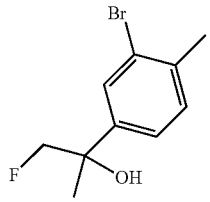

To a solution of 2-bromo-1-methyl-4-(prop-1-en-2-yl) benzene (0.170 g, 0.805 mmol) in MeCN (10 mL) was added water (2.0 mL) and Selectfluor® (0.342 g, 0.966 mmol). The mixture was heated in the microwave to 80° C. for 5 minutes. Acetonitrile was removed in vacuo and the crude reaction mixture was partitioned between DCM and water. The organic layer was dried over Na$_2$SO$_4$, filtered and concentrated. The product was purified by flash chromatography, eluting with a gradient from 0-30% EtOAc in hexanes to afford the product as a colorless oil (170 mg, 87%). LCMS calculated for C$_{10}$H$_{11}$BrF (M−H$_2$O+H)$^+$: m/z=229.0, found: 229.0. $^1$H NMR (400 MHz, CDCl$_3$) δ 7.69 (d, J=1.6 Hz, 1H), 7.32 (dd, J=7.9, 1.7 Hz, 1H), 7.25 (d, J=7.9 Hz, 1H), 4.56-4.30 (m, 2H), 2.41 (s, 3H), 1.59 (d, J=2.0 Hz, 3H).

Step 3. 1-Fluoro-2-(4-methyl-3-(4,4,5,5-tetramethyl-1,3,2-dioxaborolan-2-yl)phenyl)propan-2-ol (Racemic Mixture of Isomers)

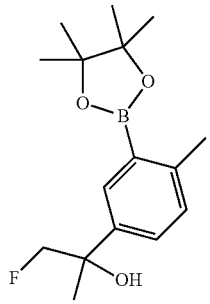 [SMILES: Cc1ccc(C(C)(O)CF)cc1B1OC(C)(C)C(C)(C)O1]

A sealable vial was charged with 2-(3-bromo-4-methylphenyl)-1-fluoropropan-2-ol (168 mg, 0.680 mmol), bis(pinacolato)diboron (207 mg, 0.816 mmol), and potassium acetate (0.220 g, 2.24 mmol) and the atmosphere in the vial was replaced with nitrogen. Tetrahydrofuran (2.5 mL) was added and the mixture was degassed with nitrogen for 5 minutes. Bis(triphenylphosphine)palladium(II) dichloride (19 mg, 0.027 mmol) was added and the mixture was degassed again for 5 minutes. The reaction mixture was then heated in an oil bath held at 120° C. for 1.5 hours. The reaction mixture was diluted with EtOAc and deionized water, then filtered through Celite®. The layers of the filtrate were separated and the aqueous layer was again extracted with ethyl acetate. The combined organic extracts were washed with brine, dried over MgSO$_4$, filtered, and concentrated to afford product which was used without further purification. LCMS calculated for C$_{16}$H$_{23}$BFO$_2$ (M−H$_2$O+H)$^+$: m/z=277.2, found: 277.1.

Step 4. 2-(3-(8-Amino-6-(trifluoromethyl)imidazo[1,2-a]pyrazin-3-yl)-4-methylphenyl)-1-fluoropropan-2-ol trifluoroacetate salt (Racemic Mixture Prepared)

A microwavable vial was charged with 1-fluoro-2-(4-methyl-3-(4,4,5,5-tetramethyl-1,3,2-dioxaborolan-2-yl)phenyl)propan-2-ol (0.050 g, 0.10 mmol), 3-bromo-6-(trifluoromethyl)imidazo[1,2-a]pyrazin-8-amine (Example 4, Step 6; 43.0 mg, 0.153 mmol), THF (2.0 mL), and K$_2$CO$_3$ solution (1.0 M, 0.41 mL, 0.41 mmol). The reaction mixture was degassed with N$_2$ and heated in the microwave to 120° C. for 20 minutes. The reaction mixture was diluted with MeCN and MeOH and filtered. The product was purified by preparative HPLC-MS (pH=2) and the eluent was frozen and lyophilized to afford the product as a white solid (14 mg, 28%). LCMS calculated for C$_{17}$H$_{17}$F$_4$N$_4$O (M+H)$^+$: m/z=369.1, found: 369.4. $^1$H NMR (400 MHz, DMSO-d$_6$) δ 7.76 (s, 1H), 7.65 (br s, 2H), 7.59-7.54 (m, 2H), 7.52 (d, J=1.7 Hz, 1H), 7.42 (d, J=8.1 Hz, 1H), 4.39 (d, J=47.9 Hz, 2H), 2.18 (s, 3H), 1.47 (d, J=1.8 Hz, 3H).

Example 25. 2-(3-(8-Amino-6-(1-(methyl-d$_3$)-1H-pyrazol-5-yl)imidazo[1,2-a]pyrazin-3-yl)-4-methylphenyl)-1,1-difluoropropan-2-ol trifluoroacetate salt (Single Enantiomer)

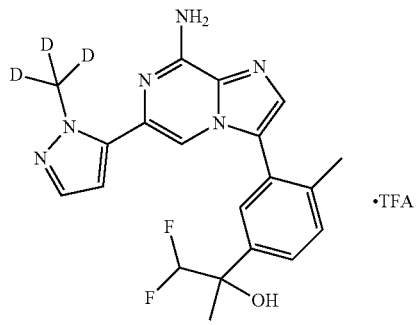 [SMILES: [2H]C([2H])([2H])n1nccc1-c1cn2c(-c3cc(C(C)(O)C(F)F)ccc3C)cnc2c(N)n1]

Step 1. 1-(Methyl-d$_3$)-5-(4,4,5,5-tetramethyl-1,3,2-dioxaborolan-2-yl)-1H-pyrazole

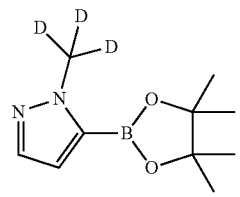

The title product was prepared via the method described in *J. Label Compd. Radiopharm* 2012, 55, 467-469 with the modification that 1H-pyrazole and iodomethane-d$_3$ were utilized as starting materials. n-Butyllithium (1.6 M in hexanes, 8.08 mL, 12.9 mmol) was added over 2 minutes to a stirred mixture of 1H-pyrazole (0.800 g, 11.8 mmol, Aldrich) in THF (23.5 mL) at 0° C. under nitrogen. Iodomethane-d$_3$ (1.87 g, 12.9 mmol, Aldrich) was then added, the reaction mixture was warmed to room temperature and was stirred for 23 hours. The reaction mixture was then cooled to 0° C. and n-butyllithium (1.6 M in hexanes, 8.81 mL, 14.1 mmol) was added. The reaction mixture was warmed to room temperature for one hour, then was cooled to −78° C. 2-Isopropoxy-4,4,5,5-tetramethyl-1,3,2-dioxaborolane (3.59 mL, 17.6 mmol) was added, and the mixture was stirred at −78° C. for 15 minutes, then warmed to room temperature and stirred overnight. Saturated NH$_4$Cl (90 mL) was added and the mixture was extracted with DCM (350 mL and 2×100 mL). The organic extracts were combined, dried over Na$_2$SO$_4$, filtered, and concentrated to give the desired product as a solid which was used without further purification.

Step 2. 2-(3-(8-Amino-6-(1-(methyl-d$_3$)-1H-pyrazol-5-yl)imidazo[1,2-a]pyrazin-3-yl)-4-methylphenyl)-1,1-difluoropropan-2-ol trifluoroacetate salt (Single Enantiomer)

A vial was charged with a single isomer of 2-(3-(8-amino-6-bromoimidazo[1,2-a]pyrazin-3-yl)-4-methylphenyl)-1,1-difluoropropan-2-ol (0.100 g, 0.252 mmol, from Example 29, Step 3), 1-(methyl-d$_3$)-5-(4,4,5,5-tetramethyl-1,3,2-dioxaborolan-2-yl)-1H-pyrazole (159 mg, 0.755 mmol) and THF (2.0 mL). The mixture was degassed and 1.0 M K$_2$CO$_3$ solution (0.63 mL, 0.63 mmol) was added. The reaction mixture was again degassed and dichloro[1,1'-bis(diphenylphosphino)ferrocene]palladium (II) dichloromethane adduct (0.041 g, 0.050 mmol) was added. The reaction was heated to 90° C. for 4 hours. The reaction mixture was cooled to room temperature and was filtered. The product was purified by preparative HPLC-MS (pH=2). LCMS calculated for C$_{20}$H$_{18}$D$_3$F$_2$N$_6$O (M+H)$^+$: m/z=402.2, found: 402.1. $^1$H NMR (500 MHz, DMSO-d$_6$) δ 7.78 (s, 1H), 7.58-7.53 (m, 2H), 7.49 (s, 1H), 7.45 (d, J=7.9 Hz, 1H), 7.42 (d, J=1.9 Hz, 1H), 6.45 (d, J=1.9 Hz, 1H), 5.98 (t, J=56.0 Hz, 1H), 2.25 (s, 3H), 1.54 (s, 3H). $^{19}$F NMR (470 MHz, DMSO-d$_6$) δ −74.66 (s), −129.27 (dd, J=56.1, 30.1 Hz).

Examples 26 and 27. 2-(3-(8-Amino-6-(trifluoromethyl)imidazo[1,2-a]pyrazin-3-yl)-4-methylphenyl)-1,1-difluoropropan-2-ol (Enantiomers 1-2)

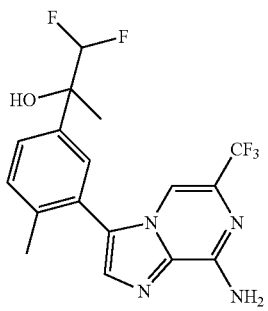 [SMILES: Cc1ccc(C(C)(O)C(F)F)cc1-c1cnc2c(N)nc(C(F)(F)F)cn12]

Step 1.
2-(3-Bromo-4-methylphenyl)-1,1-difluoropropan-2-ol

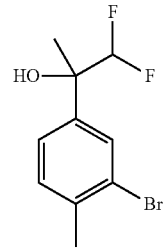

To a solution of 1-(3-bromo-4-methylphenyl)ethan-1-one (3.1 g, 15 mmol) in dry acetonitrile (15 mL) was added (bromodifluoromethyl)trimethylsilane (5.1 ml) (Combi-Blocks, QC-0668) and triphenylphosphine (4.6 g, 17 mmol), successively. Then 1,3-dimethyl-3,4,5,6-tetrahydro-2(1H)-pyrimidinone (3.5 ml, 29 mmol) was added dropwise. The reaction mixture was stirred at rt overnight. With the reaction flask in a rt water bath, aqueous KOH (15 ml, 45 mmol, 3.0 M) was added dropwise. The bath was removed, and the reaction mixture was stirred rapidly for 2 h. With the reaction flask again in art water bath, aqueous HCl (15 ml, 30 mmol, 2.0 M) was added. The mixture was extracted with MTBE (3×30 mL). The combined organic layers were dried over Na$_2$SO$_4$, filtered, and concentrated. Purification via silica gel chromatography (5-25% MTBE/hexanes) afforded the title compound as a light yellow oil (3.2 g, 73%). $^1$H NMR (400 MHz, CDCl$_3$) δ 7.70 (d, J=1.9 Hz, 1H), 7.33 (dd, J=8.0, 1.9 Hz, 1H), 7.24 (d, J=7.8 Hz, 1H), 5.67 (t, J=56 Hz, 1H), 2.40 (s, 3H), 2.28 (s, 1H), 1.63 (s, 3H). $^{19}$F NMR (376 MHz, CDCl$_3$) δ −129.39 (dd, J=280, 56 Hz, 1F), −130.48 (dd, J=280, 57 Hz, 1F).

Step 2. 1,1-Difluoro-2-(4-methyl-3-(4,4,5,5-tetramethyl-1,3,2-dioxaborolan-2-yl)phenyl)propan-2-ol

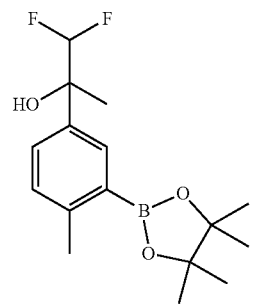 [SMILES: Cc1ccc(C(C)(O)C(F)F)cc1B1OC(C)(C)C(C)(C)O1]

A mixture of 2-(3-bromo-4-methylphenyl)-1,1-difluoropropan-2-ol (0.50 g, 1.8 mmol), bis(pinacolato)diboron (0.55 g, 2.2 mmol), potassium acetate (0.59 g, 6.0 mmol), and bis(triphenylphosphine)palladium(II) dichloride (51 mg, 0.072 mmol) in THF (7.2 mL) was degassed for 5 min with N$_2$. The mixture was heated in a microwave at 135° C. for 20 minutes. The reaction mixture was diluted with EtOAc and filtered through Celite®, rinsing with EtOAc. The filtrate was washed with water and then brine, dried over Na$_2$SO$_4$, filtered, and concentrated. Purification via silica gel chromatography (10-34% MTBE/hexanes)

afforded the title compound as clear oil (0.63 g, 93%). $^1$H NMR (400 MHz, CDCl$_3$) δ 7.86 (d, J=2.3 Hz, 1H), 7.44 (dd, J=8.1, 2.3 Hz, 1H), 7.19 (d, J=8.0 Hz, 1H), 5.75 (t, J=57 Hz, 1H), 2.53 (s, 3H), 2.27 (s 1H), 1.65 (s, 3H), 1.34 (s, 12H). $^{19}$F NMR (376 MHz, CDCl$_3$) δ −129.71 (dd, J=280, 56 Hz, 1F), −130.76 (dd, J=280, 57 Hz, 1F). LCMS for C$_{16}$H$_{22}$BF$_2$O$_2$ (M-OH)$^+$: calculated m/z=295.2; found 295.1.

Step 3. 2-(3-(8-Amino-6-(trifluoromethyl)imidazo [1,2-a]pyrazin-3-yl)-4-methylphenyl)-1,1-difluoropropan-2-ol (Isomers 1-2)

A mixture of 3-bromo-6-(trifluoromethyl)imidazo[1,2-a] pyrazin-8-amine (Example 4, Step 6; 0.13 g, 0.46 mmol), dichloro[1,1'-bis(diphenylphosphino)ferrocene]palladium (II) dichloromethane adduct (76 mg, 0.093 mmol), 1,1-difluoro-2-(4-methyl-3-(4,4,5,5-tetramethyl-1,3,2-dioxaborolan-2-yl)phenyl)propan-2-ol (0.19 g, 0.51 mmol), THF (7.8 mL), and 1.0 M K$_2$CO$_3$ (aq) (0.93 ml, 0.93 mmol) was degassed with N$_2$ for 5 min and then heated to 80° C. for 4 h. The reaction mixture was diluted with water (10 ml) and extracted with EtOAc (3×8 mL). The combined organic layers were washed with brine (15 mL), dried over Na$_2$SO$_4$, filtered, and concentrated. Purification via preparative HPLC on a C-18 column (pH=10, 32-52% MeCN/0.1% NH$_4$OH (aq) over 5 min, 60 mL/min) afforded the racemic product (65 mg). Purification via chiral HPLC on an AD column (30% hexane/iPrOH (0.1% Et$_2$NH), 17 mL/min) afforded Example 26 as a white solid (first eluting isomer, t$_R$=25.0 min, 24 mg, 13%) and Example 27 as an off-white solid (second eluting isomer, t$_R$=28.2 min, 28 mg, 16%).

Example 26 (Isomer 1): $^1$H NMR (400 MHz, DMSO-d$_6$) δ 7.77 (s, 1H), 7.66 (br s, 2H), 7.58 (s, 1H), 7.57 (d, J=1.9 Hz, 1H), 7.54 (d, J=2.0 Hz, 1H), 7.45 (d, J=8.0 Hz, 1H), 5.99 (s, 1H) 5.98 (t, J=56 Hz, 1H), 2.21 (s, 3H), 1.54 (s, 3H). $^{19}$F NMR (376 MHz, DMSO-d$_6$) δ −66.87 (s, 3F), −128.74 (dd, J=270, 56 Hz, 1F), −129.82 (dd, J=270, 56 Hz, 1F). LCMS for C$_{17}$H$_{16}$F$_5$N$_4$O$_2$ (M+H)$^+$: calculated m/z=387.1; found 387.1.

Example 27 (Isomer 2): $^1$H NMR (500 MHz, DMSO-d$_6$) δ 7.77 (s, 1H), 7.65 (br s, 2H), 7.59-7.56 (m, 2H), 7.54 (d, J=1.9 Hz, 1H), 7.45 (d, J=8.1 Hz, 1H), 5.99 (s, 1H), 5.98 (t, J=56 Hz, 1H), 2.21 (s, 3H), 1.54 (s, 3H). $^{19}$F NMR (470 MHz, DMSO-d$_6$) δ −66.87 (s, 3F), −129.04 (dd, J=270, 56 Hz, 1F), −129.72 (dd, J=270, 56 Hz, 1F). LCMS for C$_{17}$H$_{16}$F$_5$N$_4$O (M+H)$^+$: calculated m/z=387.1; found 387.1.

Example 28. 2-(3-(8-Amino-6-(2-methyloxazol-5-yl)imidazo[1,2-a]pyrazin-3-yl)-4-methylphenyl)-1,1-difluoropropan-2-ol

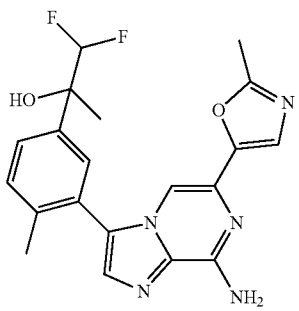 [SMILES: Cc1ncc(-c2cn3c(-c4cc(C(C)(O)C(F)F)ccc4C)cnc3c(N)n2)o1]

Step 1. 6-Bromo-3-iodoimidazo[1,2-a]pyrazin-8-amine

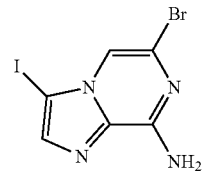

A suspension of 6,8-dibromo-3-iodoimidazo[1,2-a]pyrazine (539 mg, 1.34 mmol) in conc. NH$_4$OH (aq) (10 mL) was heated to 150° C. for 15 min in a microwave. After cooling to 0° C., the reaction mixture was diluted with cold water and filtered. The collected solid was then washed with cold water to afford the title compound as an off-white solid (356 mg, 79%). LCMS for C$_6$H$_5$BrIN$_4$ (M+H)$^+$: calculated m/z=338.9, 340.9; found 338.8, 340.9.

Step 2. 2-(3-(8-Amino-6-bromoimidazo[1,2-a] pyrazin-3-yl)-4-methylphenyl)-1,1-difluoropropan-2-ol

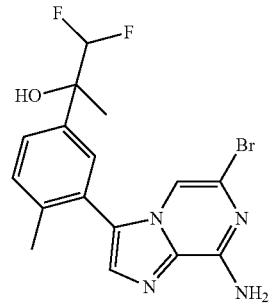 [SMILES: Cc1ccc(C(C)(O)C(F)F)cc1-c1cnc2c(N)nc(Br)cn12]

A mixture of 6-bromo-3-iodoimidazo[1,2-a]pyrazin-8-amine (0.12 g, 0.35 mmol), 1,1-difluoro-2-(4-methyl-3-(4,4,5,5-tetramethyl-1,3,2-dioxaborolan-2-yl)phenyl)propan-2-ol (0.13 g, 0.35 mmol), tetrakis(triphenylphosphine)palladium(0) (24 mg, 0.021 mmol), EtOH (5.0 mL), and 2.0 M Na$_2$CO$_3$ (aq) (0.35 mL, 0.70 mmol) was degassed for 5 min with N$_2$. The reaction mixture was then heated in a microwave reactor at 130° C. for 2×30 min. The reaction mixture was poured into water and extracted with EtOAc. The combined organic layers were washed with brine, dried over Na$_2$SO$_4$, filtered, and concentrated. Purification via silica gel chromatography (20-80% EtOAc/DCM) afforded the title compound as a yellow solid (0.14 g). LCMS for C$_{16}$H$_{16}$BrF$_2$N$_4$O (M+H)$^+$: calculated m/z=397.0, 399.0; found 397.0, 399.0.

Step 3. 2-(3-(8-Amino-6-(2-methyloxazol-5-yl)imidazo[1,2-a]pyrazin-3-yl)-4-methylphenyl)-1,1-difluoropropan-2-ol A 1-dram vial was charged with 2-(3-(8-amino-6-bromoimidazo[1,2-a]pyrazin-3-yl)-4-methylphenyl)-1,1-difluoropropan-2-ol (8 mg, 0.02 mmol), dichloro[1,1'-bis(diphenylphosphino)ferrocene]palladium (II) dichloromethane adduct (3 mg, 4 μmol), and 2-methyl-5-(4,4,5,5-tetramethyl-1,3,2-dioxaborolan-2-yl)oxazole (13 mg, 0.060 mmol). THF (0.4 mL) and then 1.0 M K$_2$CO$_3$ (aq) (50 μL, 0.050 mmol) were added. The reaction mixture was degassed with N$_2$ briefly and then heated at 80° C. for 12 h. Heating was discontinued, and the reaction mixture was stirred for 2 d. The reaction mixture filtered through a plug of Celite® and Na$_2$SO$_4$ and then concentrated. Purification via preparative HPLC on a C-18 column (pH=10, 26-46% MeCN/0.1% NH$_4$OH (aq) over 5 min, 60 mL/min) afforded the title compound as an off-white solid (2.4 mg, 30%). $^1$H NMR (400 MHz, DMSO-d$_6$) δ 7.64 (s, 1H), 7.59 (dd, J=8.1, 1.9 Hz, 1H), 7.53 (d, J=1.9 Hz, 1H), 7.46 (d, J=8.1 Hz, 1H), 7.39 (s, 1H), 7.29 (br s, 2H), 7.27 (s, 1H), 5.99 (t, J=56.0 Hz, 1H), 5.98 (s, 1H), 2.40 (s, 3H), 2.19 (s, 3H), 1.55 (s, 3H). LCMS for C$_{20}$H$_{20}$F$_2$N$_5$O$_2$ (M+H)$^+$: calculated m/z=400.2; found 400.2.

Example 29. 2-(3-(8-Amino-6-(1-methyl-1H-pyrazol-5-yl)imidazo[1,2-a]pyrazin-3-yl)-4-methylphenyl)-1,1-difluoropropan-2-ol 1.2 trifluoroacetate salt (Isomer 1)

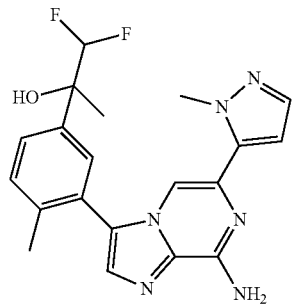 [SMILES: Cc1ccc(C(C)(O)C(F)F)cc1-c1cnc2c(N)nc(-c3ccnn3C)cn12]

Step 1. 2-(3-Bromo-4-methylphenyl)-1,1-difluoropropan-2-ol (First Eluting Isomer)

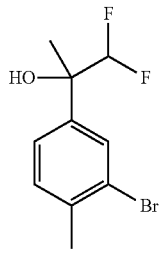

To a solution of 1-(3-bromo-4-methylphenyl)ethan-1-one (15 g, 70 mmol) (Combi-Blocks, SH-5880) in dry acetonitrle (70 mL) was added (bromodifluoromethyl)trimethylsilane (17 mL) (Combi-Blocks, QC-0668) and triphenylphosphine (22 g, 85 mmol), successively. Then 1,3-dimethyl-3,4,5,6-tetrahydro-2(1H)-pyrimidinone (3.5 mL, 29 mmol) was added dropwise. The reaction mixture was stirred at ambient temperature overnight. With the reaction flask in a rt water bath, aqueous KOH (70 mL, 210 mmol, 3.0 M) was added dropwise via addition funnel. The bath was removed, and the reaction mixture was stirred rapidly for 1.5 h. With the reaction flask again in a rt water bath, aqueous HCl (70 mL, 140 mmol, 2.0 M) was added slowly via addition funnel. The mixture was then extracted with MTBE (3×125 mL). The combined organic layers were dried over Na$_2$SO$_4$, filtered, and concentrated. Purification via silica gel chromatography (step gradient: 5%, then 19% MTBE/hexanes) afforded the racemic compound as a yellow oil (17 g). Purification via chiral preparatory HPLC on a Phenomenx Lux Amylose-1 column (5% EtOH/hexanes, 18 mL/min) afforded the title compound, which was the first eluting enantiomer (t$_R$=8.9 min), as light yellow oil (7.1 g, 38%). $^1$H NMR (400 MHz, CDCl$_3$) δ 7.70 (d, J=1.8 Hz, 1H), 7.33 (dd, J=8.3, 1.7 Hz, 1H), 7.24 (d, J=8.1 Hz, 1H), 5.67 (t, J=56 Hz, 1H), 2.40 (s, 3H), 2.24 (s, 1H), 1.63 (s, 3H). $^{19}$F NMR (376 MHz, CDCl$_3$) δ −129.40 (dd, J=280, 56 Hz, 1F), −130.49 (dd, J=280, 57 Hz, 1F).

Step 2. 1,1-Difluoro-2-(4-methyl-3-(4,4,5,5-tetramethyl-1,3,2-dioxaborolan-2-yl)phenyl)propan-2-ol (Isomer 1)

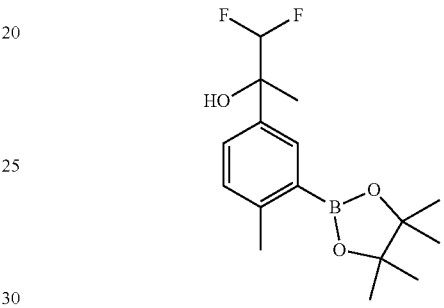

A mixture of 2-(3-bromo-4-methylphenyl)-1,1-difluoropropan-2-ol (first eluting isomer) (0.50 g, 1.8 mmol), bis(pinacolato)diboron (0.55 g, 2.2 mmol), potassium acetate (0.58 g, 5.9 mmol), and bis(triphenylphosphine)palladium(II) dichloride (50 mg, 0.072 mmol) in THF (2.5 mL) was degassed for 5 min with N$_2$. The mixture was heated in a microwave at 135° C. for 20 minutes. The reaction mixture was diluted with EtOAc and filtered through Celite®, rinsing with EtOAc. The filtrate was washed with water and then brine, dried over Na$_2$SO$_4$, filtered, and concentrated. Purification via silica gel chromatography (1-5% EtOAc/hexanes) afforded the title compound as clear oil (0.53 g, 79%). $^1$H NMR (400 MHz, CDCl$_3$) δ 7.86 (d, J=2.2 Hz, 1H), 7.44 (dd, J=8.0, 2.2 Hz, 1H), 7.19 (d, J=8.0 Hz, 1H), 5.74 (t, J=56 Hz, 1H), 2.53 (s, 3H), 2.28 (s, 1H), 1.65 (s, 3H), 1.34 (s, 12H). LCMS for C$_{16}$H$_{22}$BF$_2$O$_2$ (M-OH)$^+$: calculated m/z=295.2; found 295.1.

Step 3. 2-(3-(8-Amino-6-bromoimidazo[1,2-a]pyrazin-3-yl)-4-methylphenyl)-1,1-difluoropropan-2-ol (Isomer 1)

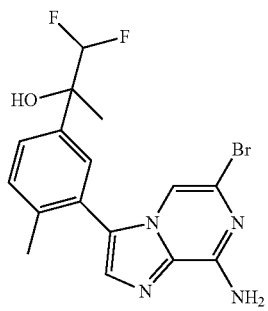 [SMILES: Cc1ccc(C(C)(O)C(F)F)cc1-c1cnc2c(N)nc(Br)cn12]

A mixture of 6-bromo-3-iodoimidazo[1,2-a]pyrazin-8-amine (1.21 g, 3.56 mmol), 1,1-difluoro-2-(4-methyl-3-(4,4,5,5-tetramethyl-1,3,2-dioxaborolan-2-yl)phenyl)propan-2-ol (Isomer 1) (1.10 g, 3.56 mmol), THF (17.8 mL), and 1.0 M K$_2$CO$_3$ (aq) (10.7 mL, 10.7 mmol) was degassed for 5 min with N$_2$ before addition of dichloro[1,1'-bis(diphenylphosphino)ferrocene]palladium (II) dichloromethane adduct (581 mg, 0.711 mmol). The mixture was degassed again for 2 min with N$_2$. The reaction mixture was then heated in a sealed vial at 80° C. overnight. The aqueous layer was removed, and the organic layer was concentrated. Purification via silica gel (50-100% EtOAc/hexanes) afforded the title compound (1.15 g, 81%). $^1$H NMR (400 MHz, DMSO-d$_6$) δ 7.62 (s, 1H), 7.58-7.51 (m, 3H), 7.49 (d, J=1.7 Hz, 1H), 7.42 (d, J=8.0 Hz, 1H), 7.26 (s, 1H), 5.98 (s, 1H), 5.97 (t, J=56 Hz, 1H), 2.17 (s, 3H), 1.53 (s, 3H). $^{19}$F NMR (376 MHz, CDCl$_3$) δ −129.26 (dd, J=280, 56 Hz, 1F), −130.28 (dd, J=280, 57 Hz, 1F). LCMS for C$_{16}$H$_{16}$BrF$_2$N$_4$O (M+H)$^+$: calculated m/z=397.0, 399.0; found 397.0, 399.0.

Step 4. 2-(3-(8-Amino-6-(1-methyl-1H-pyrazol-5-yl)imidazo[1,2-a]pyrazin-3-yl)-4-methylphenyl)-1,1-difluoropropan-2-ol, 1.2TFA (Isomer 1)

A vial was charged with 2-(3-(8-amino-6-bromoimidazo[1,2-a]pyrazin-3-yl)-4-methylphenyl)-1,1-difluoropropan-2-ol (Isomer 1) (0.87 g, 2.2 mmol), dichloro[1,1'-bis(diphenylphosphino)ferrocene]palladium (II) dichloromethane adduct (0.36 g, 0.44 mmol), and 1-methyl-1H-pyrazole-5-boronic acid pinacol ester (1.4 g, 6.6 mmol). THF (5.0 mL) and then 1.0 M K$_2$CO$_3$ (aq) (5.5 mL, 5.5 mmol) were added. The reaction mixture was degassed with N$_2$ briefly and then heated at 80° C. for 12 h. The reaction mixture was filtered through a plug of Celite® and Na$_2$SO$_4$ and then concentrated. Purification via preparative HPLC on a C-18 column (pH=2, 12-30% MeCN/0.1% TFA (aq) over 5 min, 60 mL/min) afforded the title compound (0.46 g, 40%). $^1$H NMR (500 MHz, DMSO-d$_6$) δ 7.78 (s, 1H), 7.67 (br s, 2H), 7.57-7.53 (m, 2H), 7.48 (s, 1H), 7.44 (d, J=8.0 Hz, 1H), 7.42 (d, J=1.9 Hz, 1H), 6.44 (d, J=1.9 Hz, 1H), 5.97 (t, J=56 Hz, 1H), 5.97 (s, 1H), 4.01 (s, 3H), 2.24 (s, 3H), 1.54 (s, 3H). $^{19}$F NMR (470 MHz, DMSO-d$_6$) δ −74.56 (s), −128.94 (dd, J=270, 56 Hz), −129.58 (dd, J=270, 56 Hz). LCMS for C$_{20}$H$_{21}$F$_2$N$_6$O (M+H)$^+$: calculated m/z=399.2; found 399.1.

Example 30. 2-(3-(8-Amino-6-(1-methyl-1H-pyrazol-5-yl)imidazo[1,2-a]pyrazin-3-yl)-4-methylphenyl)-1,1-difluoropropan-2-ol (Isomer 2)

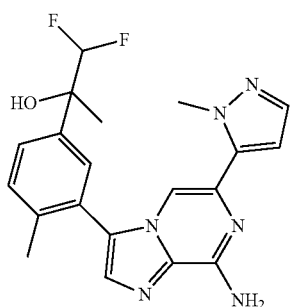

Step 1. 2-(3-Bromo-4-methylphenyl)-1,1-difluoropropan-2-ol (Isomer 2)

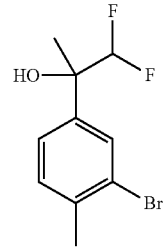

The title compound was synthesized according to an experimental procedure analogous to the synthesis of Example 29, Step 1. Purification of the racemic compound via chiral preparatory HPLC on a Phenomenx Lux Amylose-1 column (5% EtOH/hexanes, 18 mL/min) afforded the title compound, which was the second eluting enantiomer (t$_R$=11.6 min; Isomer 2). $^1$H NMR (400 MHz, CDCl$_3$) δ 7.70 (d, J=1.9 Hz, 1H), 7.33 (dd, J=8.0, 1.9 Hz, 1H), 7.24 (d, J=8.0 Hz, 1H), 5.67 (t, J=56 Hz, 1H), 2.40 (s, 3H), 2.27 (s, 1H), 1.63 (s, 3H). $^{19}$F NMR (376 MHz, CDCl$_3$) δ −129.39 (dd, J=280, 56 Hz), −130.48 (dd, J=280, 57 Hz).

Step 2. 1,1-Difluoro-2-(4-methyl-3-(4,4,5,5-tetramethyl-1,3,2-dioxaborolan-2-yl)phenyl)propan-2-ol (Isomer 2)

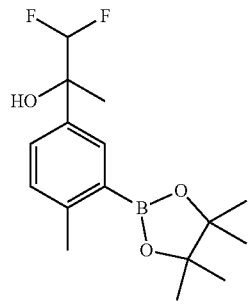 [SMILES: Cc1ccc(C(C)(O)C(F)F)cc1B1OC(C)(C)C(C)(C)O1]

The title compound was synthesized according to an experimental procedure analogous to Example 29, Step 2, substituting 2-(3-bromo-4-methylphenyl)-1,1-difluoropropan-2-ol (Isomer 2) for 2-(3-bromo-4-methylphenyl)-1,1-difluoropropan-2-ol (Isomer 1). LCMS for C$_{16}$H$_{22}$BF$_2$O$_2$ (M-OH)$^+$: calculated m/z=295.2; found 295.1.

Step 3. 2-(3-(8-Amino-6-bromoimidazo[1,2-a]pyrazin-3-yl)-4-methylphenyl)-1,1-difluoropropan-2-ol (Isomer 2)

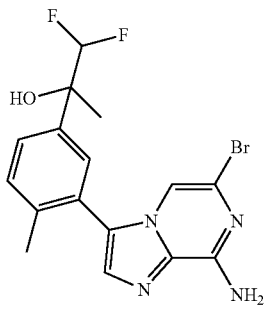 [SMILES: Cc1ccc(C(C)(O)C(F)F)cc1-c1cnc2c(N)nc(Br)cn12]

The title compound was synthesized according to an experimental procedure analogous to Example 28, Step 2, substituting 1,1-difluoro-2-(4-methyl-3-(4,4,5,5-tetramethyl-1,3,2-dioxaborolan-2-yl)phenyl)propan-2-ol (Isomer 2) for 1,1-difluoro-2-(4-methyl-3-(4,4,5,5-tetramethyl-1,3,2-dioxaborolan-2-yl)phenyl)propan-2-ol (Isomer 1). LCMS for $C_{16}H_{16}BrF_2N_4O$ $(M+H)^+$: calculated m/z=397.0, 399.0; found 397.0, 399.0.

Step 4. 2-(3-(8-Amino-6-(1-methyl-1H-pyrazol-5-yl)imidazo[1,2-a]pyrazin-3-yl)-4-methylphenyl)-1,1-difluoropropan-2-ol (Isomer 2)

The title compound was synthesized according to an experimental procedure analogous to Example 29, Step 4, substituting 2-(3-(8-amino-6-bromoimidazo[1,2-a]pyrazin-3-yl)-4-methylphenyl)-1,1-difluoropropan-2-ol (Isomer 2) for 2-(3-(8-amino-6-bromoimidazo[1,2-a]pyrazin-3-yl)-4-methylphenyl)-1,1-difluoropropan-2-ol (Isomer 1). $^1$H NMR (500 MHz, DMSO-$d_6$) δ 7.68 (s, 1H), 7.56 (d, J=1.9 Hz, 1H), 7.54 (dd, J=8.1, 1.9 Hz, 1H), 7.45 (s, 1H), 7.43 (d, J=8.3 Hz, 1H), 7.38 (d, J=1.9 Hz, 1H), 7.25 (br s, 2H), 6.40 (d, J=1.9 Hz, 1H), 5.97 (t, J=56 Hz, 1H), 5.97 (s, 1H) 4.04 (s, 3H), 2.23 (s, 3H), 1.53 (s, 3H). LCMS for $C_{20}H_{21}F_2N_6O$ $(M+H)^+$: calculated m/z=399.2; found 399.2.

Examples 31 to 48, 100, 106 and 108

Examples 31 to 48, 100, 106 and 108, were synthesized according to procedures analogous to those presented in Example 28, Step 3 (Method A); Example 29, Step 4 (Method B); or Example 30, Step 4 (Method C). The data are listed in Table 3.

TABLE 3

| Ex. No. | Name | R¹ | Method | LCMS [M + H]⁺ | NMR Spectra |
|---|---|---|---|---|---|
| 31 | 3-(8-Amino-3-(5-(1,1-difluoro-2-hydroxypropan-2-yl)-2-methylphenyl)imidazo[1,2-a]pyrazin-6-yl)-4-fluorobenzamide | 4-fluoro-3-carbamoylphenyl | A | 456.1 | |
| 32 | 2-(3-(8-Amino-6-(pyrimidin-5-yl)imidazo[1,2-a]pyrazin-3-yl)-4-methylphenyl)-1,1-difluoropropan-2-ol | pyrimidin-5-yl | A | 397.1 | |
| 33 | 2-(3-(8-Amino-6-(2-methoxypyridin-3-yl)imidazo[1,2-a]pyrazin-3-yl)-4-methylphenyl)-1,1-difluoropropan-2-ol | 2-methoxypyridin-3-yl | A | 426.1 | |

TABLE 3-continued

| Ex. No. | Name | R¹ | Method | LCMS [M + H]⁺ | NMR Spectra |
|---|---|---|---|---|---|
| 34 | 2-(3-(8-Amino-6-(2-methylthiazol-5-yl)imidazo[1,2-a]pyrazin-3-yl)-4-methylphenyl)-1,1-difluoropropan-2-ol | | A | 416.2 | |
| 35 | 2-(3-(8-Amino-6-(3-fluoro-2-methylpyridin-4-yl)imidazo[1,2-a]pyrazin-3-yl)-4-methylphenyl)-1,1-difluoropropan-2-ol | | A | 428.3 | |
| 36 | 2-(3-(8-Amino-6-(1,5-dimethyl-1H-pyrazol-4-yl)imidazo[1,2-a]pyrazin-3-yl)-4-methylphenyl)-1,1-difluoropropan-2-ol (isomer 1) | | B | 413.1 | |
| 37 | 2-(3-(8-Amino-6-(1-methyl-1H-pyrazol-4-yl)imidazo[1,2-a]pyrazin-3-yl)-4-methylphenyl)-1,1-difluoropropan-2-ol (isomer 1) | | B | 399.1 | |
| 38 | 2-(3-(8-Amino-6-(1,3-dimethyl-1H-pyrazol-4-yl)imidazo[1,2-a]pyrazin-3-yl)-4-methylphenyl)-1,1-difluoropropan-2-ol (isomer 1) | | B | 413.2 | |
| 39 | 2-(3-(8-Amino-6-(3,5-dimethyl-1H-pyrazol-4-yl)imidazo[1,2-a]pyrazin-3-yl)-4-methylphenyl)-1,1-difluoropropan-2-ol (isomer 1) | | B | 413.1 | |
| 40 | 2-(3-(8-Amino-6-(1H-pyrazol-4-yl)imidazo[1,2-a]pyrazin-3-yl)-4-methylphenyl)-1,1-difluoropropan-2-ol (isomer 1) | | B | 385.1 | |

TABLE 3-continued

| Ex. No. | Name | R¹ | Method | LCMS [M + H]⁺ | NMR Spectra |
|---|---|---|---|---|---|
| 41 | 2-(3-(8-Amino-6-(1,3-dimethyl-1H-pyrazol-5-yl)imidazo[1,2-a]pyrazin-3-yl)-4-methylphenyl)-1,1-difluoropropan-2-ol (isomer 1) | | B | 413.2 | |
| 42 | 2-(3-(8-Amino-6-(1,4-dimethyl-1H-pyrazol-5-yl)imidazo[1,2-a]pyrazin-3-yl)-4-methylphenyl)-1,1-difluoropropan-2-ol (isomer 1) | | B | 413.1 | |
| 43 | 2-(3-(8-Amino-6-(1-methyl-1H-pyrazol-3-yl)imidazo[1,2-a]pyrazin-3-yl)-4-methylphenyl)-1,1-difluoropropan-2-ol (isomer 1) | | B | 399.1 | ¹H NMR (500 MHz, DMSO-d₆) δ 7.68 (d, J = 2.2 Hz, 1H), 7.59 (dd, J = 8.0, 2.0 Hz, 1H), 7.59 (s, 1H), 7.53 (s, 1H), 7.51 (d, J = 2.0 Hz, 1H), 7.46 (d, J = 8.1 Hz, 1H), 7.08 (s, 2H), 6.59 (d, J = 2.2 Hz, 1H), 5.99 (t, J = 55.9 Hz, 1H), 5.97 (s, 1H), 3.81 (s, 3H), 2.14 (s, 3H), 1.54 (s, 3H). |
| 44 | 2-(3-(8-Amino-6-(2-(hydroxymethyl)pyridin-4-yl)imidazo[1,2-a]pyrazin-3-yl)-4-methylphenyl)-1,1-difluoropropan-2-ol (isomer 1) | | B | 426.1 | ¹H NMR (600 MHz, DMSO-d₆) δ 8.46 (d, J = 5.2 Hz, 1H), 7.98 (dd, J = 1.7, 0.9 Hz, 1H), 7.81 (s, 1H), 7.67 (s, 1H), 7.66 (dd, J = 5.2, 1.7 Hz, 1H), 7.59-7.57 (m, 2H), 7.46 (d, J = 8.7 Hz, 1H), 7.30 (s, 2H), 6.00 (t, J = 56 Hz, 1H), 5.98 (s, 1H), 5.40 (s, 1H), 4.58 (s, 2H), 2.23 (s, 3H), 1.56 (s, 3H). |
| 45 | 2-(3-(8-Amino-6-(2-(hydroxymethyl)pyridin-4-yl)imidazo[1,2-a]pyrazin-3-yl)-4-methylphenyl)-1,1-difluoropropan-2-ol (isomer 2) | | C | 426.1 | ¹H NMR (500 MHz, DMSO-d₆) δ 8.46 (d, J = 5.2 Hz, 1H), 7.98 (apparent s, 1H), 7.81 (s, 1H), 7.67 (s, 1H), 7.66 (dd, J = 5.3, 1.8 Hz, 1H), 7.62-7.54 (m, 2H), 7.46 (d, J = 8.8 Hz, 1H), 7.29 (s, 2H), 6.00 (t, J = 56.0 Hz, 2H), 5.98 (br s, 1H) 5.41 (s, 1H), 4.58 (s, 2H), 2.23 (s, 3H), 1.56 (s, 3H). |
| 46 | 2-(3-(8-Amino-6-(6-(hydroxymethyl)pyridin-3-yl)imidazo[1,2-a]pyrazin-3-yl)-4-methylphenyl)-1,1-difluoropropan-2-ol trifluoroacetate (isomer 1) | | B | 426.5 | ¹H NMR (600 MHz, DMSO-d₆) δ 8.99 (d, J = 2.2 Hz, 1H), 8.44 (d, J = 8.2 Hz, 1H), 7.84 (s, 1H), 7.71 (s, 1H), 7.65 (d, J = 8.3 Hz, 1H), 7.60-7.55 (m, 2H), 7.46 (apparent d, J = 8.6 Hz, 3H), 5.99 (t, J = 56 Hz, 1H), 5.99 (s, 1H), 4.68 (s, 2H), 2.24 (s, 3H), 1.55 (s, 3H). |

TABLE 3-continued

| Ex. No. Name | R¹ | Method | LCMS [M + H]⁺ | NMR Spectra |
|---|---|---|---|---|
| 47 2-(3-(8-Amino-6-(3-methyl-1H-pyrazol-4-yl)imidazo[1,2-a]pyrazin-3-yl)-4-methylphenyl)-1,1-difluoropropan-2-ol, 1.2TFA (isomer 1) | 3-methyl-1H-pyrazol-4-yl | B | 399¹ | ¹H NMR (500 MHz, DMSO-d₆) δ 7.83 (s, 1H), 7.80 (s, 1H), 7.60-7.53 (m, 2H), 7.45 (d, J = 8.0 Hz, 1H), 7.27 (s, 1H), 5.97 (t, J = 56.0 Hz, 1H), 5.97 (s, 1H) 2.32 (s, 3H), 2.26 (s, 3H), 1.54 (s, 3H). ¹⁹F NMR (470 MHz, DMSO-d₆) δ −74.10 (s), −128.91 (dd, J = 270, 56 Hz), −129.58 (dd, J = 270, 56 Hz). |
| 48 2-(3-(8-Amino-6-(3-methylisoxazol-5-yl)imidazo[1,2-a]pyrazin-3-yl)-4-methylphenyl)-1,1-difluoropropan-2-ol trifluoroacetate (isomer 1) | 3-methylisoxazol-5-yl | B | 400.1 | ¹H NMR (600 MHz, DMSO-d₆) δ 7.70 (s, 1H), 7.63 (s, 1H), 7.59 (dd, J = 8.0, 1.9 Hz, 1H), 7.54 (d, J = 2.0 Hz, 1H), 7.46 (d, J = 8.1 Hz, 1H), 7.40 (br s, 2H), 6.65 (s, 1H), 5.98 (t, J = 56 Hz, 1H), 5.98 (s, 1H), 2.26 (s, 3H), 2.19 (s, 3H), 1.55 (s, 3H). |
| 100 2-(3-(4-(8-amino-3-(5-(1,1-difluoro-2-hydroxypropan-2-yl)-2-methylphenyl)imidazo[1,2-a]pyrazin-6-yl)-1H-pyrazol-1-yl)-1-(cyclobutane-carbonyl)azetidin-3-yl)acetonitrile | 1-(cyclobutanecarbonyl)azetidin-3-yl substituted pyrazole | B* | 561.2 |  |
| 106 2-(3-(8-Amino-6-(5-(methylsulfonyl)pyridin-3-yl)imidazo[1,2-a]pyrazin-3-yl)-4-methylphenyl)-1,1-difluoropropan-2-ol | 5-(methylsulfonyl)pyridin-3-yl | B | 474.1 | ¹H NMR (500 MHz, DMSO-d₆) δ 9.36 (d, J = 2.1 Hz, 1H), 9.01 (d, J = 2.2 Hz, 1H), 8.75 (t, J = 2.1 Hz, 1H), 8.02 (s, 1H), 7.68 (s, 1H), 7.57 (m, 2H), 7.46 (d, J = 7.9 Hz, 1H), 7.38 (br s, 2H), 5.99 (t, J = 56 Hz, 2H), 5.97 (s, 1H), 3.35 (s, 3H), 2.24 (s, 3H), 1.56 (s, 3H). ¹⁹F NMR (470 MHz, DMSO-d₆) δ −73.4, −129.25 (apparent d, J = 56 Hz), −129.27 (apparent d, J = 56 Hz). |
| 108 (4-(8-amino-3-(5-(1,1-difluoro-2-hydroxypropan-2-yl)-2-methylphenyl)imidazo[1,2-a]pyrazin-6-yl)phenyl)boronic acid trifluoroacetate salt (1.3TFA:1 molecule Example 108) | 4-boronic acid phenyl | B | 439.1 | ¹H NMR (500 MHz, DMSO-d₆) δ 7.85 (d, J = 8.2 Hz, 2H), 7.78 (apparent d, J = 8.3 Hz, 3H), 7.67 (s, 1H), 7.61-7.56 (m, 2H), 7.50-7.44 (m, 1H), 6.00 (t, J = 56 Hz, 1H), 6.00 (s, 1H), 2.26 (s, 3H), 1.56 (s, 3H). ¹⁹F NMR (470 MHz, DMSO-d₆) δ −74.31 (s), −128.9 (dd, J = 270, 57 Hz), −129.6 (dd, J = 270, 56 Hz) |

B* indicates further derivitization after described suzuki coupling (Deprotection and or capping with acid chlorides or sulfonyl chlorides).

Example 49. 2-(3-(8-Amino-6-(1H-1,2,4-triazol-1-yl)imidazo[1,2-a]pyrazin-3-yl)-4-methylphenyl)-1,1-difluoropropan-2-ol

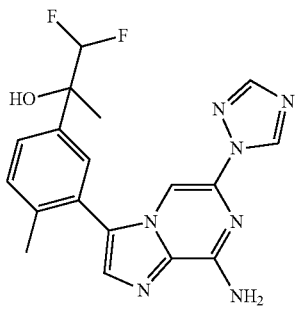 [SMILES: Cc1ccc(C(C)(O)C(F)F)cc1-c1cnc2c(N)nc(-n3cncn3)cn12]

A mixture of 2-(3-(8-amino-6-bromoimidazo[1,2-a]pyrazin-3-yl)-4-methylphenyl)-1,1-difluoropropan-2-ol (from Example 28, Step 1) (9 mg, 0.02 mmol), 1,2,4-triazole (5 mg, 0.07 mmol), and Cs$_2$CO$_3$ (22 mg, 0.07 mmol) in NMP (62 µL) was heated at 110° C. for 2 h and then at 120° C. for 3.5 h. The reaction mixture was diluted with MeOH and filtered. Purification via preparative HPLC on a C-18 column (pH=10, 30-41% MeCN/0.1% NH$_4$OH (aq) over 5 min, 60 mL/min) afforded the title compound as a white solid (1 mg, 10%). LCMS for C$_{18}$H$_{18}$F$_2$N$_7$O (M+H)$^+$: calculated m/z=386.2; found 386.1.

Example 50. 2-(3-(8-Amino-6-(1-methyl-1H-pyrazol-5-yl)imidazo[1,2-a]pyrazin-3-yl)-4-methylphenyl)-1,1-difluorobutan-2-ol trifluoroacetate

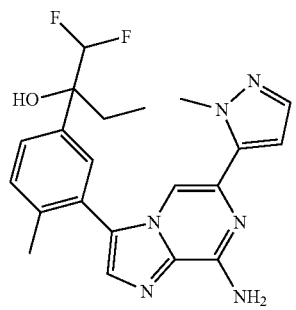 [SMILES: CCC(O)(c1ccc(C)c(-c2cnc3c(N)nc(-c4ccnn4C)cn23)c1)C(F)F]

Step 1. 1-(3-Bromo-4-methylphenyl)propan-1-one

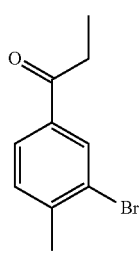

To a solution of 3-bromo-N-methoxy-N,4-dimethylbenzamide (0.36 g, 1.4 mmol) in THF (5.6 mL) at 0° C., was added dropwise ethylmagnesium bromide in THF (4.2 mL, 4.2 mmol, 1.0 M). The 0° C. bath was removed, and the reaction mixture was stirred overnight. The reaction mixture was cooled once again to 0° C., and the reaction quenched with sat. NH$_4$Cl. The mixture was extracted with EtOAc (3×). The combined organic layers were dried over MgSO$_4$, filtered, and concentrated. Purification via silica gel chromatography (1-15% EtOAc/hexanes) afforded the title compound as a white solid (0.29 g, 92%). $^1$H NMR (400 MHz, CDCl$_3$) δ 8.12 (d, J=1.7 Hz, 1H), 7.79 (dd, J=8.0, 1.7 Hz, 1H), 7.32 (d, J=7.9 Hz, 1H), 2.96 (q, J=7.2 Hz, 2H), 2.45 (s, 3H), 1.22 (t, J=7.2 Hz, 3H).

Step 2. 2-(3-Bromo-4-methylphenyl)-1,1-difluorobutan-2-ol

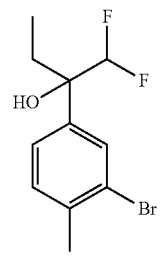

The title compound was synthesized according to an experimental procedure analogous to Examples 26 and 27, Step 1, substituting 1-(3-bromo-4-methylphenyl)propan-1-one for 1-(3-bromo-4-methylphenyl)ethan-1-one. $^1$H NMR (400 MHz, CDCl$_3$) δ 7.66 (d, J=1.7 Hz, 1H), 7.32-7.22 (m, 2H), 5.70 (t, J=56 Hz, 1H), 2.40 (s, 3H), 2.15 (s, 1H), 2.09-1.89 (m, 2H), 0.81 (t, J=7.5 Hz, 3H). $^{19}$F NMR (376 MHz, CDCl$_3$) δ −129.89 (dd, J=280, 56 Hz), −131.16 (dd, J=280, 56 Hz).

Step 3. 1,1-Difluoro-2-(4-methyl-3-(4,4,5,5-tetramethyl-1,3,2-dioxaborolan-2-yl)phenyl)butan-2-ol

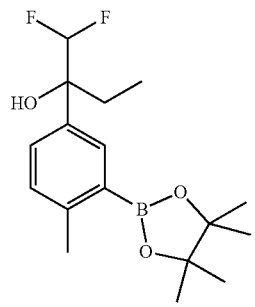 [SMILES: CCC(O)(c1ccc(C)c(B2OC(C)(C)C(C)(C)O2)c1)C(F)F]

The title compound was synthesized according to an experimental procedure analogous to Examples 26-27, Step 2, substituting 2-(3-bromo-4-methylphenyl)-1,1-difluorobutan-2-ol for 2-(3-bromo-4-methylphenyl)-1,1-difluoropropan-2-ol. LCMS for C$_{17}$H$_{24}$BF$_2$O$_2$ (M-OH)$^+$: calculated m/z=309.2; found 309.2.

Step 4. 2-(3-(8-Amino-6-bromoimidazo[1,2-a]pyrazin-3-yl)-4-methylphenyl)-1,1-difluorobutan-2-ol

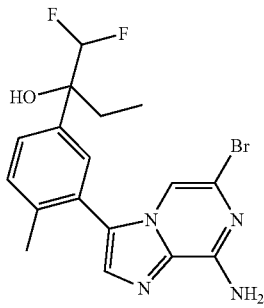

The title compound was synthesized according to an experimental procedure analogous to Example 28, Step 2, substituting 1,1-difluoro-2-(4-methyl-3-(4,4,5,5-tetramethyl-1,3,2-dioxaborolan-2-yl)phenyl)butan-2-ol for 1,1-difluoro-2-(4-methyl-3-(4,4,5,5-tetramethyl-1,3,2-dioxaborolan-2-yl)phenyl)propan-2-ol. LCMS for $C_{17}H_{18}BrF_2N_4O$ (M+H)$^+$: calculated m/z=411.1, 413.1; found 411.0, 413.1.

Step 5. 2-(3-(8-Amino-6-(1-methyl-1H-pyrazol-5-yl)imidazo[1,2-a]pyrazin-3-yl)-4-methylphenyl)-1,1-difluorobutan-2-ol trifluoroacetate The title compound was synthesized according to an experimental procedure analogous to Example 29, Step 4, substituting 2-(3-(8-amino-6-bromoimidazo[1,2-a]pyrazin-3-yl)-4-methylphenyl)-1,1-difluorobutan-2-ol for 2-(3-(8-amino-6-bromoimidazo[1,2-a]pyrazin-3-yl)-4-methylphenyl)-1,1-difluoropropan-2-ol (Isomer 1). $^1$H NMR (400 MHz, DMSO-d$_6$) δ 7.74 (s, 1H), 7.54-7.48 (m, 2H), 7.47-7.41 (m, 3H), 7.40 (d, J=1.9 Hz, 1H), 6.39 (d, J=2.0 Hz, 1H), 6.03 (t, J=56 Hz, 1H), 4.03 (s, 3H), 2.25 (s, 3H), 2.06-1.91 (m, 1H), 1.91-1.79 (m, 1H), 0.71 (t, J=7.3 Hz, 3H). $^{19}$F NMR (376 MHz, DMSO-d$_6$) δ −74.29 (s), −128.57 (dd, J=270, 56 Hz), −130.62 (dd, J=270, 56 Hz). LCMS for $C_{21}H_{23}F_2N_6O$ (M+H)$^+$: calculated m/z=413.2; found 413.2.

Example 51. 2-(3-(4-Amino-2-(1-methyl-1H-pyrazol-5-yl)imidazo[2,1-f][1,2,4]triazin-7-yl)-4-methylphenyl)-1,1-difluoropropan-2-ol trifluoroacetate salt (Single Enantiomer)

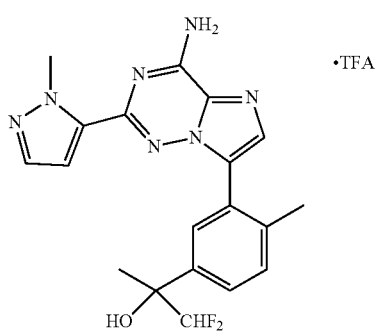 [SMILES: Cc1ccc(C(C)(O)C(F)F)cc1-c1cnc2c(N)nc(-c3ccnn3C)nn12]

Step 1. 7-Bromo-2-chloroimidazo[2,1-f][1,2,4]triazin-4-amine

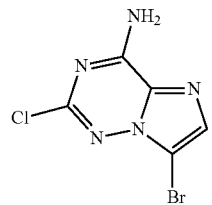 [SMILES: Nc1nc(Cl)nn2c(Br)cnc12]

A mixture of 7-bromo-2,4-dichloroimidazo[2,1-f][1,2,4]triazine (96 mg, 0.358 mmol, prepared as described in WO2016183094) in ammonia (2M/EtOH) (3 ml, 6.00 mmol) and THF (2 ml) was stirred at room temperature for 1 h, and the volatiles were removed in vacuo. The residue was washed with ether, filtered, and air dried to yield the title compound as a purple solid (79 mg, 89%). LCMS calculated for $C_5H_4BrClN_5$ (M+H)$^+$: m/z=247.9, found: 247.9.

Step 2. 2-(3-(4-Amino-2-chloroimidazo[2,1-f][1,2,4]triazin-7-yl)-4-methylphenyl)-1,1-difluoropropan-2-ol

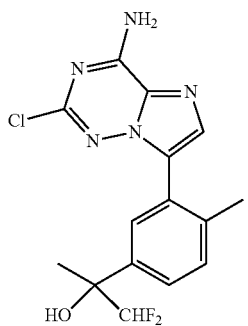 [SMILES: Cc1ccc(C(C)(O)C(F)F)cc1-c1cnc2c(N)nc(Cl)nn12]

A mixture of 7-bromo-2-chloroimidazo[2,1-f][1,2,4]triazin-4-amine (55 mg, 0.22 mmol), 1,1-difluoro-2-(4-methyl-3-(4,4,5,5-tetramethyl-1,3,2-dioxaborolan-2-yl)phenyl)propan-2-ol (isomer 1) (from Example 29, Step 2) (90 mg, 0.29 mmol), PdCl$_2$(dppf) (24.3 mg, 33 μmol), and potassium carbonate (1M/H$_2$O, 0.55 ml, 0.55 mmol) in dioxane (3 ml) was sparged with N$_2$ for 5 min and heated to 80° C. overnight. The reaction mixture was partitioned between water and EtOAc, and the layers were separated. The aqueous layer was extracted with EtOAc and the combined organic layers were washed with brine, dried over MgSO$_4$, filtered, and concentrated. The residue was purified by flash chromatography (0-100% EtOAc/hexanes) to afford the title compound as a white solid (45 mg, 58%). LCMS calculated for $C_{15}H_{15}ClF_2N_5O$ (M+H)$^+$: m/z=354.1, found: 354.0.

Step 3. 2-(3-(4-Amino-2-(1-methyl-1H-pyrazol-5-yl)imidazo[2,1-f][1,2,4]triazin-7-yl)-4-methylphenyl)-1,1-difluoropropan-2-ol trifluoroacetate salt (Isomer 1)

A mixture of 2-(3-(4-amino-2-chloroimidazo[2,1-f][1,2,4]triazin-7-yl)-4-methylphenyl)-1,1-difluoropropan-2-ol (45 mg, 0.13 mmol), 1-methyl-5-(4,4,5,5-tetramethyl-1,3,2-dioxaborolan-2-yl)-1H-pyrazole (79 mg, 0.38 mmol), PdCl$_2$(dppf)-CH$_2$Cl$_2$ adduct (20.8 mg, 25 µmol), and sodium carbonate (1M/H$_2$O, 0.38 ml, 0.38 mmol) in dioxane (3.0 ml) was sparged with N$_2$ for 5 min and heated to 130° C. in the microwave for 1 h. The reaction mixture was diluted with EtOAc, filtered through a pad of Celite®, and concentrated. The residue was dissolved in MeOH and purified by prep HPLC (pH=2) to afford the title compound (15 mg, 30%). LCMS calculated for C$_{19}$H$_{20}$F$_2$N$_7$O (M+H)$^+$: m/z=400.2, found: 400.2.

Example 52. 2-(3-(4-Amino-2-(2-methyloxazol-5-yl)imidazo[2,1-f][1,2,4]triazin-7-yl)-4-methylphenyl)-1,1-difluoropropan-2-ol trifluoroacetate salt (Single Enantiomer)

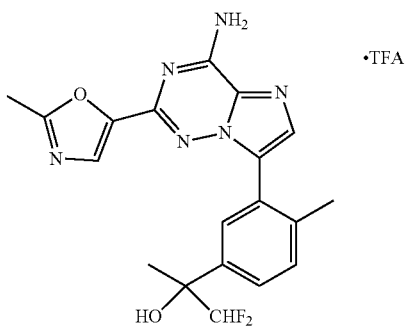

This compound was synthesized according to the procedure described for Example 51, utilizing 2-methyl-5-(4,4,5,5-tetramethyl-1,3,2-dioxaborolan-2-yl)oxazole instead of 1-methyl-5-(4,4,5,5-tetramethyl-1,3,2-dioxaborolan-2-yl)-1H-pyrazole in Step 3. $^1$H NMR (500 MHz, DMSO) δ 8.42 (s, 2H), 7.73 (s, 1H), 7.69 (d, J=1.9 Hz, 1H), 7.54 (dd, J=8.1, 1.9 Hz, 1H), 7.52 (s, 1H), 7.40 (d, J=8.1 Hz, 1H), 5.99 (t, J=56.0 Hz, 1H), 2.47 (s, 3H), 2.28 (s, 3H), 1.56 (s, 3H). LCMS calculated for C$_{19}$H$_{19}$F$_2$N$_6$O$_2$ (M+H)$^+$: m/z=401.2, found: 401.1.

Example 53. 2-(5-(8-Amino-6-(trifluoromethyl)imidazo[1,2-a]pyrazin-3-yl)-2-fluoro-4-methylphenyl)-1,1,1-trifluoropropan-2-ol

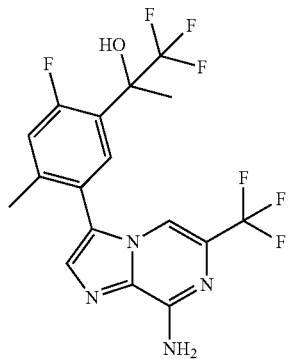

Step 1.
1-(2-fluoro-5-iodo-4-methylphenyl)ethan-1-one

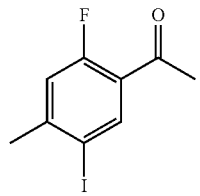

To a 0° C. solution of methyl 2-fluoro-5-iodo-4-methylbenzoate (300 mg, 1.02 mmol) and N,O-dimethylhydroxylamine hydrochloride (119 mg, 1.22 mmol) in anhydrous THF (5 ml) was added methylmagnesium bromide 3M in Et$_2$O (2.0 ml, 6.1 mmol) and the solution was allowed to gradually warm to ambient temperature while stirring overnight. The reaction mixture was cooled to 0° C. prior to quenching with saturated ammonium chloride (aq). The reaction mixture was diluted with ethyl acetate (20 mL) and water (3 mL). The layers were separated and the organic layer was washed with water (3×3 mL) and the combined aqueous phases were extracted with ethyl acetate (5 mL). The combined organic layers were washed with brine (5 mL), dried over Na$_2$SO$_4$, filtered and concentrated in vacuo. The crude product was purified by CombiFlash chromatography (40 g silica gel column, eluting with 0-20% ethyl acetate/hexanes) to afford the desired product (174 mg, 61% yield). $^1$H NMR (400 MHz, CDCl$_3$) δ 8.27-8.31 (m, 1H), 7.00 (dt, J=11.6, 3.6 Hz, 1H), 2.62 (bs, 3H), 2.47 (bs, 3H).

Step 2. 1,1,1-trifluoro-2-(2-fluoro-5-iodo-4-methylphenyl)propan-2-ol

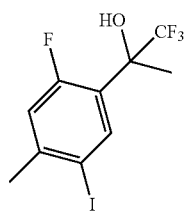 [SMILES: Cc1cc(F)c(C(C)(O)C(F)(F)F)cc1I]

To a 0° C. solution of 1-(2-fluoro-5-iodo-4-methylphenyl)ethan-1-one (174 mg, 0.626 mmol) was added sequentially trimethyl(trifluoromethyl)silane (2.0 M in THF) (0.60 ml, 1.3 mmol) and tetrabutylammonium fluoride (1.0 M in THF) (0.063 mL, 0.063 mmol) and the resulting solution was allowed to gradually warm to ambient temperature. The reaction was quenched by the addition of methanol and purified by CombiFlash chromatography (20 g silica gel column, eluting with 0-40% ethyl acetate/hexanes) to afford the desired product (150 mg, 69% yield). $^1$H NMR (400 MHz, CDCl$_3$) δ 8.0 (d, J=8 Hz, 1H), 7.0 (d, J=13 Hz, 1H), 2.96-2.98 (m, 1H), 2.44 (s, 3H), 1.86 (s, 3H).

Step 3. 1,1,1-trifluoro-2-(2-fluoro-4-methyl-5-(4,4,5,5-tetramethyl-1,3,2-dioxaborolan-2-yl)phenyl)propan-2-ol

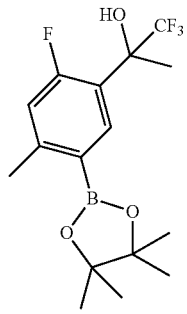 [SMILES: Cc1cc(F)c(C(C)(O)C(F)(F)F)cc1B1OC(C)(C)C(C)(C)O1]

A mixture of 1,1,1-trifluoro-2-(2-fluoro-5-iodo-4-methylphenyl)propan-2-ol (122 mg, 0.350 mmol), potassium acetate (103 mg, 1.05 mmol), 4,4,4',4',5,5,5',5'-octamethyl-2,2'-bi(1,3,2-dioxaborolane) (134 mg, 0.526 mmol), and PdCl$_2$(dppf)-CH$_2$Cl$_2$ adduct (29 mg, 0.035 mmol) in 1,4-dioxane (2.0 ml) was de-gassed and purged with N$_2$ several times prior to heating at 105° C. in a sealed vial overnight. Upon cooling to ambient temperature the crude reaction mixture was diluted with ethyl acetate (15 mL) and filtered through a pad of Celite®. The inorganics were washed thoroughly with ethyl acetate and the filtrate was concentrated in vacuo. The crude product was used directly in the next step without further purification. $^1$H NMR (400 MHz, CDCl$_3$) δ 8.0 (d, J=8 Hz, 1H), 7.0 (d, J=13 Hz, 1H), 2.43 (s, 3H), 1.35 (s, 3H), 1.29 (s, 12H).

Step 4. 2-(5-(8-Amino-6-(trifluoromethyl)imidazo[1,2-a]pyrazin-3-yl)-2-fluoro-4-methylphenyl)-1,1,1-trifluoropropan-2-ol A mixture of 3-bromo-6-(trifluoromethyl)imidazo[1,2-a]pyrazin-8-amine (Example 4, Step 6; 30 mg, 0.11 mmol), (4-fluoro-2-methyl-5-(1,1,1-trifluoro-2-hydroxypropan-2-yl)phenyl)boronic acid (40 mg, 0.15 mmol), potassium carbonate (44.3 mg, 0.320 mmol), and Pd(Ph$_3$P)$_4$ (16 mg, 14 μmol) in 1,4-dioxane (0.6 ml) and water (0.06 ml) was de-gassed and purged with N$_2$ (g) several times prior to heating via microwave irradiation in a sealed vial at 130° C. overnight. A second aliquot of (4-fluoro-2-methyl-5-(1,1,1-trifluoro-2-hydroxypropan-2-yl)phenyl)boronic acid (40 mg, 0.15 mmol) and Pd(Ph$_3$P)$_4$ (8 mg, 7 μmol) was added and stirring was continued at 130° C. for 1.5 h. Upon cooling to ambient temperature the reaction mixture was diluted with ethyl acetate (15 mL) and filtered through a pad of Celite®. The inorganics were thoroughly washed with ethyl acetate and the crude product was purified by CombiFlash chromatography (12 g silica gel column, eluting with 0-20% methanol/dichloromethane) followed by purification via preparative HPLC on a C-18 column (pH=2, 33-51% MeCN/0.1% TFA (aq) over 12 min, 60 mL/min) to afford the title compound. LCMS for C$_{17}$H$_{13}$F$_7$N$_4$O (M+H)$^+$: calculated m/z=423.3; found 423.3.

Example 54. 2-(4-(8-Amino-6-(trifluoromethyl)imidazo[1,2-a]pyrazin-3-yl)-5-methylpyridin-2-yl)-1,1,1-trifluoropropan-2-ol

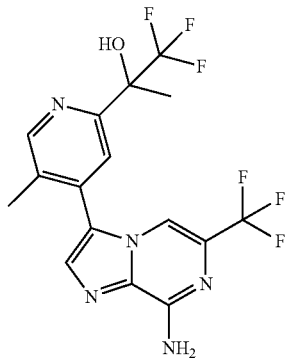 [SMILES: Cc1cnc(C(C)(O)C(F)(F)F)cc1-c1cnc2c(N)nc(C(F)(F)F)cn12]

Step 1. 4-bromo-N-methoxy-N,5-dimethylpicolinamide

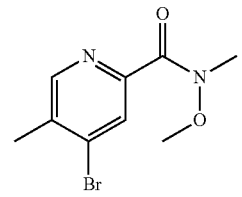

A solution of 4-bromo-5-methylpicolinic acid (368 mg, 1.70 mmol), HATU (712 mg, 1.87 mmol), DIEA (0.59 ml, 3.4 mmol), and N,O-dimethylhydroxylamine hydrochloride (199 mg, 2.04 mmol) in DCE (10 ml) was stirred at ambient temperature overnight. The crude product was purified by CombiFlash chromatography (40 g silica gel column, eluting with 0-50% ethyl acetate/hexanes) to afford the desired product (345 mg, 78% yield). LCMS for C$_9$H$_{11}$BrN$_2$O$_2$ (M+H)$^+$: calculated m/z=259.1/261.1; found 259.1/261.1.

Step 2. 1-(4-bromo-5-methylpyridin-2-yl)ethan-1-one

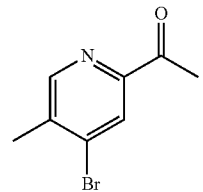

To a 0° C. solution of 4-bromo-N-methoxy-N,5-dimethylpicolinamide (345 mg, 1.33 mmol) in THF (6 ml) was added 3 M methylmagnesium bromide (0.6 ml, 1.8 mmol) drop-wise and the resulting solution was allowed to gradually warm to ambient temperature while stirring overnight. The reaction mixture was cooled to 0° C. prior to quenching with saturated ammonium chloride (aq). The reaction mixture was diluted with ethyl acetate (20 mL) and water (3 mL). The layers were separated and the organic layer was washed with water (2×3 mL) and the combined aqueous phases were extracted with ethyl acetate (5 mL). The combined organic layers were washed with brine (5 mL), dried over Na$_2$SO$_4$, filtered and concentrated in vacuo. The crude product was purified by CombiFlash chromatography (40 g silica gel column, eluting with 0-60% ethyl acetate/hexanes) to afford the desired product (155 mg, 54% yield). LCMS for C$_8$H$_8$BrNO (M+H)$^+$: calculated m/z=214.1/216.1; found 214.0/216.0.

Step 3. 2-(4-(8-Amino-6-(trifluoromethyl)imidazo[1,2-a]pyrazin-3-yl)-5-methylpyridin-2-yl)-1,1,1-trifluoropropan-2-ol A procedure analogous to that described for Example 53 steps 2-4 was used, substituting 1-(4-bromo-5-methylpyridin-2-yl)ethan-1-one as the ketone to obtain the title compound. LCMS for C$_{16}$H$_{13}$F$_6$N$_5$O (M+H)$^+$: calculated m/z=406.3; found 406.1.

Example 55. 2-(5-(8-Amino-6-(trifluoromethyl)imidazo[1,2-a]pyrazin-3-yl)-2-fluorophenyl)-1,1,1-trifluoropropan-2-ol

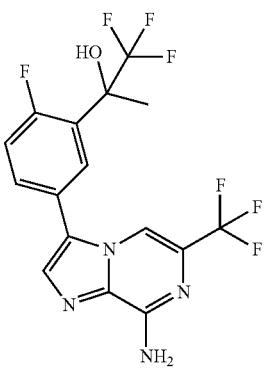 [SMILES: CC(O)(c1cc(-c2cnc3c(N)nc(C(F)(F)F)cn23)ccc1F)C(F)(F)F]

A procedure analogous to that described for Example 53 steps 2-4 was used, substituting 1-(5-bromo-2-fluorophenyl)ethan-1-one as the ketone to obtain the title compound. LCMS for C$_{16}$H$_{11}$F$_7$N$_4$O (M+H)$^+$: calculated m/z=409.3; found 409.1.

Example 56. 2-(3-(8-Amino-6-(trifluoromethyl)imidazo[1,2-a]pyrazin-3-yl)phenyl)-1,1,1-trifluoropropan-2-ol

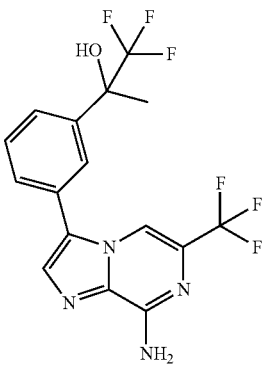 [SMILES: CC(O)(c1cccc(-c2cnc3c(N)nc(C(F)(F)F)cn23)c1)C(F)(F)F]

Step 1. 1-(3-(8-amino-6-(trifluoromethyl)imidazo[1,2-a]pyrazin-3-yl)phenyl)ethan-1-one

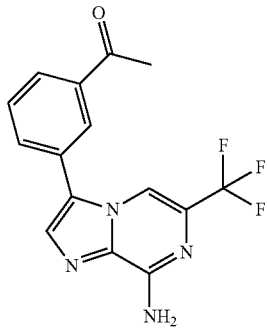 [SMILES: CC(=O)c1cccc(-c2cnc3c(N)nc(C(F)(F)F)cn23)c1]

A mixture of 3-bromo-6-(trifluoromethyl)imidazo[1,2-a]pyrazin-8-amine (Example 4, Step 6; 50 mg, 0.18 mmol), 1-(3-(4,4,5,5-tetramethyl-1,3,2-dioxaborolan-2-yl)phenyl)ethan-1-one (88 mg, 0.36 mmol), potassium carbonate (74 mg, 0.53 mmol), and Pd(Ph$_3$P)$_4$ (25 mg, 0.021 mmol) in 1,4-dioxane (2 ml) and water (0.20 ml) was de-gassed and purged with N$_2$ (g) several times prior to heating in a sealed vial at 120° C. for 2 h. Upon cooling to ambient temperature the reaction mixture was diluted with ethyl acetate (15 mL) and filtered through a pad of Celite®. The inorganics were thoroughly washed with ethyl acetate and the crude product was purified by CombiFlash chromatography (12 g silica gel column, eluting with 0-15% methanol/dichloromethane) to afford the desired product (66 mg, which was treated as 57 mg). LCMS for C$_{15}$H$_{11}$F$_3$N$_4$O (M+H)$^+$: calculated m/z=321.3; found 321.1.

Step 2. 2-(3-(8-amino-6-(trifluoromethyl)imidazo[1,2-a]pyrazin-3-yl)phenyl)-1,1,1-trifluoropropan-2-ol A procedure analogous to Example 53 step 2 was used, substituting 1-(3-(8-amino-6-(trifluoromethyl)imidazo[1,2-a]pyrazin-3-yl)phenyl)ethan-1-one as the ketone. The crude reaction mixture was purified by CombiFlash chromatography (12 g silica gel column, eluting with 0-15% methanol/dichloromethane) followed by a second purification on preparative HPLC on a C-18 column (pH=2, 30-48% MeCN/0.1% TFA (aq) over 12 min, 60 mL/min) to afford the desired product. LCMS for C$_{16}$H$_{12}$F$_6$N$_4$O (M+H)$^+$: calculated m/z=391.3; found 391.1.

Example 57. 2-(3-(8-Amino-6-(trifluoromethyl)imidazo[1,2-a]pyrazin-3-yl)-4-fluorophenyl)-1,1,1-trifluoropropan-2-ol

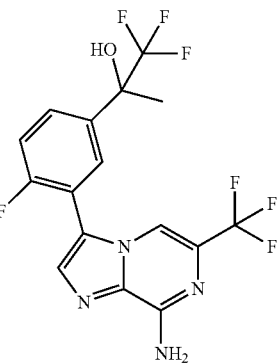

Step 1. Methyl 3-(8-amino-6-(trifluoromethyl)imidazo[1,2-a]pyrazin-3-yl)-4-fluorobenzoate

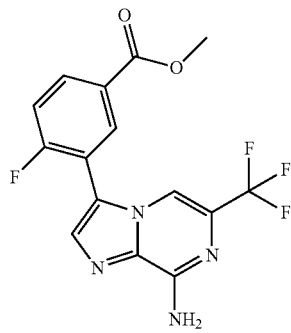 [SMILES: COC(=O)c1ccc(F)c(-c2cnc3c(N)nc(C(F)(F)F)cn23)c1]

A procedure analogous to Example 56 step 1 was used, substituting (2-fluoro-5-(methoxycarbonyl)phenyl)boronic acid as the boronic acid to obtain the desired product (41 mg, 65% yield). LCMS for $C_{15}H_{10}F_4N_4O_2$ (M+H)$^+$: calculated m/z=355.3; found 355.1.

Step 2. 1-(3-(8-Amino-6-(trifluoromethyl)imidazo[1,2-a]pyrazin-3-yl)-4-fluorophenyl)ethan-1-one

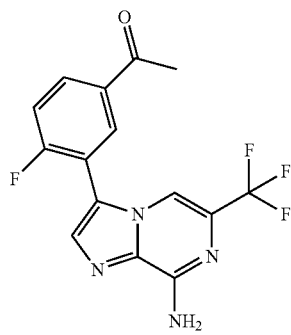 [SMILES: CC(=O)c1ccc(F)c(-c2cnc3c(N)nc(C(F)(F)F)cn23)c1]

To a 0° C. solution of ethyl 3-(8-amino-6-(trifluoromethyl)imidazo[1,2-a]pyrazin-3-yl)-4-fluorobenzoate (41 mg, 0.11 mmol) and O,N-dimethylhydroxylamine hydrochloride (11.1 mg, 0.114 mmol) in THF (0.8 ml) was added 3.0 M methylmagnesium bromide in diethyl ether (0.2 ml, 0.6 mmol) and the solution was allowed to gradually warm to ambient temperature while stirring for 4 h. The reaction mixture was cooled to 0° C. prior to quenching with saturated ammonium chloride (aq). The reaction mixture was diluted with ethyl acetate (20 mL) and water (3 mL). The layers were separated and the organic layer was washed with water (2×3 mL) and the combined aqueous phases were extracted with ethyl acetate (5 mL). The combined organic layers were washed with brine (5 mL), dried over Na$_2$SO$_4$, filtered and concentrated in vacuo. The crude product was purified by CombiFlash chromatography (12 g silica gel column, eluting with 0-15% methanol/dichloromethane) to afford the desired product (24 mg, 75% yield). LCMS for $C_{15}H_{10}F_4N_4O$ (M+H)$^+$: calculated m/z=339.3; found 339.0.

Step 3. 2-(3-(8-Amino-6-(trifluoromethyl)imidazo[1,2-a]pyrazin-3-yl)-4-fluorophenyl)-1,1,1-trifluoropropan-2-ol A procedure analogous to Example 56, step 2 was used, substituting 1-(3-(8-Amino-6-(trifluoromethyl)imidazo[1,2-a]pyrazin-3-yl)-4-fluorophenyl)ethan-1-one as the ketone to obtain the title compound. LCMS for $C_{16}H_{11}F_7N_4O$ (M+H)$^+$: calculated m/z=409.3; found 409.1.

Example 58. 2-(5-(8-Amino-6-(trifluoromethyl)imidazo[1,2-a]pyrazin-3-yl)-6-methylpyridin-3-yl)-1,1,1-trifluoropropan-2-ol

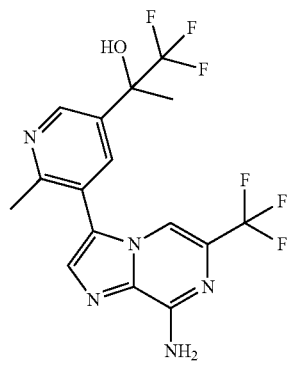 [SMILES: Cc1ncc(C(C)(O)C(F)(F)F)cc1-c1cnc2c(N)nc(C(F)(F)F)cn12]

A procedure analogous to Example 54, steps 1-3 was used, substituting 5-bromo-6-methylnicotinic acid as the starting carboxylic acid to obtain the title compound. LCMS for $C_{16}H_{13}F_6N_5O$ (M+H)$^+$: calculated m/z=406.3; found 406.1.

Examples 59-60. 2-(3-(8-Amino-6-(trifluoromethyl)imidazo[1,2-a]pyrazin-3-yl)-4-methylphenyl)-3,3,4,4,4-pentafluorobutan-2-ol (Enantiomers 1-2)

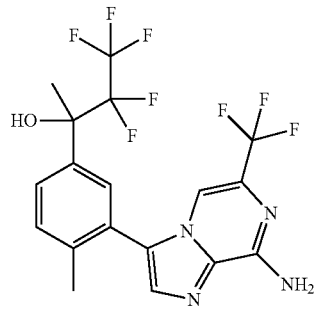 [SMILES: Cc1ccc(C(C)(O)C(F)(F)C(F)(F)F)cc1-c1cnc2c(N)nc(C(F)(F)F)cn12]

Step 1. 2-(3-Bromo-4-methylphenyl)-3,3,4,4,4-pentafluorobutan-2-ol

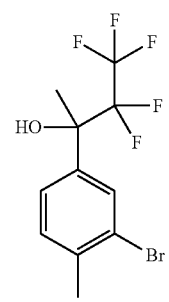

To a mixture of 1-(3-bromo-4-methylphenyl)ethan-1-one (0.10 g, 0.47 mmol) and (pentafluoroethyl)trimethylsilane (0.098 mL) (TCI, T3011) in THF (0.47 ml) at 0° C. was added tetrabutylammonium fluoride (4 µL, 4 µmol, 1.0 M in THF). The 0° C. bath was removed, and the reaction mixture was stirred overnight. The reaction mixture was again cooled to 0° C., and an additional portion of tetrabutylammonium fluoride (0.47 mL, 0.47 mmol, 1.0 M in THF) was added. The 0° C. bath was removed, and the reaction mixture was stirred for 6 h. The reaction mixture was diluted with water and extracted with Et$_2$O (3×). The combined organic layers were washed with brine, dried over MgSO$_4$, and concentrated. Purification via silica gel chromatography (2-20% EtOAc/hexanes) afforded the title compound (78 mg, 50%). $^1$H NMR (400 MHz, CDCl$_3$) δ 7.73 (s, 1H), 7.37 (d, J=8.0 Hz, 1H), 7.24 (d, J=8.1 Hz, 1H), 2.40 (s, 3H), 2.37 (s, 1H), 1.78 (s, 3H). $^{19}$F NMR (376 MHz, CDCl$_3$) δ −77.84 (s, 3F), −121.37 (d, J=280 Hz, 1F), −123.02 (d, J=280 Hz, 1F).

Step 2. 3,3,4,4,4-Pentafluoro-2-(4-methyl-3-(4,4,5,5-tetramethyl-1,3,2-dioxaborolan-2-yl)phenyl)butan-2-ol

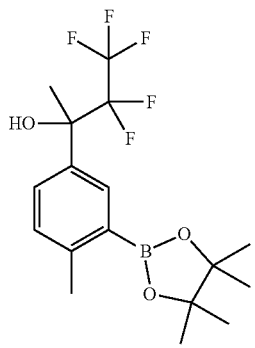

The title compound was synthesized according to an experimental procedure analogous to Examples 26-27, Step 2, substituting 2-(3-bromo-4-methylphenyl)-3,3,4,4,4-pentafluorobutan-2-ol for 2-(3-bromo-4-methylphenyl)-1,1-difluoropropan-2-ol. LCMS for C$_{17}$H$_{23}$BF$_5$O$_3$ (M+H)$^+$: calculated m/z=381.2; found 381.1.

Step 3. 2-(3-(8-Amino-6-(trifluoromethyl)imidazo[1,2-a]pyrazin-3,3,4,4,4-pentafluorobutan-2-ol (Racemic Mixture)

A mixture of 3-bromo-6-(trifluoromethyl)imidazo[1,2-a]pyrazin-8-amine (Example 4, Step 6; 15 mg, 0.053 mmol), dichloro[1,1'-bis(diphenylphosphino)ferrocene]palladium (II) dichloromethane adduct (8.7 mg, 10.7 µmol), 3,3,4,4,4-pentafluoro-2-(4-methyl-3-(4,4,5,5-tetramethyl-1,3,2-dioxaborolan-2-yl)phenyl)butan-2-ol (30 mg, 0.080 mmol) in THF (0.90 mL), and 1.0 M K$_2$CO$_3$ (aq) (100 µL, 0.11 mmol) was degassed with N$_2$ for 5 min and then heated at 80° C. for 16 h. The reaction mixture was filtered through Celite®, rinsing with MeOH. Purification via preparative HPLC on a C-18 column (pH=10, 33-53% MeCN/0.1% NH$_4$OH (aq) over 5 min, 60 mL/min) afforded the racemic compound (14 mg). $^1$H NMR (400 MHz, DMSO-d$_6$) δ 7.79 (s, 1H), 7.66 (br s, 2H), 7.61 (m, 2H), 7.53 (s 1H), 7.48 (d, J=8.0 Hz, 1H), 6.74 (s, 1H), 2.24 (s, 3H), 1.73 (s, 3H). $^{19}$F NMR (376 MHz, DMSO-d$_6$) δ −67.17 (s, 3F), −77.12 (s, 3F), −120.31 (d, J=270 Hz, 1F), −122.20 (d, J=270 Hz, 1F). LCMS for C$_{18}$H$_{15}$F$_8$N$_4$O (M+H)$^+$: calculated m/z=455.1; found 455.1.

Step 4. 2-(3-(8-Amino-6-(trifluoromethyl)imidazo[1,2-a]pyrazin-3-yl)-4-methylphenyl)-3,3,4,4,4-pentafluorobutan-2-ol (Enantiomers 1-2)

Purification of a portion of the racemic compound of Step 3 via chiral HPLC on an AM-1 column (10% hexane/EtOH, 18 mL/min) afforded Example 59 as a clear residue (Enantiomer 1; first eluting enantiomer, t$_R$=9.96 min, 3.4 mg) and Example 60 as a clear residue (Enantiomer 2; second eluting enantiomer, t$_R$=15.7 min, 3.5 mg).

Example 59 (Enantiomer 1): LCMS for C$_{18}$H$_{15}$F$_8$N$_4$O (M+H)$^+$: calculated m/z=455.1; found 455.2.

Example 60 (Enantiomer 2): LCMS for C$_{18}$H$_{15}$F$_8$N$_4$O (M+H)$^+$: calculated m/z=455.1; found 455.2.

Example 61. 1-(3-(8-Amino-6-(trifluoromethyl)imidazo[1,2-a]pyrazin-3-yl)-4-methylphenyl)-2-fluorocyclopentan-1-ol trifluoroacetate salt (Mixture of Four Isomers)

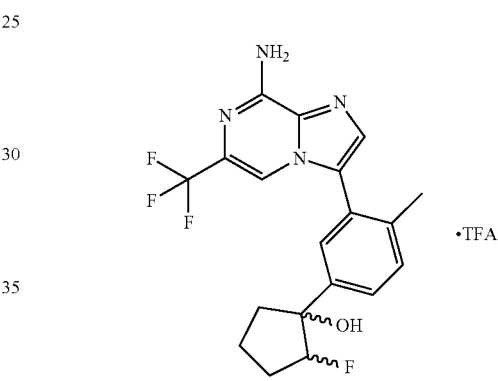

Step 1. 2-Chloro-4-(cyclopent-1-en-1-yl)-1-methylbenzene

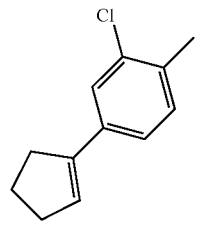

A degassed mixture of 4-bromo-2-chloro-1-methylbenzene (0.600 g, 2.92 mmol, Aldrich 528889), 2-(cyclopent-1-en-1-yl)-4,4,5,5-tetramethyl-1,3,2-dioxaborolane (0.680 g, 3.50 mmol, Combi-Blocks, PN-2510), Na$_2$CO$_3$ (2.0 M solution, 4.4 mL, 8.8 mmol) and [1,1'-bis(diphenylphosphino)ferrocene]palladium(II) dichloride complex with dichloromethane (162 mg, 0.198 mmol) in MeCN (5 mL) was heated in a sealed vial to 110° C. in an oil bath for 3 hours. The reaction was cooled to room temperature and partitioned between EtOAc and water. The organic layer was washed with water, followed by brine, dried over Na$_2$SO$_4$, filtered and concentrated. The product was purified by flash chromatography, eluting with a gradient from 0-50% EtOAc in hexanes (520 mg, 92%). $^1$H NMR (400 MHz, CDCl$_3$) δ 7.42 (d, J=0.9 Hz, 1H), 7.25 (dd, J=7.9, 1.3 Hz, 1H), 7.17 (d, J=7.9 Hz, 1H), 6.20-6.16 (m, 1H), 2.73-2.65 (m, 2H), 2.59-2.50 (m, 2H), 2.38 (s, 3H), 2.10-1.96 (m, 2H).

Step 2. 1-(3-Chloro-4-methylphenyl)-2-fluorocyclopentan-1-ol (Mixture of Four Isomers)

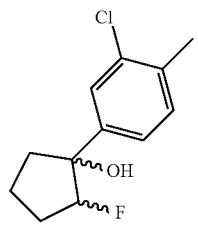

To a solution of 2-chloro-4-(cyclopent-1-en-1-yl)-1-methylbenzene (0.050 g, 0.26 mmol) in MeCN (3 mL) was added H$_2$O (0.8 mL) and Selectfluor® (0.110 g, 0.311 mmol). The mixture was heated in a microwave to 80° C. for 5 minutes. Acetonitrile was removed in vacuo and the mixture was diluted with water and extracted with DCM. The organic layer was dried over Na$_2$SO$_4$, filtered and concentrated. The product was purified by flash chromatography, eluting with a gradient of 0-30% EtOAc in hexanes to afford product as a colorless oil (0.040 g, 67%).

Step 3. 2-Fluoro-1-(4-methyl-3-(4,4,5,5-tetramethyl-1,3,2-dioxaborolan-2-yl)phenyl)cyclopentan-1-ol (Mixture of Four Isomers)

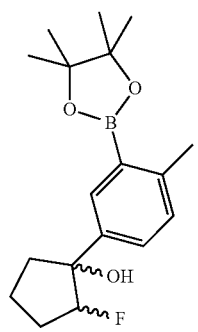 [SMILES: Cc1ccc(C2(O)CCCC2F)cc1B1OC(C)(C)C(C)(C)O1]

A degassed mixture of 1-(3-chloro-4-methylphenyl)-2-fluorocyclopentan-1-ol (0.040 g, 0.18 mmol), bis(pinacolato)diboron (89 mg, 0.350 mmol), potassium acetate (57 mg, 0.58 mmol), tris(dibenzylideneacetone)dipalladium(0) (3.2 mg, 3.5 μmol) and 2-dicyclohexylphosphino-2',4',6'-triisopropyl-1,1'-biphenyl (6.7 mg, 0.014 mmol) in dioxane (1.16 mL) was heated in a sealed vial to 120° C. for 1.5 hours. Identical quantities of each reagent were added and heating was continued at 120° C. for 2 additional hours. Upon cooling to room temperature, the reaction mixture was diluted with EtOAc and filtered through a 0.5 micrometer cartridge, rinsing with additional EtOAc. The filtrate was washed with water, followed by brine, dried over MgSO$_4$, filtered and concentrated. The product was used without further purification.

Step 4. 1-(3-(8-Amino-6-(trifluoromethyl)imidazo [1,2-a]pyrazin-3-yl)-4-methylphenyl)-2-fluorocyclopentan-1-ol trifluoroacetate salt (Mixture of Four Isomers)

A microwave vial was charged with 2-fluoro-1-(4-methyl-3-(4,4,5,5-tetramethyl-1,3,2-dioxaborolan-2-yl)phenyl)cyclopentan-1-ol (0.056 g, 0.18 mmol), 3-bromo-6-(trifluoromethyl)imidazo[1,2-a]pyrazin-8-amine (Example 4, Step 6; 0.049 g, 0.18 mmol, AFFINITY, ARI-0167) and THF (3 mL), followed by the addition of K$_2$CO$_3$ solution (1.0 M, 0.525 mL, 0.525 mmol), dichloro[1,1'-bis(diphenylphosphino)ferrocene]palladium(II) dichloromethane adduct (0.029 g, 0.035 mmol). The reaction mixture was degassed by sparging with N$_2$ and was heated in an oil bath held at 90° C. for 3 hours. Additional 3-bromo-6-(trifluoromethyl)imidazo[1,2-a]pyrazin-8-amine (Example 4, Step 6; 0.024 g, 0.086 mmol), K$_2$CO$_3$ solution (1.0 M, 0.2 mL, 0.2 mmol), dichloro[1,1'-bis(diphenylphosphino)ferrocene]palladium (II) dichloromethane adduct (0.011 g, 0.013 mmol) were added and the reaction was continued at 90° C. for 1 hour. Upon cooling to room temperature, the reaction was filtered through Celite® and the filtrate was partitioned between water and EtOAc. The organic layer was dried over MgSO$_4$, filtered and concentrated. The crude residue was diluted with MeCN and H$_2$O, filtered and purified by preparative HPLC-MS (pH=2) and lyophilized to afford product as the TFA salt (7 mg, 7%). LCMS calculated for C$_{19}$H$_{19}$F$_4$N$_4$O (M+H)$^+$: m/z=395.1, found: 395.1. $^1$H NMR (400 MHz, DMSO-d$_6$) δ 7.76 (s, 1H), 7.65 (br s, 2H), 7.59 (s, 1H), 7.57 (d, J=8.3 Hz, 1H), 7.50 (s, 1H), 7.42 (d, J=7.9 Hz, 1H), 5.41 (br s, 1H), 4.77 (m, J$_{H-F}$=52.0 Hz, 1H), 2.37-2.11 (m, 2H), 2.20 (s, 3H), 2.01-1.75 (m, 4H). $^{19}$F NMR (376 MHz, DMSO-d$_6$) δ −66.8 (s), −73.7 (s), −172.6--173.1 (m).

Examples 62-63. 8-amino-N-(2-hydroxy-2-methylpropyl)-3-(2-methyl-5-(1,1,1-trifluoro-2-hydroxypropan-2-yl)phenyl)imidazo[1,2-a]pyrazine-6-carboxamide (Enantiomers 1-2)

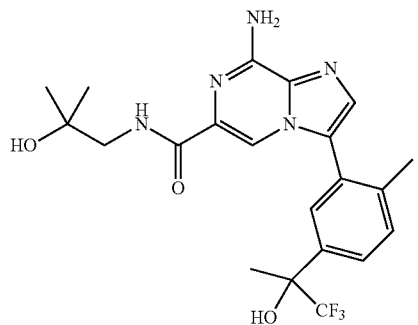 [SMILES: Cc1ccc(C(C)(O)C(F)(F)F)cc1-c1cnc2c(N)nc(C(=O)NCC(C)(C)O)cn12]

A solution of methyl 8-amino-3-(2-methyl-5-(1,1,1-trifluoro-2-hydroxypropan-2-yl)phenyl)imidazo[1,2-a]pyrazine-6-carboxylate (Example 8, 0.080 g, 0.203 mmol) in THF (3.38 mL) was treated with 1-amino-2-methylpropan-2-ol (0.181 g, 2.03 mmol) followed by trimethylaluminum (0.507 mL, 1.01 mmol) (2 M in toluene) and stirred at 80° C. overnight. The reaction mixture was treated with additional trimethylaluminum (0.70 ml, 1.40 mmol) (2 M in toluene) and stirred at 80° C. overnight. The reaction mixture was cooled to room temperature, diluted with methanol, and filtered over a pad of Celite. After rinsing with MeOH (2×), the filtrate was concentrated to an amber oil. Purification via silica gel chromatography (0-5% MeOH/DCM) afforded the title compound as an oily solid (26 mg, 28%) that was a mixture of enantiomers. The racemic mixture was separated via preparative chiral HPLC (Phenomenex Lux Amylose-1 [21.2×250 mm, 5 micron], eluting with 12% ethanol in hexanes, at flow rate of 18 mL/min, loading ~8 mg in 800 µL ethanol). The first peak that eluted had a retention time of 11.9 min (Example 62; Enantiomer 1). The second peak that eluted had a retention time of 16.1 min (Example 63, Enantiomer 2).

Example 62 (Enantiomer 1): $^1$H NMR (400 MHz, DMSO-$d_6$) δ 8.08 (t, J=6.1 Hz, 1H), 7.70 (d, J=2.8 Hz, 2H), 7.65 (d, J=8.1 Hz, 1H), 7.58 (s, 1H), 7.49 (d, J=8.2 Hz, 1H), 7.36 (s, 2H), 6.65 (s, 1H), 4.65 (s, 1H), 3.22 (d, J=6.1 Hz, 2H), 2.15 (s, 3H), 1.70 (s, 3H), 1.09 (s, 6H). LCMS for $C_{21}H_{25}F_3N_5O_3$ (M+H)$^+$: m/z=452.2; Found: 452.1.

Example 63 (Enantiomer 2): $^1$H NMR (600 MHz, DMSO-$d_6$) δ 8.08 (t, J=6.0 Hz, 1H), 7.70 (d, J=3.0 Hz, 2H), 7.65 (d, J=8.2 Hz, 1H), 7.58 (s, 1H), 7.49 (d, J=8.2 Hz, 1H), 7.36 (s, 2H), 6.65 (s, 1H), 4.65 (s, 1H), 3.22 (d, J=6.1 Hz, 2H), 2.15 (s, 3H), 1.70 (s, 3H), 1.09 (s, 6H). LCMS for $C_{21}H_{25}F_3N_5O_3$ (M+H)$^+$: m/z=452.2; Found: 452.2.

Example 64. 1-(8-Amino-3-(5-(1,1-difluoro-2-hydroxypropan-2-yl)-2-methylphenyl)imidazo[1,2-a]pyrazin-6-yl)piperidine-4-carbonitrile

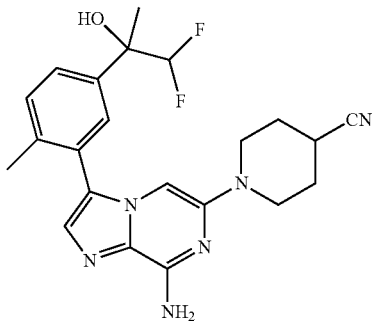 [SMILES: Cc1ccc(C(C)(O)C(F)F)cc1-c1cnc2c(N)nc(N3CCC(C#N)CC3)cn12]

Step 1. 6-Bromo-3-(5-(2-((tert-butyldimethylsilyl)oxy)-1,1-difluoropropan-2-yl)-2-methylphenyl)imidazo[1,2-a]pyrazin-8-amine

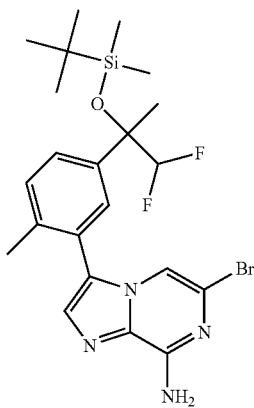 [SMILES: Cc1ccc(C(C)(O[Si](C)(C)C(C)(C)C)C(F)F)cc1-c1cnc2c(N)nc(Br)cn12]

To a solution of 2-(3-(8-amino-6-bromoimidazo[1,2-a]pyrazin-3-yl)-4-methylphenyl)-1,1-difluoropropan-2-ol (406 mg, 1.02 mmol) in anhydrous DMF (3 mL) was added sequentially 2,6-lutidine (0.59 mL, 5.1 mmol) and tert-butyldimethylsilyl trifluoromethane-sulfonate (0.70 mL, 3.0 mmol) and the resulting solution was stirred in a sealed vial at 60° C. for 4 h. The crude reaction mixture was cooled to 0° C. and quenched by the addition of saturated ammonium chloride (aq). The reaction mixture was diluted with EtOAc (30 mL) and washed successively with water (2×4 mL), 5% LiCl (aq) (3×4 mL), 50% brine/water (2×4 mL), and brine (2×4 mL). The organic layer was dried over $Na_2SO_4$, filtered, and concentrated in vacuo. The crude product was purified by CombiFlash chromatography (40 g silica gel column, eluting with 0-60% ethyl acetate/hexanes) to afford the title compound. LCMS for $C_{22}H_{30}BrF_2N_4OSi$ (M+H)$^+$: calculated m/z=511.1, 513.1; found 511.1, 513.1.

Step 2. Di-tert-butyl (6-bromo-3-(5-(2-((tert-butyldimethylsilyl)oxy)-1,1-difluoropropan-2-yl)-2-methylphenyl)imidazo[1,2-a]pyrazin-8-yl)carbamate

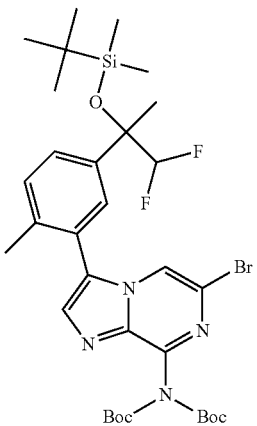 [SMILES: Cc1ccc(C(C)(O[Si](C)(C)C(C)(C)C)C(F)F)cc1-c1cnc2c(N(C(=O)OC(C)(C)C)C(=O)OC(C)(C)C)nc(Br)cn12]

A solution of 6-bromo-3-(5-(2-((tert-butyldimethylsilyl)oxy)-1,1-difluoropropan-2-yl)-2-methylphenyl)imidazo[1,2-a]pyrazin-8-amine (523 mg, 1.02 mmol), di-tert-butyl dicarbonate (0.71 mL, 3.1 mmol), and DMAP (18 mg, 0.15 mmol) in DCM (4 mL) was stirred at ambient temperature overnight. A second aliquot of di-tert-butyl dicarbonate (300 µL, 1.3 mmol) and DMAP (9 mg, 0.07 mmol) were added and stirring was continued for 5 h. The crude product was purified by CombiFlash chromatography (40 g silica gel column, eluting with 0-40% ethyl acetate/hexanes) to afford the title compound. LCMS for $C_{27}H_{38}BrF_2N_4O_3Si$ (M-Boc+2H)$^+$: calculated m/z=611.2, 613.2; found 611.3, 613.3.

Step 3. 1-(8-Amino-3-(5-(1,1-difluoro-2-hydroxypropan-2-yl)-2-methylphenyl)imidazo[1,2-a]pyrazin-6-yl)piperidine-4-carbonitrile A mixture of di-tert-butyl (6-bromo-3-(5-(2-((tert-butyldimethylsilyl)oxy)-1,1-difluoropropan-2-yl)-2-methylphenyl)imidazo[1,2-a]pyrazin-8-yl)carbamate (19 mg, 0.031 mmol), piperidine-4-carbonitrile (10 mg, 0.093 mmol), sodium tert-butoxide (11.9 mg, 0.124 mmol), and tBuXPhos Pd G3 (Aldrich, 76229, CAS [1142811-12-8]) (3.7 mg, 4.7 µmol) in dioxane (0.57 mL) was de-gassed and purged with $N_2$ several times prior to heating at 100° C. in a sealed vial overnight. Upon cooling to ambient temperature the crude reaction mixture was diluted with ethyl acetate (15 mL), filtered through a pad of celite and the filtrate was concentrated in vacuo. The residue was dissolved in DCM (2 mL), treated with TFA (1 mL), and stirred at ambient temperature for 1 h. The volatiles were removed in vacuo and the crude product was re-dissolved in MeOH and purified via preparative HPLC on a C-18 column (pH 2, 10-28% MeCN/0.1% TFA (aq) over 12 min, 60 mL/min) to afford the title compound. LCMS for $C_{22}H_{25}F_2N_6O$ (M+H)$^+$: calculated m/z=427.2; found 427.3.

Example 65. 1-(8-Amino-3-(2-methyl-5-(1,1,1-trifluoro-2-hydroxypropan-2-yl)phenyl)imidazo[1,2-a]pyrazin-6-yl)piperidin-4-ol

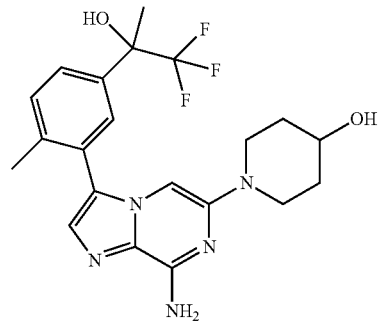 [SMILES: Cc1ccc(C(C)(O)C(F)(F)F)cc1-c1cnc2c(N)nc(N3CCC(O)CC3)cn12]

A procedure analogous to that described above in Example 64 was used with the exception that the starting material was 2-(3-(8-amino-6-bromoimidazo[1,2-a]pyrazin-3-yl)-4-methylphenyl)-1,1,1-trifluoropropan-2-ol in Step 1 and the amine was piperidin-4-ol in Step 3. LCMS for $C_{21}H_{25}F_3N_5O_2$ (M+H)$^+$: calculated m/z=436.2; found 436.3.

Example 66. 2-(3-(8-Amino-6-(1-(methyl-d3)-1H-pyrazol-5-yl)imidazo[1,2-a]pyrazin-3-yl)-4-methylphenyl)-3,3,3-trifluoropropane-1,2-diol (Isomer 1)

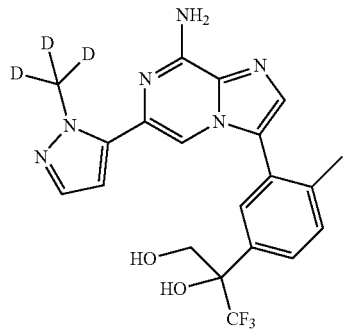 [SMILES: [2H]C([2H])([2H])n1nccc1-c1cn2c(-c3cc(C(O)(CO)C(F)(F)F)ccc3C)cnc2c(N)n1]

Step 1. 2-(3-Chloro-4-methylphenyl)-4,4,5,5-tetramethyl-1,3,2-dioxaborolane

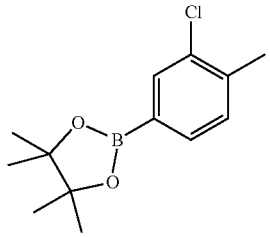

A degassed mixture of 4-bromo-2-chloro-1-methylbenzene (12.0 g, 58.4 mmol, Aldrich), KOAc (17.2 g, 175 mmol), bis(pinacolato)diboron (16.3 g, 64.2 mmol), and PdCl$_2$(dppf)-CH$_2$Cl$_2$ adduct (2.39 g, 2.92 mmol) in dioxane (120 mL) was heated to 80° C. for 5 hours. Upon cooling to room temperature, the reaction mixture was diluted with EtOAc, filtered and concentrated. The product was purified via flash chromatography, eluting with a gradient of 0-5% EtOAc in hexanes to afford the product as an off-white solid (12.2 g, 82%). LCMS calculated for $C_{13}H_{19}BClO_2$ (M+H)$^+$: m/z=253.1, found: 253.0.

Step 2. 2-Chloro-1-methyl-4-(3,3,3-trifluoroprop-1-en-2-yl)benzene

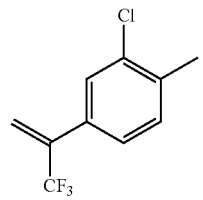

A degassed mixture of 2-(3-chloro-4-methylphenyl)-4,4,5,5-tetramethyl-1,3,2-dioxaborolane (12.2 g, 48.1 mmol), 2-bromo-3,3,3-trifluoroprop-1-ene (11.8 g, 67.4 mmol, Aldrich), K$_2$CO$_3$ (1.0 M in water, 144 mL, 144 mmol), and bis(triphenylphosphine)palladium(II) dichloride (1.69 g, 2.41 mmol) in THF (300 mL) was heated under N$_2$ to 65° C. for 5 hours in a 1 L round bottom flask fitted with a reflux condenser. Upon cooling to room temperature, the reaction mixture was partitioned between EtOAc and water. The organic layer was washed with water, followed by brine, dried over Na$_2$SO$_4$, filtered and concentrated. The product was purified via flash chromatography, eluting with 100% hexanes to afford the product as a light yellow oil (9.75 g, 92%). $^1$H NMR (400 MHz, CDCl$_3$) δ 7.47 (s, 1H), 7.27 (s, 2H), 5.98 (q, J=1.3 Hz, 1H), 5.79 (q, J=1.5 Hz, 1H), 2.42 (s, 3H); $^{19}$F NMR (376 MHz, CDCl$_3$) δ −64.93 (s).

Step 3. 2-(3-Chloro-4-methylphenyl)-3,3,3-trifluoropropane-1,2-diol

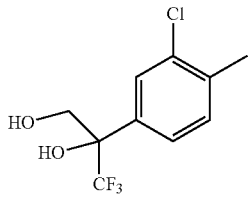 [SMILES: Cc1ccc(C(O)(CO)C(F)(F)F)cc1Cl]

To a solution of 2-chloro-1-methyl-4-(3,3,3-trifluoroprop-1-en-2-yl)benzene (8.10 g, 36.7 mmol) in acetone (75 mL) and water (75 mL) was added NMO (5.59 g, 47.7 mmol) and $OsO_4$ (4% in water, 14.0 mL, 2.20 mmol). The mixture was stirred at room temperature overnight, then was filtered and concentrated in vacuo to remove acetone. The aqueous mixture was extracted with three portions of EtOAc. The combined organic extracts were dried over $Na_2SO_4$, filtered and concentrated. The product was purified via flash chromatography, eluting with a gradient of 0-50% EtOAc in hexanes (7.02 g, 75%). LCMS calculated for $C_{10}H_{11}ClF_3O_2$ $(M+H)^+$: m/z=255.0, found: 255.0. $^1H$ NMR (400 MHz, $CDCl_3$) δ 7.61-7.57 (m, 1H), 7.37-7.33 (m, 1H), 7.29 (d, J=7.1 Hz, 1H), 4.30 (dd, J=11.9, 5.8 Hz, 1H), 3.87 (dd, J=10.6, 7.2 Hz, 1H), 3.73 (s, 1H), 2.41 (s, 3H), 1.92 (t, J=6.6 Hz, 1H); $^{19}F$ NMR (376 MHz, $CDCl_3$) δ −77.25 (s).

Step 4. 3,3,3-Trifluoro-2-(4-methyl-3-(4,4,5,5-tetramethyl-1,3,2-dioxaborolan-2-yl)phenyl)propane-1,2-diol

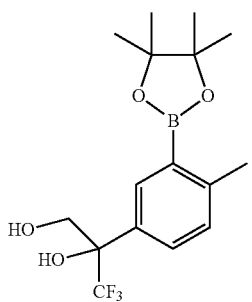 [SMILES: Cc1ccc(C(O)(CO)C(F)(F)F)cc1B1OC(C)(C)C(C)(C)O1]

A degassed mixture of 2-(3-chloro-4-methylphenyl)-3,3,3-trifluoropropane-1,2-diol (1.00 g, 3.93 mmol), bis(pinacolato)diboron (2.99 g, 11.8 mmol), KOAc (2.31 g, 23.6 mmol), $Pd_2(dba)_3$ (0.180 g, 0.196 mmol) and 2-dicyclohexylphosphino-2',4',6'-triisopropylbiphenyl (0.374 g, 0.785 mmol) in dioxane (40 mL) was heated to 120° C. in a sealed vial for 1.5 hours. Upon cooling to room temperature, the reaction mixture was diluted with EtOAc, filtered through Celite®, and concentrated. The product was purified via flash chromatography, eluting with a gradient of 0-40% EtOAc in hexanes (1.16 g, 85%).

Step 5. 2-(3-(8-Amino-6-bromoimidazo[1,2-a]pyrazin-3-yl)-4-methylphenyl)-3,3,3-trifluoropropane-1,2-diol

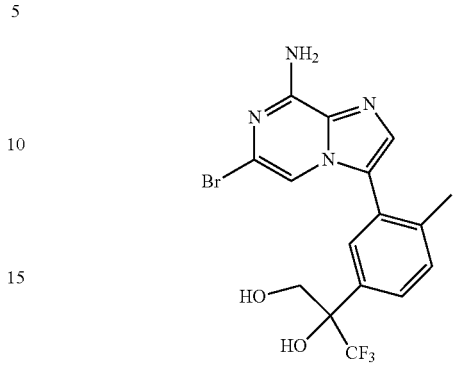

A degassed mixture of 6-bromo-3-iodoimidazo[1,2-a]pyrazin-8-amine (480 mg, 1.42 mmol, from Example 28, Step 1), 3,3,3-trifluoro-2-(4-methyl-3-(4,4,5,5-tetramethyl-1,3,2-dioxaborolan-2-yl)phenyl)propane-1,2-diol (490 mg, 1.42 mmol), and tetrakis(triphenylphosphine)palladium(0) (98 mg, 0.085 mmol) in ethanol (10 mL) and $Na_2CO_3$ (2.0 M in water, 1.77 mL, 3.54 mmol) was heated to 130° C. in a microwave reactor for 35 minutes. Upon cooling to room temperature, the mixture was diluted with EtOAc, dried over $MgSO_4$, filtered and concentrated. The product was purified via flash chromatography, eluting with a gradient of 0-8% MeOH in DCM to afford the product as a light yellow solid (0.37 g, 61%). LCMS calculated for $C_{16}H_{15}BrF_3N_4O_2$ $(M+H)^+$: m/z=431.0, found: 431.0; $^1H$ NMR (400 MHz, $CDCl_3$) δ 7.63 (dd, J=8.1, 1.3 Hz, 1H), 7.56 (d, J=1.5 Hz, 1H), 7.49 (s, 1H), 7.47 (d, J=8.1 Hz, 1H), 7.29 (s, 1H), 4.40-4.33 (m, 1H), 4.06 (s, 1H), 4.01-3.93 (m, 1H), 2.23 (s, 3H).

The enantiomers were separated via chiral HPLC (Phenomenex Lux Amylose-1, 21.2×250 mm, 5 μM, loading: 22.5 mg in 300 μL EtOH, eluting with 30% EtOH in hexanes at 20 mL/min). Peak 1 retention time: 12.0 min, Peak 2 retention time: 13.6 min. Peak 1 was used in Step 6.

Step 6. 2-(3-(8-Amino-6-(1-(methyl-d3)-1H-pyrazol-5-yl)imidazo[1,2-a]pyrazin-3-yl)-4-methylphenyl)-3,3,3-trifluoropropane-1,2-diol (Isomer 1)

A degassed mixture of 2-(3-(8-amino-6-bromoimidazo[1,2-a]pyrazin-3-yl)-4-methylphenyl)-3,3,3-trifluoropropane-1,2-diol (50.0 mg, 0.116 mmol, Peak 1 from Step 5), 1-(methyl-d3)-5-(4,4,5,5-tetramethyl-1,3,2-dioxaborolan-2-yl)-1H-pyrazole (73 mg, 0.35 mmol, prepared according to the procedure found in *Journal of Labelled Compounds and Radiopharmaceuticals*, 55(13), 467-469; 2012), and $PdCl_2$(dppf)-$CH_2Cl_2$ adduct (19 mg, 0.023 mmol) in THF (1.0 mL) and $K_2CO_3$ (1.0 M, 0.29 mL, 0.29 mmol) was heated to 95° C. for 2 hours. The product was purified via flash chromatography, eluting with a gradient from 0-8% MeOH in DCM. The fractions containing product were pooled and solvent was removed in vacuo. The residue was dissolved in a mixture of MeCN/$H_2O$, frozen and lyophilized to afford the product as an off-white solid (39 mg, 69%). LCMS calculated for $C_{20}H_{17}D_3F_3N_6O_2$ $(M+H)^+$: m/z=436.2, found: 436.1. $^1H$ NMR (500 MHz, DMSO-d6) δ 7.71 (s, 1H), 7.66-7.60 (m, 2H), 7.50 (s, 1H), 7.47 (d, J=8.0 Hz, 1H), 7.39 (d, J=1.8 Hz, 1H), 7.27 (s, 2H), 6.53 (s, 1H), 6.41 (d, J=1.8 Hz, 1H), 5.19 (t, J=5.8 Hz, 1H), 3.97 (dd, J=11.5, 5.8 Hz, 1H), 3.90 (dd, J=11.6, 5.8 Hz, 1H), 2.27 (s, 3H). $^{19}F$ NMR (471 MHz, DMSO-d6) δ −75.72 (s).

Example 67. 2-(3-(8-Amino-6-(1-(methyl-d3)-1H-pyrazol-5-yl)imidazo[1,2-a]pyrazin-3-yl)-4-methylphenyl)-3,3,3-trifluoropropane-1,2-diol trifluoroacetate salt (Isomer 2)

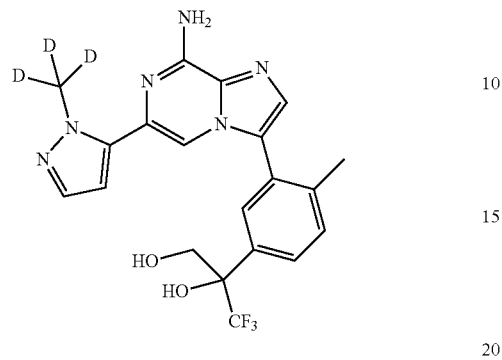

The title compound was prepared according to the procedure of Example 66, Step 6 using Peak 2 from Example 66, Step 5. The product was purified by LC-MS (pH=2). LCMS calculated for $C_{20}H_{17}D_3F_3N_6O_2$ (M+H)$^+$: m/z=436.2, found: 436.2. $^1$H NMR (400 MHz, DMSO-d6) δ 7.81 (s, 1H), 7.67-7.61 (m, 2H), 7.53 (s, 1H), 7.48 (d, J=8.9 Hz, 1H), 7.43 (d, J=1.9 Hz, 1H), 6.45 (d, J=1.9 Hz, 1H), 3.97 (d, J=11.6 Hz, 1H), 3.89 (d, J=11.5 Hz, 1H), 2.27 (s, 3H); $^{19}$F NMR (376 MHz, DMSO-d6) δ −74.71 (s), −75.72 (s).

Example 68

The compound in Table 4 was prepared according to the procedure of Example 66, using Peak 1 from Step 5 and 2-methyl-5-(4,4,5,5-tetramethyl-1,3,2-dioxaborolan-2-yl)oxazole (Ark Pharm) in Step 6.

TABLE 4

| Ex. No. | Name | R | LCMS [M + H]$^+$ | NMR Spectra |
|---|---|---|---|---|
| 68 | 2-(3-(8-Amino-6-(2-methyloxazol-5-yl)imidazo[1,2-a]pyrazin-3-yl)-4-methylphenyl)-3,3,3-trifluoropropane-1,2-diol (single enantiomer prepared) | 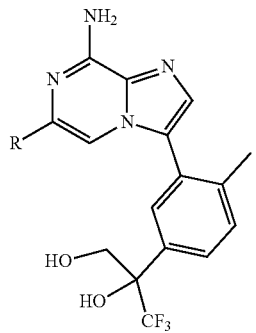 | 434.1 | $^1$H NMR (500 MHz, DMSO-d6) δ 7.67 (dd, J = 7.9, 1.7 Hz, 1H), 7.67 (s, 1H), 7.63 (d, J = 1.5 Hz, 1H), 7.50 (d, J = 8.2 Hz, 1H), 7.46 (s, 1H), 7.30 (br s, 2H), 7.27 (s, 1H), 6.54 (s, 1H), 5.20 (t, J = 5.8 Hz, 1H), 3.98 (dd, J = 11.6, 5.8 Hz, 1H), 3.91 (dd, J = 11.6, 5.7 Hz, 1H), 2.41 (s, 3H), 2.23 (s, 3H); $^{19}$F NMR (470 MHz, DMSO-d6) δ −75.81 (s) |

Examples 69-71

Examples 69-71 in Table 5 were prepared according to the procedure of Example 66, using a racemic mixture from Step 5 and appropriately substituted boronic esters or acids in Step 6. The products were purified via preparative LC-MS (pH=2).

TABLE 5

| Ex. No. | Name | R | LCMS [M + H]$^+$ | NMR Spectra |
|---|---|---|---|---|
| 69 | 2-(3-(8-Amino-6-(1-methyl-1H-pyrazol-4-yl)imidazo[1,2-a]pyrazin-3-yl)-4-methylphenyl)-3,3,3-trifluoropropane-1,2-diol trifluoroacetate salt (racemic mixture) | 1-methyl-1H-pyrazol-4-yl | 433.1 | $^1$H NMR (400 MHz, DMSO-d6) δ 8.13 (s, 1H), 7.84 (s, 1H), 7.83 (s, 1H), 7.69 (dd, J = 8.0, 1.2 Hz, 1H), 7.64 (d, J = 1.3 Hz, 1H), 7.55 (s, 1H), 7.50 (d, J = 8.2 Hz, 1H), 3.99 (d, J = 11.5 Hz, 1H), 3.91 (d, J = 11.6 Hz, 1H), 3.87 (s, 3H), 2.26 (s, 3H); $^{19}$F NMR (376 MHz, DMSO-d6) δ −74.41 (s), −75.67 (s) |
| 70 | 2-(3-(8-Amino-6-(2-methylthiazol-5-yl)imidazo[1,2-a]pyrazin-3-yl)-4-methylphenyl)-3,3,3-trifluoropropane-1,2-diol trifluoroacetate salt (racemic mixture) | 2-methylthiazol-5-yl | 450.1 | $^1$H NMR (400 MHz, DMSO-d6) δ 8.00 (s, 1H), 7.76 (s, 1H), 7.74 (s, 1H), 7.70-7.63 (m, 2H), 7.50 (d, J = 8.1 Hz, 1H), 3.99 (d, J = 11.7 Hz, 1H), 3.91 (d, J = 11.6 Hz, 1H), 2.65 (s, 3H), 2.27 (s, 3H); $^{19}$F NMR (376 MHz, DMSO-d6) δ −74.81 (s), −75.68 (s) |
| 71 | 2-(3-(8-Amino-6-(oxazol-5-yl)imidazo[1,2-a]pyrazin-3-yl)-4-methylphenyl)-3,3,3-trifluoropropane-1,2-diol trifluoroacetate salt (racemic mixture) | oxazol-5-yl | 420.1 | $^1$H NMR (400 MHz, DMSO-d6) δ 8.38 (s, 1H), 7.73 (s, 1H), 7.68 (dd, J = 8.1, 1.3 Hz, 1H), 7.66-7.63 (m, 1H), 7.53 (s, 1H), 7.50 (d, J = 8.0 Hz, 1H), 7.46 (s, 1H), 3.98 (d, J = 11.7 Hz, 1H), 3.91 (d, J = 11.7 Hz, 1H), 2.24 (s, 3H); $^{19}$F NMR (376 MHz, DMSO-d6) δ −74.63 (s), −75.77 (s) |

Examples 72-73. 2-(3-(8-Amino-6-(trifluoromethyl)imidazo[1,2-a]pyrazin-3-yl)-4-methylphenyl)-3,3,3-trifluoropropane-1,2-diol (Isomers 1-2)

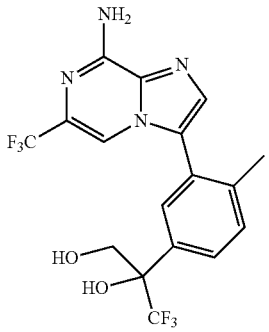 [SMILES: Cc1ccc(C(O)(CO)C(F)(F)F)cc1-c1cnc2c(N)nc(C(F)(F)F)cn12]

A degassed mixture of 3,3,3-trifluoro-2-(4-methyl-3-(4,4,5,5-tetramethyl-1,3,2-dioxaborolan-2-yl)phenyl)propane-1,2-diol (1.00 g, 2.89 mmol, from Example 66, Step 4), 3-bromo-6-(trifluoromethyl)imidazo[1,2-a]pyrazin-8-amine (0.812 g, 2.89 mmol, from Example 4, Step 6), and dichloro[1,1'-bis(diphenylphosphino)ferrocene]palladium(II) dichloromethane adduct (0.472 g, 0.578 mmol) in THF (30 mL) and $K_2CO_3$ (1.0 M, 8.67 mL, 8.67 mmol) was heated to 90° C. in a sealed vial for 5 hours. Upon cooling to room temperature, the mixture was partitioned between EtOAc and water. The aqueous layer was extracted with two further portions of EtOAc. The combined organic extracts were dried over $Na_2SO_4$, filtered and concentrated. The product was purified via flash chromatography, eluting with a gradient of 0-8% MeOH/DCM.

The enantiomers were separated via chiral HPLC (Phenomenex Lux Amylose-1, 21.2×250 mm, 5 µM, loading: 54 mg in 1.8 mL, eluting with 15% EtOH in hexanes at 20 mL/min over 30 min). Peak 1 retention time: 16.0 min, Peak 2 retention time: 21.9 min.

Peak 1 (Example 72): (2-(3-(8-Amino-6-(trifluoromethyl)imidazo[1,2-a]pyrazin-3-yl)-4-methylphenyl)-3,3,3-trifluoropropane-1,2-diol; Isomer 1): (0.20 g, 34%). LCMS calculated for $C_{17}H_{15}F_6N_4O_2$ $(M+H)^+$: m/z=421.1, found: 421.1. $^1H$ NMR (600 MHz, DMSO-d6) δ 7.79 (s, 1H), 7.68-7.64 (m, 2H), 7.63 (s, 1H), 7.61 (d, J=1.5 Hz, 1H), 7.49 (d, J=8.2 Hz, 1H), 6.54 (s, 1H), 5.17 (t, J=5.8 Hz, 1H), 3.97 (dd, J=11.6, 5.8 Hz, 1H), 3.90 (dd, J=11.6, 5.8 Hz, 1H), 2.24 (s, 3H); $^{19}F$ NMR (565 MHz, DMSO-d6) δ −66.89 (s), −75.89 (s).

Peak 2 (Example 73): (2-(3-(8-Amino-6-(trifluoromethyl)imidazo[1,2-a]pyrazin-3-yl)-4-methylphenyl)-3,3,3-trifluoropropane-1,2-diol; Isomer 2): LCMS calculated for $C_{17}H_{15}F_6N_4O_2$ $(M+H)^+$: m/z=421.1, found: 421.1.

Examples 74-75. Ethyl 2-(8-amino-3-(5-(1,1-difluoro-2-hydroxypropan-2-yl)-2-methylphenyl)imidazo[1,2-a]pyrazin-6-yl)cyclopropane-1-carboxylate trifluoroacetate salt (Isomers 1 and 2)

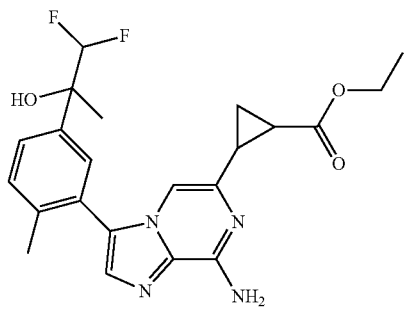 [SMILES: CCOC(=O)C1CC1c1cn2c(-c3cc(C(C)(O)C(F)F)ccc3C)cnc2c(N)n1]

Step 1. 2-(3-(8-Amino-6-vinylimidazo[1,2-a]pyrazin-3-yl)-4-methylphenyl)-1,1-difluoropropan-2-ol

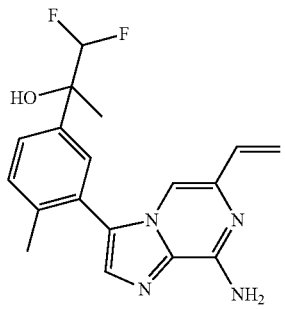 [SMILES: C=Cc1cn2c(-c3cc(C(C)(O)C(F)F)ccc3C)cnc2c(N)n1]

A microwave vial was charged with 2-(3-(8-amino-6-bromoimidazo[1,2-a]pyrazin-3-yl)-4-methylphenyl)-1,1-difluoropropan-2-ol (isomer 1) (0.20 g, 0.50 mmol) (from Example 29, Step 3), potassium vinyltrifluoroborate, (0.19 g, 1.4 mmol), and dichloro[1,1'-bis(diphenylphosphino)ferrocene] palladium (II), dichloromethane adduct (82 mg, 0.10 mmol). THF (8.1 mL) and 1.0 M $K_2CO_3$ (1.4 mL, 1.4 mmol) were added. The reaction mixture was degassed with $N_2$ for 5 min and then heated at 80° C. for 4 h. Heating was discontinued, and the reaction mixture was stirred overnight. The reaction mixture was diluted with EtOAc (20 mL) and washed with 50% sat. NaCl (20 mL) and brine (20 mL). The organic layer was dried over $Na_2SO_4$, filtered, and concentrated. Purification via silica gel chromatography (12-100% EtOAc in DCM) afforded the title compound as a red-brown solid (0.16 g, 92%). $^1H$ NMR (400 MHz, $CDCl_3$) δ 7.55 (dd, J=8.0, 2.1 Hz, 1H), 7.50 (apparent s, 2H), 7.41 (d, J=8.1 Hz, 1H), 7.07 (s, 1H), 6.46 (dd, J=17, 11 Hz, 1H), 6.14 (dd, J=17, 1.8 Hz, 1H), 5.73 (t, J=57 Hz, 1H), 5.56 (br s, 2H), 5.31 (dd, J=11, 1.8 Hz, 1H), 2.55 (br s, 1H), 2.19 (s, 3H), 1.69 (t, J=1.5 Hz, 3H). $^{19}F$ NMR (376 MHz, $CDCl_3$) δ −129.3 (dd, J=280, 56 Hz), −130.3 (dd, J=280, 57 Hz). LCMS for $C_{18}H_{19}F_2N_4O$ $(M+H)^+$: calculated m/z=345.1; found 345.1.

Step 2. Ethyl 2-(8-amino-3-(5-(1,1-difluoro-2-hydroxypropan-2-yl)-2-methylphenyl)imidazo[1,2-a]pyrazin-6-yl)cyclopropane-1-carboxylate trifluoroacetate salt (Isomers 1 and 2)

Two reactions were prepared in parallel as follows: To a solution of 2-(3-(8-amino-6-vinylimidazo[1,2-a]pyrazin-3-yl)-4-methylphenyl)-1,1-difluoropropan-2-ol (75 mg, 0.22 mmol) in toluene (1.4 mL) in a 20-mL microwave vial was slowly added a solution of ethyl diazoacetate (230 μL, 2.2 mmol) in toluene (7.0 mL). The reaction mixture was heated at 100° C. for 2.5 days. The reaction mixture was cooled to 0° C. and 2-propanol (1.7 mL, 22 mmol) was added. After warming to room temperature, the two reaction mixtures were combined and concentrated in vacuo and the pressure was kept >40 mbar. Purification via preparative HPLC on a C-18 column (pH=2, 28-38% MeCN/0.1% TFA (aq) over 5 min, 60 mL/min) afforded Example 74 as a yellow residue (Isomer 1; first eluting, $t_R$=3.7 min, 39 mg, 33%) and Example 75 as a mixture of an off-white solid and a yellow oil (Isomer 2; second eluting, $t_R$=4.5 min, 76 mg, 64%).

Example 74 (Isomer 1): LCMS for $C_{22}H_{25}F_2N_4O_3$ (M+H)$^+$: calculated m/z=431.2; found 431.1.

Example 75 (Isomer 2): LCMS for $C_{22}H_{25}F_2N_4O_3$ (M+H)$^+$: calculated m/z=431.2; found 431.1.

Example 76. 2-(8-Amino-3-(5-(1,1-difluoro-2-hydroxypropan-2-yl)-2-methylphenyl)imidazo[1,2-a]pyrazin-6-yl)-N-methylcyclopropane-1-carboxamide

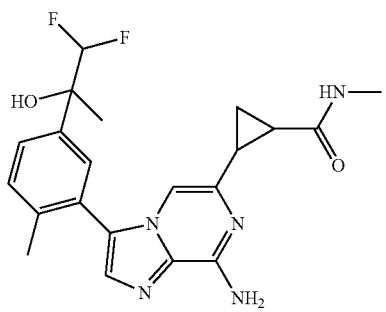 [SMILES: CNC(=O)C1CC1c1cn2c(-c3cc(C(C)(O)C(F)F)ccc3C)cnc2c(N)n1]

Step 1. 2-(8-Amino-3-(5-(1,1-difluoro-2-hydroxypropan-2-yl)-2-methylphenyl)imidazo[1,2-a]pyrazin-6-yl)cyclopropane-1-carboxylic acid

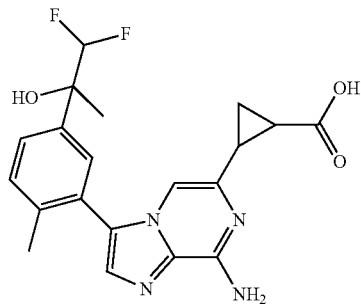 [SMILES: Cc1ccc(C(C)(O)C(F)F)cc1-c1cnc2c(N)nc(C3CC3C(=O)O)cn12]

To a solution of ethyl 2-(8-amino-3-(5-(1,1-difluoro-2-hydroxypropan-2-yl)-2-methylphenyl)imidazo[1,2-a]pyrazin-6-yl)cyclopropane-1-carboxylate trifluoroacetate salt (8.1 mg, 0.015 mmol; Isomer 2 from Examples 74-75, Step 2) in 2:1 THF/MeOH (220 μL) was added 2.0 M NaOH (74 μL, 0.15 mmol). The reaction mixture was stirred at room temperature for 2 h. Upon cooling to 0° C., 0.5 M HCl (330 μL, 0.16 mmol) was added slowly. The mixture was extracted with CHCl$_3$ (3×0.5 mL). The organic layers were filtered through a plug of Na$_2$SO$_4$, combined, and concentrated to afford the title compound as a yellow residue (6.6 mg). LCMS for $C_{20}H_{21}F_2N_4O_3$ (M+H)$^+$: calculated m/z=403.2; found 403.1.

Step 2. 2-(8-Amino-3-(5-(1,1-difluoro-2-hydroxypropan-2-yl)-2-methylphenyl)imidazo[1,2-a]pyrazin-6-yl)-N-methylcyclopropane-1-carboxamide To a mixture of methylamine (20 μL, 0.05 mmol, 2.0 M in THF), 2-(8-amino-3-(5-(1,1-difluoro-2-hydroxypropan-2-yl)-2-methylphenyl)imidazo[1,2-a]pyrazin-6-yl)cyclopropane-1-carboxylic acid (6 mg, 0.02 mmol), and N,N,N',N'-tetramethyl-O-(7-azabenzotriazol-1-yl)uronium hexafluorophosphate (8 mg, 0.02 mmol) in DMF (400 μL) was added dropwise N,N-diisopropylethylamine (5 μL, 0.03 mmol). The reaction mixture was stirred 1 h at room temperature. The reaction mixture was diluted with MeOH and purified via preparative HPLC on a C-18 column (pH=10, 27-41% MeCN/0.1% NH$_4$OH (aq) over 5 min, 60 mL/min) to afford the title compound as a white solid (2.3 mg, 37%). LCMS for $C_{21}H_{24}F_2N_5O_2$ (M+H)$^+$: calculated m/z=416.2; found 416.3.

Examples 77-78

Examples 77-78 were synthesized according to procedures analogous to the procedures of Example 76, Step 2, substituting 1-methylpiperazine (Example 77) or 2-amino-2-methyl-1-propanol (Example 78) for methylamine. The data are listed in Table 6.

TABLE 6

| Ex. No. | Name | —NR$^2$R$^3$ | LCMS [M + H]$^+$ |
|---|---|---|---|
| 77 | (2-(8-Amino-3-(5-(1,1-difluoro-2-hydroxypropan-2-yl)-2-methylphenyl)imidazo[1,2-a]pyrazin-6-yl)cyclopropyl)(4-methylpiperazin-1-yl)methanone trifluoroacetate salt | | 485.2 |

TABLE 6-continued

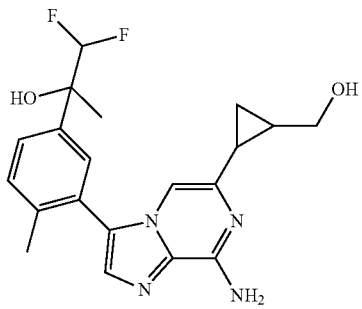 [SMILES: Cc1ccc(C(C)(O)C(F)F)cc1-c1cnc2c(N)nc(C3CC3CO)cn12]

| Ex. No. | Name | —NR²R³ | LCMS [M + H]⁺ |
|---|---|---|---|
| 78 | 2-(8-Amino-3-(5-(1,1-difluoro-2-hydroxypropan-2-yl)-2-methylphenyl)imidazo[1,2-a]pyrazin-6-yl)-N-(1-hydroxy-2-methylpropan-2-yl)cyclopropane-1-carboxamide | 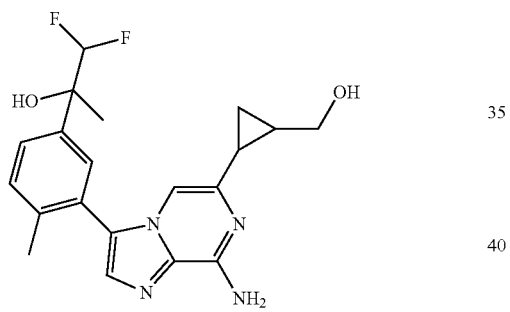 | 474.2 |

Example 79. 2-(3-(8-Amino-6-(2-(hydroxymethyl)cyclopropyl)imidazo[1,2-a]pyrazin-3-yl)-4-methylphenyl)-1,1-difluoropropan-2-ol (Isomer 2)

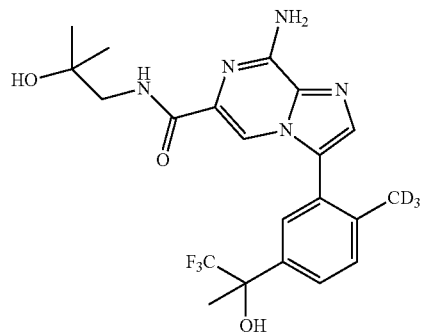 [SMILES: [2H]C([2H])([2H])c1ccc(C(C)(O)C(F)(F)F)cc1-c1cnc2c(N)nc(C(=O)NCC(C)(C)O)cn12]

To a solution of ethyl 2-(8-amino-3-(5-(1,1-difluoro-2-hydroxypropan-2-yl)-2-methylphenyl)imidazo[1,2-a]pyrazin-6-yl)cyclopropane-1-carboxylate trifluoroacetate salt (2.6 mg, 4.8 µmol; Isomer 2 from Examples 74-75, Step 2) in THF (0.25 mL) at 0° C. was added lithium aluminum hydride (9.6 µL, 9.6 µmol, 1.0 M in THF). The reaction mixture was warmed to room temperature and stirred for 1.5 h. The reaction mixture was cooled to 0° C., and the reaction was quenched with 1.0 M NaOH (50 µL) followed by addition of Na₂SO₄. Upon stirring for 5 min and warming to room temperature, the resulting slurry was diluted with MeOH and filtered through a plug of Celite. Purification via (pH=2, 18-38% MeCN/0.1% TFA (aq) over 5 min, 60 mL/min) afforded a white solid (2.1 mg). This material was dissolved in EtOAc and neutralized by the addition of 1 M NaOH. After stirring for 25 min, the organic layer was removed, and the aqueous layer was extracted with EtOAc (2×). The organic layers were filtered through a plug of Na₂SO₄, combined, and concentrated to afford the title compound as a clear residue (1.2 mg, 65%). LCMS for $C_{20}H_{23}F_2N_4O_2$ (M+H)⁺: calculated m/z=389.2; found 389.2.

Example 80. 2-(3-(8-Amino-6-(2-(hydroxymethyl)cyclopropyl)imidazo[1,2-a]pyrazin-3-yl)-4-methylphenyl)-1,1-difluoropropan-2-ol (Isomer 1)

The title compound was synthesized according to an experimental procedure analogous to Example 79, substituting ethyl 2-(8-amino-3-(5-(1,1-difluoro-2-hydroxypropan-2-yl)-2-methylphenyl)imidazo[1,2-a]pyrazin-6-yl)cyclopropane-1-carboxylate trifluoroacetate salt (Isomer 1 from Examples 74-75, Step 2) for ethyl 2-(8-amino-3-(5-(1,1-difluoro-2-hydroxypropan-2-yl)-2-methylphenyl)imidazo[1,2-a]pyrazin-6-yl)cyclopropane-1-carboxylate trifluoroacetate salt (Isomer 2 from Examples 74-75, Step 2). LCMS for $C_{20}H_{23}F_2N_4O_2$ (M+H)⁺: calculated m/z=389.2; found 389.3.

Example 81. 8-Amino-N-(2-hydroxy-2-methylpropyl)-3-(2-(methyl-d₃)-5-(1,1,1-trifluoro-2-hydroxypropan-2-yl)phenyl)imidazo[1,2-a]pyrazine-6-carboxamide Step 1. 1-(4-(Methyl-d₃)phenyl)ethan-1-one

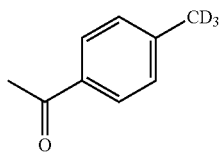

A solution of (4-acetylphenyl)boronic acid (1.00 g, 6.10 mmol) [Aldrich, 470821], bis(di-tert-butyl(4-dimethylaminophenyl)phosphine)dichloropalladium(II) (0.108 g, 0.152 mmol), and cesium fluoride (3.24 g, 21.4 mmol) in DMF (10.2 mL) and water (2.03 mL) was degassed with nitrogen for 10 min, treated with iodomethane-d₃ (1.44 mL, 23.2 mmol), and stirred at 45° C. overnight. The reaction mixture was cooled to rt and diluted with water and ethyl acetate. The aqueous layer was separated and extracted with ethyl acetate (2×). The combined organic extracts were washed with water and brine, dried over magnesium sulfate, filtered, and concentrated (60-70 Torr, 25° C. bath) to give the desired product (546 mg, 65.3%) as a yellow oil that was used without further purification. ¹H NMR (400 MHz, CDCl₃) δ 7.86 (d, J=8.0 Hz, 2H), 7.26 (d, J=8.0 Hz, 2H), 2.58 (s, 3H). LCMS for C₉H₈D₃O (M+H)⁺: m/z=138.1; Found: 138.1.

Step 2. 1-(3-Bromo-4-(methyl-d₃)phenyl)ethan-1-one

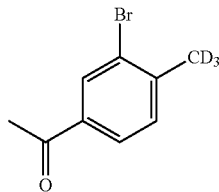

A suspension of aluminum chloride (13.6 g, 102 mmol) in dichloromethane (24 mL) was treated with 1-(4-(methyl-d₃)phenyl)ethan-1-one (6.35 g, 46.3 mmol) dropwise via syringe over 5 min. The residual material in the syringe was rinsed with dichloromethane (7.0 mL) and added to the reaction mixture dropwise. After the initial exotherm the reaction mixture was allowed to cool to rt for 3 min, stirred at 35° C. for 5 min, and treated with bromine (2.38 mL, 46.3 mmol) dropwise over 5 min. The reaction mixture was stirred for 25 min and then added slowly into a mixture of dichloromethane (50 mL), 1 N HCl (100 mL), and ice. The residual reaction mixture was rinsed into the dichloromethane/HCl/ice mixture with additional dichloromethane. The mixture was warmed to room temperature (rt) and the layers were separated. The aqueous layer was extracted with dichloromethane (2×75 mL). The combined organic layers were washed with saturated sodium bicarbonate and brine. The sodium bicarbonate and brine washes contained product and these were combined, acidified with 1M HCl, and extracted with dichloromethane (2×50 mL). The organic layers were all combined, dried over magnesium sulfate, filtered, and concentrated to a yellow oil. Purification by flash column chromatography using ethyl acetate in hexanes (0%-15%) gave the desired product (9.08 g, 90.8%) as a light yellow solid. ¹H NMR (400 MHz, CDCl₃) δ 8.11 (d, J=1.8 Hz, 1H), 7.79 (dd, J=7.9, 1.8 Hz, 1H), 7.32 (d, J=7.9 Hz, 1H), 2.57 (s, 3H). LCMS for C₉H₇D₃BrO (M+H)⁺: m/z=216.0, 218.0; Found: 216.0, 218.0.

Step 3. 2-(3-Bromo-4-(methyl-d3)phenyl)-1,1,1-trifluoropropan-2-ol

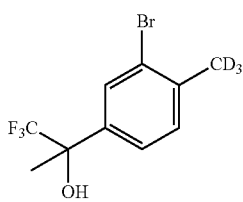 [SMILES: [2H]C([2H])([2H])c1ccc(C(C)(O)C(F)(F)F)cc1Br]

The desired compound was prepared according to the procedure of Example 1, step 1, using 1-(3-bromo-4-(methyl-d3)phenyl)ethan-1-one as the starting material. ¹H NMR (400 MHz, CDCl₃) δ 7.79-7.72 (m, 1H), 7.48-7.35 (m, 1H), 7.24 (s, 1H), 2.41 (br s, 1H), 1.76 (s, 3H).

Step 4. 1,1,1-Trifluoro-2-(4-(methyl-d₃)-3-(4,4,5,5-tetramethyl-1,3,2-dioxaborolan-2-yl)phenyl)propan-2-ol

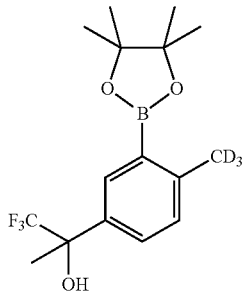 [SMILES: [2H]C([2H])([2H])c1ccc(C(C)(O)C(F)(F)F)cc1B1OC(C)(C)C(C)(C)O1]

A suspension of bis(pinacolato)diboron (12.8 g, 50.2 mmol) and potassium acetate (8.63 ml, 138 mmol) in dioxane (24 mL) was treated with 2-(3-bromo-4-(methyl-d₃)phenyl)-1,1,1-trifluoropropan-2-ol (13.3 g, 41.8 mmol). The residual 2-(3-bromo-4-(methyl-d₃)phenyl)-1,1,1-trifluoropropan-2-ol was rinsed in with dioxane (106 mL) and added to the reaction mixture which was degassed with nitrogen for 10 min. The reaction mixture was treated with bis(triphenylphosphine)palladium(II) dichloride (1.16 g, 1.67 mmol), degassed with nitrogen for another 10 min, and stirred at 100° C. overnight. The reaction mixture was cooled to rt, degassed with nitrogen for 5 min, treated with additional bis(triphenylphosphine)palladium(II) dichloride (1.16 g, 1.67 mmol), degassed with nitrogen for another 5 min, and stirred at 100° C. for 4 h. The reaction mixture was filtered over Celite and rinsed with THF and ethyl acetate. The filtrate was washed with 1:1 water/brine (300 mL). The aqueous layer was re-extracted with ethyl acetate. The combined organic layers were dried over magnesium sulfate, filtered, and concentrated to a brown oil. Purification by flash column chromatography using MTBE in hexanes (0%-20%) gave the desired product (14.4 g, 84.7%) as a pale yellow oil. ¹H NMR (400 MHz, CDCl₃) δ 7.93 (d, J=2.3 Hz, 1H), 7.55-7.45 (m, 1H), 7.19 (d, J=8.1 Hz, 1H), 2.43 (br s, 1H), 1.77 (s, 3H), 1.34 (s, 12H). LCMS for C₁₆H₂₀D₃BF₃O₃ (M+H)⁺: m/z=334.2; Found: 334.3.

Step 5. 2-(3-(8-Amino-6-bromoimidazo[1,2-a]pyrazin-3-yl)-4-(methyl-d₃)phenyl)-1,1,1-trifluoropropan-2-ol (Racemic Mixture)

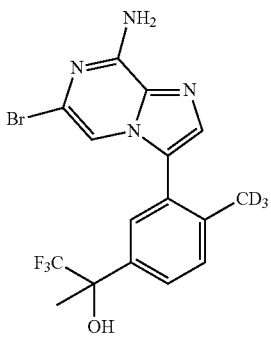 [SMILES: [2H]C([2H])([2H])c1ccc(C(C)(O)C(F)(F)F)cc1-c1cnc2c(N)nc(Br)cn12]

A solution of 1,1,1-trifluoro-2-(4-(methyl-d₃)-3-(4,4,5,5-tetramethyl-1,3,2-dioxaborolan-2-yl)phenyl)propan-2-ol (14.5 g, 35.6 mmol) in dioxane (178 mL) was treated with 6-bromo-3-iodoimidazo[1,2-a]pyrazin-8-amine (12.1 g, 35.6 mmol), degassed with nitrogen for 5 min, treated with dichloro[1,1'-bis(diphenylphosphino)ferrocene]palladium (II) dichloromethane adduct (5.81 g, 7.11 mmol), and degassed with nitrogen for another 5 min. The reaction mixture was treated with 1.0 M potassium carbonate in water (107 ml, 107 mmol), degassed with nitrogen for 5 min, and stirred at 80° C. overnight. The reaction mixture was cooled to rt and filtered over Celite. The Celite was rinsed with ethyl acetate and water. The filtrate was diluted with water (150 mL) and extracted with ethyl acetate (3×100 mL). The combined organic layers were dried over magnesium sulfate, filtered, and concentrated to a dark oil. Purification by flash column chromatography using methanol in dichloromethane (0%-5%) and repurification by flash column chromatography using ethyl acetate in hexanes (0%-100%) gave the desired product (13.8 g, 92.8%). LCMS for C₁₆H₁₂D₃BrF₃N₄O (M+H)⁺: m/z=418.1, 420.1; Found: 418.0, 420.0.

Step 6. Second eluting enantiomer of 2-(3-(8-amino-6-bromoimidazo[1,2-a]pyrazin-3-yl)-4-(methyl-d3)phenyl)-1,1,1-trifluoropropan-2-ol

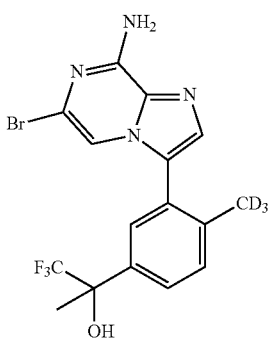 [SMILES: [2H]C([2H])([2H])c1ccc(C(C)(O)C(F)(F)F)cc1-c1cnc2c(N)nc(Br)cn12]

The racemic mixture of 2-(3-(8-amino-6-bromoimidazo[1,2-a]pyrazin-3-yl)-4-(methyl-d₃)phenyl)-1,1,1-trifluoropropan-2-ol was separated via preparative chiral HPLC (Phenomenex Lux Amylose-1 [21.2×250 mm, 5 micron], eluting with 20% ethanol in hexanes, at flow rate of 20 mL/min, loading ~200 mg in 4 mL ethanol). The first peak that eluted had a retention time of 9.6 min. The second peak that eluted had a retention time of 14.6 min.

Peak 2: ¹H NMR (400 MHz, DMSO-d₆) δ 7.66-7.59 (m, 2H), 7.59-7.53 (m, 3H), 7.46 (d, J=8.1 Hz, 1H), 7.25 (s, 1H), 6.66 (s, 1H), 1.71 (s, 3H). LCMS for C₁₆H₁₂D₃BrF₃N₄O (M+H)⁺: m/z=418.1, 420.1; Found: 418.0, 420.0.

Step 7. Methyl 8-amino-3-(2-(methyl-d₃)-5-(1,1,1-trifluoro-2-hydroxypropan-2-yl)phenyl)imidazo[1,2-a]pyrazine-6-carboxylate (Single Enantiomer Prepared)

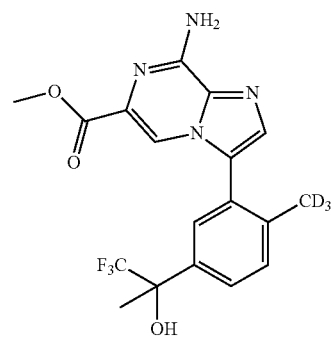 [SMILES: [2H]C([2H])([2H])c1ccc(C(C)(O)C(F)(F)F)cc1-c1cnc2c(N)nc(C(=O)OC)cn12]

The desired compound was prepared according to the procedure of Example 8, step 5, using 2-(3-(8-amino-6-bromoimidazo[1,2-a]pyrazin-3-yl)-4-(methyl-d₃)phenyl)-1,1,1-trifluoropropan-2-ol (Peak 2 from Step 6) as the starting material. LCMS for C₁₈H₁₅D₃F₃N₄O₃ (M+H)⁺: m/z=398.1; Found: 398.3.

Step 8. 8-Amino-3-(2-(methyl-d₃)-5-(1,1,1-trifluoro-2-hydroxypropan-2-yl)phenyl)imidazo[1,2-a]pyrazine-6-carboxylic acid (Single Enantiomer Prepared)

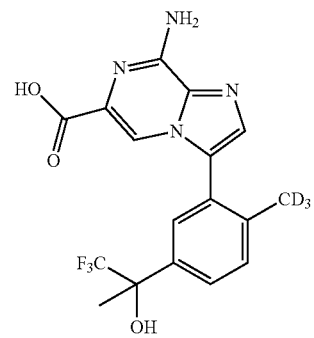 [SMILES: [2H]C([2H])([2H])c1ccc(C(C)(O)C(F)(F)F)cc1-c1cnc2c(N)nc(C(=O)O)cn12]

A solution of methyl 8-amino-3-(2-(methyl-d₃)-5-(1,1,1-trifluoro-2-hydroxypropan-2-yl)phenyl)imidazo[1,2-a]pyrazine-6-carboxylate (4.49 g, 11.3 mmol) (single enantiomer from step 7) in methanol (113 mL) was treated with 1.0 M sodium hydroxide (56.5 mL, 56.5 mmol) and stirred at room temperature. The reaction mixture was concentrated to remove methanol, diluted with water (50 mL), and extracted with ethyl acetate (50 mL, then 20 mL). The combined ethyl acetate layers were extracted with additional 1.0 M sodium hydroxide (3×20 mL). The combined basic aqueous layers were adjusted to pH~5 with citric acid (7.6 g). The aqueous layer was extracted with dichloromethane (2×150 mL). The aqueous layer was diluted with brine and extracted with ethyl acetate (150 mL). The combined organic layers were concentrated to give the desired product (4.06 g, 93.8%) as a tan solid that was used without further purification. $^1$H NMR (400 MHz, DMSO-d$_6$) δ 7.76 (s, 1H), 7.71 (s, 1H), 7.65 (dd, J=8.2, 2.0 Hz, 1H), 7.59 (d, J=2.0 Hz, 1H), 7.49 (d, J=8.1 Hz, 1H), 7.30 (br s, 2H), 6.66 (s, 1H), 1.71 (s, 3H). LCMS for $C_{17}H_{13}D_3F_3N_4O_3$ (M+H)$^+$: m/z=384.1; Found: 384.2.

Step 9. 8-Amino-N-(2-hydroxy-2-methylpropyl)-3-(2-(methyl-d$_3$)-5-(1,1,1-trifluoro-2-hydroxypropan-2-yl)phenyl)imidazo[1,2-a]pyrazine-6-carboxamide A solution of 8-amino-3-(2-(methyl-d$_3$)-5-(1,1,1-trifluoro-2-hydroxypropan-2-yl)phenyl)imidazo[1,2-a]pyrazine-6-carboxylic acid (4.06 g, 10.6 mmol) (single enantiomer from step 8) in DMF (106 mL) was treated with 1-amino-2-methylpropan-2-ol (1.44 g, 16.2 mmol) [Ark Pharm, AK-37803] and HATU (6.16 g, 16.2 mmol), stirred for 15 min, treated with triethylamine (4.43 mL, 31.8 mmol), and stirred at rt for 3.5 h. The reaction mixture was diluted with water (500 mL) and brine (100 mL) and extracted with ethyl acetate (3×150 mL). The combined organics were washed with saturated ammonium chloride (150 mL), 11% sodium carbonate (150 mL), and brine (100 mL), dried over magnesium sulfate, filtered, and concentrated to an amber oil. Purification by flash column chromatography using methanol in dichloromethane (0%-5%) gave the desired product (4.28 g, 89.0%) as a foam. $^1$H NMR (600 MHz, DMSO-d$_6$) δ 8.14-8.05 (m, 1H), 7.74-7.69 (m, 2H), 7.66 (d, J=7.9 Hz, 1H), 7.62-7.54 (m, 1H), 7.50 (dd, J=8.2, 2.0 Hz, 1H), 7.38 (s, 2H), 6.67 (s, 1H), 4.67 (s, 1H), 3.23 (d, J=5.6 Hz, 2H), 1.71 (s, 3H), 1.10 (s, 6H). LCMS for $C_{21}H_{22}D_3F_3N_5O_3$ (M+H)$^+$: m/z=455.2; Found: 455.2.

Example 82. 2-(3-(8-Amino-6-(trifluoromethyl)imidazo[1,2-a]pyrazin-3-yl)-4-methylphenyl)-3,3,3-trifluoro-2-hydroxypropanamide

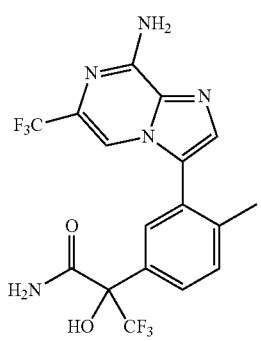 [SMILES: Cc1ccc(C(O)(C(N)=O)C(F)(F)F)cc1-c1cnc2c(N)nc(C(F)(F)F)cn12]

Step 1. 1-(3-Bromo-4-methylphenyl)-2,2,2-trifluoroethan-1-ol

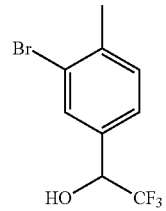

A solution of 3-bromo-4-methylbenzaldehyde (6.51 g, 32.7 mmol) [Aldrich, 565334] in tetrahydrofuran (65.4 mL) was cooled to 0° C. and treated with trimethyl(trifluoromethyl)silane (6.28 mL, 42.5 mmol). The yellow mixture was treated with 1.0 M tetrabutylammonium fluoride in tetrahydrofuran (0.654 mL, 0.654 mmol) at 0° C. and stirred for a few minutes at 0° C. The ice bath was removed and the resulting reaction mixture was stirred for 1.5 h. The reaction mixture was cooled back to 0° C. and treated with water (6.48 mL, 360 mmol) and 1.0 M tetrabutylammonium fluoride in tetrahydrofuran (6.54 mL, 6.54 mmol). The ice bath was removed and the reaction mixture was stirred at ambient temperature for 30 min. The yellow reaction mixture was diluted with brine (150 mL) and extracted with ethyl acetate (200 mL). The organic layer was washed with saturated ammonium chloride (100 mL), dried over sodium sulfate, filtered, and concentrated to give a tan oil. Purification by flash column chromatography using methyl tert-butyl ether (MTBE) in hexanes (0% to 50%) gave the desired product (8.42 g, 95.7%) as a yellow oil. LCMS for $C_9H_7BrF_3$ (M-OH)$^+$: m/z=251.0, 253.0; Found: 250.9, 252.8.

Step 2. 1-(3-Bromo-4-methylphenyl)-2,2,2-trifluoroethan-1-one

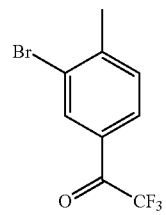

A mixture of 1-(3-bromo-4-methylphenyl)-2,2,2-trifluoroethan-1-ol (8.41 g, 31.3 mmol) in dichloromethane (125 mL) at 0° C. was treated with Dess-Martin periodinane (19.9 g, 46.9 mmol) and stirred at RT for 2.5 h. The reaction mixture was concentrated (by rotary evaporation with the water bath set at 30° C.) to an oily solid that was diluted with diethyl ether (200 mL) which precipitated more solids. This mixture was filtered over Celite® and the Celite® was rinsed with additional diethyl ether (200 mL). The filtrate was washed with saturated sodium bicarbonate solution (3×200 mL) and brine, dried over sodium sulfate, filtered, and concentrated to give an oily solid. The oily solid was partioned between diethyl ether (150 mL) and water (100 mL). The organic layer was separated and washed with saturated sodium bicarbonate solution (2×75 mL) and brine, Step 3. 2-(3-Bromo-4-methylphenyl)-3,3,3-trifluoro-2-hydroxypropanenitrile

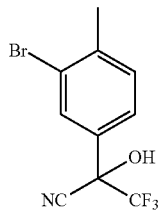

A solution of 1-(3-bromo-4-methylphenyl)-2,2,2-trifluoroethan-1-one (7.92 g, 29.7 mmol) in dichloromethane (29.7 mL) was treated with trimethylsilyl cyanide (8.70 mL, 65.2 mmol), potassium cyanide (0.290 g, 4.45 mmol), and 18-crown-6 (0.290 g, 1.10 mmol) and stirred for 1 h. The reaction was cooled with an ice bath due to an exotherm after the addition of 18-crown-6. The reaction mixture was concentrated (by rotary evaporation with the water bath set at 28° C.) to give a rust colored solid. The solid was dissolved in THF (29.6 mL), cooled to 0° C., treated with 1.8 M HCl (10.9 mL, 19.6 mmol), and stirred at room temperature (rt) for 1.5 h. The reaction mixture was diluted with water (75 mL) and extracted with diethyl ether (3×75 mL). The combined organic extracts were washed with brine, dried over sodium sulfate, filtered, and concentrated. Reconcentration from hexanes gave the desired product (8.70 g, 99.8%) as an orange solid that was used without further purification. LCMS for $C_9H_7BrF_3O$ (M-CN)$^+$: m/z=267.0, 269.0; Found: 266.9, 269.0.

Step 4. 2-(3-Bromo-4-methylphenyl)-3,3,3-trifluoro-2-hydroxypropanamide (Second Eluting Enantiomer)

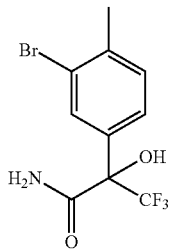 [SMILES: Cc1ccc(C(O)(C(N)=O)C(F)(F)F)cc1Br]

A solution of 2-(3-bromo-4-methylphenyl)-3,3,3-trifluoro-2-hydroxypropanenitrile (8.70 g, 29.6 mmol) in 1,4-dioxane (59.2 mL) at 0° C. was treated with concentrated HCl (9.00 mL, 108 mmol) that had been pre-cooled in an ice bath. While stirring at 0° C., the reaction mixture was bubbled with HCl gas for 45 min. The cooling bath was removed and the reaction mixture was stirred at rt for 61 h. The reaction mixture was bubbled with nitrogen for 10 min to remove some of the HCl, cooled to 0° C., and diluted with brine (200 mL), water (50 mL), and ethyl acetate (200 mL). The organic layer was separated and the aqueous layer was diluted with water (100 mL) to dissolve the remaining solids. The aqueous layer was extracted with ethyl acetate (100 mL). The combined organic extracts were washed with brine, dried over sodium sulfate, filtered, and concentrated to give a brown oil. Purification by flash column chromatography using MTBE in hexanes (0% to 60%) gave the racemic product as a yellow oily solid. The racemic mixture was separated via preparative chiral HPLC (Phenomenex Lux Amylose-1 [21.2×250 mm, 5 micron], eluting with 95% ethanol in hexanes, at flow rate of 18 mL/min, loading about 100 mg in 2 mL ethanol) to give the desired second eluting enantiomer (4.50 g, 48.8%) as a viscous yellow oil. The first enantiomer that eluted had a retention time of 4.0 min. The second enantiomer that eluted had a retention time of 5.3 min.

Second eluting enantiomer: $^1$H NMR (400 MHz, DMSO-$d_6$) δ 7.85 (d, J=1.9 Hz, 1H), 7.75 (s, 1H), 7.67 (s, 1H), 7.63-7.53 (m, 2H), 7.41 (d, J=8.1 Hz, 1H), 2.35 (s, 3H). LCMS for $C_{10}H_{10}BrF_3NO_2$ (M+H)$^+$: m/z=312.0, 314.0; Found: 312.0, 314.0.

Step 5. 3,3,3-Trifluoro-2-hydroxy-2-(4-methyl-3-(4,4,5,5-tetramethyl-1,3,2-dioxaborolan-2-yl)phenyl)propanamide

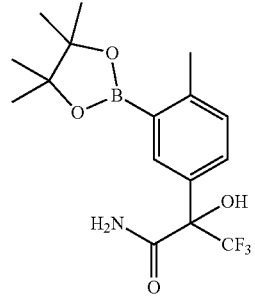 [SMILES: Cc1ccc(C(O)(C(N)=O)C(F)(F)F)cc1B1OC(C)(C)C(C)(C)O1]

A solution of 2-(3-bromo-4-methylphenyl)-3,3,3-trifluoro-2-hydroxypropanamide (3.57 g, 11.5 mmol) (Example 1, Step 4, second eluting enantiomer) in 1,4-dioxane (57.2 mL) was treated with bis(pinacolato)diboron (3.49 g, 13.7 mmol) and potassium acetate (3.71 g, 37.8 mmol) and degassed with nitrogen for 5 min. The reaction mixture was treated with bis(triphenylphosphine)palladium(II)chloride (0.482 g, 0.687 mmol), degassed for 5 min, and stirred at 100° C. for 2.5 h. The reaction mixture was diluted with ethyl acetate (50 mL), filtered over Celite®, and rinsed with additional ethyl acetate (100 mL). The filtrate was washed with brine, dried over sodium sulfate, filtered, and concentrated to a brown foam. Purification by flash column chromatography using MTBE in hexanes (0% to 100%) gave the desired product (3.35 g, 81.5%) as a thick yellow foam. $^1$H NMR (400 MHz, DMSO-$d_6$) δ 7.96 (d, J=2.2 Hz, 1H), 7.63 (dd, J=7.9, 2.1 Hz, 1H), 7.58 (s, 1H), 7.54 (s, 1H), 7.51-7.40 (m, 1H), 7.21 (d, J=8.2 Hz, 1H), 2.46 (s, 3H), 1.30 (s, 12H). LCMS for $C_{16}H_{22}BF_3NO_4$ (M+H)$^+$: m/z=360.2; Found: 360.1.

Step 6. 2-(3-(8-Amino-6-(trifluoromethyl)imidazo[1,2-a]pyrazin-3-yl)-4-methylphenyl)-3,3,3-trifluoro-2-hydroxypropanamide A solution of 3-bromo-6-(trifluoromethyl)imidazo[1,2-a]pyrazin-8-amine (7.50 g, 26.7 mmol) and 3,3,3-trifluoro-2- hydroxy-2-(4-methyl-3-(4,4,5,5-tetramethyl-1,3,2-dioxaborolan-2-yl)phenyl)propanamide (10.5 g, 29.4 mmol, Example 82, Step 5) in 1,4-dioxane (133 mL) was treated with 1.0 M potassium carbonate in water (53.4 mL, 53.4 mmol), degassed with nitrogen 5 min, treated with dichloro[1,1'-bis(diphenylphosphino)ferrocene]palladium (II) dichloromethane adduct (3.27 g, 4.00 mmol), degassed with nitrogen an additional 5 min, and stirred at 100° C. for 19 h. The reaction mixture was treated with ethyl acetate (200 mL) and brine (50 mL), filtered over Celite and the Celite was rinsed with additional ethyl acetate. The aqueous layer from the filtrate was separated and extracted with ethyl acetate (200 mL). The combined organic extracts were dried over sodium sulfate, filtered, and concentrated to a brown foam. Purification by flash column chromatography using MeOH in dichloromethane (0% to 10%) gave the desired product as a red/brown foam that was not completely pure. This material was repurified by flash column chromatography using MeOH in dichloromethane (0% to 15%) to give the desired product as an orange/brown foam that was still not completely pure. This material was repurified by flash column chromatography using ethyl acetate (containing 5% MeOH) in hexanes (0% to 100%) to give the desired product as a white foam that still contained an impurity. This material was repurified by flash column chromatography using acetonitrile (containing 5% MeOH) in dichloromethane (0% to 100%) to give the desired product (4.67 g, 40.4%) as a white foam. $^1$H NMR (600 MHz, DMSO-$d_6$) δ 7.79 (s, 1H), 7.76-7.71 (m, 2H), 7.71-7.64 (m, 4H), 7.61 (d, J=3.5 Hz, 2H), 7.51 (d, J=8.2 Hz, 1H), 2.23 (s, 3H). LCMS for $C_{17}H_{14}F_6N_5O_2$ (M+H)$^+$: m/z=434.1; Found: 434.1.

Example 83. 8-Amino-3-(5-(3-amino-1,1,1-trifluoro-2-hydroxy-3-oxopropan-2-yl)-2-methylphenyl)-N-(3-cyclopropyltetrahydrofuran-3-yl)imidazo[1,2-a]pyrazine-6-carboxamide trifluoroacetate salt

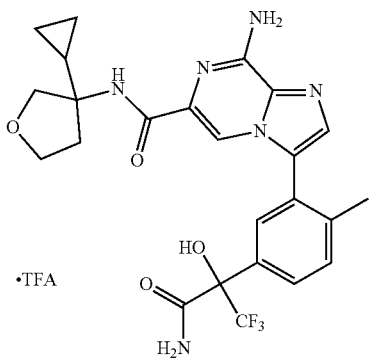 [SMILES: Cc1ccc(C(O)(C(N)=O)C(F)(F)F)cc1-c1cnc2c(N)nc(C(=O)NC3(C4CC4)CCOC3)cn12]

Step 1. N-(Dihydrofuran-3(2H)-ylidene)-2-methylpropane-2-sulfinamide

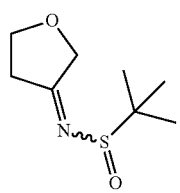

A solution of dihydrofuran-3(2H)-one (300 mg, 3.48 mmol), 2-methylpropane-2-sulfinamide (422 mg, 3.48 mmol), and titanium(IV) isopropoxide (1.07 ml, 3.66 mmol) in THF (5 ml) was heated to 60° C. overnight. The reaction mixture was cooled to room temperature, diluted with EtOAc, and poured into brine. The suspension was filtered and the layers were separated. The organic layer was dried over MgSO$_4$, filtered, and concentrated. The residue was used without purification. LCMS calculated for $C_8H_{16}NO_2S$ (M+H)$^+$: m/z=190.1, found: 190.1.

Step 2. N-(3-Cyclopropyltetrahydrofuran-3-yl)-2-methylpropane-2-sulfinamide

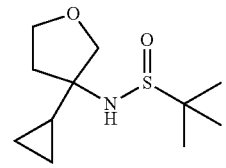

To a solution of N-(dihydrofuran-3(2H)-ylidene)-2-methylpropane-2-sulfinamide (40 mg, 0.21 mmol) in toluene (1 ml) at −78° C. was added trimethylaluminum (0.12 ml, 0.23 mmol) and the reaction mixture was stirred at this temperature for 30 min. In a separate reaction vessel, a solution of bromocyclopropane (60 μl, 0.75 mmol) in Et$_2$O (1.0 ml) at −78° C. was treated with sec-butyllithium (0.54 ml, 0.75 mmol) and the reaction mixture was stirred at −78° C. for 1 h. The solution containing the sulfinamide complex was transferred dropwise via cannula to the freshly prepared solution of cyclopropyllithium (0.85 ml, 0.63 mmol) in Et$_2$O (1 ml). The reaction mixture was allowed to warm to room temperature overnight. The reaction was quenched with saturated NH$_4$Cl and extracted with EtOAc. The layers were separated and the organic layer was washed with brine, dried over MgSO$_4$, filtered and concentrated. The residue was used without purification. LCMS calculated for $C_{11}H_{22}NO_2S$ (M+H)$^+$: m/z=232.1, found: 232.2.

Step 3. 3-Cyclopropyltetrahydrofuran-3-amine hydrochloride

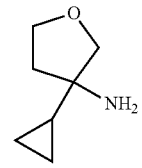

N-(3-Cyclopropyltetrahydrofuran-3-yl)-2-methylpropane-2-sulfinamide (49 mg, 0.21 mmol) was stirred in HCl (4M/dioxane) (2 ml)/MeOH (2 ml) for 30 min and concentrated. The residual solid was triturated with ether and used without purification. Quantitative yield assumed and no analytical data was collected.

Step 4. 8-Amino-3-(5-(3-amino-1,1,1-trifluoro-2-hydroxy-3-oxopropan-2-yl)-2-methylphenyl)-N-(3-cyclopropyltetrahydrofuran-3-yl)imidazo[1,2-a]pyrazine-6-carboxamide, trifluoroacetate To a solution of 8-amino-3-(5-(3-amino-1,1,1-trifluoro-2-hydroxy-3-oxopropan-2-yl)-2-methylphenyl)imidazo[1,2-a]

pyrazine-6-carboxylic acid (10 mg, 24 µmol), 3-cyclopropyltetrahydrofuran-3-amine hydrochloride (10 mg, 73 µmol), and HATU (11 mg, 29 µmol) in DMF (1.0 ml) was added DIPEA (13 µl, 73 µmol), and the reaction mixture was stirred at room temperature for 30 min. The reaction mixture was diluted with MeOH and purified by prep HPLC (pH 2). LCMS calculated for $C_{24}H_{26}F_3N_6O_4$ (M+H)$^+$: m/z=519.2, found: 519.2.

Examples 84-85

These compounds were synthesized according to the procedure outlined in Example 83, utilizing the appropriate commercially available amine in Step 4.

TABLE 7

| Ex. No. | Name | R | LCMS [M + H]$^+$ |
|---|---|---|---|
| 84 | 8-Amino-3-(5-(3-amino-1,1,1-trifluoro-2-hydroxy-3-oxopropan-2-yl)-2-methylphenyl)-N-(2,3-dimethyltetrahydrofuran-3-yl)imidazo[1,2-a]pyrazine-6-carboxamide, trifluoroacetate (mixture of diastereomers) | | 507.2 |
| 85 | 8-Amino-3-(5-(3-amino-1,1,1-trifluoro-2-hydroxy-3-oxopropan-2-yl)-2-methylphenyl)-N-(4-(trifluoromethyl)tetrahydro-2H-pyran-4-yl)imidazo[1,2-a]pyrazine-6-carboxamide, trifluoroacetate | | 561.2 |

Example 86. 3-(4-(8-Amino-3-(2-(methyl-d$_3$)-5-(1,1,1-trifluoro-2-hydroxypropan-2-yl)phenyl)imidazo[1,2-a]pyrazin-6-yl)-1H-pyrazol-1-yl)-3-cyclobutyl-propanenitrile, trifluoroacetate

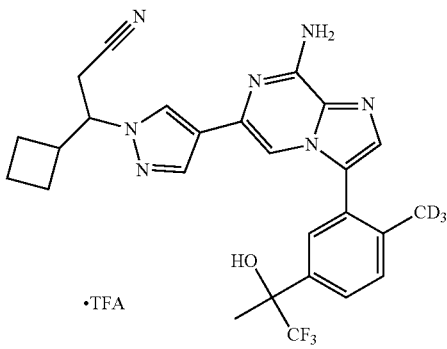 [SMILES: [2H]C([2H])([2H])c1ccc(C(C)(O)C(F)(F)F)cc1-c1cnc2c(N)nc(-c3cnn(C(CC#N)C4CCC4)c3)cn12]

To a solution of 2-(3-(8-amino-6-bromoimidazo[1,2-a]pyrazin-3-yl)-4-(methyl-d$_3$)phenyl)-1,1,1-trifluoropropan-2-ol [Example 81, Step 5] (10 mg, 24 µmol), 3-cyclobutyl-3-(4-(4,4,5,5-tetramethyl-1,3,2-dioxaborolan-2-yl)-1H-pyrazol-1-yl)propanenitrile (10.8 mg, 36 µmol, as described in WO2009064835), and PdCl$_2$(dppf)-CH$_2$Cl$_2$ adduct (2 mg, 2.4 µmol) in dioxane (1 ml) and water (0.5 mL) was added sodium carbonate (7.6 mg, 72 µmol). The reaction mixture was sparged with N$_2$ and heated to 100° C. for 2 h. The reaction mixture was diluted with MeOH, filtered, and purified by prep HPLC (pH 2). LCMS calculated for $C_{26}H_{24}D_3F_3N_7O$ (M+H)$^+$: m/z=513.2, found: 513.3.

Example 87. 2-(3-(8-Amino-6-(5,6-dihydro-4H-pyrrolo[1,2-b]pyrazol-3-yl)imidazo[1,2-a]pyrazin-3-yl)-4-(methyl-d$_3$)phenyl)-1,1,1-trifluoropropan-2-ol, trifluoroacetate

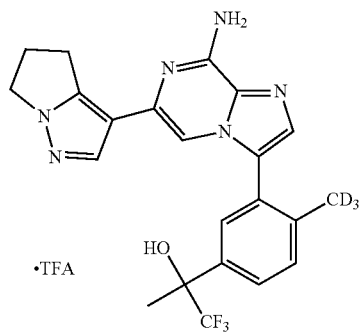 [SMILES: [2H]C([2H])([2H])c1ccc(C(C)(O)C(F)(F)F)cc1-c1cnc2c(N)nc(-c3cnn4c3CCC4)cn12]

This compound was prepared following a procedure identical to that described for Example 86, utilizing 3-(4,4,5,5-tetramethyl-1,3,2-dioxaborolan-2-yl)-5,6-dihydro-4H-pyrrolo[1,2-b]pyrazole (Aurum Pharmatech) instead of 3-cyclobutyl-3-(4-(4,4,5,5-tetramethyl-1,3,2-dioxaborolan-2-yl)-1H-pyrazol-1-yl)propanenitrile. LCMS calculated for $C_{22}H_{19}D_3F_3N_6O$ (M+H)$^+$: m/z=446.2, found: 446.1.

Example 88. Methyl 3-(4-(8-amino-3-(2-(methyl-d3)-5-(1,1,1-trifluoro-2-hydroxypropan-2-yl)phenyl)imidazo[1,2-a]pyrazin-6-yl)-1H-pyrazol-1-yl)-3-(cyanomethyl)cyclobutane-1-carboxylate, trifluoroacetate

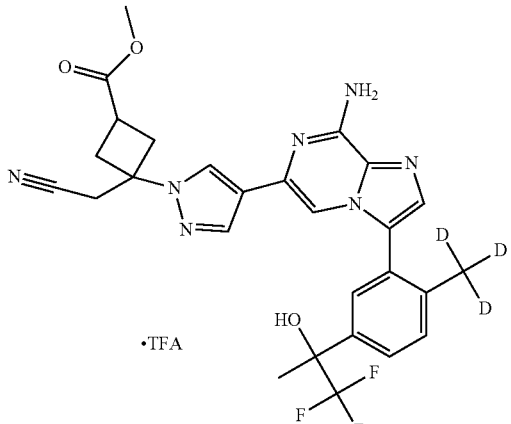

Step 1. 2-(3-(8-Amino-6-(1H-pyrazol-4-yl)imidazo[1,2-a]pyrazin-3-yl)-4-(methyl-d3)phenyl)-1,1,1-trifluoropropan-2-ol

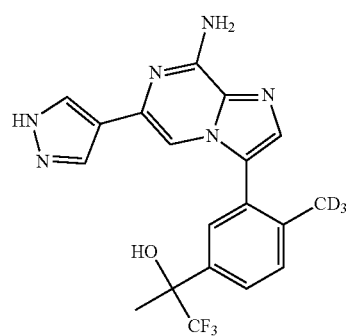 [SMILES: [2H]C([2H])([2H])c1ccc(C(C)(O)C(F)(F)F)cc1-c1cnc2c(N)nc(-c3cn[nH]c3)cn12]

A mixture of 2-(3-(8-amino-6-bromoimidazo[1,2-a]pyrazin-3-yl)-4-(methyl-d₃)phenyl)-1,1,1-trifluoropropan-2-ol (150 mg, 0.36 mmol), tert-butyl 4-(4,4,5,5-tetramethyl-1,3,2-dioxaborolan-2-yl)-1H-pyrazole-1-carboxylate (158 mg, 0.54 mmol), PdCl₂(dppf)-CH₂Cl₂ adduct (14.6 mg, 0.018 mmol), and sodium carbonate (114 mg, 1.08 mmol) in dioxane (2 ml) and water (0.5 ml) was sparged with N₂ and heated to 100° C. for 3 h. The reaction mixture was partitioned between water and EtOAc, and the layers were separated. The aqueous layer was extracted with EtOAc and the combined organic layers were washed with brine, dried over MgSO₄, filtered, and concentrated. The residue was purified by flash chromatography (0-100% EtOAc/hexanes followed by 0-25% MeOH/DCM) to afford the title compound (quantitative yield assumed). LCMS calculated for $C_{19}H_{15}D_3F_3N_6O$ (M+H)⁺: m/z=406.2, found: 406.2.

Step 2. Methyl 3-(4-(8-amino-3-(2-(methyl-d3)-5-(1,1,1-trifluoro-2-hydroxypropan-2-yl)phenyl)imidazo[1,2-a]pyrazin-6-yl)-1H-pyrazol-1-yl)-3-(cyanomethyl)cyclobutane-1-carboxylate, trifluoroacetate To a solution of 2-(3-(8-amino-6-(1H-pyrazol-4-yl)imidazo[1,2-a]pyrazin-3-yl)-4-(methyl-d₃)phenyl)-1,1,1-trifluoropropan-2-ol (20 mg, 49 μmol) in acetonitrile (1 ml) was added methyl 3-(cyanomethylene)cyclobutane-1-carboxylate (37 mg, 0.25 mmol) and DBU (37 μl, 0.25 mmol, as described in WO2009114512), and the reaction mixture was stirred at 60° C. for 5 h. The reaction mixture was diluted with MeCN, filtered, and purified by prep HPLC (pH 2). LCMS calculated for $C_{27}H_{24}D_3F_3N_7O_3$ (M+H)⁺: m/z=557.2, found: 557.2.

Examples P1-P6

In the below Examples P1-P6, X-Ray Powder Diffraction analysis was carried out on a Bruker D8 Advance ECO X-ray Powder Diffractometer (XRPD) instrument with the following parameters: radiation source is Cu at 1.5418 Å and LYNXEYE™ detector and X-ray power of 40 KV, 25 mA. The sample powder was dispersed on a zero-background sample holder. General measurement conditions were: Start Angle—3°; Stop Angle—30°; Sampling—0.015 deg.; and Scan speed—2 deg/min.

Differential Scanning Calorimetry (DSC) was carried out on a TA Instrument Differential Scanning Calorimetry, Discovery DSC2500 with autosampler. The general experimental conditions were: 20-300° C. at 10° C./min, nitrogen gas flow at 50 mL/min, using an aluminum sample pan.

Thermogravimetric analysis (TGA) was carried out on a TA Instrument Thermogravimetric Analyzer, TGA5500 with an autosampler at the following conditions: Ramp at 10° C./min. from 25° C. to 600° C.; nitrogen gas at 25 mL/min balance purge flow; and platinum sample pan.

Example P1. Preparation and Characterization of 2-(3-(8-amino-6-(trifluoromethyl)imidazo[1,2-a]pyrazin-3-yl)-4-methylphenyl)-3,3,3-trifluoro-2-hydroxypropanamide, Crystalline Form I (Free Base)

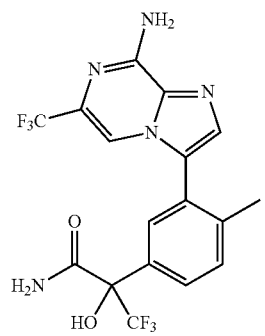 [SMILES: Cc1ccc(C(O)(C(N)=O)C(F)(F)F)cc1-c1cnc2c(N)nc(C(F)(F)F)cn12]

A vial was charged with 2-(3-(8-amino-6-(trifluoromethyl)imidazo[1,2-a]pyrazin-3-yl)-4-methylphenyl)-3,3,3-trifluoro-2-hydroxypropanamide (0.050 g, 0.115 mmol) and stirred at 80° C. while a 1:2 premixed solution of isopropyl acetate (0.676 mL)/heptane (1.34 mL) was added dropwise. After 2 mL was added the solid was not completely dissolved and some remained on the bottom of the vial. After almost all of the solids had dissolved, new solids were forming on the walls of the vial. More solids had formed after stirring at 80° C. for 2 h. After cooling to ambient temperature the solids were filtered and washed with heptane. The solids were collected and dried under reduced pressure for 30 min to give 2-(3-(8-amino-6-(trifluoromethyl)imidazo[1,2-a]pyrazin-3-yl)-4-methylphenyl)-3,3,3-trifluoro-2-hydroxypropanamide (Form I) (33.2 mg, 66.4%) as a white solid.

Form I was confirmed as a crystalline solid according to XRPD analysis. The XRPD pattern of Form I is shown in FIG. 1 and the peak data is given in Table 8 below.

TABLE 8

XRPD Peak Data for Form I.

| 2-Theta (°) | Relative Intensity (%) |
|---|---|
| 8.2 | 0.9 |
| 8.6 | 21.5 |
| 9.5 | 34.3 |
| 10.3 | 92.1 |
| 10.8 | 1.0 |
| 12.8 | 1.1 |
| 13.0 | 5.0 |
| 13.6 | 7.8 |
| 14.2 | 4.1 |
| 14.9 | 100 |
| 16.5 | 2.3 |
| 17.3 | 43.8 |
| 17.8 | 22.6 |
| 18.1 | 1.3 |
| 19.0 | 29.9 |
| 19.2 | 49.7 |
| 19.5 | 8.1 |
| 19.9 | 1.6 |
| 20.1 | 25.4 |
| 20.4 | 15.1 |
| 20.6 | 39.6 |
| 21.2 | 16.8 |
| 21.5 | 6.6 |
| 21.8 | 0.6 |
| 22.2 | 26.6 |
| 22.5 | 4.0 |
| 23.0 | 0.8 |
| 23.6 | 3.2 |
| 24.0 | 42.4 |
| 24.3 | 8.2 |
| 24.6 | 4.2 |
| 25.6 | 7.4 |
| 25.8 | 7.6 |
| 26.3 | 4.3 |
| 26.8 | 12.9 |
| 27.4 | 9.9 |
| 27.9 | 4.4 |
| 28.2 | 1.7 |
| 28.7 | 37.4 |
| 29.6 | 1.3 |

Figure 2:
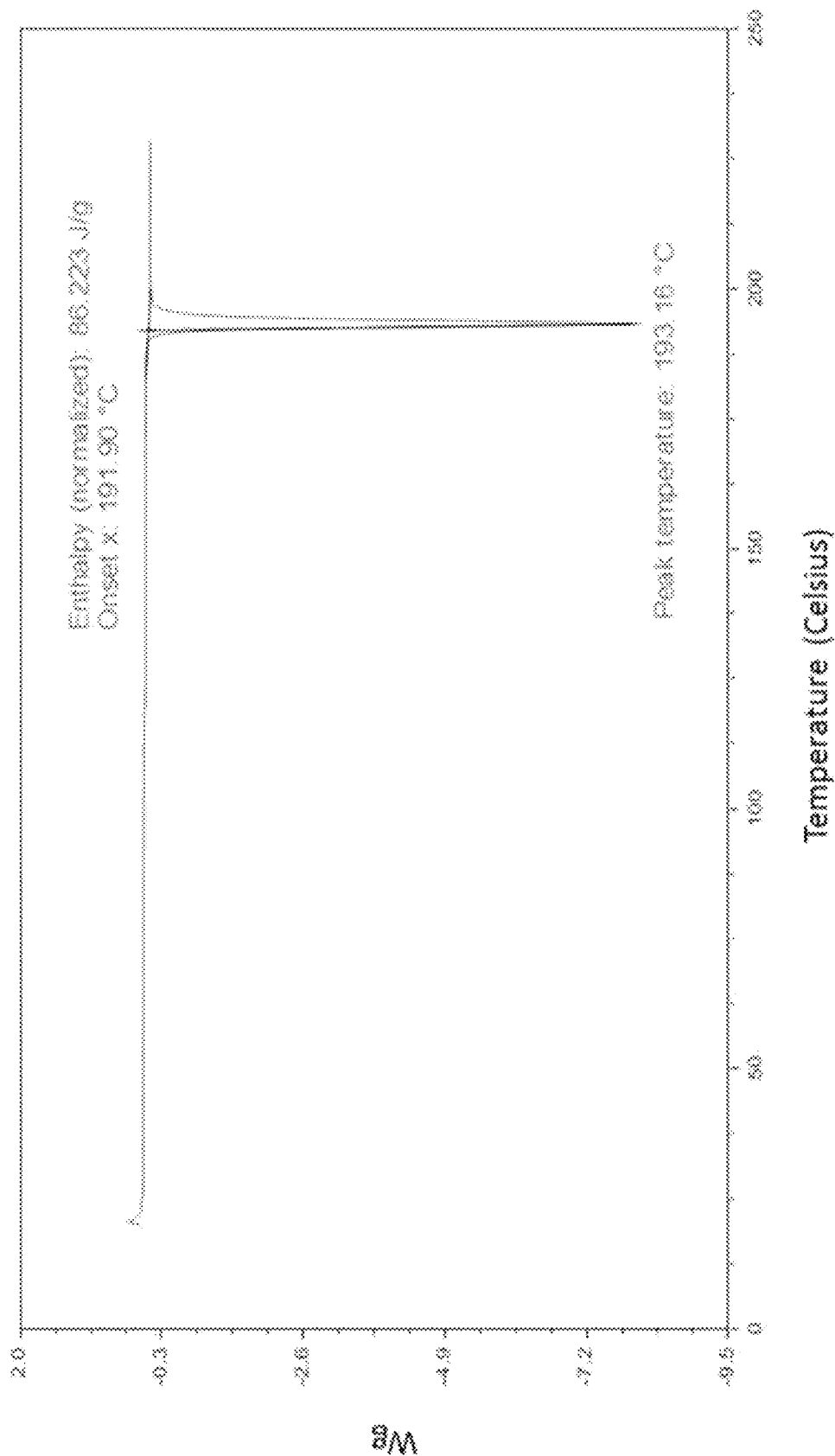
FIG. 2 shows the results of a DSC experiment for crystalline Form I of Example P1.

DSC analysis of Form I revealed one peak with an onset temperature of 191.9° C. and a maximum at 193.2° C. The DSC thermogram is provided in FIG. 2.

Figure 3:
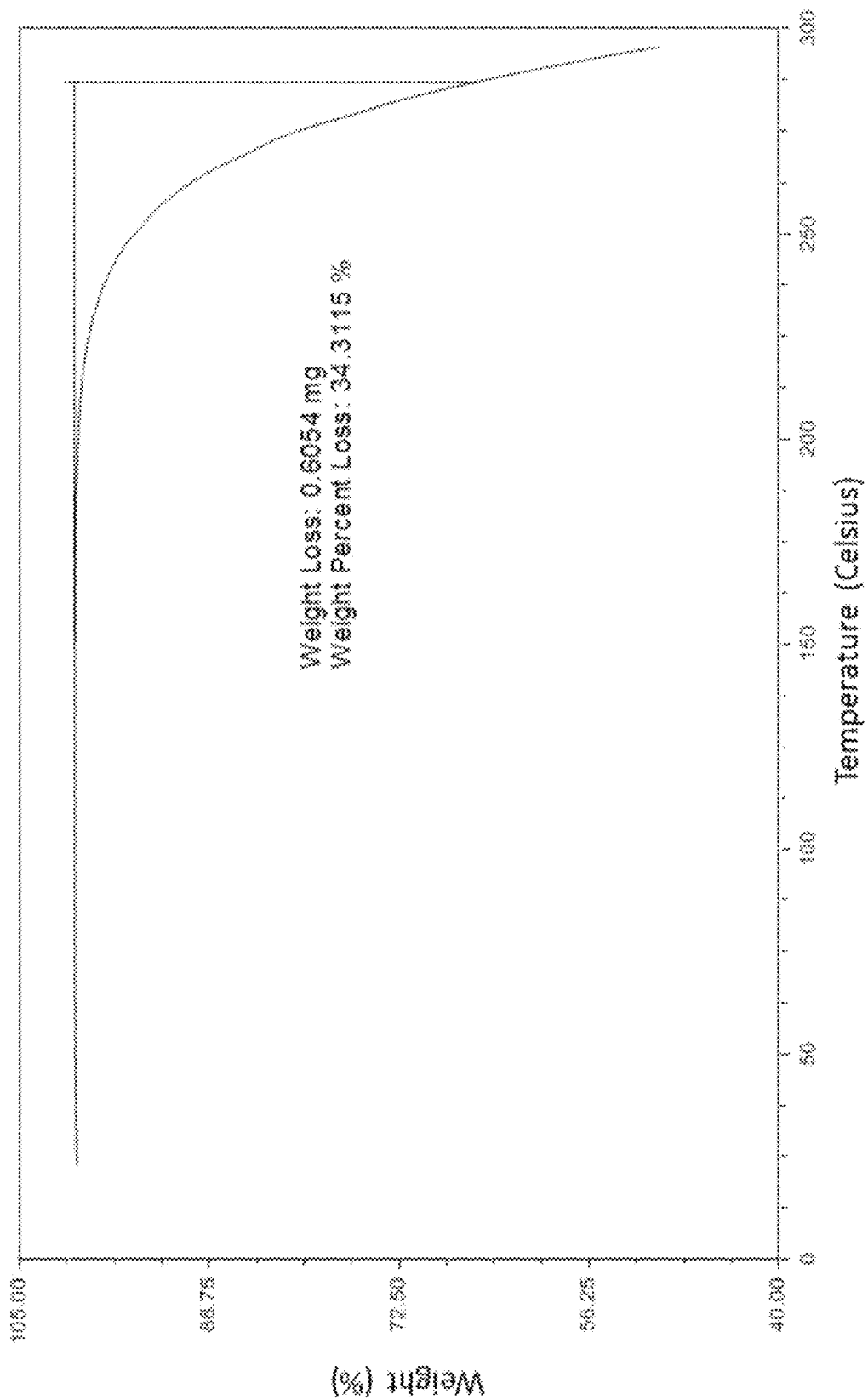
FIG. 3 shows the results of a TGA experiment for crystalline Form I of Example P1.

TGA analysis of Form I revealed significant weight loss above 200° C. due to decomposition of the sample. The TGA thermogram is provided in FIG. 3.

Form I was confirmed as an anhydrous, non-solvated crystalline form.

Example P2. Preparation and Characterization of 2-(3-(8-amino-6-(trifluoromethyl)imidazo[1,2-a]pyrazin-3-yl)-4-methylphenyl)-3,3,3-trifluoro-2-hydroxypropanamide, Crystalline Form II (Free Base)

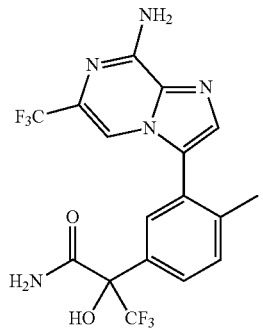 [SMILES: Cc1ccc(C(O)(C(N)=O)C(F)(F)F)cc1-c1cnc2c(N)nc(C(F)(F)F)cn12]

Approximately 100 mg of 2-(3-(8-amino-6-(trifluoromethyl)imidazo[1,2-a]pyrazin-3-yl)-4-methylphenyl)-3,3,3-trifluoro-2-hydroxypropanamide free base was dissolved in 1 mL of isopropyl acetate in a 4 mL clear glass vial. To the solution, 2 mL of heptane was added with stirring at ambient temperature. The mixture was heated at 80° C. with stirring for 2 h. The mixture was cooled to ambient temperature and stirred for 1 h. The solid was collected by filtration and air dried to give 2-(3-(8-amino-6-(trifluoromethyl)imidazo[1,2-a]pyrazin-3-yl)-4-methylphenyl)-3,3,3-trifluoro-2-hydroxypropanamide (Form II).

Figure 4:
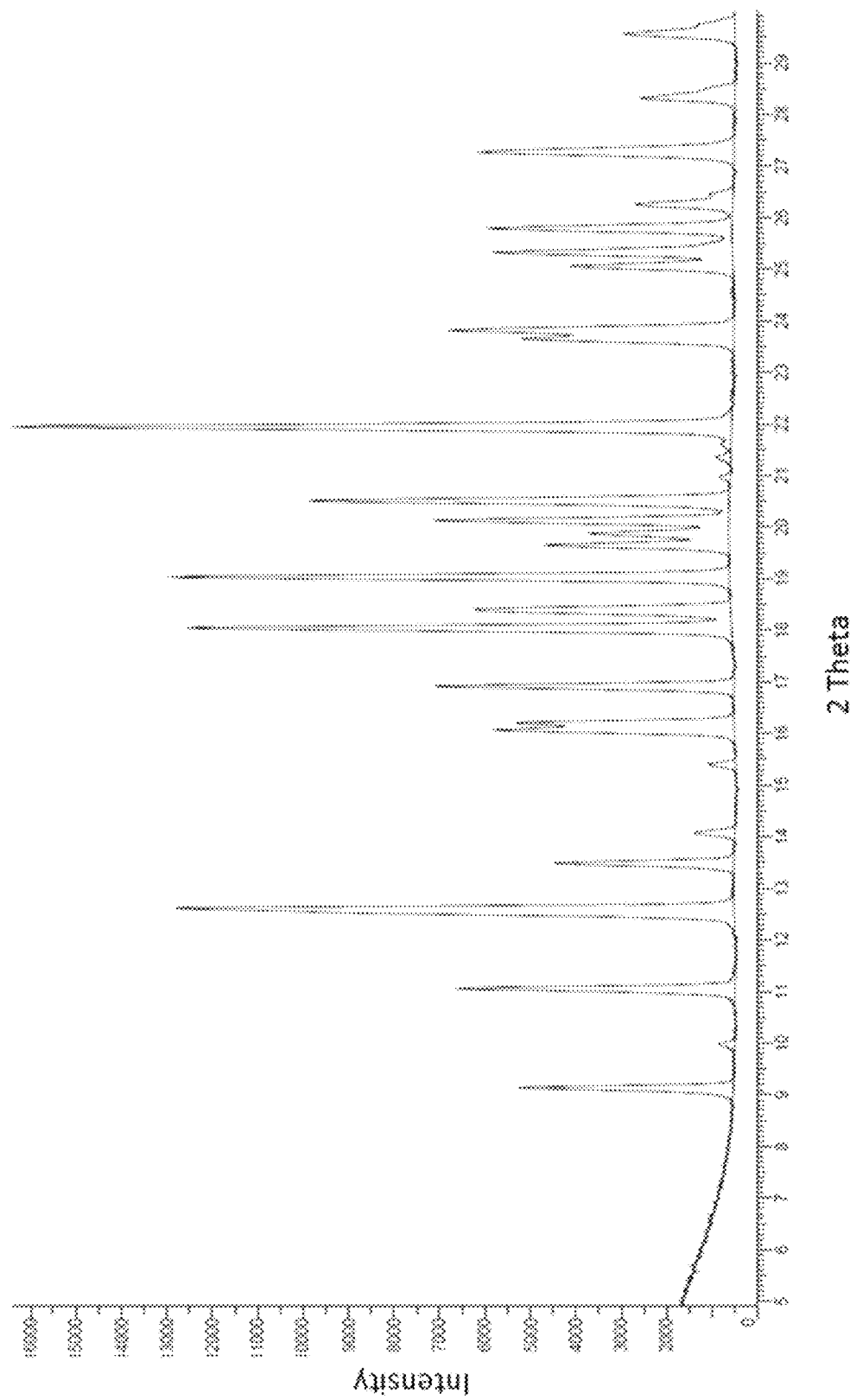
FIG. 4 shows an XRPD pattern for crystalline Form II of Example P2.

Form II was confirmed as a crystalline solid according to XRPD analysis. The XRPD pattern of Form II is shown in FIG. 4 and the peak data is given in Table 9 below.

TABLE 9

XRPD Peak Data for Form II.

| 2-Theta (°) | Relative Intensity (%) |
|---|---|
| 9.1 | 29.8 |
| 10.0 | 2.2 |
| 11.1 | 38.6 |
| 12.6 | 77.6 |
| 13.5 | 24.8 |
| 14.1 | 5.6 |
| 15.4 | 3.6 |
| 16.1 | 24.0 |
| 16.9 | 41.4 |
| 18.0 | 75.7 |
| 18.4 | 35.0 |
| 19.0 | 77.5 |
| 19.7 | 25.5 |
| 19.9 | 19.5 |
| 20.1 | 40.9 |
| 20.5 | 58.2 |
| 21.0 | 1.1 |
| 21.4 | 2.1 |
| 21.6 | 1.3 |
| 21.9 | 100 |
| 23.7 | 29.4 |
| 23.8 | 39.7 |
| 25.1 | 22.5 |
| 25.3 | 33.1 |
| 25.8 | 33.9 |
| 26.3 | 13.6 |

TABLE 9-continued

XRPD Peak Data for Form II.

| 2-Theta (°) | Relative Intensity (%) |
|---|---|
| 26.4 | 3.3 |
| 27.3 | 35.5 |
| 28.3 | 13.2 |
| 29.6 | 15.4 |

Figure 5:
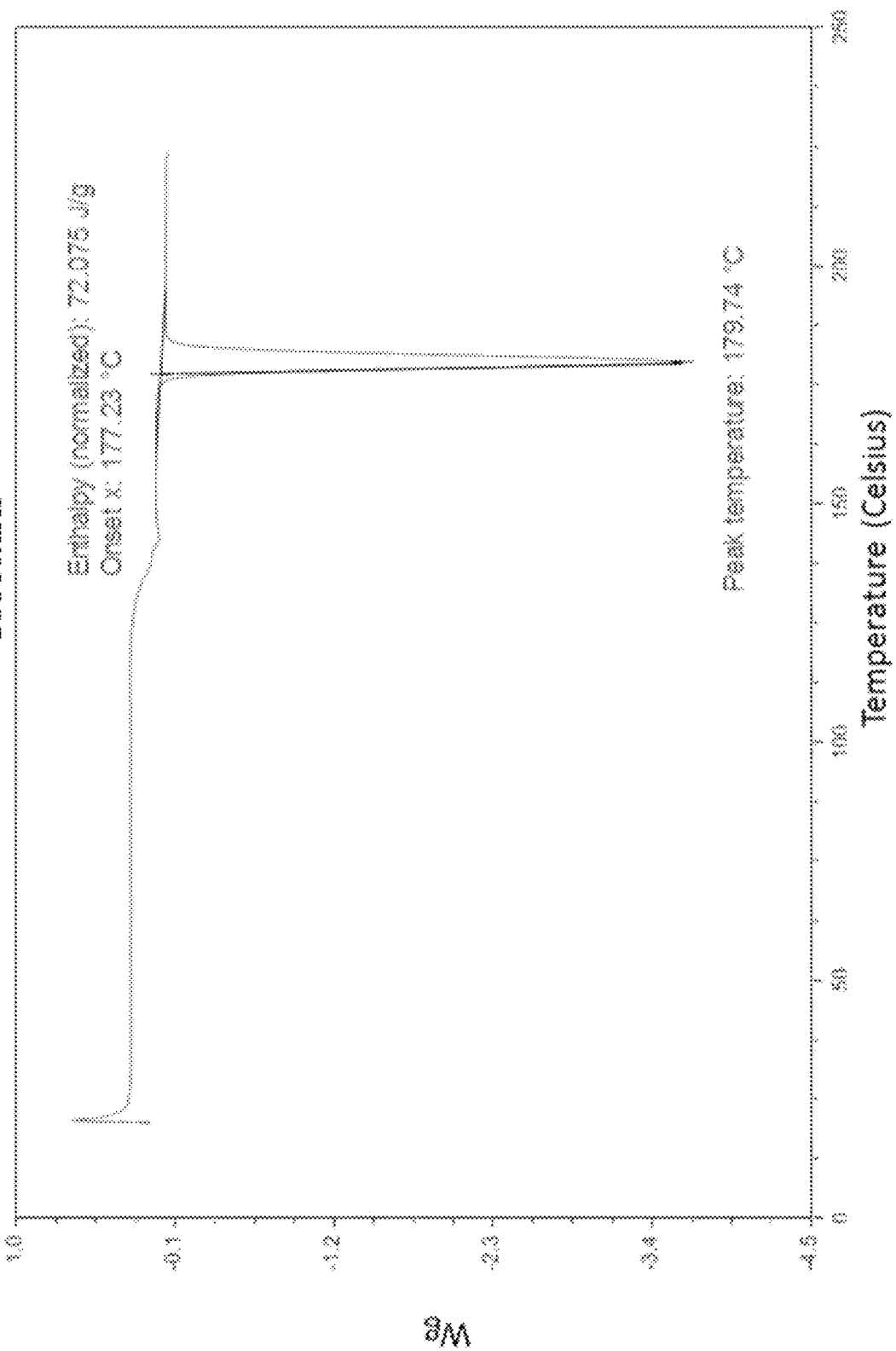
FIG. 5 shows the results of a DSC experiment for crystalline Form II of Example P2.

DSC analysis of Form II revealed one peak with an onset temperature of 177.2° C. and a maximum at 179.7° C. The DSC thermogram is provided in FIG. 5.

Figure 6:
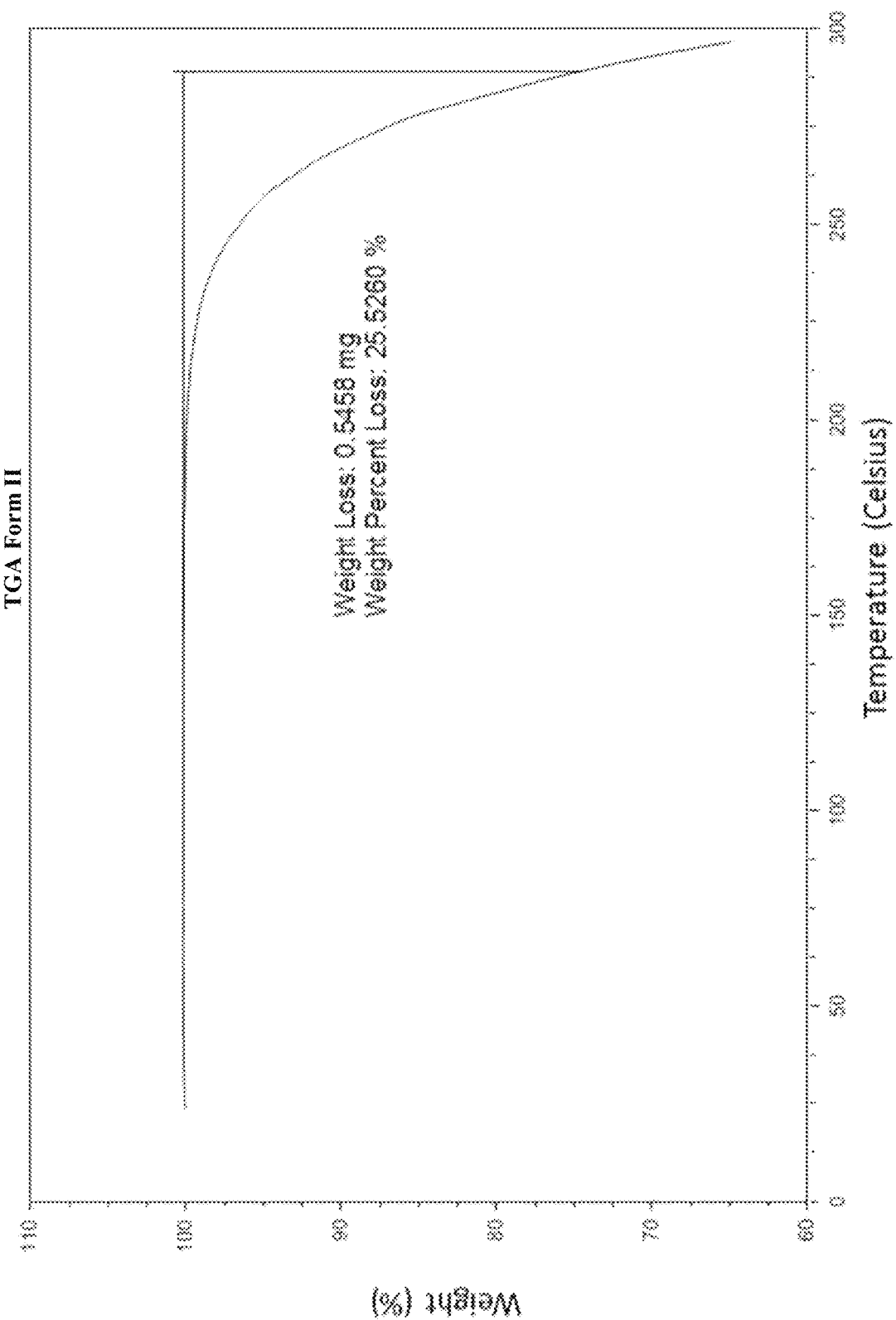
FIG. 6 shows the results of a TGA experiment for crystalline Form II of Example P2.

TGA analysis of Form II revealed significant weight loss above 200° C. due to decomposition of the sample. The TGA thermogram is provided in FIG. 6.

Form II was confirmed as an anhydrous, non-solvated crystalline form.

Example P3. Preparation and Characterization of 2-(3-(8-amino-6-(trifluoromethyl)imidazo[1,2-a]pyrazin-3-yl)-4-methylphenyl)-3,3,3-trifluoro-2-hydroxypropanamide, Crystalline Form III (Free Base)

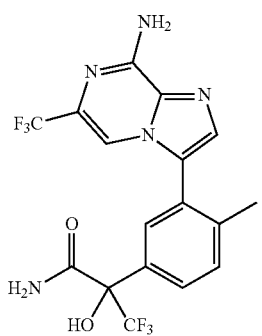 [SMILES: Cc1ccc(C(O)(C(N)=O)C(F)(F)F)cc1-c1cnc2c(N)nc(C(F)(F)F)cn12]

Approximately 72 mg of 2-(3-(8-amino-6-(trifluoromethyl)imidazo[1,2-a]pyrazin-3-yl)-4-methylphenyl)-3,3,3-trifluoro-2-hydroxypropanamide free base was dissolved in 1 mL of MeOH in a 4 mL clear glass vial. The solution was evaporated to dryness at ambient temperature. The resultant solid, which is a MeOH solvate, was dried at 60° C. under vacuum overnight to afford 2-(3-(8-amino-6-(trifluoromethyl)imidazo[1,2-a]pyrazin-3-yl)-4-methylphenyl)-3,3,3-trifluoro-2-hydroxypropanamide (Form III).

Figure 7:
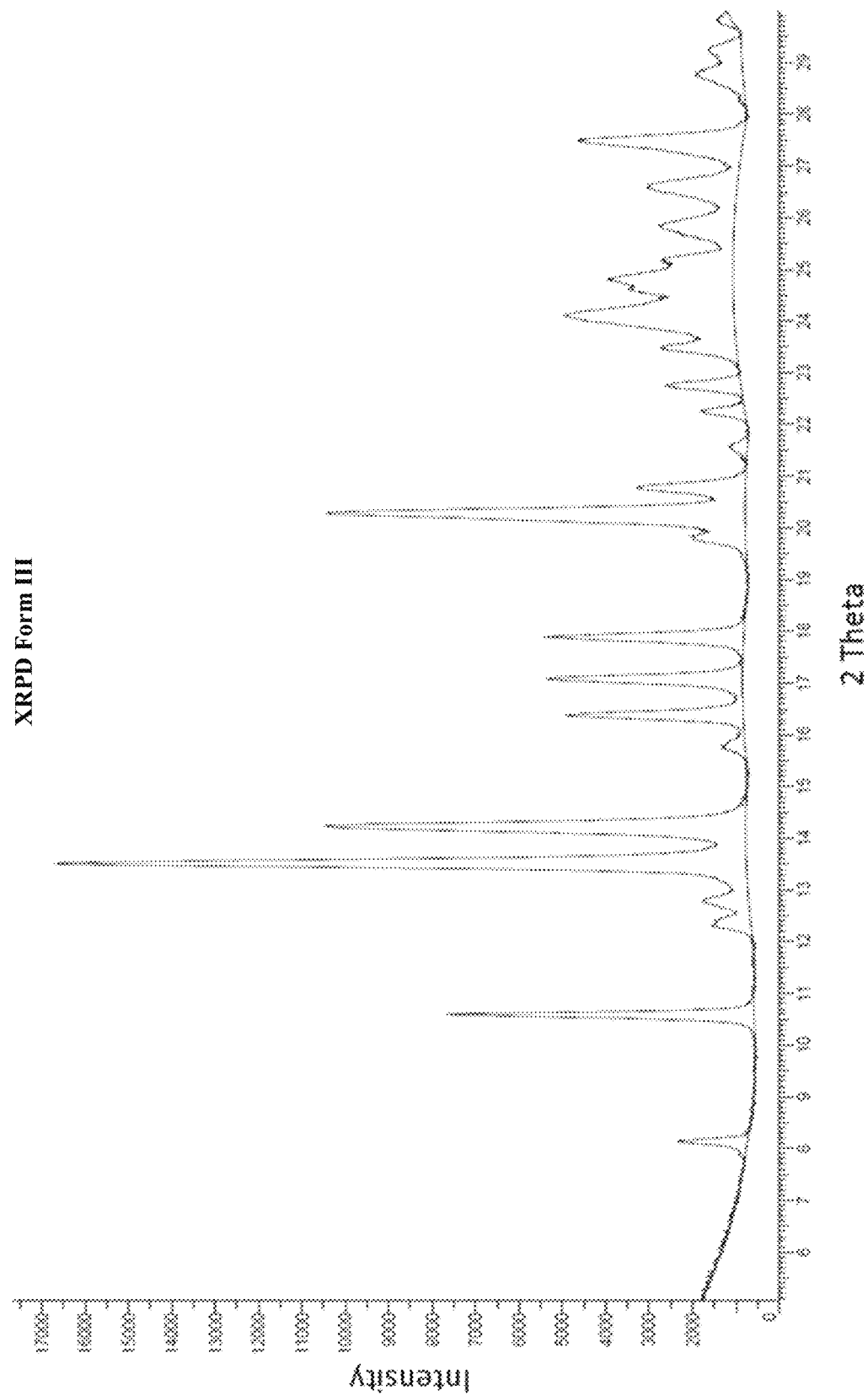
FIG. 7 shows an XRPD pattern for crystalline Form III in Example P3.

Form III was confirmed as a crystalline solid according to XRPD analysis. The XRPD pattern of Form III is shown in FIG. 7 and the peak data is given in Table 10 below.

TABLE 10

XRPD Peak Data for Form III.

| 2-Theta (°) | Relative Intensity (%) |
|---|---|
| 8.1 | 10.0 |
| 10.6 | 44.4 |
| 12.4 | 5.0 |
| 12.8 | 6.7 |
| 13.5 | 100 |
| 14.2 | 60.9 |
| 15.8 | 3.3 |
| 16.4 | 25.7 |
| 17.1 | 28.3 |

TABLE 10-continued

XRPD Peak Data for Form III.

| 2-Theta (°) | Relative Intensity (%) |
|---|---|
| 17.9 | 29.1 |
| 19.8 | 7.8 |
| 20.3 | 60.6 |
| 20.8 | 15.8 |
| 21.6 | 2.7 |
| 22.3 | 6.5 |
| 22.8 | 10.9 |
| 23.5 | 10.8 |
| 24.1 | 24.6 |
| 24.6 | 15.0 |
| 24.8 | 18.0 |
| 25.2 | 10.0 |
| 25.8 | 10.8 |
| 26.6 | 13.0 |
| 27.5 | 24.0 |
| 28.8 | 6.8 |
| 29.2 | 4.8 |
| 29.8 | 2.1 |

Figure 8:
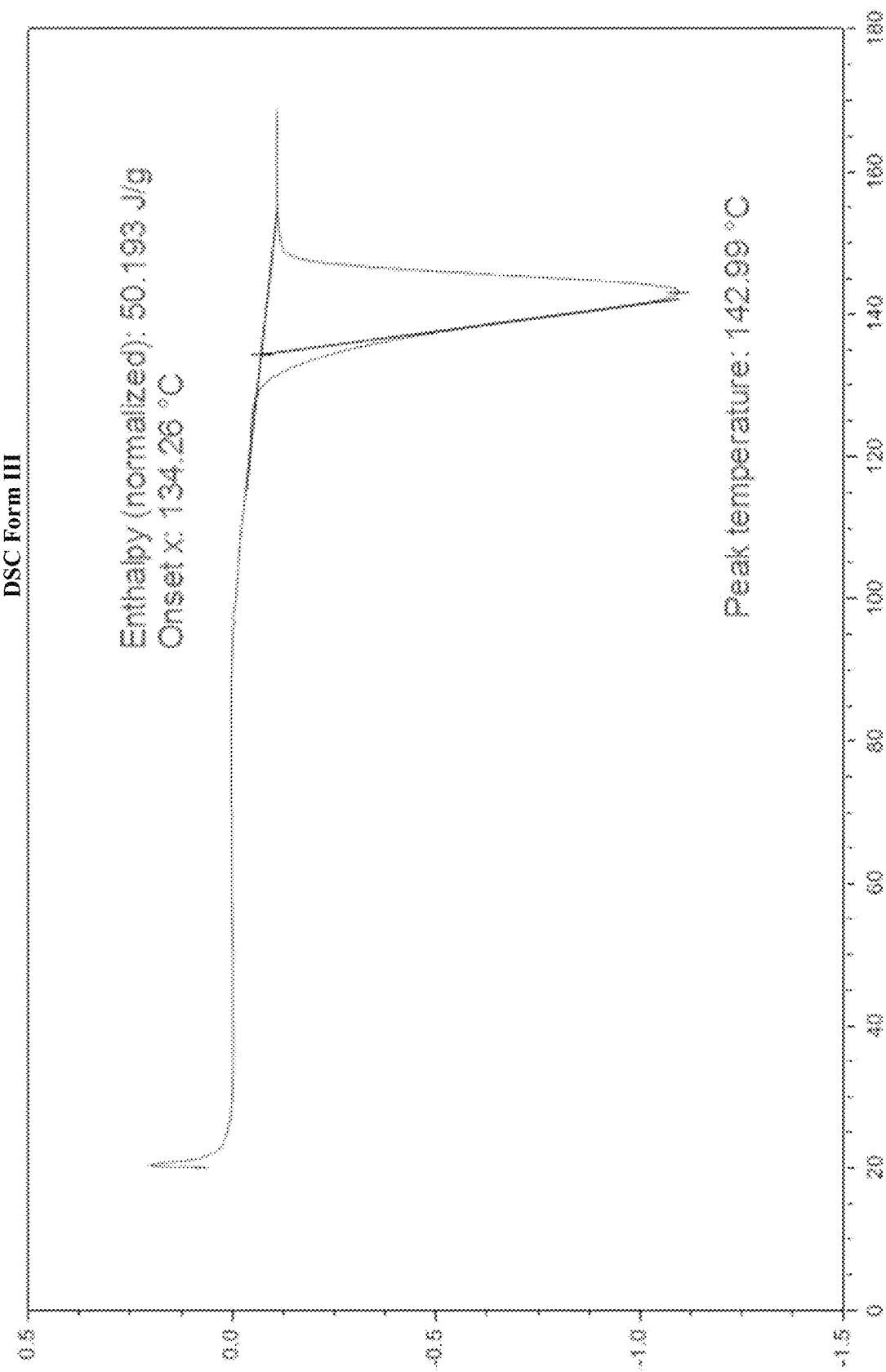
FIG. 8 shows the results of a DSC experiment for crystalline Form III of Example P3.

DSC analysis of Form III revealed one peak with an onset temperature of 134.3° C. and a maximum at 143.0° C. The DSC thermogram is provided in FIG. 8.

Figure 9:
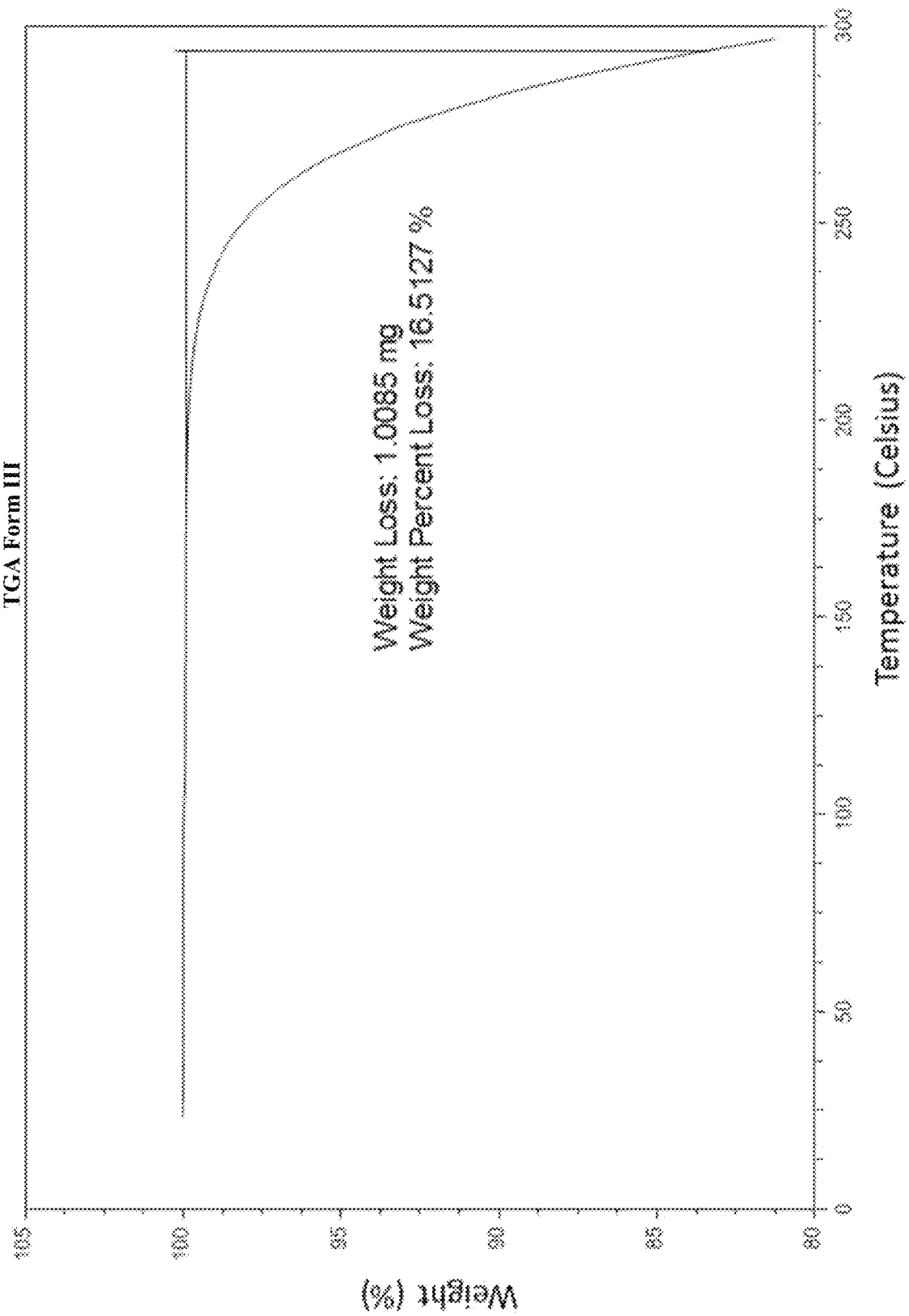
FIG. 9 shows the results of a TGA experiment for crystalline Form III of Example P3.

TGA analysis of Form II revealed significant weight loss above 200° C. due to decomposition of the sample. The TGA thermogram is provided in FIG. 9.

Form III was confirmed as an anhydrous, non-solvated crystalline form.

Example P4. Preparation and Characterization of 8-amino-N-(2-hydroxy-2-methylpropyl)-3-(2-(methyl-d3)-5-(1,1,1-trifluoro-2-hydroxypropan-2-yl)phenyl)imidazo[1,2-a]pyrazine-6-carboxamide, Crystalline Form I (Free Base)

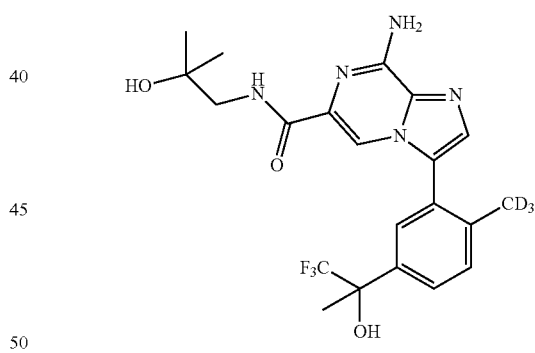

A round bottom was charged with 8-amino-N-(2-hydroxy-2-methylpropyl)-3-(2-(methyl-d$_3$)-5-(1,1,1-trifluoro-2-hydroxypropan-2-yl)phenyl)imidazo[1,2-a]pyrazine-6-carboxamide (4.60 g, 10.1 mmol) and isopropyl acetate (25.5 mL) that was heated at 80° C. The mixture was stirred at 80° C. and solids began to form within 5 min. The mixture was stirred at 80° C. for 1 h. The heat was discontinued and the mixture was stirred for 1 h while cooling to rt. The mixture was treated with heptane (25.5 mL) dropwise from an addition funnel over 35 min and stirred at rt for 40 min. The solids were collected, washed with 1:1 isopropyl acetate/heptane (10 mL) and dried under reduced pressure at 60° C. for 24 h to give 8-amino-N-(2-hydroxy-2-methylpropyl)-3-(2-(methyl-d$_3$)-5-(1,1,1-trifluoro-2-hydroxypropan-2-yl)phenyl)imidazo[1,2-a]pyrazine-6-carboxamide (Form I) (4.16 g, 90.4%).

Figure 10:
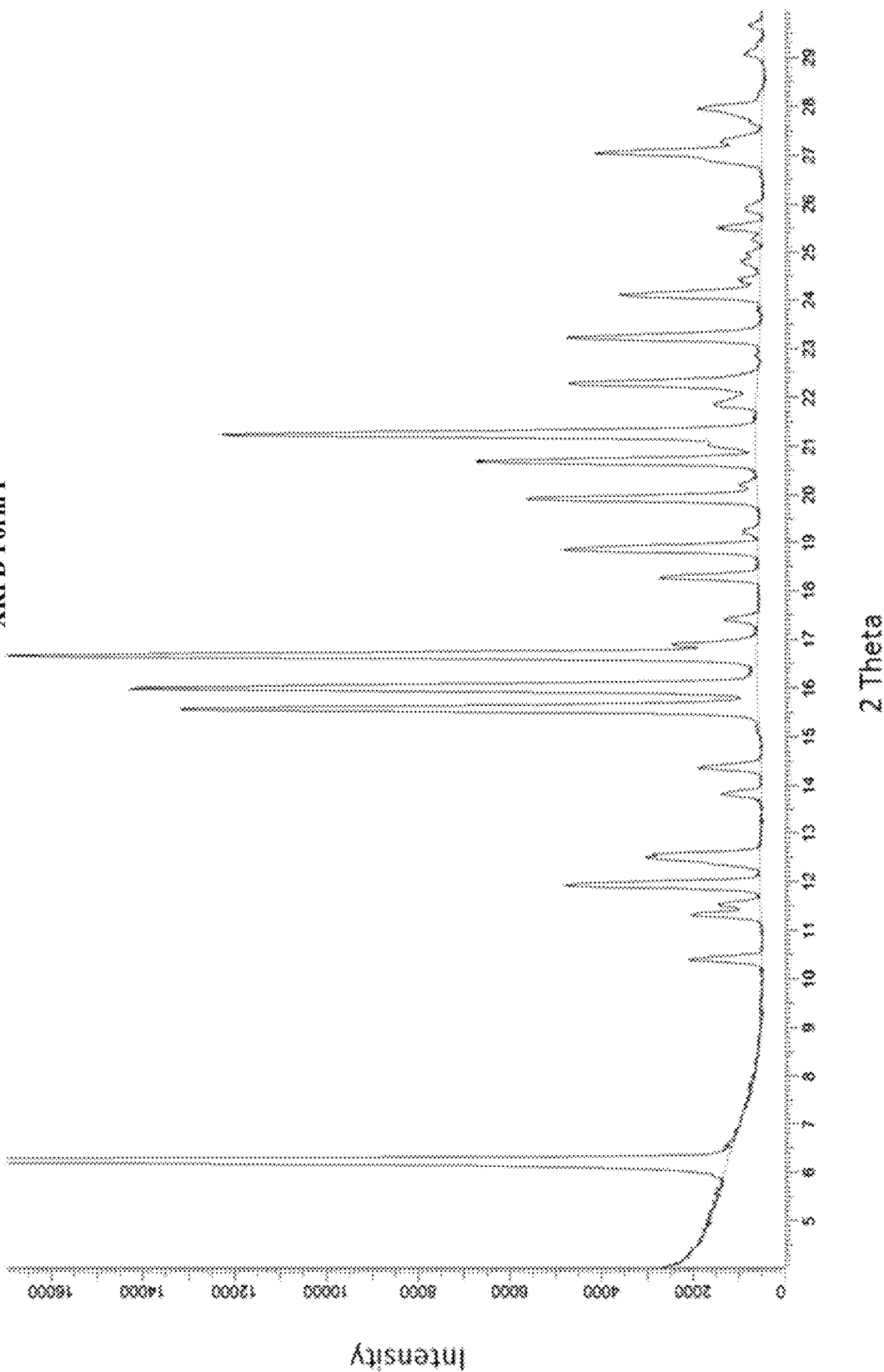
FIG. 10 shows an XRPD pattern for crystalline Form I of Example P4.

Form I was confirmed as a crystalline solid according to XRPD analysis. The XRPD pattern of Form I is shown in FIG. 10 and the peak data is given in Table 11 below.

TABLE 11

XRPD Peak Data for Form I.

| 2-Theta (°) | Relative Intensity (%) |
|---|---|
| 6.2 | 100 |
| 10.4 | 6.4 |
| 11.3 | 6.0 |
| 11.5 | 3.7 |
| 11.9 | 17.3 |
| 12.5 | 10.1 |
| 13.8 | 3.5 |
| 14.4 | 5.5 |
| 15.6 | 51.0 |
| 16.0 | 55.2 |
| 16.7 | 66.3 |
| 16.9 | 7.5 |
| 17.4 | 2.9 |
| 18.3 | 8.6 |
| 18.8 | 17.1 |
| 19.2 | 1.4 |
| 19.9 | 20.4 |
| 20.2 | 1.4 |
| 20.7 | 24.4 |
| 21.0 | 4.1 |
| 21.2 | 47.0 |
| 21.8 | 3.7 |
| 22.3 | 16.6 |
| 23.2 | 17.0 |
| 24.1 | 12.4 |
| 24.4 | 1.9 |
| 24.8 | 1.7 |
| 24.9 | 0.9 |
| 25.3 | 0.8 |
| 25.5 | 3.9 |
| 25.9 | 1.5 |
| 27.0 | 14.7 |
| 27.3 | 3.4 |
| 27.9 | 5.8 |
| 29.1 | 1.4 |
| 29.7 | 1.2 |

Figure 11:
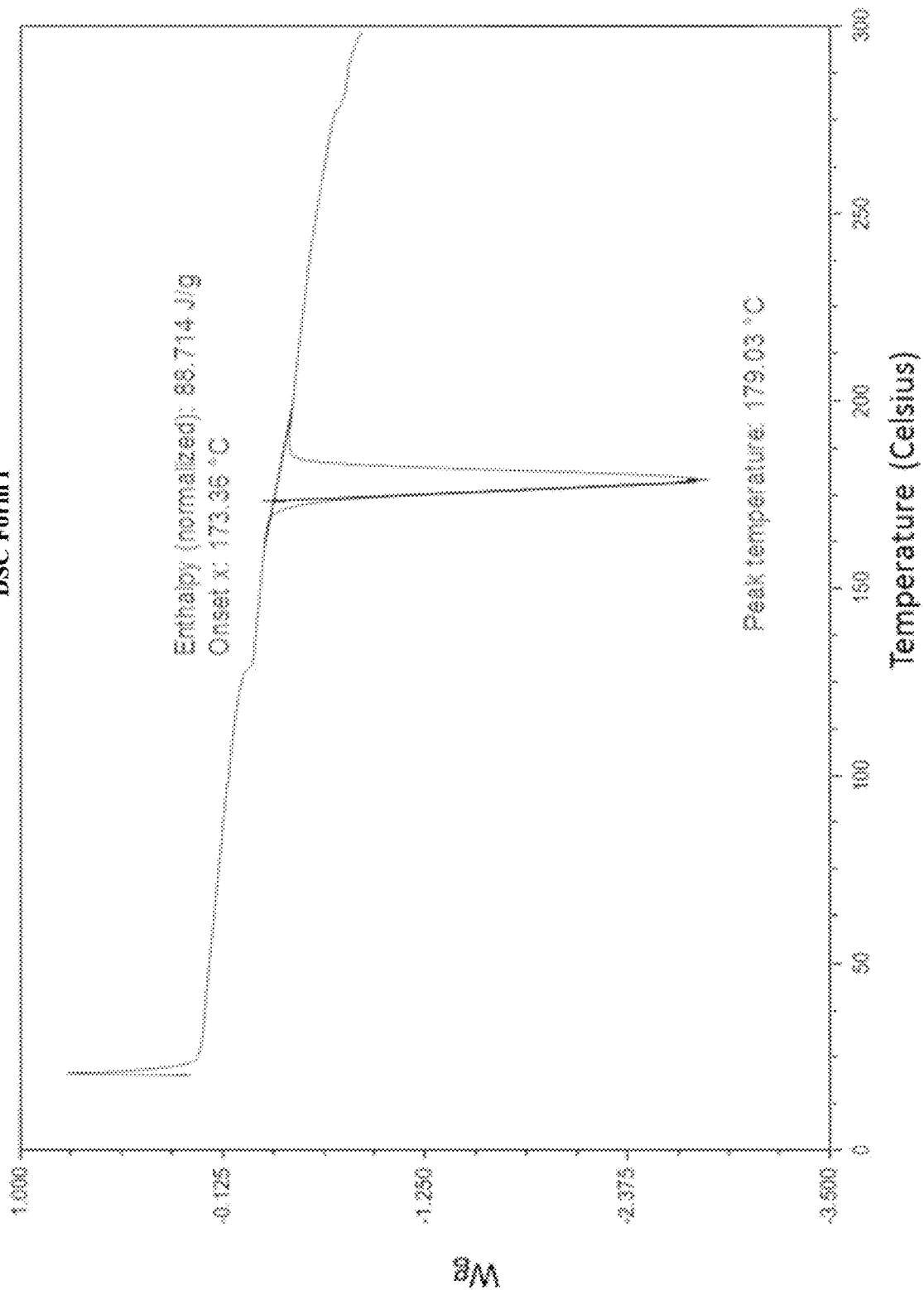
FIG. 11 shows the results of a DSC experiment for crystalline Form I of Example P4.
Figure 16A:
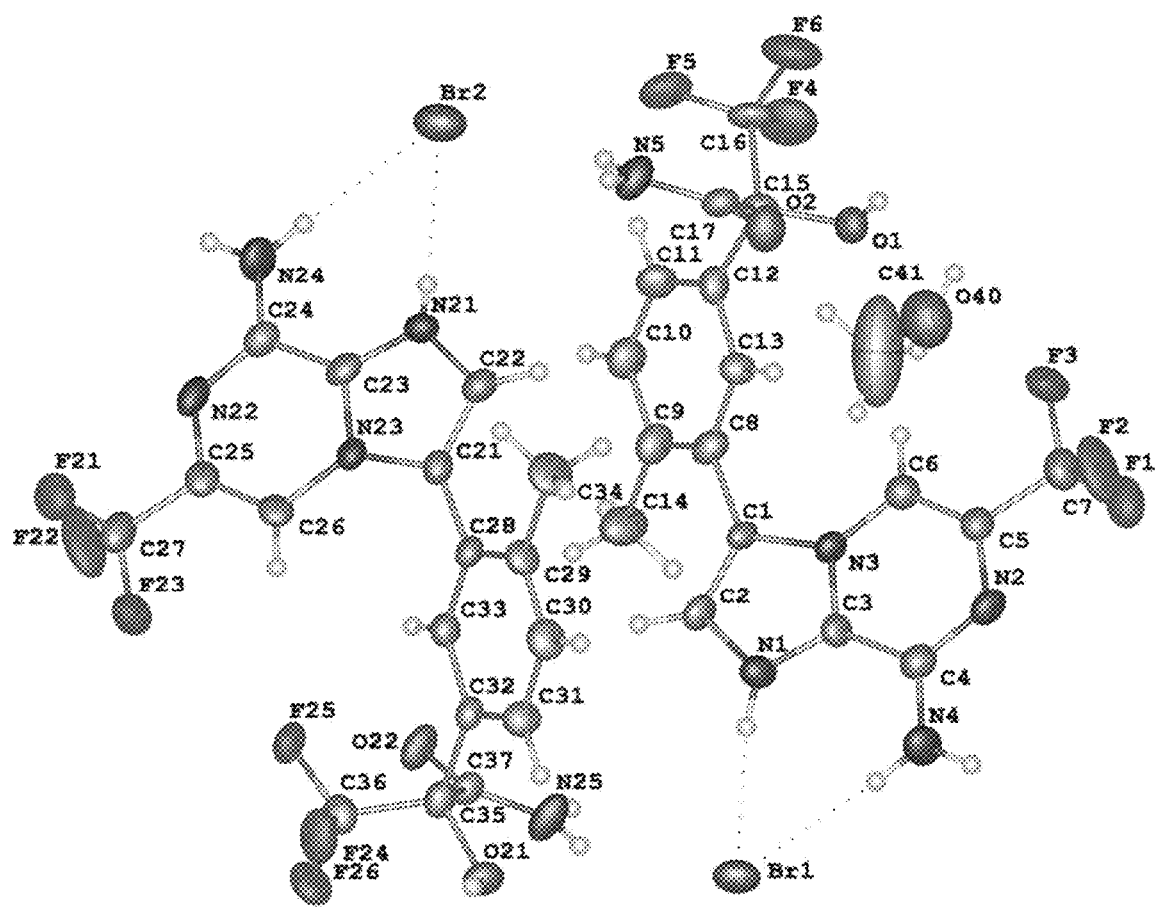
FIG. 16A shows the asymmetric crystalline unit of the hydrobromic acid salt, methanol solvent form of Example P7, with thermal ellipsoids drawn to the 30% probability level.
Figure 16B:
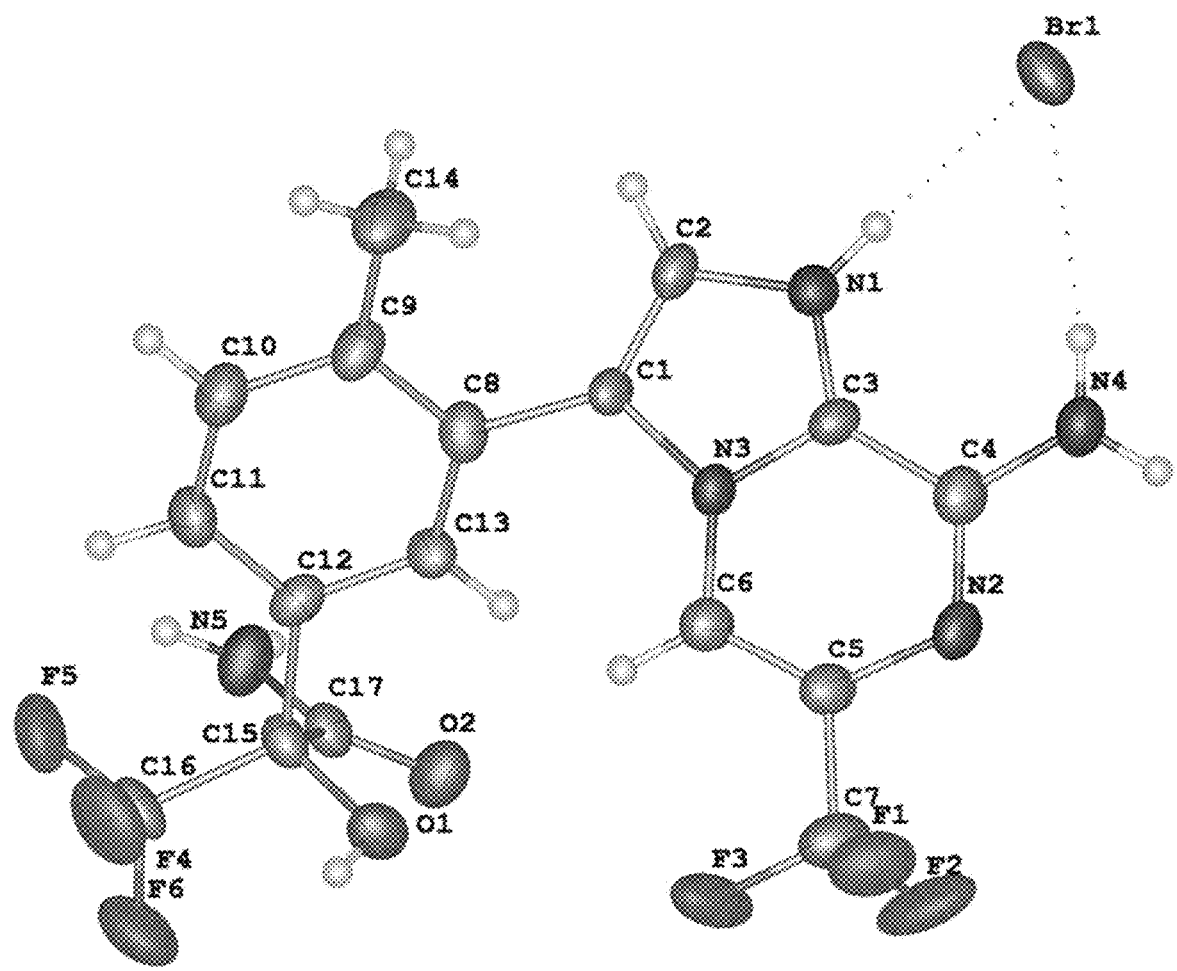
FIG. 16B shows a crystalline unit of the hydrobromic acid salt of Example P7, with thermal ellipsoids drawn to the 30% probability level.

DSC analysis of Form I revealed one peak with an onset temperature of 173.4° C. and a maximum at 179.0° C. The DSC thermogram is provided in FIG. 11. Form I was confirmed as an anhydrous, non-solvated crystalline form.

Example P5. Preparation and Characterization of 8-amino-N-(2-hydroxy-2-methylpropyl)-3-(2-methyl-5-(1,1,1-trifluoro-2-hydroxypropan-2-yl)phenyl)imidazo[1,2-a]pyrazine-6-carboxamide, Crystalline Form I (Free Base)

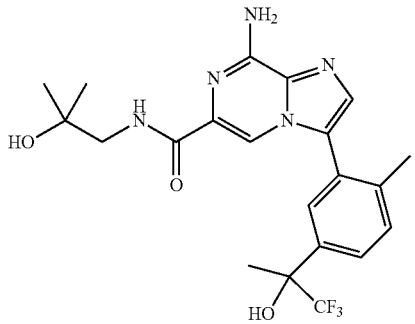 [SMILES: Cc1ccc(C(C)(O)C(F)(F)F)cc1-c1cnc2c(N)nc(C(=O)NCC(C)(C)O)cn12]

A round bottom flask was charged with 8-amino-N-(2-hydroxy-2-methylpropyl)-3-(2-methyl-5-(1,1,1-trifluoro-2-hydroxypropan-2-yl)phenyl)imidazo[1,2-a]pyrazine-6-carboxamide (Enantiomer 2 from Example 2, Step 8; 184 g, 408 mmol) and isopropyl acetate (950 mL). The mixture was stirred at 80° C. for 1 h, cooled to room temperature (RT), and stirred at RT overnight. The solids were collected to give 8-amino-N-(2-hydroxy-2-methylpropyl)-3-(2-methyl-5-(1,1,1-trifluoro-2-hydroxypropan-2-yl)phenyl)imidazo[1,2-a]pyrazine-6-carboxamide (Form I, 152 g, 82.8%).

Form I was confirmed as a crystalline solid according to XRPD analysis. The XRPD pattern of Form I is shown in FIG. 12 and the peak data is given in Table 12 below.

TABLE 12

XRPD Peak Data for Form I.

| 2-Theta (°) | Relative Intensity (%) |
|---|---|
| 6.2 | 31.8 |
| 9.6 | 0.6 |
| 10.4 | 8.8 |
| 11.4 | 12.4 |
| 11.6 | 6.7 |
| 12.0 | 15.6 |
| 12.4 | 4.2 |
| 12.6 | 3.9 |
| 13.9 | 6.0 |
| 14.4 | 10.6 |
| 15.1 | 0.5 |
| 15.6 | 100 |
| 16.0 | 26.8 |
| 16.7 | 49.1 |
| 16.9 | 12.6 |
| 17.4 | 2.9 |
| 18.3 | 9.0 |
| 18.9 | 5.4 |
| 19.3 | 4.3 |
| 19.9 | 19.4 |
| 20.2 | 2.6 |
| 20.7 | 68.4 |
| 21.0 | 4.0 |
| 21.3 | 21.9 |
| 21.9 | 5.2 |
| 22.3 | 10.4 |
| 22.9 | 0.6 |
| 23.2 | 29.4 |
| 23.8 | 0.5 |
| 24.1 | 8.9 |
| 24.4 | 1.3 |
| 24.8 | 1.5 |
| 25.0 | 1.1 |
| 25.5 | 8.2 |
| 26.0 | 2.3 |
| 27.1 | 16.8 |
| 27.3 | 2.2 |
| 28.0 | 7.9 |
| 29.1 | 3.0 |
| 29.7 | 0.4 |

DSC analysis of Form I revealed one peak with an onset temperature of 172.2° C. and a maximum at 174.2° C. The DSC thermogram is provided in FIG. 13. Form I was confirmed as an anhydrous, non-solvated crystalline form.

Example P6. Preparation and Characterization of 8-amino-N-(2-hydroxy-2-methylpropyl)-3-(2-methyl-5-(1,1,1-trifluoro-2-hydroxypropan-2-yl)phenyl)imidazo[1,2-a]pyrazine-6-carboxamide, Crystalline Form II (Free Base)

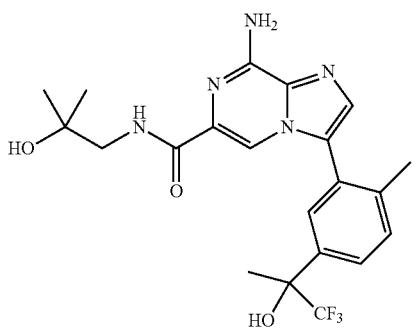 [SMILES: Cc1ccc(C(C)(O)C(F)(F)F)cc1-c1cnc2c(N)nc(C(=O)NCC(C)(C)O)cn12]

A vial was charged with 8-amino-N-(2-hydroxy-2-methylpropyl)-3-(2-methyl-5-(1,1,1-trifluoro-2-hydroxypropan-2-yl)phenyl)imidazo[1,2-a]pyrazine-6-carboxamide (Enantiomer 2 from Example 2, Step 8; 252 mg, 0.559 mmol) and isopropyl acetate (1.25 mL) and the solids slowly dissolved. The mixture was treated with heptane (0.35 mL) until the solids persisted. The mixture was heated at 80° C. for 30 min and stirred at RT overnight. The solids were collected to give 8-amino-N-(2-hydroxy-2-methylpropyl)-3-(2-methyl-5-(1,1,1-trifluoro-2-hydroxypropan-2-yl)phenyl)imidazo[1,2-a]pyrazine-6-carboxamide (Form II, 116 mg, 46.0%).

Form II was confirmed as a crystalline solid according to XRPD analysis. The XRPD pattern of Form II is shown in FIG. 14 and the peak data is given in Table 13 below.

TABLE 13

| XRPD Peak Data for Form II. | |
|---|---|
| 2-Theta (°) | Relative Intensity (%) |
| 4.3 | 59.1 |
| 6.2 | 0.5 |
| 7.4 | 100 |
| 8.6 | 7.6 |
| 11.3 | 2.1 |
| 13.3 | 34.1 |
| 14.7 | 10.5 |
| 14.9 | 4.1 |
| 15.3 | 58.1 |
| 15.5 | 47.3 |
| 17.0 | 78.5 |
| 17.2 | 41.1 |
| 18.1 | 34.9 |
| 18.8 | 63.6 |
| 19.6 | 15.1 |
| 19.8 | 10.0 |
| 20.1 | 79.7 |
| 20.8 | 0.6 |
| 21.4 | 32.3 |
| 22.4 | 1.5 |
| 22.7 | 6.9 |
| 23.5 | 36.0 |
| 24.1 | 6.8 |
| 25.1 | 6.3 |
| 25.8 | 28.3 |
| 26.2 | 18.0 |
| 26.5 | 13.9 |
| 26.9 | 1.0 |
| 27.3 | 19.5 |

TABLE 13-continued

| XRPD Peak Data for Form II. | |
|---|---|
| 2-Theta (°) | Relative Intensity (%) |
| 27.9 | 14.6 |
| 28.4 | 3.1 |
| 28.6 | 4.0 |
| 29.0 | 3.9 |
| 29.3 | 3.8 |
| 29.6 | 2.4 |

DSC analysis of Form II revealed one peak with an onset temperature of 161.7° C. and a maximum at 165.4° C. The DSC thermogram is provided in FIG. 15. Form II was confirmed as an anhydrous, non-solvated crystalline form.

Example P7. Preparation and Single Crystal Characterization of 2-(3-(8-Amino-6-(trifluoromethyl)imidazo[1,2-a]pyrazin-3-yl)-4-methylphenyl)-3,3,3-trifluoro-2-hydroxypropanamide hydrobromic acid (HBr) salt 2-(3-(8-amino-6-(trifluoromethyl)imidazo[1,2-a]pyrazin-3-yl)-4-methylphenyl)-3,3,3-trifluoro-2-hydroxypropanamide free base (98.81 mg) was dissolved in 2.5 mL of methanol in a 4 mL clear glass vial. To the solution, 42.4 µL of 6M aqueous HBr solution (1.2 eq.) was added and mixed well. The solution was evaporated at room temperature to obtain HBr salt crystal.

Crystal Data:

C35 H32 Br$_2$ F12 N10 O5, from methanol, colorless, irregular plate, ~0.450×0.210×0.060 mm, monoclinic, C2, a=20.055(7) Å, b=10.115(4) Å, c=21.363(8) Å, beta=94.953(7), Vol=4318(3) Å$^3$, Z=4, T=−40° C., Formula weight=1060.52, Density=1.631 g/cm$^3$, µ(Mo)=1.98 mm$^{−1}$.

Data Collection:

Data collection was performed using a Bruker SMART APEX-II CCD system, MoKalpha radiation, standard focus tube, anode power=50 kV×30 mA, crystal to plate distance=5.0 cm, 512×512 pixels/frame, beam center=(259.19, 253.13), total frames=2635, oscillation/frame=0.50°, exposure/frame=40.1 sec/frame, SAINT integration, hkl min/max=(−26,26,−12,13,−27,27), data input to shelx=38968, unique data=9756, two-theta range=4.51 to 55.43°, completeness to two-theta 55.43=99.60%, R(int-xl)=0.0672, SADABS correction applied.

Solution And Refinement:

The crystal structure was solved using XS(Shelxtl) and refined using shelxtl software package. Refinement was by full-matrix least squares on F$^2$, scattering factors from Int. Tab. Vol C Tables 4.2.6.8 and 6.1.1.4, number of data=9756, number of restraints=1, number of parameters=584, data/parameter ratio=16.71, goodness-of-fit on F2=1.14, R indices [I>4sigma(I)] R1=0.0648, wR2=0.1560, R indices (all data) R1=0.1004, wR2=0.1719, max difference peak and hole=1.795 and −0.642 e/Å$^3$, refined flack parameter=0.038(6). All of the hydrogen atoms were idealized using a riding model.

Results:

This analysis confirmed the structure of 2-(3-(8-amino-6-(trifluoromethyl)imidazo[1,2-a]pyrazin-3-yl)-4-methylphenyl)-3,3,3-trifluoro-2-hydroxypropanamide hydrobromic acid salt. The asymmetric unit contains two molecules of 2-(3-(8-amino-6-(trifluoromethyl)imidazo[1,2-a]pyrazin-3-yl)-4-methylphenyl)-3,3,3-trifluoro-2-hydroxypropanamide, two bromides to balance the charge, and one methanol solvent molecule, as shown in FIGS. 16A-16B. The enantiomeric setting was based on the Flack parameter that refined to 0.038(6). This study determined the absolute configuration at the chiral centers C15=S— and C35=S—.

Example 89. 2-(3-(8-Amino-6-(trifluoromethyl) imidazo[1,2-a]pyrazin-3-yl)-4-methylphenyl)-3,3-difluoro-2-hydroxypropanamide

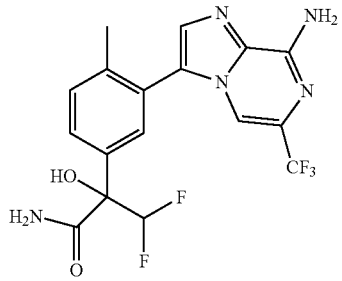 [SMILES: Cc1ccc(C(O)(C(N)=O)C(F)F)cc1-c1cnc2c(N)nc(C(F)(F)F)cn12]

Step 1.
1-(3-Bromo-4-methylphenyl)-2,2-difluoroethan-1-ol

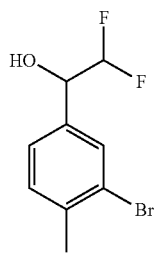

To solution of (difluoromethyl)trimethylsilane (5.1 g, 42 mmol) in dry DMF (20 ml) at 0° C. was added 3-bromo-4-methylbenzaldehyde (4.1 g, 21 mmol) followed by cesium fluoride (0.44 g, 2.9 mmol). The ice bath was removed, and the resulting reaction mixture was stirred for 2 h. The mixture was cooled back to 0° C., water (2.0 ml) and 1.0 M tetra-n-butylammonium fluoride in tetrahydrofuran (4.2 ml, 4.2 mmol) were added. The ice bath was removed and the mixture was stirred for 30 min at rt. The yellow reaction mixture was diluted with water (100 ml), and was extracted with $Et_2O$ (150 ml). The organic layer was washed with saturated $NH_4Cl$ solution (25 ml), dried over anhydrous sodium sulfate, filtered and concentrated to give a rust colored oil. Purification on silica gel using ethyl acetate/hexane, 0-60% gave the desired compound as a yellow oil, 3.6 g, 69%. LCMS calculated for $C_9H_8BrF_2$ $(M-OH)^+$: m/z=233.0, 235.0; Found: 232.9, 235.1

Step 2.
1-(3-Bromo-4-methylphenyl)-2,2-difluoroethan-1-one

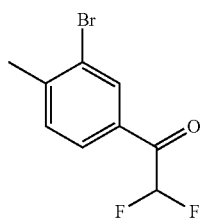

A mixture of 1-(3-bromo-4-methylphenyl)-2,2-difluoroethan-1-ol (3.6 g, 14 mmol) in dichloromethane (57 ml) at 0° C. was treated with Dess-Martin periodinane (9.1 g, 22 mmol). The ice bath was removed and the reaction mixture was stirred at rt for 1.0 h. The reaction mixture was concentrated to an oil. $Et_2O$ was added and solid precipitated. The suspended mixture was filtered. The filtrate was washed with saturated $NaHCO_3$ solution and saturated NaCl solution, dried over anhydrous $Na_2SO_4$, and filtered. The solution was concentrated to yellow oil, 2.3 g, 64%. LCMS for $C_9H_8BrF_2O(M+H)^+$ calculated for $(M+H)^+$: m/z=249.0, 251.0; Found: 248.9, 251.0

Step 3. 2-(3-Bromo-4-methylphenyl)-3,3-difluoro-2-hydroxypropanenitrile

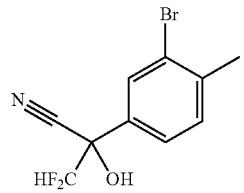

To a solution of 1-(3-bromo-4-methylphenyl)-2,2-difluoroethan-1-one (2.3 g, 9.0 mmol) in dichloromethane (9.0 ml) under $N_2$ was added trimethylsilyl cyanide (2.7 ml, 20 mmol), potassium cyanide (88 mg, 1.4 mmol), and 18-crown-6 (88 mg, 0.33 mmol). The reaction mixture was stirred for 1 h. The reaction mixture was concentrated under nitrogen. The solid was dissolved in THF (9.0 ml) and cooled to 0° C. Aqueous HCl (1.8 M, 0.37 ml), was added with stirring at 0° C. The ice bath was removed, and the reaction mixture was stirred for 1.5 h. Water (75 ml) was added to the reaction mixture. The reaction mixture was extracted with $Et_2O$ (3×75 ml). The combined $Et_2O$ extracts were washed with saturated NaCl solution, dried over anhydrous $Na_2SO_4$, filtered, and concentrated to give orange solid, 2.5 g, 100%.

Step 4. 2-(3-Bromo-4-methylphenyl)-3,3-difluoro-2-hydroxypropanamide

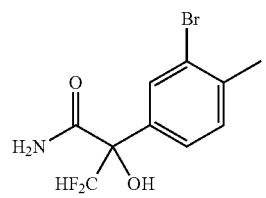

To a solution of 2-(3-bromo-4-methylphenyl)-3,3-difluoro-2-hydroxypropanenitrile (21.5 g, 78 mmol) in dioxane (156 ml) under $N_2$ at 0° C. was added HCl (concentrated) (24 ml, 284 mmol) (precooled in a ice bath). While cooling at 0° C., the reaction mixture was vigorously bubbled with HCl gas for 10 min. The reaction vessel was capped tightly. The cooling bath was removed and the mixture stirred for 16 h. The reaction mixture was cooled at 0° C. and diluted with saturated $NH_4Cl$ solution (20 ml), water (10 ml), and of EtOAc (250 ml). The EtOAc layer was separated and washed with water, dried over anhydrous $Na_2SO_4$, filtered, and concentrated to brown oil. The oil was dissolved in CH$_2$Cl$_2$ and purified on a silica gel column, EtOAc/hexane, 0-60%. The product fractions were concentrated to yellow oil, 17 g. The racemic mixture was separated via preparative chiral HPLC (Phenomenex Lux Amylose-1 [21.2×250 mm, 5 micron], eluting with 85% ethanol in hexanes, at flow rate of 20 mL/min, loading about 100 mg in 2 mL ethanol) to give the desired second eluting enantiomer (8.0 g, 35%) as a viscous oil. The first enantiomer that eluted had a retention time of 4.2 min. The second enantiomer that eluted had a retention time of 6.4 min. Second eluting enantiomer: LCMS calculated for C$_{10}$H$_{11}$BrF$_2$NO$_2$ (M+H)$^+$: m/z=294.0, 296.0; Found: 294.0, 296.0.

Step 5. 3,3-Difluoro-2-hydroxy-2-(4-methyl-3-(4,4,5,5-tetramethyl-1,3,2-dioxaborolan-2-yl)phenyl)propanamide

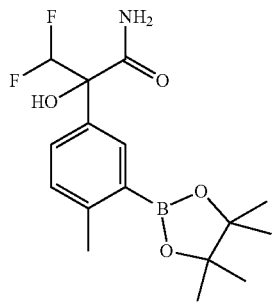 [SMILES: Cc1ccc(C(O)(C(N)=O)C(F)F)cc1B1OC(C)(C)C(C)(C)O1]

A mixture of 2-(3-bromo-4-methylphenyl)-3,3-difluoro-2-hydroxypropanamide (1.1 g, 3.7 mmol), (step 4, second eluting isomer), 4,4,4',4',5,5,5',5'-octamethyl-2,2'-bi(1,3,2-dioxaborolane) (1.2 g, 4.5 mmol), potassium acetate (1.2 g, 12.3 mmol), and dichlorobis(triphenylphosphine)palladium (II) (105 mg, 0.15 mmol) in THF (12 ml) was degassed for 5 min with N$_2$. The mixture was heated in a microwave at 135° C. for 20 minutes. The reaction mixture was diluted with EtOAc and filtered through Celite®, rinsing with EtOAc. The filtrate was concentrated. Purification via silica gel chromatography (0-100% EtOAc/hexanes) afforded the desired product as clear oil. The yield for the product is: 78%, 1.0 g. LCMS calculated for C$_{16}$H$_{23}$BF$_2$NO$_4$ (M+H)$^+$: m/z=342.2; Found 342.2.

Step 6. 2-(3-(8-Amino-6-(trifluoromethyl)imidazo[1,2-a]pyrazin-3-yl)-4-methylphenyl)-3,3-difluoro-2-hydroxypropanamide A vial was charged with 3-bromo-6-(trifluoromethyl)imidazo[1,2-a]pyrazin-8-amine (700.0 mg, 2.5 mmol), and 3,3-difluoro-2-hydroxy-2-(4-methyl-3-(4,4,5,5-tetramethyl-1,3,2-dioxaborolan-2-yl)phenyl)propanamide (1.1 g, 3.2 mmol) in THF (12.5 ml). To the mixture was added aqueous potassium carbonate (5.0 ml, 5.0 mmol) and the mixture was bubbled with N$_2$ for 5 Min. To the mixture was added [1,1'-bis(diphenylphosphino)ferrocene]dichloropalladium (II) complex with dichloromethane (407 mg, 0.50 mmol) and bubbled N$_2$ for 5 min. The reaction was heated to 80° C. for 15 h. The reaction mixture was cooled to rt and the aqueous layer was separated. The organic layer was evaporated and the residue was dried under vac for 2 hours. The crude material was dissolved in DCM and loaded to a silica gel column (1% load). Purification on silica gel column using 0-100% EtOAc in hexane. The yield for the product is 620 mg, 60%, LCMS calculated for C$_{17}$H$_{15}$F$_5$N$_5$O$_2$ (M+H)$^+$: m/z=416.1; Found 416.2. $^1$H NMR (600 MHz, DMSO-d$_6$) δ 7.77 (s, 1H), 7.67 (m, 4H), 7.61 (s, 1H), 7.51 (m, 2H), 7.47 (m, 1H), 6.92 (s, 1H), 6.76 (m, 1H), 2.21 (s, 3H).

Example 112. 2-(3-(4-Amino-2-methylimidazo[2,1-f][1,2,4]triazin-7-yl)-4-methylphenyl)-1,1,3,3-tetrafluoropropan-2-ol trifluoroacetate salt (1.3 TFA:1 Molecule Example 112)

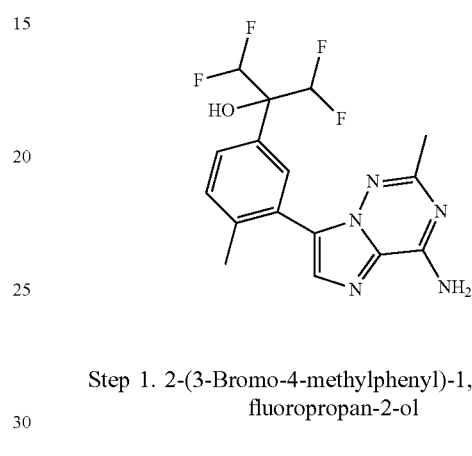

Step 1. 2-(3-Bromo-4-methylphenyl)-1,1,3,3-tetrafluoropropan-2-ol

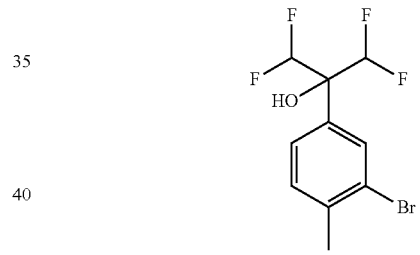

A mixture of 3-bromo-4-methylbenzoic acid (0.50 g, 2.3 mmol), N,N-dimethylformamide (9.0 µL, 0.12 mmol), and oxalyl chloride (1.6 mL, 3.3 mmol, 2.0 M in CH$_2$Cl$_2$) in CH$_2$Cl$_2$ (0.70 ml) was stirred at room temperature (rt) for 1 h. The reaction mixture was concentrated under inert atmosphere. The resulting yellow solid was dissolved in anhydrous MeCN (2.3 mL). Trimethyl(bromodifluoromethyl)silane (1.1 mL, 7.0 mmol) (Combi-Blocks, QC-0668), triphenylphosphine (1.5 g, 5.8 mmol), and 1,3-dimethyl-3,4,5,6-tetrahydro-2(1H)-pyrimidinone (1.1 mL, 9.3 mmol) were added successively. The reaction flask was equipped with a reflux condensor, and the reaction mixture was stirred at rt for 2.5 d. The reaction was quenched via the addition of aqueous pyridine (2.3 mL, 9.3 mmol, 4.0 M). The reaction mixture was then heated at 80° C. for 1.5 h. After cooling to rt, the reaction mixture was diluted with water (10 mL) and extracted with tert-butyl methyl ether (3×10 mL). The combined organic layers were dried over Na$_2$SO$_4$, filtered, and concentrated. Purification via silica gel chromatography (10-50% tert-butyl methyl ether/hexanes) afforded the title compound as a yellow oil (0.57 g, 77%). $^1$H NMR (600 MHz, CDCl$_3$) δ 7.76 (d, J=1.9 Hz, 1H), 7.39 (dd, J=8.0, 1.9 Hz, 1H), 7.30 (d, J=8.0 Hz, 1H), 6.24-5.87 (m, 2H), 3.00 (s, 1H), 2.42 (s, 3H). ¹⁹F NMR (565 MHz, CDCl₃) δ −130.50--131.46 (m), −131.74--132.68 (m).

Step 2. 1,1,3,3-Tetrafluoro-2-(4-methyl-3-(4,4,5,5-tetramethyl-1,3,2-dioxaborolan-2-yl)phenyl)propan-2-ol

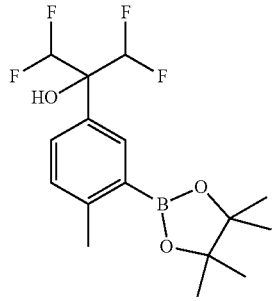 [SMILES: Cc1ccc(C(O)(C(F)F)C(F)F)cc1B1OC(C)(C)C(C)(C)O1]

A mixture of 2-(3-bromo-4-methylphenyl)-1,1,3,3-tetrafluoropropan-2-ol (78 mg, 0.26 mmol), bis(pinacolato)diboron (79 mg, 0.31 mmol), potassium acetate (84 mg, 0.86 mmol), and bis(triphenylphosphine)palladium(II) dichloride (7 mg, 10 μmol) in tetrahydrofuran (1.0 mL) was degassed for 5 min with N₂. The mixture was heated in a microwave at 135° C. for 20 min. The reaction mixture was filtered through Celite®, rinsing with EtOAc. The filtrate was washed with water and then brine, dried over Na₂SO₄, filtered, and concentrated to afford the title compound, which was used without further purification. LCMS for $C_{16}H_{22}BF_4O_3$ (M+H)⁺: calculated m/z=349.2; found 349.1.

Step 3. 2-(3-(4-Amino-2-methylimidazo[2,1-f][1,2,4]triazin-7-yl)-4-methylphenyl)-1,1,3,3-tetrafluoropropan-2-ol trifluoroacetate salt (1.3 TFA:1 Molecule Example 112)

A mixture of 7-bromo-2-methylimidazo[2,1-f][1,2,4]triazin-4-amine 2,2,2-trifluoroacetate (17 mg, 0.053 mmol) (from Example 2, Step 5), [1,1'-bis(diphenylphosphino)ferrocene]dichloropalladium(II), complex with dichloromethane (8.7 mg, 11 μmol), 1,1,3,3-tetrafluoro-2-(4-methyl-3-(4,4,5,5-tetramethyl-1,3,2-dioxaborolan-2-yl)phenyl)propan-2-ol (30 mg, 0.085 mmol) in tetrahydrofuran (1.0 mL), and 1.0 M K₂CO₃ (110 μL, 0.11 mmol) was degassed with N₂ for 5 min and then heated to 80° C. for 16 h. The reaction mixture was filtered through a plug of Na₂SO₄ and Celite®, rinsing with MeOH. Purification via preparative HPLC on a C-18 column (pH=2, 21-41% MeCN/0.1% TFA (aq) over 5 min, 60 mL/min) afforded the title compound as a white solid (14 mg, 54%). ¹H NMR (500 MHz, DMSO-d₆) δ 8.35 (s, 1H), 8.23 (s, 1H), 7.64 (s, 1H), 7.63 (d, J=2.0 Hz, 1H), 7.59 (dd, J=8.0, 2.0 Hz, 1H), 7.43 (d, J=8.1 Hz, 1H), 6.43 (apparent t, J=53.9 Hz, 2H), 2.28 (s, 3H), 2.21 (s, 3H). ¹⁹F NMR (470 MHz, DMSO-d₆) δ −74.78 (s), −129.06--131.20 (m), −131.72--133.01 (m). LCMS for $C_{16}H_{16}F_4N_5O$ (M+H)⁺: calculated m/z=370.1; found 370.1.

Example 117. ((1S)-(8-Amino-3-(2-methyl-5-(1,1,1-trifluoro-2-hydroxypropan-2-yl)phenyl)imidazo[1,2-a]pyrazine-6-carboxamido)(cyclobutyl)methyl)boronic acid

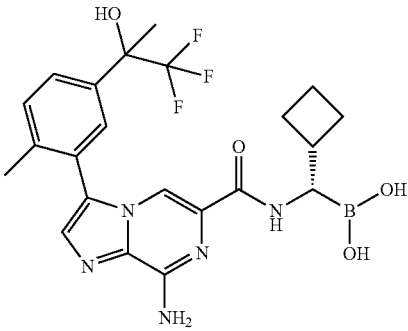 [SMILES: Cc1ccc(C(C)(O)C(F)(F)F)cc1-c1cnc2c(N)nc(C(=O)N[C@@H](B(O)O)C3CCC3)cn12]

Step 1. (S,E)-N-(Cyclobutylmethylene)-2-methylpropane-2-sulfinamide

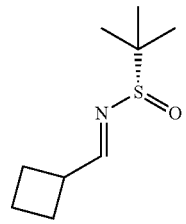

A mixture of (S)-2-methylpropane-2-sulfinamide (0.50 g, 4.1 mmol) (Aldrich, 513210), cyclobutanecarbaldehyde (0.37 ml, 4.1 mmol), and titanium(IV) ethoxide (1.7 ml, 8.3 mmol) was heated at 70° C. in a microwave for 10 min. The reaction mixture was diluted with EtOAc (20 mL) and poured into brine (1 mL) while stirring rapidly. After stirring for 10 min, the resulting slurry was filtered through Celite®, and the filter cake was washed with EtOAc. The combined filtrate was concentrated. Purification via silica gel chromatography (15-45% tert-butyl methyl ether/hexanes) afforded the title compound as a clear liquid (0.64 g, 83%). ¹H NMR (400 MHz, CDCl₃) δ 8.11 (d, J=4.8 Hz, 1H), 3.46-3.25 (m, 1H), 2.35-2.12 (m, 4H), 2.12-1.99 (m, 1H), 1.99-1.85 (m, 1H), 1.20 (s, 9H). LCMS for $C_9H_{18}NOS$ (M+H)⁺: calculated m/z=188.1; found 188.1.

Step 2. (S)—N—((S)-Cyclobutyl(4,4,5,5-tetramethyl-1,3,2-dioxaborolan-2-yl)methyl)-2-methylpropane-2-sulfinamide

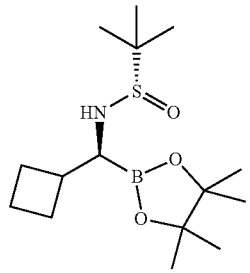 [SMILES: CC(C)(C)[S@](=O)N[C@@H](B1OC(C)(C)C(C)(C)O1)C1CCC1]

A mixture of tricyclohexylphosphine tetrafluoroborate (1.2 mg, 3.2 μmol), toluene (53 μL), aqueous copper(II) sulfate (110 μL, 3.2 μmol, 30 mM), and benzylamine (1.5 μL, 0.013 mmol) was stirred rapidly at rt for 10 min. A solution of (S,E)-N-(cyclobutylmethylene)-2-methylpropane-2-sulfinamide (50 mg, 0.27 mmol) in toluene (480 μL) was added. The reaction mixture was cooled to 0° C., and bis(pinacolato)diboron (140 mg, 0.53 mmol) was added. The reaction mixture was stirred rapidly overnight during which it warmed to rt. The reaction mixture was diluted with EtOAc and filtered through a plug of deactivated silica gel (100:35 SiO₂/H₂O). The filtrate was concentrated to afford the crude product (>95:5 dr), which was carried on without further purification. While not wishing to be bound by theory, the carbinamine stereochemistry was assigned by analogy to a previous literature report (see e.g., Buesking, A. W.; Bacauanu, V.; Cai, I.; Ellman, J. A. *J. Org. Chem.* 2014, 79, 3671). LCMS for $C_{15}H_{31}BNO_3S$ (M+H)⁺: calculated m/z=316.2; found 316.1.

Step 3. (S)-Cyclobutyl(4,4,5,5-tetramethyl-1,3,2-dioxaborolan-2-yl)methanamine hydrochloride

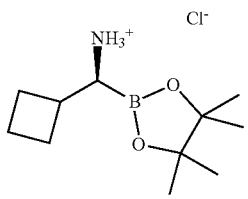

To a solution of (S)—N—((S)-cyclobutyl(4,4,5,5-tetramethyl-1,3,2-dioxaborolan-2-yl)methyl)-2-methylpropane-2-sulfinamide (84 mg, 0.27 mmol) in 1,4-dioxane (1.3 mL) and MeOH (0.10 mL) at 0° C. was added dropwise HCl (70 μL, 0.3 mmol, 4.0 N in HCl in 1,4-dioxane). After stirring 10 min at 0° C., the reaction mixture was warmed to rt. After stirring 1 h, the reaction mixture was concentrated to about a third the original volume, 2:1 hexanes/diethyl ether was added, and the precipitate was collected via filtration. The white solid that had been collected was then triturated with 2:1 hexanes/diethyl ether (2×) to afford the title compound as a white solid (55 mg, 83%). ¹H NMR (400 MHz, DMSO-d₆) δ 7.80 (br s, 3H), 2.74-2.59 (m, 1H), 2.59-2.43 (m, 1H), 2.05-1.67 (m, 6H), 1.25 (s, 6H), 1.23 (s, 6H).

Step 4. Methyl 8-amino-3-(2-methyl-5-(1,1,1-trifluoro-2-hydroxypropan-2-yl)phenyl)imidazo[1,2-a] pyrazine-6-carboxylate (Single Isomer)

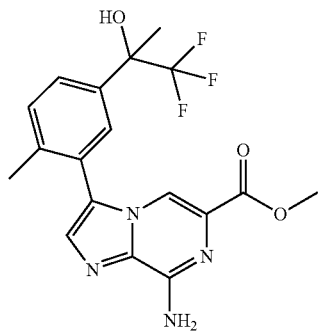

The title compound was synthesized according to an experimental procedure analogous to Example 8, Step 5, substituting the second eluting enantiomer of 2-(3-(8-amino-6-bromoimidazo[1,2-a]pyrazin-3-yl)-4-methylphenyl)-1,1,1-trifluoropropan-2-ol (from Example 64, Step 1) for 2-(3-(8-amino-6-bromoimidazo[1,2-a]pyrazin-3-yl)-4-methylphenyl)-1,1,1-trifluoropropan-2-ol. LCMS for $C_{18}H_{18}F_3N_4O_3$ (M+H)⁺: calculated m/z=395.1; found 395.1.

Step 5. 8-Amino-3-(2-methyl-5-(1,1,1-trifluoro-2-hydroxypropan-2-yl)phenyl)imidazo[1,2-a]pyrazine-6-carboxylic acid (Single Isomer)

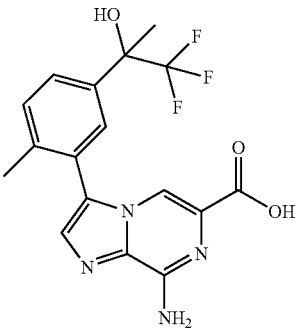 [SMILES: Cc1ccc(C(C)(O)C(F)(F)F)cc1-c1cnc2c(N)nc(C(=O)O)cn12]

The title compound was synthesized according to an experimental procedure analogous to Example 81, Step 8, substituting methyl 8-amino-3-(2-methyl-5-(1,1,1-trifluoro-2-hydroxypropan-2-yl)phenyl)imidazo[1,2-a]pyrazine-6-carboxylate (single isomer from Step 4) for methyl 8-amino-3-(2-(methyl-d₃)-5-(1,1,1-trifluoro-2-hydroxypropan-2-yl)phenyl)imidazo[1,2-a]pyrazine-6-carboxylate. LCMS for $C_{17}H_{16}F_3N_4O_3$ (M+H)⁺: calculated m/z=381.1; found 381.1.

Step 6. ((1S)-(8-Amino-3-(2-methyl-5-(1,1,1-trifluoro-2-hydroxypropan-2-yl)phenyl)imidazo[1,2-a] pyrazine-6-carboxamido)(cyclobutyl)methyl)boronic acid A 1-dram vial was charged with 8-amino-3-(2-methyl-5-(1,1,1-trifluoro-2-hydroxypropan-2-yl)phenyl)imidazo[1,2-a]pyrazine-6-carboxylic acid (15 mg, 0.039 mmol) (single isomer from Step 5), O-(7-azabenzotriazol-1-yl)-N,N,N',N'-tetramethyluronium hexafluorophosphate (15 mg, 0.039 mmol), and (S)-cyclobutyl(4,4,5,5-tetramethyl-1,3,2-dioxaborolan-2-yl)methanamine hydrochloride (12 mg, 0.047 mmol) (from Step 3). N,N-Dimethylformamide (0.40 mL) and N,N-diisopropylethylamine (20 μL, 0.12 mmol) were added consecutively. The reaction mixture was stirred at rt overnight. The reaction mixture was diluted with MeCN/H₂O and filtered. Purification via preparative HPLC on a C-18 column (pH=6.5, 44-59% MeCN/98 mM NH₄OAc (aq) over 5 min, 60 mL/min) afforded fractions containing the desired boronate ester intermediate. These fractions were combined and concentrated to remove MeCN, and the resulting aqueous mixture was extracted with EtOAc (3×). The combined organic layers were dried over Na₂SO₄, filtered, and concentrated to afford a residue (12 mg). To a mixture of this residue and (2-methylpropyl)boronic acid (16 mg, 0.16 mmol) in 1:1 pentane/methanol (420 μL) was added 1.0 N HCl (42 μl, 0.042 mmol). The reaction mixture was stirred vigorously for 23 h at rt. The reaction mixture was concentrated and then diluted with MeOH/water. Purification via preparative HPLC on a C-18 column (pH=6.5, 28-47% MeCN/98 mM NH$_4$OAc (aq) over 5 min, 60 mL/min) afforded the title compound as a white solid (3.2 mg, 16%). $^1$H NMR (400 MHz, 5:1 DMSO-d$_6$/D$_2$O) δ 7.68 (s, 1H), 7.66 (s, 1H), 7.61 (d, J=8.5 Hz, 1H), 7.53 (s, 1H), 7.48 (d, J=8.1 Hz, 1H), 3.23 (d, J=7.9 Hz, 1H), 2.12 (s, 3H), 1.94-1.55 (m, 9H). $^{19}$F NMR (376 MHz, 5:1 DMSO-d$_6$/D$_2$O) δ −79.76. LCMS for C$_{22}$H$_{26}$BF$_3$N$_5$O$_4$ (M+H)$^+$: calculated m/z=492.2; found 492.2.

Example 118. 2-(3-(8-Amino-6-(trifluoromethyl)imidazo[1,2-a]pyrazin-3-yl)-4-methylphenyl)-3,3,3-trifluoro-2-hydroxy-N-methylpropanamide

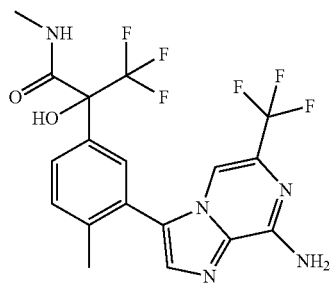 [SMILES: CNC(=O)C(O)(c1ccc(C)c(-c2cnc3c(N)nc(C(F)(F)F)cn23)c1)C(F)(F)F]

Step 1. 2-(3-Chloro-4-methylphenyl)-3,3,3-trifluoropropane-1,2-diol (Single Isomer)

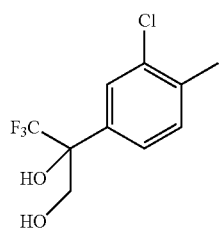

To a suspension of AD-mix-α (54 g, 120 mmol) in water (100 mL) at 0° C. was added a solution of 2-chloro-1-methyl-4-(3,3,3-trifluoroprop-1-en-2-yl)benzene (8.6 g, 39 mmol) (from Example 66, Step 2) in t-BuOH (100 mL). The mixture was then stirred at 6° C. for 46 hours. The reaction was cooled in an ice bath to 0° C., and sodium sulfite (18 g) was added. The reaction mixture was warmed to room temperature and stirred for 30 minutes. tert-Butanol was removed in vacuo and the aqueous mixture was extracted twice with EtOAc. The combined organic extracts were dried over Na$_2$SO$_4$, filtered, and the solvent was removed in vacuo. Purification via flash chromatography, eluting with a gradient of 0-40% EtOAc in hexanes afforded the scalemic product as a colorless oil (8.7 g, 88%). Subsequent purification via chiral preparatory HPLC on a Phenomenx Lux Amylose-1 column (5% EtOH/hexanes, 20 mL/min) afforded the title compound, which was further enriched (>98:2 er) in the first eluting enantiomer (t$_R$=19.3 min). Due to use of AD-mix-α, it is believed that the title compound was predominantly the (S)-enantiomer (for stereochemical rationale, vida supra). $^1$H NMR (400 MHz, CDCl$_3$) δ 7.59 (s, 1H), 7.36 (d, J=8.0 Hz, 1H), 7.30 (d, J=8.0 Hz, 1H), 4.31 (dd, J=11.9, 6.1 Hz, 1H), 3.91-3.84 (m, 1H), 3.70 (s, 1H), 2.41 (s, 3H), 1.88-1.79 (dd, J=7.1, 6.3 Hz, 1H). $^{19}$F NMR (376 MHz, CDCl$_3$) δ −77.25 (s).

Step 2. 2-(3-Chloro-4-methylphenyl)-3,3,3-trifluoro-2-hydroxypropanoic acid

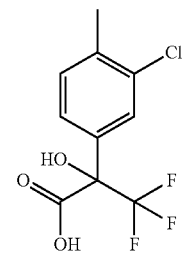 [SMILES: Cc1ccc(C(O)(C(=O)O)C(F)(F)F)cc1Cl]

To a mixture of 2-(3-chloro-4-methylphenyl)-3,3,3-trifluoropropane-1,2-diol (single isomer) (0.40 g, 1.6 mmol) (from Step 1), sodium bicarbonate (0.14 g, 1.6 mmol), and 5% platinum on carbon (0.31 g, 0.079 mmol) in water (11.2 mL) was added one drop of antifoam A concentrate (Aldrich A5633). The mixture was then heated at 75° C. for 2.5 d while air was bubbled through the reaction mixture. After cooling to rt, the reaction mixture was diluted with water and filtered through Celite®. The Celite® was rinsed with water (3×), and the combined filtrate was acidified to pH 2 via slow addition of 1 N H$_2$SO$_4$. The aqueous mixture was extracted with EtOAc (3×). The combined organic layers were dried over MgSO$_4$, filtered, and concentrated to afford the title compound as an off-white solid (0.36 g, 79%). $^1$H NMR (500 MHz, DMSO-d$_6$) δ 7.63 (d, J=1.9 Hz, 1H), 7.49 (dd, J=8.1, 1.9 Hz, 1H), 7.42 (d, J=8.1 Hz, 1H), 2.34 (s, 3H). $^{19}$F NMR (471 MHz, DMSO-d$_6$) δ −75.31. LCMS for C$_{10}$H$_7$ClF$_3$O$_3$ (M−H)$^-$: calculated m/z=267.0; found 267.0.

Step 3. 2-(3-Chloro-4-methylphenyl)-3,3,3-trifluoro-2-hydroxy-N-methylpropanamide

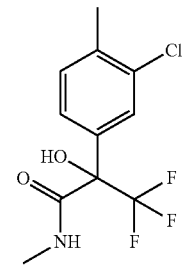

To a suspension of 2-(3-chloro-4-methylphenyl)-3,3,3-trifluoro-2-hydroxypropanoic acid (0.11 g, 0.398 mmol) (from Step 4) in DCM (3.6 mL) at 0° C. was added oxalyl chloride (0.070 mL, 0.80 mmol) and one drop of DMF. The reaction mixture was stirred 2 h during which it slowly warmed to rt. Methylamine (1.0 mL, 12 mmol, 40 wt % in water) was added dropwise, and the biphasic reaction mixture was stirred for 3 h at rt. The reaction mixture was diluted with water (10 mL), and extracted with EtOAc (3×). The combined organic layers were washed with brine (20 mL), dried over MgSO$_4$, and concentrated. Purification via silica gel chromatography (1-20% MTBE/DCM) afforded the title compound as a light yellow solid (94 mg, 84%). $^1$H NMR (400 MHz, CDCl$_3$) δ 7.62 (s, 1H), 7.43 (d, J=7.7 Hz, 1H), 7.27 (d, J=8.0 Hz, 1H), 6.12 (br s, 1H), 4.85 (s, 1H), 2.90 (d, J=4.9 Hz, 3H), 2.38 (s, 3H). $^{19}$F NMR (376 MHz, CDCl$_3$) δ −74.48. LCMS for C$_{11}$H$_{12}$ClF$_3$NO$_2$ (M+H)$^+$: calculated m/z=282.0; found 282.0.

Step 4. 3,3,3-Trifluoro-2-hydroxy-N-methyl-2-(4-methyl-3-(4,4,5,5-tetramethyl-1,3,2-dioxaborolan-2-yl)phenyl)propanamide

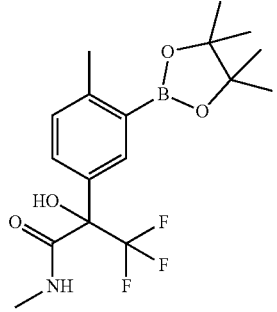 [SMILES: CNC(=O)C(O)(c1ccc(C)c(B2OC(C)(C)C(C)(C)O2)c1)C(F)(F)F]

A mixture of 2-(3-chloro-4-methylphenyl)-3,3,3-trifluoro-2-hydroxy-N-methylpropanamide (42 mg, 0.15 mmol) (from Step 5), bis(pinacolato)diboron (110 mg, 0.45 mmol), potassium acetate (88 mg, 0.90 mmol), tris(dibenzylideneacetone)dipalladium(0) (11 mg, 0.012 mmol), and 2-dicyclohexylphosphino-2',4',6'-triisopropylbiphenyl (23 mg, 0.048 mmol) (Aldrich 638064) in 1,4-dioxane (1.2 mL) was degassed with N$_2$ for 3 min and then heated at 120° C. for 1 h. The reaction mixture was diluted with EtOAc and filtered through Celite®. The filtrate was concentrated. Purification via silica gel chromatography (1-100% MTBE/hexanes) afforded a red-brown residue (39 mg). This material was carried forward without further purification. LCMS for C$_{17}$H$_{24}$BF$_3$NO$_4$ (M+H)$^+$: calculated m/z=374.2; found 374.1.

Step 5. 2-(3-(8-Amino-6-(trifluoromethyl)imidazo[1,2-a]pyrazin-3-yl)-4-methylphenyl)-3,3,3-trifluoro-2-hydroxy-N-methylpropanamide A 1-dram vial was charged with 3-bromo-6-(trifluoromethyl)imidazo[1,2-a]pyrazin-8-amine (14 mg, 0.050 mmol), 3,3,3-trifluoro-2-hydroxy-N-methyl-2-(4-methyl-3-(4,4,5,5-tetramethyl-1,3,2-dioxaborolan-2-yl)phenyl)propanamide (19 mg, 0.050 mmol) (from Step 6), and dichloro[1,1'-bis(diphenylphosphino)ferrocene]palladium(II) dichloromethane adduct (8.14 mg, 9.96 μmol). Tetrahydrofuran (0.80 mL) and aqueous K$_2$CO$_3$ (0.10 mL, 0.10 mmol, 1.0 M) were then added. The reaction mixture was degassed for 4 min with N$_2$ and then heated at 80° C. for 3 h. The reaction mixture was diluted with MeOH/water and filtered. Purification via preparative HPLC on a C-18 column (pH=2, 37-49% MeCN/0.1% TFA (aq) over 5 min, 60 mL/min) and then repurification via preparative HPLC on a C-18 column (pH=10, 28-41% MeCN/0.1% NH$_4$OH (aq) over 5 min, 60 mL/min) afforded the title compound as an off-white solid (3.3 mg, 15%). Due to use of AD-mix-α in Step 1, it is believed that the title compound was enriched (>98:2 er) in the (S)-enantiomer (for stereochemical rationale, vida supra), (S)-2-(3-(8-amino-6-(trifluoromethyl)imidazo[1,2-a]pyrazin-3-yl)-4-methylphenyl)-3,3,3-trifluoro-2-hydroxy-N-methylpropanamide. LCMS for C$_{18}$H$_{16}$F$_6$N$_5$O$_2$ (M+H)$^+$: calculated m/z=448.1; found 448.1.

Example 120. 2-(3-(8-amino-6-(trifluoromethyl)imidazo[1,2-a]pyrazin-3-yl)-4-methylphenyl)-3,3,3-trifluoro-2-hydroxypropanoic acid (Ammonium Salt)

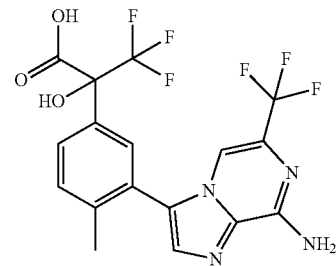 [SMILES: Cc1ccc(C(O)(C(=O)O)C(F)(F)F)cc1-c1cnc2c(N)nc(C(F)(F)F)cn12]

A suspension of 2-(3-(8-amino-6-(trifluoromethyl)imidazo[1,2-a]pyrazin-3-yl)-4-methylphenyl)-3,3,3-trifluoro-2-hydroxypropanamide (0.25 g, 0.58 mmol) (single enantiomer, from Example 82, Step 6) in 12 N HCl (2.1 ml) was stirred at 80° C. for 30 min. Water (1 mL) was added, and the reaction mixture was stirred at 80° C. for 1.5 h. 1,4-Dioxane (1.0 mL) and additional 12 N HCl (1.0 ml) were added, and the reaction mixture was stirred for 20 h at 80° C. The reaction mixture was then concentrated. The resulting solids were partitioned between water (20 mL) and 3:1 CHCl$_3$/iPrOH (20 mL). The organic layer was removed, and the aqueous layer was extracted with 3:1 CHCl$_3$/iPrOH (2×20 mL). The combined organic layers were dried over Na$_2$SO$_4$, filtered, and concentrated. The resulting residue was dissolved in CH$_2$Cl$_2$ and concentrated to afford 2-(3-(8-amino-6-(trifluoromethyl)imidazo[1,2-a]pyrazin-3-yl)-4-methylphenyl)-3,3,3-trifluoro-2-hydroxypropanoic acid as a red-brown solid (0.27 g, 83% yield, 77% purity). A portion of this material (8.4 mg) was purified via preparative HPLC on a C-18 column (pH=10, 16-30% MeCN/0.1% NH$_4$OH (aq) over 5 min, 60 mL/min) to afford the title compound as a white solid (3.5 mg, 40%). LCMS for C$_{17}$H$_{13}$F$_6$N$_4$O$_3$ (M+H)$^+$: calculated m/z=435.1; found 435.0.

Example 128. 2-(3-(8-Amino-6-(trifluoromethyl)imidazo[1,2-a]pyrazin-3-yl)-4-methylphenyl)-3,3,3-trifluoro-2-hydroxy-N-(3-methylazetidin-3-yl)propanamide trifluoroacetate salt

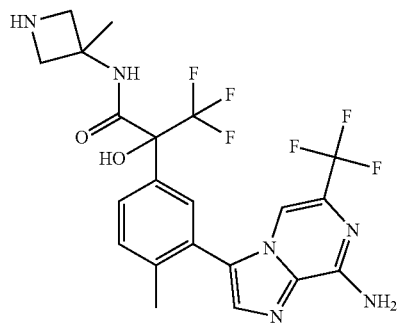 [SMILES: Cc1ccc(C(O)(C(=O)NC2(C)CNC2)C(F)(F)F)cc1-c1cnc2c(N)nc(C(F)(F)F)cn12]

To a suspension of 2-(3-(8-amino-6-(trifluoromethyl)imidazo[1,2-a]pyrazin-3-yl)-4-methylphenyl)-3,3,3-trifluoro-2-hydroxypropanoic acid (20 mg, 0.046 mmol) (from Example 120) in CH$_2$Cl$_2$ (0.72 mL) at 0° C. was added oxalyl chloride (46 μL, 0.092 mmol, 2.0 M in CH$_2$Cl$_2$) and one drop of N,N-dimethylformamide. The reaction mixture was stirred 2 h during which the 0° C. bath slowly warmed to rt. A solution of 3-amino-1-Boc-3-methyl-azetidine (130 mg, 0.69 mmol) (Advanced ChemBlocks, C-2457) in CH$_2$Cl$_2$ (0.25 mL) was added dropwise. The bath was removed, and the reaction mixture was stirred for 2 h at rt. The reaction mixture was concentrated, and the resulting residue dissolved in TFA (0.36 mL). After stirring 1 h at rt, the reaction mixture was added dropwise to MeOH. Purification via preparative HPLC on a C-18 column (pH=2, 30-42% MeCN/0.1% TFA (aq) over 5 min, 60 mL/min) afforded the title compound as a yellow residue (2.4 mg, 8.5%). LCMS for C$_{21}$H$_{21}$F$_6$N$_6$O$_2$ (M+H)$^+$: calculated m/z=503.2; found 503.1.

Example 129. 2-(3-(8-Amino-6-(trifluoromethyl)imidazo[1,2-a]pyrazin-3-yl)-4-methylphenyl)-N-(bicyclo[1.1.1]pentan-1-yl)-3,3,3-trifluoro-2-hydroxypropanamide trifluoroacetate salt

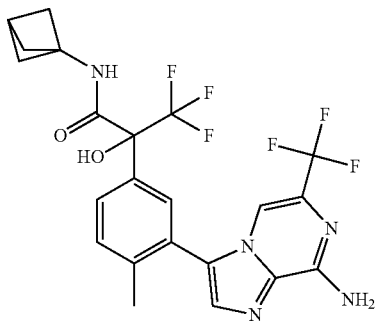 [SMILES: Cc1ccc(C(O)(C(=O)NC23CC(C2)C3)C(F)(F)F)cc1-c1cnc2c(N)nc(C(F)(F)F)cn12]

Step 1. N-(Bicyclo[1.1.1]pentan-1-yl)-2-(3-bromo-4-methylphenyl)-3,3,3-trifluoro-2-hydroxypropanamide

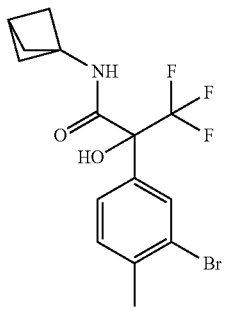 [SMILES: Cc1ccc(C(O)(C(=O)NC23CC(C2)C3)C(F)(F)F)cc1Br]

A microwave vial was charged with ethyl 2-(3-bromo-4-methylphenyl)-3,3,3-trifluoro-2-hydroxypropanoate (53 mg, 0.16 mmol) (single enantiomer from Example 82, Step 3) and bicyclo[1.1.1]pentan-1-amine hydrochloride (93 mg, 0.78 mmol). The vial was placed under nitrogen, and then tetrahydrofuran (1.3 mL) and triethylamine (0.22 mL, 1.6 mmol) were added. The vial was placed in 0° C. bath, and trimethylaluminum (0.39 mL, 0.78 mmol, 2 M in toluene) was added dropwise. The reaction mixture was warmed to rt. The vial was sealed, and the reaction mixture was heated at 80° C. After heating for 15 min, the reaction mixture was cooled slightly and vented to relieve pressure. The reaction mixture was then heated for 2.5 h at 80° C. Heating was discontinued, and the reaction mixture sat at rt for 2 d. The reaction mixture was added slowly into 1 N HCl (5.5 mL) that was cooled to 0° C., resulting in gas evolution. The aqueous mixture was warmed to rt and extracted with ethyl acetate (3×4 mL). The combined organics were washed with sat. NaHCO$_3$ (8 mL) and brine (8 mL). The organic layer was then dried over MgSO$_4$, filtered, and concentrated. Purification via silica gel chromatography (1-4% MeOH/CH$_2$Cl$_2$) afforded the title compound as a white solid (50 mg, 84%). LCMS for C$_{15}$H$_{16}$BrF$_3$NO$_2$ (M+H)$^+$: calculated m/z=378.0, 380.0; found 378.0, 380.0.

Step 2. N-(Bicyclo[1.1.1]pentan-1-yl)-3,3,3-trifluoro-2-hydroxy-2-(4-methyl-3-(4,4,5,5-tetramethyl-1,3,2-dioxaborolan-2-yl)phenyl)propanamide

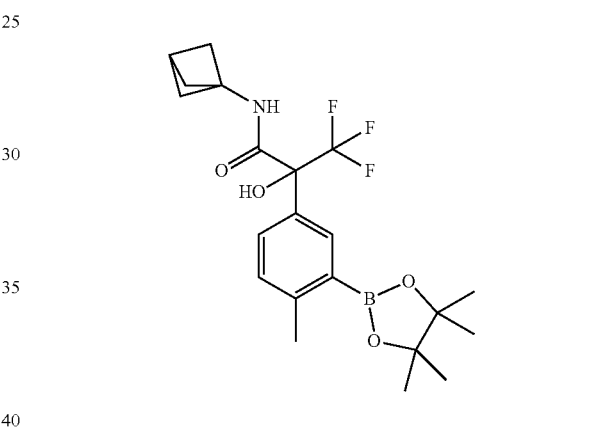

A mixture of N-(bicyclo[1.1.1]pentan-1-yl)-2-(3-bromo-4-methylphenyl)-3,3,3-trifluoro-2-hydroxypropanamide (49 mg, 0.13 mmol), bis(pinacolato)diboron (40 mg, 0.16 mmol), potassium acetate (45 mg, 0.45 mmol), and dichlorobis(triphenylphosphine)palladium(II) (4 mg, 5 μmol) in tetrahydrofuran (0.50 mL) was degassed for 3 min with N$_2$. The mixture was heated in a microwave at 135° C. for 20 min. The reaction mixture was filtered through Celite®, rinsing with EtOAc. The filtrate was washed with water and brine, dried over Na$_2$SO$_4$, filtered, and concentrated to afford the title compound as an orange, waxy solid. This material was used without further purification. LCMS for C$_{21}$H$_{28}$BF$_3$NO$_4$ (M+H)$^+$: calculated m/z=426.2; found 426.2.

Step 3. 2-(3-(8-Amino-6-(trifluoromethyl)imidazo[1,2-a]pyrazin-3-yl)-4-methylphenyl)-N-(bicyclo[1.1.1]pentan-1-yl)-3,3,3-trifluoro-2-hydroxypropanamide trifluoroacetate salt A mixture of 3-bromo-6-(trifluoromethyl)imidazo[1,2-a]pyrazin-8-amine (14 mg, 0.050 mmol), N-(bicyclo[1.1.1]pentan-1-yl)-3,3,3-trifluoro-2-hydroxy-2-(4-methyl-3-(4,4,5,5-tetramethyl-1,3,2-dioxaborolan-2-yl)phenyl)propanamide (28 mg, 0.065 mmol), dichloro[1,1'-bis(diphenylphosphino)ferrocene]palladium(II) dichloromethane adduct (8 mg, 10 μmol), tetrahydrofuran (0.80 mL), and K₂CO₃ (0.10 mL, 0.10 mmol, 1.0 M in water) was degassed for 5 min with N₂ and then heated at 80° C. for 15 h. The reaction mixture was diluted with MeOH/water and filtered. Purification via preparative HPLC on a C-18 column (pH=2, 42-54% MeCN/0.1% TFA (aq) over 5 min, 60 mL/min) afforded the title compound as an orange-brown solid (3.8 mg, 12%). LCMS for $C_{22}H_{20}F_6N_5O_2$ (M+H)⁺: calculated m/z=500.1; found 500.1.

Example 136. 2-(3-(8-Amino-6-(6-(1-hydroxyethyl) pyridin-3-yl)imidazo[1,2-a]pyrazin-3-yl)-4-methylphenyl)-1,1-difluoropropan-2-ol (Single Isomer)

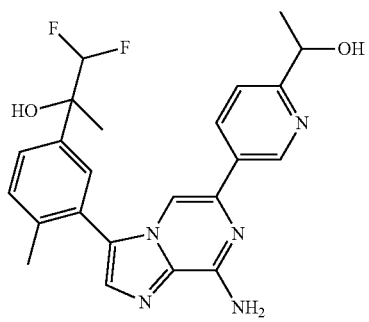 [SMILES: Cc1ccc(C(C)(O)C(F)F)cc1-c1cnc2c(N)nc(-c3ccc(C(C)O)nc3)cn12]

Step 1. 1-(5-Bromopyridin-2-yl)ethan-1-ol (Single Isomer)

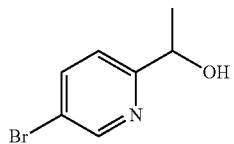

In a 200 mL round bottom flask, 1-(5-bromopyridin-2-yl)ethan-1-one (20 g, 0.10 mol) and RuCl(p-cymene)[(S,S)-Ts-DPEN] (0.64 g, 1.0 mmol) (Aldrich, 703915) were dissolved in CH₂Cl₂ (0.10 L). A premixed solution of formic acid (17 mL, 0.43 mol) in triethylamine (35 mL, 0.25 mol) was added to the reaction mixture. After stirring at rt overnight, the resulting mixture was diluted with CH₂Cl₂ and poured into aq. sat. Na₂HCO₃ (400 mL). The organic layer was separated, and the aqueous layer extracted with CH₂Cl₂. The combined organic layers were dried over MgSO₄, filtered, and concentrated. Purification via silica gel chromatography afforded the product as a yellow oil (20 g, 97% yield, 80% ee). Further purification via chiral preparatory HPLC on a Phenomenx Lux Amylose-1 column (3% EtOH/hexanes, 20 mL/min) afforded the title compound as a single isomer, the first eluting enantiomer ($t_R$=3 min). ¹H NMR (400 MHz, CDCl₃) δ 8.60 (d, J=2.2 Hz, 1H), 7.81 (dd, J=8.4, 2.3 Hz, 1H), 7.22 (d, J=8.4 Hz, 1H), 5.04-4.61 (m, 1H), 3.73 (d, J=5.0 Hz, 1H), 1.49 (d, J=6.6 Hz, 3H).

Step 2. (6-(1-Hydroxyethyl)pyridin-3-yl)boronic acid (Single Isomer)

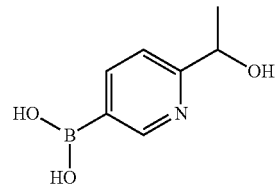

A mixture of 1-(5-bromopyridin-2-yl)ethan-1-ol (0.50 g, 2.5 mmol), bis(pinacolato)diboron (0.75 g, 2.97 mmol), potassium acetate (0.73 g, 7.4 mmol), and dichloro[1,1'-bis (diphenylphosphino)ferrocene]palladium(II) dichloromethane adduct (0.081 g, 0.099 mmol) in tetrahydrofuran (6.5 mL) was degassed briefly with N₂. The mixture was then heated at 140° C. in a microwave for 30 min. The reaction mixture was diluted with tetrahydrofuran and filtered through Celite®, rinsing with tetrahydrofuran. The filtrate was concentrated via rotary evaporation and then placed under high vacuum for 1 h to afford the title compound as a brown oil, which was used directly in the next step without further purification. LCMS for C₇H₁₁BNO₃ (M+H)⁺: calculated m/z=168.1; found 168.1.

Step 3. 2-(3-(8-Amino-6-(6-(1-hydroxyethyl)pyridin-3-yl)imidazo[1,2-a]pyrazin-3-yl)-4-methylphenyl)-1,1-difluoropropan-2-ol (Single Isomer)

A 3-neck, 50-mL round-bottom flask was charged with 2-(3-(8-amino-6-bromoimidazo[1,2-a]pyrazin-3-yl)-4-methylphenyl)-1,1-difluoropropan-2-ol (0.54 g, 1.2 mmol) (from Example 29, Step 3) and [1,1'-bis(di-cyclohexylphosphino)ferrocene]dichloropalladium(II) (0.092 g, 0.12 mmol). A solution of (6-(1-hydroxyethyl)pyridin-3-yl)boronic acid (from Step 2) in tetrahydrofuran (9.4 mL) and then 1.0 M K₂CO₃ (3.1 ml, 3.1 mmol) were added. The reaction mixture was degassed by bubbling N₂ through the mixture for 5 min and then heated at reflux overnight. After cooling to rt, the reaction mixture was diluted with EtOAc (15 mL) and washed with water (15 mL) and brine (15 mL). The organic layer was dried over Na₂SO₄, filtered, and concentrated via rotary evaporation. The resulting brown oil was then placed under high vacuum for 1 h to afford the crude product as a brown foamy solid (1.1 g). Purification via silica gel chromatography (3-25% EtOH/CH₂Cl₂) and subsequent purification via preparative HPLC on a C-18 column (pH=10, 26-31% MeCN/0.15% NH₄OH (aq) over 5 min, 60 mL/min) afforded fractions containing the desired product, which were combined and concentrated. The resulting aqueous mixture was extracted with EtOAc (2×300 mL). The combined extracts were dried with Na₂SO₄, filtered, and concentrated to afford the title compound as a white solid (0.26 g, 49%). ¹H NMR (500 MHz, DMSO-d₆) δ 8.94 (d, J=2.2 Hz, 1H), 8.20 (dd, J=8.2, 2.3 Hz, 1H), 7.74 (s, 1H), 7.66 (s, 1H), 7.59 (d, J=1.9 Hz, 1H), 7.56 (dd, J=8.0, 2.0 Hz, 1H), 7.53 (d, J=8.3 Hz, 1H), 7.45 (d, J=8.1 Hz, 1H), 7.23 (br s, 2H), 6.00 (t, J=56 Hz, 1H), 5.99 (s, 1H), 5.36 (d, J=4.5 Hz, 1H), 4.75 (m, 1H), 2.24 (s, 3H), 1.56 (s, 3H), 1.37 (d, J=6.5 Hz, 3H). ¹⁹F NMR (376 MHz, DMSO-d₆) -128.9 (dd, J=270, 56 Hz), -129.6 (dd, J=270, 56 Hz). LCMS for C₂₃H₂₄F₂N₅O₂ (M+H)⁺: calculated m/z=440.2; found 440.4.

Example 162. 2-(3-(8-Amino-6-(cyclopropylethynyl)imidazo[1,2-a]pyrazin-3-yl)-4-methylphenyl)-1,1,1-trifluoropropan-2-ol trifluoroacetate salt

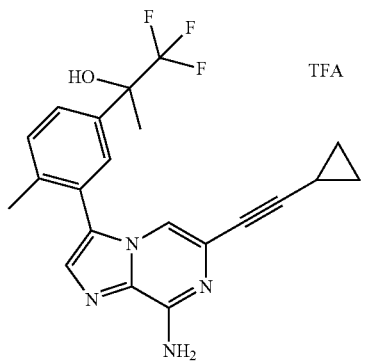 [SMILES: Cc1ccc(C(C)(O)C(F)(F)F)cc1-c1cnc2c(N)nc(C#CC3CC3)cn12]

A mixture of ethynylcyclopropane (0.031 mL, 0.36 mmol), 2-(3-(8-amino-6-bromoimidazo[1,2-a]pyrazin-3-yl)-4-methylphenyl)-1,1,1-trifluoropropan-2-ol (15 mg, 0.036 mmol), Pd(Ph$_3$P)$_4$ (6 mg, 5 μmol), copper(I) iodide (2 mg, 10 μmol), and triethylamine (0.050 mL, 0.36 mmol) in DMF (0.5 mL) was heated at 80° C. in a sealed vial overnight. The crude reaction mixture was filtered through a pad of Celite® and the inorganics were thoroughly washed with MeOH. The filtrate was concentrated in-vacuo and purified via preparative HPLC on a C-18 column (23-41% MeCN/0.1% TFA (aq) over 12 min, 60 mL/min) to afford the title compound. LCMS for C$_{21}$H$_{20}$F$_3$N$_4$O (M+H)$^+$: calculated m/z=401.2; found 401.2.

Example 169. 2-(8-amino-3-(2-methyl-5-(1,1,1-trifluoro-2-hydroxypropan-2-yl)phenyl)imidazo[1,2-a]pyrazin-6-yl)-N,N-dimethylacetamide trifluoroacetate salt

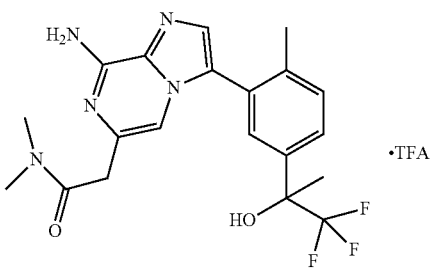 [SMILES: Cc1ccc(C(C)(O)C(F)(F)F)cc1-c1cnc2c(N)nc(CC(=O)N(C)C)cn12]

Step 1. (E)-2-(3-(8-amino-6-(2-ethoxyvinyl)imidazo[1,2-a]pyrazin-3-yl)-4-methylphenyl)-1,1,1-trifluoropropan-2-ol

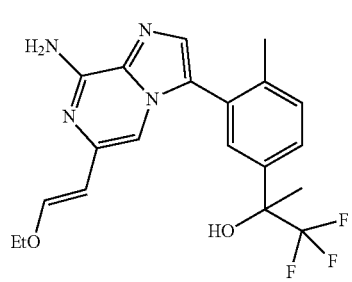 [SMILES: CCO/C=C/c1cn2c(-c3cc(C(C)(O)C(F)(F)F)ccc3C)cnc2c(N)n1]

A solution of 2-(3-(8-amino-6-bromoimidazo[1,2-a]pyrazin-3-yl)-4-methylphenyl)-1,1,1-trifluoropropan-2-ol (400 mg, 0.96 mmol, enatiomer 2) and (E)-2-(2-ethoxyvinyl)-4,4,5,5-tetramethyl-1,3,2-dioxaborolane (477 mg, 2.41 mmol) in THF (12 mL) was treated with 1 M aqueous potassium carbonate (2.5 mL) and dichloro[1,1'-bis(diphenylphosphino)ferrocene]palladium (II) dichloromethane adduct (157 mg, 0.19 mmol). The reaction mixture was degassed with nitrogen for 5 min, and stirred at 80° C. for 12 h. The resulting mixture was diluted with MeOH and passed through a Celite pad and concentrated. Purification via flash column chromatography using ethyl acetate in hexanes (0% to 100%) gave the desired product (250 mg, 0.61 mmol, 64%) as yellow oil. LCMS for C$_{20}$H$_{22}$F$_3$N$_4$O$_2$ (M+H)$^+$: m/z=407.2; Found: 407.2.

Step 2. 2-(8-amino-3-(2-methyl-5-(1,1,1-trifluoro-2-hydroxypropan-2-yl)phenyl)imidazo[1,2-a]pyrazin-6-yl)acetaldehyde

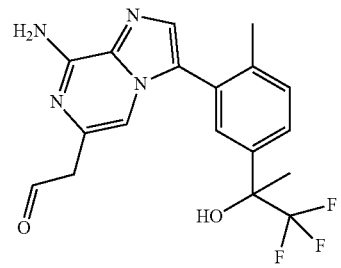 [SMILES: Cc1ccc(C(C)(O)C(F)(F)F)cc1-c1cnc2c(N)nc(CC=O)cn12]

A solution of (E)-2-(3-(8-amino-6-(2-ethoxyvinyl)imidazo[1,2-a]pyrazin-3-yl)-4-methylphenyl)-1,1,1-trifluoropropan-2-ol (50 mg, 0.12 mmol) in THF/H$_2$O (1 mL/0.5 mL) was treated with 0.5 mL conc. HCl at 0° C. The reaction mixture was stirred at room temperature for 12 h. The resulting mixture was diluted with EtOAc and quenched with sat. aq. NaHCO$_3$. The aqueous layer was extracted with EtOAc and the combined organic layers was dried (MgSO$_4$) and concentrated. Purification via flash column chromatography using ethyl acetate in hexanes (0% to 100%) gave the desired product (25 mg, 0.066 mmol, 55%) as yellow oil. LCMS for C$_{18}$H$_{18}$F$_3$N$_4$O$_2$ (M+H)$^+$: m/z=379.1; Found: 379.2.

Step 3. 2-(8-amino-3-(2-methyl-5-(1,1,1-trifluoro-2-hydroxypropan-2-yl)phenyl)imidazo[1,2-a]pyrazin-6-yl)acetic acid

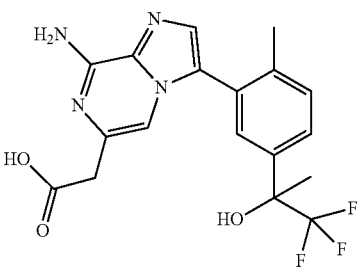 [SMILES: Cc1ccc(C(C)(O)C(F)(F)F)cc1-c1cnc2c(N)nc(CC(=O)O)cn12]

A solution of in 2-(8-amino-3-(2-methyl-5-(1,1,1-trifluoro-2-hydroxypropan-2-yl)phenyl)imidazo[1,2-a]pyrazin- 6-yl)acetaldehyde (40 mg, 0.11 mmol) in t-BuOH/H₂O/2-methyl-2-butene (1 mL/0.5 mL/0.25 mL) was treated with NaClO₂ (50 mg, 0.55 mmol) and NaH₂PO₄ (50 mg, 0.42 mmol) at 0° C. The reaction mixture was stirred at room temperature for 1 h. The resulting mixture was diluted with EtOAc/water. The aqueous layer was extracted with EtOAc and the combined organic layers was dried (MgSO₄) and concentrated. Purification via flash column chromatography using ethyl acetate in hexanes (50% to 100%) gave the desired product (25 mg, 0.063 mmol, 58%) as yellow oil. LCMS for $C_{18}H_{18}F_3N_4O_3$ (M+H)⁺: m/z=395.1; Found: 395.2.

Step 4. 2-(8-amino-3-(2-methyl-5-(1,1,1-trifluoro-2-hydroxypropan-2-yl)phenyl)imidazo[1,2-a]pyrazin-6-yl)-N,N-dimethylacetamide trifluoroacetate A solution of (2-(8-amino-3-(2-methyl-5-(1,1,1-trifluoro-2-hydroxypropan-2-yl)phenyl)imidazo[1,2-a]pyrazin-6-yl) acetic acid (20 mg, 0.051 mmol) and dimethyl amine (11 mg, 0.25 mmol) in DMF/Hünig's base (1 mL/0.1 mL) was treated with HATU (30 mg, 0.079 mmol). The resulting mixture was stirred for 30 mins before it was diluted with MeOH (3 mL). After filtered through a cartridge. The filtrate was purified via preparative LCMS (XBridge C18 Column, eluting with a gradient of acetonitrile in water with 0.1% trifluoroacetic acid, at flow rate of 60 mL/min) to give the desired product (15 mg, 0.036 mmol, 70%) as a white solid. ¹H NMR (500 MHz, DMSO-d₆) δ 7.89 (s, 1H), 7.62 (d, J=8.1 Hz, 1H), 7.56 (s, 1H), 7.49 (d, J=6.3 Hz, 1H), 7.16 (s, 1H), 6.68 (s, 1H), 3.80 (s, 2H), 2.89 (s, 6H), 2.21 (s, 3H), 1.73 (s, 3H). LCMS for $C_{20}H_{23}F_3N_5O_2$ (M+H)⁺: m/z=422.2; Found: 422.2.

Example 173

Example 173 was synthesized according to procedures analogous to Example 169 and the data are listed in Table 18.

TABLE 18

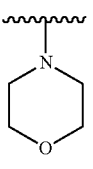

| Ex. No. | Name | NRᵃRᵇ | LCMS [M + H]⁺ |
|---|---|---|---|
| 173 | 2-(8-amino-3-(2-methyl-5-(1,1,1-trifluoro-2-hydroxypropan-2-yl)phenyl)imidazo[1,2-a]pyrazin-6-yl)-1-morpholinoethanone trifluoroacetate salt | morpholine | 464.2 |

Example 207-208. 2-(3-(8-amino-6-(3-(hydroxymethyl)cyclobutyl)imidazo[1,2-a]pyrazin-3-yl)-4-methylphenyl)-1,1,1-trifluoropropan-2-ol trifluoroacetate (Diastereomers 1-2)

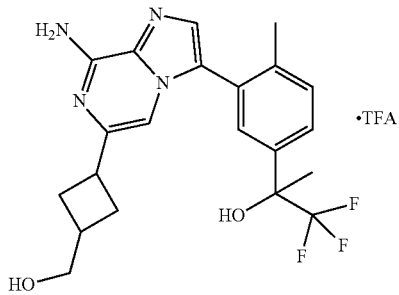 [SMILES: Cc1ccc(C(C)(O)C(F)(F)F)cc1-c1cnc2c(N)nc(C3CC(CO)C3)cn12]

A solution of ethyl 3-(8-amino-3-(2-methyl-5-(1,1,1-trifluoro-2-hydroxypropan-2-yl)phenyl)imidazo[1,2-a]pyrazin-6-yl)cyclobutane-1-carboxylate (17 mg, 0.036 mmol) in THF (1 mL) was treated with LiAlH₄ (10 mg, 0.26 mmol). The resulting mixture was stirred for 2 hours before it was diluted with MeOH (3 mL). After filtered through a cartridge. The filtrate was purified via preparative LCMS (XBridge C18 Column, eluting with a gradient of acetonitrile in water with 0.1% trifluoroacetic acid, at flow rate of 60 mL/min) to give the desired products eluted as two peaks. The first peak that eluted (Example 207, 3 mg, 0.0071 mmol, 20%) had a retention time of 4.1 min. The second peak that eluted (Example 208, 4 mg, 0.0094 mmol, 26%) had a retention time of 4.3 min.

Example 207 (Diastereomer 1): LCMS for $C_{21}H_{24}F_3N_4O_2$ (M+H)⁺: m/z=421.2; Found: 421.2.

Example 208 (Diastereomer 2): LCMS for $C_{21}H_{24}F_3N_4O_2$ (M+H)⁺: m/z=421.2; Found: 421.2.

Example 211. N-(2-(3-(8-amino-6-(trifluoromethyl)imidazo[1,2-a]pyrazin-3-yl)-4-methylphenyl)-3,3,3-trifluoro-2-hydroxypropyl)acetamide trifluoroacetate

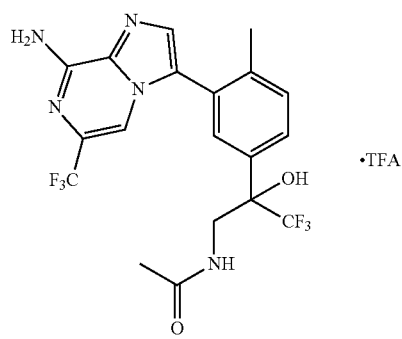 [SMILES: CC(=O)NCC(O)(c1ccc(C)c(-c2cnc3c(N)nc(C(F)(F)F)cn23)c1)C(F)(F)F]

Step 1. 3-amino-2-(3-(8-amino-6-(trifluoromethyl)imidazo[1,2-a]pyrazin-3-yl)-4-methylphenyl)-1,1,1-trifluoropropan-2-ol

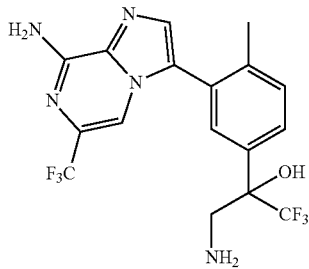 [SMILES: Cc1ccc(C(O)(CN)C(F)(F)F)cc1-c1cnc2c(N)nc(C(F)(F)F)cn12]

A solution of 3-bromo-6-(trifluoromethyl)imidazo[1,2-a]pyrazin-8-amine (1.06 g, 3.77 mmol) and 3-amino-1,1,1-trifluoro-2-(4-methyl-3-(4,4,5,5-tetramethyl-1,3,2-dioxaborolan-2-yl)phenyl)propan-2-ol (Intermediate 1, 1.00 g, 2.90 mmol, racemic) in dioxane (42.6 mL) was added 1.0 M aqueous potassium carbonate (8.69 mL, 8.69 mmol) and dichloro[1,1'-bis(diphenylphosphino)ferrocene]palladium (II) dichloromethane adduct (0.473 g, 0.579 mmol). The resulting mixture was degassed by sparging with $N_2$ for 10 mins. The resulting mixture was stirred at 100° C. for 36 h before it was diluted with MeOH and passed through a Celite pad and concentrated. Purification via flash column chromatography using ethyl acetate in hexanes (0% to 100%) gave the desired product (405 mg, 0.97 mmol, 33%) as yellow oil. LCMS for $C_{17}H_{16}F_6N_5O$ $(M+H)^+$: m/z=420.1; Found: 420.2.

Step 2. N-(2-(3-(8-amino-6-(trifluoromethyl)imidazo[1,2-a]pyrazin-3-yl)-4-methylphenyl)-3,3,3-trifluoro-2-hydroxypropyl)acetamide trifluoroacetate salt A solution of 3-amino-2-(3-(8-amino-6-(trifluoromethyl)imidazo[1,2-a]pyrazin-3-yl)-4-methylphenyl)-1,1,1-trifluoropropan-2-ol (5 mg, 0.012 mmol) and acetic acid (7.2 mg, 0.12 mmol) in DMF/Hünig's base (1 mL/0.1 mL) was treated with HATU (10 mg, 0.026 mmol). The resulting mixture was stirred for 30 mins before it was diluted with MeOH (3 mL). After filtered through a cartridge. The filtrate was purified via preparative LCMS (XBridge C18 Column, eluting with a gradient of acetonitrile in water with 0.1% trifluoroacetic acid, at flow rate of 60 mL/min) to give the desired product as a white solid. $^1$H NMR (500 MHz, DMSO-$d_6$) δ 7.94 (m, 1H), 7.78 (s, 1H), 7.66 (s, 1H),7.62 (s, 1H), 7.56 (s, 1H), 7.49 (d, J=6.8 Hz, 1H), 7.01 (s, 1H), 3.97 (dd, J=14.2, 3.9 Hzm 1H), 3.73 (dd, J=14.2, 4.9 Hz, 1H), 2.23 (s, 3H), 1.75 (s, 3H). LCMS for $C_{19}H_{18}F_6N_5O_2$ $(M+H)^+$: m/z=462.1; Found: 462.2.

Example 212. N-(2-(3-(8-amino-6-(trifluoromethyl)imidazo[1,2-a]pyrazin-3-yl)-4-methylphenyl)-3,3,3-trifluoro-2-hydroxypropyl)benzamide trifluoroacetate salt

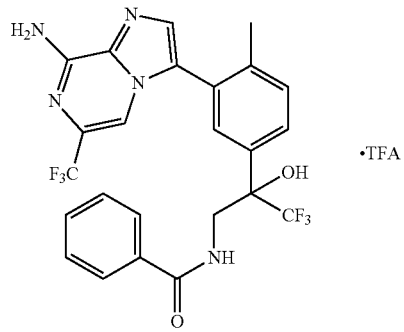 [SMILES: Cc1ccc(C(O)(CNC(=O)c2ccccc2)C(F)(F)F)cc1-c1cnc2c(N)nc(C(F)(F)F)cn12]

Example 212 was synthesized according to procedures analogous to Example 211, utilizing benzoic acid as starting material instead of acetic acid. $^1$H NMR (500 MHz, DMSO-$d_6$) δ 8.43 (m, 1H), 7.73 (s, 1H), 7.71-7.37 (m, 9H), 7.12 (s, 1H), 4.22 (dd, J=14.2, 3.9 Hzm 1H), 3.92 (dd, J=14.2, 4.9 Hz, 1H), 2.17 (s, 3H). LCMS for $C_{24}H_{20}F_6N_5O_2$ $(M+H)^+$: m/z=524.1; Found: 524.2.

Example 214

Example 214 was synthesized according to procedures analogous to Example 212 and the data are listed in Table 19.

TABLE 19

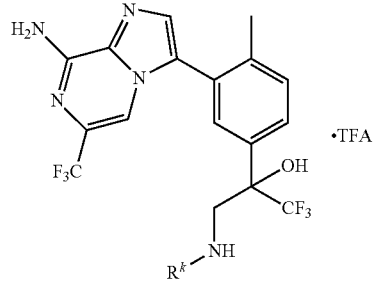

| Ex. No. | Name | $NHR^k$ | LCMS $[M + H]^+$ |
|---|---|---|---|
| 214 | N-(2-(3-(8-amino-6-(trifluoromethyl)imidazo[1,2-a]pyrazin-3-yl)-4-methylphenyl)-3,3,3-trifluoro-2-hydroxypropyl)-2-fluoroacetamide trifluoroacetate salt |  | 480.2 |

Example 221. 3-(5-(3-acetamido-1,1,1-trifluoro-2-hydroxypropan-2-yl)-2-methylphenyl)-8-amino-N-ethylimidazo[1,2-a]pyrazine-6-carboxamide trifluoroacetate

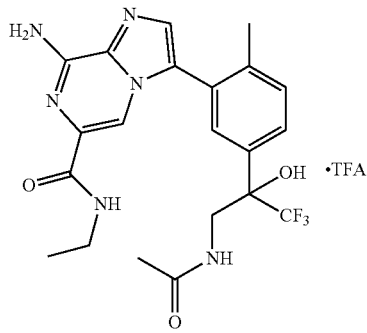 [SMILES: CCNC(=O)c1cn2c(-c3cc(C(O)(CNC(C)=O)C(F)(F)F)ccc3C)cnc2c(N)n1]

Step 1. 3-amino-2-(3-(8-amino-6-bromoimidazo[1,2-a]pyrazin-3-yl)-4-methylphenyl)-1,1,1-trifluoropropan-2-ol

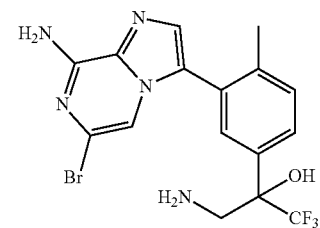 [SMILES: Cc1ccc(C(O)(CN)C(F)(F)F)cc1-c1cnc2c(N)nc(Br)cn12]

A solution of 6-bromo-3-iodoimidazo[1,2-a]pyrazin-8-amine (305 mg, 0.90 mmol) and 3-amino-2-(3-(5-amino-6-(2-cyclopropylthiazol-5-yl)pyrazin-2-yl)-4-methylphenyl)-1,1,1-trifluoropropan-2-ol (200 mg, 0.58 mmol, racemic) in dioxane/water (5 mL/1 mL) was treated with sodium carbonate (184 mg, 1.74 mmol) and dichloro[1,1'-bis(diphenylphosphino)ferrocene]palladium (II) dichloromethane adduct (24 mg, 0.029 mmol). The reaction mixture was degassed with nitrogen for 5 min, and stirred at 120° C. for 2.5 h. The resulting mixture was diluted with MeOH and passed through a Celite pad and concentrated. Purification vis flash column chromatography using ethyl acetate (containing 5% MeOH) in hexanes (0% to 100%) gave the desired product (103 mg, 41%) as a yellow oil. LCMS for $C_{16}H_{16}BrF_3N_5O$ (M+H)$^+$: m/z=430.0; Found: 430.1.

Step 2. 8-amino-3-(5-(3-amino-1,1,1-trifluoro-2-hydroxypropan-2-yl)-2-methylphenyl)-N-ethylimidazo[1,2-a]pyrazine-6-carboxamide

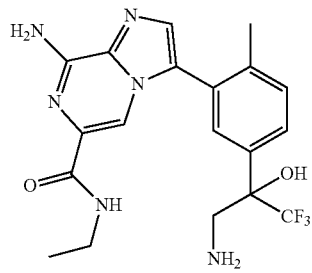 [SMILES: CCNC(=O)c1cn2c(-c3cc(C(O)(CN)C(F)(F)F)ccc3C)cnc2c(N)n1]

To a microwave vial was added 3-amino-2-(3-(5-amino-6-chloropyrazin-2-yl)-4-methylphenyl)-1,1,1-trifluoropropan-2-ol (103 mg, 0.24 mmol), [1,1'-bis(diphenylphosphino)ferrocene]dichloropalladium (47.0 mg, 0.058 mmol), ethyl amine (2M in THF, 1.0 mL, 2.0 mmol), sodium carbonate (61.1 mg, 0.58 mmol), dioxane (5 mL) and water (1 mL). The vial was capped and degassed with a stream of nitrogen for 5 min and the solution saturated with CO by bubbling the gas through the reaction mixture for 10 min followed by addition of additional isopropyl amine (2M in THF, 0.4 mL, 0.8 mmoL). The reaction was heated at 80° C. overnight. The reaction mixture was diluted with methanol and passed through a Celite® pad. The resulting mixture was concentrated and purified by flash column chromatography using MeOH in $CH_2Cl_2$ (5% to 10%) to give the desired product (70 mg, 69%) as a thick yellow foam. LCMS for $C_{19}H_{22}F_3N_6O_2$ (M+H)$^+$: m/z=423.2; found: 423.2.

Step 3. 3-(5-(3-acetamido-1,1,1-trifluoro-2-hydroxypropan-2-yl)-2-methylphenyl)-8-amino-N-ethylimidazo[1,2-a]pyrazine-6-carboxamide trifluoroacetate A solution of 8-amino-3-(5-(3-amino-1,1,1-trifluoro-2-hydroxypropan-2-yl)-2-methylphenyl)-N-ethylimidazo[1,2-a]pyrazine-6-carboxamide (5 mg, 11.84 µmol) (racemic) and acetic acid (20 mg, 0.33 mmol) in DMF/Hünig's base (0.5 mL/0.05 mL) was treated with HATU (10 mg, 26.32 µmol). The resulting mixture was stirred for 1 h before it was diluted with MeOH (3 mL). After filtered through a cartridge. The filtrate was purified via preparative LCMS (XBridge C18 Column, eluting with a gradient of acetonitrile in water with 0.1% trifluoroacetic acid, at flow rate of 60 mL/min) to give the desired product (2.5 mg, 45%) as a white solid. $^1$H NMR (400 MHz, DMSO-d$_6$) δ 8.25 (s, 1H), 8.00 (s, 1H), 7.74 (s, 2H), 7.65 (d, J=8.6 Hz, 1H), 7.55 (s, 1H), 7.51 (d, J=7.6 Hz, 1H), 7.04 (s, 1H), 4.00 (dd, J=15.0, 7.7 Hz, 1H), 3.73 (dd, J=15.0, 4.0 Hz, 1H), 3.30 (q, J=7.7 Hz, 2H), 2.17 (s, 3H), 1.78 (s, 3H), 1.04 (t, J=7.7 Hz, 3H).; LCMS for $C_{21}H_{24}F_3N_6O_3$ (M+H)$^+$: m/z=465.2; found: 465.2

Example 224. 2-(4-(8-Amino-6-(trifluoromethyl)imidazo[1,2-a]pyrazin-3-yl)-1-(phenylsulfonyl)-1H-indol-6-yl)-1,1,1-trifluoropropan-2-ol (Racemic)

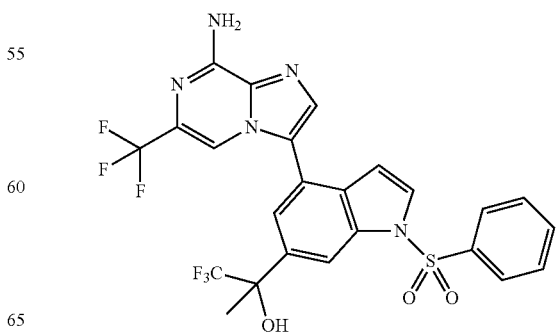

Step 1. 4-Bromo-N-methoxy-N-methyl-1H-indole-6-carboxamide

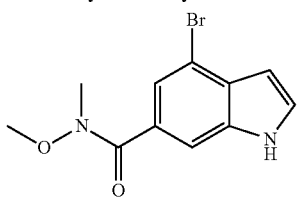

To 4-bromo-1H-indole-6-carboxylic acid (1.0 g, 4.2 mmol, Synthonix B15140), N,O-dimethylhydroxylamine hydrochloride (0.45 g, 4.6 mmol) and pyridine (0.84 mL, 10 mmol) in THF (21 mL) at 0° C. was added EDC (0.88 g, 4.6 mmol). The reaction was allowed to warm to room temperature and stir overnight. Water was added to the reaction mixture, and the mixture was extracted with EtOAc (3×). The combined organic extracts were dried over Na$_2$SO$_4$, filtered, and concentrated. The product was purified by flash chromatography, eluting with a gradient from 0-100% EtOAc in hexanes, to afford the title compound (0.15 g, 67%). LCMS for C$_{11}$H$_{12}$BrN$_2$O$_2$ (M+H)$^+$: calculated m/z=283.0; found 283.0.

Step 2. 4-Bromo-N-methoxy-N-methyl-1-(phenylsulfonyl)-1H-indole-6-carboxamide

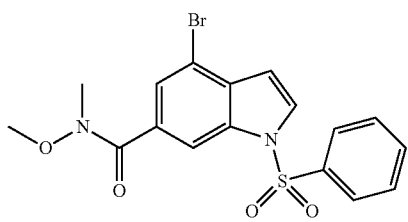 [SMILES: CON(C)C(=O)c1cc(Br)c2ccn(S(=O)(=O)c3ccccc3)c2c1]

To 4-bromo-N-methoxy-N-methyl-1H-indole-6-carboxamide (0.93 g, 3.3 mmol in DMF (16.5 mL at 0° C. was added NaH (60% in mineral oil, 0.63 g, 16 mmol) and the reaction was stirred for 10 minutes. Benzenesulfonyl chloride (0.47 mL, 3.6 mmol) was added, and the reaction was stirred for 10 minutes. The reaction mixture was poured into water, and the aqueous mixture was extracted with EtOAc (3×). The combined organic extracts were washed with water, dried over Na$_2$SO$_4$, filtered, and concentrated. The product was purified by flash chromatography, eluting with a gradient from 0-50% EtOAc in hexanes, to afford the title compound (1.1 g, 80%). $^1$H NMR (400 MHz, CDCl$_3$) δ 8.39-8.34 (m, 1H), 7.95-7.92 (m, 1H), 7.92-7.89 (m, 1H), 7.80 (d, J=1.2 Hz, 1H), 7.75 (d, J=3.7 Hz, 1H), 7.65-7.57 (m, 1H), 7.54-7.45 (m, 2H), 6.79 (dd, J=3.6, 0.9 Hz, 1H), 3.56 (s, 3H), 3.42 (s, 3H).

Step 3. 1-(4-Bromo-1-(phenylsulfonyl)-1H-indol-6-yl)ethan-1-one

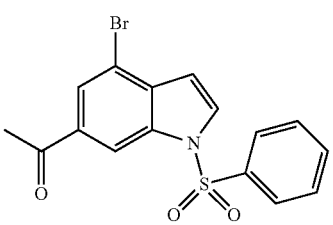 [SMILES: CC(=O)c1cc(Br)c2ccn(S(=O)(=O)c3ccccc3)c2c1]

To 4-bromo-N-methoxy-N-methyl-1-(phenylsulfonyl)-1H-indole-6-carboxamide (1.1 g, 2.7 mmol) in THF (27 mL) at 0° C. was added methylmagnesium bromide (3.0 M in Et$_2$O, 2.9 mL, 8.7 mmol). The reaction was stirred at 0° C. for 1 hour, then at room temperature overnight. The reaction was cooled in an ice bath, and was quenched by the addition of water, followed by saturated NH$_4$Cl solution. The mixture was extracted with EtOAc (3×), and the combined extracts were dried over Na$_2$SO$_4$, filtered, and concentrated. The product was used without further purification, theoretical yield assumed. LCMS for C$_{16}$H$_{13}$BrNO$_3$S (M+H)$^+$: calculated m/z=378.0; found 377.9.

Step 4. 2-(4-Bromo-1-(phenylsulfonyl)-1H-indol-6-yl)-1,1,1-trifluoropropan-2-ol (Racemic)

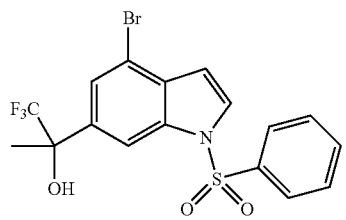 [SMILES: CC(O)(c1cc(Br)c2ccn(S(=O)(=O)c3ccccc3)c2c1)C(F)(F)F]

A solution of 1-(4-bromo-1-(phenylsulfonyl)-1H-indol-6-yl)ethan-1-one (0.20 g, 0.53 mmol) in dry THF (1.1 mL) was cooled to 0° C., and trimethyl(trifluoromethyl)silane (0.11 mL, 0.74 mmol, Combi Blocks QA-3660) was added. The solution was treated with a catalytic amount of TBAF (1.0 M in THF, 0.026 mL, 0.026 mmol) at 0° C. After 5 minutes, the ice bath was removed, and the resulting reaction mixture was stirred at room temperature overnight. The reaction mixture was again cooled to 0° C., and trimethyl(trifluoromethyl)silane (0.11 mL, 0.74 mmol) and TBAF (1.0 M in THF, 0.026 mL, 0.026 mmol) were added. After 5 minutes, the cooling bath was removed, and the reaction was stirred over three nights. Water was added, and the reaction was stirred for 4 hours. The reaction mixture was then extracted with EtOAc (2×). The combined organic extracts were dried over Na$_2$SO$_4$, filtered, and concentrated. The product was purified by flash chromatography, eluting with a gradient from 0-50% EtOAc in hexanes, to afford the title compound (0.15 g, 63%). LCMS for C$_{17}$H$_{14}$BrF$_3$NO$_3$S (M+H)$^+$: calculated m/z=448.0; found 447.9.

Step 5. 1,1,1-Trifluoro-2-(1-(phenylsulfonyl)-4-(4,4,5,5-tetramethyl-1,3,2-dioxaborolan-2-yl)-1H-indol-6-yl)propan-2-ol (Racemic)

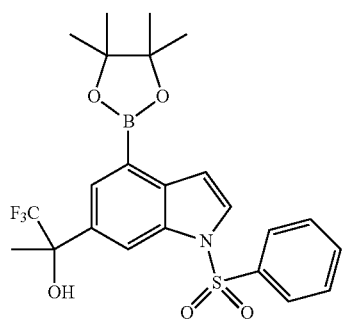 [SMILES: CC1(C)OB(c2cc(C(C)(O)C(F)(F)F)cc3c2ccn3S(=O)(=O)c2ccccc2)OC1(C)C]

A degassed mixture of 2-(4-bromo-1-(phenylsulfonyl)-1H-indol-6-yl)-1,1,1-trifluoropropan-2-ol (0.15 g, 0.34 mmol), bis(pinacolato)diboron (0.10 g, 0.40 mmol), potassium acetate (0.11 g, 1.1 mmol) and bis(triphenylphosphine)palladium(II) dichloride (9.4 mg, 0.013 mmol) in THF (1.2 mL) was heated in a sealed vial in an oil bath held at 120° C. for 1.5 hours, then the reaction mixture was stirred at room temperature overnight. The reaction mixture was diluted with water, and extracted with EtOAc (3×). The combined organic extracts were washed with brine, dried over $Na_2SO_4$, filtered, and concentrated. The product was purified by flash chromatography, eluting with a gradient from 0-50% EtOAc in hexanes, to afford the title compound (0.11 g, 67%). LCMS for $C_{23}H_{25}BF_3NO_5S$ (M+H)$^+$: calculated m/z=496.2; found 496.1.

Step 6. 2-(4-(8-Amino-6-(trifluoromethyl)imidazo[1,2-a]pyrazin-3-yl)-1-(phenylsulfonyl)-1H-indol-6-yl)-1,1,1-trifluoropropan-2-ol (Racemic)

A microwave vial was charged with 1,1,1-trifluoro-2-(1-(phenylsulfonyl)-4-(4,4,5,5-tetramethyl-1,3,2-dioxaborolan-2-yl)-1H-indol-6-yl)propan-2-ol (0.030 g, 0.061 mmol), 3-bromo-6-(trifluoromethyl)imidazo[1,2-a]pyrazin-8-amine (26 mg, 0.091 mmol, Example 4, Step 6) and THF (2.0 mL). To the solution was added aq. $K_2CO_3$ solution (1.0 M, 0.24 mL, 0.24 mmol). The reaction mixture was sparged with $N_2$, and dichloro[1,1'-bis(diphenylphosphino)ferrocene]palladium(II) dichloromethane adduct (9.9 mg, 0.012 mmol) was added. The reaction mixture was sparged with $N_2$, and was heated in the microwave to 120° C. for 50 minutes. An aliquot of the reaction mixture was purified via sequential preparative HPLC-MS purifications (pH=2, followed by repurification at pH=6.5) to afford the title compound (5.0 mg, 14%). LCMS for $C_{24}H_{18}F_6N_5O_3S$ (M+H)$^+$: calculated m/z=570.1; found 570.1. $^1$H NMR (400 MHz, $CD_3OD$) δ 8.48 (s, 1H), 8.02-8.00 (m, 1H), 8.00-7.97 (m, 1H), 7.89 (d, J=3.7 Hz, 1H), 7.83 (s, 1H), 7.81 (s, 1H), 7.71 (s, 1H), 7.70-7.63 (m, 1H), 7.60-7.50 (m, 2H), 6.71 (d, J=3.7 Hz, 1H), 1.87 (s, 3H). $^{19}$F NMR (376 MHz, $CD_3OD$) δ −70.04 (s), −82.17 (s).

Example 233. 2-(3-(8-Amino-6-(trifluoromethyl)imidazo[1,2-a]pyrazin-3-yl)-4-(methyl-d$_3$)phenyl)-1,1,1-trifluorobutane-2,3-diol trifluoroacetate salt (Single Diastereomer, Racemic)

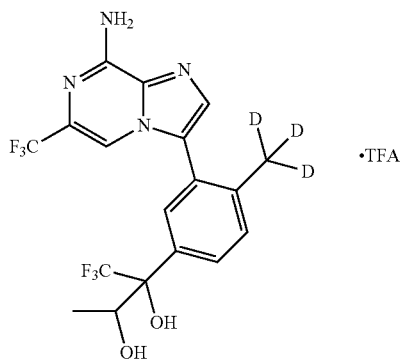 [SMILES: [2H]C([2H])([2H])c1ccc(C(O)(C(C)O)C(F)(F)F)cc1-c1cnc2c(N)nc(C(F)(F)F)cn12]

Step 1. 2,2,2-Trifluoro-1-(4-(methyl-d$_3$)phenyl)ethan-1-one

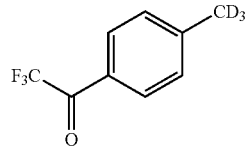 [SMILES: [2H]C([2H])([2H])c1ccc(C(=O)C(F)(F)F)cc1]

1,4-Dibromobenzene (10.0 g, 42.4 mmol, Aldrich) in THF (94 mL) and $Et_2O$ (94 mL) at −78° C. was treated dropwise with n-butyllithium (1.6 M in hexanes, 26.5 mL, 42.4 mmol). Ethyl 2,2,2-trifluoroacetate (6.02 g, 42.4 mmol, Aldrich T5521) was then added, and the reaction was stirred for 30 minutes. A further portion of n-butyllithium (1.6 M in hexanes, 26.5 mL, 42.4 mmol) was added, and after stirring for 10 minutes, iodomethane-d$_3$ (6.76 g, 46.6 mmol, Aldrich 176036) was added. After stirring for 30 minutes, a precooled solution of conc. HCl (12.5 mL) in EtOH (6.25 mL) was added. The reaction mixture was then poured into 2.0 N HCl (250 mL). The layers were separated, and the organic layer was dried over $MgSO_4$, filtered, and concentrated, to afford the title compound (7.2 g, 89%). $^1$H NMR (400 MHz, $CDCl_3$) δ 8.00 (d, J=7.7 Hz, 2H), 7.37 (d, J=8.4 Hz, 2H). $^{19}$F NMR (376 MHz, $CDCl_3$) δ −71.33 (s).

Step 2. 1-(3-Bromo-4-(methyl-d$_3$)phenyl)-2,2,2-trifluoroethan-1-one

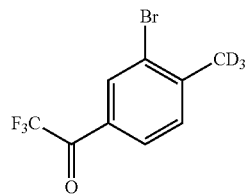 [SMILES: [2H]C([2H])([2H])c1ccc(C(=O)C(F)(F)F)cc1Br]

A solution of 2,2,2-trifluoro-1-(4-(methyl-d$_3$)phenyl)ethan-1-one (7.20 g, 37.7 mmol) in 1,2-dichloroethane (10 mL) was added slowly dropwise to a mixture of $AlCl_3$ (11.0 g, 82.9 mmol) in 1,2-dichloroethane (25 mL). The reaction mixture was then heated at 35° C. for 5 minutes. Bromine (1.94 mL, 37.7 mmol) was then added dropwise to the heated mixture. The reaction was stirred at 35° C. for 1.5 hours, then at 45° C. for 7 hours. Upon cooling to room temperature, the reaction was quenched by slowly pouring the reaction mixture into a mixture of ice-cold DCM and 1.0 N HCl. The layers were separated, and the aqueous layer was extracted with DCM (2×). The combined organic extracts were washed with saturated $NaHCO_3$ solution, washed with brine, dried over $Na_2SO_4$, filtered, and concentrated to afford the title compound (9.9 g, 98%). $^1$H NMR (400 MHz, $CDCl_3$) δ 8.28-8.22 (m, 1H), 7.96-7.89 (m, 1H), 7.44 (d, J=8.0 Hz, 1H). $^{19}$F NMR (376 MHz, $CDCl_3$) δ −71.50 (s).

Step 3. (E)- and (Z)-2-Bromo-1-(methyl-d₃)-4-(1,1,1-trifluorobut-2-en-2-yl)benzene

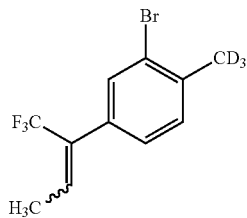

Ethyltriphenylphosphonium bromide (0.86 g, 2.3 mmol) was suspended in THF (4.1 mL) and the mixture was cooled to 0° C. n-Butyllithium (1.6 M in hexanes, 1.4 mL, 2.2 mmol) was added dropwise, and the reaction was stirred for 20 minutes. A solution of 1-(3-bromo-4-(methyl-d₃)phenyl)-2,2,2-trifluoroethan-1-one (0.50 g, 1.9 mmol) in THF (2.0 mL) was added dropwise, and the cooling bath was removed. The mixture was allowed to warm to room temperature, and to stir for 2 hours. The reaction mixture was diluted with water, and was extracted with DCM (3×). The combined organic extracts were dried over Na₂SO₄, filtered, and concentrated. The product was purified via flash chromatography, eluting with 100% hexanes, to afford the title compound as a 1.3:1 mixture of olefin isomers (0.51 g, 98%). ¹H NMR (400 MHz, CDCl₃) δ 7.49 (d, J=1.3 Hz, 1H, major isomer), 7.45 (d, J=1.3 Hz, 1H, minor isomer), 7.28 (d, J=7.8 Hz, 1H, minor isomer), 7.22 (d, J=7.8 Hz, 1H, major isomer), 7.17-7.13 (m, 1H, major isomer), 7.11 (dd, J=7.8, 1.7 Hz, 1H, minor isomer), 6.60-6.52 (m, 1H, minor isomer), 6.19-6.11 (m, 1H, major isomer), 2.05 (dq, J=7.5, 3.0 Hz, 3H, major isomer), 1.70 (dq, J=7.3, 2.6 Hz, 3H, minor isomer).

Step 4. 2-(3-Bromo-4-(methyl-d₃)phenyl)-1,1,1-trifluorobutane-2,3-diol (Two Diastereomers Isolated, Each as Racemate)

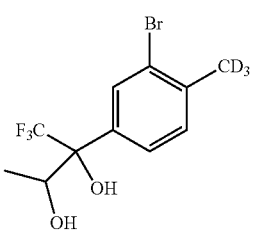 [SMILES: [2H]C([2H])([2H])c1ccc(C(O)(C(C)O)C(F)(F)F)cc1Br]

To a solution of 2-bromo-1-(methyl-d₃)-4-(1,1,1-trifluorobut-2-en-2-yl)benzene (0.50 g, 1.8 mmol, a mixture of (E)- and (Z)-isomers from Step 3) in acetone (6.0 mL) and water (6.0 mL) was added N-methylmorpholine N-oxide (0.27 g, 2.3 mmol), osmium tetroxide (4% in water, 0.68 mL, 0.11 mmol), and methane sulfonamide (0.17 g, 1.8 mmol). The reaction mixture was stirred at ambient temperature overnight, then at 50° C. for 4.5 hours, then at 60° C. for 1.5 hours, then at ambient temperature again overnight. One olefin isomer reacted at a slower rate than the other and was incompletely consumed. The reaction mixture was filtered, through Celite®, and the filtrate was concentrated in vacuo. The residue was partitioned between EtOAc and water. The layers were separated, and the aqueous layer was extracted with EtOAc. The combined organic extracts were dried over Na₂SO₄, filtered, and concentrated. Purification via flash chromatography, eluting with a gradient of 0-30% EtOAc in hexanes, afforded partial separation of the diastereomers. Peak 1 (first diastereomer to elute): 40 mg, Peak 2 (second diastereomer to elute): 180 mg. Mixed fractions pooled: 150 mg. Total yield: 370 mg, 66%. Peak 1 was used in Step 5.

Step 5. 1,1,1-Trifluoro-2-(4-(methyl-d₃)-3-(4,4,5,5-tetramethyl-1,3,2-dioxaborolan-2-yl)phenyl)butane-2,3-diol (Single Diastereomer, Racemic)

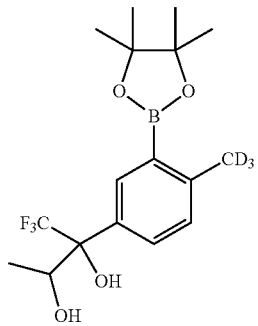 [SMILES: [2H]C([2H])([2H])c1ccc(C(O)(C(C)O)C(F)(F)F)cc1B1OC(C)(C)C(C)(C)O1]

A mixture of 2-(3-bromo-4-(methyl-d₃)phenyl)-1,1,1-trifluorobutane-2,3-diol (0.040 g, 0.13 mmol, Peak 1 from Step 4), bis(pinacolato)diboron (58 mg, 0.23 mmol), potassium acetate (37 mg, 0.38 mmol) and triphenylphosphine palladium chloride (5.3 mg, 7.6 µmol) in THF (0.8 mL) was heated in a sealed vial in an oil bath held at 120° C. for 2 hours, then the reaction mixture was heated at 70° C. overnight. Upon cooling to room temperature, the reaction mixture was diluted with EtOAc, filtered, through Celite®, and the filtrate was concentrated. The product was purified via flash chromatography, eluting with a gradient from 0-20% EtOAc in hexanes, to afford the title compound (0.030 g, 65%). LCMS calculated for $C_{17}H_{25}D_3BF_3NO_4$ $(M+NH_4)^+$: m/z=381.2, found: 381.2.

Step 6. 2-(3-(8-Amino-6-(trifluoromethyl)imidazo[1,2-a]pyrazin-3-yl)-4-(methyl-d₃)phenyl)-1,1,1-trifluorobutane-2,3-diol trifluoroacetate salt (Single Diastereomer, Racemic)

A mixture of 1,1,1-trifluoro-2-(4-(methyl-d₃)-3-(4,4,5,5-tetramethyl-1,3,2-dioxaborolan-2-yl)phenyl)butane-2,3-diol (0.030 g, 0.083 mmol), 3-bromo-6-(trifluoromethyl)imidazo[1,2-a]pyrazin-8-amine (23 mg, 0.083 mmol, Example 4, Step 6) and dichloro[1,1'-bis(diphenylphosphino)ferrocene]palladium(II) dichloromethane adduct (14 mg, 0.017 mmol) in THF (0.5 mL) and aq. K₂CO₃ solution (1.0 M, 0.25 mL, 0.25 mmol) was degassed by sparging with N₂. The reaction mixture was heated at 120° C. in the microwave for 35 minutes. A further portion of 3-bromo-6-(trifluoromethyl)imidazo[1,2-a]pyrazin-8-amine (4.6 mg, 0.017 mmol) was added, and the reaction was heated at 120° C. in the microwave for 15 minutes. Upon cooling to room temperature, the reaction mixture was diluted with MeCN and MeOH and purified via preparative HPLC-MS (pH=2) to afford the title compound (7.7 mg, 17%). LCMS calculated for $C_{18}H_{14}D_3F_6N_4O_2$ $(M+H)^+$: m/z=438.1, found: 438.1. ¹H NMR (400 MHz, DMSO-d₆) δ 7.81 (s, 1H), 7.67 (br s, 2H), 7.61-7.51 (m, 3H), 7.48 (d, J=8.1 Hz, 1H), 4.45-4.37 (m, 1H), 0.85 (d, J=6.3 Hz, 3H). ¹⁹F NMR (376 MHz, DMSO-d₆) δ −67.05 (s), −72.49 (s), −74.42 (s).

Example 235. 2-(3-(8-Amino-6-(trifluoromethyl) imidazo[1,2-a]pyrazin-3-yl)-4-(methyl-d₃)phenyl)-1,1,1-trifluoro-3-methylbutane-2,3-diol trifluoroacetate salt (Racemic)

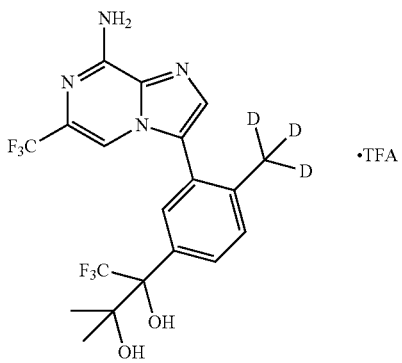 [SMILES: [2H]C([2H])([2H])c1ccc(C(O)(C(C)(C)O)C(F)(F)F)cc1-c1cnc2c(N)nc(C(F)(F)F)cn12]

Step 1. 2-Bromo-1-(methyl-d₃)-4-(1,1,1-trifluoro-3-methylbut-2-en-2-yl)benzene

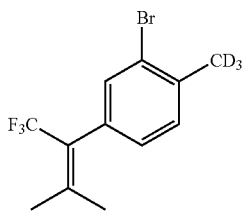 [SMILES: [2H]C([2H])([2H])c1ccc(C(=C(C)C)C(F)(F)F)cc1Br]

The procedure of Example 233, Step 3, was followed, using isopropyltriphenylphosphonium iodide instead of ethyltriphenylphosphonium bromide, to afford the title compound. ¹H NMR (400 MHz, CDCl₃) δ 7.36 (d, J=1.8 Hz, 1H), 7.24 (d, J=7.7 Hz, 1H), 7.01 (dd, J=7.8, 1.8 Hz, 1H), 2.08 (q, J=2.5 Hz, 3H), 1.66 (q, J=2.3 Hz, 3H).

Step 2. 2-(3-Bromo-4-(methyl-d₃)phenyl)-1,1,1-trifluoro-3-methylbutane-2,3-diol (Racemic)

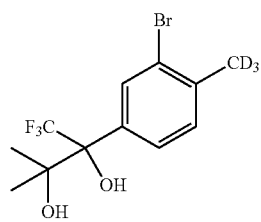 [SMILES: [2H]C([2H])([2H])c1ccc(C(O)(C(C)(C)O)C(F)(F)F)cc1Br]

To a solution of 2-bromo-1-(methyl-d₃)-4-(1,1,1-trifluoro-3-methylbut-2-en-2-yl)benzene (190 mg, 0.64 mmol) in acetone (3.0 mL) and water (3.0 mL) was added N-methylmorpholine N-oxide (160 mg, 1.4 mmol), followed by osmium tetroxide (4% in water, 0.64 mL, 0.10 mmol), and methanesulfonamide (120 mg, 1.3 mmol). The reaction mixture was heated at 60° C. in a sealed vial for 5 hours. Upon cooling to ambient temperature, the reaction mixture was filtered, and the filtrate was concentrated in vacuo. The residue was partitioned between EtOAc and water. The aqueous layer was extracted with EtOAc (2×). The combined organic extracts were dried over Na₂SO₄, filtered, and concentrated. The product was purified via flash chromatography, eluting with a gradient of 0-30% EtOAc in hexanes, to afford the title compound (67 mg, 32%). ¹H NMR (400 MHz, CDCl₃) δ 7.90 (d, J=2.0 Hz, 1H), 7.54-7.49 (m, 1H), 7.25 (d, J=8.2 Hz, 1H), 4.24 (s, 1H), 1.63 (q, J=1.7 Hz, 3H), 1.01 (s, 3H). ¹⁹F NMR (376 MHz, CDCl₃) δ −70.81 (s).

Step 3. 2-(3-(8-Amino-6-(trifluoromethyl)imidazo [1,2-a]pyrazin-3-yl)-4-(methyl-d₃)phenyl)-1,1,1-trifluoro-3-methylbutane-2,3-diol, trifluoroacetate salt (Racemic)

The procedure of Example 233, Steps 5 and 6 were followed, using 2-(3-bromo-4-(methyl-d₃)phenyl)-1,1,1-trifluoro-3-methylbutane-2,3-diol (racemic) instead of 2-(3-bromo-4-(methyl-d₃)phenyl)-1,1,1-trifluorobutane-2,3-diol. LCMS calculated for C₁₉H₁₆D₃F₆N₄O₂ (M+H)⁺: m/z=452.2, found: 452.2. ¹H NMR (400 MHz, CD₃OD) δ 7.80 (dd, J=8.4, 1.6 Hz, 1H), 7.72 (s, 2H), 7.66 (d, J=1.4 Hz, 1H), 7.48 (d, J=8.2 Hz, 1H), 1.31 (s, 3H), 1.27 (s, 3H). ¹⁹F NMR (376 MHz, CD₃OD) δ −69.90 (s), −70.50 (s), −77.28 (s).

Example 253. 2-(3-(8-Amino-6-(2-hydroxypropan-2-yl)imidazo[1,2-a]pyrazin-3-yl)-4-(methyl-d₃)phenyl)-1,1,1-trifluoropropan-2-ol trifluoroacetate salt (Single Enantiomer)

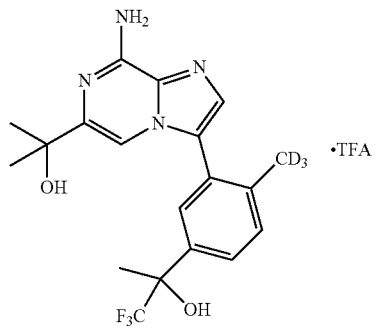 [SMILES: [2H]C([2H])([2H])c1ccc(C(C)(O)C(F)(F)F)cc1-c1cnc2c(N)nc(C(C)(C)O)cn12]

To methyl 8-amino-3-(2-(methyl-d₃)-5-(1,1,1-trifluoro-2-hydroxypropan-2-yl)phenyl)imidazo[1,2-a]pyrazine-6-carboxylate (0.020 g, 0.050 mmol, from Example 81, Step 7) in THF (1.0 mL) at 0° C. was added methylmagnesium bromide (3.0 M in diethyl ether. 0.12 mL, 0.35 mmol). After 1.5 h at 0° C., the reaction was quenched by the dropwise addition of water (1.0 mL). The reaction mixture was diluted with MeOH, and was filtered. Purification via preparative HPLC-MS (pH=2) afforded the title compound (9.0 mg, 35%). LCMS calculated for C₁₉H₁₉D₃F₃N₄O₂ (M+H)⁺: m/z=398.2, found: 398.1. ¹H NMR (400 MHz, DMSO-d₆) δ 7.93 (s, 1H), 7.69 (dd, J=8.1, 2.1 Hz, 1H), 7.61 (d, J=2.1 Hz, 1H), 7.51 (d, J=8.1 Hz, 1H), 7.23 (s, 1H), 6.70 (br s, 1H), 1.72 (s, 3H), 1.45 (s, 6H). ¹⁹F NMR (376 MHz, DMSO-d₆) δ −74.23 (s), −79.75 (s).

Example 255

Example 255 was synthesized according to procedures analogous to those in Example 253, using ethyl 8-amino-3-(5-(3-amino-1,1,1-trifluoro-2-hydroxy-3-oxopropan-2-yl)-2-methylphenyl)imidazo[1,2-a]pyrazine-6-carboxylate (Example 288), Step 1)) instead of methyl 8-amino-3-(2-(methyl-d$_3$)-5-(1,1,1-trifluoro-2-hydroxypropan-2-yl)phenyl)imidazo[1,2-a]pyrazine-6-carboxylate as starting material, and the appropriate Grignard reagent. The data are listed in Table 20.

TABLE 20

| Ex. No. | Name | R | LCMS [M + H]$^+$ |
|---|---|---|---|
| 255 | 2-(3-(8-Amino-6-(2-hydroxypropan-2-yl)imidazo[1,2-a]pyrazin-3-yl)-4-methylphenyl)-3,3,3-trifluoro-2-hydroxypropanamide trifluoroacetate salt (single enantiomer) | Me | 424.2 |

Example 262. 3-(3-(8-Amino-6-(trifluoromethyl)imidazo[1,2-a]pyrazin-3-yl)-4-methylphenyl)-4,4,4-trifluoro-3-hydroxy-N,2,2-trimethylbutanamide

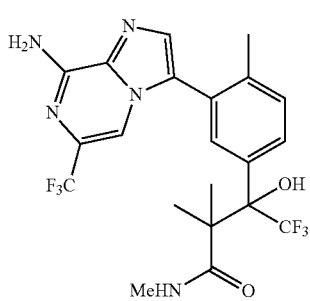 [SMILES: CNC(=O)C(C)(C)C(O)(c1ccc(C)c(-c2cnc3c(N)nc(C(F)(F)F)cn23)c1)C(F)(F)F]

Step 1. 3-(3-(8-Amino-6-(trifluoromethyl)imidazo[1,2-a]pyrazin-3-yl)-4-methylphenyl)-4,4,4-trifluoro-3-hydroxy-2,2-dimethylbutanoic acid

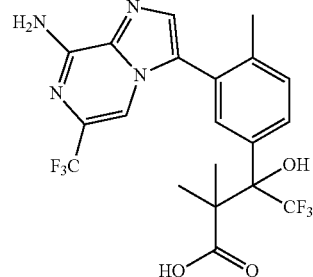 [SMILES: Cc1ccc(C(O)(C(F)(F)F)C(C)(C)C(=O)O)cc1-c1cnc2c(N)nc(C(F)(F)F)cn12]

A solution of methyl 3-(3-(8-amino-6-(trifluoromethyl)imidazo[1,2-a]pyrazin-3-yl)-4-methylphenyl)-4,4,4-trifluoro-3-hydroxy-2,2-dimethylbutanoate (0.261 g, 0.532 mmol) in methanol (1.77 mL) and tetrahydrofuran (1.77 mL) at 0° C. was treated with 1.0 M sodium hydroxide in water (1.60 mL, 1.60 mmol) dropwise and stirred at RT for 20 h. The reaction mixture was cooled to 0° C., diluted with 1.0 M HCl (2.13 mL, 2.13 mmol), water (15 mL), and brine (15 mL), and extracted with ethyl acetate (50 mL). The organic layer was separated, dried over sodium sulfate, filtered, and concentrated to give the desired product (0.247 g, 97.2%) as a white solid that was used without further purification. LCMS for C$_{20}$H$_{19}$F$_6$N$_4$O$_3$ (M+H)$^+$: m/z=477.1; Found: 477.1.

Step 2. 3-(3-(8-Amino-6-(trifluoromethyl)imidazo[1,2-a]pyrazin-3-yl)-4-methylphenyl)-4,4,4-trifluoro-3-hydroxy-N,2,2-trimethylbutanamide The desired compound was prepared according to the procedure of Example 76, Step 2, using 3-(3-(8-amino-6-(trifluoromethyl)imidazo[1,2-a]pyrazin-3-yl)-4-methylphenyl)-4,4,4-trifluoro-3-hydroxy-2,2-dimethylbutanoic acid in place of 2-(8-amino-3-(5-(1,1-difluoro-2-hydroxypropan-2-yl)-2-methylphenyl)imidazo[1,2-a]pyrazin-6-yl)cyclopropane-1-carboxylic acid as the starting material. $^1$H NMR (400 MHz, DMSO-d$_6$) δ 8.15-8.05 (m, 2H), 7.80 (s, 1H), 7.72-7.61 (m, 4H), 7.58 (d, J=2.1 Hz, 1H), 7.50 (d, J=8.2 Hz, 1H), 2.62 (d, J=4.3 Hz, 3H), 2.25 (s, 3H), 1.29 (s, 3H), 1.01 (s, 3H). LCMS for C$_{21}$H$_{22}$F$_6$N$_5$O$_2$ (M+H)$^+$: m/z=490.1; Found: 490.1.

Example 264. 2-(3-(8-Amino-6-(1-methyl-1H-pyrazol-5-yl)imidazo[1,2-a]pyrazin-3-yl)-4-methylphenyl)-1,1,1,3,3,3-hexafluoropropan-2-ol

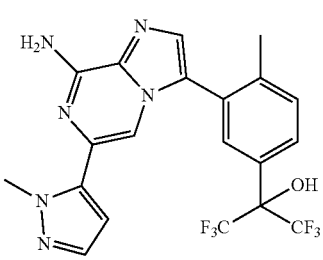 [SMILES: Cc1ccc(C(O)(C(F)(F)F)C(F)(F)F)cc1-c1cnc2c(N)nc(-c3ccnn3C)cn12]

Step 1. Perfluorophenyl 3-bromo-4-methylbenzoate

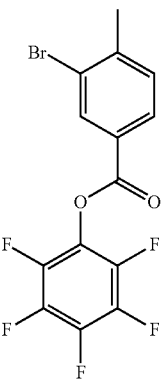 [SMILES: Cc1ccc(C(=O)Oc2c(F)c(F)c(F)c(F)c2F)cc1Br]

A solution of 3-bromo-4-methylbenzoic acid (0.750 g, 3.49 mmol) [Combi-Blocks, CA-5008] in tetrahydrofuran (12.9 mL) was treated with 2,3,4,5,6-pentafluorophenol (0.719 g, 3.91 mmol) followed by N,N'-dicyclohexylcarbodiimide (0.813 g, 3.94 mmol) and stirred at RT for 14 h. The reaction mixture was filtered to remove the solids which were washed with tetrahydrofuran. The filtrate was concentrated to a tan solid. Purification by flash column chromatography using MTBE in hexanes (0%-30%) gave the desired product (1.29 g, 97.0%) as a tan solid. LCMS for $C_{14}H_7BrF_5O_2$ (M+H)$^+$: m/z=381.0, 383.0; Found: 380.9, 382.9.

Step 2. 2-(3-Bromo-4-methylphenyl)-1,1,1,3,3,3-hexafluoropropan-2-ol

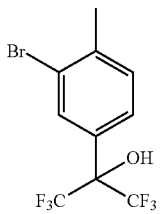

A solution of perfluorophenyl 3-bromo-4-methylbenzoate (0.737 g, 1.93 mmol) in toluene (9.67 mL) at 0° C. was treated with trimethyl(trifluoromethyl)silane (2.00 mL, 13.5 mmol) followed by 1.0 M tetrabutylammonium fluoride in tetrahydrofuran (0.677 ml, 0.677 mmol) and stirred at RT for 17 h. The reaction mixture was diluted with saturated ammonium chloride (20 mL) and extracted with ethyl acetate (40 mL). The organic layer was separated, washed with brine, dried over sodium sulfate, filtered, and concentrated to give a tan oily solid. The oily solid was dissolved in tetrahydrofuran (9.67 mL), treated with 6.0 M HCl (4.83 mL, 29.0 mmol), and stirred for 14 h. The reaction mixture was diluted with water (50 mL) and extracted with ethyl acetate (50 mL). The organic layer was separated, washed with brine, dried over sodium sulfate, filtered, and concentrated to give a tan oily solid. Purification by flash column chromatography using MTBE in hexanes (0%-50%) gave the desired product (578 mg, 88.7%) as a yellow oil. $^1$H NMR (400 MHz, DMSO-d$_6$) δ 8.91 (s, 1H), 7.83 (d, J=2.1 Hz, 1H), 7.64-7.55 (m, 1H), 7.52 (d, J=8.1 Hz, 1H), 2.40 (s, 3H).

Step 3. 1,1,1,3,3,3-Hexafluoro-2-(4-methyl-3-(4,4,5,5-tetramethyl-1,3,2-dioxaborolan-2-yl)phenyl)propan-2-ol

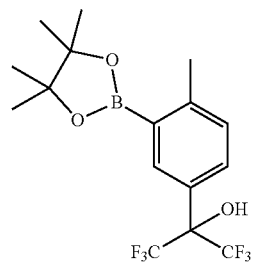 [SMILES: Cc1ccc(C(O)(C(F)(F)F)C(F)(F)F)cc1B1OC(C)(C)C(C)(C)O1]

The desired compound was prepared according to the procedure of Example 1, Step 2, using 2-(3-bromo-4-methylphenyl)-1,1,1,3,3,3-hexafluoropropan-2-ol as the starting material. LCMS for $C_{16}H_{20}BF_6O_3$ (M+H)$^+$: m/z=385.1; Found: 385.1.

Step 4. 2-(3-(8-Amino-6-bromoimidazo[1,2-a]pyrazin-3-yl)-4-methylphenyl)-1,1,1,3,3,3-hexafluoropropan-2-ol

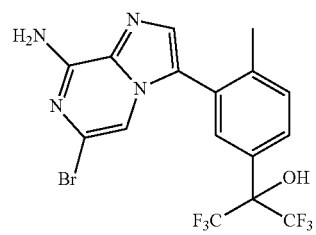 [SMILES: Cc1ccc(C(O)(C(F)(F)F)C(F)(F)F)cc1-c1cnc2c(N)nc(Br)cn12]

The desired compound was prepared according to the procedure of Example 28, Step 2, using 1,1,1,3,3,3-hexafluoro-2-(4-methyl-3-(4,4,5,5-tetramethyl-1,3,2-dioxaborolan-2-yl)phenyl)propan-2-ol in place of 1,1-difluoro-2-(4-methyl-3-(4,4,5,5-tetramethyl-1,3,2-dioxaborolan-2-yl)phenyl)propan-2-ol as the starting material. LCMS for $C_{16}H_{12}BrF_6N_4O$ (M+H)$^+$: m/z=469.0, 471.0; Found: 469.0, 471.0.

Step 5. 2-(3-(8-Amino-6-(1-methyl-1H-pyrazol-5-yl)imidazo[1,2-a]pyrazin-3-yl)-4-methylphenyl)-1,1,1,3,3,3-hexafluoropropan-2-ol The desired compound was prepared according to the procedure of Example 10 using 2-(3-(8-amino-6-bromoimidazo[1,2-a]pyrazin-3-yl)-4-methylphenyl)-1,1,1,3,3,3-hexafluoropropan-2-ol in place of 2-(3-(8-amino-6-bromoimidazo[1,2-a]pyrazin-3-yl)-4-methylphenyl)-1,1,1-trifluoropropan-2-ol and 1-methyl-5-(4,4,5,5-tetramethyl-1,3,2-dioxaborolan-2-yl)-1H-pyrazole in place of (2-(hydroxymethyl)pyridin-4-yl)boronic acid as the starting materials. $^1$H NMR (400 MHz, DMSO-d$_6$) δ 8.84 (s, 1H), 7.81-7.65 (m, 3H), 7.61 (d, J=8.2 Hz, 1H), 7.45 (s, 1H), 7.40

(s, 1H), 7.31 (s, 2H), 6.38 (d, J=2.0 Hz, 1H), 4.04 (s, 3H), 2.30 (s, 3H). LCMS for C$_{20}$H$_{17}$F$_6$N$_6$O (M+H)$^+$: m/z=471.1; Found: 471.1.

Example 267. 2-(3-(8-Amino-6-(6-(1-hydroxyethyl) pyridin-3-yl)imidazo[1,2-a]pyrazin-3-yl)-4-(methyl-d$_3$)phenyl)-1,1,1-trifluoropropan-2-ol

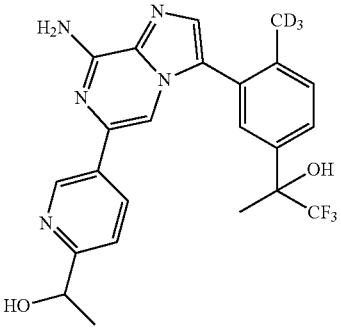 [SMILES: [2H]C([2H])([2H])c1ccc(C(C)(O)C(F)(F)F)cc1-c1cnc2c(N)nc(-c3ccc(C(C)O)nc3)cn12]

The desired compound was prepared according to the procedure of Example 10 using 2-(3-(8-amino-6-bromoimidazo[1,2-a]pyrazin-3-yl)-4-(methyl-d$_3$)phenyl)-1,1,1-trifluoropropan-2-ol (from Example 81, Step 6) in place of 2-(3-(8-amino-6-bromoimidazo[1,2-a]pyrazin-3-yl)-4-methylphenyl)-1,1,1-trifluoropropan-2-ol and (6-(1-hydroxyethyl)pyridin-3-yl)boronic acid (single isomer from Example 136, Step 2) in place of (2-(hydroxymethyl)pyridin-4-yl)boronic acid as the starting materials. $^1$H NMR (500 MHz, DMSO-d$_6$) δ 8.92 (d, J=2.3 Hz, 1H), 8.19 (dd, J=8.3, 2.4 Hz, 1H), 7.72 (s, 1H), 7.70-7.59 (m, 3H), 7.53 (d, J=8.2 Hz, 1H), 7.48 (d, J=8.0 Hz, 1H), 7.23 (s, 2H), 6.66 (s, 1H), 5.36 (s, 1H), 4.75 (q, J=6.5 Hz, 1H), 1.73 (s, 3H), 1.37 (d, J=6.5 Hz, 3H). LCMS for C$_{23}$H$_{20}$D$_3$F$_3$N$_5$O$_2$ (M+H)$^+$: m/z=461.2; Found: 461.2.

Example 268. 2-(3-(8-Amino-6-(trifluoromethyl)imidazo[1,2-a]pyrazin-3-yl)-4-methylphenyl)-1-chloro-1,1-difluoropropan-2-ol

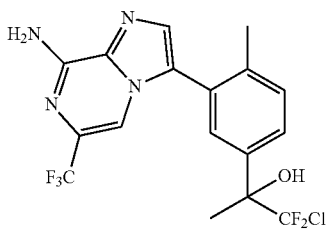

Step 1. 2-Chloro-1-(3-chloro-4-methylphenyl)-2,2-difluoroethan-1-one

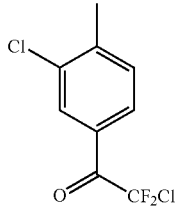

A solution of 2-chloro-4-iodo-1-methylbenzene (0.561 g, 2.22 mmol) in diethyl ether (4.94 mL) at −78° C. was treated with butyllithium (2.5 M in hexanes) (0.933 mL, 2.33 mmol) and stirred at −78° C. for 30 min. The reaction mixture was treated with ethyl chlorodifluoroacetate (0.338 ml, 2.67 mmol), warmed slowly to 0° C., and stirred at 0° C. for 1 h. The reaction mixture was quenched with saturated ammonium chloride solution at 0° C. and diluted with diethyl ether and water. The organic layer was separated and washed with brine, dried over sodium sulfate, filtered, and concentrated to give the desired product (0.45 g, 84.7%) as a yellow oil that was used without further purification. LCMS for C$_9$H$_7$Cl$_2$F$_2$O (M+H)$^+$: m/z=239.0, 241.0; Found: 239.0, 241.0.

Step 2. 1-Chloro-2-(3-chloro-4-methylphenyl)-1,1-difluoropropan-2-ol

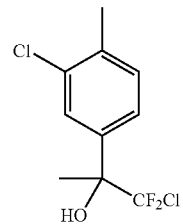

A solution of 2-chloro-1-(3-chloro-4-methylphenyl)-2,2-difluoroethan-1-one (0.598 g, 2.50 mmol) in tetrahydrofuran (10.0 mL) at 0° C. was added was treated with methylmagnesium bromide (3.0 M in diethyl ether) (1.67 mL, 5.00 mmol) dropwise and stirred at 0° C. for 1 h. The cooling bath was removed and the reaction mixture was allowed to warm to ambient temperature. The reaction mixture was cooled to 0° C. and quenched with saturated ammonium chloride (30 mL) dropwise. The resulting mixture was diluted with water (20 mL) to dissolve all solids and extracted with diethyl ether (100 mL). The organic layer was separated and washed with brine, dried over sodium sulfate, filtered, and concentrated to give a tan oil. Purification by flash column chromatography using diethyl ether in hexanes (0%-50%) gave the desired product (465 mg, 72.9%) as a colorless oil. LCMS for C$_{10}$H$_9$Cl$_2$F$_2$ (M-OH)$^+$: m/z=237.0, 239.0; Found: 237.1, 238.9.

Step 3. 1-Chloro-1,1-difluoro-2-(4-methyl-3-(4,4,5,5-tetramethyl-1,3,2-dioxaborolan-2-yl)phenyl)propan-2-ol

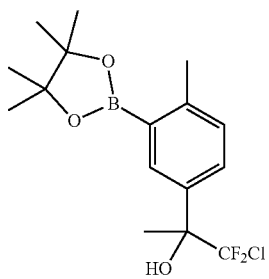

285

The desired compound was prepared according to the procedure of Example 61, Step 3, using 1-chloro-2-(3-chloro-4-methylphenyl)-1,1-difluoropropan-2-ol in place of 1-(3-chloro-4-methylphenyl)-2-fluorocyclopentan-1-ol as the starting material. LCMS for $C_{16}H_{23}BClF_2O_3$ (M+H)⁺: m/z=347.1; Found: 347.1.

Step 4. 2-(3-(8-Amino-6-(trifluoromethyl)imidazo[1,2-a]pyrazin-3-yl)-4-methylphenyl)-1-chloro-1,1-difluoropropan-2-ol The desired compound was prepared according to the procedure of Example 1, Step 7, using 3-bromo-6-(trifluoromethyl)imidazo[1,2-a]pyrazin-8-amine in place of 7-bromo-2-(trifluoromethyl)imidazo[2,1-f][1,2,4]triazin-4-amine and 1-chloro-1,1-difluoro-2-(4-methyl-3-(4,4,5,5-tetramethyl-1,3,2-dioxaborolan-2-yl)phenyl)propan-2-ol in place of 1,1,1-trifluoro-2-(4-methyl-3-(4,4,5,5-tetramethyl-1,3,2-dioxaborolan-2-yl)phenyl)propan-2-ol as the starting materials. ¹H NMR (400 MHz, DMSO-d₆) δ 7.79 (s, 1H), 7.70-7.61 (m, 4H), 7.58 (s, 1H), 7.47 (d, J=7.9 Hz, 1H), 6.75 (s, 1H), 2.24 (s, 3H), 1.75 (s, 3H). LCMS for $C_{17}H_{15}ClF_5N_4O$ (M+H)⁺: m/z=421.0; Found: 421.0.

Examples 277-279

Examples 277-279 were synthesized according to procedures analogous to those in Example 283 (Method B). The data are listed in Table 21.

TABLE 21

| Ex. No. | Name | R¹ | Method | LCMS [M + H]⁺ | NMR Spectra |
|---|---|---|---|---|---|
| 277 | 8-Amino-N-(1-azabicyclo[2.2.1]heptan-4-yl)-3-(2-methyl-5-(1,1,1-trifluoro-2-hydroxypropan-2-yl)phenyl)imidazo[1,2-a]pyrazine-6-carboxamide trifluoroacetate salt | | B | 475.1 | |
| 278 | 8-Amino-N-(3-cyanobicyclo[1.1.1]pentan-1-yl)-3-(2-methyl-5-(1,1,1-trifluoro-2-hydroxypropan-2-yl)phenyl)imidazo[1,2-a]pyrazine-6-carboxamide trifluoroacetate salt | | B | 471.1 | |
| 279 | 8-Amino-N-(1-(hydroxymethyl)-2-oxabicyclo[2.1.1]hexan-4-yl)-3-(2-methyl-5-(1,1,1-trifluoro-2-hydroxypropan-2-yl)phenyl)imidazo[1,2-a]pyrazine-6-carboxamide trifluoroacetate salt | | B | 492.1 | ¹H NMR (400 MHz, DMSO-d₆) δ 8.74 (s, 1H), 7.80-7.70 (m, 2H), 7.70-7.64 (m, 1H), 7.59 (d, J = 2.1 Hz, 1H), 7.50 (d, J = 8.1 Hz, 1H), 6.68 (s, 1H), 3.77 (s, 2H), 3.58 (s, 2H), 2.17 (s, 3H), 2.04 (dd, J = 4.3, 1.6 Hz, 2H), 1.81 (dd, J = 4.3, 1.7 Hz, 2H), 1.71 (s, 3H). |

Example 283. 8-Amino-N-((1-cyanocyclobutyl)methyl)-3-(2-methyl-5-(1,1,1-trifluoro-2-hydroxypropan-2-yl)phenyl)imidazo[1,2-a]pyrazine-6-carboxamide trifluoroacetate salt

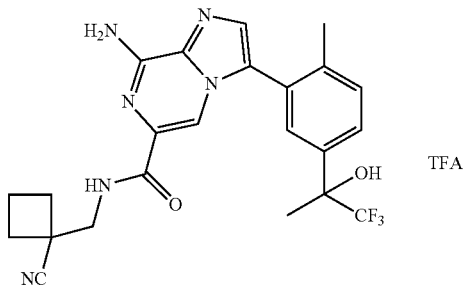 [SMILES: Cc1ccc(C(C)(O)C(F)(F)F)cc1-c1cnc2c(N)nc(C(=O)NCC3(C#N)CCC3)cn12]

Step 1. 8-Amino-3-(2-methyl-5-(1,1,1-trifluoro-2-hydroxypropan-2-yl)phenyl)imidazo[1,2-a]pyrazine-6-carboxylic acid

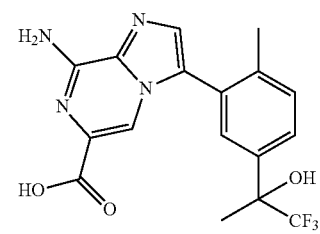

The desired compound was prepared according to the procedure of Example 81, Step 8, using methyl 8-amino-3-(2-methyl-5-(1,1,1-trifluoro-2-hydroxypropan-2-yl)phenyl)imidazo[1,2-a]pyrazine-6-carboxylate in place of methyl 8-amino-3-(2-(methyl-$d_3$)-5-(1,1,1-trifluoro-2-hydroxypropan-2-yl)phenyl)imidazo[1,2-a]pyrazine-6-carboxylate as the starting material. LCMS for $C_{17}H_{16}F_3N_4O_3$ (M+H)$^+$: m/z=381.1; Found: 381.1.

Step 2. 8-Amino-N-((1-cyanocyclobutyl)methyl)-3-(2-methyl-5-(1,1,1-trifluoro-2-hydroxypropan-2-yl)phenyl)imidazo[1,2-a]pyrazine-6-carboxamide trifluoroacetate salt The desired compound was prepared according to the procedure of Example 81, Step 9, using 8-amino-3-(2-methyl-5-(1,1,1-trifluoro-2-hydroxypropan-2-yl)phenyl)imidazo[1,2-a]pyrazine-6-carboxylic acid in place of 8-amino-3-(2-(methyl-$d_3$)-5-(1,1,1-trifluoro-2-hydroxypropan-2-yl)phenyl)imidazo[1,2-a]pyrazine-6-carboxylic acid and 1-(aminomethyl)cyclobutane-1-carbonitrile in place of 1-amino-2-methylpropan-2-ol as the starting materials. LCMS for $C_{23}H_{24}F_3N_6O_2$ (M+H)$^+$: m/z=473.2; Found: 473.1.

Example 284. 8-Amino-3-(5-(3-amino-1,1,1-trifluoro-2-hydroxy-3-oxopropan-2-yl)-2-methylphenyl)-N-(2-hydroxy-2-methylpropyl)imidazo[1,2-a]pyrazine-6-carboxamide

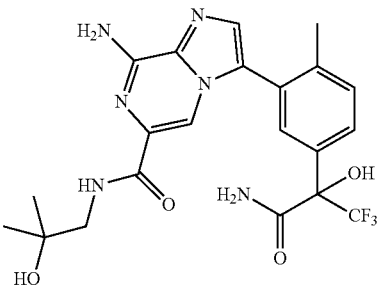 [SMILES: Cc1ccc(C(O)(C(N)=O)C(F)(F)F)cc1-c1cnc2c(N)nc(C(=O)NCC(C)(C)O)cn12]

Step 1. 2-(3-(8-Amino-6-bromoimidazo[1,2-a]pyrazin-3-yl)-4-methylphenyl)-3,3,3-trifluoro-2-hydroxypropanamide

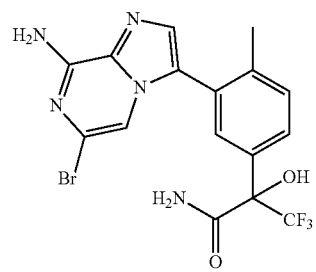 [SMILES: Cc1ccc(C(O)(C(N)=O)C(F)(F)F)cc1-c1cnc2c(N)nc(Br)cn12]

The desired compound was prepared according to the procedure of Example 28, Step 2, using 3,3,3-trifluoro-2-hydroxy-2-(4-methyl-3-(4,4,5,5-tetramethyl-1,3,2-dioxaborolan-2-yl)phenyl)propanamide (Example 82, Step 5) in place of 1,1-difluoro-2-(4-methyl-3-(4,4,5,5-tetramethyl-1,3,2-dioxaborolan-2-yl)phenyl)propan-2-ol as the starting material. LCMS for $C_{16}H_{14}BrF_3N_5O_2$ (M+H)$^+$: m/z=444.0, 446.0; Found: 444.1, 446.1.

Step 2. 8-Amino-3-(5-(3-amino-1,1,1-trifluoro-2-hydroxy-3-oxopropan-2-yl)-2-methylphenyl)-N-(2-hydroxy-2-methylpropyl)imidazo[1,2-a]pyrazine-6-carboxamide In a microwave vial, 2-(3-(8-amino-6-bromoimidazo[1,2-a]pyrazin-3-yl)-4-methylphenyl)-3,3,3-trifluoro-2-hydroxypropanamide (0.010 g, 0.023 mmol) and 1-amino-2-methylpropan-2-ol (0.020 g, 0.23 mmol) were dissolved in 1,4-dioxane (0.375 mL) and treated with triethylamine (0.013 ml, 0.090 mmol). The reaction mixture was degassed with nitrogen for 5 min, treated with dichloro[1,1'-bis(diphenylphosphino)ferrocene]palladium (II) dichloromethane adduct (3.68 mg, 4.50 µmol), and degassed with nitrogen for another 5 min. The vial was capped and the solution was saturated with CO by bubbling the gas through the reaction subsurface for 5 minutes. The reaction mixture was heated at 80° C. overnight. The reaction mixture was cooled to RT, dissolved in methanol and DI water, and passed through a 0.45 µm filter. The filtrate was purified via preparative LCMS (XBridge® C18 Column, eluting with a gradient of acetonitrile in water with 0.1% trifluoroacetic acid, at flow rate of 60 mL/min) to give the desired product (6.30 mg, 58.2%) as a white solid. $^1$H NMR (400 MHz, DMSO-$d_6$) δ 8.27-8.02 (m, 1H), 7.77 (dd, J=8.2, 2.1 Hz, 1H), 7.74-7.68 (m, 3H), 7.66 (d, J=2.1 Hz, 2H), 7.60 (s, 1H), 7.53 (d, J=8.3 Hz, 1H), 7.47 (br s, 2H), 3.23 (d, J=6.0 Hz, 2H), 2.15 (s, 3H), 1.10 (s, 6H). LCMS for $C_{21}H_{24}F_3N_6O_4$ (M+H)$^+$: m/z=481.2; Found: 481.2.

Examples 260 and 285

Examples 260 and 285 were synthesized according to procedures analogous to those presented in Example 284. The data are listed in Table 22.

Step 1. Ethyl 8-amino-3-(5-(3-amino-1,1,1-trifluoro-2-hydroxy-3-oxopropan-2-yl)-2-methylphenyl)imidazo[1,2-a]pyrazine-6-carboxylate

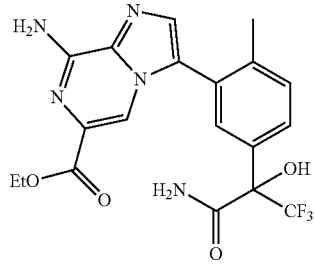

TABLE 22

| Ex. No. | Name | R$^1$ | LCMS [M + H]$^+$ | NMR Spectra |
|---|---|---|---|---|
| 260 | 8-Amino-3-(5-(3-amino-1,1,1-trifluoro-2-hydroxy-3-oxopropan-2-yl)-2-methylphenyl)-N-(4-hydroxybicyclo[2.2.1]heptan-1-yl)imidazo[1,2-a]pyrazine-6-carboxamide trifluoroacetate salt (single enantiomer) | | 519.2 | $^1$H NMR (400 MHz, DMSO-$d_6$) δ 8.12 (br s, 1H), 7.78 (dd, J = 8.3, 2.0 Hz, 1H), 7.75-7.71 (m, 2H), 7.71-7.63 (m, 3H), 7.61 (s, 1H), 7.58-7.42 (br s, 1H), 7.54 (d, J = 8.3 Hz, 1H), 2.15 (s, 3H), 2.05-1.90 (m, 2H), 1.88-1.77 (m, 2H), 1.82 (s, 3H), 1.76-1.63 (m, 2H), 1.63-1.49 (m, 2H). |
| 285 | 8-Amino-3-(5-(3-amino-1,1,1-trifluoro-2-hydroxy-3-oxopropan-2-yl)-2-methylphenyl)-N-(tetrahydro-2H-pyran-4-yl)imidazo[1,2-a]pyrazine-6-carboxamide | | 493.2 | |

Example 288. 8-Amino-3-(5-(3-amino-1,1,1-trifluoro-2-hydroxy-3-oxopropan-2-yl)-2-methylphenyl)-N-(3-fluorobicyclo[1.1.1]pentan-1-yl)imidazo[1,2-a]pyrazine-6-carboxamide trifluoroacetate salt

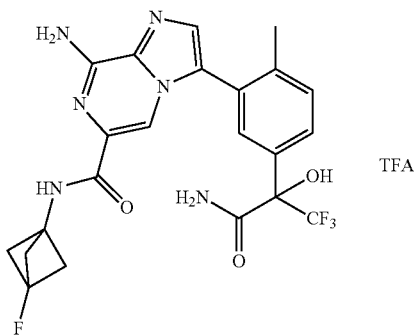 [SMILES: Cc1ccc(C(O)(C(N)=O)C(F)(F)F)cc1-c1cnc2c(N)nc(C(=O)NC34CC(F)(C3)C4)cn12]

In a microwave vial, 2-(3-(8-amino-6-bromoimidazo[1,2-a]pyrazin-3-yl)-4-methylphenyl)-3,3,3-trifluoro-2-hydroxypropanamide (0.233 g, 0.525 mmol) (single enantiomer) was dissolved in ethanol (14.0 mL) and treated with triethylamine (0.292 mL, 2.10 mmol). The reaction mixture was degassed with nitrogen for 5 min, treated with dichloro[1,1'-bis(diphenylphosphino)ferrocene]palladium (II) dichloromethane adduct (0.043 g, 0.052 mmol), and degassed with nitrogen for another 5 min. The vial was capped and the solution was saturated with CO by bubbling the gas through the reaction subsurface for 5 min. The reaction mixture was heated at 80° C. overnight. The reaction mixture was cooled to RT, passed through a 0.45 μm filter, and rinsed with methanol. The filtrate was purified by flash column chromatography using methanol in dichloromethane (0%-10%) to give the desired product (172 mg, 75.1%) as a white solid. LCMS for $C_{19}H_{19}F_3N_5O_4$ (M+H)$^+$: m/z=438.1; Found: 438.0.

Step 2. 8-Amino-3-(5-(3-amino-1,1,1-trifluoro-2-hydroxy-3-oxopropan-2-yl)-2-methylphenyl)imidazo[1,2-a]pyrazine-6-carboxylic acid

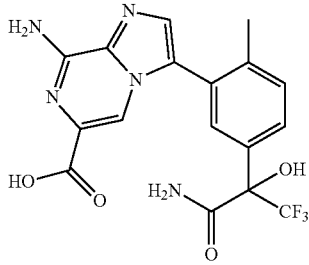 [SMILES: Cc1ccc(C(O)(C(N)=O)C(F)(F)F)cc1-c1cnc2c(N)nc(C(=O)O)cn12]

The desired compound was prepared according to the procedure of Example 81, Step 8, using ethyl 8-amino-3-(5-(3-amino-1,1,1-trifluoro-2-hydroxy-3-oxopropan-2-yl)-2-methylphenyl)imidazo[1,2-a]pyrazine-6-carboxylate in place of methyl 8-amino-3-(2-(methyl-d₃)-5-(1,1,1-trifluoro-2-hydroxypropan-2-yl)phenyl)imidazo[1,2-a]pyrazine-6-carboxylate as the starting material. LCMS for $C_{17}H_{15}F_3N_5O_4$ $(M+H)^+$: m/z=410.1; Found: 410.0.

Step 3. 8-Amino-3-(5-(3-amino-1,1,1-trifluoro-2-hydroxy-3-oxopropan-2-A-2-methylphenyl)-N-(3-fluorobicyclo[1.1.1]pentan-1-yl)imidazo[1,2-a]pyrazine-6-carboxamide, TFA A vial was charged with HATU (6.97 mg, 0.018 mmol), 8-amino-3-(5-(3-amino-1,1,1-trifluoro-2-hydroxy-3-oxopropan-2-yl)-2-methylphenyl)imidazo[1,2-a]pyrazine-6-carboxylic acid (0.005 g, 0.012 mmol), and 3-fluorobicyclo[1.1.1]pentan-1-amine, HCl (2.52 mg, 0.018 mmol) followed by DMF (0.244 mL) and stirred at RT for 5 min. The reaction mixture was treated with triethylamine (5.11 μl, 0.037 mmol) and stirred at RT for 30 min. The reaction mixture was diluted with methanol and water and purified via preparative LCMS (XBridge® C18 Column, eluting with a gradient of acetonitrile in water with 0.1% trifluoroacetic acid, at flow rate of 60 mL/min) to give the desired product (2.20 mg, 29.7%) as a white solid. LCMS for $C_{22}H_{21}F_4N_6O_3$ $(M+H)^+$: m/z=493.2; Found: 493.1.

Example 289. 8-Amino-N-(3-cyano-1,1,1-trifluoropropan-2-yl)-3-(2-methyl-5-(1,1,1-trifluoro-2-hydroxy-3-((methyl-d3)amino)-3-oxopropan-2-yl)phenyl)imidazo[1,2-a]pyrazine-6-carboxamide trifluoroacetate salt

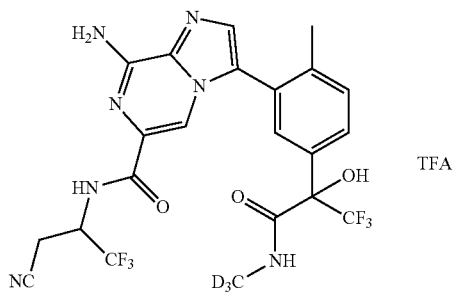 [SMILES: [2H]C([2H])([2H])NC(=O)C(O)(c1ccc(C)c(-c2cnc3c(N)nc(C(=O)NC(CC#N)C(F)(F)F)cn23)c1)C(F)(F)F]

Step 1. Ethyl 2-(3-bromo-4-methylphenyl)-2-oxoacetate

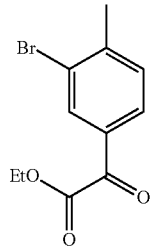

A round bottom flask containing ethyl 2-oxo-2-(p-tolyl)acetate (4.26 g, 22.16 mmol) [Oakwood 023031] was cooled to 0° C. and treated with sulfuric acid (11.8 mL, 222 mmol) slowly. The reaction mixture was maintained at 0° C., treated with N-bromosuccinimide (4.14 g, 23.3 mmol) portionwise, and stirred at 0° C. for 1 h. A mixture of water (25 mL) and MTBE (25 mL) was cooled to 0° C. The reaction mixture was added slowly to the water/MTBE mixture. The aqueous layer was separated and re-extracted with MTBE. The combined organic layers were washed with 10% $Na_2S_2O_3$ and brine, dried over magnesium sulfate, filtered, and concentrated to a light yellow oil. Purification by flash column chromatography using ethyl acetate in hexanes (0%-20%) gave the desired product (5.71 g, 95.0%) as a light yellow oil. $^1$H NMR (400 MHz, $CDCl_3$) δ 8.22 (d, J=1.8 Hz, 1H), 7.89 (dd, J=7.9, 1.8 Hz, 1H), 7.40 (d, J=7.9 Hz, 1H), 4.48 (q, J=7.1 Hz, 2H), 2.51 (s, 3H), 1.45 (t, J=7.1 Hz, 3H).

Step 2. Ethyl 2-(3-bromo-4-methylphenyl)-3,3,3-trifluoro-2-hydroxypropanoate

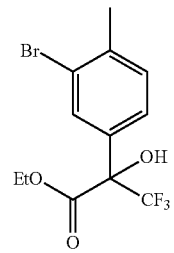

A solution of ethyl 2-(3-bromo-4-methylphenyl)-2-oxoacetate (4.75 g, 17.5 mmol) in tetrahydrofuran (35.0 mL) was treated with trimethyl(trifluoromethyl)silane (3.63 ml, 24.5 mmol) followed by cesium carbonate (2.85 g, 8.76 mmol) and stirred at 20° C. for 1 h. The reaction mixture was filtered to remove the cesium carbonate. The filtrate was concentrated to an oil that was placed under vacuum for 1 h. The crude oil was diluted with tetrahydrofuran (35.0 mL), treated with 1.0 M tetrabutylammonium fluoride in tetrahydrofuran (1.75 ml, 1.75 mmol) and water (4.10 mL), and stirred at 20° C. for 30 min. The reaction mixture was diluted with water and ethyl acetate. The organic layer was separated and the aqueous layer was extracted with ethyl acetate (2×). The combined organic layers were washed with brine, dried over magnesium sulfate, filtered, and concentrated to give a light yellow oil. Purification by flash column chromatography using ethyl acetate in hexanes (0%-20%) gave the desired product (5.90 g, 98.7%) as a light yellow oil. LCMS for $C_{12}H_{13}BrF_3O_3$ (M+H)$^+$: m/z=341.0, 343.0; Found: 341.0, 343.0.

Step 3. First Eluting Enantiomer of ethyl 2-(3-bromo-4-methylphenyl)-3,3,3-trifluoro-2-hydroxypropanoate

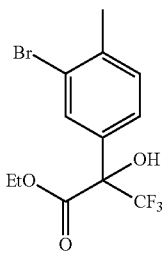

The racemic mixture of ethyl 2-(3-bromo-4-methylphenyl)-3,3,3-trifluoro-2-hydroxypropanoate was separated via preparative chiral HPLC (Phenomenex Lux Amylose-1 [21.2×250 mm, 5 micron], eluting with 10% ethanol in hexanes, at flow rate of 20 mL/min, loading ~81 mg in 1 mL ethanol). The first eluting enantiomer had a retention time of 5.1 min. The second eluting enantiomer had a retention time of 6.5 min.

Peak 1: $^1$H NMR (400 MHz, CDCl$_3$) δ 7.96 (d, J=1.7 Hz, 1H), 7.72-7.56 (m, 1H), 7.25-7.21 (m, 1H), 4.52-4.33 (m, 2H), 4.31 (d, J=1.0 Hz, 1H), 2.40 (s, 3H), 1.37 (t, J=7.1 Hz, 3H).

Step 4. 2-(3-Bromo-4-methylphenyl)-3,3,3-trifluoro-2-hydroxy-N-(methyl-d3)propanamide

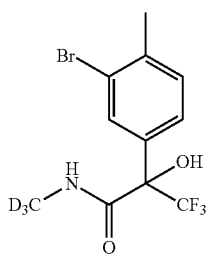 [SMILES: [2H]C([2H])([2H])NC(=O)C(O)(c1ccc(C)c(Br)c1)C(F)(F)F]

A solution of ethyl 2-(3-bromo-4-methylphenyl)-3,3,3-trifluoro-2-hydroxypropanoate (1.50 g, 4.40 mmol) (first eluting enantiomer from Step 3) and methan-d$_3$-amine hydrochloride (1.55 g, 22.0 mmol) in tetrahydrofuran (36.6 mL) was treated with triethylamine (6.12 mL, 44.0 mmol) and cooled to 0° C. The reaction mixture was treated with 2.0 M trimethylaluminum in toluene (11.0 mL, 22.0 mmol) over 5 min, stirred at RT for 2 h and then at 80° C. overnight. The reaction mixture was cooled to RT and diluted with 1 N HCl (150 mL) that had been cooled in an ice bath. The reaction mixture was warmed to RT and extracted with ethyl acetate (3×100 mL). The combined organic layers were washed with saturated aqueous sodium bicarbonate and brine, dried over magnesium sulfate, filtered, and concentrated to a pale yellow oil. Purification by flash column chromatography using methanol in dichloromethane (0%-10%) gave the desired product (1.46 g, 98.7%) as a colorless oil. LCMS for $C_{11}H_9D_3BrF_3NO_2$ (M+H)$^+$: m/z=329.0, 331.0; Found: 329.1, 331.1.

Step 5. 3,3,3-Trifluoro-2-hydroxy-N-(methyl-d3)-2-(4-methyl-3-(4,4,5,5-tetramethyl-1,3,2-dioxaborolan-2-yl)phenyl)propanamide

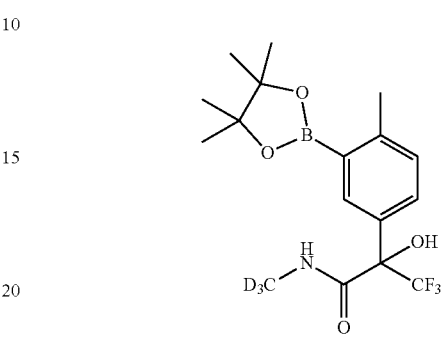

The desired compound was prepared according to the procedure of Example 1, Step 5, using 2-(3-bromo-4-methylphenyl)-3,3,3-trifluoro-2-hydroxy-N-(methyl-d3)propanamide in place of 2-(3-bromo-4-methylphenyl)-3,3,3-trifluoro-2-hydroxypropanamide as the starting material. LCMS for $C_{17}H_{21}D_3BF_3NO_4$ (M+H)$^+$: m/z=377.2; Found: 377.1.

Step 6. 2-(3-(8-Amino-6-bromoimidazo[1,2-a]pyrazin-3-yl)-4-methylphenyl)-3,3,3-trifluoro-2-hydroxy-N-(methyl-d3)propanamide

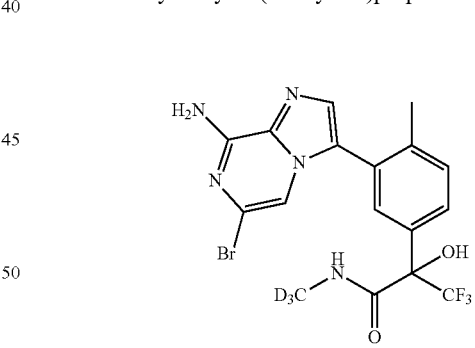

The desired compound was prepared according to the procedure of Example 28, Step 2, using 3,3,3-trifluoro-2-hydroxy-N-(methyl-d$_3$)-2-(4-methyl-3-(4,4,5,5-tetramethyl-1,3,2-dioxaborolan-2-yl)phenyl)propanamide in place of 1,1-difluoro-2-(4-methyl-3-(4,4,5,5-tetramethyl-1,3,2-dioxaborolan-2-yl)phenyl)propan-2-ol as the starting material. LCMS for $C_{17}H_{13}D_3BrF_3N_5O_2$ (M+H)$^+$: m/z=461.1, 463.1; Found: 461.0, 463.0.

Step 7. Ethyl 8-amino-3-(2-methyl-5-(1,1,1-trifluoro-2-hydroxy-3-((methyl-d3)amino)-3-oxopropan-2-yl)phenyl)imidazo[1,2-a]pyrazine-6-carboxylate

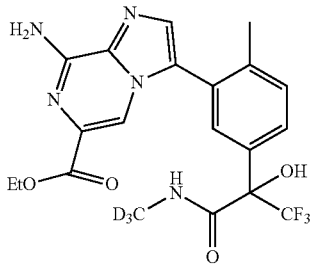 [SMILES: [2H]C([2H])([2H])NC(=O)C(O)(c1ccc(C)c(-c2cnc3c(N)nc(C(=O)OCC)cn23)c1)C(F)(F)F]

The desired compound was prepared according to the procedure of Example 288, Step 1, using 2-(3-(8-amino-6-bromoimidazo[1,2-a]pyrazin-3-yl)-4-methylphenyl)-3,3,3-trifluoro-2-hydroxy-N-(methyl-d$_3$)propanamide in place of 2-(3-(8-amino-6-bromoimidazo[1,2-a]pyrazin-3-yl)-4-methylphenyl)-3,3,3-trifluoro-2-hydroxypropanamide as the starting material. LCMS for $C_{20}H_{18}D_3F_3N_5O_4$ $(M+H)^+$: m/z=455.2; Found: 455.1.

Step 8. 8-Amino-3-(2-methyl-5-(1,1,1-trifluoro-2-hydroxy-3-((methyl-d3)amino)-3-oxopropan-2-yl)phenyl)imidazo[1,2-a]pyrazine-6-carboxylic acid

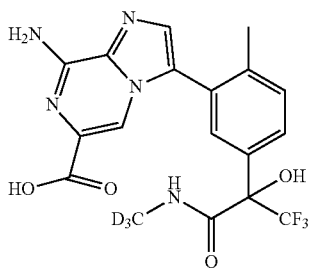 [SMILES: [2H]C([2H])([2H])NC(=O)C(O)(c1ccc(C)c(-c2cnc3c(N)nc(C(=O)O)cn23)c1)C(F)(F)F]

The desired compound was prepared according to the procedure of Example 81, Step 8, using ethyl 8-amino-3-(2-methyl-5-(1,1,1-trifluoro-2-hydroxy-3-((methyl-d3)amino)-3-oxopropan-2-yl)phenyl)imidazo[1,2-a]pyrazine-6-carboxylate in place of methyl 8-amino-3-(2-(methyl-d$_3$)-5-(1,1,1-trifluoro-2-hydroxypropan-2-yl)phenyl)imidazo[1,2-a]pyrazine-6-carboxylate as the starting material. LCMS for $C_{18}H_{14}D_3F_3N_5O_4$ $(M+H)^+$: m/z=427.1; Found: 427.2.

Step 9. 8-Amino-N-(3-cyano-1,1,1-trifluoropropan-2-yl)-3-(2-methyl-5-(1,1,1-trifluoro-2-hydroxy-3-((methyl-d3)amino)-3-oxopropan-2-yl)phenyl)imidazo[1,2-a]pyrazine-6-carboxamide, TFA The desired compound was prepared according to the procedure of Example 288, Step 3, using 8-amino-3-(2-methyl-5-(1,1,1-trifluoro-2-hydroxy-3-((methyl-d3)amino)-3-oxopropan-2-yl)phenyl)imidazo[1,2-a]pyrazine-6-carboxylic acid in place of 8-amino-3-(5-(3-amino-1,1,1-trifluoro-2-hydroxy-3-oxopropan-2-yl)-2-methylphenyl)imidazo[1,2-a]pyrazine-6-carboxylic acid and 3-amino-4,4,4-trifluorobutanenitrile in place of 3-fluorobicyclo[1.1.1]pentan-1-amine hydrochloride as the starting materials. LCMS for $C_{22}H_{17}D_3F_6N_7O_3$ $(M+H)^+$: m/z=547.2; Found: 547.2.

Example A. THP-1 RPS6 ELISA Assay

To measure the Phosphorylated Ribosomal Protein S6 (RPS6) in cell lysates, THP-1 cells (Human Acute Monocytic Leukemia) are purchased from ATCC (Manassas, Va.) and maintained in RPMI with 10% FBS (Gibco/Life Technologies, Carlsbad, Calif.). For the assay, THP-1 cells are serum starved overnight in RPMI, then plated in RPMI (2×10$^5$ cells/well in 90 µL) into 96-well flat-bottom tissue culture treated plates (Corning, Corning, N.Y.), in the presence or absence of a concentration range of test compounds. Covered plates are incubated for 2 hours at 37° C., 5% CO$_2$ then treated with or without 10 nM MCP-1 (MYBioSource, San Diego, Calif.) for 15 minutes at 37° C., 5% CO$_2$. Plates are centrifuged at 1600 RPM and supernatants are removed. Cells are lysed in Lysis Buffer (Cell Signaling, Danvers, Mass.) with Protease Inhibitor (Calbiochem/EMD, Germany), PMSF (Sigma, St Louis Mo.), HALTS (Thermo Fisher, Rockford, Ill.) for 30 min on wet ice. Cell lysates are frozen at −80° C. before testing. The lysates are tested in the Human/Mouse/Rat Phospho-RPS6 ELISA (R&D Systems, Inc. Minn, Minn.). The plate is measured using a microplate reader (SpectraMax M5—Molecular Devices, LLC Sunnyvale, Calif.) set to 450 nm with a wavelength correction of 540. IC$_{50}$ determination is performed by fitting the curve of inhibitor percent inhibition versus the log of the inhibitor concentration using the GraphPad Prism 5.0 software.

Example B. PI3K-γ Scintillation Proximity Assay

Materials

[γ-$^{33}$P]ATP (10 mCi/mL) and Wheat Germ Agglutinin (WGA) YSi SPA Scintillation Beads was purchased from PerkinElmer (Waltham, Mass.). Lipid kinase substrate, D-myo-Phosphatidylinositol 4,5-bisphosphate (PtdIns(4,5)P2)D (+)-sn-1,2-di-O-octanoylglyceryl, 3-O-phospho linked (PIP2), CAS 204858-53-7, was purchased from Echelon Biosciences (Salt Lake City, Utah). PI3Kγ (p110γ) Recombinant Human Protein was purchased from Life technology (Grand Island, N.Y.). ATP, MgCl$_2$, DTT, EDTA, MOPS and CHAPS were purchased from SigmaAldrich (St. Louis, Mo.).

The kinase reaction was conducted in polystyrene 384-well Greiner Bio-one white plate from Thermo Fisher Scientific in a final volume of 25 µL. Inhibitors were first diluted serially in DMSO and added to the plate wells before the addition of other reaction components. The final concentration of DMSO in the assay was 2%. The PI3Kγ assay was carried out at room temperature in 20 mM MOPS, pH 6.7, 10 mM MgCl$_2$, 5 mM DTT and CHAPS 0.03%. Reactions were initiated by the addition of ATP, the final reaction mixture consisted of 20 µM PIP2, 2 µM ATP, 0.5 µCi [γ-$^{33}$P] ATP, 13 nM PI3Kγ. Reactions were incubated for 120 min and terminated by the addition of 40 µL SPA beads suspended in quench buffer: 163 mM potassium phosphate pH 7.8, 20% glycerol, 25 mM EDTA. The final concentration of SPA beads is 1.0 mg/mL. After the plate sealing, plates were shaken overnight at room temperature and centrifuged at 1500 rpm for 10 min, the radioactivity of the product was determined by scintillation counting on Topcount (Perkin-Elmer). IC$_{50}$ determination was performed by fitting the curve of percent of the solvent control activity versus the log of the inhibitor concentration using the GraphPad Prism 6.0 software.

Example C. PI3Kδ Scintillation Proximity Assay

Materials

[γ-$^{33}$P]ATP (10 mCi/mL) and Wheat Germ Agglutinin (WGA) YSi SPA Scintillation Beads was purchased from PerkinElmer (Waltham, Mass.). Lipid kinase substrate, D-myo-Phosphatidylinositol 4,5-bisphosphate (PtdIns(4,5) P2)D (+)-sn-1,2-di-O-octanoylglyceryl, 3-O-phospho linked (PIP2), CAS 204858-53-7, was purchased from Echelon Biosciences (Salt Lake City, Utah). PI3Kδ (p110δ/p85α) Recombinant Human Protein was purchased from Eurofins (St Charles, Mo.). ATP, $MgCl_2$, DTT, EDTA, MOPS and CHAPS were purchased from SigmaAldrich (St. Louis, Mo.).

The kinase reaction was conducted in polystyrene 384-well Greiner Bio-one white plate from Thermo Fisher Scientific in a final volume of 25 μL. Inhibitors were first diluted serially in DMSO and added to the plate wells before the addition of other reaction components. The final concentration of DMSO in the assay was 2%. The PI3Kδ assay was carried out at room temperature in 20 mM MOPS, pH 6.7, 10 mM $MgCl_2$, 5 mM DTT and CHAPS 0.03%. Reactions were initiated by the addition of ATP, the final reaction mixture consisted of 20 μM PIP2, 2 μM ATP, 0.5 μCi [γ-$^{33}$P] ATP, 3.4 nM PI3Kδ. Reactions were incubated for 120 min and terminated by the addition of 40 μL SPA beads suspended in quench buffer: 163 mM potassium phosphate pH 7.8, 20% glycerol, 25 mM EDTA. The final concentration of SPA beads is 1.0 mg/mL. After the plate sealing, plates were shaken overnight at room temperature and centrifuged at 1500 rpm for 10 min, the radioactivity of the product was determined by scintillation counting on Topcount (PerkinElmer). $IC_{50}$ determination was performed by fitting the curve of percent of the solvent control activity versus the log of the inhibitor concentration using the GraphPad Prism 6.0 software.

The compounds of the Examples were tested in the assays described in Examples A, B and C, and found to have the $IC_{50}$ values shown in Table 23.

TABLE 23

| Ex. No. | PI3Kγ $IC_{50}$ (nM) | PI3Kδ $IC_{50}$ (nM) | PI3Kγ_THP1_RPS6_ELISA $IC_{50}$ (nM) |
|---|---|---|---|
| 1 | + | ++ | ## |
| 2 | + | +++ | ### |
| 3 | + | +++ | — |
| 4 | + | ++ | ## |
| 5 | + | ++ | ### |
| 6 | + | ++ | ## |
| 7 | + | ++ | — |
| 8 | + | +++ | ### |
| 9 | + | ++ | ## |
| 10 | + | + | ## |
| 11 | + | + | ## |
| 12 | + | + | # |
| 13 | + | ++ | ## |
| 14 | + | ++ | # |
| 15 | + | ++ | ## |
| 16 | + | ++ | ### |
| 17 | + | +++ | — |
| 18 | + | ++ | ## |
| 19 | + | ++ | #### |
| 20 | + | + | ## |
| 21 | + | + | ## |
| 22 | + | + | ## |
| 23 | + | +++ | ### |

TABLE 23-continued

| Ex. No. | PI3Kγ $IC_{50}$ (nM) | PI3Kδ $IC_{50}$ (nM) | PI3Kγ_THP1_RPS6_ELISA $IC_{50}$ (nM) |
|---|---|---|---|
| 24 | + | +++ | ### |
| 25 | + | ++ | ## |
| 26 | + | +++ | ### |
| 27 | + | ++ | ## |
| 28 | + | + | ## |
| 29 | + | ++ | ## |
| 30 | + | ++ | ## |
| 31 | + | ++ | ## |
| 32 | + | +++ | — |
| 33 | + | ++ | # |
| 34 | + | + | ## |
| 35 | + | + | # |
| 36 | + | + | ## |
| 37 | + | + | # |
| 38 | + | + | # |
| 39 | + | + | # |
| 40 | + | + | ## |
| 41 | + | ++ | ## |
| 42 | + | ++ | ## |
| 43 | + | ++ | ### |
| 44 | + | + | # |
| 45 | + | + | ## |
| 46 | + | ++ | # |
| 47 | + | + | # |
| 48 | + | ++ | ## |
| 49 | + | ++ | ## |
| 50 | + | ++ | ## |
| 51 | + | + | # |
| 52 | + | ++ | ## |
| 53 | + | — | — |
| 54 | + | — | — |
| 55 | + | — | — |
| 56 | + | — | — |
| 57 | + | — | — |
| 58 | ++ | — | — |
| 59 | + | +++ | — |
| 60 | + | +++ | #### |
| 61 | + | ++ | ## |
| 62 | + | ++ | #### |
| 63 | + | ++ | ## |
| 64 | + | +++ | — |
| 65 | + | ++ | — |
| 66 | + | + | # |
| 67 | + | ++ | — |
| 68 | + | + | — |
| 69 | + | + | # |
| 70 | + | + | # |
| 71 | + | + | # |
| 72 | + | ++ | # |
| 73 | + | ++ | ### |
| 74 | +++ | +++ | — |
| 75 | + | ++ | ## |
| 76 | + | ++ | ## |
| 77 | + | ++ | — |
| 78 | + | ++ | ## |
| 79 | + | +++ | ## |
| 80 | + | +++ | — |
| 81 | + | + | ## |
| 82 | + | + | # |
| 83 | + | ++ | # |
| 84 | + | ++ | ## |
| 85 | + | +++ | ## |
| 86 | + | ++ | ## |
| 87 | + | + | ## |
| 88 | + | ++ | ## |
| 89 | + | + | # |
| 100 | + | ++ | ## |
| 106 | + | ++ | ## |
| 108 | + | + | # |
| 112 | + | +++ | ### |
| 117 | + | +++ | #### |
| 118 | + | + | # |
| 120 | + | ++ | #### |
| 128 | + | + | # |
| 129 | + | + | # |
| 136 | + | ++ | # |
| 162 | + | ++ | ## |

TABLE 23-continued

| Ex. No. | PI3Kγ IC$_{50}$ (nM) | PI3Kδ IC$_{50}$ (nM) | PI3Kγ_THP1_RPS6_ELISA IC$_{50}$ (nM) |
|---|---|---|---|
| 169 | ++ | +++ | — |
| 173 | ++ | +++ | — |
| 207 | + | + | # |
| 208 | + | + | # |
| 211 | + | ++ | — |
| 212 | + | ++ | — |
| 214 | + | ++ | ## |
| 221 | + | ++ | — |
| 224 | ++ | +++ | — |
| 233 | + | ++ | ## |
| 235 | + | ++ | — |
| 253 | + | ++ | ## |
| 255 | + | + | # |
| 260 | + | ++ | ### |
| 262 | + | ++ | #### |
| 264 | + | + | # |
| 267 | + | + | # |
| 268 | + | ++ | ## |
| 277 | ++ | ++ | — |
| 278 | + | ++ | ## |
| 279 | + | ++ | — |
| 283 | + | + | #### |
| 284 | + | ++ | # |
| 285 | + | +++ | ## |
| 288 | + | ++ | # |
| 289 | + | ++ | # |

+ refers to IC50 of ≤100 nM;
++ refers to IC50 of ≤500 nM;
+++ refers to an IC50 of <2000 nM;
++++ refers to an IC50 of ≥2000 nM.
# refers to IC50 of ≤100 nM;
## refers to IC50 of ≤500 nM;
### refers to IC50 of <1000 nM;
#### refers to an IC50 of ≥1000 nM.
— refers to data not available.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula (I):

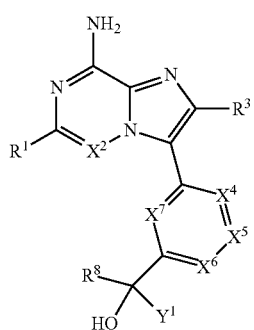

(I)

or a pharmaceutically acceptable salt thereof; wherein:

$X^2$ is N or $CR^2$;
$X^4$ is N or $CR^4$;
$X^5$ is N or $CR^5$;
$X^6$ is N or $CR^6$;
$X^7$ is N or $CR^7$;
provided that $X^4$, $X^5$, and $X^6$ are not all N;
$Y^1$ is a $C_{1-6}$ haloalkyl, wherein each halogen is selected from F or Cl, wherein the haloalkyl is optionally substituted with 1 or 2 independently selected $Y^2$ substituents;
$R^1$ is selected from H, D, halo, $C_{1-6}$ alkyl, $C_{2-6}$ alkenyl, $C_{2-6}$ alkynyl, $C_{1-6}$ haloalkyl, 6-10 membered aryl, $C_{3-10}$-cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NR$^a$R$^a$, NR$^a$NR$^a$R$^a$, NR$^a$C(O)R$^a$, NR$^a$C(O)OR$^a$, NR$^a$C(O)NR$^a$R$^a$, C(=NR$^i$)R$^a$, C(=NR$^i$)NR$^a$R$^a$, NR$^a$C(=NR$^i$)NR$^a$R$^a$, NR$^a$C(=NOH)NR$^a$R$^a$, NR$^a$C(=NCN)NR$^a$R$^a$, NR$^a$S(O)R$^a$, NR$^a$S(O)$_2$R$^a$, NR$^a$S(O)(=NR$^i$)R$^a$, NR$^a$S(O)$_2$NR$^a$R$^a$, S(O)R$^a$, S(O)NR$^a$R$^a$, S(O)$_2$R$^a$, OS(O)(=NR$^i$)R$^a$, SF$_5$, P(O)R$^a$R$^a$, P(O)(OR$^a$)(OR$^a$), B(OR$^a$)$_2$, and S(O)$_2$NR$^a$R$^a$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^1$ are each optionally substituted with 1, 2, 3, 4, 5, 6, 7, or 8 independently selected $R^b$ substituents;
$R^2$, $R^3$, $R^4$, $R^5$, $R^6$ and $R^7$ are each independently selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl, OH, NO$_2$, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^2$, $R^3$, $R^4$, $R^5$, $R^6$ and $R^7$ are each optionally substituted with 1, 2, 3, or 4 independently selected $R^h$ substituents;
$R^8$ is selected from H, D, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$cycloalkyl-$C_{1-6}$ alkyl-, 5-10 membered heteroaryl-$C_{1-6}$ alkyl-, 4-10 membered heterocycloalkyl-$C_{1-6}$ alkyl-, NO$_2$, C(O)R$^a$, C(O)NR$^a$R$^a$, C(O)OR$^a$, C(=NR$^i$)R$^a$, $C(=NR^i)NR^aR^a$, $SF_5$, $-P(O)R^aR^a$, $-P(O)(OR^a)(OR^a)$, $B(OR^a)_2$, and $S(O)_2NR^aR^a$, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^8$ are each optionally substituted with 1, 2, 3, or 4 independently selected $R^9$ substituents;

or any two $R^4$, $R^5$, $R^6$ and $R^7$ substituents, together with the ring atoms to which they attached form a 4-, 5-, 6-, or 7-membered aryl, cycloalkyl, heteroaryl, or heterocycloalkyl group optionally substituted with 1, 2, 3, or 4 independently selected $R^b$ substituents;

or $Y^1$ and $R^8$, together with the carbon atom to which they are attached, form a 4-, 5-, 6-, or 7-membered cycloalkyl or heterocycloalkyl group optionally substituted with 1, 2, 3, or 4 independently selected $R^9$ substituents;

each $R^i$ is independently selected from H, CN, OH, $C_{1-4}$ alkyl, and $C_{1-4}$ alkoxy;

each $Y^2$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-10}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^a$ is independently selected from H, D, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl- and 4-10 membered heterocycloalkyl-$C_{1-6}$ alkyl- of $R^a$ is each optionally substituted with 1, 2, 3, or 4 independently selected $R^b$ substituents;

each $R^b$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^c$, $SR^c$, $NHOR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^cC(O)OR^c$, $NR^cC(O)NR^cR^c$, $C(=NR^i)R^c$, $C(=NR^i)NR^cR^c$, $NR^cC(=NR^i)NR^cR^c$, $NR^cC(=NOH)NR^cR^c$, $NR^cC(=NCN)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$, $SF_5$, $-P(O)R^cR^c$, $-P(O)(OR^c)(OR^c)$, $B(OR^c)_2$, and $S(O)_2NR^cR^c$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^b$ is each optionally substituted with 1, 2, 3, or 4 independently selected $R^d$ substituents;

each $R^9$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^k$, $SR^k$, $NHOR^k$, $C(O)R^k$, $C(O)NR^kR^k$, $C(O)OR^k$, $OC(O)R^k$, $OC(O)NR^kR^k$, $NR^kR^k$, $NR^kC(O)R^k$, $NR^k-C(O)OR^k$, $NR^kC(O)NR^kR^k$ $C(=NR^i)R^k$, $C(=NR^i)NR^kR^k$, $NR^kC(=NR^i)NR^kR^k$, $NR^kC(=NOH)NR^kR^k$ $NR^kC(=NCN)NR^kR^k$, $NR^kS(O)R^k$, $NR^kS(O)_2R^k$, $NR^kS(O)_2NR^kR^k$, $S(O)R^k$, $S(O)NR^kR^k$, $S(O)_2R^k$, $SF_5$, $-P(O)R^kR^k$, $-P(O)(OR^k)(OR^k)$, $B(OR^k)_2$, and $S(O)_2NR^kR^k$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^9$ is each optionally substituted with 1, 2, 3, or 4 independently selected $R^q$ substituents;

each $R^c$ is independently selected from H, D, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl- and 4-10 membered heterocycloalkyl-$C_{1-6}$ alkyl- of $R^c$ is each optionally substituted with 1, 2, 3, or 4 independently selected $R^d$ substituents;

or two $R^c$ substituents, together with the nitrogen atom to which they attached form a 4-, 5-, 6-, or 7-membered heteroaryl or heterocycloalkyl group optionally substituted with 1, 2, 3, or 4 independently selected $R^d$ substituents;

each $R^d$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^e$, $SR^e$, $NHOR^e$, $C(O)R^e$, $C(O)NR^eR^e$, $C(O)OR^e$, $OC(O)R^e$, $OC(O)NR^eR^e$, $NR^eR^e$, $NR^eC(O)R^e$, $NR^e-C(O)OR^e$, $NR^eC(O)NR^eR^e$, $C(=NR^i)R^e$, $C(=NR^i)NR^eR^e$, $NR^eC(=NR^i)NR^eR^e$, $NR^eC(=NOH)NR^eR^e$, $NR^eC(=NCN)NR^eR^e$, $NR^eS(O)R^e$, $NR^eS(O)_2R^e$, $NR^eS(O)_2NR^eR^e$, $S(O)R^e$, $S(O)NR^eR^e$, $S(O)_2R^e$, $SF_5$, $-P(O)R^eR^e$, $-P(O)(OR^e)(OR^e)$, $B(OR^e)_2$, and $S(O)_2NR^eR^e$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^d$ is each optionally substituted with 1, 2, 3 or 4 independently selected $R^f$ substituents;

each $R^e$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl- and 4-7 membered heterocycloalkyl-$C_{1-6}$ alkyl- of $R^e$ is each optionally substituted with 1, 2, 3 or 4 independently selected $R^f$ substituents;

each $R^f$ is independently selected from D, halo, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, 4-7 membered heterocycloalkyl-$C_{1-6}$ alkyl-, CN, $NO_2$, $OR^g$, $SR^g$, $NHOR^g$, $C(O)R^g$, $C(O)NR^gR^g$, $C(O)OR^g$, $OC(O)R^g$, $OC(O)NR^gR^g$, $NR^gR^g$, $NR^gC(O)R^g$, $NR^gC(O)OR^g$, $NR^gC(O)NR^gR^g$, $C(=NR^i)R^g$, $C(=NR^i)NR^gR^g$, $NR^gC(=NR^i)NR^gR^g$, $NR^gC(=NOH)NR^gR^g$, $NR^gC(=NCN)NR^gR^g$, $NR^gS(O)R^g$, $NR^gS(O)_2R^g$, $NR^gS(O)_2NR^gR^g$, $S(O)R^g$, $S(O)NR^gR^g$, $S(O)_2R^g$, $SF_5$, $-P(O)R^gR^g$, $-P(O)(OR^g)(OR^g)$, $B(OR^g)_2$, and $S(O)_2NR^gR^g$, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl- of $R^f$ is each optionally substituted with 1, 2, 3 or 4 independently selected $R^h$ substituents;

each $R^g$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl- and 4-7 membered heterocycloalkyl-$C_{1-6}$ alkyl- of $R^g$ is each optionally substituted with 1, 2, 3 or 4 independently selected $R^h$ substituents;

each $R^h$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl) aminocarbonylamino;

each $R^k$ is independently selected from H, D, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl- and 4-10 membered heterocycloalkyl-$C_{1-6}$ alkyl- of $R^k$ is each optionally substituted with 1, 2, 3, or 4 independently selected $R^q$ substituents;

each $R^q$ is independently selected from D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, 4-10 membered heterocycloalkyl-$C_{1-6}$ alkyl-, CN, $NO_2$, $OR^m$, $SR^m$, $NHOR^m$, $C(O)R^m$, $C(O)NR^mR^m$, $C(O)OR^m$, $OC(O)R^m$, $OC(O)NR^mR^m$, $NHR^m$, $NR^mR^m$, $NR^mC(O)R^m$, $NR^mC(O)OR^m$, $NR^mC(O)NR^mR^m$, $C(=NR^i)R^m$, $C(=NR^i)NR^mR^m$, $NR^mC(=NR^i)NR^mR^m$, $NR^mC(=NOH)NR^mR^m$, $NR^mC(=NCN)NR^mR^m$, $NR^mS(O)R^m$, $NR^mS(O)_2R^m$, $NR^mS(O)_2NR^mR^m$, $S(O)R^m$, $S(O)NR^mR^m$, $S(O)_2R^m$, $SF_5$, $-P(O)R^mR^m$, $P(O)(OR^m)(OR^m)$, $B(OR^m)_2$, and $S(O)_2NR^mR^m$, wherein the $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, 6-10 membered aryl-$C_{1-6}$ alkyl-, $C_{3-10}$ cycloalkyl-$C_{1-6}$ alkyl-, 5-10 membered heteroaryl-$C_{1-6}$ alkyl-, and 4-10 membered heterocycloalkyl-$C_{1-6}$ alkyl- of $R^q$ is each optionally substituted with 1, 2, 3 or 4 independently selected $R''$ substituents;

each $R^m$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl- and 4-7 membered heterocycloalkyl-$C_{1-6}$ alkyl- of $R^m$ is each optionally substituted with 1, 2, 3 or 4 independently selected $R''$ substituents;

each $R''$ is independently selected from D, halo, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl- $C_{1-6}$ alkyl-, 4-7 membered heterocycloalkyl-$C_{1-6}$ alkyl-, CN, NO$_2$, OR$^o$, SR$^o$, NHOR$^o$, C(O)R$^o$, C(O)NR$^o$R$^o$, C(O)OR$^o$, OC(O)R$^o$, OC(O)NR$^o$R$^o$, NR$^o$R$^o$, NR$^o$C(O)R$^o$, NR$^o$C(O)OR$^o$, NR$^o$C(O)NR$^o$R$^o$, C(=NR$^i$)R$^o$, C(=NR$^i$)NR$^o$R$^o$, NR$^o$C(=NR$^i$)NR$^o$R$^o$, NR$^o$C(=NOH)NR$^o$R$^o$, NR$^o$C(=NCN)NR$^o$R$^o$, NR$^o$S(O)R$^o$, NR$^o$S(O)$_2$R$^o$, NR$^o$S(O)$_2$NR$^o$R$^o$, S(O)R$^o$, S(O)NR$^o$R$^o$, S(O)$_2$R$^o$, and S(O)$_2$NR$^o$R$^o$, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl- of R$^n$ is each optionally substituted with 1, 2, 3 or 4 independently selected R$^h$ substituents; and each R$^o$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl- and 4-7 membered heterocycloalkyl-$C_{1-6}$ alkyl- of R$^o$ is each optionally substituted with 1, 2, 3 or 4 independently selected R$^h$ substituents.

2. The compound of claim 1, or a pharmaceutically acceptable salt thereof, wherein X$^2$ is N or CH.

3. The compound of claim 1, or a pharmaceutically acceptable salt thereof, wherein X$^4$ is CR$^4$.

4. The compound of claim 1, or a pharmaceutically acceptable salt thereof, wherein R$^4$ is selected from H, D, halo, $C_{1-6}$ alkyl, $C_{2-6}$ alkenyl, $C_{2-6}$ alkynyl, $C_{1-6}$ haloalkyl, and $C_{1-6}$ haloalkoxy.

5. The compound of claim 1, or a pharmaceutically acceptable salt thereof, wherein X$^4$ is N.

6. The compound of claim 1, or a pharmaceutically acceptable salt thereof, wherein X$^5$ is CH.

7. The compound of claim 1, or a pharmaceutically acceptable salt thereof, wherein X$^5$ is N.

8. The compound of claim 1, or a pharmaceutically acceptable salt thereof, wherein X$^6$ is CR$^6$.

9. The compound of claim 1, or a pharmaceutically acceptable salt thereof, wherein R$^6$ is selected from H, D, and halo.

10. The compound of claim 1, or a pharmaceutically acceptable salt thereof, wherein X$^6$ is N.

11. The compound of claim 1, or a pharmaceutically acceptable salt thereof, wherein X$^7$ is CH.

12. The compound of claim 1, or a pharmaceutically acceptable salt thereof, wherein X$^7$ is N.

13. The compound of claim 1, or a pharmaceutically acceptable salt thereof, wherein R$^2$, R$^3$, R$^4$, R$^5$, R$^6$ and R$^7$ are each independently selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OR$^a$, and SR$^a$, wherein the $C_{1-6}$ alkyl, $C_{1-6}$ alkoxy, $C_{2-6}$ alkenyl, $C_{2-6}$ alkynyl, $C_{1-6}$ haloalkyl and $C_{1-6}$ haloalkoxy of R$^2$, R$^3$, R$^4$, R$^5$, R$^6$ and R$^7$ are each optionally substituted with 1, 2, 3, or 4 independently selected R$^h$ substituents.

14. The compound of claim 1, or a pharmaceutically acceptable salt thereof, wherein R$^1$ is selected from H, D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, OR$^a$, C(O)R$^a$, C(O)NR$^a$R$^a$, C(O)OR$^a$, NR$^a$R$^a$, NR$^a$C(O)R$^a$, NR$^a$C(O)OR$^a$, NR$^a$C(O)NR$^a$R$^a$, NR$^a$S(O)$_2$NR$^a$R$^a$, NR$^a$S(O)$_2$R$^a$, S(O)$_2$R$^a$, and S(O)$_2$NR$^a$R$^a$, wherein the $C_{1-6}$ alkyl, $C_{2-6}$ alkenyl, $C_{2-6}$ alkynyl, 6-10 membered aryl, $C_{3-10}$ cycloalkyl, 5-10 membered heteroaryl, and 4-10 membered heterocycloalkyl are each optionally substituted with 1, 2, 3, or 4 independently selected R$^b$ substituents.

15. The compound of claim 1, wherein Y$^1$ is selected from CF$_3$, CCl$_3$, CF$_2$H, CCl$_2$H, CF$_2$Y$^2$, CCl$_2$Y$^2$, CFH$_2$, CClH$_2$, CFHY$^2$, CClHY$^2$, CF(Y$^2$)$_2$ and CCl(Y$^2$)$_2$.

16. The compound of claim 1, or a pharmaceutically acceptable salt thereof, wherein R$^8$ is selected from H, D, $C_{1-6}$ alkyl, $C_{1-6}$ alkoxy, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, and 4-10 membered heterocycloalkyl, wherein the $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, 6-10 membered aryl, $C_{3-10}$ cycloalkyl, 5-10 membered heteroaryl, and 4-10 membered heterocycloalkyl are each optionally substituted with 1, 2, 3, or 4 independently selected R$^9$ substituents.

17. The compound of claim 1, or a pharmaceutically acceptable salt thereof, wherein each R$^9$ is independently selected from halo, $C_{1-6}$ alkyl, $C_{1-6}$ haloalkyl, phenyl, $C_{3-6}$ cycloalkyl, 5-6 membered heteroaryl, 4-6 membered heterocycloalkyl, phenyl-$C_{1-3}$ alkyl-, $C_{3-6}$ cycloalkyl-$C_{1-3}$ alkyl-, 5-6 membered heteroaryl-$C_{1-3}$ alkyl-, 4-6 membered heterocycloalkyl-$C_{1-3}$ alkyl-, CN, OR$^k$, C(O)R$^k$, C(O)NR$^k$R$^k$, C(O)OR$^k$, NR$^k$R$^k$, NR$^k$C(O)R$^k$, NR$^k$C(O)OR$^k$, NR$^k$C(O)NR$^k$R$^k$, NR$^k$S(O)$_2$R$^k$, NR$^k$S(O)$_2$NR$^k$R$^k$, S(O)$_2$R$^k$, and S(O)$_2$NR$^k$R$^k$, wherein the $C_{1-6}$ alkyl, $C_{1-6}$ haloalkyl, phenyl, $C_{3-6}$ cycloalkyl, 5-6 membered heteroaryl, 4-6 membered heterocycloalkyl, phenyl-$C_{1-3}$ alkyl-, $C_{3-6}$ cycloalkyl-$C_{1-3}$ alkyl-, 5-6 membered heteroaryl-$C_{1-3}$ alkyl-, and 4-6 membered heterocycloalkyl-$C_{1-3}$ alkyl- of R$^9$ is each optionally substituted with 1, 2, 3, or 4 independently selected R$^q$ substituents.

18. The compound of claim 1, or a pharmaceutically acceptable salt thereof, wherein:

each R$^k$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, 5-6 membered heteroaryl-$C_{1-4}$ alkyl-, and 4-7 membered heterocycloalkyl-$C_{1-4}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, 5-6 membered heteroaryl-$C_{1-4}$ alkyl-, and 4-7 membered heterocycloalkyl-$C_{1-4}$ alkyl- of R$^k$ is each optionally substituted with 1, 2, 3, or 4 independently selected R$^q$ substituents;

each R$^q$ is independently selected from D, halo, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, 4-7 membered heterocycloalkyl-$C_{1-6}$ alkyl-, OH, NO$_2$, CN, halo, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, 4-7 membered heterocycloalkyl-$C_{1-6}$ alkyl- of $R^q$ is each optionally substituted with 1, 2, 3 or 4 independently selected $R^n$ substituents; and each $R^n$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

19. The compound of claim 1, or a pharmaceutically acceptable salt thereof, wherein:

each $R^k$ is independently selected from H, $C_{1-6}$ alkyl, $C_{1-6}$ haloalkyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, 5-6 membered heteroaryl-$C_{1-4}$ alkyl-, and 4-7 membered heterocycloalkyl-$C_{1-4}$ alkyl-, wherein the $C_{1-6}$ alkyl, $C_{1-6}$ haloalkyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, 5-6 membered heteroaryl-$C_{1-4}$ alkyl-, and 4-7 membered heterocycloalkyl-$C_{1-4}$ alkyl- of $R^k$ is each optionally substituted with 1, 2, 3, or 4 independently selected $R^q$ substituents; and each $R^q$ is independently selected halo, $C_{1-6}$ alkyl, $C_{1-6}$ haloalkyl, OH, CN, $C_{1-6}$ alkoxy, $C_{1-6}$ haloalkoxy, amino, $C_{1-6}$ alkylamino, di($C_{1-6}$ alkyl)amino, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, and di($C_{1-6}$ alkyl)aminosulfonyl.

20. The compound of claim 1, or a pharmaceutically acceptable salt thereof, wherein $Y^1$ and $R^8$, together with the carbon atom to which they are attached, form a 4-, 5-, 6-, or 7-membered cycloalkyl group which is optionally substituted by 1 or 2 substituents independently selected from Cl and F.

21. The compound of claim 1, or a pharmaceutically acceptable salt thereof, wherein $R^3$ is H.

22. The compound of claim 1, or a pharmaceutically acceptable salt thereof, wherein $R^3$, $R^5$, and $R^7$ are each H.

23. The compound of claim 1, or a pharmaceutically acceptable salt thereof, wherein each $R^a$ is independently selected from H, D, $C_{1-6}$ alkyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl- of $R^a$ is each optionally substituted with 1, 2, or 3 independently selected $R^b$ substituents.

24. The compound of claim 1, or a pharmaceutically acceptable salt thereof, wherein each $R^b$ is independently selected from halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, $OR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^cC(O)OR^c$, $NR^cC(O)NR^cR^c$, $S(O)R^c$, $S(O)NR^cR^c$, $S(O)_2R^c$, and $S(O)_2NR^cR^c$, wherein the $C_{1-6}$ alkyl, $C_{2-6}$ alkenyl, $C_{2-6}$ alkynyl, 6-10 membered aryl, $C_{3-10}$ cycloalkyl, 5-10 membered heteroaryl, and 4-10 membered heterocycloalkyl are each optionally substituted with 1 or 2 independently selected $R^d$ substituents.

25. The compound of claim 1, or a pharmaceutically acceptable salt thereof, wherein:

each $R^c$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, 5-6 membered heteroaryl-$C_{1-4}$ alkyl-, and 4-7 membered heterocycloalkyl-$C_{1-4}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, 5-6 membered heteroaryl-$C_{1-4}$ alkyl-, and 4-7 membered heterocycloalkyl-$C_{1-4}$ alkyl- of $R^c$ is each optionally substituted with 1, 2, 3, or 4 independently selected $R^d$ substituents;

each $R^d$ is independently selected from D, halo, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, 4-7 membered heterocycloalkyl-$C_{1-6}$ alkyl-, OH, $NO_2$, CN, halo, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, 4-7 membered heterocycloalkyl-$C_{1-6}$ alkyl- of $R^d$ is each optionally substituted with 1, 2, 3 or 4 independently selected $R^f$ substituents; and each $R^f$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

26. The compound of claim 1, or a pharmaceutically acceptable salt thereof, wherein:

$X^2$ is N or $CR^2$;
$X^4$ is $CR^4$;
$X^5$ is N or $CR^5$;
$X^6$ is N or $CR^6$;
$X^7$ is $CR^7$;
wherein 0 or 1 of $X^5$ and $X^6$ are N;
$R^2$ is H, halo, CN, $C_{1-6}$ alkyl, or $C_{1-6}$ haloalkyl;
$R^3$ is H, halo, CN, $C_{1-6}$ alkyl, or $C_{1-6}$ haloalkyl;
$R^4$ is H, halo, CN, $C_{1-6}$ alkyl, or $C_{1-6}$ haloalkyl;
$R^5$ is H, halo, CN, $C_{1-6}$ alkyl, or $C_{1-6}$ haloalkyl;
$R^6$ is H, halo, CN, $C_{1-6}$ alkyl, or $C_{1-6}$ haloalkyl;
$R^7$ is H, halo, CN, $C_{1-6}$ alkyl, or $C_{1-6}$ haloalkyl;
$R^1$ is selected from H, D, halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, $OR^a$, $C(O)R^a$, $C(O)NR^aR^a$, $C(O)OR^a$, $NR^aR^a$, $NR^aC(O)R^a$, $NR^aC(O)OR^a$, $NR^aC(O)NR^aR^a$, $NR^aS(O)_2NR^aR^a$, $NR^aS(O)_2R^a$, $S(O)_2R^a$, and $S(O)_2NR^aR^a$, wherein the $C_{1-6}$ alkyl, $C_{2-6}$ alkenyl, $C_{2-6}$ alkynyl, 6-10 membered aryl, $C_{3-10}$ cycloalkyl, 5-10 membered heteroaryl, and 4-10 membered heterocycloalkyl are each optionally substituted with 1, 2, 3, or 4 independently selected $R^b$ substituents;
$Y^1$ is $C_{1-6}$ haloalkyl, wherein each halo is independently selected from Cl and F;
$R^8$ is selected from H, D, $C_{1-6}$ alkyl, $C_{1-6}$ alkoxy, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, and 4-10 membered heterocycloalkyl, wherein the $C_{1-6}$ alkyl, $C_{1-6}$ alkoxy, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, and 4-10 membered heterocycloalkyl are each optionally substituted with 1, 2, 3, or 4 independently selected $R^9$ substituents; or
$Y^1$ and $R^8$, together with the carbon atom to which they are attached, form a 4-, 5-, 6-, or 7-membered cycloalkyl group which is optionally substituted by 1 or 2 substituents independently selected from Cl and F;
each $R^9$ is independently selected from halo, $C_{1-6}$ alkyl, $C_{1-6}$ haloalkyl, phenyl, $C_{3-6}$ cycloalkyl, 5-6 membered heteroaryl, 4-6 membered heterocycloalkyl, phenyl-$C_{1-3}$ alkyl-, $C_{3-6}$ cycloalkyl-$C_{1-3}$ alkyl-, 5-6 membered heteroaryl-$C_{1-3}$ alkyl-, 4-6 membered heterocycloalkyl-$C_{1-3}$ alkyl-, CN, $OR^k$, $C(O)R^k$, $C(O)NR^kR^k$, $C(O)OR^k$, $NR^kR^k$, $NR^kC(O)R^k$, $NR^kC(O)OR^k$, $NR^kC(O)NR^kR^k$, $NR^kS(O)_2R^k$, $NR^kS(O)_2NR^kR^k$, $S(O)_2R^k$, and $S(O)_2NR^kR^k$, wherein the $C_{1-6}$ alkyl, $C_{1-6}$ haloalkyl, phenyl, $C_{3-6}$ cycloalkyl, 5-6 membered heteroaryl, 4-6 membered heterocycloalkyl, phenyl-$C_{1-3}$ alkyl-, $C_{3-6}$ cycloalkyl-$C_{1-3}$ alkyl-, 5-6 membered heteroaryl-$C_{1-3}$ alkyl-, and 4-6 membered heterocycloalkyl-$C_{1-3}$ alkyl- of $R^9$ is each optionally substituted with 1, 2, 3, or 4 independently selected $R^q$ substituents;
each $R^a$ is independently selected from H, D, $C_{1-6}$ alkyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl- of $R^a$ is each optionally substituted with 1, 2, or 3 independently selected $R^b$ substituents;
each $R^b$ is independently selected from halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, $OR^c$, $C(O)R^c$, $C(O)NR^cR^c$, $C(O)OR^c$, $OC(O)R^c$, $OC(O)NR^cR^c$, $NR^cR^c$, $NR^cC(O)R^c$, $NR^cC(O)OR^c$, $NR^cC(O)NR^cR^c$, $S(O)R^c$, $S(O)NR^cR^c$, $S(O)_2R^c$, and $S(O)_2NR^cR^c$, wherein the $C_{1-6}$ alkyl, $C_{2-6}$ alkenyl, $C_{2-6}$ alkynyl, 6-10 membered aryl, $C_{3-10}$ cycloalkyl, 5-10 membered heteroaryl, and 4-10 membered heterocycloalkyl are each optionally substituted with 1 or 2 independently selected $R^d$ substituents;
each $R^d$ is independently selected from D, halo, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, 4-7 membered heterocycloalkyl-$C_{1-6}$ alkyl-, OH, $NO_2$, CN, halo, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, 4-7 membered heterocycloalkyl-$C_{1-6}$ alkyl- of $R^d$ is each optionally substituted with 1, 2, 3 or 4 independently selected $R^f$ substituents;
each $R^f$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;
each $R^k$ is independently selected from H, D, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, 5-6 membered heteroaryl-$C_{1-4}$ alkyl-, and 4-7 membered heterocycloalkyl-$C_{1-4}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, 5-6 membered heteroaryl-$C_{1-4}$ alkyl-, and 4-7 membered heterocycloalkyl-$C_{1-4}$ alkyl- of $R^k$ is each optionally substituted with 1, 2, 3, or 4 independently selected $R^q$ substituents;

each $R^q$ is independently selected from D, halo, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, 4-7 membered heterocycloalkyl-$C_{1-6}$ alkyl-, OH, $NO_2$, CN, halo, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, 4-7 membered heterocycloalkyl-$C_{1-6}$ alkyl- of R is each optionally substituted with 1, 2, 3 or 4 independently selected $R^n$ substituents; and each $R^n$ is independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-6}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

27. The compound of claim 1, or a pharmaceutically acceptable salt thereof, wherein:

$X^2$ is N or $CR^2$;
$X^4$ is $CR^4$;
$X^5$ is N or $CR^5$;
$X^6$ is N or $CR^6$;
$X^7$ is $CR^7$;
wherein 0 or 1 of $X^5$ and $X^6$ are N;
$R^2$ is H;
$R^3$ is H;
$R^4$ is H, halo, or $C_{1-6}$ alkyl;
$R^5$ is H;
$R^6$ is H or halo;
$R^7$ is H;
$R^1$ is selected from H, $C_{1-6}$ alkyl, $C_{1-6}$ haloalkyl, phenyl, 3-6 membered cycloalkyl, 5-6 membered heteroaryl, 5-6 membered heterocycloalkyl, C(O)$NR^aR^a$, and C(O)$OR^a$, wherein the $C_{1-6}$ alkyl, phenyl, 3-6 membered cycloalkyl, 5-6 membered heteroaryl, 5-6 membered heterocycloalkyl are each optionally substituted with 1 or 2 independently selected $R^b$ substituents;
$Y^1$ is $C_{1-6}$ haloalkyl, wherein each halo is F;
$R^8$ is selected from H, $C_{1-6}$ alkyl, 6-10 membered aryl, $C_{3-10}$ cycloalkyl, 5-10 membered heteroaryl, and 4-10 membered heterocycloalkyl, wherein the $C_{1-6}$ alkyl, 6-10 membered aryl, $C_{3-10}$ cycloalkyl, 5-10 membered heteroaryl, and 4-10 membered heterocycloalkyl are each optionally substituted with 1, 2, 3, or 4 independently selected $R^9$ substituents; or $Y^1$ and $R^8$, together with the carbon atom to which they are attached, form a 4-, 5-, or 6-membered cycloalkyl group which is optionally substituted by 1 or 2 F;

each $R^9$ is independently selected from halo, $C_{1-6}$ alkyl, $C_{1-6}$ haloalkyl, CN, $OR^k$, and $NR^kR^k$; wherein the $C_{1-6}$ alkyl of $R^9$ is each optionally substituted with 1, 2, 3, or 4 independently selected $R^q$ substituents;

each $R^a$ is independently selected from H, $C_{1-6}$ alkyl, $C_{1-6}$ haloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl-, wherein the $C_{1-6}$ alkyl, $C_{1-6}$ haloalkyl, phenyl-$C_{1-6}$ alkyl-, $C_{3-7}$ cycloalkyl-$C_{1-6}$ alkyl-, 5-6 membered heteroaryl-$C_{1-6}$ alkyl-, and 4-7 membered heterocycloalkyl-$C_{1-6}$ alkyl- of $R^a$ is each optionally substituted with 1, 2, or 3 independently selected $R^b$ substituents;

each $R^b$ is independently selected from halo, $C_{1-6}$ alkyl, $C_{2-6}$ alkenyl, $C_{2-6}$ alkynyl, $C_{1-6}$ haloalkyl, 6-10 membered aryl, $C_{3-10}$ cycloalkyl, 5-10 membered heteroaryl, 4-10 membered heterocycloalkyl, $OR^c$, C(O)$R^c$, C(O)$NR^cR^c$, C(O)$OR^c$, OC(O)$R^c$, OC(O)$NR^cR^c$, $NR^cR^c$, $NR^cC(O)R^c$, $NR^cC(O)OR^c$, $NR^cC(O)NR^cR^c$, S(O)$R^c$, S(O)$NR^cR^c$, S(O)$_2R^c$, and S(O)$_2NR^cR^c$, wherein the $C_{1-6}$ alkyl, $C_{2-6}$ alkenyl, $C_{2-6}$ alkynyl, 6-10 membered aryl, $C_{3-10}$ cycloalkyl, 5-10 membered heteroaryl, and 4-10 membered heterocycloalkyl are each optionally substituted with 1 or 2 independently selected $R^d$ substituents;

each $R^c$ is independently selected from H, $C_{1-6}$ alkyl, and $C_{1-6}$ haloalkyl, wherein the $C_{1-6}$ alkyl and $C_{1-6}$ haloalkyl of $R^c$ is each optionally substituted with 1, 2, 3, or 4 independently selected $R^d$ substituents;

each $R^d$ is independently selected from D, halo, $C_{1-6}$ alkyl, $C_{1-6}$ haloalkyl, OH, CN, $C_{1-6}$ alkoxy, $C_{1-6}$ haloalkoxy, amino, $C_{1-6}$ alkylamino, and di($C_{1-6}$ alkyl)amino;

each $R^k$ is independently selected from H, $C_{1-6}$ alkyl, $C_{1-6}$ haloalkyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, 5-6 membered heteroaryl-$C_{1-4}$ alkyl-, and 4-7 membered heterocycloalkyl-$C_{1-4}$ alkyl-, wherein the $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, 5-6 membered heteroaryl-$C_{1-4}$ alkyl-, and 4-7 membered heterocycloalkyl-$C_{1-4}$ alkyl- of $R^k$ is each optionally substituted with 1, 2, 3, or 4 independently selected $R^q$ substituents; and each $R^q$ is independently selected halo, $C_{1-6}$ alkyl, $C_{1-6}$ haloalkyl, OH, CN, $C_{1-6}$ alkoxy, $C_{1-6}$ haloalkoxy, amino, $C_{1-6}$ alkylamino, di($C_{1-6}$ alkyl)amino, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, and di($C_{1-6}$ alkyl)aminosulfonyl.

28. The compound of claim 1, or a pharmaceutically acceptable salt thereof, wherein:

$X^2$ is N or $CR^2$;
$X^4$ is $CR^4$;
$X^5$ is N or $CR^5$;

$X^6$ is N or $CR^6$;
$X^7$ is $CR^7$;
wherein 0 or 1 of $X^5$ and $X^6$ are N;
$R^2$ is H;
$R^3$ is H;
$R^4$ is H, halo, or $C_{1-6}$ alkyl;
$R^5$ is H;
$R^6$ is H or halo;
$R^7$ is H;
$R^1$ is selected from H, $C_{1-6}$ alkyl, $C_{1-6}$ haloalkyl, C(O)$OR^a$, C(O)$NR^aR^a$, phenyl, cyclopropyl, thiazolyl, pyrazolyl, oxazolyl, pyrimidinyl, pyridinyl, isoxazolyl, 1,2,4-triazolyl, and piperidinyl; wherein said $C_{1-6}$ alkyl, $C_{1-6}$ haloalkyl, phenyl, cyclopropyl, thiazolyl, pyrazolyl, oxazolyl, pyrimidinyl, pyridinyl, isoxazolyl, 1,2,4-triazolyl, and piperidinyl are each optionally substituted by 1, 2, 3, or 4 independently selected $R^b$ substituents;
$Y^1$ is $C_{1-6}$ haloalkyl, wherein each halo is F;
$R^8$ is selected from H, $C_{1-6}$ alkyl, $C_{3-6}$ cycloalkyl, 5-6 membered heteroaryl, wherein the $C_{1-6}$ alkyl, $C_{3-6}$ cycloalkyl, and 5-6 membered heteroaryl are each optionally substituted with 1 or 2 independently selected $R^9$ substituents; or
$Y^1$ and $R^8$, together with the carbon atom to which they are attached, form a 4-5-, or 6-membered cycloalkyl group which is optionally substituted by one F;
each $R^9$ is independently selected from $C_{1-6}$ alkyl, $OR^k$, and $NR^kR^k$;
each $R^a$ is selected from H, $C_{1-6}$ alkyl, and isoxazol-5-ylmethyl; wherein said isoxazol-5-ylmethyl is substituted by methyl and said $C_{1-6}$ alkyl is optionally substituted by OH;
each $R^b$ is independently selected from halo, $C_{1-6}$ alkyl, $C_{3-6}$ cycloalkyl, $OR^c$, and C(O)$NR^cR^c$, wherein the $C_{1-6}$ alkyl and $C_{3-6}$ cycloalkyl are each optionally substituted with 1 or 2 independently selected $R^d$ substituents;
each $R^c$ group is independently selected from H and $C_{1-6}$ alkyl;
each $R^d$ is independently selected from D, $C_{1-6}$ alkyl and OH; and
each $R^k$ is independently selected from H, $C_{1-6}$ alkyl, $C_{3-7}$ cycloalkyl, and 4-7 membered heterocycloalkyl, wherein the $C_{1-6}$ alkyl, $C_{3-7}$ cycloalkyl, and 4-7 membered heterocycloalkyl of $R^k$ is each optionally substituted with 1 or 2 independently selected $C_{1-6}$ alkyl groups.

29. The compound of claim 1, or a pharmaceutically acceptable salt thereof, wherein:
$X^2$ is N or $CR^2$;
$X^4$ is $CR^4$;
$X^5$ is N or $CR^5$;
$X^6$ is N or $CR^6$;
$X^7$ is $CR^7$;
wherein 0 or 1 $X^5$ and $X^6$ are N;
$R^2$ is H;
$R^3$ is H;
$R^4$ is H, F, methyl, or $CD_3$;
$R^5$ is H;
$R^6$ is H or F;
$R^7$ is H;
$Y^1$ is $CF_3$, $CHF_2$, $CH_2F$, or $CF_2CF_3$;
$R^1$ is selected from H, methyl, $CF_3$, C(O)$OR^a$, C(O)$NR^aR^a$, phenyl, cyclopropyl, pyrazolyl, oxazolyl, pyrimidinyl, pyridinyl, isoxazolyl, 1,2,4-triazolyl, and piperindinyl, wherein the phenyl, cyclopropyl, thiazolyl, pyrazolyl, oxazolyl, pyrimidinyl, pyridinyl, isoxazolyl, 1,2,4-triazolyl, and piperidinyl are each optionally substituted by 1 or 2 independently selected $R^b$ substituents;
$R^8$ is selected from H, methyl, hydroxymethyl, ethyl, 2-hydroxyethyl, 2-(N-methylamino)ethyl, 2-(N-{tetrahydro-2H-pyran-4-yl}amino)ethyl, cyclopropyl, and 1-methyl-1H-tetrazol-5-yl;
or $Y^1$ and $R^8$, together with the carbon atom to which they are attached, form a 2-flourocyclopentyl ring;
each $R^a$ is independently selected from H, methyl, 2-hydroxy-2-methylpropyl, and (3-methylisoxazol-5-yl)methyl; and
each $R^b$ is independently selected from fluoro, methyl, $CD_3$, hydroxymethyl, methoxy, C(O)$NH_2$, and cyclopropyl.

30. The compound of claim 1, wherein the compound of Formula (I) is a compound of Formula (II):

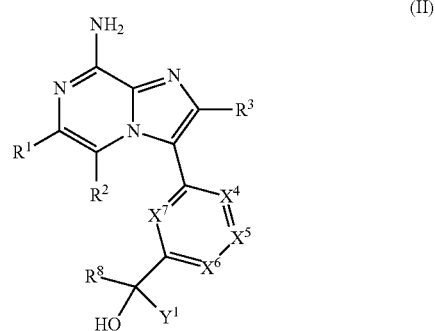

(II)

or a pharmaceutically acceptable salt thereof.

31. The compound of claim 1, wherein the compound of Formula (I) is a compound of Formula (III):

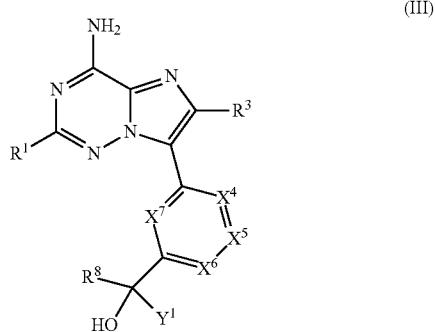

(III)

or a pharmaceutically acceptable salt thereof.

32. The compound of claim 1, wherein the compound of Formula (I) is a compound of Formula (IV):

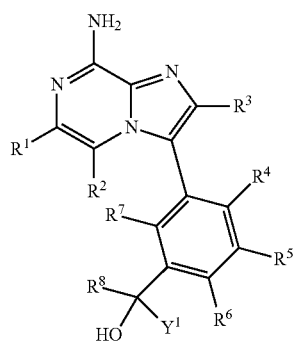

(IV)

or a pharmaceutically acceptable salt thereof.

33. The compound of claim 1, wherein the compound of Formula (I) is a compound of Formula (V):

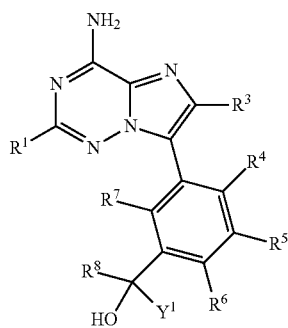

(V)

or a pharmaceutically acceptable salt thereof.

34. The compound of claim 1, selected from:
2-(3-(4-Amino-2-(trifluoromethyl)imidazo[2,1-f][1,2,4] triazin-7-yl)-4-methylphenyl)-1,1,1-trifluoropropan-2-ol;
2-(3-(4-Amino-2-methylimidazo[2,1-f][1,2,4]triazin-7-yl)-4-methylphenyl)-1,1,1-trifluoropropan-2-ol;
2-(3-(4-Aminoimidazo[2,1-f][1,2,4]triazin-7-yl)-4-methylphenyl)-1,1,1-trifluoropropan-2-ol;
2-(3-(8-Amino-6-(trifluoromethyl)imidazo[1,2-a] pyrazin-3-yl)-4-methylphenyl)-1,1,1-trifluoropropan-2-ol;
2-(3-(8-Amino-6-methylimidazo[1,2-a]pyrazin-3-yl)-4-methylphenyl)-1,1,1-trifluoropropan-2-ol;
Methyl 8-amino-3-(2-methyl-5-(1,1,1-trifluoro-2-hydroxypropan-2-yl)phenyl)imidazo[1,2-a]pyrazine-6-carboxylate;
8-Amino-N-methyl-3-(2-methyl-5-(1,1,1-trifluoro-2-hydroxypropan-2-yl)phenyl)imidazo[1,2-a]pyrazine-6-carboxamide;
8-Amino-3-(2-methyl-5-(1,1,1-trifluoro-2-hydroxypropan-2-yl)phenyl)-N-((3-methylisoxazol-5-yl)methyl) imidazo[1,2-a]pyrazine-6-carboxamide;
2-(3-(8-Amino-6-(2-(hydroxymethyl)pyridin-4-yl)imidazo[1,2-a]pyrazin-3-yl)-4-methylphenyl)-1,1,1-trifluoropropan-2-ol;
2-(3-(8-Amino-6-(2-cyclopropylthiazol-5-yl)imidazo[1,2-a]pyrazin-3-yl)-4-methylphenyl)-1,1,1-trifluoropropan-2-ol;
2-(3-(8-Amino-6-(5-methoxythiazol-2-yl)imidazo[1,2-a] pyrazin-3-yl)-4-methylphenyl)-1,1,1-trifluoropropan-2-ol;
1-(3-(8-Amino-6-(trifluoromethyl)imidazo[1,2-a] pyrazin-3-yl)-4-methylphenyl)-2,2,2-trifluoro-1-(1-methyl-1H-tetrazol-5-yl)ethan-1-ol;
2-(3-(8-Amino-6-(trifluoromethyl)imidazo[1,2-a] pyrazin-3-yl)-4-methylphenyl)-1,1,1-trifluoro-4-(methylamino)butan-2-ol;
2-(3-(8-Amino-6-(trifluoromethyl)imidazo[1,2-a] pyrazin-3-yl)-4-methylphenyl)-1,1,1-trifluoro-4-((tetrahydro-2H-pyran-4-yl)amino)butan-2-ol;
3-(3-(8-Amino-6-(trifluoromethyl)imidazo[1,2-a] pyrazin-3-yl)-4-methylphenyl)-4,4,4-trifluorobutane-1,3-diol;
1-(3-(8-Amino-6-(trifluoromethyl)imidazo[1,2-a] pyrazin-3-yl)-4-methylphenyl)-1-cyclopropyl-2,2,2-trifluoroethan-1-ol;
1-(3-(8-Amino-6-(trifluoromethyl)imidazo[1,2-a] pyrazin-3-yl)-4-methylphenyl)-2,2,2-trifluoroethan-1-ol;
2-(3-(8-Amino-6-(trifluoromethyl)imidazo[1,2-a] pyrazin-3-yl)-4-methylphenyl)-1-fluoropropan-2-ol;
2-(3-(8-Amino-6-(1-(methyl-d$_3$)-1H-pyrazol-5-yl)imidazo[1,2-a]pyrazin-3-yl)-4-methylphenyl)-1,1-difluoropropan-2-ol;
2-(3-(8-Amino-6-(trifluoromethyl)imidazo[1,2-a] pyrazin-3-yl)-4-methylphenyl)-1,1-difluoropropan-2-ol;
2-(3-(8-Amino-6-(2-methyloxazol-5-yl)imidazo[1,2-a] pyrazin-3-yl)-4-methylphenyl)-1,1-difluoropropan-2-ol;
2-(3-(8-Amino-6-(1-methyl-1H-pyrazol-5-yl)imidazo[1,2-a]pyrazin-3-yl)-4-methylphenyl)-1,1-difluoropropan-2-ol;
3-(8-Amino-3-(5-(1,1-difluoro-2-hydroxypropan-2-yl)-2-methylphenyl)imidazo[1,2-a]pyrazin-6-yl)-4-fluorobenzamide;
2-(3-(8-Amino-6-(pyrimidin-5-yl)imidazo[1,2-a]pyrazin-3-yl)-4-methylphenyl)-1,1-difluoropropan-2-ol;
2-(3-(8-Amino-6-(2-methoxypyridin-3-yl)imidazo[12-a] pyrazin-3-yl)-4-methylphenyl)-1,1-difluoropropan-2-ol;
2-(3-(8-Amino-6-(2-methylthiazol-5-yl)imidazo[1,2-a] pyrazin-3-yl)-4-methylphenyl)-1,1-difluoropropan-2-ol;
2-(3-(8-Amino-6-(3-fluoro-2-methylpyridin-4-yl)imidazo[1,2-a]pyrazin-3-yl)-4-methylphenyl)-1,1-difluoropropan-2-ol;
2-(3-(8-Amino-6-(1,5-dimethyl-1H-pyrazol-4-yl)imidazo[1,2-a]pyrazin-3-yl)-4-methylphenyl)-1,1-difluoropropan-2-ol;
2-(3-(8-Amino-6-(1-methyl-1H-pyrazol-4-yl)imidazo[1,2-a]pyrazin-3-yl)-4-methylphenyl)-1,1-difluoropropan-2-ol;
2-(3-(8-Amino-6-(1,3-dimethyl-1H-pyrazol-4-yl)imidazo[1,2-a]pyrazin-3-yl)-4-methylphenyl)-1,1-difluoropropan-2-ol;
2-(3-(8-Amino-6-(3,5-dimethyl-1H-pyrazol-4-yl)imidazo[1,2-a]pyrazin-3-yl)-4-methylphenyl)-1,1-difluoropropan-2-ol;
2-(3-(8-Amino-6-(1H-pyrazol-4-yl)imidazo[1,2-a] pyrazin-3-yl)-4-methylphenyl)-1,1-difluoropropan-2-ol;
2-(3-(8-Amino-6-(1,3-dimethyl-1H-pyrazol-5-yl)imidazo[1,2-a]pyrazin-3-yl)-4-methylphenyl)-1,1-difluoropropan-2-ol;
2-(3-(8-Amino-6-(1,4-dimethyl-1H-pyrazol-5-yl)imidazo[1,2-a]pyrazin-3-yl)-4-methylphenyl)-1,1-difluoropropan-2-ol;

2-(3-(8-Amino-6-(1-methyl-1H-pyrazol-3-yl)imidazo[1,
2-a]pyrazin-3-yl)-4-methylphenyl)-1,1-difluoropropan-2-ol;
2-(3-(8-Amino-6-(2-(hydroxymethyl)pyridin-4-yl)imidazo[1,2-a]pyrazin-3-yl)-4-methylphenyl)-1,1-difluoropropan-2-ol;
2-(3-(8-Amino-6-(6-(hydroxymethyl)pyridin-3-yl)imidazo[1,2-a]pyrazin-3-yl)-4-methylphenyl)-1,1-difluoropropan-2-ol;
2-(3-(8-Amino-6-(3-methyl-1H-pyrazol-4-yl)imidazo[1,
2-a]pyrazin-3-yl)-4-methylphenyl)-1,1-difluoropropan-2-ol;
2-(3-(8-Amino-6-(3-methylisoxazol-5-yl)imidazo[1,2-a]pyrazin-3-yl)-4-methylphenyl)-1,1-difluoropropan-2-ol;
2-(3-(8-Amino-6-(1H-1,2,4-triazol-1-yl)imidazo[1,2-a]pyrazin-3-yl)-4-methylphenyl)-1,1-difluoropropan-2-ol;
2-(3-(8-Amino-6-(1-methyl-1H-pyrazol-5-yl)imidazo[1,
2-a]pyrazin-3-yl)-4-methylphenyl)-1,1-difluorobutan-2-ol;
2-(3-(4-Amino-2-(1-methyl-1H-pyrazol-5-yl)imidazo[2,
1-f][1,2,4]triazin-7-yl)-4-methylphenyl)-1,1-difluoropropan-2-ol;
2-(3-(4-Amino-2-(2-methyloxazol-5-yl)imidazo[2,1-f][1,
2,4]triazin-7-yl)-4-methylphenyl)-1,1-difluoropropan-2-ol;
2-(5-(8-Amino-6-(trifluoromethyl)imidazo[1,2-a]pyrazin-3-yl)-2-fluoro-4-methylphenyl)-1,1,1-trifluoropropan-2-ol;
2-(4-(8-Amino-6-(trifluoromethyl)imidazo[1,2-a]pyrazin-3-yl)-5-methylpyridin-2-yl)-1,1,1-trifluoropropan-2-ol;
2-(5-(8-Amino-6-(trifluoromethyl)imidazo[1,2-a]pyrazin-3-yl)-2-fluorophenyl)-1,1,1-trifluoropropan-2-ol;
2-(3-(8-Amino-6-(trifluoromethyl)imidazo[1,2-a]pyrazin-3-yl)phenyl)-1,1,1-trifluoropropan-2-ol;
2-(3-(8-Amino-6-(trifluoromethyl)imidazo[1,2-a]pyrazin-3-yl)-4-fluorophenyl)-1,1,1-trifluoropropan-2-ol;
2-(5-(8-Amino-6-(trifluoromethyl)imidazo[1,2-a]pyrazin-3-yl)-6-methylpyridin-3-yl)-1,1,1-trifluoropropan-2-ol;
2-(3-(8-Amino-6-(trifluoromethyl)imidazo[1,2-a]pyrazin-3-yl)-4-methylphenyl)-3,3,4,4,4-pentafluorobutan-2-ol;
1-(3-(8-Amino-6-(trifluoromethyl)imidazo[1,2-a]pyrazin-3-yl)-4-methylphenyl)-2-fluorocyclopentan-1-ol; and
8-amino-N-(2-hydroxy-2-methylpropyl)-3-(2-methyl-5-(1,1,1-trifluoro-2-hydroxypropan-2-yl)phenyl)imidazo[1,2-a]pyrazine-6-carboxamide;
or a pharmaceutically acceptable salt thereof.
35. The compound of claim 1, selected from:
1-(8-Amino-3-(5-(1,1-difluoro-2-hydroxypropan-2-yl)-2-methylphenyl)imidazo[1,2-a]pyrazin-6-yl)piperidine-4-carbonitrile;
1-(8-Amino-3-(2-methyl-5-(1,1,1-trifluoro-2-hydroxypropan-2-yl)phenyl)imidazo[1,2-a]pyrazin-6-yl)piperidin-4-ol;
2-(3-(8-Amino-6-(1-(methyl-d3)-1H-pyrazol-5-yl)imidazo[1,2-a]pyrazin-3-yl)-4-methylphenyl)-3,3,3-trifluoropropane-1,2-diol;
2-(3-(8-Amino-6-(2-methyloxazol-5-yl)imidazo[1,2-a]pyrazin-3-yl)-4-methylphenyl)-3,3,3-trifluoropropane-1,2-diol;
2-(3-(8-Amino-6-(1-methyl-1H-pyrazol-4-yl)imidazo[1,
2-a]pyrazin-3-yl)-4-methylphenyl)-3,3,3-trifluoropropane-1,2-diol;
2-(3-(8-Amino-6-(2-methylthiazol-5-yl)imidazo[1,2-a]pyrazin-3-yl)-4-methylphenyl)-3,3,3-trifluoropropane-1,2-diol;
2-(3-(8-Amino-6-(oxazol-5-yl)imidazo[1,2-a]pyrazin-3-yl)-4-methylphenyl)-3,3,3-trifluoropropane-1,2-diol;
2-(3-(8-Amino-6-(trifluoromethyl)imidazo[1,2-a]pyrazin-3-yl)-4-methylphenyl)-3,3,3-trifluoropropane-1,2-diol;
Ethyl 2-(8-amino-3-(5-(1,1-difluoro-2-hydroxypropan-2-yl)-2-methylphenyl)imidazo[1,2-a]pyrazin-6-yl)cyclopropane-1-carboxylate;
2-(8-Amino-3-(5-(1,1-difluoro-2-hydroxypropan-2-yl)-2-methylphenyl)imidazo[1,2-a]pyrazin-6-yl)-N-methylcyclopropane-1-carboxamide;
(2-(8-Amino-3-(5-(1,1-difluoro-2-hydroxypropan-2-yl)-2-methylphenyl)imidazo[1,2-a]pyrazin-6-yl)cyclopropyl)(4-methylpiperazin-1-yl)methanone;
2-(8-Amino-3-(5-(1,1-difluoro-2-hydroxypropan-2-yl)-2-methylphenyl)imidazo[1,2-a]pyrazin-6-yl)-N-(1-hydroxy-2-methylpropan-2-yl)cyclopropane-1-carboxamide;
2-(3-(8-Amino-6-(2-(hydroxymethyl)cyclopropyl)imidazo[1,2-a]pyrazin-3-yl)-4-methylphenyl)-1,1-difluoropropan-2-ol; and
8-Amino-N-(2-hydroxy-2-methylpropyl)-3-(2-(methyl-d3)-5-(1,1,1-trifluoro-2-hydroxypropan-2-yl)phenyl)imidazo[1,2-a]pyrazine-6-carboxamide;
or a pharmaceutically acceptable salt thereof.
36. The compound of claim 1, selected from:
2-(3-(8-Amino-6-(trifluoromethyl)imidazo[1,2-a]pyrazin-3-yl)-4-methylphenyl)-3,3,3-trifluoro-2-hydroxypropanamide;
8-Amino-3-(5-(3-amino-1,1,1-trifluoro-2-hydroxy-3-oxopropan-2-yl)-2-methylphenyl)-N-(3-cyclopropyltetrahydrofuran-3-yl)imidazo[1,2-a]pyrazine-6-carboxamide;
8-Amino-3-(5-(3-amino-1,1,1-trifluoro-2-hydroxy-3-oxopropan-2-yl)-2-methylphenyl)-N-(2,3-dimethyltetrahydrofuran-3-yl)imidazo[1,2-a]pyrazine-6-carboxamide;
8-Amino-3-(5-(3-amino-1,1,1-trifluoro-2-hydroxy-3-oxopropan-2-yl)-2-methylphenyl)-N-(4-(trifluoromethyl)tetrahydro-2H-pyran-4-yl)imidazo[1,2-a]pyrazine-6-carboxamide;
3-(4-(8-Amino-3-(2-(methyl-d3)-5-(1,1,1-trifluoro-2-hydroxypropan-2-yl)phenyl)imidazo[1,2-a]pyrazin-6-yl)-1H-pyrazol-1-yl)-3-cyclobutylpropanenitrile;
2-(3-(8-Amino-6-(5,6-dihydro-4H-pyrrolo[1,2-b]pyrazol-3-yl)imidazo[1,2-a]pyrazin-3-yl)-4-(methyl-d3)phenyl)-1,1,1-trifluoropropan-2-ol; and
Methyl 3-(4-(8-amino-3-(2-(methyl-d3)-5-(1,1,1-trifluoro-2-hydroxypropan-2-yl)phenyl)imidazo[1,2-a]pyrazin-6-yl)-1H-pyrazol-1-yl)-3-(cyanomethyl)cyclobutane-1-carboxylate;
or a pharmaceutically acceptable salt thereof.
37. The compound of claim 1, selected from:
2-(3-(8-Amino-6-(trifluoromethyl)imidazo[1,2-a]pyrazin-3-yl)-4-methylphenyl)-3,3-difluoro-2-hydroxypropanamide;
2-(3-(4-(8-amino-3-(5-(1,1-difluoro-2-hydroxypropan-2-yl)-2-methylphenyl)imidazo[1,2-a]pyrazin-6-yl)-1H-pyrazol-1-yl)-1-(cyclobutanecarbonyl)azetidin-3-yl)acetonitrile;

2-(3-(8-Amino-6-(5-(methylsulfonyl)pyridin-3-yl)imidazo[1,2-a]pyrazin-3-yl)-4-methylphenyl)-1,1-difluoropropan-2-ol;
(4-(8-amino-3-(5-(1,1-difluoro-2-hydroxypropan-2-yl)-2-methylphenyl)imidazo[1,2-a]pyrazin-6-yl)phenyl)boronic acid;
2-(3-(4-Amino-2-methylimidazo[2,1-f][1,2,4]triazin-7-yl)-4-methylphenyl)-1,1,3,3-tetrafluoropropan-2-ol;
((1S)-(8-Amino-3-(2-methyl-5-(1,1,1-trifluoro-2-hydroxypropan-2-yl)phenyl)imidazo[1,2-a]pyrazine-6-carboxamido)(cyclobutyl)methyl)boronic acid;
2-(3-(8-Amino-6-(trifluoromethyl)imidazo[1,2-a]pyrazin-3-yl)-4-methylphenyl)-3,3,3-trifluoro-2-hydroxy-N-methylpropanamide;
2-(3-(8-amino-6-(trifluoromethyl)imidazo[1,2-a]pyrazin-3-yl)-4-methylphenyl)-3,3,3-trifluoro-2-hydroxypropanoic acid;
2-(3-(8-Amino-6-(trifluoromethyl)imidazo[1,2-a]pyrazin-3-yl)-4-methylphenyl)-3,3,3-trifluoro-2-hydroxy-N-(3-methylazetidin-3-yl)propanamide;
2-(3-(8-Amino-6-(trifluoromethyl)imidazo[1,2-a]pyrazin-3-yl)-4-methylphenyl)-N-(bicyclo[1.1.1]pentan-1-yl)-3,3,3-trifluoro-2-hydroxypropanamide;
2-(3-(8-Amino-6-(6-(1-hydroxyethyl)pyridin-3-yl)imidazo[1,2-a]pyrazin-3-yl)-4-methylphenyl)-1,1-difluoropropan-2-ol;
2-(3-(8-Amino-6-(cyclopropylethynyl)imidazo[1,2-a]pyrazin-3-yl)-4-methylphenyl)-1,1,1-trifluoropropan-2-ol;
2-(8-amino-3-(2-methyl-5-(1,1,1-trifluoro-2-hydroxypropan-2-yl)phenyl)imidazo[1,2-a]pyrazin-6-yl)-N,N-dimethylacetamide;
2-(8-amino-3-(2-methyl-5-(1,1,1-trifluoro-2-hydroxypropan-2-yl)phenyl)imidazo[1,2-a]pyrazin-6-yl)-1-morpholinoethanone;
2-(3-(8-amino-6-(3-(hydroxymethyl)cyclobutyl)imidazo[1,2-a]pyrazin-3-yl)-4-methylphenyl)-1,1,1-trifluoropropan-2-ol;
N-(2-(3-(8-amino-6-(trifluoromethyl)imidazo[1,2-a]pyrazin-3-yl)-4-methylphenyl)-3,3,3-trifluoro-2-hydroxypropyl)acetamide;
N-(2-(3-(8-amino-6-(trifluoromethyl)imidazo[1,2-a]pyrazin-3-yl)-4-methylphenyl)-3,3,3-trifluoro-2-hydroxypropyl)benzamide;
N-(2-(3-(8-amino-6-(trifluoromethyl)imidazo[1,2-a]pyrazin-3-yl)-4-methylphenyl)-3,3,3-trifluoro-2-hydroxypropyl)-2-fluoroacetamide;
3-(5-(3-acetamido-1,1,1-trifluoro-2-hydroxypropan-2-yl)-2-methylphenyl)-8-amino-N-ethylimidazo[1,2-a]pyrazine-6-carboxamide;
2-(4-(8-Amino-6-(trifluoromethyl)imidazo[1,2-a]pyrazin-3-yl)-1-(phenylsulfonyl)-1H-indol-6-yl)-1,1,1-trifluoropropan-2-ol;
2-(3-(8-Amino-6-(trifluoromethyl)imidazo[1,2-a]pyrazin-3-yl)-4-(methyl-d$_3$)phenyl)-1,1,1-trifluorobutane-2,3-diol;
2-(3-(8-Amino-6-(trifluoromethyl)imidazo[1,2-a]pyrazin-3-yl)-4-(methyl-d$_3$)phenyl)-1,1,1-trifluoro-3-methylbutane-2,3-diol;
2-(3-(8-Amino-6-(2-hydroxypropan-2-yl)imidazo[1,2-a]pyrazin-3-yl)-4-(methyl-d3)phenyl)-1,1,1-trifluoropropan-2-ol;
2-(3-(8-Amino-6-(2-hydroxypropan-2-yl)imidazo[1,2-a]pyrazin-3-yl)-4-methylphenyl)-3,3,3-trifluoro-2-hydroxypropanamide;
3-(3-(8-Amino-6-(trifluoromethyl)imidazo[1,2-a]pyrazin-3-yl)-4-methylphenyl)-4,4,4-trifluoro-3-hydroxy-N,2,2-trimethylbutanamide;
2-(3-(8-Amino-6-(1-methyl-1H-pyrazol-5-yl)imidazo[1,2-a]pyrazin-3-yl)-4-methylphenyl)-1,1,1,3,3,3-hexafluoropropan-2-ol;
2-(3-(8-Amino-6-(6-(1-hydroxyethyl)pyridin-3-yl)imidazo[1,2-a]pyrazin-3-yl)-4-(methyl-d$_3$)phenyl)-1,1,1-trifluoropropan-2-ol;
2-(3-(8-Amino-6-(trifluoromethyl)imidazo[1,2-a]pyrazin-3-yl)-4-methylphenyl)-1-chloro-1,1-difluoropropan-2-ol;
8-Amino-N-(1-azabicyclo[2.2.1]heptan-4-yl)-3-(2-methyl-5-(1,1,1-trifluoro-2-hydroxypropan-2-yl)phenyl)imidazo[1,2-a]pyrazine-6-carboxamide;
8-Amino-N-(3-cyanobicyclo[1.1.1]pentan-1-yl)-3-(2-methyl-5-(1,1,1-trifluoro-2-hydroxypropan-2-yl)phenyl)imidazo[1,2-a]pyrazine-6-carboxamide;
8-Amino-N-(1-(hydroxymethyl)-2-oxabicyclo[2.1.1]hexan-4-yl)-3-(2-methyl-5-(1,1,1-trifluoro-2-hydroxypropan-2-yl)phenyl)imidazo[1,2-a]pyrazine-6-carboxamide;
8-Amino-N-((1-cyanocyclobutyl)methyl)-3-(2-methyl-5-(1,1,1-trifluoro-2-hydroxypropan-2-yl)phenyl)imidazo[1,2-a]pyrazine-6-carboxamide;
8-Amino-3-(5-(3-amino-1,1,1-trifluoro-2-hydroxy-3-oxopropan-2-yl)-2-methylphenyl)-N-(2-hydroxy-2-methylpropyl)imidazo[1,2-a]pyrazine-6-carboxamide;
8-Amino-3-(5-(3-amino-1,1,1-trifluoro-2-hydroxy-3-oxopropan-2-yl)-2-methylphenyl)-N-(4-hydroxybicyclo[2.2.1]heptan-1-yl)imidazo[1,2-a]pyrazine-6-carboxamide;
8-Amino-3-(5-(3-amino-1,1,1-trifluoro-2-hydroxy-3-oxopropan-2-yl)-2-methylphenyl)-N-(tetrahydro-2H-pyran-4-yl)imidazo[1,2-a]pyrazine-6-carboxamide;
8-Amino-3-(5-(3-amino-1,1,1-trifluoro-2-hydroxy-3-oxopropan-2-yl)-2-methylphenyl)-N-(3-fluorobicyclo[1.1.1]pentan-1-yl)imidazo[1,2-a]pyrazine-6-carboxamide; and
8-Amino-N-(3-cyano-1,1,1-trifluoropropan-2-yl)-3-(2-methyl-5-(1,1,1-trifluoro-2-hydroxy-3-((methyl-d$_3$)amino)-3-oxopropan-2-yl)phenyl)imidazo[1,2-a]pyrazine-6-carboxamide;
or a pharmaceutically acceptable salt thereof.

38. A pharmaceutical composition comprising a compound of claim 1, or a pharmaceutically acceptable salt thereof, and a pharmaceutically acceptable excipient or carrier.

* * * * *

UNITED STATES PATENT AND TRADEMARK OFFICE
CERTIFICATE OF CORRECTION

PATENT NO. : 10,738,057 B2
APPLICATION NO. : 16/163341
DATED : August 11, 2020
INVENTOR(S) : Brent Douty et al.

It is certified that error appears in the above-identified patent and that said Letters Patent is hereby corrected as shown below:

In the Claims

Column 302, Lines 21-22, Claim 1, delete "$NR^kC(=NOH)NR^kR^k$" and insert -- $NR^kC(=NOH)NR^kR^k$, --;

Column 303, Line 33, Claim 1, delete "$NR^gC(O)OR^9$," and insert -- $NR^gC(O)OR^g$, --;

Column 304, Line 39, Claim 1, delete "$P(O)(OR^m)(OR^m)$," and insert -- $—P(O)(OR^m)(OR^m)$, --;

Column 306, Line 27, Claim 17, delete "phenyl-$C_1$-3 alkyl-" and insert -- phenyl-$C_{1-3}$ alkyl- --;

Column 310, Line 10, Claim 26, delete "$NR^cR^c$" and insert -- $NR^cR^c$, --;

Column 313, Line 67, Claim 29, delete "piperindinyl," and insert -- piperidinyl, --;

Column 314, Line 11, Claim 29, delete "2-flourocyclopentyl" and insert -- 2-fluorocyclopentyl --; and Column 316, Line 38, Claim 34, delete "[12-a]" and insert -- [1,2-a] --.

Signed and Sealed this
Seventeenth Day of November, 2020

Andrei Iancu
*Director of the United States Patent and Trademark Office*